US012226440B2

(12) United States Patent
Thorne et al.

(10) Patent No.: US 12,226,440 B2
(45) **Date of Patent: *Feb. 18, 2025**

(54) PLATFORM ONCOLYTIC VECTOR FOR SYSTEMIC DELIVERY

(71) Applicant: KaliVir Immunotherapeutics, Inc., Pittsburgh, PA (US)

(72) Inventors: Stephen H. Thorne, Pittsburgh, PA (US); Daniel J. Byrd, Pittsburgh, PA (US); Mingrui Zhang, Pittsburgh, PA (US)

(73) Assignee: KaliVir Immunotherapeutics, Inc., Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/513,034

(22) Filed: Oct. 28, 2021

(65) Prior Publication Data

US 2022/0054565 A1 Feb. 24, 2022

Related U.S. Application Data

(63) Continuation of application No. 17/192,736, filed on Mar. 4, 2021, which is a continuation of application (Continued)

(51) Int. Cl.
*A61K 35/768* (2015.01)
*A61P 35/00* (2006.01)
(Continued)

(52) U.S. Cl.
CPC ............ *A61K 35/768* (2013.01); *A61P 35/00* (2018.01); *C07K 14/7158* (2013.01); *C12N 7/00* (2013.01);
(Continued)

(58) Field of Classification Search
CPC ....... A61K 35/768; A61K 38/47; A61P 35/00; C07K 14/7158; C12N 7/00; C12N 15/86;
(Continued)

(56) References Cited

U.S. PATENT DOCUMENTS 4,458,066 A 7/1984 Caruthers
4,797,368 A 1/1989 Carter
(Continued)

FOREIGN PATENT DOCUMENTS

CN 101381742 A 3/2009
CN 1754002 B 9/2010
(Continued)

OTHER PUBLICATIONS

Hiley CT, Yuan M, Lemoine NR, Wang Y. Lister strain vaccinia virus, a potential therapeutic vector targeting hypoxic tumours. Gene therapy. Feb. 2010;17(2):281-7. (Year: 2010).*
(Continued)

*Primary Examiner* — Jeremy C Flinders
*Assistant Examiner* — Thomas R. Amick
(74) *Attorney, Agent, or Firm* — Greenberg Traurig, LLP

(57) ABSTRACT

Described herein are modified oncolytic viruses that can contain modifications in the viral genome and exogenous nucleic acids coding for proteins. The modified oncolytic virus can be utilized as a platform vector for systemic delivery. Further described herein are oncolytic viruses having an exogenous nucleic acid that codes for a protein or a functional variant thereof that enhances degradation of an extracellular matrix (ECM) associated with a tumor, wherein the protein is a membrane associated protein.

18 Claims, 45 Drawing Sheets

Specification includes a Sequence Listing.

Related U.S. Application Data

No. 16/759,705, filed as application No. PCT/US2018/058456 on Oct. 31, 2018, now Pat. No. 12,036,257.

(60) Provisional application No. 62/579,517, filed on Oct. 31, 2017.

(51) Int. Cl.

| | |
|---|---|
| ***C07K 14/715*** | (2006.01) |
| ***C12N 7/00*** | (2006.01) |
| ***C12N 15/86*** | (2006.01) |

(52) U.S. Cl.
CPC ...... *C12N 15/86* (2013.01); *C12Y 302/01035* (2013.01)

(58) Field of Classification Search
CPC ........... C12N 2710/24132; C12N 2710/24143; C12N 9/2474; C12Y 302/01035; Y02A 50/30
See application file for complete search history.

(56) References Cited

U.S. PATENT DOCUMENTS

| | | | | |
|---|---|---|---|---|
| 5,139,941 | A | 8/1992 | Muzyczka | |
| 5,530,020 | A | 6/1996 | Gunawardana | |
| 5,543,158 | A | 8/1996 | Gref | |
| 5,912,264 | A | 6/1999 | Wittman | |
| 6,194,388 | B1 | 2/2001 | Krieg | |
| 6,198,323 | B1 | 3/2001 | Offord | |
| 6,207,646 | B1 | 3/2001 | Krieg | |
| 6,352,856 | B1 | 3/2002 | Falkner | |
| 6,506,559 | B1 | 1/2003 | Fire | |
| 6,573,099 | B2 | 6/2003 | Graham | |
| 6,579,865 | B2 | 6/2003 | Mak | |
| 6,610,860 | B2 | 8/2003 | Holton | |
| 6,967,023 | B1 | 11/2005 | Eini | |
| 6,994,863 | B2 | 2/2006 | Eini | |
| 7,105,184 | B2 | 9/2006 | Pauly | |
| 7,368,122 | B1 | 5/2008 | Dow | |
| 8,383,774 | B2 | 2/2013 | Hill | |
| 8,536,380 | B2 | 9/2013 | Scheffler | |
| 8,940,534 | B2 | 1/2015 | Sandig | |
| 9,180,091 | B2 | 11/2015 | Bernick | |
| 9,289,382 | B2 | 3/2016 | Bernick | |
| 10,232,003 | B2 | 3/2019 | Mulvey | |
| 10,238,700 | B2 | 3/2019 | Szalay | |
| 10,434,136 | B2 | 10/2019 | Rammensee | |
| 10,640,542 | B2 | 5/2020 | Tavernier | |
| 10,647,963 | B2 * | 5/2020 | Hemminki | A61K 35/761 |
| 11,529,402 | B2 | 12/2022 | Hanahan | |
| 11,685,904 | B2 | 6/2023 | Kirn | |
| 2002/0041864 | A1 | 4/2002 | William, III | |
| 2002/0123099 | A1 | 9/2002 | Weiner | |
| 2003/0180352 | A1 | 9/2003 | Patel | |
| 2004/0143026 | A1 | 7/2004 | Shah | |
| 2004/0214783 | A1 * | 10/2004 | Terman | A61P 35/00 514/33 |
| 2004/0248787 | A1 | 12/2004 | Naito | |
| 2005/0031643 | A1 | 2/2005 | Szalay | |
| 2005/0152903 | A1 | 7/2005 | Newman | |
| 2006/0057553 | A1 | 3/2006 | Aguilar-Cordova | |
| 2006/0099188 | A1 | 5/2006 | Tagawa | |
| 2006/0099224 | A1 | 5/2006 | Kirn | |
| 2006/0111278 | A1 | 5/2006 | Thim | |
| 2006/0111287 | A1 | 5/2006 | Bianchi | |
| 2007/0041941 | A1 | 2/2007 | Weiner | |
| 2007/0148195 | A1 | 6/2007 | Ebert | |
| 2007/0178592 | A1 | 8/2007 | McArthur | |
| 2007/0298054 | A1 | 12/2007 | Shida | |
| 2009/0004723 | A1 | 1/2009 | Kirn | |
| 2009/0208562 | A1 | 8/2009 | Morein | |
| 2009/0285860 | A1 | 11/2009 | Martuza | |
| 2010/0016224 | A1 | 1/2010 | Bowie | |
| 2010/0094560 | A1 | 4/2010 | Lois | |
| 2010/0112001 | A1 | 5/2010 | Djurup | |
| 2010/0137198 | A1 | 6/2010 | Eini | |
| 2010/0291139 | A1 | 11/2010 | Sutter | |
| 2011/0053247 | A1 * | 3/2011 | Baker | C12N 9/2408 435/201 |
| 2011/0206640 | A1 | 8/2011 | Bell | |
| 2011/0274711 | A1 | 11/2011 | Favier | |
| 2012/0114612 | A1 | 5/2012 | Evans | |
| 2013/0183348 | A1 | 7/2013 | Taniguchi | |
| 2014/0162342 | A1 | 6/2014 | Kirn | |
| 2015/0105276 | A1 | 4/2015 | Hofmann | |
| 2016/0060311 | A1 | 3/2016 | Jo | |
| 2016/0152678 | A1 | 6/2016 | Bancel | |
| 2016/0235793 | A1 | 8/2016 | Thorne | |
| 2017/0016028 | A1 | 1/2017 | Yla-Herttuala | |
| 2017/0173092 | A1 | 6/2017 | Mulvey | |
| 2017/0368169 | A1 * | 12/2017 | Loew | C07K 14/70596 |
| 2018/0148694 | A1 | 5/2018 | Shah | |
| 2018/0214538 | A1 | 8/2018 | Kirn | |
| 2019/0054131 | A1 | 2/2019 | Deng | |
| 2019/0345204 | A1 | 11/2019 | Carrió | |
| 2020/0009203 | A1 | 1/2020 | Sobol | |
| 2020/0054677 | A1 * | 2/2020 | McColl | C12N 5/0636 |
| 2020/0140824 | A1 | 5/2020 | Fernandez Santidrian | |
| 2020/0268831 | A1 | 8/2020 | Tobin | |
| 2020/0330534 | A1 | 10/2020 | Delgoffe | |
| 2020/0330596 | A1 | 10/2020 | Borriello | |
| 2021/0093684 | A1 | 4/2021 | Thorne | |
| 2022/0033784 | A1 | 2/2022 | Binder | |
| 2022/0125865 | A1 | 4/2022 | Thorne | |
| 2023/0002740 | A1 | 1/2023 | Kirn | |
| 2023/0201283 | A1 | 6/2023 | Binder | |
| 2023/0405105 | A1 | 12/2023 | Bendjama | |

FOREIGN PATENT DOCUMENTS

| | | | | |
|---|---|---|---|---|
| CN | 111556757 | A | 8/2020 | |
| CN | 108350434 | B | 6/2022 | |
| EP | 0119621 | A1 | 9/1984 | |
| EP | 185573 | A | 6/1986 | |
| EP | 488528 | A | 6/1992 | |
| EP | 0689454 | B1 | 3/1994 | |
| EP | 0102703 | | 3/2001 | |
| JP | 6012986 | A | 4/1985 | |
| KR | 20140122603 | A | 10/2014 | |
| WO | 9118088 | A1 | 11/1991 | |
| WO | 9309239 | A1 | 5/1993 | |
| WO | 9412649 | A1 | 6/1994 | |
| WO | 9426914 | A1 | 11/1994 | |
| WO | 9428152 | A1 | 12/1994 | |
| WO | 9428938 | A1 | 12/1994 | |
| WO | 9502697 | A1 | 1/1995 | |
| WO | 9622378 | A1 | 7/1996 | |
| WO | 1999032619 | A1 | 7/1999 | |
| WO | 2001036646 | A1 | 5/2001 | |
| WO | 0168820 | A1 | 9/2001 | |
| WO | 2001068836 | A2 | 9/2001 | |
| WO | 2003035683 | A2 | 5/2003 | |
| WO | 2004018478 | A2 | 3/2004 | |
| WO | 2008023077 | A2 | 2/2008 | |
| WO | 2008100292 | A2 | 8/2008 | |
| WO | 2008142479 | A2 | 11/2008 | |
| WO | 2012089225 | A1 | 7/2012 | |
| WO | 2015027163 | A1 | 2/2015 | |
| WO | 2016033555 | A1 | 3/2016 | |
| WO | 2016061286 | A1 | 4/2016 | |
| WO | 2017013419 | A1 | 1/2017 | |
| WO | 2017043815 | A1 | 3/2017 | |
| WO | 2017112741 | A1 | 6/2017 | |
| WO | WO-2017165464 | A1 * | 9/2017 | A61K 38/1764 |
| WO | 2018057755 | A1 | 3/2018 | |
| WO | 2018058258 | A1 | 4/2018 | |
| WO | 2018091680 | A1 | 5/2018 | |
| WO | 2019089755 | A1 | 5/2019 | |
| WO | 2019148109 | A1 | 8/2019 | |

(56) References Cited

FOREIGN PATENT DOCUMENTS

| | | | |
|---|---|---|---|
| WO | 2019213452 | A1 | 11/2019 |
| WO | 2020033791 | A1 | 2/2020 |

OTHER PUBLICATIONS

Buijs PR, Verhagen JH, van Eijck CH, van den Hoogen BG. Oncolytic viruses: From bench to bedside with a focus on safety. Human vaccines & immunotherapeutics. Jul. 3, 2015;11(7):1573-84. (Year: 2015).*

Guedan S, Rojas JJ, Gros A, Mercade E, Cascallo M, Alemany R. Hyaluronidase expression by an oncolytic adenovirus enhances its intratumoral spread and suppresses tumor growth. Molecular Therapy. Jul. 1, 2010;18(7):1275-83. (Year: 2010).*

Goldufsky J, Sivendran S, Harcharik S, Pan M, Bernardo S, Stern RH, Friedlander P, Ruby CE, Saenger Y, Kaufman HL. Oncolytic virus therapy for cancer. Oncolytic Virotherapy. 2013;2:31. (Year: 2013).*

Kaufman HL, Kohlhapp FJ, Zloza A. Oncolytic viruses: a new class of immunotherapy drugs. Nature reviews Drug discovery. Sep. 2015;14(9):642-62; (Year: 2015).*

Binz E, Lauer UM. Chemovirotherapy: Combining chemotherapeutic treatment with oncolytic virotherapy. Oncolytic Virotherapy. 2015;4:39 (Year: 2015).*

Choi AH, O'Leary MP, Fong Y, Chen NG. From benchtop to bedside: a review of oncolytic virotherapy. Biomedicines. Sep. 2016;4(3):18. (Year: 2016).*

Arming S, Strobl B, Wechselberger C, Kreil G. In vitro mutagenesis of PH-20 hyaluronidase from human sperm. European journal of biochemistry. Aug. 1997;247(3):810-4. (Year: 1997).*

Farrell AM, Taylor D, Holland KT. Cloning, nucleotide sequence determination and expression of the *Staphylococcus aureus* hyaluronate lyase gene. FEMS microbiology letters. Jul. 1, 1995;130(1):81-5. (Year: 1995).*

Hynes WL, Hancock L, Ferretti JJ. Analysis of a second bacteriophage hyaluronidase gene from *Streptococcus pyogenes*: evidence for a third hyaluronidase involved in extracellular enzymatic activity. Infection and immunity. Aug. 1995;63(8):3015-20. (Year: 1995).*

Andre B, Duterme C, Van Moer K, Mertens-Strijthagen J, Jadot M, Flamion B. Hyal2 is a glycosylphosphatidylinositol-anchored, lipid raft-associated hyaluronidase. Biochemical and biophysical research communications. Jul. 22, 2011;411(1):175-9. (Year: 2011).*

Arming S, Strobl B, Wechselberger C, Kreil G. In vitro mutagenesis of PH-20 hyaluronidase from human sperm. European journal of biochemistry. Aug. 1997;247(3):810-4. (Year: 1995).*

Hart ME, Hart MJ, Roop AJ. Genotypic and phenotypic assessment of hyaluronidase among type strains of a select group of *staphylococcal* species. International Journal of Microbiology. Oct. 2009;2009. (Year: 2009).*

Goldufsky J, Sivendran S, Harcharik S, Pan M, Bernardo S, Stern RH, Friedlander P, Ruby CE, Saenger Y, Kaufman HL. Oncolytic virus therapy for cancer. Oncolytic Virotherapy. 2013;2:31. (Year: 2016).*

Choi AH, O'Leary MP, Fong Y, Chen NG. From benchtop to bedside: a review of oncolytic virotherapy. Biomedicines. Sep. 2016;4(3):18. (Year: 1997).*

Sampath P, Thorne SH. Novel therapeutic strategies in human malignancy: combining immunotherapy and oncolytic virotherapy. Oncolytic virotherapy. 2015;4:75. (Year: 2015).*

Gil M, Seshadri M, Komorowski MP, Abrams SI, Kozbor D. Targeting CXCL12/CXCR4 signaling with oncolytic virotherapy disrupts tumor vasculature and inhibits breast cancer metastases. Proceedings of the National Academy of Sciences. Apr. 2, 2013;110(14):E1291-300. (Year: 2013).*

Kochneva G, Sivolobova G, Tkacheva A, Grazhdantseva A, Troitskaya O, Nushtaeva A, Tkachenko A, Kuligina E, Richter V, Koval O. Engineering of double recombinant vaccinia virus with enhanced oncolytic potential for solid tumor virotherapy. Oncotarget. Nov. 8, 2016;7(45):74171 (Year: 2016).*

Gmachl M, Sagan S, Ketter S, Kreil G. The human sperm protein PH-20 has hyaluronidase activity. FEBS letters. Dec. 28, 1993;336(3):545-8. (Year: 1993).*

Cantoni C, Grauwet K, Pietra G, Parodi M, Mingari MC, Maria AD, Favoreel H, Vitale M. Role of NK cells in immunotherapy and virotherapy of solid tumors. Immunotherapy. Aug. 2015;7(8):861-82. (Year: 2015).*

Von Beust BR. In vivo priming of bovine T lymphocytes with vaccinia viruses expressing the bovine leukemia virus envelope gene together with bovine interleukin-4 or bovine interleukin-12. Washington State University; 1997. (Year: 1997).*

Wu B, Chien EYT, Mol CD, Fenalti G, Liu W, Katritch V, et al. Structures of the CXCR4 chemokine GPCR with small-molecule and cyclic peptide antagonists. Science. (2010) 330:1066-71 (Year: 2010).*

Furusato, B., Rhim, J.S. (2009). CXCR4 and Cancer. In: Fulton, A. (eds) Chemokine Receptors in Cancer. Cancer Drug Discovery and Development. Humana Press.) (Year: 2009).*

Zhang JM, An J. Cytokines, inflammation, and pain. Int Anesthesiol Clin. 2007 Spring;45(2):27-37. doi: 10.1097/AIA.0b013e318034194e (Year: 2007).*

Malvoisin E, et al., Soluble chemokine receptor CXCR4 is present in human sera. Anal Biochem. Jul. 15, 2011;414(2):202-7 (Year: 2011).*

Schönbeck U, Jan. 2001. "The CD40/CD154 receptor/ligand dyad". Cellular and Molecular Life Sciences. 58 (1): 4-43 (Year: 2001).*

Manthey et al. (Nov. 2009). "Complement component 5a (C5a)". The International Journal of Biochemistry & Cell Biology. 41 ( 11): 2114-2117 (Year: 2009).*

Asagoe, et al; Down-Regulation of CXCR2 Expression on Human Polymorphonuclear Leukocytes by TNF-$\alpha$1. J Immunol May 1, 1998; 160 (9): 4518-4525). (Year: 1998).*

Rein, D.T.,et al (2004), Evaluation of tissue-specific promoters in carcinomas of the cervix uteri. J. Gene Med., 6: 1281-12 (Year: 2004).*

Cohen, Ivan J, and Ronald Blasberg. "Impact of the Tumor Microenvironment on Tumor-Infiltrating Lymphocytes: Focus on Breast Cancer." Breast cancer : basic and clinical research vol. 11 1178223417731565. Sep. 25, 2017 (Year: 2017).*

Wallace et al. / Progress in Retinal and Eye Research 23 (2004) 435-448) (Year: 2004).*

Gil, Margaret et al. "Targeting CXCL12/CXCR4 signaling with oncolytic virotherapy disrupts tumor vasculature and inhibits breast cancer metastases." Proceedings of the National Academy of Sciences of the United States of America vol. 110, 14 (2013): E1291-300. (Year: 2013).*

Chen , Nanhai G et al. "Oncolytic viruses." Advances in virology vol. 2012 (2012): 320206 (Year: 2010).*

Hannon, G J., A Conserved Biological Response to Double-stranted RNA, RNA Interference, Nature, vol. 418, p. 244-251, 2002.

Hennessy, et al., Targeting Toll-like Receptors: Emerging Therapeutics? Nature Reviews. Drug Discovery, vol. 9, p. 293-307 (2010).

Herbst et al., Predictive Correlates of Response to the Anti-PD-L1 Antibody MPDL3280A in Cancer Patients, Nature, vol. 515(7528), p. 563-567, 2014.

Higgins, et al., CLUSTAL: a package for performing multiple sequence alignment ona microcomputer, Gene, vol. 73, p. 237-244, 1988.

Higgins, et al., Fast and Sensitive Multiple Sequence Alignments on a Microcomputer, CABIOS, vol. 5, No., p. 151-153, 1989.

Hokey et al., Tumor Cell Loaded Type-I Polarized Dendritic Cells Induce Thl-mediated Tumor Immunity. Cancer Research, vol. 65, p. 10059-67 (2005).

Hornemann et al., Replication of Modified Vaccinia Virus Ankara . . . Inteferon Resistance Gene E3L, Journal of Virology, vol. 77, No. 15, p. 394-8407, 2003.

Hsu et al., Leptin-Induced Mitochondrial Fusioni Mediates Hepatic Lipid Accumulation, Int J Obes (Lond) 2015, vol. 39(12), p. 1750-6.

Iwasaki, et al., Enhanced CTL Responses Mediated by Plasmid DNA Immunogens Encoding Costimulatory Molecules and Cytokines. Journal of Immunology, vol. 158, p. 4591-601, 1997.

(56) References Cited

OTHER PUBLICATIONS

Janssens and Beyaert, Role of Toll-Like Receptors in Pathgen Recognition, Clinical Microb. Revs., vol. 16, p. 637-646, 2003.
Jhawar et al., Oncolytic Viruses—Natural Genetically Engineered Cancer Immunotherapies, Front. Oncol., vol. 7, p. 1-11, 2017.
Jiang et al., Toll-like Receptor 3-Mediated Activation of NF-kappaB and IRF3 Diverges at Toll-IL-I Receptor Domain-Containing Adapter Inducing IFN-beta. Proceedings of the National Academy of Sciences of the United States of America, vol. 101, p. 3533-8 (2004).
Jinushi, et al., MFG-ES-mediated Uptake of Apoptotic Cells by APCs Links the Pro-and-anti-inflammatory activities of GM-CSF. The Journal of Clinical Investigation, vol. 117, p. 1902-13 (2007).
Jones et al., Therapeutic Strategies for the Clinical Blockade of IL-6/gpl30 Signaling. The Journal of Clinical Investigation, vol. 121, p. 3375-83 (2011).
Kafri et al., A Packaging Cell Line for Lentivirus Vectors, J. Virol., vol. 73, No. 1, p. 576-584, 1999.
Kalinski et al., Regulation of Immune Responses by Prostaglandin E2. Journal of Immunology, vol. 188, p. 21-8 (2012).
Kalinski et al., T-cell Priming by Type-I and Type-2 Polarized Dendritic Cells: The Concept of a Third Signal. Immunol Today, vol. 20, 561-7 (1999).
Kalinski, P. & Okada, H. Polarized dendritic cells as cancer vaccines: directing effector-type T cells to tumors. Seminars in immunology 22, 173-82 (2010).
Karlin et al., Applications and Statistics for Multiple High-scoring Segments in Molecular Sequences, Proc. Natl. Acad. Sci. USA, vol. 90, p. 5873-5877 (1993).
Kelly et al., Real-time Intraoperative Detection of Melanoma Lymph Node Metastases using Recombinant Vaccinia Virus GL V-1 h68 in an Immunocompetent Animal Model. International Journal of Cancer. Vol 124, p. 911-8 (2009).
Kendrew et al. (eds.), The Encyclopedia of Molecular Biology, published by Blackwell Science Ltd., 1994.
Khuri et al., A Controlled Trial of Onyx-015, an EIB Gene-deleted Adenovirus, in Combination with Chemotherapy in Patients with Recurrent Head and Neck Cancer. Nature Medicine, vol. 6, p. 879-885 (2000).
Kim et al., Oncolytic and Immunotherapeutic Vaccinia Induces Antibody-mediated Complement-dependent Cancer Cell Lysis in Humans. Science Translational Medicine, vol. 5, 185ra63 (2013).
Kim et al., Systemic Armed Oncolytic and Immunologic Therapy for Cancer with JX-594, a Targeted Poxvirus Expressing GM-CSF. Mol Ther, vol. 14, p. 361-70 (2006).
Kirn et al., Antibody Association with HER-2/neu-targeted Vaccine Enhances CD8 T Cell Responses in Mice Through Fe-mediated Activation of DCs. The Journal of Clinical Investigation, vol. 118, p. 1700-11 (2008).
Kirn et al., Enhancing Poxvirus Oncolytic Effects through Increased Spread and Immune Evasion. Cancer Res, vol. 68, p. 2071-5 (2008).
Kirn et al., Replication-selective Virotherapy for Cancer: Biological Principles, Risk Management and Future Directions. Nat Med, vol. 7, p. 781-7 (2001).
Kirn et al., Targeted and Armed Oncolytic Poxviruses: A Novel Multi-mechanistic Therapeutic Class for Cancer. Nat Rev Cancer, vol. 9, p. 64-71 (2009).
Kirn et at., Targeting of Interferon-beta to Produce a Specific, Multi-mechanistic Oncolytic Vaccinia Virus. PLoS Med, vol. 4, e353 (2007).
Kobayashi, et al., Bacterial Pathogens Modulate an Apoptosis Differentiation Program in Human Neutrophils, Proc. Natl. Acad. Sci. USA, vol. 100, p. 10948-10953, 2003.
Kolb-Maurer et al., Listeria Monocytogenes-Infected Human Dendritic Cells: Uptake and Host Cell Response, Infection Immunity, vol. 68, p. 3680-3688, 2000.
La Cava et al., The Weight of Leptin in Immunity, Nat Rev Immunol, vol. 4, p. 371-379, 2004.
Lalvani et al., Rapid Effector Function in CD8+ Memory T Cells, J. Exp. Med., vol. 186, p. 859-865, 1997.
Langland et al., The Role of the PKR-Inhibitory Genes, E3L and K3L, in Determining Vaccinia Virus Host Range, Virology. vol. 299(1), p. 133-41, 2002.
Lawler et al. Oncolytic Viruses in Cancer Treatment, JAMA Oncology, Jun. 1, 2017, vol. 3, No. 6, pp. 841-849.
Le et al., CDS(+) Foxp3(+) Tumor Infiltrating Lymphocytes Accumulate in the Context of an Effective Anti-tumor Response. International Journal of Cancer. Journal International du Cancer, vol. 129, p. 636-47 (2011).
Lemoine et al., Massive Expansion of Regulatory T-cells Following Interleukin 2 Treatment During a Phase 1-11 Dendritic Cell-based Immunotherapy of Metastatic Renal Cancer. International Journal of Oncology, vol. 35, No. 569-81 (2009).
Levero et al., Defective and Nondefective Adenovirus Vectors for Expressing Foreign Genes in Vitro and in Vivo, Gene, 1991, vol. 101, p. 195-202, 1991.
Liu et al., The Targeted Oncolytic Poxvirus JX-594 Demonstrates Antitumoral, Antivascular, and Anti-HBV Activities in Patients with Hepatocellular Carcinoma. Mol Ther, vol. 16, p. 1637-42 (2008).
Loffreda et al., Leptin Regulates Proinflammatory Immune Responses, FASEB J, vol. 12, 57-65, 1998.
Longhi, M.P., et al., Dendritic cells require a systemic type I interferon response to mature and induce CD4+ Thl immunity with poly IC as adjuvant. The Journal of Experimental Medicine, vol. 206, p. 1589-1602 (2009).
Mailliard et al., Alpha-type-I Polarized Dendritic Cells: A Novel Immunization Tool with Optimized CTL-inducing Activity. Cancer Res, vol. 64, p. 5934-7, (2004).
Martin-Romero et al., Human Leptin Enhances Activation and Proliferation of Human Circulating T Lymphocytes, Cell Immunol, vol. 199(1), p. 15-24, 2000.
McCart et al., Systemic cancer therapy with a tumor-selective vaccinia virus mutant lacking thymidine kinase and vaccinia growth factor genes. Cancer Res, vol. 61, p. 8751-7 (2001).
McHeyzer-Williams et al., Enumeration and Characterization of Memory Cells in the Th Compartment, Immunol. Rev., vol. 150, p. 5-21, 1996.
McIntosh et al., Vaccinia Virus Glycoprotein A34R is Required for Infectivity of Extracellular Enveloped Virus. J Virol, vol. 70:, p. 272-81, 1996.
McManus et al., Gene Silencing Using Micro-RNA Designed Hairpins, RNA, vol. 8, p. 842-850, (2002).
McMichael et al., A New Look at T Cells, J. Exp. Med., vol. 187(9), p. 1367-1371, 1998.
Meyer et al., Mapping of Deletions in the Genome of the Highly Attenuated Vaccinia Virus MVA and Their Influence on Virulence, J. of General Virology, vol. 72, p. 1031-1038, 1991.
Hou et al., Oncolytic vaccinia vrius demonstrates antiangiogenic effects mediated by targeting of VEGF, Internal Journal of Cancer, 2014, vol. 35, p. 1238-1246.
Moss B. Poxviridae: The Viruses and Their Replication. Field's Virology (eds. D.M., K., Fields, B.N. & Howley, P.M.) Ch.84 (Lippincott-Raven, Philadelphia, 2001).
Myers and Miller, CABIOS (1989).
Najjar et al., Clinical Perspectives on Targeting of Myeloid Derived Suppressor Cells in the Treatment of Cancer, Frontiers in Oncology, vol. 3(49), p. 1-9, 2013.
Naldini, Nuclear Acid Delivery: Lentiviral and Retroviral Vectors, Curr. Opin. Biotechnol., vol. 9, p. 457-63, 1998.
Narang et al., Improved Phosphotriester Method for Synthesis of Gene Fragments, Meth. Enzymol., vol. 68, p. 90-99, 1979.
Needham-Vandevanter et al., Characterization of an Adduct between CC-1065 and a Defined Oligodeoxynucleotide Duplex, Nucl. Acids Res., vol. 12, p. 6159-6168, 1984.
Needleman et al., A General Method Applicable to the Search for Similarities in the Amino Acid Sequence of Two Proteins,, J. Mol. Biol., vol. 48, p. 443-453, 1970.
Nestle et al., Cancer Vaccines: The Next Generation of Tools to Monitor the Anticancer Immune Response. PLoS Med 2, e339 (2005).
Ning et al., Cancer Stem Cell Vaccination Confers Significant Antitumor Immunity. Cancer Research, vol. 72, p. 1853-64 (2012).

(56) References Cited

OTHER PUBLICATIONS

Nishio et al., Oncolytic Virus Expressing RANTES and IL-15 Enhances Function of CAR-Modified T Cells in Solid Tumors, Oncoimmunology, Mar. 6, 2015 (Mar. 6, 2015), vol. 4, No. 2, pp. 1-3.
O'Gorman et al., Alternate Mechanisms of Initial Pattern Recognition Drive Differential Immune Responses to Related Poxviruses. Cell Host & Microbe, vol. 8, p. 174-85 (2010).
Okada et al., Induction of CD8+ T-cell Responses Against Novel Glioma-associated Antigen Peptides and . . . Carboxymethylcellulose in Patients with Recurrent Malignant Glioma. Journal of Clinical Oncology : Official Journal of the American Society of Clinical Oncology, vol. 29, p. 330-6 (2011).
Okamura, H., et al. Cloning of a new cytokine that induces IFN-gamma production by T cells. Nature, vol. 378, p. 88-91 (1995).
O'Neill et al., Therapeutic Targeting of Toll-like Receptors for Infectious and Inflammatory Diseases and Cancer. Pharmacological Reviews, vol. 61, p. 177-97 (2009).
Orubu et al., Expression and Cellular Immunogenicity of a Transgenic Antigen Driven by Endogenous Poxviral Early Promoters at Their Authentic Loci in MVA, PLOS One 7:e40167, 2012.
Ottolino-Perry et al. Intelligent Design: Combination Therapy With Oncolytic Viruses, Molecular Therapy, Feb. 28, 2010, vol. 18, No. 2, pp. 251-263.
Parato et al., The Oncolytic Poxvirus JX-594 Selectively Replicates in and Destroys Cancer Cells Driven by Genetic Pathways Commonly Activated in Cancers, Molecular Therapy, vol. 20, No. 4, p. 749-758, 2012.
Park et al., Use of a Targeted Oncolytic Poxvirus, JX-594, in Patients with Refractory Primary or Metastatic Liver Cancer: A Phase I Trial. Lancet Oncol, vol. 9, p. 533-42 (2008).
Paul et al., Tumor Gene Therapy by MVA-Mediated Expression of T-Cell-Stimulating Antibodies, Cancer Gene Ther., vol. 9, p. 470-7, 2002.
Pearson et al., Improved Tools for Biological Sequence Comparison, Proc. Natl. Acad. Sci. USA vol. 85, p. 2444-2448, 1988.
Penna, et al., Cutting Edge: Differential Chemokine Production by Myeloid and Plasmacytoid Dendritic Cells, J. Immunol., vol. 69, p. 6673-6676, (2002).
Peritt, et al., Cutting Edge: Differentiation of Human NK Cells into NK1 and NK2 Subsets, J. Immunol., vol. 161, p. 5821-5824 (1998).
Persing et al., Taking Toll: Lipid A Mimetics as Adjuvants and Immunomodulators, Trends in Microbiology, vol. 10, No. 10, S32-S37, 2002.
Pipiya et al., Hypoxia reduces adenoviral replication in cancer cells by downregulation of viral protein expression, Gene Ther 2005, vol. 12(11). pp. 911-917.
Pol et al., Preclinical Evaluation of an Oncolytic Mamba Virus Vaccine in a Simian Model. 7th International Oncolytic Viruses Meeting (Quebec City, 2013).
Prestwich et al., Immune-mediated Antitumor Activity of Reovirus is Required for Therapy and is Independent of Direct Viral Oncolysis and Replication. Clin Cancer Res, vol. 15, o4374-81 (2009).
Prestwich et al., Tumor Infection by Oncolytic Reovirus Primes Adaptive Antitumor Immunity. Clinical Cancer Research : An Official Journal of the American Association for Cancer Research, vol. 14(22), p. 7358-66 (2008).
Puhlmann et al., Vaccinia is a vector for tumor-directed gene therapy: Biodistribution of a thymidine kinase-deleted mutant, Cancer Gene Ther, vol. 7, p. 676-73, 2000.
Pulido et al., Using Virally Expressed Melanoma cDNA Libraries to Identify Tumor-associated Antigens that Cure Melanoma. Nature Biotechnology, vol. 30, p. 337-43 (2012).
Putz et al., Quantification of Antibody Responses Against Multiple Antigens of the Two Infectious Forms of Vaccinia Virus Provides a Benchmark for Smallpox Vaccination. Nat Med, vol. 12, p. 1310-5 (2006).
Rakoff-Nahoum et al. Toll-like Receptors and Cancer. Nature Reviews. Cancer, vol. 9, p. 57-63 (2009).
Reading et al., Vaccinia Virus Interleukin-18-Binding Protein Promotes Virulence by Reducing Gamma Interferon Production and Natural Killer and T-cell Activity. J Virol, vol. 77, p. 9960-8 (2003).
Rehm et al., Vaccinia Virus A35R Inhibit MHC Class II Antigen Presentation, Virology, vol. 397(1), p. 176-86, 2010.
Ricca et al., Pre-existing Immunity to Oncolytic Virus Potentiates Its Immunotherapeutic Efficacy, Mol Ther 2018, vol. 26(4), pp. 1008-1019.
Robins et al., Comprehensive assessment of T-cell receptor B-chain diversity in aβ T cells, Blood 2009, vol. 114(19), p. 4099-107.
Roman et al., Central Leptin Action Improves Skeletal Muscle AKT, AMPK, and PGC1a Activation by Hypothalamic PI3k-Dependent Mechanism, Mol Cell Endocrinol, vol. 314(1), p. 62-9, 2010.
Rommelfanger et al., Systemic Combination Virotherapy for Melanoma with Tumor Antigen-Expressing Vesicular Stomatitis Virus and Adoptive T-Cell Transfer. Cancer Research, p. 2753-4764 (2012).
Roper et al., Characterization of the Vaccinia Vrius A35R Protein and its Role in Virulence, J of Virology, vol. 80, No. 1, p. 306-313, 2006.
Rosenberg et al., Cancer Immunotherapy: Moving Beyond Current Vaccines. Nat Med, vol. 10, p. 909-15 (2004).
Russell et al., Oncolytic Viruses as Antigen-Agnostic Cancer Vaccines, Cancer Cell 2018, vol. 33(4), pp. 599-605.
Saikh, et al., Toll-Like Receptor and Cytokine Expression Patterns of CD56+ T Cells Are Similar to Natural Killer Cells in Response to Infection with Venezuelan Equine Encephalitis Virus Replicons, J. Infect. Dis., vol. 188, p. 1562-1570, 2003.
Sakamoto, et al., Characteristics of T-cell Receptor Va24JaQ T Cells, a Human Counterpart of Murine NK1+ T Cells, from Normal Subjects, J. Allergy Clin. Immunol., vol. 103, S445-S451, 1999.
Sambrook et al. (ed.), Molecular Cloning: A Laboratory Manual 2nd ed., vol. 1-3, Cold Spring Harbor Laboratory Press, Cold Spring, Harbor, N.Y., 1989.
Sampath et al., Crosstalk Between Immune Cell and Oncolytic Vaccinia Therapy Enhances Tumor Trafficking and Antitumor Effects, Molecular Ther., vol. 21, No. 3, p. 620-628, 2013.
Samuelsson et al., Survival of Lethal Poxvirus Infection in Mice Depends on TLR9, and Therapeutic Vaccination Provides Protection. J Clin Invest, vol. 118, p. 1776-84 (2008).
Santos-Alvarez et al., Human Leptin Stimulates Proliferation and Activation of Human Circulating Monocytes, Cell Immunol, vol. 194, p. 6-11, 1999.
Sasaki et al., Regulation of DNA-raised Immune Responses by Cotransfected Interferon Regulatory Factors. Journal of Virology, vol. 76, 6652-9 (2002).
Satija et al., Spatial reconstruction of single-cell gene expression, Nat Biotechnol 2015, vol. 33(5), pp. 495-502.
Sato et al., Toll/IL-1 Receptor Domain-Containing Adaptor Inducing IFN-B (TRIF) Associates . . . in the Toll-Like Receptor Signaling1, Journal of Immunology, vol. 171, p. 4304-10 (2003).
International Search Report and Written Opinion for PCT/US2018/058456 mailed Feb. 5, 2019.
International Search Report and Written Opinion for PCT/US2020/012611, mailed Apr. 20, 2020.
International Search Report and Written Opinion for PCT/US2020/056107, mailed Mar. 1, 2021.
International Search Report and Written Opinion for PCT/US2020/056130, mailed Feb. 8, 2021.
International Search Report for PCT/US2017/042910, mailed Mar. 6, 2018.
International Search Report for PCT/US2017/052746, mailed Feb. 13, 2018.
International Search Report for PCT/US2019/015434, mailed Apr. 5, 2019.
International Search Report for PCT/US2019/062643, mailed Mar. 31, 2020.
Alcami et al., A Soluble Receptor for Interleukin-1B Encoded by Vaccinia Virus: A Novel Mechanism of Virus Modulation of the Host Response to Infection, 1992, Cell. 71(1), p. 153-67.
Alferink et al., Compartmentalized Production of CCL17 In Vivo . . . (2003) J. Exp. Med. 197, p. 585-599.

(56) References Cited

OTHER PUBLICATIONS

Altschul et al., BLAST, Basic local alignment search tool; J Mol Biol. Oct. 5, 1990; vol. 215(3), p. 403-410.
Altschul et al., Issues in Searching Molecular Sequence Databases, Nature Genet., vol. 6, p. 119-129, 1994.
Altschul, S. et al., Gapped BLAST and PSI-BLAST: a new generation of protein database search programs, Nucleic Acids Res., 25:3389-3402 (1997).
Alvarez-Breckenridge et al., NK Cells Impede Glioblastoma Virotherapy Through NKp30 and NKp46 Natural Cytotoxicity Receptors. Nature Medicine, vol. 18, p. 1827-34 (2012).
Andtbacka et al., Talimogene Laherparepvec Improves Durable Response Rate in Patients with Advanced Melanoma.J Clin Oncol 2015; vol. 33(25), p. 2780-8.
Bahar et al., Structure and Function of A41, a Vaccinia Virus Chemokine Binding Protein. PLoS Pathog 4, e5 (2008).
Baldrick et al., Safety Evaluation of a New Allergy Vaccine Containing the Adjuvant Monophosphoryl Lipid A (MPL) for the Treatment of Grass Pollen Allergy, Journal of Applied Toxicology, vol. 24, p. 261-268, 2004.
Baldrick et al., Safety Evaluation of Monophosphoryl Lipid A (MPL): An Immunostimulatory Adjuvant, Reg. Toxi. and Pharma., vol. 35, p. 398-413, 2002.
Banaszynski et al., Chemical control of protein stability and function in living mice. Nat Med, vol. 14(10), p. 1123-127, 2008.
Banchereau et al., Dendritic cells as therapeutic vaccines against cancer. Nat Rev Immunol, vol. 5, 296-306 (2005).
Barve et al., Induction of Immune Responses and Clinical Efficacy in a Phase II Trial of IDM-2101, a 10-Epitope Cytotoxic T-Lymphocyte Vaccine, in Metastatic Non-Small-Cell Lung Cancer, J Clin Oncol 2008; vol. 26(27), p. 4418-25.
Beard et al., Transcription Mapping of Mouse Adenovirus Type 1 Early Region 3, Virology, 1990, 175, p. 81-90.
Beaucage & Caruthers, Deoxynucleoside Phosphoramidites—A New Class of Key Intermediates for Deoxypolynucleotide Synthesis, Tetra. Letts. 22(20):1859-1862, 1981.
Belyakov, et al., What Role does the Route of Immunization Play in the Generation of Protective Immunity Against Mucosal Pathogens? Journal of Immunology, vol. 183, p. 6883-92 (2009).
Bischoff, et al., An Adenovirus Mutant that Replicates selectively in p53-Deficient Human Tumor Cells. Science, vol. 274, p. 373-6 (1996).
Bitter et al., Expression and Secretion Vectors for Yeast, Methods in Enzymology, vol. 153, p. 516-544, 1987.
Blasco el al., Dissociation of progeny vaccinia virus from the cell membrane is regulated by a viral envelope glycoprotein: effect of a point mutation in the lectin homology domain of the A34R gene, J Virol. Jun. 1993;67(6):3319-3325.
Boonstra, et al., Flexibility of mouse classical and plasmacytoid-derived dendritic cells in directing T helper type 1 and 2 cell development: dependency on antigen dose and differential toll-like receptor ligation, J. Exp. Med., vol. 197, p. 101-109, 2003.
Brader, et al., Imaging of Lymph Node Micrometastases using an Oncolytic Herpes Virus and [18F]FEAU PET. PLoS One, vol. 4, e4789 (2009).
Breitbach, et al., Intravenous Delivery of a Multi-Mechanistic Cancer-Targeted Oncolytic Poxvirus in Humans. Nature, vol. 477, p. 99-102 (2011).
Brown et al., Cancer Immunotherapy with Recombinant Poliovirus Induces IFN-Dominant Activation of Dendritic Cells and Tumor Antigen-Specific CTLs; Sci Trans Med. 2017; vol. 9, No. 408, pp. 1-37.
Brown, et al., Chemical Synthesis and Cloning of a Tyrosine tRNA Gene, Meth. Enzymol., vol. 68, p. 109-151, 1979.
Brummelkamp et al., Stable Suppression of Tumorigenicity by Virus-Mediated RNA Interference, Cancer Cell, vol. 2, p. 243-247 (2002).
Brzoza, et al., Cytoplasmic Entry of Listeria Monocytogenes Enhances Dendritic Cell Maturation and T Cell Differentiation and Function, J. Immunol., vol. 173, p. 2641-2651.
Bu et al., GRIM-19 Inhibits the STAT3 Signaling Pathway and Sensitizes Gastric Cancer Cells to Radiation, Gene, vol. 512(2), p. 198-205 (2013).
Buller et al., Decreased virulence of recombinant vaccinia virus expression vectors is associated with a thymidine kinase-negative phenotype, Nature 1985, vol. 317(6040), p. 813-5.
Buller et al., Poxvirus Pathogenesis, Microbiological Reviews, vol. 55, No. 1, Mar. 1991, p. 80-122.
Carine, et al., Mouse Strain Differences in Plasmacytoid Dendritic Cell Frequency and Function Revealed by a Novel Monoclonal Antibody, J. Immunol., vol. 171, p. 6466-6477, 2003.
Carpenter et al., STAT3 Target Genes Relevant to Human Cancers, Cancers, vol. 6, p. 897-925, 2014.
Chakir, et al., Differential of Murine NK Cells into Distinct Subsets Based on Variable Expression of the IL-12Rb2 Subunit, J. Immunol., vol. 165, p. 4985-4993, 2000.
Chakrabarti et al., Compact, Synthetic, Vaccinia Virus Early/Late Promoter for Protein Expression, Biotechniques, vol. 23, p. 1094-1097, Dec. 1997.
Chang et al., The E3L Gene of Vaccinia Virus Encodes an Inhibitor of the Interferon-Induced, Double-Stranded RNA-Dependent Protein Kinase, Proc. Natl. Acad. Sci., vol. 89(11), p. 4825-9, Jun. 1992.
Chang, et al., Treatment with Cyclooxygenase-2 Inhibitors Enables Repeated Administration of Vaccinia Virus for Control of Ovarian Cancer, Molecular Therapy, The Journal of the American Society of Gene Therapy 17, 1365-72 (2009).
Charafe, Jauffret et al., Breast Cancer Cell Lines Contain Functional Cancer Stem Cells with Metastatic Capacity and a Distinct Molecular Signature. Cancer Research, vol. 69, p. 1302-13 (2009).
Chen, et al., Cancers take Their Toll—The Function and Regulation of Toll-like Receptors in Cancer Cells. Oncogene, vol. 27, p. 225-33 (2008).
Chen, et al., Regulating Cytokine Function Enhances Safety and Activity of Genetic Cancer Therapies. Molecular Therapy : The Journal of the American Society of Gene Therapy, vol. 21, p. 167-74 (2013).
Cheng et al., Anticancer Function of Polyinosinic-Polycytidylic Acid. Cancer Biology & Therapy, vol. 10, p. 1219-23 (2011).
Chertova et al. "Characterization and Favorable in Vivo Properties of Heterodimeric Soluble IL-15/IL-15Rα Cytokine Compared to IL-15 Monomer," Journal of Biological Chemistry, May 6, 2013, vol. 288, p. 18093-18103.
Cho, et al., Isolation and Molecular Characterization of Cancer Stem Cells in MMTV-Wnt-1 Murine Breast Tumors. Stem Cells, vol. 26, p. 364-71, 2008.
Coffin, R. Clinical Updates with oncolytic HSV. in 7th International Oncolytic Virus Meeting (Quebec City, 2013).
Colamonici et al., Vaccinia Virus B18R Gene Encodes a Type 1 Interferon-Binding Protein that Blocks Interferon a Transmembrane Signaling, J. Biol. Chem. Vol 270(27):, p. 5974-8. 1005.
Contag, et al., Definition of an Enhanced Immune Cell Therapy in Mice that can Target Stem-like Lymphoma Cells. Cancer Research, vol. 70, p. 9837-45 (2010).
Corpet et al., Multiple Sequence Alignment with Hierarchical Clustering, Nucleic Acids Research, vol. 16, p. 10881-10890, 1988.
Couedel et al., Diverse CD1d-Restricted Reactivity Patterns of Human T Cells Bearing "invariant" AV24BV11 TCR, Eur. J. Immunol., vol. 28, p. 4391-4397, 1988.
Albelda et al., Giving Oncolytic Vaccinia Virus More BiTE, Molecular Therapy, vol. 22, No. 1, p. 6-8.
Baldridge et al., Monophosphoryl lipid A enhances mucosal and systemic immunity to vaccine antigens following intranasal administration, Vaccine 18, Elsevier, 2000, p. 2416-2425.
Becker, Immunological and Regulatory Functions of Uninfected and Virus Infected Immature and Mature Subtypes of Dendritic Cells—a Review, Virus Genes, 2003, vol. 26, p. 119-130.
Wei et al., Interleukin-2 administration alters the CD4+FOXP3+ T-cell pool and tumor trafficking in patients with ovarian carcinoma. Cancer Research, vol. 67, p. 7487-94 (2007).
Weiss et al., Trafficking of high avidity HER-2/neu-specific T cells into HER-2/neu-expressing tumors after depletion of effector/memory-like regulatory T cells. PLoS One 7, vol. 7, e31962 (2012).

(56) References Cited

OTHER PUBLICATIONS

Wesa et al., Polarized type-I dendritic cells (DCI) producing high levels of IL-12 family members rescue patient THI-type antimelanoma CD4+ T cell responses in vitro. J Immunother, vol. 30, p. 75-82 (2007).
Whitman et al., In vitro and in vivo kinetics of recombinant vaccinia virus cancer-gene therapy. Surgery. Surgery 1994; vol. 116(2), p. 183-8.
Workenhe et al., Mitoxantrone synergizes with oncolytic herpes simplex virus to regress established breast tumors in part by increasing recruitment of CDS+ T cells. 7th International Oncolytic Viruses Meeting (Quebec City, 2013).
Worschech A., et al., Systemic treatment of xenografts with vaccinia virus GLV-I h68 reveals the immunologic facet of oncolytic therapy. BMC Genomics vol. 10, 301 (2009).
Yang et al., Persistent Toll-like receptor signals are required for reversal of regulatory T cell-mediated CD8 tolerance. Nature Immunology, vol. 5, p. 508-15 (2004).
Yu et al., Visualization of tumors and metastases in live animals with bacteria and vaccinia virus encoding light-emitting proteins. Nat Biotechnol, vol. 22, p. 313-20 (2004).
Yue et al., Targeting STAT3 in cancer: how successful are we? Expert Opin. Investig. Drugs, vol. 18(1), p. 45-56 (2009).
Zhu et al., High-throughput screening for TLR3-IFN regulatory factor 3 signaling pathway modulators identifies several antipsychotic drugs as TLR inhibitors. Journal of Immunology, vol. 184, p. 5768-76 (2010).
Zhu et al., Innate immunity against vaccinia virus is mediated by TLR2 and requires TLR-independent production of IFN-B. Blood, vol. 109, p. 619-25 (2007).
Zufferey et al., Self-Inactivating Lentivirus Vector for Safe and Efficient In Vivo Gene Delivery, J. Virol., 1998, vol. 72, p. 9873-80.
Kang et al., HMGB1 in Cancer: Good, Bad, or Both? Clin Cancer Res., 2013, vol. 19, p. 4046-4057.
Labeck, Checkpoint Inhibitors: New Insights and Current Place in Cancer Therapy, ERRATUM, Pharmcotherapy Publications, Inc., 2015.
Li et al., CCL5-armed oncolytic virus augments CCR5-engineered NK cell infiltration and antitumor efficiency. J Immunother Cancer, vol. 8(1), e000131, 2020.
Li J, et al., (2011) Chemokine Expression From Oncolytic Vaccinia Virus Enhances Vaccine Therapies of Cancer. Molecular Therapy, vol. 19, No. 5, pp. 650-657, 2011.
Mahoney et al., Cancer Immunotherapy, Nature Reviews, Drug Discovery, vol. 14, Aug. 2015, p. 561-584.
Moon EK et al., Intra-tumoral delivery of CXCL11 via a vaccinia virus, but not by modified T cells, enhances the efficacy of adoptive T cell therapy and vaccines. Oncoimmunology, vol. 7, Issue 3, 2018.
Perry et al., Clinical Scale Expansion of Human Pluripotent Stem Cells, Blood, vol. 106(11), (2005), Abstract Only.
Rivadeneira et al. Oncolytic Viruses Engineered to Enforce Leptin Expression Reprogram Tumor-Infiltrating T Cell Metabolism and Promote Tumor Clearance. Immunity, vol. 51, p. 548-560, 2019.
Rojas J, Sampath P, Hou W, Thorne SH, Defining Effective Combinations of Immune Checkpoint Blockade and Oncolytic Virotherapy. Clin. Cancer Res., (2015), PMID: 26187615.
Sampath P, et al., Novel therapeutic strategies in human malignancy: Combining immunotherapy and oncolytic virotherapy. Oncolytic Virotherapy, vol. 4, p. 75-82, (2015).
Shao et al., (2019) IRF1 Inhibits Antitumor Immunity through the Up-regulation of PD-L1 in the Tumor Cell. Cancer Immunol Res., vol. 7, Issue 8, p. 1258-1266.
Tang et al., Endogenous HMGB1 regulates autophagy, J Cell Biol, vol. 190, No. 5, p. 881-892.
Thorne, Virus fuels NK cell killing of leukemia, 2016, Blood, vol. 127, Issue21, 2509.
Thorne SH, Design and testing of novel oncolytic vaccinia strains. Methods Mol Biol., Gene Therapy of Cancer, vol. 542, p. 635-647, 2009.
Thorne, Next-generation oncolytic vaccinia vectors, Methods Mol Biol., 2012, Abstract.
Yan et al., (2012) High mobility group box 1 activates caspase-1 and promotes hepatocellular carcinoma invasiveness and metastases. Hepatology. Jan. 11, 2012, vol. 55, Issue 6, pp. 1863-1875.
Zamarin et al., Intratumoral modulation of the inducible co-stimulator ICOS by recombinant oncolytic virus promotes systemic anti-tumour immunity, Nature Communication, 2017, vol. 8, p. 1-14.
Sautes-Fridman et al., Tumor Microenvironment is Multifaceted. Cancer Metastasis Reviews, vol. 30, vol. 13-25, 2011.
Schafer et al., Vaccinia virus-mediated intra-tumoral expression of matrix metalloproteinase 9 enhances oncolysis of PC-3 xenograft tumors, BMC Cancer, 2012, vol. 12, No. 366, p. 1-9.
Scharping et al., Efficacy of PD-1 Blockade is Potentiated by Metformin-induced Reduction of Tumor Hypoxia, Cancer Immunol. Res., vol. 5, p. 9-16, 2017.
Scharping et al., The Tumor Microenvironment Represses T Cell Mitochondrial Biogenesis to Drive Intratumoral T Cell Metabolic Insufficiency and DysfunctionImmunity 2016; vol. 45(3), p. 374-388, 2016.
Schmidt, Amgen Spikes Interest in Live Virus Vaccines for Hard-to-Treat Cancers. Nature Biotechnology, vol. 29, p. 295-6 (2011).
Senzer et al., Phase II Clinical Trial of a Granulocyte-Macrophage Colony-stimulating Factor-encoding, Second-generation Oncolytic Herpesvirus in Patients with Unresectable Metastatic Melanoma. J Clin Oncol, vol. 27, p. 5763-71 (2009).
Setoguchi et al., Homeostatic Maintenance of Natural Foxp3(+) CD25(+) CD4(+) Regulatory T Cells by Interleukin (IL)-2 and Induction of Autoimmune Disease by IL-2 Neutralization. The Journal of Experimental Medicine, vol. 201, p. 723-35 (2005).
Sharma et al., The PTEN Pathway in Tregs is a Critical Driver of the Suppressive Tumor Microenvironment, Sci. Advance, p. 1-15, 2015.
Sharma et al., Primary, Adaptive, and Acquired Resistance to Cancer Immunotherapy, Cell, vol. 168(4), p. 707-23, 2017.
Sibelius et al., Role of Listeria Monocytogenes Exotoxins Listeriolysin and Phosphatidylinositol-Specific Phospholipase C in Activation of Human Neutrophils, Infection Immunity, vol. 67, p. 1125-1130, 1999.
Sidobre, et al., The T Cell Antigen Receptor Expressed by Va14i NKT Cells has a Unique Mode of Glycosphingolipid Antigen Recognition, Proc. Natl. Acad. Sci., vol. 101, p. 12254-12259, 2004.
Silva et al., Aldehyde Dehydrogenase in Combination with CD 133 Defines Angiogenic Ovarian Cancer Stem Cells hat Portend Poor Patient Survival. Cancer Research, vol. 71, p. 3991-4001 (2011).
Siveen et al., Targeting the STAT3 Signaling Pathway in Cancer: Role of Synthetic and Natural Inhibitors, Biochimica et Biophysica Acta, vol. 1845, p. 136-154 (2014).
Smith et al., Comparison of Biosequences, Adv. Appl. Math., vol. 2, p. 482-489, 1981.
Smith et al., Immune Modulation by Proteins Secreted from Cells Infected by Vaccinia Virus. Arch Virol, Suppl 15, p. 111-29 (1999).
Smith et al., Infectious Poxvirus Vectors have Capacity for at Least 25 000 Base Pairs of Foreign DNA. Gene, vol. 25, p. 21-28 (1983).
Smith et al., Intracellular Cytokine Staining and Flow Cytometry: Considerations for Application in Clinical Trials of Novel Tuberculosis Vaccines, PLoS One (2015), vol. 10(9), e0138042.
Smith et al., Nonstochastic Coexpression of Activation Receptors on Murine Natural Killer Cells, J. Exp. Med., vol. 191, p. 1341-1354, (2000).
Smith G.L., et al., Vaccinia virus immune evasion. Immunol Rev, vol. 159, p. 137-154 (1997).
Sukumar et al., Mitochondrial Membrane Potential Identifies Cells with Enhanced Stemness for Cellular Therapy, Cell Metab, vol. 23(1), p. 63-76, 2016.
Sunderkotter, et al., Subpopulations of Mouse Blood Monocytes Differ in Maturation Stage and Inflammatory Response, J. Immunol., vol. 172, p. 4410-4417, 2004.
Sutter et al., A Recombinant Vector Derived from the Host Range-restricted and Highly Attenuated MVA Strain of Vaccinia Virus Stimulates Protective Immunity in Mice to Influenza Virus, Vaccine, vol. 12, No. 11, p. 1032-1040, 1994.

(56) References Cited

OTHER PUBLICATIONS

Symons et al., The vaccinia virus C 12L protein inhibits mouse IL-18 and promotes virus virulence in the murine intranasal model. J Gen Virol 83, 2833-2844 (2002).
Symons et al., Vaccinia Virus Encodes a Soluble Type I Interferon Receptor of Novel Structure and Broad Species Specificity, Cell., vol. 81(4), p. 551-60, 1995.
Takeshita et al., Toll-like Receptor Adaptor Molecules Enhance DNA-raised Adaptive Immune Responses Against Influenza and Tumors Through Activation of Innate Immunity. Journal of Virology, vol. 80, p. 6218-6224, 2006.
Taniguchi et al., The Regulatory Role of Va14 NKT Cells in Innate and Acquired Immune Response, Annu. Rev. Immunol., vol. 21, p. 483-513, 2003.
Terajima et al., Role of Indoleamine 2,3-Dioxygenase in Antiviral Activity of Interferon-gamma Against Vaccinia Virus. Viral Immunology, vol. 18, 722-9 (2005).
Thorne et al., Rational strain selection and engineering creates a broad-spectrum, systemically effective oncolytic poxvirus, JX-963. J Clin Invest, vol. 117, p. 3350-3358 (2007).
Thorne et al., Targeted and Armed Oncolytic Poxviruses: A Novel Multi-mechanistic Therapeutic Class for Cancer, Nat Rev Cancer, vol. 9, p. 64-71, 2009.
Thorne et al., Targeting localized immune suppression within the tumor through repeat cycles of immune cell-oncolytic virus combination therapy. Molecular Therapy : The Journal of the American Society of Gene Therapy, vol. 18, p. 1698-705 (2010).
Thorne, Enhancing Biological Therapy through Conditional Regulation of Protein Stability. Expert Reviews in Molecular Medicine, vol. 12, e2 (2010).
Thorne, Immunotherapeutic Potential of Oncolytic Vaccinia Virus. Immunologic Research, vol. 50, p. 286-93 (2011).
Thorne, S. H. "Immunotherapeutic potential of oncolytic vaccinia virus," Frontiers in Oncology, Jun. 17, 2014, vol. 4, No. 155, pp. 1-5.
Torres et al., Toll-Like Receptor 2 is Required for Optimal Control of Listeria monocytogenes Infection, Infection and Immunity, vol. 72, p. 2131-2139, 2004.
Trumpfheller et al., The microbial mimic poly IC induces durable and protective CD4+ T cell immunity together with a dendritic cell targeted vaccine. Proceedings of the National Academy of Sciences of the United States of America, vol. 105, p. 2574-9 (2008).
Tsukamoto et al., Expression of the int-I gene in transgenic mice is associated with mammary gland hyperplasia and adenocarcinomas in male and female mice. Cell, vol. 55, p. 619-625, 1988.
Tuschl T. et al., Targeted mRNA degradation by double-stranded RNA in vitro, Genes & Development, vol. 13, p. 3191-3197, 1999.
Tvinnereim et al., Neutrophil Involvement in Cross-Priming CD8+ T Cell Responses to Bacterial Antigens, J. Immunol., vol. 17. p. 1994-2002, 2004.
Umemura et al. Defective NF-kappaB signaling in metastatic head and neck cancer cells leads to enhanced apoptosis by double-stranded RNA. Cancer Research, vol. 72, p. 45-55 (2012).
Van Der Windt et al., CD8 memory T cells have a bioenergetic advantage that underlies their rapid recall ability, PNAS, vol. 110(35), p. 14336-41, 2013.
Van Der Windt et al., Mitochondrial Respiratory Capacity Is A Critical Regulator Of CD8+ T Cell Memory Development, Immunity, vol. 36(1), p. 68-78, 2012.
Van Eiji H, et al.; The Vaccinia Virus A36R Protein Is a Type Ib Membrane Protein Present on Intracellular but Not Extracellular Enveloped Virus Particles, Virology 271; p. 26-36; 2000.
Vella et al., Healthy individuals have T-cell and antibody responses to the tumor antigen cyclin BI that when elicited In mice protect from cancer. Proceedings of the National Academy of Sciences of the United States of America, vol. 106, p. 14010-5 (2009).
Visus et al., Targeting ALDH (bright) human carcinoma-initiating cells with ALDHIAI-specific CDS(+) T cells. Clinical Cancer Research : An Official Journal of the American Association for Cancer Research, vol. 17, p. 6174-84 (2011).
Walzer et al., Differential In Vivo Persistence of Two Subsets of Memory Phenotype CD8 T Cells Defined by CD44 and CD122 Expression Levels, J. Immunol., vol. 168, p. 2704-2711, 2002.
Wang et al., Treating Tumors With a Vaccinia Virus Expressing IFNbeta Illustrates the Complex Relationships Between Oncolytic Ability and Immunogenicity. Molecular Therapy : The Journal of the American Society of Gene Therapy, vol. 20, No. 4, p. 736-748, (2012).
Weber et al., antiSMASH 3.0—a comprehensive resource for the genome mining of biosynthetic gene clusters, Nucleic Acids Research, vol. 43, W237-W243, 2015.
Wong et al., Helper Activity of Natural Killer Cells During the Dendritic Cell-mediated Induction of Melanoma-specific Cytotoxic T Cells. Journal of Immunotherapy, vol. 34, 270-8 (2011).
Dankort et al., BRafV600E cooperates with Pten silencing to elicit metastatic melanoma, Nat. Genet. 2009; vol. 41, No. 5, pp. 544-552.
Davies et al., The E3L and K3L vaccinia virus gene products stimulate translation through inhibition of the double-stranded RNA-dependent protein kinase by different mechanisms, J. Virol., vol. 67(3), p. 1688-92, 1993.
Dehoon et al., Open source clustering software, Bioinformatics 2004, vol. 20(9), pp. 1453-1454.
Delgoffe et al., Enhanced interaction between Hsp90 and raptor regulates mTOR signaling upon T cell activation, Mol. Immunol. 2009; vol. 46(13), p. 2694-8.
Di Pilato M, et al., Distinct Roles of Vaccinia Virus NF-KB Inhibitor Proteins A52,B15, and K7 in the Immune Response, J Virology, vol. 91, Issue 13, e00575-17.
Donnenberg, et al., Rare-Event Analysis of Circulating Human Dendritic Cell Subsets and Their Presumptive Mouse Counterparts, Transplantation, vol. 72, p. 1946-1951, 2001.
Dowty and Wolff, ed, Gene Therapeutics, Methods and Applications of Direct Gene Transfer, Birkhauser, Boston, USA (1994).
Drugs and Pharmaceutical Sciences, Pharmaceutical Preformulation and Formulation, 2nd Edition, Gibson Ed., CRC Press LLC: Boca Raton, FL, 2004.
Durham et al. "Oncolytic VSV Primes Differential Responses to Immuno-oncology Therapy," Molecular Therapy, Aug. 30, 2017 (Aug. 30, 2017), vol. 25, No. 8, pp. 1917-1932.
Earl et al., Native oligomeric human immunodeficiency virus type 1 envelope glycoprotein elicits diverse monoclonal antibody reactivities, J of Virology, vol. 68, No. 5, 1994.
Earl et al., Removal of cryptic poxvirus transcription termination signals from the human immunodeficiency virus type 1 envelope gene enhances expression and immunogenicity of a recombinant vaccinia virus, J. Virol., vol. 64, p. 2448-2451, 1990.
Ehrlich, et al., Engagement of NKG2D by cognate ligand or antibody alone is insufficient to mediate costimulation of human and mouse CD8+ T cells, J. Immunol., vol. 174, p. 1922-1931, 2005.
Eisenberg, et al., Real-time Intraoperative Detection of Breast Cancer Axillary Lymph Node Metastases using a Green Fluorescent Protein-expressing Herpes Virus. Annals of surgery, vol. 243, p. 824-30; discussion 830-2 (2006).
Elbashir, S. M. et al., RNA Interference is Mediated by 21- and 22-Nucleotide RNAs, Genes & Development, vol. 15; p. 188-200, 2001.
Emoto, et al., Transient Control of Interleukin-4-Producing Natural Killer T Cells in Liver of Listeria Monocytogenes-Infected Mice by Interleukin 12, Infection Immunity, vol. 65, p. 5003-5009, 1997.
Enzler, et al., Deficiencies of GM-CSF and Interferon Gamma Link Inflammation and Cancer. The Journal of Experimental Medicine, vol. 197, p. 1213-9 (2003).
Ercolini et al., Recruitment of Latent Pools of High-avidity CDS(+) T Cells to the Antitumor Immune Response. The Journal of Experimental Medicine, vol. 201, p. 1591-602 (2005).
Erickson et al., Hepatitis C Virus-Specific CTL Responses in the Liver of Chimpanzees with Acute and Chronic Hepatitis C, J. Immunol., vol. 151. p. 4189-4199, 1993.
Errington, F., et al., Fusogenic membrane glycoprotein-mediated tumour cell fusion activates human dendritic cells for enhanced IL-12 production and T-cell priming. Gene Therapy, vol. 13, p. 138-49 (2006).

(56) References Cited

OTHER PUBLICATIONS

Evans et al., Enhancement of Antigen-Specific Immunity via the TLR4 Ligands MPL Adjuvant and Ribi.529, Summary of Clinical Trials, Expert Review Vaccines, vol. 2, No. 2, 2003.
Fahy et al., Vaccinia Virus Protein C16 Acts Intracellularly to Modulate the Host Response and Promote Virulence, J. Gen. Virol., vol. 89, p. 2377-2387, 2008.
Falivene et al., Improving the MVA vaccine Potential by Deleting the Viral Gene Coding for the IL-18 Binding Protein. PLoS One 7, e32220, 2012.
Falkner et al., Transient Dominant Selection of Recombinant Vaccinia Viruses, J Virol., vol. 64(6), p. 3108-3111, 1990.
Feoktistova, et al., cIAPs Block Ripoptosome Formation, a RIPI/caspase-8 Containing Intracellular Cell Death Complex Differentially Regulated by cFLIP Isoforrns. Molecular Cell, vol. 43, p. 449-63 (2011).
Feuerer et al., Fat Treg Cells: a Liaison Between the Immune and Metabolic Systems, Nat Med, vol. 15(8), p. 930-9, 2009.
Filipazzi et al., Identification of a New Subset of Myeloid Suppressor Cells . . . Antitumor Vaccine. Journal of Clinical Oncology : Official Journal of the American Society of Clinical Oncology, vol. 25, p. 2546-53 (2007).
Fountzilas et al., Review: Oncolytic Virotherapy, Updates and Future Directions, Oncotarget, vol. 8, p. 102617-39, 2017.
Freund's Incomplete Adjuvant and Complete Adjuvant (Difco Laboratories, Detroit, Mich.).
Friedman et al., Hypoxia Moderates y134.5-Deleted Herpes Simplex Virus Oncolytic Activity in Human Glioma Xenoline Primary Cultures, Transl Oncol 2012, vol. 5(3), p. 200-7.
Fujita, et al.COX-2 Blockade Suppresses Gliomagenesis by Inhibiting Myeloid-Derived Suppressor Cells. Cancer Research, vol. 71, p. 2664-74, 2011.
Fukata et al., Role of Toll-like Receptors in Gastrointestinal Malignancies. Oncogene, vol. 27, p. 234-43 (2008).
Furtek et al., Strategies and Approaches of Targeting STAT3 for Cancer Treatment, ACS Chem. Biol., vol. 11(2), p. 308-318 (2016).
Galon J. et al., Type, Density, and Location of Immune Cells within Human Colorectal Tumors Predict Clinical Outcome. Science, vol. 313, p. 1960-4 (2006).
Garber, K., China Approves World's First Oncolytic Virus Therapy for Cancer Treatment. J Natl Cancer Inst, vol. 98, p. 298-300 (2006).
Gil et al., Targeting CXCL 12/CXCR4 Signaling with Oncolytic Virotherapy Disrupts Tumor, Vasculature and Inhibits Breast Cancer Metastases, Proceedings of the National Academy of Sciences, Mar. 13, 2013, vol. 110, No. 14, pp. 1291-1300.
Ginestier, et al. CXCR1 Blockade Selectively Targets Human Breast Cancer Stem Cells in Vitro and in Xenografts. The Journal of Clinical Investigation, vol. 120, p. 485-97 (2010).
Gnant et al., Tumor-specific Gene Delivery using Recombinant Vaccinia Virus in a Rabbit Model of Liver Metastases. J Natl Cancer Inst, vol. 91, p. 1744-50 (1999).
Godin-Ethier, et al., Indoleamine 2,3-dioxygenase Expression in Human Cancers: Clinical and Immunologic Perspectives. Clinical Cancer Research: An Official Journal of the American Association for Cancer Research, vol. 17, p. 6985-91 (2011).
Graham et al., Characteristics of a Human Cell Line Transformed by DNA from Human Adenovirus Type 5, J. Gen. Virol., vol. 36, p. 59-72, 1977.
Graham, Covalently Closed Circles of Human Adenovirus DNA are Infectious, EMBO J., vol. 3, p. 2917, 1984.
Green, D.R. et al., Immunogenic and Tolerogenic Cell Death. Nature Reviews, Immunology, vol. 9, p. 353-63 (2009).
Guo et al., Oncolytic Immunotherapy: Conceptual Evolution, Current Strategies, and Future Perspectives, Front. Oncol., vol. 8, p. 1-15, 2017.
Guo et al., Oncolytic Immunotherapy: Dying the Right Way is a Key to Eliciting Potent Antitumor Immunity, Frontiers in Oncology, Apr. 10, 2014 (Apr. 10, 2014), vol. 4, No. 74, pp. 1-11.
Guo, et al., Oncolytic Virotherapy: Molecular Targets in Tumor-Selective Replication and Carrier Cell-mediated Delivery of Oncolytic Viruses. Biochim Biophys Acta (2008).
Guo, et al., The Enhanced Tumor Selectivity of an Oncolytic Vaccinia Lacking the Host Range and Antiapoptosis Genes SPI-1 and SPI-2. Cancer Res, vol. 65, p. 9991-8 (2005).
Guy, et al., Expression of the Neu Protooncogene in the Mammary Epithelium of Transgenic Mice Induces Metastatic Disease. Proceedings of the National Academy of Sciences of the United States of America, vol. 89, p. 10578-82 (1992).
International Search Report and Written Opinion for PCT/US2021/059887, mailed Feb. 2, 2022.
Gaston et al., Production of Bioactive Soluble Interleukin-15 in Complex with Interleukin-15 Receptor Alpha from a Conditionally-Replicating Oncolytic HSV-1, PLOS One, 2013, vol. 8, No. 11, p. 81768.
Kowalsky et al., Superagonist IL-15Armed Oncolytic Virus Elicits Potent Antitumor Immunity and Therapy that are Enchanced with PD-1 Blockadge, Molecular Therapy, Nature Publishing Group, 2018, vol. 26, No. 10, p. 2476-2486.
Tosic et al., Myxoma Virus Expressing a Fusion Protein of Interleukin-15 (IL15) and IL 15 Receptor Alpha has Enhanced Antitumor Activity, PLOS One, 2014, vol. 9, No. 10, p. 3109801.
Albarnaz, Modulating Vaccinia Virus Immunomodulators to Improve Immunological Memory, Viruses, 2018, vol. 10, p. 1-33.
Brown et al., "The pl4 FAST Protein of Reptilian Reovirus Increases Vesicular Stomatitis Virus Neuropathogenesis", Journal of Virology, 2009, vol. 83, No. 2, p. 552-561.
Carrillo et al., "Enhanced adaptation of vesicular stomatitis virus in cells infected with vaccinia virus", Infection, Genetics and Evolution, Elsevier, Amsterdam, NL, 2008, vol. 8, No. 5, pp. 614-620.
Guo et al., Rapid Generation of Multiple Loci-Engineered Marker-free Poxvirus and Characterization of a Clinical-Grade Oncolytic Vaccinia Virus, Molecular Therapy, Methods and Clinical Development, 2017, vol. 7, p. 112-122.
Hughes et al., A rapid Orthopoxvirus purification protocol suitable for high-containment laboratories, Journal of Virological Methods, 2017, vol. 243, p. 68-73.
International Search Report and Written Opinion for PCT/US2022/026703, mailed Oct. 5, 2022.
Kim, P.S., et al., Antibody association with HER-2/neu-targeted vaccine enhances CD8 T cell responses in mice through Fe-mediated activation of DCs. The Journal of Clinical Investigation, vol. 118, p. 1700-11 (2008).
Lun et al., "Effects of Intravenously Administered Recombinant Vesicular Stomatitis Virus (VSV-delta-M51) on Multifocal and Invasive Gliomas", Journal of the National Cancer Institute, 2006, vol. 98, No. 21, p. 1546-1556.
Millipore Sigma, Benzonase endonuclease, SAFC, 2018, pp. 1-40.
Moleirinho et al., Clinical-grade Oncolytic Adenovirus Purification Using Polysorbate 20 as an Alternative for Cell Lysis, Current Gene Therapy, 2018, vol. 18, p. 366-374.
Pharmaceutical Preformulation and Formulation, CRC Press LLC: Boca Raton, FL, 2004).
International Search Report and Written Opinion for PCT/US2022/033524, mailed Nov. 23, 2022.
KaliVir Poster Presentation 894; A novel oncolytic immunotherapy, VET3-TGI, overcomes TGFB1 mediated immunosuppression, augments type-1 immune response, and displays potent therapeutic activity in multiple mouse tumor models; Published Nov. 7, 2022.
Muthuswamy et al., A novel oncolytic immunotherapy, VET3-TGI, overcomes TGFB1 mediated Immunosuppression, augments type-1 immune response, and displays potent therapeutic activity in multiple mouse tumor models, Journal for Immuno Therapy of Cancer 2022, vol. 10, Abstract.
Yoshie, Chemokine receptors as therapeutic targets, Japanese Journal of Clinical Immunology, 2013, vol. 36, No. 4, pp. 189-196.
Wu et al., Structures of the CXCR4 Chemokine GPCR with Small-Molecule and Cyclic Peptide Antagonists, Science, 2010, vol. 330, p. 1066-1071.
Billottet et al., CXCR3, a double-edged sword in tumor progression and angiogenesis, Biochimica et Biophysica Acta, 2013, vol. 1836, p. 287-295.

(56) References Cited

OTHER PUBLICATIONS

Cronin et al., Bacterial-Mediated Knockdown of Tumor Resistance to an Oncolytic Virus Enhances Therapy, Mol Ther, 2014, vol. 22, No. 6, p. 1188-1197.
Dey et al., Intranasal Oncolytic Virotherapy with CXCR4-Enhanced Stem Cells Extends Survival in Mouse Model of Glioma, Stem Cell Reports, 2016, vol. 7, p. 471-482.
Genbank Accession No. NM_00586.4 *Homo Sapiens* Interleukin 2 (IL2), mRNSA, Earliest priority 1992, 4 pages.
Genbank Accession No. NM_01123041.3 Human CCR2 mRNA, Earliest priority 1988, 5 pages.
Lin et al., Direct Priming of CD8+ T Cells Persists in the Face of Cowpox Virus Inhibitors of Antigen Presentation, Journal of Virology, 2021, vol. 95, Issue 10, e00186_21, p. 1-15.
Pettit et al., Vaccinia Virus Transfection of Hippocampal Slice Neurons, Neuron, 1995, vol. 14, p. 685-688.
Wang et al., An optimized HMGB1 expressed by recombinant rabies virus enhances immunogenicity through activation of dendritic cells in mice, Oncotarget, 2017, vol. 8, No. 48, p. 83539-83554.
Zhou et al., Tumor-targeting bacteria engineered to fight cancer, Nat Rev Cancer, 2018, vol. 18, p. 727-743.
Bernard, et al. Chronic Inhibition of Cyclooxygenase-2 Attenuates Antibody Responses Against Vaccinia Infection. Vaccine, vol. 28, p. 1363-72 (2010).
Chartier et al., Efficient Generation of Recombinant Adenovirus Vectors by Homologous Recombination in *Escherichia coli*, Journal of Virology, Jul. 1996, vol. 7, No. 7, p. 4805-4810.
Gulley, et al., Pilot Study of Vaccination with Recombinant CEA-MUC-1-TRICOM Poxviral-based Vaccines in Patients with Metastatic Carcinoma. Clin Cancer Res, vol. 14, p. 3060-9 (2008).
Hynes, et al., Analysis of a Second Bacteriophage Hyaluronidase Gene from *Streptococcus pyogenes*: Evidence for a Third Hyaluronidase Involved in Extracellular Enzymatic Activity, Infection and Immunity, 1995, vol. 63, No. 8, p. 3015-3020.
Konetschny et al., Generation of Transduction-Competent Retroviral Vectors by Infection with a Single Hybrid Vaccinia Virus, Journal of Virology, 2003, vol. 77, No. 12, p. 7017-7025.
Paolino et al., Drug delivery systems, Encyclopedia of Medical Devices and Instrumentation, 2006, p. 437-495.
Yan et al., (2012) High mobility group box 1 activates caspase-1 and promotes hepatocellular carcinoma invasiveness and metastases. Hepatology. Jan. 1, 20121, vol. 55, Issue 6, pp. 1863-1875.
Yang et al., Mechanisms of Monophosphoryl Lipid A Augmentation of Host Responses to Recombinant HagB from Porphyromonas gingivalis, Infection and Immunity, Jul. 2002, p. 3557-3565.
Zamarin et al., Intratumoral modulation of the inducible co-stimulator ICOS by recombinant oncolytic virus promotes systemic anti-tumour immunity, Nature Communication, 2017; 8: p. 1-14.
Zeh H, et al., First-in-man Study of Western Reserve Strain Oncolytic Vaccinia Virus: Safety, Systemic Spread and Anti-tumor Activity. Molecular Therapy, vol. 23, No. 1, Jan. 2015.
Zhang et al., Eradication of solid human breast tumors in nude mice with an intravenously injected light-emitting oncolytic vaccinia virus. Cancer Res, vol. 67, p. 10038-46 (2007).
Deng et al., Oncolytic efficacy of thymidine kinase-deleted vaccinia virus strain Guang9. Oncotarget, 2017, vol. 8, No. 25, p. 40533-40543.
Harte et al. The poxvirus protein A52R targets Toll-like receptor signaling complexes to suppress host defense. J Exp Med. 2003, vol. 197, No. 3, p. 343-351.
Muller et al., Engineering NK Cells Modified with an EGFRvIII-specific Chimeric Antigen Receptor to Overexpress CXCR4 Improves Immunotherapy of CXCL12/SDF-1α-secreting Gliobastoma, J Immunother, 2015, vol. 38, No. 5, p. 197-210.
Sanchez-Puig et al., Susceptibility of different leukocyte cell types to Vaccinnia virus infection, Virgology Journal, 2004, vol. 1, No. 10, p. 1-7.
Schcheilkunov, Human Monkeypox and small pox viruses: genomic comparison, FEBS Letters, 2001, vol. 509, p. 66-70.
Wendel et al., Natural Killer Cell Accumulation in Tumors is Dependent on IFN-γ and CXCR3 Ligands, Cancer Res., 2008, vol. 68, No. 20, p. 8437-8445.
Zhao et al., CXCR4 over-expression and survival in cancer: A system review and meta-analysis, Oncotarget, 2014, vol. 6, No. 7, p. 5022-5044.
Benfield et al., Vaccinia virus protein K7 is a virulence factor that alters the acute immune response to infection; Journal of General Virology, 2013, vol. 94, p. 1647-1657.
Di Pilato et al., NFkB activation by modified vaccinia virus as a novel strategy to enhance neutrophil migration and HIV-specific T-cell responses, PNAS, 2015, p. E1333-E1342.
Kleinpeter et al., Vectorization in an oncolytic vaccinia virus of an antibody, a Fab and a scFv against programmed cell death-1 (PD-1) allows their intratumorial delivery and an improved tumor-growth inhibition, Oncoimmunology, 2016; vol. 5, No. 10, e1220467, p. 1-14.
Lim et al., Targeting the CCL2-CCR2 signaling axis in cancer metastasis, Oncotarget, 2016, vol. 7, No. 19, p. 28697-28710.
Ogata et al., Overexpression of PIAS3 Suppresses Cell Growth and Restores the Drug Sensitivity of Human Lung Cancer Cells in Association with PI3-K/Akt Inactivation, Neoplasia, 2006, vol. 8, No. 10, p. 817-825.
Oghumu et al., Transgenic Expression of CXCR3 on T Cells Enhances Susceptibility to Cutaneous Leishmania major Infection by Inhibiting Monocyte Maturation and Promoting Th2 Response, Infection and Immunity, 2015, vol. 83, No. 1, p. 67-76.
Pozzobon et al., CXCR4 signaling in health and disease, Immunology Letters, 2015, vol. 177, p. 6-15.
Raemdonck et al., CXCR3 ligands in disease and therapy, Cytokine & Growth Factor Reviews, 2015, vol. 26, p. 311-327.
Wu et al., Altered CXCR3 isoform expression regulates prostate cancer cell migration and invasion, Molecular Cancer, 2012, vol. 11, No. 3, p. 1-16.

* cited by examiner

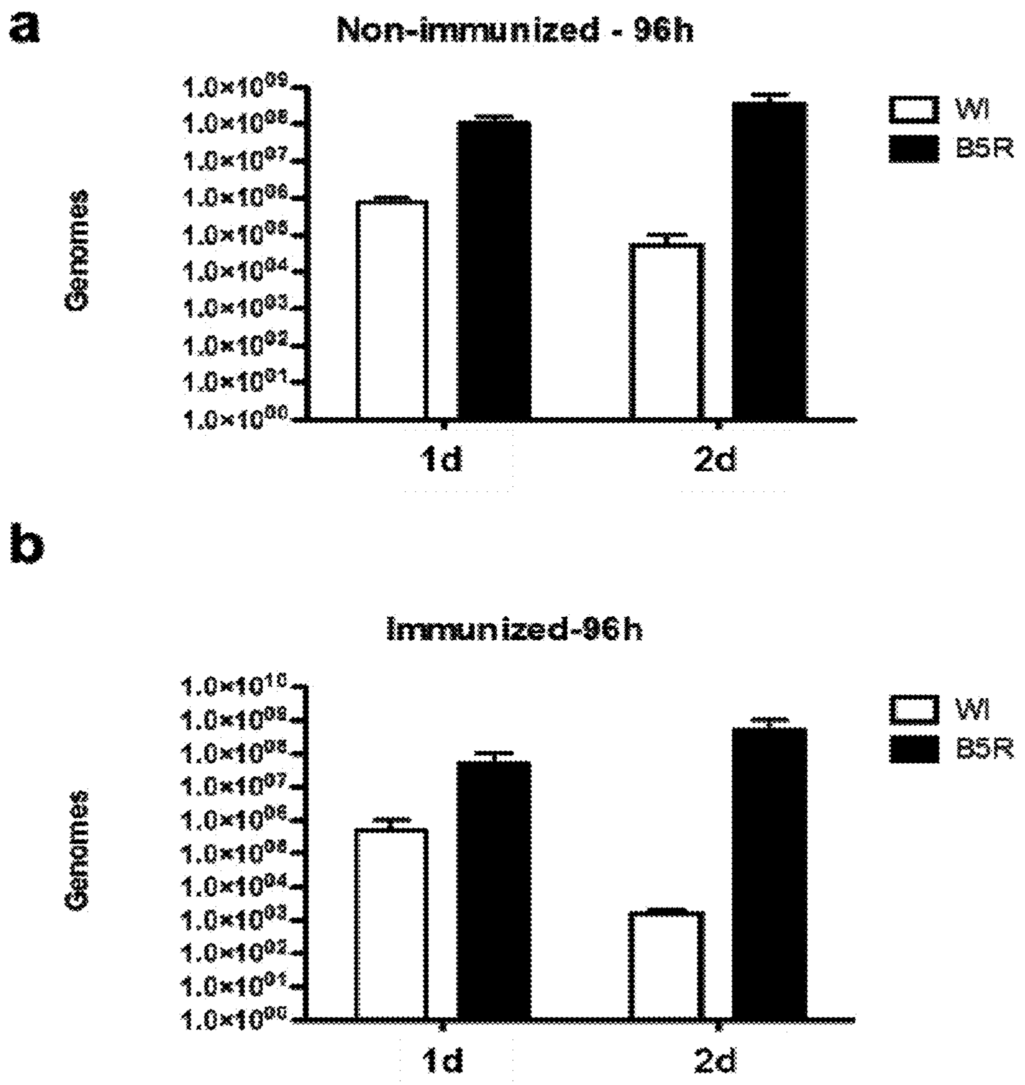
a
Non-immunized - 96h
Genomes
1.0×10^09
1.0×10^08
1.0×10^07
1.0×10^06
1.0×10^05
1.0×10^04
1.0×10^03
1.0×10^02
1.0×10^01
1.0×10^00
1d
2d
Wl
B5R
b
Immunized-96h
Genomes
1.0×10^10
1.0×10^09
1.0×10^08
1.0×10^07
1.0×10^06
1.0×10^05
1.0×10^04
1.0×10^03
1.0×10^02
1.0×10^01
1.0×10^00
1d
2d
Wl
B5R

| | PBS vs TK- | PBS vs CCR5 | PBS vs CXCR4 | TK- vs CCR5 | TK- vs CXCR4 | CCR5 vs CXCR4 |
|---|---|---|---|---|---|---|
| Day07 | ns | ns | ** | * | ns | *** |
| Day10 | ns | ** | * | ns | ** | *** |
| Day14 | ns | ns | * | ns | ** | *** |
| Day17 | * | * | * | ns | ns | ns |

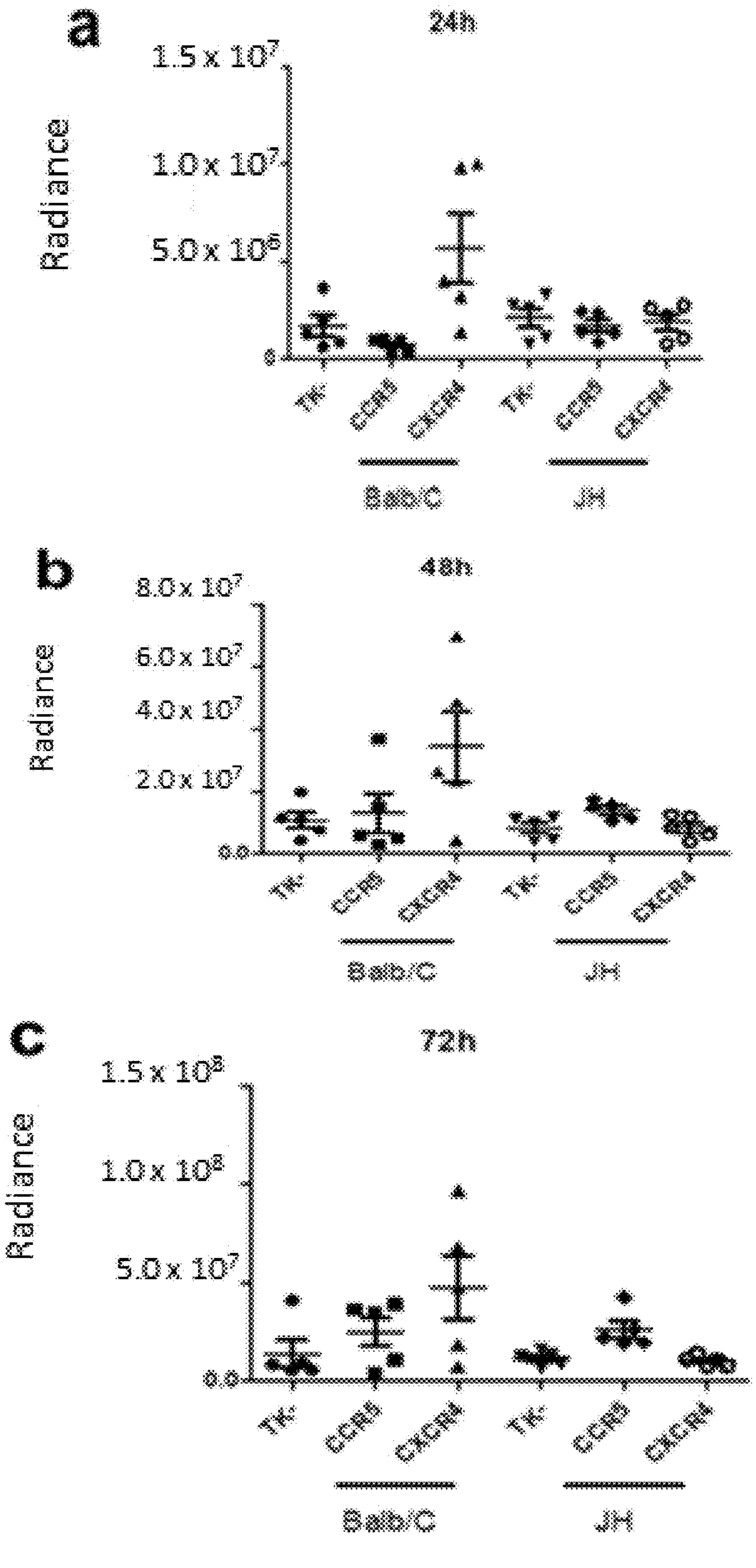
a
24h
Radiance
1.5 x 10^7
1.0 x 10^7
5.0 x 10^6
0
TK-
CCR5
CXCR4
TK-
CCR5
CXCR4
Balb/C
JH
b
48h
Radiance
8.0 x 10^7
6.0 x 10^7
4.0 x 10^7
2.0 x 10^7
0.0
TK-
CCR5
CXCR4
TK-
CCR5
CXCR4
Balb/C
JH
c
72h
Radiance
1.5 x 10^8
1.0 x 10^8
5.0 x 10^7
0.0
TK-
CCR5
CXCR4
TK-
CCR5
CXCR4
Balb/C
JH

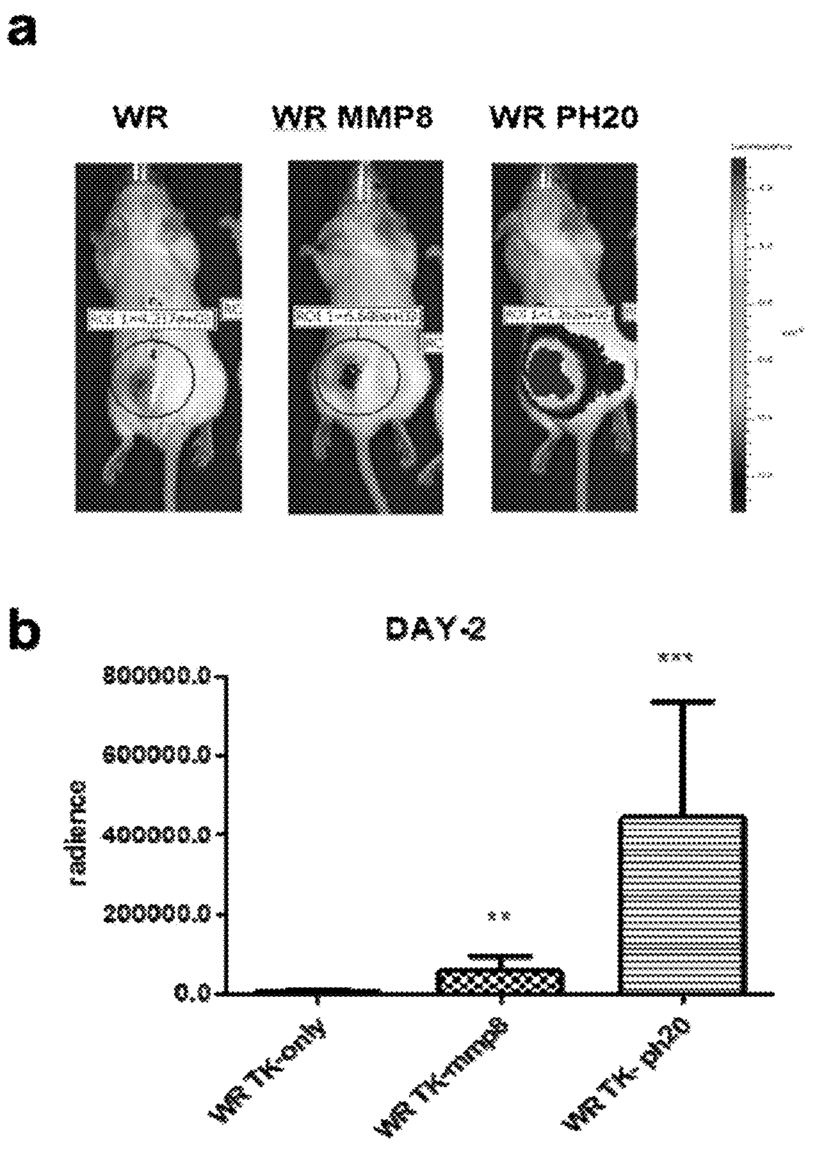
a
WR
WR MMP8
WR PH20
b
DAY-2
800000.0
600000.0
400000.0
200000.0
0.0
radience
***
**
WR TK-only
WR TK-mmp8
WR TK- ph20

PLATFORM ONCOLYTIC VECTOR FOR SYSTEMIC DELIVERY

CROSS-REFERENCE

This application is a continuation of U.S. application Ser. No. 17/192,736, filed on Mar. 4, 2021, which is a continuation of U.S. application Ser. No. 16/759,705, filed on Apr. 27, 2020, which is a national stage of International Application No. PCT/US18/058456 filed on Oct. 31, 2018, which claims the benefit of U.S. Provisional Application No. 62/579,517 filed on Oct. 31, 2017, each incorporated by reference herein in their entirety.

SEQUENCE LISTING

The instant application contains a Sequence Listing which has been submitted electronically in ASCII format and is hereby incorporated by reference in its entirety. Said ASCII copy, created on Oct. 27, 2021, is named 199249_706303_SL.txt and is 510,289 bytes in size.

INCORPORATION BY REFERENCE

All publications, patents, patent applications, and NCBI accession numbers mentioned in this specification are herein incorporated by reference to the same extent as if each individual publication, patent, or patent application was specifically and individually indicated to be incorporated by reference, and as if set forth in their entireties. In the event of a conflict between a term as used herein and the term as defined in the incorporated reference, the definition of this disclosure controls.

SUMMARY

One aspect of the present disclosure provides a modified oncolytic virus, comprising an exogenous nucleic acid that codes for a chemokine receptor, a membrane associated protein that can be capable of degrading hyaluronan, a microbial protein that is capable of degrading hyaluronan, or any combinations thereof.

In some embodiments, the chemokine receptor can comprise at least one of CXCR4 and CCR2.

In some embodiments, the modified oncolytic virus can comprise the exogenous nucleic acid that can code for the membrane associated protein. In some embodiments, the exogenous nucleic acid that codes for the membrane associated protein can code for a hyaluronidase. In some embodiments, the hyaluronidase can be PH-20. In some embodiments, the PH-20 can be GPI-anchored. In some embodiments, the modified oncolytic virus can comprise the exogenous nucleic acid that can code for the microbial protein. In some embodiments, the microbial protein comprises a secreted hyaluronidase. In some embodiments, the secreted hyaluronidase comprises at least one of HysA, lin, sko, rv, or any combinations thereof. In some embodiments, the microbial protein comprises HysA.

In some embodiments, the modification can enhance production of enveloped extracellular form (EEV) of the virus.

In some embodiments, the modified oncolytic virus can comprise the modification in the genome of the virus. In some embodiments, the modification can comprise a mutation or a deletion of the B5R gene, wherein said deletion is a partial deletion. In some embodiments, the modification can comprise a mutation or a deletion in a SCR region of the B5R gene, wherein said SCR region comprises SCR1, SCR3, SCR4, or any combinations thereof, and wherein the SCR region does not comprise SCR2.

In some embodiments, the modified oncolytic virus can comprise the deletion of the B5R gene, and the deletion can be a partial deletion of the B5R gene.

In some embodiments, the modified oncolytic virus can comprise a modification in the genome of the virus, wherein the modification can comprise a mutation or a deletion of the A52R gene. In some embodiments, the modification can comprise the deletion of the A52R gene.

In some embodiments, the modified oncolytic virus can further comprise at least one additional modification in the genome of the virus, wherein the additional modification can comprise a mutation or a deletion of a further viral gene.

In some embodiments, the further viral gene can comprise at least one of F13L, A36R, A34R, A33R, B8R, B18R, SPI-1, SPI-2, B15R, VGF, E3L, K3L, A41L, K7R, and N1L, and a functional domain or fragment or variant thereof, or any combinations thereof.

In some embodiments, the modified oncolytic virus can further comprise at least one additional exogenous nucleic acid.

In some embodiments, the at least one additional exogenous nucleic acid can comprise a nucleic acid sequence that codes for a protein or a fragment thereof that: modulates NFκB (NF-kappaB) signaling, promotes reduction of interstitial fluid pressure (IFP) in a tumor, modulates STAT3-mediated gene activation, promotes T cell activation, promotes attraction of NK cells to virus-infected cells, modulates metabolic program of virus-infected cells, modulates fatty acid uptake by virus-infected cells, promotes therapeutic targeting of MDSCs, or any combinations thereof.

In some embodiments, the at least one additional exogenous nucleic acid can comprise a nucleic acid coding for at least one of HMGB1, PIAS3, IL15, IL15-Rα, LIGHT, ITAC, fractalkine, CCL5, and a functional domain or fragment or variant thereof, or any combinations thereof.

In some embodiments, the modified oncolytic virus can comprise: (a) the exogenous nucleic acid that codes for at least one of CXCR4 and CCR2; and (b) the exogenous nucleic acid that codes for a hyaluronidase.

In some embodiments, the modified oncolytic virus can comprise: (a) the exogenous nucleic acid that codes for at least one of CXCR4 and CCR2; and (b) the mutation or the deletion of B5R gene.

In some embodiments, the modified oncolytic virus can comprise: (a) the exogenous nucleic acid that codes for a hyaluronidase; and (b) the mutation or the deletion of B5R gene.

In some embodiments, the modified oncolytic virus can comprise: (a) the exogenous nucleic acid that codes for at least one of CXCR4 and CCR2; (b) the exogenous nucleic acid that codes for a hyaluronidase; and (c) the mutation or the deletion of B5R gene.

In some embodiments, the modified oncolytic virus can comprise: (a) the exogenous nucleic acid that codes for at least one of CXCR4 and CCR2; and (b) the mutation or the deletion of the further viral gene can comprise at least one of F13L, A36R, A34R, A33R, B8R, B18R, SPI-1, SPI-2, B15R, VGF, E3L, K3L, A41L, K7R, N1L, and a functional domain or fragment or variant thereof, or any combinations thereof.

In some embodiments, the modified oncolytic virus can comprise: (a) the exogenous nucleic acid that codes for a hyaluronidase; and (b) the mutation or the deletion of the further viral gene can comprise at least one of F13L, A36R, A34R, A33R, B8R, B18R, SPI-1, SPI-2, B15R, VGF, E3L, K3L, A41L, K7R, N1L, and a functional domain or fragment or variant thereof, or any combinations thereof.

In some embodiments, the modified oncolytic virus can comprise: (a) the exogenous nucleic acid that codes for at least one of CXCR4 and CCR2; (b) the exogenous nucleic acid that codes for a hyaluronidase; and (c) the mutation or the deletion of the further viral gene can comprise at least one of F13L, A36R, A34R, A33R, B8R, B18R, SPI-1, SPI-2, B15R, VGF, E3L, K3L, A41L, K7R, N1L, and a functional domain or fragment or variant thereof, or any combinations thereof.

In some embodiments, the modified oncolytic virus can comprise: (a) the exogenous nucleic acid that codes for at least one of CXCR4 and CCR2; (b) the mutation or the deletion of B5R gene; and (c) the mutation or the deletion of the further viral gene can comprise at least one of F13L, A36R, A34R, A33R, B8R, B18R, SPI-1, SPI-2, B15R, VGF, E3L, K3L, A41L, I7R, N1L, and a functional domain or fragment or variant thereof, or any combinations thereof.

In some embodiments, the modified oncolytic virus can comprise: (a) the exogenous nucleic acid that codes for a hyaluronidase; (b) the mutation or the deletion of B5R gene; and (c) the mutation or the deletion of the further viral gene can comprise at least one of F13L, A36R, A34R, A33R, B8R, B18R, SPI-1, SPI-2, B15R, VGF, E3L, K3L, A41L, I7R, N1L, and a functional domain or fragment or variant thereof, or any combinations thereof.

In some embodiments, the modified oncolytic virus can comprise: (a) the exogenous nucleic acid that codes for at least one of CXCR4 and CCR2; (b) the exogenous nucleic acid that codes for a hyaluronidase; (c) the mutation or the deletion of B5R gene; and (d) the mutation or the deletion of the further viral gene can comprise at least one of F13L, A36R, A34R, A33R, B8R, B18R, SPI-1, SPI-2, B15R, VGF, E3L, K3L, A41L, I7R, N1L, and a functional domain or fragment or variant thereof, or any combinations thereof.

In some embodiments, the modified oncolytic virus can comprise: (a) the exogenous nucleic acid that codes for at least one of CXCR4 and CCR2; and (b) the at least one additional exogenous nucleic acid that codes for at least one of HMGB1, PIAS3, IL15, IL15-Rα, LIGHT, ITAC, fractalkine, CCL5, and a functional domain or fragment or variant thereof, or any combinations thereof.

In some embodiments, the modified oncolytic virus can comprise: (a) the exogenous nucleic acid that codes for a hyaluronidase; and (b) the at least one additional exogenous nucleic acid that codes for at least one of HMGB1, PIAS3, IL15, IL15-Rα, LIGHT, ITAC, fractalkine, CCL5, and a functional domain or fragment or variant thereof, or any combinations thereof.

In some embodiments, the modified oncolytic virus can comprise: (a) the exogenous nucleic acid that codes for at least one of CXCR4 and CCR2; (b) the exogenous nucleic acid that codes for a hyaluronidase; and (c) the at least one additional exogenous nucleic acid that codes for at least one of HMGB1, PIAS3, IL15, IL15-Rα, LIGHT, ITAC, fractalkine, CCL5, and a functional domain or fragment or variant thereof, or any combinations thereof.

In some embodiments, the modified oncolytic virus can comprise: (a) the exogenous nucleic acid that codes for at least one of CXCR4 and CCR2; (b) the mutation or the deletion of B5R gene; and (c) the at least one additional exogenous nucleic acid that codes for at least one of HMGB1, PIAS3, IL15, IL15-Rα, LIGHT, ITAC, fractalkine, CCL5, and a functional domain or fragment or variant thereof, or any combinations thereof.

In some embodiments, the modified oncolytic virus can comprise: (a) the exogenous nucleic acid that codes for a hyaluronidase; (b) the mutation or the deletion of B5R gene; and (c) the at least one additional exogenous nucleic acid that codes for at least one of HMGB1, PIAS3, IL15, IL15-Rα, LIGHT, ITAC, fractalkine, CCL5, and a functional domain or fragment or variant thereof, or any combinations thereof.

In some embodiments, the modified oncolytic virus can comprise: (a) the exogenous nucleic acid that codes for at least one of CXCR4 and CCR2; (b) the exogenous nucleic acid that codes for a hyaluronidase; (c) the mutation or the deletion of B5R gene; and (d) the at least one additional exogenous nucleic acid that codes for at least one of HMGB1, PIAS3, IL15, IL15-Rα, LIGHT, ITAC, fractalkine, CCL5, and a functional domain or fragment or variant thereof, or any combinations thereof.

In some embodiments, the modified oncolytic virus can comprise: (a) the exogenous nucleic acid that codes for at least one of CXCR4 and CCR2; (b) the exogenous nucleic acid that codes for a hyaluronidase; (c) the mutation or the deletion of B5R gene; (d) the mutation or the deletion of the further viral gene can comprise at least one of F13L, A36R, A34R, A33R, B8R, B18R, SPI-1, SPI-2, B15R, VGF, E3L, K3L, A41L, K7R, N1L, and a functional domain or fragment or variant thereof, or any combinations thereof; and (e) the at least one additional exogenous nucleic acid that codes for at least one of HMGB1, PIAS3, IL15, IL15-Rα, LIGHT, ITAC, fractalkine, CCL5, and a functional domain or fragment or variant thereof, or any combinations thereof.

In some embodiments, the hyaluronidase comprises PH-20. In some embodiments, the hyaluronidase comprises HysA. In some embodiments, the modified oncolytic virus can further comprise an exogenous nucleic acid that codes for a viral VH1 protein.

In some embodiments, the modified oncolytic virus can comprise the exogenous nucleic acid coding for the viral VH1 protein, wherein the exogenous nucleic acid can be from a genome of a poxvirus, wherein the poxvirus can be not vaccinia virus. In some embodiments, the poxvirus can comprise a measles virus, a poliovirus, a poxvirus, a vaccinia virus, an adenovirus, an adeno associated virus, a herpes simplex virus, a vesicular stomatitis virus, a reovirus, a Newcastle disease virus, a senecavirus, a lentivirus, a mengovirus, or a myxoma virus.

In some embodiments, the viral genome can comprise a thymidine kinase gene. In some embodiments, a thymidine kinase gene can be deleted from the viral genome.

In some embodiments, the modified oncolytic virus can further comprise a thymidine kinase gene from a herpes simplex virus.

In some embodiments, the modified oncolytic virus exhibits enhanced intratumoral and intertumoral spreading, enhanced immune evasion, enhanced tumor-specific replication, enhanced tumor-targeted delivery, compared to an otherwise identical oncolytic virus that does not comprise the modifications as disclosed herein.

In some embodiments, the modified oncolytic virus can comprise a vaccinia virus, an adeno associated virus, an adenovirus, a reovirus, a lentivirus, a herpes simplex virus, a vesicular stomatitis virus, a mengovirus, or a myxoma virus. In some embodiments, the modified oncolytic virus can be a vaccinia virus.

Another aspect of the present disclosure provides an oncolytic vaccinia virus that can comprise at least two of the following: (a) a modification that enhances intratumoral and intertumoral spreading of the virus; (b) a modification that enhances systemic delivery of the virus; (c) a modification that enhances tumor-specific replication of the virus; and (d) a modification that enhances immune evasion of the virus.

Yet another aspect of the present disclosure provides an oncolytic vaccinia virus that can comprise an exogenous nucleic acid that codes for a protein, or a fragment thereof, that enhances degradation of an extracellular matrix (ECM) of a tumor.

In some embodiments of the oncolytic vaccinia virus, the protein or the fragment thereof that enhances degradation of the ECM can be a hyaluronidase. In some embodiments, the hyaluronidase can be a membrane associated hyaluronidase, such as PH-20. In some embodiments, the PH-20 can be GPI-anchored. In some embodiments, the hyaluronidase can be a microbial hyaluronidase, such as HysA.

In some embodiments, the oncolytic vaccinia virus can comprise at least one of the following: (a) a modification that enhances intratumoral and intertumoral spreading of the virus; (b) a modification that enhances systemic delivery of the virus; (c) a modification that enhances tumor-specific replication of the virus; and (d) a modification that enhances immune evasion of the virus.

Yet another aspect of the present disclosure provides an oncolytic vaccinia virus that can comprise an exogenous nucleic acid that codes for a chemokine receptor, wherein expression of the chemokine receptor from the virus enhances systemic delivery of the virus.

In some embodiments, the chemokine receptor can comprise at least one of CXCR4 and CCR2.

In some embodiments, the oncolytic vaccinia virus can comprise the exogenous nucleic acid that codes for the chemokine receptor, and can further comprise at least one of the following: (a) a modification that enhances degradation of an ECM of a tumor; and (b) a modification that enhances production of EEV form of the virus;

Yet another aspect of the present disclosure provides an oncolytic vaccinia virus that can comprise a first modification in the genome of the virus that enhances production of EEV form of the virus, and at least one of the following further modifications: (a) a modification that enhances intratumoral and intertumoral spreading of the virus; (b) a modification that enhances systemic delivery of the virus; (c) a modification that enhances tumor-specific replication of the virus; and (d) a modification that enhances immune evasion of the virus.

In some embodiments, the first modification can comprise a mutation or a deletion of the B5R gene.

In some embodiments, the oncolytic vaccinia virus can comprise a mutation or a deletion of a further viral gene, wherein the further viral gene can comprise at least one of F13L, A36R, A34R, A33R, B8R, B18R, SPI-1, SPI-2, B15R, VGF, E3L, K3L, A41L, K7R, N1L, and A52R, and a functional domain or fragment or variant thereof, or any combinations thereof.

In some embodiments, the oncolytic vaccinia virus can further comprise a nucleic acid sequence that codes for a protein or a fragment thereof that: modulates NFκB signaling, promotes reduction of interstitial fluid pressure (IFP), modulates STAT3-mediated gene activation, promotes T cell activation, promotes attraction of NK cells to virus-infected cells, modulates metabolic program of virus-infected cells, modulates fatty acid uptake by virus-infected cells, promotes therapeutic targeting of MDSCs, or any combinations thereof.

In some embodiments, the at least one additional exogenous nucleic acid can comprise a nucleic acid coding for at least one of HMGB1, PIAS3, IL15, IL15-Rα, LIGHT, ITAC, fractalkine, CCL5, and a functional domain or fragment or variant thereof, or any combinations thereof.

In some embodiments, the oncolytic vaccinia virus can comprise: (a) the exogenous nucleic acid that codes for at least one of CXCR4 and CCR2; and (b) the exogenous nucleic acid that codes for a hyaluronidase.

In some embodiments, the oncolytic vaccinia virus can comprise: (a) the exogenous nucleic acid that codes for at least one of CXCR4 and CCR2; and (b) the mutation or the deletion of B5R gene.

In some embodiments, the oncolytic vaccinia virus can comprise: (a) the exogenous nucleic acid that codes for a hyaluronidase; and (b) the mutation or the deletion of B5R gene.

In some embodiments, the oncolytic vaccinia virus can comprise: (a) the exogenous nucleic acid that codes for at least one of CXCR4 and CCR2; (b) the exogenous nucleic acid that codes for a hyaluronidase; and (c) the mutation or the deletion of B5R gene.

In some embodiments, the oncolytic vaccinia virus can comprise: (a) the exogenous nucleic acid that codes for at least one of CXCR4 and CCR2; and (b) the mutation or the deletion of the further viral gene can comprise at least one of F13L, A36R, A34R, A33R, B8R, B18R, SPI-1, SPI-2, B15R, VGF, E3L, K3L, A41L, K7R, N1L, A52R, and a functional domain or fragment or variant thereof, or any combinations thereof.

In some embodiments, the oncolytic vaccinia virus can comprise: (a) the exogenous nucleic acid that codes for a hyaluronidase; and (b) the mutation or the deletion of the further viral gene can comprise at least one of F13L, A36R, A34R, A33R, B8R, B18R, SPI-1, SPI-2, B15R, VGF, E3L, K3L, A41L, K7R, N1L, A52R, and a functional domain or fragment or variant thereof, or any combinations thereof a functional domain thereof, or any combinations thereof.

In some embodiments, the oncolytic vaccinia virus can comprise: (a) the exogenous nucleic acid that codes for at least one of CXCR4 and CCR2; (b) the exogenous nucleic acid that codes for a hyaluronidase; and (c) the mutation or the deletion of the further viral gene can comprise at least one of F13L, A36R, A34R, A33R, B8R, B18R, SPI-1, SPI-2, B15R, VGF, E3L, K3L, A41L, K7R, N1L, A52R, and a functional domain or fragment or variant thereof, or any combinations thereof.

In some embodiments, the oncolytic vaccinia virus can comprise: (a) the exogenous nucleic acid that codes for at least one of CXCR4 and CCR2; (b) the mutation or the deletion of B5R gene; and (c) the mutation or the deletion of the further viral gene can comprise at least one of F13L, A36R, A34R, A33R, B8R, B18R, SPI-1, SPI-2, B15R, VGF, E3L, K3L, A41L, K7R, N1L, A52R, and a functional domain or fragment or variant thereof, or any combinations thereof.

In some embodiments, the oncolytic vaccinia virus can comprise: (a) the exogenous nucleic acid that codes for a hyaluronidase; (b) the mutation or the deletion of B5R gene; and (c) the mutation or the deletion of the further viral gene can comprise at least one of F13L, A36R, A34R, A33R, B8R, B18R, SPI-1, SPI-2, B15R, VGF, E3L, K3L, A41L, K7R, N1L, A52R, and a functional domain or fragment or variant thereof, or any combinations thereof.

In some embodiments, the oncolytic vaccinia virus can comprise: (a) the exogenous nucleic acid that codes for at least one of CXCR4 and CCR2; (b) the exogenous nucleic acid that codes for a hyaluronidase; (c) the mutation or the deletion of B5R gene; and (d) the mutation or the deletion of the further viral gene can comprise at least one of F13L, A36R, A34R, A33R, B8R, B18R, SPI-1, SPI-2, B15R, VGF, E3L, K3L, A41L, K7R, N1L, A52R, and a functional domain or fragment or variant thereof, or any combinations thereof.

In some embodiments, the oncolytic vaccinia virus can comprise: (a) the exogenous nucleic acid that codes for at least one of CXCR4 and CCR2; and (b) the at least one additional exogenous nucleic acid that codes for at least one of HMGB1, PIAS3, IL15, IL15-R, LIGHT, ITAC, fractalkine, CCL5, and a functional domain or fragment or variant thereof, or any combinations thereof.

In some embodiments, the oncolytic vaccinia virus can comprise: (a) the exogenous nucleic acid that codes for the hyaluronidase; and (b) the at least one additional exogenous nucleic acid that codes for at least one of HMGB1, PIAS3, IL15, IL15-R, LIGHT, ITAC, fractalkine, CCL5, and a functional domain or fragment or variant thereof, or any combinations thereof.

In some embodiments, the oncolytic vaccinia virus can comprise: (a) the exogenous nucleic acid that codes for at least one of CXCR4 and CCR2; (b) the exogenous nucleic acid that codes for the hyaluronidase; and (c) the at least one additional exogenous nucleic acid that codes for at least one of HMGB1, PIAS3, IL15, IL15-R, LIGHT, ITAC, fractalkine, CCL5, and a functional domain or fragment or variant thereof, or any combinations thereof.

In some embodiments, the oncolytic vaccinia virus can comprise: (a) the exogenous nucleic acid that codes for at least one of CXCR4 and CCR2; (b) the mutation or the deletion of B5R gene; and (c) the at least one additional exogenous nucleic acid that codes for at least one of HMGB1, PIAS3, IL15, IL15-R, LIGHT, ITAC, fractalkine, CCL5, and a functional domain or fragment or variant thereof, or any combinations thereof.

In some embodiments, the oncolytic vaccinia virus can comprise: (a) the exogenous nucleic acid that codes for the hyaluronidase; (b) the mutation or the deletion of B5R gene; and (c) the at least one additional exogenous nucleic acid that codes for at least one of HMGB1, PIAS3, IL15, IL15-R, LIGHT, ITAC, fractalkine, CCL5, and a functional domain or fragment or variant thereof, or any combinations thereof.

In some embodiments, the oncolytic vaccinia virus can comprise: (a) the exogenous nucleic acid that codes for at least one of CXCR4 and CCR2; (b) the exogenous nucleic acid that codes for the hyaluronidase; (c) the mutation or the deletion of B5R gene; and (d) the at least one additional exogenous nucleic acid that codes for at least one of HMGB1, PIAS3, IL15, IL15-R, LIGHT, ITAC, fractalkine, CCL5, and a functional domain or fragment or variant thereof, or any combinations thereof.

In some embodiments, the oncolytic vaccinia virus can comprise: (a) the exogenous nucleic acid that codes for at least one of CXCR4 and CCR2; (b) the exogenous nucleic acid that codes for the hyaluronidase; (c) the mutation or the deletion of B5R gene; (d) the mutation or the deletion of the further viral gene can comprise at least one of F13L, A36R, A34R, A33R, B8R, B18R, SPI-1, SPI-2, B15R, VGF, E3L, K3L, A41L, K7R, N1L, A52R, and a functional domain or fragment or variant thereof, or any combinations thereof; and (e) the at least one additional exogenous nucleic acid that codes for at least one of HMGB1, PIAS3, IL15, IL15-Rα, LIGHT, ITAC, fractalkine, CCL5, and a functional fragment or domain or variant thereof, or any combinations thereof.

One aspect provides an oncolytic vaccinia virus, comprising an exogenous nucleic acid that can code for a chemokine receptor, a protein that is capable of degrading hyaluronan, or any combinations thereof. In some embodiments, the protein that is capable of degrading hyaluronan, wherein the protein comprises PH-20 or HysA.

One aspect provides a modified oncolytic virus that can comprise a mutation or a deletion of A52R gene. In some embodiments, the modified oncolytic virus can comprise the deletion of A52R gene.

In some embodiments, the modified oncolytic virus can comprise an exogenous nucleic acid that can code for a chemokine receptor, a protein that is capable of degrading hyaluronan, or any combinations thereof. In some embodiments, the modified oncolytic virus can comprise the exogenous nucleic acid that can code for the chemokine receptor, wherein the chemokine receptor can comprise CXCR4 or CCR2. In some embodiments, the modified oncolytic virus can comprise the exogenous nucleic acid that codes for the protein that is capable of degrading hyaluronan, wherein the protein can comprise a membrane associated hyaluronidase or a secreted hyaluronidase. In some embodiments, the modified oncolytic virus can comprise the exogenous nucleic acid that can code for the membrane associated hyaluronidase, wherein the membrane associated hyaluronidase can be PH-20. In some embodiments, the PH-20 can be GPI-anchored. In some embodiments, the modified oncolytic virus can comprise the exogenous nucleic acid that can code for the secreted hyaluronidase, wherein the secreted hyaluronidase can be HysA.

One aspect provides a modified oncolytic virus that can comprise a mutation or a deletion of K7R gene. In some embodiments, the modified oncolytic virus can comprise the deletion of the K7R gene. In some embodiments, the modified oncolytic virus can further comprise at least one of an exogenous nucleic acid that can code for a cytokine, an exogenous nucleic acid that can code for a cytokine receptor, and an exogenous nucleic acid that can code for a chemokine. In some embodiments, the modified oncolytic virus comprises the exogenous nucleic acid that can code for the cytokine, wherein the cytokine can comprise IL15. In some embodiments, the modified oncolytic virus can comprise the exogenous nucleic acid that can code for the cytokine receptor, wherein the cytokine receptor can comprise IL15-Ra. In some embodiments, the modified oncolytic virus can comprise exogenous nucleic acid that can code for the chemokine, wherein the chemokine can comprise CCL5. In some embodiments, the modified oncolytic virus can further comprise an exogenous nucleic acid that codes for at least one of HMGB1, PIAS3, LIGHT, ITAC, a fractalkine, and a functional domain or fragment or variant thereof, or any combinations thereof. In some embodiments, the modified oncolytic virus can further comprise a mutation or a deletion of a further viral gene comprising at least one of F13L, A36R, A34R, A33R, B8R, B18R, SPI-1, SPI-2, B15R, VGF, E3L, K3L, A41L, N1L, A52R, and a functional domain or fragment or a variant thereof, or any combinations thereof.

One aspect provides a modified oncolytic virus that can comprise exogenous nucleic acids that can code for IL15 and IL15-Ra. One aspect provides a modified oncolytic virus that can comprise exogenous nucleic acids that can code for IL15 and CCL5. One aspect provides a modified oncolytic virus that can comprise an exogenous nucleic acid that can code for at least one of: IL15, IL15-Rα, ITAC, fractalkine, and a functional domain or fragment or variant thereof, or any combinations thereof. In some embodiments, the virus can exhibit enhanced activation and attraction of natural killer cells.

In some embodiments, the modified oncolytic virus can exhibit enhanced intratumoral and intertumoral spreading, enhanced immune evasion, enhanced tumor-specific replication, enhanced tumor-targeted delivery, compared to an otherwise identical oncolytic virus that does not comprise the modifications as disclosed herein. In some embodiments, the modified oncolytic virus can comprise a poxvirus, an adeno associated virus, an adenovirus, a reovirus, a lentivirus, a herpes simplex virus, a vesicular stomatitis virus, a mengovirus, or a myxoma virus. In some embodiments, the modified oncolytic virus can comprise the poxvirus. In some embodiments, the poxvirus can be a vaccinia virus. In some embodiments, the modified oncolytic virus can be suitable for systemic delivery.

In some embodiments, the oncolytic vaccinia virus can exhibit enhanced intratumoral and intertumoral spreading, enhanced immune evasion, enhanced tumor-specific replication, enhanced tumor-targeted delivery, compared to an otherwise identical vaccinia virus that does not comprise the modifications as disclosed herein.

In some embodiments, the oncolytic vaccinia virus can be suitable for systemic delivery.

In some embodiments, the oncolytic vaccinia virus may be capable of immune evasion.

In some embodiments, the systemic delivery can comprise oral administration, parenteral administration, intranasal administration, sublingual administration, rectal administration, transdermal administration, or any combinations thereof.

In some embodiments, the parenteral delivery can comprise an intravenous injection.

In some embodiments, the oncolytic vaccinia virus can be suitable for intratumoral delivery.

In some embodiments, the oncolytic vaccinia virus can comprise an exogenous nucleic acid that codes for a viral VH1 protein.

In some embodiments, the exogenous nucleic acid can be from a genome of a poxvirus, wherein the poxvirus can be not vaccinia virus. In some embodiments, the poxvirus can comprise a betaentomopoxvirus, a yatapoxvirus, a cervidpoxvirus, a gammaentomopoxvirus, a leporipoxvirus, a suipoxvirus, a molluscipoxvirus, a crocodylidpoxvirus, an alphaentomopoxvirus, a capripoxvirus, an avipoxvirus, a parapoxvirus.

In some embodiments, the viral genome can comprise a thymidine kinase gene. In some embodiments, a thymidine kinase gene can be deleted from the viral genome.

In some embodiments, the oncolytic vaccinia virus can comprise a thymidine kinase gene from a herpes simplex virus.

Yet another aspect of the present disclosure provides a pharmaceutical composition can comprise a modified oncolytic virus as disclosed herein, or an oncolytic vaccinia virus as disclosed herein. In some embodiments, the pharmaceutical composition can comprise a solubilizing agent and an excipient. In some embodiments, the excipient can comprise one or more of a buffering agent, a stabilizer, an antioxidant, a binder, a diluent, a dispersing agent, a rate controlling agent, a lubricant, a glidant, a disintegrant, a plasticizer, a preservative, or any combinations thereof. In some embodiments, the excipient can comprise di-sodium hydrogen phosphate dihydrate, sodium dihydrogen phosphate dihydrate, sodium chloride, myo-inositol, sorbitol, or any combinations thereof. In some embodiments, the pharmaceutical composition does not comprise a preservative. In some embodiments, the pharmaceutical composition can comprise one or more of a preservative, a diluent, and a carrier. In some embodiments, the pharmaceutical composition can comprise an additional active ingredient or a salt thereof. In some embodiments, the solubilizing agent can be sterile water. In some embodiments, the pharmaceutical composition can comprise an additional active ingredient, wherein the additional active ingredient can be a further oncolytic virus.

Yet another aspect of the present disclosure provides a method of enhancing therapeutic effect of an oncolytic virus upon systemic delivery of the virus to a subject, comprising a systemic administration of a modified oncolytic virus as disclosed herein, an oncolytic vaccinia virus as disclosed herein, or a pharmaceutical composition as disclosed herein.

In some embodiments, the systemic administration can comprise oral administration, parenteral administration, intranasal administration, sublingual administration, rectal administration, transdermal administration, or any combinations thereof. In some embodiments, the parenteral administration can comprise intravenous injection.

Yet another aspect of the present disclosure provides a process for engineering a modified oncolytic virus can comprise: (i) obtaining a modified oncolytic virus DNA backbone vector, the modified oncolytic virus DNA backbone vector can comprise one or more modifications as disclosed herein; (ii) further modifying the modified oncolytic virus DNA vector to produce an engineered DNA vector; (iii) transfecting mammalian cells with the engineered DNA vector; (iv) culturing the mammalian cells under conditions suitable for viral replication; and (v) harvesting the viral particles.

Yet another aspect of the present disclosure provides a process for engineering an oncolytic vaccinia virus can comprise: (i) obtaining an oncolytic vaccinia virus DNA backbone vector, the oncolytic vaccinia virus DNA backbone vector can comprise one or more modifications as disclosed herein; (ii) further modifying the oncolytic vaccinia virus DNA vector to produce an engineered DNA vector; (iii) transfecting mammalian cells with the engineered DNA vector; (iv) culturing the mammalian cells under conditions suitable for viral replication; and (v) harvesting the viral particles.

Yet another aspect of the present disclosure provides a process for producing a modified oncolytic virus as disclosed herein, comprising: (i) generating a modified oncolytic virus DNA vector, the modified oncolytic virus DNA vector can comprise the modifications as disclosed herein; (ii) transfecting mammalian cells with the modified oncolytic virus DNA vector; (iii) culturing the mammalian cells under conditions suitable for viral replication; and (iv) harvesting the viral particles.

Yet another aspect of the present disclosure provides a process for producing an oncolytic vaccinia virus as disclosed herein, comprising: (i) generating an oncolytic vaccinia virus DNA vector, the oncolytic vaccinia virus DNA vector can comprise the modifications as disclosed herein; (ii) transfecting mammalian cells with the oncolytic vaccinia virus DNA vector; (iii) culturing the mammalian cells under conditions suitable for viral replication; and (iv) harvesting the viral particles. In some embodiments, the mammalian cells comprise HeLa cells, 293 cells, or Vero cells.

Yet another aspect of the present disclosure provides a kit that can comprise: a modified oncolytic virus as disclosed herein, an oncolytic vaccinia virus as disclosed herein, or a pharmaceutical composition as disclosed herein, and instruction for administering the modified oncolytic virus, the oncolytic vaccinia virus, or a pharmaceutical composition; and instructions for administering said pharmaceutical composition to a subject to treat a disorder associated with pathological angiogenesis.

Yet another aspect of the present disclosure provides a kit, comprising: a modified oncolytic virus as disclosed herein, an oncolytic vaccinia virus as disclosed herein, or a pharmaceutical composition as disclosed herein, and instruction for administering the modified oncolytic virus, the oncolytic vaccinia virus, or a pharmaceutical composition; a container; and instructions for administering said pharmaceutical composition to a subject to treat a disorder associated with pathological angiogenesis.

Yet another aspect of the present disclosure provides a kit for treating a cancer, comprising: a modified oncolytic virus as disclosed herein, an oncolytic vaccinia virus as disclosed herein, or a pharmaceutical composition as disclosed herein, and instruction for administering the modified oncolytic virus, the oncolytic vaccinia virus, or the pharmaceutical composition; and instructions for administering said pharmaceutical composition to a subject to treat a disorder associated with pathological angiogenesis.

Yet another aspect of the present disclosure provides a kit for treating a cancer, comprising: a modified oncolytic virus as disclosed herein, an oncolytic vaccinia virus as disclosed herein, or a pharmaceutical composition as disclosed herein, and instruction for administering the modified oncolytic virus, the oncolytic vaccinia virus, or the pharmaceutical composition; a container; and instructions for administering said pharmaceutical composition to a subject to treat a disorder associated with pathological angiogenesis. In some embodiments, the cancer can be a solid tumor, a leukemia, or a lymphoma.

Yet another aspect of the present disclosure provides a kit for treating a tumor, comprising: a modified oncolytic virus as disclosed herein, an oncolytic vaccinia virus as disclosed herein, or a pharmaceutical composition as disclosed herein, and instruction for administering the modified oncolytic virus, the oncolytic vaccinia virus, or the pharmaceutical composition; and instructions for administering said pharmaceutical composition to a subject to treat a disorder associated with pathological angiogenesis.

Yet another aspect of the present disclosure provides a kit for treating a tumor, comprising: a modified oncolytic virus as disclosed herein, an oncolytic vaccinia virus as disclosed herein, or a pharmaceutical composition as disclosed herein, and instruction for administering the modified oncolytic virus, the oncolytic vaccinia virus, or the pharmaceutical composition; a container; and instructions for administering said pharmaceutical composition to a subject to treat a disorder associated with pathological angiogenesis. In some embodiments, the tumor can be a solid tumor, a leukemia, or a lymphoma. In some embodiments, the subject can be in need of the treatment. In some embodiments, the subject can be human. In some embodiments, the instructions for administering can comprise instructions for a systemic administration. In some embodiments, the systemic administration can comprise oral administration, parenteral administration, intranasal administration, sublingual administration, rectal administration, transdermal administration, or any combinations thereof. In some embodiments, the parenteral administration can comprise intravenous injection.

Yet another aspect of the present disclosure provides a method of treating a tumor, comprising: administering to a subject a therapeutically effective amount of a modified oncolytic virus as disclosed herein, an oncolytic vaccinia virus as disclosed herein, or a pharmaceutical composition as disclosed herein.

In some embodiments, the method of treating a tumor can comprise administering to a subject a therapeutically effective amount of a modified oncolytic virus as disclosed herein, an oncolytic vaccinia virus as disclosed herein, or a pharmaceutical composition as disclosed herein, wherein the tumor can be a solid tumor, a leukemia, or a lymphoma.

Yet another aspect of the present disclosure provides a method of treating a cancer, comprising administering to a subject a therapeutically effective amount of a modified oncolytic virus as disclosed herein, an oncolytic vaccinia virus as disclosed herein, or a pharmaceutical composition as disclosed herein.

In some embodiments, the method of treating a cancer can comprise administering to a subject a therapeutically effective amount of a modified oncolytic virus as disclosed herein, an oncolytic vaccinia virus as disclosed herein, or a pharmaceutical composition as disclosed herein, wherein the cancer can be a solid tumor, a leukemia, or a lymphoma.

In some embodiments, the method of treating a cancer can comprise administering to a subject a therapeutically effective amount of a modified oncolytic virus as disclosed herein, an oncolytic vaccinia virus as disclosed herein, or a pharmaceutical composition as disclosed herein, wherein the method further can comprise administration of a further therapy.

In some embodiments, the further therapy can comprise chemotherapy, radiation, oncolytic viral therapy with an additional virus, treatment with immunomodulatory proteins, a CAR T cellular therapy (chimeric antigen receptor T cell therapy), an anti-cancer agent, or any combinations thereof.

In some embodiments, the further therapy can comprise administration of an immunomodulatory agent can comprise anti-CD33 antibody and variable region thereof, an anti-CD11b antibody and variable region thereof, a COX2 inhibitor, a cytokine, a chemokine, an anti-CTLA4 antibody or an antigen binding fragment thereof, an anti-PD-1 antibody or an antigen binding fragment thereof, an anti-PD-L1 antibody or an antigen binding fragment thereof, or a TLR agonist.

In some embodiments, the method of treating a cancer can comprise administration of the further therapy, wherein the further therapy can comprise administration of the anti-cancer agent, wherein the anti-cancer agent can be a chemotherapeutic agent. In some embodiments, the chemotherapeutic agent can be a prodrug. In some embodiments, upon administration of the prodrug in combination with the oncolytic vaccinia virus, the modified vaccinia virus, or a pharmaceutical composition can comprise the same, the prodrug can be converted to an active form. In some embodiments, the prodrug can comprise ganciclovir. In some embodiments, the method of treating a cancer can comprise administration of the further therapy, wherein the further therapy can be administered concurrently or sequentially. In some embodiments, the method of treating a cancer can comprise sequential administration of the further therapy, wherein the further therapy can be administered prior to administering the modified oncolytic virus as disclosed herein, the oncolytic vaccinia virus as disclosed herein, or the pharmaceutical composition as disclosed herein. In some embodiments, the method of treating a cancer can comprise sequential administration of the further therapy, wherein the further therapy can be administered after administering the modified oncolytic virus as disclosed herein, the oncolytic vaccinia virus as disclosed herein, or the pharmaceutical composition as disclosed herein.

Yet another aspect of the present disclosure provides a method of producing a toxic effect in a cancer cell, comprising: administering to a cancer cell a therapeutically effective amount of a modified oncolytic virus as disclosed herein, an oncolytic vaccinia virus as disclosed herein, or a pharmaceutical composition as disclosed herein. In some embodiments, the cancer cell can be present in a subject. In some embodiments, the subject can be in need of the method that producing the toxic effect in the cancer cell.

Yet another aspect of the present disclosure provides a method of treating a subject, comprising: producing a toxic effect in a cancer cell that can be present in the subject by administering to the cancer cell a therapeutically effective amount of a modified oncolytic virus as disclosed herein, an oncolytic vaccinia virus as disclosed herein, or a pharmaceutical composition as disclosed herein. In some embodiments, the subject can be in need of the treatment.

Yet another aspect of the present disclosure provides a method of treating cancer in a subject, comprising, infecting a cancer cell of the subject by administration of a therapeutically effective amount of a modified oncolytic virus as disclosed herein, an oncolytic vaccinia virus as disclosed herein, or a pharmaceutical composition as disclosed herein, wherein the administration can be a systemic administration.

Yet another aspect of the present disclosure provides a method of treating cancer in a subject, comprising administering cells infected with a modified oncolytic virus as disclosed herein or an oncolytic vaccinia virus as disclosed herein.

In some embodiments, the cancer can comprise melanoma, hepatocellular carcinoma, breast cancer, lung cancer, peritoneal cancer, prostate cancer, bladder cancer, ovarian cancer, leukemia, lymphoma, renal carcinoma, pancreatic cancer, epithelial carcinoma, gastric cancer, colon carcinoma, duodenal cancer, pancreatic adenocarcinoma, mesothelioma, glioblastoma multiforme, astrocytoma, multiple myeloma, prostate carcinoma, hepatocellular carcinoma, cholangiosarcoma, pancreatic adenocarcinoma, head and neck squamous cell carcinoma, colorectal cancer, intestinal-type gastric adenocarcinoma, cervical squamous-cell carcinoma, osteosarcoma, epithelial ovarian carcinoma, acute lymphoblastic lymphoma, myeloproliferative neoplasms, or sarcoma.

In some embodiments, the cancer cell can be present in an organ of the subject selected from the group consisting of: the bladder, blood, bone, bone marrow, brain, breast, colon, esophagus, gastrointestine, gum, head, kidney, liver, lung, nasopharynx, neck, ovary, prostate, skin, stomach, testis, tongue, or uterus. In some embodiments, the cancer can be metastatic.

Yet another aspect of the present disclosure provides a method of treating a cancer in a subject, comprising: administering a modified oncolytic virus as disclosed herein or pharmaceutical composition can comprise the same in combination with a chemotherapeutic prodrug.

Yet another aspect of the present disclosure provides a method of treating a cancer in a subject, comprising: administering an oncolytic vaccinia virus as disclosed herein or a pharmaceutical composition can comprise the same in combination with a chemotherapeutic prodrug.

Yet another aspect of the present disclosure provides a method of treating a cancer in a subject, comprising: (i) administering a modified oncolytic virus as disclosed herein or a pharmaceutical compositions can comprise the same; (ii) assaying a viral titer in a first and a second biological sample isolated from the subject, wherein the first biological sample can comprise a cancer cell and the second biological sample can comprise a non-cancer cell; and (iii) administering a chemotherapeutic prodrug if the viral titer can be equal to or higher in the second sample than the first sample, wherein administration of the chemotherapeutic prodrug results in inhibition of replication of the modified oncolytic virus in the subject.

Yet another aspect of the present disclosure provides a method of treating a cancer in a subject, comprising: (i) administering an oncolytic vaccinia virus as disclosed herein or a pharmaceutical compositions can comprise the same; (ii) assaying a viral titer in a first and a second biological sample isolated from the subject, wherein the first biological sample can comprise a cancer cell and the second biological sample can comprise a non-cancer cell; and (iii) administering a chemotherapeutic prodrug if the viral titer can be equal to or higher in the second sample than the first sample, wherein administration of the chemotherapeutic prodrug results in inhibition of replication of the oncolytic vaccinia virus in the subject.

In some embodiments, the method of treating a cancer in a subject can increase efficacy of oncolytic virus based cancer therapy. In some embodiments, the method of treating a cancer in a subject, can comprise the administration of the modified oncolytic virus as disclosed herein, the oncolytic vaccinia virus as disclosed herein, or the pharmaceutical composition as disclosed herein, wherein the modified oncolytic virus, the oncolytic vaccinia virus, or a pharmaceutical composition can be administered at a dosage that can comprise about $10^6$ PFU/mL to about $10^{10}$ PFU/mL of the oncolytic vaccinia virus.

In some embodiments, the method of treating a cancer in a subject can comprise the administration of the modified oncolytic virus as disclosed herein, the oncolytic vaccinia virus as disclosed herein, or the pharmaceutical composition as disclosed herein, wherein the modified oncolytic virus, the oncolytic vaccinia virus, or a pharmaceutical composition can be administered at a dosage that can comprise about $5\times10^9$ PFU/mL of the oncolytic vaccinia virus.

In some embodiments, the method of treating a cancer in a subject can comprise the administration of the modified oncolytic virus as disclosed herein, the oncolytic vaccinia virus as disclosed herein, or the pharmaceutical composition as disclosed herein, wherein the modified oncolytic virus, the oncolytic vaccinia virus, or a pharmaceutical composition can be administered, independently, in an initial dose for a first period of time, an intermediate dose for a second period of time, and a high dose for a third period of time. In some embodiments, the method of treating a cancer in a subject can comprise administration of the initial, the intermediate, and the high dose, independently, wherein the initial dose can be lower than the intermediate dose and the intermediate dose can be lower than the high dose.

In some embodiments, wherein the first, second, and third periods of time can be each from about 1 week to about 3 weeks. In some embodiments, the method of treating a cancer in a subject can comprise administering the modified oncolytic virus as disclosed herein, the oncolytic vaccinia virus as disclosed herein, or the pharmaceutical composition as disclosed herein, wherein the modified oncolytic virus, the oncolytic vaccinia virus, and a pharmaceutical composition independently can comprise a liquid dosage form that can be administered at a volume of about 1 mL to about 5 mL, about 5 mL to 10 mL, about 15 mL to about 20 mL, about 25 mL to about 30 mL, about 30 mL to about 50 mL, about 50 mL to about 100 mL, about 100 mL to 150 mL, about 150 mL to about 200 mL, about 200 mL to about 250 mL, about 250 mL to about 300 mL, about 300 mL to about 350 mL, about 350 mL to about 400 mL, about 400 mL to about 450 mL, about 450 mL to 500 mL, about 500 mL to 750 mL, or about 750 mL to 1000 mL.

In some embodiments, the method of treating a cancer in a subject can comprise administering the modified oncolytic virus as disclosed herein, the oncolytic vaccinia virus as disclosed herein, or the pharmaceutical composition as disclosed herein, wherein the modified oncolytic virus, the oncolytic vaccinia virus, or a pharmaceutical composition can be administered in a liquid dosage form, a solid dosage form, an inhalable dosage form, an intranasal dosage form, a liposomal formulation, a dosage form can comprise nanoparticles, a dosage form can comprise microparticles, a polymeric dosage form, or any combinations thereof.

In some embodiments, the method of treating a cancer in a subject can comprise administering the modified oncolytic virus as disclosed herein, the oncolytic vaccinia virus as disclosed herein, or the pharmaceutical composition as disclosed herein, wherein the modified oncolytic virus, the oncolytic vaccinia virus, or the pharmaceutical composition can be administered for a duration of about 1 week, about 2 week, about 3 weeks, about 4 weeks, about 6 weeks, about 7 weeks, about 8 weeks, about 9 weeks, about 10, weeks, or about 12 weeks.

In some embodiments, the method of treating a cancer in a subject can comprise administering the modified oncolytic virus as disclosed herein, the oncolytic vaccinia virus as disclosed herein, or a pharmaceutical composition as disclosed herein, wherein the modified oncolytic virus, the oncolytic vaccinia virus, or the pharmaceutical composition can be administered once daily, twice daily, once every week, once every two weeks, or once every three weeks.

In some embodiments, the method of treating a cancer in a subject can comprise administering the modified oncolytic virus as disclosed herein, the oncolytic vaccinia virus as disclosed herein, or a pharmaceutical composition as disclosed herein, wherein the modified oncolytic virus, the oncolytic vaccinia virus, or a pharmaceutical composition can be administered intravenously, intraperitoneally, or by an intratumoral injection.

In some embodiments, the method of treating a cancer in a subject can comprise administering the modified oncolytic virus as disclosed herein, the oncolytic vaccinia virus as disclosed herein, or a pharmaceutical composition as disclosed herein, wherein the modified oncolytic virus, the oncolytic vaccinia virus, or a pharmaceutical composition can be administered as a bolus injection or a slow infusion.

In some embodiments, the method of treating a cancer in a subject can comprise administering the modified oncolytic virus as disclosed herein, the oncolytic vaccinia virus as disclosed herein, or a pharmaceutical composition as disclosed herein, wherein the administration of the modified oncolytic virus, the oncolytic vaccinia virus, or the pharmaceutical composition results in a first peak viral load after about 1 hour to about 3 days and a second peak viral load after about 3 days to about 10 days from administration of a first dose.

In some embodiments, the method of treating a cancer in a subject can comprise administration of the further therapy, wherein the further therapy can be administered for a duration of about 1 week, about 2 week, about 3 weeks, about 4 weeks, about 6 weeks, about 7 weeks, about 8 weeks, about 9 weeks, about 10, weeks, or about 12 weeks. In some embodiments, the method of treating a cancer in a subject can comprise administration of the further therapy, wherein the further therapy can be administered once daily, once every week, once every two weeks, or once every three weeks. In some embodiments, the method of treating a cancer in a subject can comprise administration of the further therapy, wherein the further therapy can be administered in a liquid dosage form, a solid dosage form, an inhalable dosage form, an intranasal dosage form, a liposomal formulation, a dosage form can comprise nanoparticles, a dosage form can comprise microparticles, a polymeric dosage form, or any combinations thereof. In some embodiments, the method of treating a cancer in a subject can comprise administration of the further therapy, wherein the further therapy can be administered orally, intravenously, by an intratumoral injection, or by radiation. In some embodiments, the method of treating a cancer in a subject can comprise the administration of the modified oncolytic virus as disclosed herein, the oncolytic vaccinia virus as disclosed herein, or the pharmaceutical composition as disclosed herein to a subject in need thereof, wherein the subject can be human. In some embodiments, the method of treating a cancer in a subject can comprise the administration of the modified oncolytic virus as disclosed herein, the oncolytic vaccinia virus as disclosed herein, or the pharmaceutical composition as disclosed herein to the subject in need thereof, wherein prior to administration of the modified oncolytic virus, the oncolytic vaccinia virus, or the pharmaceutical composition the subject has been diagnosed with a cancer. In some embodiments, the method of treating a subject can comprise the administration of the modified oncolytic virus as disclosed herein, the oncolytic vaccinia virus as disclosed herein, or the pharmaceutical composition as disclosed herein to the subject in need thereof, wherein prior to administration of the modified oncolytic virus, the oncolytic vaccinia virus, or the pharmaceutical composition the subject has been diagnosed with a tumor. In some embodiments, the method of treating a cancer in a subject can comprise the administration of the modified oncolytic virus as disclosed herein, the oncolytic vaccinia virus as disclosed herein, or a pharmaceutical composition as disclosed herein to the subject in need thereof in combination with the further therapy, wherein prior to administration of the modified oncolytic virus, the oncolytic vaccinia virus, or the pharmaceutical composition or the further therapy the subject has been diagnosed with a cancer or a tumor. In some embodiments, the method of treating a subject can comprise the administration of the modified oncolytic virus as disclosed herein, the oncolytic vaccinia virus as disclosed herein, or a pharmaceutical composition as disclosed herein to the subject in need thereof in combination with the further therapy, wherein prior to administration of the modified oncolytic virus, the oncolytic vaccinia virus, or the pharmaceutical composition or the further therapy the subject has been diagnosed with a tumor.

BRIEF DESCRIPTION OF THE DRAWINGS

The novel features of the disclosure are set forth with particularity in the appended claims. A better understanding of the features and advantages of this disclosure will be obtained by reference to the following detailed description that sets forth illustrative embodiments, in which the principles of this disclosure are utilized, and the accompanying drawings of which.

FIGS. 2A-2B show the effects of an exemplary mutation in B5R gene on the delivery and spreading of an exemplary modified vaccinia virus (WR.B5RmutTK- virus) (referred to as B5R in FIGS. 2A and 2B), in tumors. FIG. 2A and FIG. 2B are graphs showing the quantification of the viral genomes per gram of tumor collected from non-immunized and immunized C57/BL6 mice bearing B16 tumors, respectively. The mice treated with a single injection of the WR.B5RmutTK- virus were compared with mice treated with another modified vaccinia virus WR.TK-A34R K151E, where TK was deleted and the viral A34R gene was mutated with an amino acid change, K151 to E (referred to as WI in FIGS. 2A and 2B).

FIG. 3A and FIG. 3B are graphs quantifying the plaque forming capability of the viruses, WR.TK-A34R K151E, where TK was deleted and the viral A34R gene was mutated with an amino acid change, K151 to E (referred to as WI in FIGS. 3A and 3B) and B5R, per gram of collected tumor (PFU/g) in an in vitro plaque assay.

FIG. 5A includes a graph showing the relative tumor size over the days post implantation in mice bearing orthotopic (mammary fat pad) 4T1 tumors, which were treated with a single dose a modified vaccinia virus where TK gene was deleted and an exogenous nucleic acid encoding mouse CCR5 was added (CCR5- virus), a modified vaccinia virus where TK gene was deleted and an exemplary exogenous nucleic acid encoding mouse CXCR4 was added (CXCR4- virus), or a TK- virus, where TK gene was deleted. FIG. 5A also includes a chart listing statistic difference for each pair of comparison. FIG. 5B shows the survival curves of these mice.

FIG. 6A is a graph quantifying the luciferase-mediated photon intensity in the tumors during bioluminescence imaging in C57/BL6 mice bearing B16 tumors. The mice were treated with a single dose of a modified vaccinia virus where TK gene was deleted and an exogenous nucleic acid encoding mouse CCR5 was added (mCCR5/TK- virus), a modified vaccinia virus where TK gene was deleted and an exemplary exogenous nucleic acid encoding mouse CXCR4 was added (mCXCR4/TK- virus), or a TK- virus, where TK gene was deleted. FIG. 6B is a representative picture showing the luminescence signal from the bioluminescence imaging of the mice treated with the viruses on day 1 post injection. All viruses were engineered to express luciferase.

FIG. 8A and FIG. 8B are graphs showing quantification of plaque-forming capability of three different viruses (mCCR5/TK- virus, mCXCR4/TK- virus, and TK- virus) in tumor cell line 4T1, starting at multiplicity of infection of 0.1 (4T1-MOI0.1) and 1 (4T1-MOI1), respectively. FIG. 8C and FIG. 8D are similar graphs showing quantification of plaque-forming capability of three different viruses (mCCR5/TK- virus, mCXCR4/TK- virus, and TK- virus) in tumor cell line B16, starting at MOI of 0.1 (B16-MOI0.1) and 1 (B16-MOI1), respectively.

FIGS. 9A-9C show the effects of B cells depletion on the increased viral expression of luciferase in tumors treated with an exemplary modified vaccinia virus having an exemplary exogenous nucleic acid that codes for CXCR4. FIG. 9A, FIG. 9B, and FIG. 9C are graphs quantifying the luciferase-mediated photon intensity in tumors measured at 24 h, 48 h, and 72 hours post viral injection, respectively. Balb/C mice are wild type mice having B cells, while JH mice are B cell-depleted mice. The mice were injected with a single dose of a modified vaccinia virus where TK gene was deleted and an exogenous nucleic acid encoding mouse CCR5 was added (mCCR5/TK- virus), a modified vaccinia virus where TK gene was deleted and an exemplary exogenous nucleic acid encoding mouse CXCR4 was added (mCXCR4/TK- virus), or a TK- virus, where TK gene was deleted.

FIG. 10A, FIG. 10B, and FIG. 10C are graphs quantifying the percentage of B cells in the lymphocytes collected from spleen, lymph node (LN), and tumor, respectively, in BALB/c mice bearing subcutaneous 4T1 tumor. The mice were treated with a single dose of a modified vaccinia virus where TK gene was deleted and an exemplary exogenous nucleic acid encoding mouse CXCR4 was added (mCXCR4/TK- virus), a TK- virus, where TK gene was deleted, or PBS.

FIG. 11A and FIG. 11B are graphs quantifying IFNgamma release by T cells in response to tumor cell 4T1 lysate and inactivated vaccinia virus (VV) mixed with tumor cell 4T1 lysate, respectively. The T cells were collected from mice bearing 4T1 tumors treated with a single dose of a modified vaccinia virus where TK gene was deleted and an exemplary exogenous nucleic acid encoding mouse CXCR4 was added (mCXCR4/TK- virus), or a TK- virus, where TK gene was deleted, or PBS. T cells were recovered from spleens after 14 days.

FIGS. 12A-12B show the effects of exemplary modified vaccinia viruses having an exemplary exogenous nucleic acid that encodes hyaluronidase PH-20 or matrix metalloprotease MMP8, on viral expression of luciferase in tumors. FIG. 12A is a representative picture showing the luminescence signal in three BALB/c mice bearing RENCA tumors, which were treated with a single dose of an unmodified vaccinia virus (WR), a modified vaccinia virus having an exemplary exogenous nucleic acid that codes for MMP8 (WR MMP8), or a modified vaccinia virus having an exemplary exogenous nucleic acid that codes for PH-20 (WR PH20 virus), respectively. FIG. 12B is a graph quantifying the photon intensity in the mice on day 2 after viral injection.

FIG. 13A is a graph quantifying the luciferase-mediated photon intensity over the days after the viral injection in BALB/c mice bearing 4T1 tumors treated with either a modified vaccinia virus where the TK gene was deleted (TK-), or a modified vaccinia virus where the TK gene was deleted and which has an exemplary exogenous nucleic acid that codes for PH-20 TK-PH20DCK virus. FIG. 13B is a graph quantifying the relative tumor volume over the days after the viral injection in mice treated with a PBS, gemcitabine alone, TK-PH20 DCK virus alone, TK- virus alone, TK- virus combined with gemcitabine, or TK-PH20 DCK virus combined with gemcitabine.

DETAILED DESCRIPTION

Figure 1:
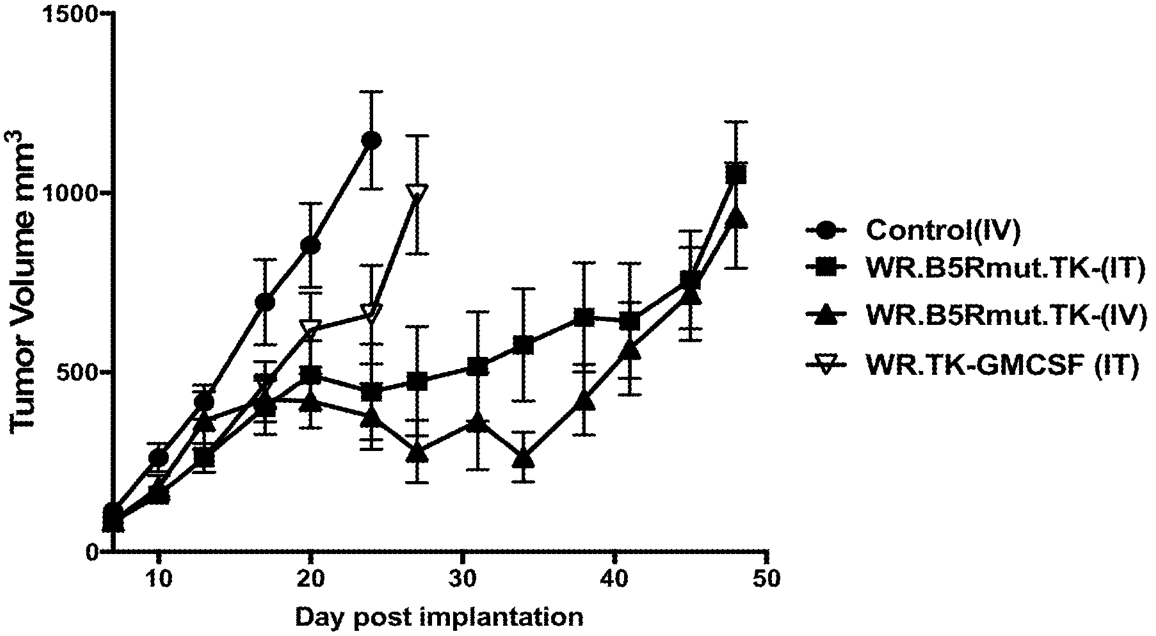
FIG. 1 shows the effect of an exemplary modified vaccinia virus of this disclosure, containing an exemplary mutation in B5R gene, on tumor growth. The graph quantifies the relative tumor size over the days post implantation in BALB/c mice bearing subcutaneous RENCA tumors, which were treated with a single dose of a control vaccinia virus injected intravenously (Control (IV)), a modified WR.TK-GMCSF vaccinia virus, where TK gene was deleted and an exogenous nucleic acid encoding GMCSF was added, injected intratumorally (WR.TK-GMCSF (IT)), or the exemplary modified vaccinia virus (WR.B5Rmut.TK-) where TK gene was deleted and a mutation was introduced in B5R gene, injected intravenously (WR.B5Rmut.TK-(IV)) or intratumorally (WR.B5Rmut.TK-(IT)).

While preferred embodiments of this disclosure have been shown and described herein, it will be obvious to those skilled in the art that such embodiments are provided by way of example only. Numerous variations, changes, and substitutions will now occur to those skilled in the art without departing from this disclosure. It should be understood that various alternatives to the embodiments of this disclosure described herein may be employed in practicing the disclosure. It is intended that the following claims define the scope of the disclosure and that methods and structures within the scope of these claims and their equivalents be covered thereby.

Certain Definitions

The terminology used herein is for the purpose of describing particular cases only and is not intended to be limiting. As used herein, the singular forms “a”, “an” and “the” can include the plural forms as well, unless the context clearly indicates otherwise.

Furthermore, to the extent that the terms “contains,” “containing,” “including”, “includes,” “having,” “has”, “with”, or variants thereof are used in either the detailed description and/or the claims, such terms are intended to be inclusive in a manner similar to the term “comprising.”

The term “about” or “approximately” can mean within an acceptable error range for the particular value as determined by one of ordinary skill in the art, which will depend in part on how the value is measured or determined, e.g., the limitations of the measurement system. For example, “about” can mean within 1 or more than 1 standard deviation, per the practice in the given value. Where particular values are described in the application and claims, unless otherwise stated the term “about” should be assumed to mean an acceptable error range for the particular value, such as +10% of the value modified by the term “about”.

The terms “individual,” “patient,” or “subject” can be used interchangeably. None of the terms require or are limited to situation characterized by the supervision (e.g. constant or intermittent) of a health care worker (e.g. a doctor, a registered nurse, a nurse practitioner, a physician’s assistant, an orderly, or a hospice worker). In some embodiments, patients, subjects, or individuals can be under the supervision of a health care worker.

The terms “heterologous nucleic acid sequence,” or “exogenous nucleic acid sequence,” or “transgenes,” as used herein, in relation to a specific virus can refer to a nucleic acid sequence that originates from a source other than the specified virus.

The term “mutation,” as used herein, can refer to a deletion, an insertion of a heterologous nucleic acid, an inversion or a substitution, including an open reading frame ablating mutations as commonly understood in the art.

The term “gene,” as used herein, can refer to a segment of nucleic acid that encodes an individual protein or RNA (also referred to as a “coding sequence” or “coding region”), optionally together with associated regulatory regions such as promoters, operators, terminators and the like, which may be located upstream or downstream of the coding sequence.

The terms “mutant virus” and “modified virus,” as used interchangeably herein, can refer to a virus comprising one or more mutations in its genome, including but not limited to deletions, insertions of heterologous nucleic acids, inversions, substitutions or combinations thereof.

The term “naturally-occurring,” as used herein with reference to a virus, can indicate that the virus can be found in nature, i.e., it can be isolated from a source in nature and has not been intentionally modified.

The terms “inhibiting,” “reducing” or “prevention,” or any variation of these terms, referred to herein, can include any measurable decrease or complete inhibition to achieve a desired result.

A “promoter,” as used herein, can be a control sequence that is a region of a nucleic acid sequence at which initiation and rate of transcription are controlled. In certain embodiments, a promoter may contain genetic elements at which regulatory proteins and molecules may bind such as RNA polymerase and other transcription factors.

The terms “operatively positioned,” “operatively linked,” “under control” and “under transcriptional control” can mean that a promoter is in a correct functional location and/or orientation in relation to a nucleic acid sequence to control transcriptional initiation and/or expression of that sequence. In certain embodiments, a promoter may or may not be used in conjunction with an “enhancer,” which refers to a cis-acting regulatory sequence involved in the transcriptional activation of a nucleic acid sequence.

The term “homology,” as used herein, may be to calculations of “homology” or “percent homology” between two or more nucleotide or amino acid sequences that can be determined by aligning the sequences for optimal comparison purposes (e.g., gaps can be introduced in the sequence of a first sequence). The nucleotides at corresponding positions may then be compared, and the percent identity between the two sequences may be a function of the number of identical positions shared by the sequences (i.e., % homology=# of identical positions/total # of positions×100). For example, a position in the first sequence may be occupied by the same nucleotide as the corresponding position in the second sequence, then the molecules are identical at that position. The percent homology between the two sequences may be a function of the number of identical positions shared by the sequences, taking into account the number of gaps, and the length of each gap, which need to be introduced for optimal alignment of the two sequences. In some embodiments, the length of a sequence aligned for comparison purposes may be at least about: 30%, 40%, 50%, 60%, 65%, 70%, 75%, 80%, 85%, 90%, 91%, 92%, 93%, 94%, 95%, 96%, 97%, 98%, or 95%, of the length of the reference sequence. A BLAST® search may determine homology between two sequences. The homology can be between the entire lengths of two sequences or between fractions of the entire lengths of two sequences. The two sequences can be genes, nucleotides sequences, protein sequences, peptide sequences, amino acid sequences, or fragments thereof. The actual comparison of the two sequences can be accomplished by well-known methods, for example, using a mathematical algorithm. A non-limiting example of such a mathematical algorithm may be described in Karlin, S. and Altschul, S., Proc. Natl. Acad. Sci. USA, 90-5873-5877 (1993). Such an algorithm may be incorporated into the NBLAST and XBLAST programs (version 2.0), as described in Altschul, S. et al., Nucleic Acids Res., 25:3389-3402 (1997). When utilizing BLAST and Gapped BLAST programs, any relevant parameters of the respective programs (e.g., NBLAST) can be used. For example, parameters for sequence comparison can be set at score=100, word length=12, or can be varied (e.g., W=5 or W=20). Other examples include the algorithm of Myers and Miller, CABIOS (1989), ADVANCE, ADAM, BLAT, and FASTA. In another embodiment, the percent identity between two amino acid sequences can be accomplished using, for example, the GAP program in the GCG software package (Accelrys, Cambridge, UK).

The term “subject” can refer to an animal, including, but not limited to, a primate (e.g., human), cow, sheep, goat, horse, dog, cat, rabbit, rat, or mouse. The terms “subject” and “patient” are used interchangeably herein in reference, for example, to a mammalian subject, such as a human subject.

The terms “treat,” “treating,” and “treatment” can be meant to include alleviating or abrogating a disorder, disease, or condition; or one or more of the symptoms associated with the disorder, disease, or condition; or alleviating or eradicating the cause(s) of the disorder, disease, or condition itself. Desirable effects of treatment can include, but are not limited to, preventing occurrence or recurrence of disease, alleviation of symptoms, diminishing any direct or indirect pathological consequences of the disease, preventing metastasis, decreasing the rate of disease progression, amelioration or palliation of the disease state and remission or improved prognosis.

The term “therapeutically effective amount” can refer to the amount of a compound that, when administered, can be sufficient to prevent development of, or alleviate to some extent, one or more of the symptoms of the disorder, disease, or condition being treated. The term “therapeutically effective amount” can also refer to the amount of a compound that is sufficient to elicit the biological or medical response of a cell, tissue, system, animal, or human that is being sought by a researcher, veterinarian, medical doctor, or clinician.

The term “pharmaceutically acceptable carrier,” “pharmaceutically acceptable excipient,” “physiologically acceptable carrier,” or “physiologically acceptable excipient” can refer to a pharmaceutically-acceptable material, composition, or vehicle, such as a liquid or solid filler, diluent, excipient, solvent, or encapsulating material. A component can be “pharmaceutically acceptable” in the sense of being compatible with the other ingredients of a pharmaceutical formulation. It can also be suitable for use in contact with the tissue or organ of humans and animals without excessive toxicity, irritation, allergic response, immunogenicity, or other problems or complications, commensurate with a reasonable benefit/risk ratio. See, *Remington: The Science and Practice of Pharmacy,* 21st Edition; Lippincott Williams & Wilkins: Philadelphia, Pa., 2005; *Handbook of Pharmaceutical Excipients,* 5th Edition; Rowe et al., Eds., The Pharmaceutical Press and the American Pharmaceutical Association: 2005; and *Handbook of Pharmaceutical Additives,* 3rd Edition; Ash and Ash Eds., Gower Publishing Company: 2007; *Pharmaceutical Preformulation and Formulation*, Gibson Ed., CRC Press LLC: Boca Raton, Fla., 2004).

The term “pharmaceutical composition” can refer to a mixture of a compound disclosed herein with other chemical components, such as diluents or carriers. The pharmaceutical composition can facilitate administration of the compound to an organism. Multiple techniques of administering a compound exist in the art including, but not limited to, oral, injection, aerosol, parenteral, and topical administration. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid and the like.

An “anti-cancer agent,” as used herein, can refer to an agent or therapy that is capable of negatively affecting cancer in a subject, for example, by killing cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer. Non-limiting examples of anti-cancer agents can include biological agents (biotherapy), chemotherapy agents, and radiotherapy agents.

The term “oncolytic,” as used herein, can refer to killing of cancer or tumor cells by an agent, such as an oncolytic pox virus, such as an oncolytic vaccinia virus, e.g., through the direct lysis of said cells, by stimulating immune response towards said cells, apoptosis, expression of toxic proteins, autophagy and shut-down of protein synthesis, induction of anti-tumoral immunity, or any combinations thereof. The direct lysis of the cancer or tumor cells infected by the agent, such as an oncolytic vaccinia virus, can be a result of replication of the virus within said cells. In certain examples, the term “oncolytic,” can refer to killing of cancer or tumor cells without lysis of said cells.

The term “oncolytic virus” as used herein can refer to a virus that preferentially infects and kills tumor cells. Under certain non-limiting circumstances, it is understood that oncolytic viruses can promote anti-tumor responses through dual mechanisms dependent on not only the selective killing of tumor cells, but also the stimulation of host anti-tumor immune responses.

In some embodiments, the oncolytic viruses can include, but are not limited to, (i) viruses that naturally replicate preferentially in cancer cells and are non-pathogenic in humans often due to elevated sensitivity to innate antiviral signaling or dependence on oncogenic signaling pathways; and (ii) viruses that are genetically-manipulated for use. In some embodiments, the oncolytic virus can be a measles virus, a poliovirus, a poxvirus, a vaccinia virus, an adenovirus, an adeno associated virus, a herpes simplex virus, a vesicular stomatitis virus, a reovirus, a Newcastle disease virus, a senecavirus, a lentivirus, a mengovirus, or a myxoma virus. In certain embodiments, the oncolytic virus can be a pox virus. In certain embodiments, the oncolytic virus can be a vaccinia virus.

The term "modified oncolytic virus" as used herein can refer to an oncolytic virus that comprises a modification to its constituent, such as, but not limited to, a modification in the native genome ("backbone") of the virus like a mutation or a deletion of a viral gene, introduction of an exogenous nucleic acid, a chemical modification of a viral nucleic acid or a viral protein, and introduction of a exogenous protein or modified viral protein to the viral capsid. In general, oncolytic viruses may be modified (also known as "engineered") in order to gain improved therapeutic effects against tumor cells. In certain embodiments, the modified oncolytic virus can be a modified pox virus. In certain embodiments, the modified oncolytic virus can be a modified pox virus.

The terms "systemic delivery," and "systemic administration," used interchangeably herein, in some cases can refer to a route of administration of medication, oncolytic virus or other substances into the circulatory system. The systemic administration may comprise oral administration, parenteral administration, intranasal administration, sublingual administration, rectal administration, transdermal administration, or any combinations thereof.

Modified Oncolytic Viruses

Provided herein, in some embodiments, is a modified oncolytic virus that can have one or more modifications that can result in a greater therapeutic effect against tumor cells, as compared to an otherwise identical virus that does not comprises the modifications. Some non-limiting examples of the greater therapeutic effect may include each or any combinations of: enhanced immune evasion of the virus, enhanced tumor-targeted systemic delivery of the virus, enhanced intratumoral and intertumoral spreading of the virus, and enhanced tumor-specific replication of the virus. The modified oncolytic virus of this disclosure, in some instances, can be utilized as a platform vector for systemic delivery.

Provided herein is a modified oncolytic virus having one or more modifications that can, in some embodiments, result in enhanced immune evasion of the virus, enhanced tumor-targeted systemic delivery of the virus, enhanced intratumoral and intertumoral spreading of the virus, and enhanced tumor-specific replication of the virus.

In some embodiments of this disclosure, provided is a modified oncolytic virus comprising a modification that can enhance immune evasion of the virus. Virus infection very often can induce immune responses from the host body against the viral invasion, which may consequently, deplete the inoculated viruses or diminish the toxic effect the virus is expected to produce against the tumor cells in therapeutic settings. Appropriate immune evasion therefore may significantly increase the efficacy of the therapeutic application of oncolytic viruses.

In some embodiments of the present disclosure, provided is a modified oncolytic virus comprising a modification that can enhance tumor-targeted systemic delivery of the virus. Typically, oncolytic viruses can be either be (a) administered systemically or (b) inoculated topically over the tumor or, in many cases, injected directly into the tumor ("intratumoral delivery"). It is believed that systemic delivery of the oncolytic virus can afford the opportunity to treat both the primary tumor and any overt or undiagnosed metastatic deposits simultaneously. As a result, this method of delivery can be a very attractive option for the treatment of patients with advanced/metastatic disease or patients with inaccessible disease such as those with pancreatic cancer or brain cancer, where access is difficult for example due to physiological barriers, such as blood-brain barrier. However, barriers can exist for successful systemic delivery of many oncolytic viruses. For instance, in some cases, as described above, host defense limits most oncolytic viruses' ability to infect tumors after systemic administration. Blood cells, complement, antibodies, and antiviral cytokines, as well as nonspecific uptake by other tissues such as the lung, liver and spleen, tissue-resident macrophages, and additionally poor virus escape from the vascular compartment are among the main barriers to systemic delivery of oncolytic viruses. In order to have effective systemic administration, in many cases, the oncolytic virus may need to persist in the circulation without depletion or degradation while selectively infecting tumor cells. In some embodiments of the present disclosure, disclosed oncolytic viruses can comprise a modification that can promote the persistent existence of the virus in the circulation system, at least through, as abovementioned, enhancement of immune evasion. On the other hand, enhanced tumor-targeted delivery of the virus can also be desirable under certain circumstances, as it may not only increase therapeutic efficacy against cancer, but may also alleviate the safety concerns around virus-mediated oncotherapy as the non-tumor infection can be limited, avoiding the undesired side effects of viral infection. Certain embodiments herein relate to an oncolytic virus comprising a modification that can promote the tumor-targeted delivery of the virus.

In some embodiments of the present disclosure, provided is a modified oncolytic virus comprising a modification that can enhance intratumoral and intertumoral spreading of the virus. Enhanced spreading of the oncolytic virus within and between tumors may be an effective manner to boost the therapeutic efficacy by increasing the number of the cancer cells that are infected by the virus.

In some embodiments of the present disclosure, provided is a modified oncolytic virus comprising a modification that can enhance tumor-specific replication of the virus. By enhancing the selective replication of the oncolytic viruses in tumor cells, both the safety and efficacy of the therapeutic application of the oncolytic viruses could be improved.

Provided herein, in some embodiments, is a modified oncolytic virus that can comprise an exogenous nucleic acid. Provided herein, in some embodiments, is a modified oncolytic virus that can comprise a modification to in the genome of the virus. Provided herein, in some embodiments, is a modified oncolytic virus that can comprise an exogenous nucleic acid as well as a modification in the genome of the virus.

Exogenous Nucleic Acids

In some embodiments, provided herein is a modified oncolytic virus comprising an exogenous nucleic acid, also referred to herein as a transgene, that can code for a chemokine receptor. In some cases, the exogenous nucleic acid can be a therapeutic transgene. In some embodiments, provided herein is a modified oncolytic virus comprising an exogenous nucleic acid that can code for a membrane associated protein that can degrade hyaluronan, such as a hyaluronidase. In some embodiments, provided herein is a modified oncolytic virus comprising exogenous nucleic acids that can code for both a chemokine receptor and a hyaluronidase.

Chemokines are chemotactic cytokines that regulate the trafficking and positioning of cells by activating the seven-transmembrane spanning chemokine receptors. In some cases, chemokines can be divided into four subfamilies based on the position of the first two N-terminal cysteine residues, including the CC, CXC, CX3C and XC subfamilies. Differential expression of chemokine receptors on leukocytes may result in selective recruitment of specific cell types under particular conditions, providing appropriate and efficient immune responses tailored to the infecting pathogen or foreign insult. Beyond their pivotal role in the coordinated migration of immune cells to the site of inflammation, in many cases, chemokines may also play important roles in the development of lymphoid tissues, in the maturation of immune cells, and in the generation and delivery of adaptive immune responses.

Tumors are increasingly recognized as a complex microenvironment made up of many different cell types that cohabit and communicate with each other in a complicated signaling network. Chemokines are essential coordinators of cellular migration and cell-cell interactions and therefore have great impact on tumor development. In the tumor microenvironment, tumor-associated host cells and cancer cells release an array of different chemokines, resulting in the recruitment and activation of different cell types that mediate the balance between antitumor and pro-tumor responses. In addition to their primary role as chemoattractants, chemokines, in many cases, are also involved in other tumor-related processes, including tumor cell growth, angiogenesis and metastasis.

Tumor cells have been shown to acquire the ability to produce growth-promoting chemokines. For instance, melanoma has been found to express a number of chemokines, including CXCL1, CXCL2, CXCL3, CXCL8, CCL2 and CCL5, which have been implicated in tumor growth and progression. CCL2 level can be found increased in neuroblastoma cell lines and primary tumor cells isolated from human patients. Immunostaining studies also suggest an elevated expression level of CXCL12 in a variety of cancers, including breast cancer, carcinoid, cervical cancer, colorectal cancer, endometrial cancer, liver cancer, lung cancer, lymphoma, melanoma, ovarian cancer, pancreatic cancer, prostate cancer, stomach cancer.

Chemokine receptors are cytokine receptors found on the surface of certain cells that interact with chemokines. There have been 20 distinct chemokine receptors discovered in humans. Each has a 7-transmembrane structure and couples to G-protein for signal transduction within a cell, making them members of a large protein family of G protein-coupled receptors. Following interaction with their specific chemokine ligands, chemokine receptors may trigger a flux in intracellular calcium ($Ca^{2+}$) ions (calcium signaling). This may cause cell responses, including the onset of a process known as chemotaxis that traffics the cell to a desired location within the organism. In general, the term "chemokine receptor" as used herein can refer to a membrane associated protein that selectively binds to a chemokine ligand and induces the chemotaxis toward the chemokine ligand.

It is to be understood the chemokine receptor as disclosed herein in some cases can refer to not only the naturally occurring chemokine receptors identified in human bodies, but also include chemokine receptors from other sources, such as, but not limited to: (1) naturally occurring chemokine receptors identified in animals, like pigs, dogs, cows, sheep; (2) non-naturally occurring chemokine receptors, like mutant proteins, chimeric receptors, design proteins with binding affinity to a certain type(s) of chemokines. In some examples, a fragment of a naturally occurring chemokine receptor can be also considered a chemokine receptor, if the function of binding and responding to the corresponding chemokine and directing the chemotaxis of the cell is retained in the fragment. As provided herein, in some embodiments, the virus that comprises the exogenous nucleic acid coding for the chemokine receptor may force a virus-infected cell to express the chemokine receptor as the virus hijacks the host cell's gene expression machinery.

In some cases, the modified oncolytic viruses can comprise exogenous nucleic acid that can code for a cytokine receptor whose cognate cytokine can be expressed in tumor microenvironments (e.g., IL15-R can have a cognate cytokine IL15 expressed in a tumor microenvironment). In some cases, the modified oncolytic viruses can express selected chemokine receptors whose cognate chemokines are likely to be expressed on tumors (e.g., CXCR4 can have a cognate chemokine CXCL12 expressed on a tumor; CCR2 can have a target CCL2 expressed on a tumor) and can be delivered systemically as a naked virus. Subsequent to entry of the modified oncolytic viruses into the blood stream, by systemic delivery, the viruses can infect lymphocytes, such as B-cells, and can re-direct the infected B-cells to the tumor, resulting in significantly increased viral load in the tumor. In certain embodiments, the increased viral load in the tumor can be achieved soon after the systemic delivery. Ability to deliver the modified oncolytic viruses disclosed herein, in a systemic manner, can provide an advantage over traditional intratumoral delivery methods for oncolytic viruses. While intratumoral delivery can be helpful in treating easily accessible tumors, in some instances, it is critical to treat inaccessible or metastatic cancer which is allegedly the predominant cause of death from the disease. In this context, it may be ineffective to rely on oncolytic viruses delivered intratumorally, as it will need systemic dissemination after administration to the distant sites. However, this dissemination often may be transient and ineffective, at least in part, due to the development of immune responses to the viral infection.

Chemokine receptors can be divided into different families. Non-limiting examples of chemokine receptors, as described herein can include CXC chemokine receptors, CC chemokine receptors, CX3C chemokine receptors and XC chemokine receptors that correspond to the 4 distinct subfamilies of chemokines they bind. Among the CXC chemokine receptors, CXCR1 and CXCR2 are closely related, while CXCR1 binds to CXCL8 and CXCL6, and CXCR2 binds to CXCL1 and CXCL7; CXCR3 binds to CXCL9, CXCL10, and CXCL11; CXCR4 binds to CXCL12 (or SDF-1); CXCR5 binds to CXCL13; CXCR6 binds to CXCL16. Among the CC chemokine receptors, CCR1's ligands include CCL4, CCL5, CCL6, CCL14, CCL15, CCL16, CCL23; CCR2's ligands include CCL2, CCL8, and CCL16; CCR3's ligands include CCL11, CCL26, CCL7, CCL13, CCL15, CCL24, CCL5, CCL28, and CCL18; CCR4's ligands include CCL3, CCL5, CCL17, and CCL22; CCR5's ligands include CCL3, CCL4, CCL5, CCL8, CCL11, CCL13, CCL14, and CCL16; CCR6's ligands include CCL20; CCR7's ligands include CCL19 and CCL21. CX3C chemokine receptor CX3CR1 has a ligand CXCL1. XC chemokine receptor XCR1 binds to both XCL1 and XCL2.

Non-limiting embodiments of the present disclosure provide a modified oncolytic virus that comprises an exogenous nucleic acid that can code for a chemokine receptor. In some embodiments, the chemokine receptor can be a CXC chemokine receptor, a CC chemokine receptor, a CX3C chemokine receptor, a XC chemokine receptor, or any combinations thereof. In some embodiments, the chemokine receptor can be CXCR1, CXCR2, CXCR2, CXCR3, CXCR4, CXCR5, CXCR6, CXCR7, CCR1, CCR2, CCR3, CCR4, CCR5, CCR6, CCR7, CX3CR1, XCR1, or any combinations thereof.

In certain embodiments, the modified oncolytic virus comprises an exogenous CXCR4-expressing nucleic acid. In certain embodiments, the modified oncolytic virus comprises an exogenous CCR2-expressing nucleic acid. Certain embodiments disclose a modified oncolytic virus comprising an exogenous nucleic acid that codes for both CXCR4 and CCR2, and both chemokines are expressed form the same virus. Under certain circumstances, CXCL12 and/or CCL2 typically expressed in the tumor microenvironment may attract the CXCR4 and/or CCR2-expressing lymphocytes or other migrating cells that are infected by the modified oncolytic virus, thereby enhancing the tumor-targeted delivery of the modified oncolytic virus.

In some embodiments, the modification of the oncolytic virus can result in at least about 1.1, 1.2, 1.5, 1.8, 2, 2.2, 2.5, 2.8, 3, 3.2, 3.5, 3.8, 4, 4.2, 4.5, 4.8, 5, 5.2, 5.5, 5.8, 6, 6.2, 6.5, 6.8, 7, 7.2, 7.5, 7.8, 8, 8.2, 8.5, 8.8, 9, 9.2, 9.5, 9.8, 10, 12, 14, 15, 16, 18, 20, 25, 30, 35, 40, 45, 50, 55, 60, 65, 70, 75, 80, 85, 90, 95, 100, 150, 200, 250, 500, 800, 1000, 2500, 5000, $10^4$, $2.5\times10^4$, $5\times10^4$, $7.5\times10^4$, $2.5\times10^5$, $5\times10^5$, $7.5\times10^5$, $10^6$, $2.5\times10^6$, $5\times10^6$, $7.5\times10^6$, $10^7$, $2.5\times10^7$, $5\times10^7$, $7.5\times10^7$, $10^8$, $2.5\times10^8$, $5\times10^8$, $7.5\times10^8$, $10^9$, $2.5\times10^9$, $5\times10^9$, $7.5\times10^9$, $10^{10}$ or even more folds increase in the efficacy of tumor-targeted systemic delivery of the virus, as compared to an otherwise identical oncolytic virus that does not comprise the modification. In certain embodiments, the efficacy of tumor-targeted systemic delivery of the virus can be measured by quantifying the viruses infecting the tumor cells, and optionally, in contrast with the viruses infecting non-tumor cells in the body. For instance, in some cases, the quantification of the virus can be performed by staining the viral particles in tissue sections, or blood smear in the cases of leukemia, lymphoma, or myeloma. In some cases, such quantification can be performed by reporter molecule(s) that is/are engineered to be expressed by the viruses, e.g., luciferase, and fluorescent proteins. In some cases, such quantification can be performed by quantifying the viral genome in the tumor. Without being limited, it is also possible to measure the tumor-targeted systemic delivery of the virus by quantifying certain downstream effect(s) of viral infection in tumor cells, like cytokines in response to viral infection or lymphocyte accumulation. In some embodiments, the oncolytic virus comprises an exogenous nucleic acid that can code for CXCR4, CCR2, or both, and the presence of the exogenous nucleic acid can result in about 5 to 10 folds increase in the efficacy of tumor-target systemic delivery of the virus, as compared to an otherwise identical oncolytic virus that does not comprise the exogenous nucleic acid.

In some embodiments, provided herein is a modified oncolytic virus that comprises an exogenous nucleic acid that can code for a chemokine receptor, and the forced expression of chemokine receptor by the modified oncolytic virus can result in boosted immune responses against the infected tumor. Following infecting the tumor, the modified oncolytic viruses can replicate in the tumor cells and result in the expression of the chemokine receptors on the surface of the tumor cells. These membrane receptors may function as decoy receptors, binding and sequestering the immunosuppressive chemokines within the tumor (e.g., CXCL12 and/or CCL2). Consequently, the immunosuppressive microenvironment in the tumor can be altered, leading to enhanced immunotherapeutic activity of the modified oncolytic virus, as compared to an otherwise identical virus that does comprise the nucleic acid coding for the chemokine receptor. In some embodiments, the increase in immunotherapeutic activity can be at least about 1.1, 1.1, 1.2, 1.5, 1.8, 2, 2.2, 2.5, 2.8, 3, 3.2, 3.5, 3.8, 4, 4.2, 4.5, 4.8, 5, 5.2, 5.5, 5.8, 6, 6.2, 6.5, 6.8, 7, 7.2, 7.5, 7.8, 8, 8.2, 8.5, 8.8, 9, 9.2, 9.5, 9.8, 10, 12, 14, 15, 16, 18, 20, 25, 30, 35, 40, 45, 50, 55, 60, 65, 70, 75, 80, 85, 90, 95, 100, 150, 200, 250, 500, 800, 1000, 2500, 5000, $10^4$, $2.5\times10^4$, $5\times10^4$, $7.5\times10^4$, $2.5\times10^5$, $5\times10^5$, $10^6$ or even higher folds. Without being limited, the increased immunotherapeutic activity can be reflected by increased B cell accumulation in the tumor, increased T cell response to tumor-related immunogens, or both. B cell accumulation can be measured, for example, by quantifying the B cells in the tumor, and T cell immunoactivity may be measured by, for example, interferon-γ (interferon-gamma) secretion in ELISPOT assays.

In some embodiments, provided herein is a modified oncolytic virus that comprises an exogenous nucleic acid that can code for a chemokine receptor, and the forced expression of chemokine receptor by the modified oncolytic virus can result in increased replication of the virus in tumor cells, as compared to an otherwise identical virus that does not comprise the nucleic acid coding for the chemokine receptor. In certain embodiments, the modified oncolytic virus can comprise an exogenous CCR2-expressing nucleic acid, which can increase the tumor-specific replication of the virus. In some embodiments, the modified oncolytic virus can comprise an exogenous CCR5-expressing nucleic acid, which can increase the tumor-specific replication of the virus. In some embodiments, the increase in tumor-specific replication can be at least about 1.1, 1.1, 1.2, 1.5, 1.8, 2, 2.2, 2.5, 2.8, 3, 3.2, 3.5, 3.8, 4, 4.2, 4.5, 4.8, 5, 5.2, 5.5, 5.8, 6, 6.2, 6.5, 6.8, 7, 7.2, 7.5, 7.8, 8, 8.2, 8.5, 8.8, 9, 9.2, 9.5, 9.8, 10, 12, 14, 15, 16, 18, 20, 25, 30, 35, 40, 45, 50, 55, 60, 65, 70, 75, 80, 85, 90, 95, 100, 150, 200, 250, 500, 800, 1000, 2500, 5000, $10^4$, $2.5\times10^4$, $5\times10^4$, $7.5\times10^4$, $2.5\times10^5$, $5\times10^5$, $10^6$ or even higher folds. Exemplary methods for measuring the increase in viral delivery and spread in tumors can include, but are not limited to, fluorescence or bioluminescence based imaging of expression of a reporter gene, quantitative PCR for detection of tumor concentrations of viral genomes or plaque determination of plaque forming units or immunohistochemistry of viral proteins.

In some embodiments, the modified oncolytic virus comprises an exogenous nucleic acid that can code for a chemokine receptor that is a chimeric protein. At least part of its extracellular domain can be from a chemokine receptor that promotes the tumor-targeted delivery of the virus, and at least part of its intracellular domain can be from a chemokine receptor that promotes the tumor-specific replication, inhibits immunosuppressive activity, or conveys some other beneficial effects, or vice versa. For instance, the modified oncolytic virus can comprise a nucleic acid that codes for a protein having an intracellular GTPase domain of CCR5, and an extracellular chemokine-binding domain of CXCR4 or CCR2. In some case, by combining domains with different functionalities one may achieve further improvement in therapeutic performance of the modified oncolytic virus. It is one embodiment of this disclosure that the modified oncolytic virus can comprise exogenous nucleic acids that can code for at least one chemokine receptor. In some cases, the modified oncolytic virus can comprise exogenous nucleic acids that can code for two or more different chemokine receptors, which may be expressed simultaneously by the virus. Exemplary chemokine receptors that can be expressed simultaneously from the modified oncolytic viruses described herein can include CXCR4 and CCR2. In modified oncolytic viruses expressing more than one chemokine receptors, a combinatorial or synergistic effect against tumor cells may be achieved as to the therapeutic application of the oncolytic virus.

Therapeutic effects of oncolytic viruses can often be limited by their ineffective spreading in and between the solid tumors, at least in part due to the high amounts of extracellular matrix (ECM) and high interstitial fluid pressure (IFP) that exist in tumor. Certain embodiments of the present disclosure relate to a modified oncolytic virus that comprises an exogenous nucleic acid that can code for a protein that degrades ECM of a tumor. Exemplary proteins that can degrade ECM can be a membrane associated protein. In some cases, the membrane associated protein can comprise a glycosylphosphatidylinositol (GPI) anchor.

Hyaluronan (HA) is an important structural element of ECM and a high molecular weight linear glycosaminoglycan consisting of repeating disaccharide units. It can be distributed widely throughout connective, epithelial, and neural tissues, and its expression level can be significantly elevated in many types of tumors. Hyaluronidases are a family of enzymes that catalyze the degradation of HA. There are at least five functional hyaluronidases identified so far in human: HYAL1, HYAL2, HYAL3, HYAL4 and HYAL5 (also known as PH-20 or SPAM1), among which PH-20 is the only one known so far to be functional at relatively neutral pH. In some embodiments of the present disclosure, combining hyaluronidase with other tumor-targeting therapeutic agents (such as transgenes, also referred to herein as exogenous nucleic acid) can promote the therapeutic effect of the modified oncolytic virus at least by diminishing the ECM and enhancing the transportation of the therapeutic agent inside and between the tumors.

Some embodiments herein disclose a modified oncolytic virus that can comprise an exogenous nucleic acid coding for a membrane associated protein that is capable of degrading hyaluronan, such as a hyaluronidase. It should be noted that the term "hyaluronidase" as used herein can refer to any enzyme or a fragment thereof that catalyzes the degradation of HA in a tumor, including, but not limited to, PH-20 and its homologs from other species, as well as other engineered/design proteins with similar enzymatic function. As used herein, hyaluronidase can refer to a class of hyaluronan degrading enzymes.

Hyaluronidases can include bacterial hyaluronidases (EC 4.2.2.1 or EC 4.2.99.1), hyaluronidases from leeches, other parasites, and crustaceans (EC 3.2.1.36), and mammalian-type hyaluronidases (EC 3.2.1.35). Hyaluronidases can be of any non-human origin including, but not limited to, murine, canine, feline, leporine, avian, bovine, ovine, porcine, equine, piscine, ranine, bacterial, and any from leeches, other parasites, and crustaceans. Exemplary non-human hyaluronidases include, hyaluronidases from cows, yellow-jacket wasp, honey bee, white-face hornet, paper wasp, mouse, pig, rat, rabbit, sheep, chimpanzee, Rhesus monkey, orangutan, cynomolgus monkey, guinea pig, *Arthrobacter* sp. (strain FB24), *Bdellovibrio bacteriovorus, Propionibacterium acnes, Streptococcus agalactiae, Staphylococcus aureus*; strain MRSA252, *Streptococcus pneumoniae, Streptococcus pyogenes, Streptococcus suis, Vibrio fischeri*, and the *Streptomyces hyaluronolyticus* hyaluronidase enzyme, which is specific for hyaluronic acid and does not cleave chondroitin or chondroitin sulfate.

In some embodiments, the modified oncolytic virus can comprise an exogenous nucleic acid that can code for PH-20. In some embodiments, the modified oncolytic virus can comprise an exogenous nucleic acid that can code for PH-20, and the PH-20 can comprise a GPI-anchor. In some embodiments, the modified oncolytic virus can comprise an exogenous nucleic acid that can code for PH-20, and the PH-20 may lack a GPI-anchor. GPI can function as an anchor of the protein to a cell membrane, therefore, generally, GPI-containing PH-20 may be anchored to the cell membrane, while PH-20 that does not have GPI may be in secretory form.

In some embodiments, exemplary amino acid sequences for the PH-20 can be SEQ ID NO: 36, SEQ ID NO: 130, or sequences that can be about 70%, about 75%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identical to SEQ ID NO: 36 or SEQ ID NO: 130.

The present disclosure identifies that retention of the C-terminal GPI anchor, unexpectedly, improves the spread of oncolytic viruses expressing the GPI-anchor containing PH-20, within a tumor microenvironment. In some examples, the modified oncolytic virus comprising an exogenous nucleic that can code for a GPI-anchored PH-20 can unexpectedly degrade tumor ECM and promote viral spreading to a greater extent, as compared to an otherwise identical virus that can comprise an exogenous nucleic acid that can code for a PH-20 lacking a GPI-anchor. In some other embodiments, the modified oncolytic virus can comprise nucleic acids that can code for both a GPI-anchored PH-20 and secretory PH-20 without the GPI-anchor.

In some cases, expression of the GPI-anchored PH-20 from the modified oncolytic vaccinia virus can have at least one of the following effect: (i) the PH-20 can be incorporated into the EEV outer envelope, and thereby may allow the EEV to spread more effectively, (ii) the viral infection may result in movement of infected cells, which may be enhanced if they express PH20 on their surface. Some embodiments of this disclosure identify that the secreted form of the PH-20, without the GPI-anchor can be less active in promoting production of the EEV form of the virus.

In some embodiments, at least some of the hyaluronidase-encoding nucleic acid can be derived from other sources than human beings. Hyaluronidases in different species can hydrolyze tumor HA in different manners, with different efficiencies, combinations thereof. Some embodiments herein relate to a modified oncolytic virus that can comprise an exogenous nucleic acid coding for multiple hyaluronidases from different species. The combination may provide a greater ECM degrading capability and subsequently lead to enhanced therapeutic effects.

In some embodiments, the oncolytic virus comprises an exogenous nucleic acid that can code for a hyaluronidase of microbial origin. In some examples, the hyaluronidase of microbial origin can be HysA from *Staphylococcus aureus*, lin from *Loxosceles intermedia*, sko from *Streptomyces koganeiensis*, rv from *Mycobacterium tuberculosis*. In some examples, the hyaluronidase of microbial origin can be a secreted hyaluronidase. In some examples, the exogenous nucleic acid hysA can comprise a sequence as set forth in GenBank: CP020020.1, (*Staphylococcus aureus* subsp.

*aureus* strain ATCC 6538 chromosome, complete genome) range of nucleotides: 2248602 to 2250899). In some cases, the exogenous nucleic acid hysA can code for a protein that comprises an amino acid sequence as set forth in SEQ ID NO: 122. In some cases, the exogenous nucleic acid hysA can code for a protein that comprises an amino acid sequence as set forth in UniProtKB Accession No. Q59801 (HYAS_STAA8) (SEQ ID NO: 123). In some embodiments, expression of a secreted hyaluronidase, such as HysA, enhances replication, spread, therapeutic activity (e.g., cancer cell killing potential) of a modified oncolytic virus as described herein. In some cases, the exogenous nucleic acid lin can code for a protein that comprises an amino acid sequence as set forth in SEQ ID NO: 124 or SEQ ID NO: 127. In some cases, the exogenous nucleic acid rv can code for a protein that comprises an amino acid sequence as set forth in SEQ ID NO: 125 or SEQ ID NO: 128. In some cases, the exogenous nucleic acid sko can code for a protein that comprises an amino acid sequence as set forth in SEQ ID NO: 126 or SEQ ID NO: 129. In some embodiments, exemplary amino acid sequences for the microbial hyaluronidase can be SEQ ID NO: 122, SEQ ID NO: 123, SEQ ID NO: 124, SEQ ID NO: 125, SEQ ID NO: 126, SEQ ID NO: 127, SEQ ID NO: 128, or SEQ ID NO: 129, or sequences that can be about 70%, about 75%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identical to S SEQ ID NO: 122, SEQ ID NO: 123, SEQ ID NO: 124, SEQ ID NO: 125, SEQ ID NO: 126, SEQ ID NO: 127, SEQ ID NO: 128, or SEQ ID NO: 129.

Furthermore, in some embodiments, the modified oncolytic virus can comprise exogenous nucleic acids that can code for both a hyaluronidase and a matrix metalloprotease. Collectively, matrix metalloproteases are capable of degrading all kinds of ECM proteins. The addition of a matrix metalloprotease may further enhance the ECM degradation effect and promote virus spreading. One example of matrix metalloproteases can be MMP8. Other examples can include, but not limited to, MMP1, MMP2, MMP3, MMP7, MMP9, MMP10, MMP11, MMP12, MMP13, MMP14, MMP15, MMP17, MMP18, MMP19, MMP20, MMP21, MMP23A, MMP23B, MMP24, MMP25, MMP26, MMP27, and MMP28.

In some embodiments, the modified oncolytic virus that comprises the nucleic acid that can code for a hyaluronidase may have increased virus spreading in and between tumors as compared to an otherwise identical virus that does not comprise the hyaluronidase-encoding nucleic acid. In some embodiments, such increase can be at least about 1.1, 1.1, 1.2, 1.5, 1.8, 2, 2.2, 2.5, 2.8, 3, 3.2, 3.5, 3.8, 4, 4.2, 4.5, 4.8, 5, 5.2, 5.5, 5.8, 6, 6.2, 6.5, 6.8, 7, 7.2, 7.5, 7.8, 8, 8.2, 8.5, 8.8, 9, 9.2, 9.5, 9.8, 10, 12, 14, 15, 16, 18, 20, 25, 30, 35, 40, 45, 50, 55, 60, 65, 70, 75, 80, 85, 90, 95, 100, 150, 200, 250, 500, 800, 1000, 2500, 5000, $10^4$, $2.5\times10^4$, $5\times10^4$, $7.5\times10^4$, $2.5\times10^5$, $5\times10^5$, $\mathbf{10^6}$ or even higher folds. In certain embodiments, the modified oncolytic virus comprises an exogenous nucleic acid coding PH-20, and the viral spreading within tumor can be increased at least about 100 folds, as compared to an otherwise identical virus that does not comprise the PH-20-encoding nucleic acid. Exemplary methods for measuring the increase in viral spread can include, but are not limited to, fluorescence or bioluminescence based imaging of expression of a reporter gene, quantitative PCR for detection of tumor concentrations of viral genomes or plaque determination of plaque forming units or immunohistochemistry of viral proteins.

VH1 is a viral protein, identified as a dual specificity phosphatase against both phosphoserine- and phosphotyrosine-containing substrates. In particular, VH1 can inhibit phosphorylation and nuclear translocation of STAT1, a transcription factor responsive to a number of immune factors, such as interferon alpha and interferon gamma, suppressing immune response against virus-infected cells, at least in part through reduction in antigen presentation. More active VH1 expressed by the virus may have better immunosuppressive effect as to the virus-infected cells.

In some embodiments, the modified oncolytic virus can comprise an exogenous nucleic acid that can code for a viral VH1 protein. In some embodiments, the exogenous nucleic acid coding for the viral VH1 protein can be from a genome of poxvirus that is a different species than the modified oncolytic virus. In some embodiments, the poxvirus can comprise a betaentomopoxvirus, a yatapoxvirus, a cervidpoxvirus, a gammaentomopoxvirus, a leporipoxvirus, a suipoxvirus, a molluscipoxvirus, a crocodylidpoxvirus, an alphaentomopoxvirus, a capripoxvirus, an avipoxvirus, or a parapoxvirus. In some embodiments, the modified oncolytic virus can comprise a partial or a complete deletion of the native VH1 gene, and can comprise an exogenous VH1-encoding nucleic acid. The VH1 protein can also be a chimeric/fusion protein that has components from different species, artificially designed/engineered, or only a functional fragment of a naturally occurring VH1 protein that can retains the phosphatase activity. The VH1 protein encoded by the exogenous nucleic acid may be more active than the native VH1 protein of the backbone oncolytic virus.

In some embodiments, the modified oncolytic virus can comprise a vaccinia virus, wherein its native VH1 gene can be deleted from the genome, and a VH1 gene from other poxviruses can be inserted in its genome. In this case, a more active VH1 protein may lead to a lower toxicity of the virus. Alternatively, or additionally, it may lead to a greater therapeutic benefit, at least partially due to the adaptive immune response more actively targeting the tumor antigens, and less potently targeting viral antigens.

In some embodiments, the modified oncolytic virus can comprise an exogenous nucleic acid that can code for a therapeutic protein. Examples of therapeutic proteins that can be coded by the exogenous nucleic acid contained with the modified oncolytic vaccinia virus described herein, can include, but are not limited to, antibodies or antigen binding fragments thereof, cytokines, growth factors, peptide hormones, cytokines, coagulation factors, plasma proteins, fusion proteins. In some embodiments, the modified oncolytic virus can comprise an exogenous nucleic acid that codes for proteins or fragment thereof that are immune checkpoint inhibitors, T-cell activators, therapeutic nanobodies, chemokines and immune activators, prodrug converting enzymes, directly cytotoxic compounds, or any combinations thereof. Each or any combinations of these proteins may contribute to a greater therapeutic benefit of the backbone oncolytic virus.

The exogenous nucleic acid, in some cases, can code for a transgene comprising a humanized anti-CD20 monoclonal antibody (e.g., Gazyva), a VEGFR Fc-fusion (e.g., Eylea), a CTLA-4 Fc-fusion (e.g., Nulojix), a glucagon-like peptide-1 receptor agonist Fc-fusion (e.g., Trulicity), VEGFR Fc-fusion (e.g., Zaltrap), a recombinant factor IX Fc fusion (e.g., Alprolix), a recombinant factor VIII Fc-fusion (e.g., Eloctate), a GLP-1 receptor agonist-albumin fusion (e.g., Tanzeum), a recombinant factor IX albumin fusion (e.g., Idelvion), a PEGylated IFNβ-1a (e.g., Plegridy), a recombinant factor VIII PEGylated (e.g., Adynovate), a humanized anti-HER2/neu conjugated to emtansine (e.g., Kadcyla), a mouse/human chimeric anti-CD30 (e.g., Adcetris), an anti-human epidermal growth factor receptor 2 (HER2) (e.g., Perjeta), Anti-IL-6 receptor (Actemra), an anti-CD20 (e.g., obinutuzumab; Gazyva), an anti-integrin a4b7 (LPAM-1) (e.g., Entyvio), an anti-PD-1 (e.g., Keytruda), an anti-dabigatran (e.g., Praxbind), an anti-IL-5 (e.g., Nucala), an Anti-CD319 (SLAMF7) (e.g., Empliciti), an anti-IL-17a (e.g., Taltz), an anti-IL-5 (e.g., Cinqair), an anti-PD-L1 (e.g., Tecentriq), an anti-CD25 (e.g., Zinbryta), an anti-CD30 (e.g., Adcetris), an anti-IL-6 (e.g., Sylvant), an anti-GD2 (e.g., Unituxin), an anti-*Bacillus anthracis* (e.g., Anthim), an anti-TNFα (e.g., Inflectra), a human anti-B-cell activating factor (BAFF) (e.g., belimumab), a human anti-CTLA-4 (e.g., ipilimumab), a CTLA-4 Fc-fusion (e.g., belatacept), humanized anti-human epidermal growth factor receptor 2 (HER2) (e.g., pertuzumab), a VEGFR Fc fusion (e.g., ziv-afilbercept), a G-CSF (e.g., tbo-filgrastim), human anti-VEGFR2 (KDR) (e.g., ramucirumab), a mouse/human chimeric anti-IL-6 (e.g., siltuximab), pembrolizumab, mouse bispecific anti-CD19/anti-CD3 (e.g., blintumomab), nivolumab, a parathyroid hormone, a mouse/human chimeric anti-GD2 (e.g., dinutuximab), a human anti-CD38 (e.g., daratumumab), a human anti-epidermal growth factor receptor (EGFR)(e.g., necitumumab), humanized anti-CD319 (SLAMF7) (e.g., elotuzumab), atezolizumab. In some embodiments, the modified oncolytic virus can comprise an exogenous nucleic acid coding for a protein or a fragment thereof that: can modulate NFκB signaling, can promote reduction of interstitial fluid pressure (IFP) in a tumor, can modulate STAT3-mediated gene activation, can promote T cell activation, can promote attraction of NK cells to virus-infected cells, can modulate metabolic program of virus-infected cells, can modulate fatty acid uptake by virus-infected cells, can promote therapeutic targeting of MDSCs, or any combinations thereof.

In some embodiments, the modified oncolytic virus can comprise an exogenous nucleic acid that can code for at least one of HMGB1, PIAS3, IL15, CCL5, a fragment thereof, or any combinations thereof. Each or any combinations of these proteins may contribute to a greater therapeutic benefit of the backbone oncolytic virus.

In some embodiments, the modified oncolytic virus can comprise an exogenous nucleic acid that codes for a fractalkine (such as CX3CL1), ITAC (such as CXCL11), LIGHT (such as tumor necrosis factor superfamily member 14, or TNFSF14), a fragment thereof, or any combinations thereof. Each or any combinations of these proteins may contribute to a greater therapeutic benefit of the backbone oncolytic virus.

In some embodiments, the immune checkpoint inhibitors can refer to inhibitors of immune checkpoint molecules such as, but not limited to, PD-1, PD-L1, PD-L2, CTLA4, TIM-3, LAG-3, CEACAM-1, CEACAM-5, VISTA, BTLA, TIGIT, LAIR1, CD 160, 2B4, TGFR-beta, and any combinations thereof.

In some embodiments, the T-cell activators can include, but not limited to, interleukin-1, interleukin-2, interleukin-4, interleukin-5, interleukin-6, interleukin-7, interleukin-11, interleukin-12, interleukin-13, interleukin-15 (IL15/IL-15), IL15-α (IL15-alpha), IL15-receptor (IL15-R), IL15-Rα (IL15-receptor alpha), interferon-alpha, interferon-gamma, tumor necrosis factors, anti-CD3 antibodies, anti-CD28 antibodies, anti-CTLA4 antibodies, anti-TGF-beta antibodies, anti-4-1BB antibodies, cell-based vaccines peptide vaccines, DNA vaccines, growth factors, phytohemagglutinin, concanavalin-A, phorbol esters, and any combinations thereof.

In some embodiments, the therapeutic nanobody can refer to an antibody fragment consisting of a single monomeric variable antibody domain and having therapeutic effects against a tumor cell or a tumor.

In some embodiments, the other cytokines, chemokines, and immune activators can refer to any other proteins belonging to the corresponding category that may have therapeutic effects against a tumor cell or a tumor.

In some embodiments, the prodrug converting enzyme can refer to an enzyme that converts a molecule with less activity against a target into a molecule with more activity against a target. In some cases, the target can be a tumor cell or a tumor. The prodrug converting enzyme can include, but not limited to, cytosine deaminase, uracil phosphoribosyltransferase, thymidine kinase, and any combinations thereof.

In some embodiments, the directly cytotoxic compounds can refer to any molecules that are directly cytotoxic to the tumor cell without effecting through other cells or compounds. In some embodiments, the directly cytotoxic compound can include, but not limited to, proteins, peptides, mRNAs, or oligomers that may be expressed from the exogenous nucleic acids that are added to the modified oncolytic virus.

In various examples, the modified oncolytic virus can comprise one or more of exogenous nucleic acids described above, that can code for proteins, as described above, wherein the proteins can be the full-length proteins, truncated versions of the full-length proteins, functional domains of the full-length proteins, fragments of the full-length proteins, or variants of the full-length proteins, truncated versions, functional domains, or fragments. Variants can comprise, in some examples, amino acid substitutions (conservative or non-conservative), deletions, additions, modifications, or any combinations thereof.

Modifications of Viral Genome

Some embodiments of this disclosure can include a modified oncolytic virus that can comprise a modification in the genome of the virus. In some embodiments, the modified oncolytic virus can comprise at least one modification in the genome of the virus.

In some embodiments, the modified oncolytic virus can comprise at least 2, 3, 4, 5, 6, 7, 8, 9, 10, 11, 12, 13, 14, 15, 20, or even more modifications in the genome of the virus. The modification of the viral genome can comprise a mutation, a deletion, or both of a viral gene.

A deletion of a viral gene may include a partial or a complete deletion of the viral gene. It should be noted that as used herein, "partial deletion" or "mutation" may refer to an in situ partial deletion or mutation of an endogenous viral gene, respectively. Alternatively, they may refer to replacing the endogenous viral gene with an otherwise identical exogenous nucleic acid that lacks a portion of the gene ("partial deletion") or has one or more nucleotide change in the gene ("mutation").

Replication of many viruses, including poxviruses, involves several stages with different morphologies in the various stages. One non-limiting example may be vaccinia virus, which is a large DNA virus that may replicate entirely within the cytoplasm of an infected cell. Generally, vaccinia virus has a complex morphogenic pathway that culminates in the formation of two distinct infectious virions that are surrounded by different numbers of membranes. The first virion produced, which is called intracellular mature virus (IMV), is surrounded by a single membrane and remains within the cell until cell lysis. The other virion is surrounded by a second membrane and is exported from the cell before cell death. This virion is called cell-associated enveloped virus (CEV) if it is retained on the cell surface and extracellular enveloped virus (EEV) if it is released from the cell surface.

In the therapeutic applications of oncolytic vaccinia virus, the second membrane of the virion in its EEV form may significantly reduce the virus' sensitivity to neutralizing antibodies and complement that exist in the circulating system and other tissue environments, as compared to single membrane-wrapped IMV. Moreover, as EEV is in the released form, administration of EEV may make it easier for the virus to spread within and between tumors, thereby increasing the chance of infecting tumor cells. Therefore, increasing the production of EEV may result in greater therapeutic benefits when oncolytic viruses, such as poxviruses, e.g., oncolytic vaccinia viruses, other oncolytic poxviruses, or other similar viruses are used at clinical settings. Some embodiments herein disclose a modified oncolytic virus that can comprise a modification in the viral genome that can enhance production of the EEV form of the virus and thereby the spreading of the virus within and between tumors. B5R, F13L, A36R, A34R, A33Rare examples of EEV-specific membrane proteins.

In some embodiments, the modified oncolytic virus can comprise a modification in the viral B5R gene, provided that said modification is not in the SCR2 domain. The B5R protein includes the following regions: (Signal peptide)-(Short Consensus Repeat (SCR) regions 1 to 4 (Transmembrane domain)-(Cytoplasmic Tail). SCR1 domain can contain a neutralizing antibody epitope found on the EEV. SCR3 can contain a P189S mutation site that can result in increased EEV release.

A modified oncolytic virus of this disclosure, in some examples, can comprise modifications in at least one of the SCR1, SCR3 and SCR4 domains of the B5R gene. For example, the modification can be a partial deletion of the B5R gene. In some cases, the modification of the B5R gene, e.g., deletions in the SCR3 and SCR4 domains, can, at least partially, disrupt binding of neutralizing antibodies to B5R. Thus, a modified oncolytic virus according to this disclosure can be at least partially resistant to neutralization.

Additional modifications in the B5R SCR regions are also included in this disclosure, such that the modified oncolytic viruses may be optimized for EEV release, replication and antibody evasion. The B5R mutations, e.g., removal of antibody binding site in B5R SCR1, can be combined with other EEV enhancing mutations, e.g., random mutagenesis in A34R. In some cases, such combinations of modifications can result in increased EEV production.

In some embodiments, the modification comprises a deletion or mutation in B5R. The deletion may be a complete or partial deletion.

In some embodiments, the modified oncolytic virus can comprise a modification in the viral gene B5R, F13L, A36R, A34R, A33R, or any combinations thereof that increases production of EEV. In some embodiments, the modified oncolytic virus can comprise one or more of the following mutations: partial deletion of A33R, A34R Lys151 to Glu (K 151 E); complete or partial deletion of B5R; and/or mutation/deletion of A36R.

In some embodiments, the modified oncolytic virus can comprise a mutation or a deletion of a further viral gene. The further viral gene can comprise genes encoding certain secreted cytokine binding proteins, e.g., B8R or B18R. Or it can comprise genes that may be responsible for immune suppressive activity, e.g., N1L or A41L. It can also comprise genes coding for proteins with NFκB (NF-kappaB) inhibitory functions, e.g., K7R, B15R, A52R. Alternatively, it is also possible that the modified oncolytic virus comprises a mutation or a deletion of any one or combination of the genes that can code for B8R, B18R, SPI-1, SPI-2, B15R, VGF, E3L, K3L, A41L, K7R, N1L, or A52R. The protein B8R can, in some embodiments, refer to a secreted viral protein with homology to the IFN-gamma receptor, which in some cases can inhibit the interaction between host IFN-gamma and its receptor, thereby counteracting the antiviral effects of host IFNγ. The protein B18R can, in some embodiments, refer to a viral ankyrin-like protein that is secreted and, in some cases, can bind to type 1 interferon. The protein SPI-1 can, in some embodiments, refer to a viral seine proteinase inhibitor 1 and SPI-2 can refer to a viral serine proteinase inhibitor 2. The protein B15R (also referred to as B14R in Vaccinia virus strain Copenhagen) can, in some embodiments, refer to a viral protein that, in some cases, can bind to the IKBKB subunit of the IKK complex, thereby preventing host NF-kappa-B activation in response to pro-inflammatory stimuli such as TNF-alpha or IL1B. The protein VGF can, in some embodiments, refer to pro-vaccinia growth factor that can stimulate cellular proliferation around infected cells. The protein E3L, in some embodiments, can refer to a viral protein that, in some cases, can bind to and sequester double-stranded RNA (dsRNA) synthesized during viral infection, thereby preventing recognition of the dsRNA by and subsequent activation of EIF2AK2/PKR. The protein K3L can, in some embodiments, refer to a viral protein that, in some cases, can act as a pseudosubstrate of EIF2AK2/PKR, thereby inhibiting eIF2α activation by PKR kinase and preventing translation shutoff in host cell. The protein A41L can, in some embodiments, refer to a secreted viral chemokine binding protein that, in some cases, can interact with certain cellular chemokines to interfere with chemokine-glycosaminoglycan (GAG) interactions at the cell surface to alter chemotaxis of nearby responsive cells. The protein K7R can, in some embodiments, refer to a viral Bcl-2-like protein that, in some cases, can bind to Toll-like receptor-adaptor proteins and the DEAD-box RNA helicase DDX3, thereby inhibiting the activation of NFκB and interferon regulatory factor 3. The protein N1L can, in some embodiments, refer to another viral Bcl-2-like protein that, in some cases, can bind to BH3 peptides of pro-apoptotic Bcl-2 family proteins. In some cases, N1L can inhibit NFκB activation and host cell apoptosis. The protein A52R can, in some embodiments, refer to another viral Bcl-2-like protein, which, in some cases can target host toll-like receptor signaling complexes to suppress innate immune response, in some cases can interact with host TRAF6 to activate p38 and subsequently induce the expression of several cytokines such as IL-10, and in some cases can interact with host IRAK2 to inhibit NF-kappa-B signaling. In some cases, a deletion in the N1L gene can, in some embodiments, result in increased memory T-cell response, upon administration of the modified oncolytic virus. Additional effects can, in some embodiments, include one or more of the following: deletion of A41L can, in some embodiments, result in increased CTL response; K7R deletion can, in some embodiments, lead to increased natural killer and T-cell response, modified B15R can, in some embodiments, reduce NFκB activation and a deletion of the B15R gene can, in some embodiments, enhance immune response, modified A52R can, in some embodiments, reduce NFκB activation and a deletion of the A52R gene can, in some embodiments, enhance immune response.

In some embodiments, the modified oncolytic virus can comprise an exogenous nucleic acid that can code for LIGHT. In some embodiments, the modified oncolytic virus can comprise an exogenous nucleic acid that can code for IL15. In some embodiments, the modified oncolytic virus can comprise an exogenous nucleic acid that can code for IL15, and exogenous nucleic acid that can code for CCL5. In some embodiments, the modified oncolytic virus can comprise an exogenous nucleic acid that can code for IL15, and exogenous nucleic acid that can code for IL15-Ra. In some embodiments, the modified oncolytic virus can comprise an exogenous nucleic acid that can code for ITAC (CXCL11), and an exogenous nucleic acid that can code for a fractalkine (CX3CL1). In some embodiments, the modified oncolytic virus can comprise an exogenous nucleic acid that can code for ITAC (CXCL11), an exogenous nucleic acid that can code for a fractalkine (CX3CL1), an exogenous nucleic acid that can code for IL15, and exogenous nucleic acid that can code for IL15-Rα.

In some embodiments, the modified oncolytic virus can comprise a mutation or deletion of the K7R gene, and can further comprise an exogenous nucleic acid that can code for a cytokine, e.g., IL15. In some embodiments, the modified oncolytic virus can comprise a mutation or deletion of the K7R gene, and can further comprise an exogenous nucleic acid that can code for a chemokine, e.g., IL15, and an exogenous nucleic acid that can code for a chemokine, e.g., CCL5. In some embodiments, the modified oncolytic virus can comprise a mutation or deletion of the K7R gene, and can further comprise an exogenous nucleic acid that can code for a cytokine, e.g., IL15, and an exogenous nucleic acid that can code for a receptor for the cytokine, e.g., IL15Rα. In some embodiments, the modified oncolytic virus can comprise a mutation or deletion of the K7R gene, and can further comprise exogenous nucleic acid that can code for LIGHT. In some embodiments, the modified oncolytic virus can comprise a mutation or deletion of the K7R gene, and can further comprise an exogenous nucleic acid that can code for ITAC (CXCL11). In some embodiments, the modified oncolytic virus can comprise a mutation or deletion of the K7R gene, and comprise an exogenous nucleic acid that can code for a fractalkine (CX3CL1). In some embodiments, the modified oncolytic virus can comprise a mutation or deletion of the K7R gene, and can further comprise an exogenous nucleic acid that can code for ITAC (CXCL11), and an exogenous nucleic acid that can code for a fractalkine (CX3CL1).

In some embodiments, the modified oncolytic virus can comprise a mutation or deletion of the A52R gene, and can further comprise an exogenous nucleic acid that can code for a cytokine, e.g., IL15. In some embodiments, the modified oncolytic virus can comprise a mutation or deletion of the A52R gene, and can further comprise an exogenous nucleic acid that can code for a chemokine, e.g., IL15, and an exogenous nucleic acid that can code for a chemokine, e.g., CCL5. In some embodiments, the modified oncolytic virus can comprise a mutation or deletion of the A52R gene, and can further comprise an exogenous nucleic acid that can code for a cytokine, e.g., IL15, and an exogenous nucleic acid that can code for a receptor for the cytokine, e.g., IL15Rα. In some embodiments, the modified oncolytic virus can comprise a mutation or deletion of the A52R gene, and can further comprise exogenous nucleic acid that can code for LIGHT. In some embodiments, the modified oncolytic virus can comprise a mutation or deletion of the A52R gene, and can further comprise an exogenous nucleic acid that can code for ITAC (CXCL11). In some embodiments, the modified oncolytic virus can comprise a mutation or deletion of the A52R gene, and comprise an exogenous nucleic acid that can code for a fractalkine (CX3CL1). In some embodiments, the modified oncolytic virus can comprise a mutation or deletion of the A52R gene, and can further comprise an exogenous nucleic acid that can code for ITAC (CXCL11), and an exogenous nucleic acid that can code for a fractalkine (CX3CL1).

In some examples, the co-expression of a cytokine (e.g., IL15) and its receptor (e.g., IL15-Ru), from the modified oncolytic virus, can, in some cases, lead to enhanced immunomodulatory effects of the oncolytic virus, for example, due to improved ability of a complex formed by IL15 and IL15-Rα (IL15:IL15-R complex) to activate natural killer cells and promote T cell response. Without being bound by any specific theory, it is contemplated that the IL15 in the IL15:IL15-Rα complex can be presented to the IL15-Roy (IL15-receptor beta gamma complex) displayed on the surface of T cells and natural killer (NK) cells, thereby imparting potent immunomodulatory effects on the NK cells and the T cells.

In certain embodiments are provided modified oncolytic viruses wherein the A52R gene can be mutated or deleted, and further, wherein the modified oncolytic viruses can comprise an exogenous nucleic acid that can code for a secreted hyaluronidase, such as HysA. In certain embodiments are provided modified oncolytic viruses wherein the A52R gene can be mutated or deleted, and further, wherein the modified oncolytic viruses can comprise an exogenous nucleic acid that can code for a chemokine receptor, such as CXCR4. In certain embodiments are provided modified oncolytic viruses wherein the A52R gene can be mutated or deleted, and further, wherein the modified oncolytic viruses can comprise an exogenous nucleic acid that can code for a chemokine receptor, such as CXCR4, and an exogenous nucleic acid that can code for a secreted hyaluronidase, such as HysA.

In certain embodiments are provided modified oncolytic viruses wherein the A52R gene can be mutated or deleted, and further, wherein the modified oncolytic viruses can comprise an exogenous nucleic acid that can code for a membrane associated hyaluronidase, such as PH-20 (also known as SPAM-1). In certain embodiments are provided modified oncolytic viruses wherein the A52R gene can be mutated or deleted, and further, wherein the modified oncolytic viruses can comprise an exogenous nucleic acid that can code for a chemokine receptor, such as CXCR4. In certain embodiments are provided modified oncolytic viruses wherein the A52R gene can be mutated or deleted, and further, wherein the modified oncolytic viruses can comprise an exogenous nucleic acid that can code for a chemokine receptor, such as CXCR4, and an exogenous nucleic acid that can code for a membrane associated hyaluronidase, such as PH-20 (or SPAM-1).

In certain embodiments, the modified oncolytic virus can comprise a complete or a partial deletion of the viral thymidine kinase (TK) gene. According to certain embodiments, in the genome of the modified oncolytic virus disclosed herein, one or more of the exogenous nucleic acids are inserted in the loci of the deleted TK gene. Exemplary nucleic acid sequences for the viral genes disclosed herein, and amino acid sequences for the proteins coded by said genes, are provided in Table 3.

In some embodiments, in the modified oncolytic virus, such as in an oncolytic vaccinia virus, the viral TK gene may be replaced with a TK gene from a herpes simplex virus (HSV-TK). The HSV TK may function as a substitute for the deleted TK and may have multifaceted advantages. For instance, (i) HSV TK can be used as an additional therapeutic prodrug converting enzyme for converting ganciclovir (GCV) into its cytotoxic metabolite in a tumor. In addition to the added therapeutic effect this modification can also serve as a suicide gene, e.g., vaccinia expressing cells can be killed efficiently through addition of GCV, thereby shutting down the virus in the case of an adverse event or uncontrolled replication. Thus, in some instances, the modified oncolytic virus of this disclosure can act as a safety switch). In additional examples, a mutated version of the HSV TK can be used to allow for PET imaging of labelled substrates with greatly increased sensitivity. Thus, in some cases, the modified oncolytic virus, comprising a HSV TK that can be used in PET imaging, can act as a reporter of viral replication in vivo to determine therapeutic activity early after treatment.

In some cases, the modified oncolytic virus can comprise a full-length viral backbone gene or viral backbone protein described above, or truncated versions thereof, or functional domains thereof, or fragments thereof, or variants thereof. In various examples, the modified oncolytic virus can comprise mutation or deletion of one or more of viral backbones genes or viral backbone proteins, as described above. Mutations of the viral backbone genes and viral backbone proteins can comprise insertion, deletion, substitution, or modifications of nucleotides in nucleic acid sequences and amino acids in protein sequences. Deletion can comprise, in some examples, a complete or partial deletion of the viral backbone gene or protein.

Cancer Targets

In an embodiment of this disclosure, a method of treatment for a hyperproliferative disease, such as a cancer or a tumor, by the delivery of a modified oncolytic virus, such as an oncolytic vaccinia virus as described herein, is contemplated. Cancers that can be treated by a modified oncolytic virus, as described herein, can include, but are not limited to, melanoma, hepatocellular carcinoma, breast cancer, lung cancer, peritoneal cancer, prostate cancer, bladder cancer, ovarian cancer, leukemia, lymphoma, renal carcinoma, pancreatic cancer, epithelial carcinoma, gastric cancer, colon carcinoma, duodenal cancer, pancreatic adenocarcinoma, mesothelioma, glioblastoma multiforme, astrocytoma, multiple myeloma, prostate carcinoma, hepatocellular carcinoma, cholangiosarcoma, pancreatic adenocarcinoma, head and neck squamous cell carcinoma, colorectal cancer, intestinal-type gastric adenocarcinoma, cervical squamous-cell carcinoma, osteosarcoma, epithelial ovarian carcinoma, acute lymphoblastic lymphoma, myeloproliferative neoplasms, and sarcoma.

Cancer cells that can be treated by the methods of this disclosure include cells from the bladder, blood, bone, bone marrow, brain, breast, colon, esophagus, gastrointestine, gum, head, kidney, liver, lung, nasopharynx, neck, ovary, prostate, skin, stomach, testis, tongue, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extramammary paraganglioma, malignant; pheochromocytoma; glomangiosarcoma; malignant melanoma; amelanotic melanoma; superficial spreading melanoma; malignant melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; Kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; Ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; hodgkin's disease; hodgkin's; paragranuloma; malignant lymphoma, small lymphocytic; malignant lymphoma, large cell, diffuse; malignant lymphoma, follicular; mycosis fungoides; other specified non-hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia. In some cases, solid cancers that are metastatic can be treated using the modified oncolytic viruses of this disclosure, such as a modified oncolytic vaccinia virus that is advantageous for systemic delivery. In some cases, solid cancers that are inaccessible or difficult to access, such as for purpose of intratumoral delivery of therapeutic agents, can be treated using the modified oncolytic viruses of this disclosure, such as a modified oncolytic vaccinia virus that is advantageous for systemic delivery. Cancers that are associated with increased expression of free fatty acids can, in some examples, be treated using the modified oncolytic viruses of this disclosure, such as a modified oncolytic vaccinia virus that is advantageous for systemic delivery and forms increased amounts of EEV.

This disclosure also contemplates methods for inhibiting or preventing local invasiveness or metastasis, or both, of any type of primary cancer. For example, the primary cancer can be melanoma, non-small cell lung, small-cell lung, lung, hepatocarcinoma, retinoblastoma, astrocytoma, glioblastoma, gum, tongue, leukemia, neuroblastoma, head, neck, breast, pancreatic, prostate, renal, bone, testicular, ovarian, mesothelioma, cervical, gastrointestinal, lymphoma, brain, colon, or bladder. In certain embodiments, the primary cancer can be lung cancer. For example, the lung cancer can be non-small cell lung carcinoma. Moreover, this disclosure can be used to prevent cancer or to treat pre-cancers or premalignant cells, including metaplasias, dysplasias, and hyperplasias. It can also be used to inhibit undesirable but benign cells, such as squamous metaplasia, dysplasia, benign prostate hyperplasia cells, hyperplastic lesions, and the like. In some embodiments, the progression to cancer or to a more severe form of cancer can be halted, disrupted, or delayed by methods of this disclosure involving the modified oncolytic virus as discussed herein.

Furthermore, the modified oncolytic virus as disclosed herein can be administered for treatment of tumors with high bioavailability of free fatty acids in the tumor microenvironment. In some instances, free fatty acids released by adipocytes in tumors in obese patients can feed and enhance the replication of the modified oncolytic virus within the tumor, and formation of EEV form of the virus. The advantage can also be realized in non-obese patients, especially patients who have peritoneal cancer. For example, several peritoneal cancers can be targets for therapy using the modified oncolytic viruses of this disclosure as these tend to grow in omentum wall and can be fed by adipocytes, and as mentioned above free fatty acids released by adipocytes in tumors can feed and enhance the replication of the modified oncolytic virus within the tumor. The modified oncolytic virus as disclosed herein can form an increased titer of extracellular enveloped virus (EEV) in tumors with high bioavailability of free fatty acids.

Methods of Treatment and Assaying the Efficacy and Pharmacokinetics

This disclosure provides methods for treating a subject by administration of one or more modified oncolytic viruses, as disclosed herein. An "individual" or "subject," as used interchangeably herein, refers to a human or a non-human subject. Non-limiting examples of non-human subjects include non-human primates, dogs, cats, mice, rats, guinea pigs, rabbits, pigs, fowl, horses, cows, goats, sheep, cetaceans, etc. In some embodiments, the subject is human.

Provided is a method of producing a toxic effect in a cancer cell comprising administering, to the cancer cell, a therapeutically effective amount of a modified virus, such as an oncolytic vaccinia virus, as described above, or a pharmaceutical composition containing the same. This disclosure further provides a method of inhibiting at least one of growth and proliferation of a second cancer cell comprising administering, to a first cancer cell, a modified oncolytic virus as described above such that the first cancer cell is infected with said virus. Thus, in some embodiments of the methods disclosed here, it is contemplated that not every cancer or tumor cell is infected upon administering a therapeutically effective amount of an oncolytic vaccinia virus, as described herein, or a pharmaceutical composition containing the same, and growth of non-infected cells can be inhibited without direct infection.

In some examples, to induce oncolysis, kill cells, inhibit growth, inhibit metastases, decrease tumor size and otherwise reverse or reduce the malignant phenotype of tumor cells, using the methods and compositions of the present disclosure, a cancer cell or a tumor can be contacted with a therapeutically effective dose of an exemplary oncolytic vaccinia virus as described herein or a pharmaceutical composition containing the same. In certain embodiments, an effective amount of a modified oncolytic virus of the present disclosure, such as an oncolytic vaccinia virus as described herein or a pharmaceutical composition thereof, can include an amount sufficient to induce oncolysis, the disruption or lysis of a cancer cell or the inhibition or reduction in the growth or size of a cancer cell. Reducing the growth of a cancer cell may be manifested, for example, by cell death or a slower replication rate or reduced growth rate of a tumor comprising the cell or a prolonged survival of a subject containing the cancer cell.

Provided, in some embodiments, is a method of treating a subject having a cancer or a tumor comprising administering, to the subject, an effective amount of a modified virus, as described above. An effective amount in such method can include an amount that reduces growth rate or spread of the cancer or that prolongs survival in the subject. This disclosure provides a method of reducing the growth of a tumor, which method can comprise administering, to the tumor, an effective amount of a modified oncolytic virus as described above. In certain embodiments, an effective amount of a modified virus, or a pharmaceutical composition thereof, can include an amount sufficient to induce the slowing, inhibition or reduction in the growth or size of a tumor and can include the eradication of the tumor. Reducing the growth of a tumor may be manifested, for example, by reduced growth rate or a prolonged survival of a subject containing the tumor.

This disclosure also provides a method of determining the infectivity or anti-tumor activity, or amount of tumor specific viral replication of an oncolytic vaccinia virus as described herein, which method can comprise; (i) administering to a subject a therapeutically effective amount of an oncolytic vaccinia virus or a pharmaceutical composition according to the present disclosure, which further expresses a luciferase reporter gene, alone or in combination with a further therapy; (ii) collecting a first biological sample from the subject immediately after administering the virus and determining the level of the luciferase reporter in the first biological sample (iii) collecting a second biological sample from the subject following the administration in step (ii) and (iii) detecting the level of the luciferase reporter in the second biological sample, wherein the oncolytic vaccinia virus is determined to be infective, demonstrate anti-tumor activity, exhibit tumor specific viral replication if the level of luciferase is higher in step (iii) than in step (ii). The second biological sample is collected about 30 mins, about 1 hour, about 2 hours, about 3 hours, about 4 hours, about 5 hours, about 6 hours, about 7 hours, about 8 hours, about 9 hours, about 10 hours, about 12 hours, about 15 hours, about 24 hours, about 36 hours, about 48 hours, about 72 hours, about 4 days, about 5 days, about 6 days, about 7 days, about 8 days, about 9 days, about 10 days, about 11 days, about 12 days, about 13 days, about 14 days, about 15 days, about 1 month, to about 2 months after the administration in step (i).

In some embodiments, the method of mentioned above can further comprise, detecting in steps (i) and (iii), the level of one or more assaying cytokine levels, e.g., IL-2, IL-7, IL-8, IL-10, IFN-γ, GM-CSF, TNF-α, IL-6, IL-4, IL-5, and IL-13, in plasma samples collected from a subject after administering to said subject a therapeutically effective amount of a modified oncolytic virus of the present disclosure, such as an oncolytic vaccinia virus as described herein or a pharmaceutical composition comprising the same. In some embodiments of this disclosure, the increase in luciferase bioluminescence between steps (ii) and (iv) mentioned above is higher for a modified oncolytic virus as described herein, compared to that in an otherwise identical virus that does not comprise the modifications in the modified oncolytic virus. Other exemplary techniques for detecting and monitoring viral load after administration of the modified oncolytic viruses include real-time quantitative PCR.

Further provided is a method of monitoring the pharmacokinetics following administration of a therapeutically effective amount of modified oncolytic viruses according to the present disclosure, such as oncolytic vaccinia virus or a pharmaceutical composition containing the vaccinia virus, as described herein. An exemplary method for monitoring the pharmacokinetics can comprise the following steps: (i) administering to the subject a therapeutically effective amount of an oncolytic vaccinia virus or a pharmaceutical composition comprising the same, alone or in combination with a further therapy; (ii) collecting biological samples from the subject at one or more time points selected from about 15 minutes, about 30 minutes, about 45 mins, about 60 mins, about 75 mins, about 90 mins, about 120 mins, about 180 mins, and about 240 mins, about 5 hours, about 6 hours, about 7 hours, about 8 hours, about 9 hours, about 10 hours, about 12 hours, about 15 hours, about 24 hours, about 36 hours, about 48 hours, about 72 hours, about 4 days, about 5 days, about 6 days, about 7 days, about 8 days, about 9 days, about 10 days, about 11 days, about 12 days, about 13 days, about 14 days, about 15 days, about 1 month, to about 2 months after the administration in step (i) and (iii) detecting the quantity of the viral genome (or a reporter gene inserted within the viral genome, such as luciferase) in the biological samples collected at the above mentioned time points. In some instances, viral genome copies/mL can be highest in the sample collected at the 15 mins time point and further the sample collected at the 240 mins time point may not contain a detectable quantity of the viral genome. Therefore, in some instances, a viral peak can be observed at about 15 mins following administration and majority of the viruses can be cleared from the subject's system after about 240 mins (or 4 hours). In some instances, a first viral peak can be observed after about 15 mins following administration and a second viral peak can be observed in the biological samples collected in the subsequent time points, e.g., at about 30 mins, about 45 mins, about 60 mins, or about 90 mins. The biological sample can be, in exemplar embodiments, blood, and the quantity of viral genome/mL can be determined by quantitative PCR or other appropriate techniques. In some examples, a first viral peak can be observed after about 15 mins following administration and a second viral peak can be observed after about 30 mins, about 1 hour, about 2 hours, about 3 hours, about 4 hours, about 5 hours, about 6 hours, about 7 hours, about 8 hours, about 9 hours, about 10 hours, about 12 hours, about 15 hours, about 24 hours, about 36 hours, about 48 hours, about 72 hours, about 4 days, about 5 days, about 6 days, about 7 days, about 8 days, about 9 days, about 10 days, about 11 days, about 12 days, about 13 days, about 14 days, about 15 days, about 1 month, to about 2 months following administration of a modified oncolytic virus of the present disclosure, such as an oncolytic vaccinia virus as described herein.

In some instances, tumor-selective replication of a modified virus, such as an oncolytic vaccinia virus can be measured through use of a reporter gene, such as a luciferase gene. In some embodiments, the luciferase gene can be inserted into the genome of a virus, and a tumor cell can be infected with the virus. Bioluminescence in infected tumor cells can be measured to monitor tumor-selective replication. Some examples show an increase in luciferase reporter bioluminescence in a modified oncolytic virus of this disclosure, compared to that in an otherwise identical oncolytic vaccinia virus that does not contain the modifications in the modified oncolytic virus.

Delivery of Modified Oncolytic Viruses

In some embodiments, amount of a modified oncolytic virus of this disclosure, such as an oncolytic vaccinia virus, administered to a subject can be between about $10^3$ and $10^{12}$ infectious viral particles or plaque forming units (PFU), or between about $10^5$ and $10^{10}$ PFU, or between about $10^5$ and $10^8$ PFU, or between about $10^8$ and $10^{10}$ PFU. In some embodiments, the amount of a modified oncolytic virus of this disclosure, such as an oncolytic vaccinia virus administered to a subject can be between about $10^3$ and $10^{12}$ viral particles or plaque forming units (PFU), or between about $10^5$ and $10^{10}$ PFU, or between about $10^5$ and $10^8$ PFU, or between about $10^8$ and $10^{10}$ PFU. In some embodiments, a modified oncolytic virus of this disclosure, such as an oncolytic vaccinia virus, can be administered at a dose that can comprise about $10^3$ PFU/dose to about $10^4$ PFU/dose, about $10^4$ PFU/dose to about $10^5$ PFU/dose, about $10^5$ PFU/dose to about $10^6$ PFU/dose, about $10^7$ PFU/dose to about $10^8$ PFU/dose, about $10^9$ PFU/dose to about $10^{10}$ PFU/dose, about $10^{10}$ PFU/dose to about $10^{11}$ PFU/dose, about $10^{11}$ PFU/dose to about $10^{12}$ PFU/dose, about $10^{12}$ PFU/dose to about $10^{13}$ PFU/dose, about $10^{13}$ PFU/dose to about $10^{14}$ PFU/dose, or about $10^{14}$ PFU/dose to about $10^{15}$ PFU/dose. In some embodiments, a modified oncolytic virus of this disclosure, such as an oncolytic vaccinia virus, can be administered at a dose that can comprise about $2\times10^3$ PFU/dose, $3\times10^3$ PFU/dose, $4\times10^3$ PFU/dose, $5\times10^3$ PFU/dose, $6\times10^3$ PFU/dose, $7\times10^3$ PFU/dose, $8\times10^3$ PFU/dose, $9\times10^3$ PFU/dose, about $10^4$ PFU/dose, about $2\times10^4$ PFU/dose, about $3\times10^4$ PFU/dose, about $4\times10^4$ PFU/dose, about $5\times10^4$ PFU/dose, about $6\times10^4$ PFU/dose, about $7\times10^4$ PFU/dose, about $8\times10^4$ PFU/dose, about $9\times10^4$ PFU/dose, about $10^5$ PFU/dose, $2\times10^5$ PFU/dose, $3\times10^5$ PFU/dose, $4\times10^5$ PFU/dose, $5\times10^5$ PFU/dose, $6\times10^5$ PFU/dose $7\times10^5$ PFU/dose, $8\times10^5$ PFU/dose, $9\times10^5$ PFU/dose, about $10^6$ PFU/dose, about $2\times10^6$ PFU/dose, about $3\times10^6$ PFU/dose, about $4\times10^6$ PFU/dose, about $5\times10^6$ PFU/dose, about $6\times10^6$ PFU/dose, about $7\times10^6$ PFU/dose, about $8\times10^6$ PFU/dose, about $9\times10^6$ PFU/dose about $10^7$ PFU/dose, about $2\times10^7$ PFU/dose, about $3\times10^7$ PFU/dose, about $4\times10^7$ PFU/dose, about $5\times10^7$ PFU/dose, about $6\times10^7$ PFU/dose, about $7\times10^7$ PFU/dose, about $8\times10^7$ PFU/dose, about $9\times10^7$ PFU/dose, about $10^8$ PFU/dose, about $2\times10^8$ PFU/dose, about $3\times10^8$ PFU/dose, about $4\times10^8$ PFU/dose, about $5\times10^8$ PFU/dose, about $6\times10^8$ PFU/dose, about $7\times10^8$ PFU/dose, about $8\times10^8$ PFU/dose, about $9\times10^8$ PFU/dose, about $10^9$ PFU/dose, about $2\times10^9$ PFU/dose, about $3\times10^9$ PFU/dose, about $4\times10^9$ PFU/dose, about $5\times10^9$ PFU/dose, about $6\times10^9$ PFU/dose, about $7\times10^9$ PFU/dose, about $8\times10^9$ PFU/dose, about $9\times10^9$ PFU/dose, about $10^{10}$ PFU/dose, about $2\times10^{10}$ PFU/dose, about $3\times10^{10}$ PFU/dose, about $4\times10^{10}$ PFU/dose, about $5\times10^{10}$ PFU/dose, about $6\times10^{10}$ PFU/dose, about $7\times10^{10}$ PFU/dose, about $8\times10^{10}$ PFU/dose, about $9\times10^{10}$ PFU/dose, about $10^{10}$ PFU/dose, about $2\times10^{10}$ PFU/dose, about $3\times10^{10}$ PFU/dose, about $4\times10^{10}$ PFU/dose, about $5\times10^{10}$ PFU/dose, about $6\times10^{10}$ PFU/dose, about $7\times10^{10}$ PFU/dose, about $8\times10^{10}$ PFU/dose, about $9\times10^{10}$ PFU/dose, about $10^{11}$ PFU/dose, about $2\times10^{11}$ PFU/dose, about $3\times10^{11}$ PFU/dose, about $4\times10^{11}$ PFU/dose, about $5\times10^{11}$ PFU/dose, about $6\times10^{11}$ PFU/dose, about $7\times10^{11}$ PFU/dose, about $8\times10^{11}$ PFU/dose, about $9\times10^{11}$ PFU/dose, or about $10^{12}$ PFU/dose, about $10^{12}$ PFU/dose to about $10^{13}$ PFU/dose, about $10^{13}$ PFU/dose to about $10^{14}$ PFU/dose, or about $10^{14}$ PFU/dose to about $10^{15}$ PFU/dose. In some embodiments, a modified oncolytic virus of this disclosure, such as an oncolytic vaccinia virus, can be administered at a dose that can comprise $5\times10^{9}$ PFU/dose. In some embodiments, a modified oncolytic virus of this disclosure, such as an oncolytic vaccinia virus, can be administered at a dose that can comprise up to $5\times10^{9}$ PFU/dose.

In some embodiments, a modified oncolytic virus of this disclosure, such as an oncolytic vaccinia virus, can be administered at a dose that can comprise about $10^{3}$ viral particles/dose to about $10^{4}$ viral particles/dose, about $10^{4}$ viral particles/dose to about $10^{5}$ viral particles/dose, about $10^{5}$ viral particles/dose to about $10^{6}$ viral particles/dose, about $10^{7}$ viral particles/dose to about $10^{8}$ viral particles/dose, about $10^{9}$ viral particles/dose to about $10^{10}$ viral particles/dose, about $10^{10}$ viral particles/dose to about $10^{11}$ viral particles/dose, about $10^{11}$ viral particles/dose to about $10^{12}$ viral particles/dose, about $10^{12}$ viral particles/dose to about $10^{13}$ viral particles/dose, about $10^{13}$ viral particles/dose to about $10^{14}$ viral particles/dose, or about $10^{14}$ viral particles/dose to about $10^{15}$ viral particles/dose.

In some embodiments, a modified oncolytic virus of this disclosure can be administered at a dose that can comprise about $10^{3}$ PFU/kg to about $10^{4}$ PFU/kg, about $10^{4}$ PFU/kg to about $10^{5}$ PFU/kg, about $10^{5}$ PFU/kg to about $10^{6}$ PFU/kg, about $10^{7}$ PFU/kg to about $10^{8}$ PFU/kg, about $10^{9}$ PFU/kg to about $10^{10}$ PFU/kg, about $10^{10}$ PFU/kg to about $10^{11}$ PFU/kg, about $10^{11}$ PFU/kg to about $10^{12}$ PFU/kg, about $10^{12}$ PFU/kg to about $10^{13}$ PFU/kg, about $10^{13}$ PFU/kg to about $10^{14}$ PFU/kg, or about $10^{14}$ PFU/kg to about $10^{15}$ PFU/kg. In some embodiments, a modified oncolytic virus of this disclosure, such as an oncolytic vaccinia virus, can be administered at a dose that can comprise about $2\times10^{3}$ PFU/kg, $3\times10^{3}$ PFU/kg, $4\times10^{3}$ PFU/kg, $5\times10^{3}$ PFU/kg, $6\times10^{3}$ PFU/kg, $7\times10^{3}$ PFU/kg, $8\times10^{3}$ PFU/kg, $9\times10^{3}$ PFU/kg, about $10^{4}$ PFU/kg, about $2\times10^{4}$ PFU/kg, about $3\times10^{4}$ PFU/kg, about $4\times10^{4}$ PFU/kg, about $5\times10^{4}$ PFU/kg, about $6\times10^{4}$ PFU/kg, about $7\times10^{4}$ PFU/kg, about $8\times10^{4}$ PFU/kg, about $9\times10^{4}$ PFU/kg, about $10^{5}$ PFU/kg, $2\times10^{5}$ PFU/kg, $3\times10^{5}$ PFU/kg, $4\times10^{5}$ PFU/kg, $5\times10^{5}$ PFU/kg, $6\times10^{5}$ PFU/kg, $7\times10^{5}$ PFU/kg, $8\times10^{5}$ PFU/kg, $9\times10^{5}$ PFU/kg, about $10^{6}$ PFU/kg, about $2\times10^{6}$ PFU/kg, about $3\times10^{6}$ PFU/kg, about $4\times10^{6}$ PFU/kg, about $5\times10^{6}$ PFU/kg, about $6\times10^{6}$ PFU/kg, about $7\times10^{6}$ PFU/kg, about $8\times10^{6}$ PFU/kg, about $9\times10^{6}$ PFU/kg, about $10^{7}$ PFU/kg, about $2\times10^{7}$ PFU/kg, about $3\times10^{7}$ PFU/kg, about $4\times10^{7}$ PFU/kg, about $5\times10^{7}$ PFU/kg, about $6\times10^{7}$ PFU/kg, about $7\times10^{7}$ PFU/kg, about $8\times10^{7}$ PFU/kg, about $9\times10^{7}$ PFU/kg, about $10^{8}$ PFU/kg, about $2\times10^{8}$ PFU/kg, about $3\times10^{8}$ PFU/kg, about $4\times10^{8}$ PFU/kg, about $5\times10^{8}$ PFU/kg, about $6\times10^{8}$ PFU/kg, about $7\times10^{8}$ PFU/kg, about $8\times10^{8}$ PFU/kg, about $9\times10^{8}$ PFU/kg, about $10^{9}$ PFU/kg, about $2\times10^{9}$ PFU/kg, about $3\times10^{9}$ PFU/kg, about $4\times10^{9}$ PFU/kg, about $5\times10^{9}$ PFU/kg, about $6\times10^{9}$ PFU/kg, about $7\times10^{9}$ PFU/kg, about $8\times10^{9}$ PFU/kg, about $9\times10^{9}$ PFU/kg, about $10^{10}$ PFU/kg, about $2\times10^{10}$ PFU/kg, about $3\times10^{10}$ PFU/kg, about $4\times10^{10}$ PFU/kg, about $5\times10^{10}$ PFU/kg, about $6\times10^{10}$ PFU/kg, about $7\times10^{10}$ PFU/kg, about $8\times10^{10}$ PFU/kg, about $9\times10^{10}$ PFU/kg, about $10^{10}$ PFU/kg, about $2\times10^{10}$ PFU/kg, about $3\times10^{10}$ PFU/kg, about $4\times10^{10}$ PFU/kg, about $5\times10^{10}$ PFU/kg, about $6\times10^{10}$ PFU/kg, about $7\times10^{10}$ PFU/kg, about $8\times10^{10}$ PFU/kg, about $9\times10^{10}$ PFU/kg, about $10^{11}$ PFU/kg, about $2\times10^{11}$ PFU/kg, about $3\times10^{11}$ PFU/kg, about $4\times10^{11}$ PFU/kg, about $5\times10^{11}$ PFU/kg, about $6\times10^{11}$ PFU/kg, about $7\times10^{11}$ PFU/kg, about $8\times10^{11}$ PFU/kg, about $9\times10^{11}$ PFU/kg, or about $10^{12}$ PFU/kg, about $10^{12}$ PFU/kg to about $10^{13}$ PFU/kg, about $10^{13}$ PFU/kg to about $10^{14}$ PFU/kg, or about $10^{14}$ PFU/kg to about $10^{15}$ PFU/kg. In some embodiments, a modified oncolytic virus of this disclosure, such as an oncolytic vaccinia virus, can be administered at a dose that can comprise $5\times10^{9}$ PFU/kg. In some embodiments, a modified oncolytic virus of this disclosure, such as an oncolytic vaccinia virus, can be administered at a dose that can comprise up to $5\times10^{9}$ PFU/kg.

In some embodiments, a modified oncolytic virus of this disclosure can be administered at a dose that can comprise about $10^{3}$ viral particles/kg to about $10^{4}$ viral particles/kg, about $10^{4}$ viral particles/kg to about $10^{5}$ viral particles/kg, about $10^{5}$ viral particles/kg to about $10^{6}$ viral particles/kg, about $10^{7}$ viral particles/kg to about $10^{8}$ viral particles/kg, about $10^{9}$ viral particles/kg to about $10^{10}$ viral particles/kg, about $10^{10}$ viral particles/kg to about $10^{11}$ viral particles/kg, about $10^{11}$ viral particles/kg to about $10^{12}$ viral particles/kg, about $10^{12}$ viral particles/kg to about $10^{13}$ viral particles/kg, about $10^{13}$ viral particles/kg to about $10^{14}$ viral particles/kg, or about $10^{14}$ viral particles/kg to about $10^{15}$ viral particles/kg.

A liquid dosage form of an oncolytic vaccinia virus as described herein can comprise, in certain embodiments, a viral dose of about $10^{3}$ PFU/mL to about $10^{4}$ PFU/mL, about $10^{4}$ PFU/mL to about $10^{5}$ PFU/mL, about $10^{5}$ PFU/mL to about $10^{6}$ PFU/mL, about $10^{7}$ PFU/mL to about $10^{8}$ PFU/mL, about $10^{9}$ PFU/mL to about $10^{10}$ PFU/mL, about $10^{10}$ PFU/mL to about $10^{11}$ PFU/mL, about $10^{11}$ PFU/mL to about $10^{12}$ PFU/mL, about $10^{12}$ PFU/mL to about $10^{13}$ PFU/mL, about $10^{13}$ PFU/mL to about $10^{14}$ PFU/mL, or about $10^{14}$ PFU/mL to about $10^{15}$ PFU/mL. In some embodiments, a modified oncolytic virus of this disclosure, such as an oncolytic vaccinia virus, can be administered at a dose that can comprise about $2\times10^{3}$ PFU/mL, $3\times10^{3}$ PFU/mL, $4\times10^{3}$ PFU/mL, $5\times10^{3}$ PFU/mL, $6\times10^{3}$ PFU/mL, $7\times10^{3}$ PFU/mL, $8\times10^{3}$ PFU/mL, $9\times10^{3}$ PFU/mL, about $10^{4}$ PFU/mL, about $2\times10^{4}$ PFU/mL, about $3\times10^{4}$ PFU/mL, about $4\times10^{4}$ PFU/mL, about $5\times10^{4}$ PFU/mL, about $6\times10^{4}$ PFU/mL, about $7\times10^{4}$ PFU/mL, about $8\times10^{4}$ PFU/mL, about $9\times10^{4}$ PFU/mL, about $10^{5}$ PFU/mL, $2\times10^{5}$ PFU/mL, $3\times10^{5}$ PFU/mL, $4\times10^{5}$ PFU/mL, $5\times10^{5}$ PFU/mL, $6\times10^{5}$ PFU/mL, $7\times10^{5}$ PFU/mL, $8\times10^{5}$ PFU/mL, $9\times10^{5}$ PFU/mL, about $10^{6}$ PFU/mL, about $2\times10^{6}$ PFU/mL, about $3\times10^{6}$ PFU/mL, about $4\times10^{6}$ PFU/mL, about $5\times10^{6}$ PFU/mL, about $6\times10^{6}$ PFU/mL, about $7\times10^{6}$ PFU/mL, about $8\times10^{6}$ PFU/mL, about $9\times10^{6}$ PFU/mL, about $10^{7}$ PFU/mL, about $2\times10^{7}$ PFU/mL, about $3\times10^{7}$ PFU/mL, about $4\times10^{7}$ PFU/mL, about $5\times10^{7}$ PFU/mL, about $6\times10^{7}$ PFU/mL, about $7\times10^{7}$ PFU/mL, about $8\times10^{7}$ PFU/mL, about $9\times10^{7}$ PFU/mL, about $10^{8}$ PFU/mL, about $2\times10^{8}$ PFU/mL, about $3\times10^{8}$ PFU/mL, about $4\times10^{8}$ PFU/mL, about $5\times10^{8}$ PFU/mL, about $6\times10^{8}$ PFU/mL, about $7\times10^{8}$ PFU/mL, about $8\times10^{8}$ PFU/mL, about $9\times10^{8}$ PFU/mL, about $10^{9}$ PFU/mL, about $2\times10^{9}$ PFU/mL, about $3\times10^{9}$ PFU/mL, about $4\times10^{9}$ PFU/mL, about $5\times10^{9}$ PFU/mL, about $6\times10^{9}$ PFU/mL, about $7\times10^{9}$ PFU/mL, about $8\times10^{9}$ PFU/mL, about $9\times10^{9}$ PFU/mL, about $10^{10}$ PFU/mL, about $2\times10^{10}$ PFU/mL, about $3\times10^{10}$ PFU/mL, about $4\times10^{10}$ PFU/mL, about $5\times10^{10}$ PFU/mL, about $6\times10^{10}$ PFU/mL, about $7\times10^{10}$ PFU/mL, about $8\times10^{10}$ PFU/mL, about $9\times10^{10}$ PFU/mL, about $10^{10}$ PFU/mL, about $2\times10^{10}$ PFU/mL, about $3\times10^{10}$ PFU/mL, about $4\times10^{10}$ PFU/mL, about $5\times10^{10}$ PFU/mL, about $6\times10^{10}$ PFU/mL, about $7\times10^{10}$ PFU/mL, about $8\times10^{10}$ PFU/mL, about $9\times10^{10}$ PFU/mL, about $10^{11}$ PFU/mL, about $2\times10^{11}$ PFU/mL, about $3\times10^{11}$ PFU/mL, about $4\times10^{11}$ PFU/mL, about $5\times10^{11}$ PFU/mL, about $6\times10^{11}$ PFU/mL, about $7\times10^{11}$ PFU/mL, about $8\times10^{11}$ PFU/mL, about $9\times10^{11}$ PFU/mL, or about $10^{12}$ PFU/mL, about $10^{12}$ PFU/mL to about $10^{13}$ PFU/mL, about $10^{13}$ PFU/mL to about $10^{14}$ PFU/mL, or about $10^{14}$ PFU/mL to about $10^{15}$ PFU/mL. In some embodiments, a modified oncolytic virus of this disclosure, such as an oncolytic vaccinia virus, can be administered at a dose that can comprise $5\times10^{9}$ PFU/mL. In some embodiments, a modified oncolytic virus of this disclosure, such as an oncolytic vaccinia virus, can be administered at a dose that can comprise up to $5\times10^{9}$ PFU/mL.

In some instances, where the modified oncolytic virus is administered by an injection, the dosage can comprise about $10^{3}$ viral particles per injection, $10^{4}$ viral particles per injection, $10^{5}$ viral particles per injection, $10^{6}$ viral particles per injection, $10^{7}$ viral particles per injection, $10^{8}$ viral particles per injection, $10^{9}$ viral particles per injection, $10^{10}$ viral particles per injection, $10^{11}$ viral particles per injection, $10^{12}$ viral particles per injection, $2\times10^{12}$ viral particles per injection, $10^{13}$ viral particles per injection, $10^{14}$ viral particles per injection, or $10^{15}$ viral particles per injection. In further instances, where the modified oncolytic virus is administered by an injection, the dosage can comprise about $10^{3}$ infectious viral particles per injection, $10^{4}$ infectious viral particles per injection, $10^{5}$ infectious viral particles per injection, $10^{6}$ infectious viral particles per injection, $10^{7}$ infectious viral particles per injection, $10^{8}$ infectious viral particles per injection, $10^{9}$ infectious viral particles per injection, $10^{10}$ infectious viral particles per injection, $10^{11}$ infectious viral particles per injection, $10^{12}$ infectious viral particles per injection, $2\times10^{12}$ infectious viral particles per injection, $10^{13}$ infectious viral particles per injection, $10^{14}$ infectious viral particles per injection, or $10^{15}$ infectious viral particles per injection. In additional embodiments, a modified oncolytic virus of this disclosure can be administered at a dose that can be about $10^{3}$ Tissue Culture Inhibitor Dose 50% ($TCID_{50}$)/kg, $10^{4}$ $TCID_{50}$/kg, $10^{4}$ $TCID_{50}$/kg, $10^{4}$ $TCID_{50}$/kg, $10^{4}$ $TCID_{50}$/kg, $10^{4}$ $TCID_{50}$/kg, $10^{4}$ $TCID_{50}$/kg, $10^{4}$ $TCID_{50}$/kg, $10^{4}$ $TCID_{50}$/kg, $10^{4}$ $TCID_{50}$/kg, $10^{4}$ $TCID_{50}$/kg, $10^{4}$ $TCID_{50}$/kg, $10^{4}$ $TCID_{50}$/kg, $3\times10^{8}$ $TCID_{50}$/kg, $4\times10^{8}$ $TCID_{50}$/kg, $5\times10^{8}$ $TCID_{50}$/kg, $3\times10^{9}$ $TCID_{50}$/kg, $4\times10^{9}$ $TCID_{50}$/kg, $5\times10^{9}$ $TCID_{50}$/kg, $3\times10^{10}$ $TCID_{50}$/kg, $4\times10^{10}$ $TCID_{50}$/kg, or $4\times10^{10}$ $TCID_{50}$/kg. Note that herein $10^{x}$ is alternatively expressed as 1 eX.

In certain embodiments, the modified oncolytic virus can be administered in one or more doses. In certain embodiments, the virus can be administered in an amount sufficient to induce oncolysis in at least about 20% of cells in a tumor, in at least about 30% of cells in a tumor, in at least about 40% of cells in a tumor, in at least about 50% of cells in a tumor, in at least about 60% of cells in a tumor, in at least about 70% of cells in a tumor, in at least about 80% of cells in a tumor, or in at least about 90% of cells in a tumor. In certain embodiments, a single dose of virus can refer to the amount administered to a subject or a tumor over a 1, 2, 5, 10, 15, 20 or 24 hour period. In certain embodiments, the dose can be spread over time or by separate injection. In certain embodiments, multiple doses (e.g., 2, 3, 4, 5, 6 or more doses) of the vaccinia virus can be administered to the subject, for example, where a second treatment can occur within 1, 2, 3, 4, 5, 6, 7 days or weeks of a first treatment. In certain embodiments, multiple doses of the modified oncolytic virus can be administered to the subject over a period of 1, 2, 3, 4, 5, 6, 7 or more days or weeks. In certain embodiments, the oncolytic vaccinia virus or the pharmaceutical composition as described herein can be administered over a period of about 1 week to about 2 weeks, about 2 weeks to about 3 weeks, about 3 weeks to about 4 weeks, about 4 weeks to about 5 weeks, about 6 weeks to about 7 weeks, about 7 weeks to about 8 weeks, about 8 weeks to about 9 weeks, about 9 weeks to about 10 weeks, about 10 weeks to about 11 weeks, about 11 weeks to about 12 weeks, about 12 weeks to about 24 weeks, about 24 weeks to about 48 weeks, about 48 weeks or about 52 weeks, or longer. The frequency of administration of the oncolytic vaccinia virus or the pharmaceutical composition as described herein can be, in certain instances, once daily, twice daily, once every week, once every three weeks, once every four weeks (or once a month), once every 8 weeks (or once every 2 months), once every 12 weeks (or once every 3 months), or once every 24 weeks (once every 6 months). In some embodiments of the methods disclosed herein, the oncolytic vaccinia virus or the pharmaceutical composition can be administered, independently, in an initial dose for a first period of time, an intermediate dose for a second period of time, and a high dose for a third period of time. In some embodiments, the initial dose is lower than the intermediate dose and the intermediate dose is lower than the high dose. In some embodiments, the first, second, and third periods of time are, independently, about 1 week to about 2 weeks, about 2 weeks to about 3 weeks, about 3 weeks to about 4 weeks, about 4 weeks to about 5 weeks, about 6 weeks to about 7 weeks, about 7 weeks to about 8 weeks, about 8 weeks to about 9 weeks, about 9 weeks to about 10 weeks, about 10 weeks to about 11 weeks, about 11 weeks to about 12 weeks, about 12 weeks to about 24 weeks, about 24 weeks to about 48 weeks, about 48 weeks or about 52 weeks, or longer.

In some examples, the subject can be put on a reduced carbohydrate diet, e.g., a ketogenic diet prior to, concurrent with, and following administration of the modified oncolytic viruses, such as the oncolytic vaccinia viruses or the pharmaceutical composition comprising the same, as described herein, according to any of the methods of treatment described herein. In certain embodiments, the subject is put on a diet that can comprise consuming less than 500 grams of carbohydrates per day, less than 450 grams of carbohydrates per day, less than 450 grams of carbohydrates per day, less than 400 grams of carbohydrates per day, less than 350 grams of carbohydrates per day, less than 300 grams of carbohydrates per day, less than 250 grams of carbohydrates per day, less than 200 grams of carbohydrates per day, less than 150 grams of carbohydrates per day, less than 100 grams of carbohydrates per day, less than 90 grams of carbohydrates per day, less than 80 grams of carbohydrates per day, less than 70 grams of carbohydrates per day, less than 60 grams of carbohydrates per day, less than 50 grams of carbohydrates per day, less than 40 grams of carbohydrates per day, less than 30 grams of carbohydrates per day, less than 20 grams of carbohydrates per day, less or than 10 grams of carbohydrates per day.

An exemplary method for the delivery of a modified oncolytic virus of the present disclosure, such as an oncolytic vaccinia virus as described herein or a pharmaceutical composition comprising the same, to cancer or tumor cells can be via intratumoral injection. However, alternate methods of administration can also be used, e.g., intravenous, via infusion, parenteral, intravenous, intradermal, intramuscular, transdermal, rectal, intraurethral, intravaginal, intranasal, intrathecal, or intraperitoneal. The routes of administration can vary with the location and nature of the tumor. In certain embodiments, the route of administration can be intradental, transdermal, parenteral, intravenous, intramuscular, intranasal, subcutaneous, regional (e.g., in the proximity of a tumor, particularly with the vasculature or adjacent vasculature of a tumor), percutaneous, intrathecal, intratracheal, intraperitoneal, intraarterial, intravesical, intratumoral, inhalation, perfusion, by lavage or orally. An injectable dose of the oncolytic virus can be administered as a bolus injection or as a slow infusion. In certain embodiments, the modified oncolytic virus can be administered to the patient from a source implanted in the patient. In certain embodiments, administration of the modified oncolytic virus can occur by continuous infusion over a selected period of time. In some instances, an oncolytic vaccinia virus as described herein, or a pharmaceutical composition containing the same can be administered at a therapeutically effective dose by infusion over a period of about 15 mins, about 30 mins, about 45 mins, about 50 mins, about 55 mins, about 60 minutes, about 75 mins, about 90 mins, about 100 mins, or about 120 mins or longer. The oncolytic vaccinia virus or the pharmaceutical composition of the present disclosure can be administered as a liquid dosage, wherein the total volume of administration is about 1 mL to about 5 mL, about 5 mL to 10 mL, about 15 mL to about 20 mL, about 25 mL to about 30 mL, about 30 mL to about 50 mL, about 50 mL to about 100 mL, about 100 mL to 150 mL, about 150 mL to about 200 mL, about 200 mL to about 250 mL, about 250 mL to about 300 mL, about 300 mL to about 350 mL, about 350 mL to about 400 mL, about 400 mL to about 450 mL, about 450 mL to 500 mL, about 500 mL to 750 mL, or about 750 mL to 1000 mL.

Pharmaceutical Compositions

Pharmaceutical compositions containing a modified virus, such as an oncolytic vaccinia virus, as described herein, can be prepared as solutions, dispersions in glycerol, liquid polyethylene glycols, and any combinations thereof in oils, in solid dosage forms, as inhalable dosage forms, as intranasal dosage forms, as liposomal formulations, dosage forms comprising nanoparticles, dosage forms comprising microparticles, polymeric dosage forms, or any combinations thereof. In some embodiments, a pharmaceutical composition as described herein can comprise a stabilizer and a buffer. In some embodiments, a pharmaceutical composition as described herein can comprise a solubilizer, such as sterile water, Tris-buffer. In some embodiments, a pharmaceutical composition as described herein can comprise an excipient. An excipient can be an excipient described in the Handbook of Pharmaceutical Excipients, American Pharmaceutical Association (1986). Non-limiting examples of suitable excipients can include a buffering agent, a preservative, a stabilizer, a binder, a compaction agent, a lubricant, a chelator, a dispersion enhancer, a disintegration agent, a flavoring agent, a sweetener, a coloring agent.

In some embodiments an excipient can be a buffering agent. Non-limiting examples of suitable buffering agents can include sodium citrate, magnesium carbonate, magnesium bicarbonate, calcium carbonate, and calcium bicarbonate. As a buffering agent, sodium bicarbonate, potassium bicarbonate, magnesium hydroxide, magnesium lactate, magnesium gluconate, aluminum hydroxide, sodium citrate, sodium tartrate, sodium acetate, sodium carbonate, sodium polyphosphate, potassium polyphosphate, sodium pyrophosphate, potassium pyrophosphate, disodium hydrogen phosphate, dipotassium hydrogen phosphate, trisodium phosphate, tripotassium phosphate, potassium metaphosphate, magnesium oxide, magnesium hydroxide, magnesium carbonate, magnesium silicate, calcium acetate, calcium glycerophosphate, calcium chloride, calcium hydroxide and other calcium salts or combinations thereof can be used in a pharmaceutical formulation.

In some embodiments an excipient can comprise a preservative. Non-limiting examples of suitable preservatives can include antioxidants, such as alpha-tocopherol and ascorbate, and antimicrobials, such as parabens, chlorobutanol, and phenol. Antioxidants can further include but not limited to EDTA, citric acid, ascorbic acid, butylated hydroxytoluene (BHT), butylated hydroxy anisole (BHA), sodium sulfite, p-amino benzoic acid, glutathione, propyl gallate, cysteine, methionine, ethanol and N-acetyl cysteine. In some instances a preservatives can include validamycin A, TL-3, sodium ortho vanadate, sodium fluoride, N-a-tosyl-Phe-chloromethylketone, N-a-tosyl-Lys-chloromethylketone, aprotinin, phenylmethylsulfonyl fluoride, diisopropylfluorophosphate, kinase inhibitor, phosphatase inhibitor, caspase inhibitor, granzyme inhibitor, cell adhesion inhibitor, cell division inhibitor, cell cycle inhibitor, lipid signaling inhibitor, protease inhibitor, reducing agent, alkylating agent, antimicrobial agent, oxidase inhibitor, or other inhibitor.

In some embodiments a pharmaceutical composition as described herein can comprise a binder as an excipient. Non-limiting examples of suitable binders can include starches, pregelatinized starches, gelatin, polyvinylpyrolidone, cellulose, methylcellulose, sodium carboxymethylcellulose, ethylcellulose, polyacrylamides, polyvinyloxoazolidone, polyvinylalcohols, $C_{12}$-$C_{18}$ fatty acid alcohol, polyethylene glycol, polyols, saccharides, oligosaccharides, and combinations thereof. The binders that can be used in a pharmaceutical formulation can be selected from starches such as potato starch, corn starch, wheat starch; sugars such as sucrose, glucose, dextrose, lactose, maltodextrin; natural and synthetic gums; gelatine; cellulose derivatives such as microcrystalline cellulose, hydroxypropyl cellulose, hydroxyethyl cellulose, hydroxypropyl methyl cellulose, carboxymethyl cellulose, methyl cellulose, ethyl cellulose; polyvinylpyrrolidone (povidone); polyethylene glycol (PEG); waxes; calcium carbonate; calcium phosphate; alcohols such as sorbitol, xylitol, mannitol and water or a combination thereof.

In some embodiments a pharmaceutical composition as described herein can comprise a lubricant as an excipient. Non-limiting examples of suitable lubricants can include magnesium stearate, calcium stearate, zinc stearate, hydrogenated vegetable oils, sterotex, polyoxyethylene monostearate, talc, polyethyleneglycol, sodium benzoate, sodium lauryl sulfate, magnesium lauryl sulfate, and light mineral oil. The lubricants that can be used in a pharmaceutical formulation can be selected from metallic stearates (such as magnesium stearate, calcium stearate, aluminum stearate), fatty acid esters (such as sodium stearyl fumarate), fatty acids (such as stearic acid), fatty alcohols, glyceryl behenate, mineral oil, paraffins, hydrogenated vegetable oils, leucine, polyethylene glycols (PEG), metallic lauryl sulphates (such as sodium lauryl sulphate, magnesium lauryl sulphate), sodium chloride, sodium benzoate, sodium acetate and talc or a combination thereof.

In some embodiments a pharmaceutical formulation can comprise a dispersion enhancer as an excipient. Non-limiting examples of suitable dispersants can include starch, alginic acid, polyvinylpyrrolidones, guar gum, kaolin, bentonite, purified wood cellulose, sodium starch glycolate, isoamorphous silicate, and microcrystalline cellulose as high HLB emulsifier surfactants.

In some embodiments a pharmaceutical composition as described herein can comprise a disintegrant as an excipient. In some embodiments a disintegrant can be a non-effervescent disintegrant. Non-limiting examples of suitable non-effervescent disintegrants can include starches such as corn starch, potato starch, pregelatinized and modified starches thereof, sweeteners, clays, such as bentonite, micro-crystalline cellulose, alginates, sodium starch glycolate, gums such as agar, guar, locust bean, karaya, pectin, and tragacanth. In some embodiments a disintegrant can be an effervescent disintegrant. Non-limiting examples of suitable effervescent disintegrants can include sodium bicarbonate in combination with citric acid, and sodium bicarbonate in combination with tartaric acid.

In some embodiments an excipient can comprise a flavoring agent. Flavoring agents incorporated into an outer layer can be chosen from synthetic flavor oils and flavoring aromatics; natural oils; extracts from plants, leaves, flowers, and fruits; and combinations thereof. In some embodiments a flavoring agent can be selected from the group consisting of cinnamon oils; oil of wintergreen; peppermint oils; clover oil; hay oil; anise oil; eucalyptus; vanilla; citrus oil such as lemon oil, orange oil, grape and grapefruit oil; and fruit essences including apple, peach, pear, strawberry, raspberry, cherry, plum, pineapple, and apricot.

In some embodiments an excipient can comprise a sweetener. Non-limiting examples of suitable sweeteners can include glucose (corn syrup), dextrose, invert sugar, fructose, and mixtures thereof (when not used as a carrier); saccharin and its various salts such as a sodium salt; dipeptide sweeteners such as aspartame; dihydrochalcone compounds, glycyrrhizin; *Stevia Rebaudiana* (Stevioside); chloro derivatives of sucrose such as sucralose; and sugar alcohols such as sorbitol, mannitol, sylitol, and the like.

In some instances, a pharmaceutical composition as described herein can comprise a coloring agent. Non-limiting examples of suitable color agents can include food, drug and cosmetic colors (FD&C), drug and cosmetic colors (D&C), and external drug and cosmetic colors (Ext. D&C). A coloring agents can be used as dyes or their corresponding lakes.

In some instances, a pharmaceutical composition as described herein can comprise a chelator. In some cases, a chelator can be a fungicidal chelator. Examples can include, but are not limited to: ethylenediamine-N,N,N',N'-tetraacetic acid (EDTA); a disodium, trisodium, tetrasodium, dipotassium, tripotassium, dilithium and diammonium salt of EDTA; a barium, calcium, cobalt, copper, dysprosium, europium, iron, indium, lanthanum, magnesium, manganese, nickel, samarium, strontium, or zinc chelate of EDTA; trans-1,2-diaminocyclohexane-N,N,N',N'-tetraaceticacid monohydrate; N,N-bis(2-hydroxyethyl)glycine; 1,3-diamino-2-hydroxypropane-N,N,N',N'-tetraacetic acid; 1,3-diaminopropane-N,N,N',N'-tetraacetic acid; ethylenediamine-N,N'-diacetic acid; ethylenediamine-N,N'-dipropionic acid dihydrochloride; ethylenediamine-N,N'-bis (methylenephosphonic acid) hemihydrate; N-(2-hydroxyethyl)ethylenediamine-N,N',N'-triacetic acid; ethylenediamine-N,N,N',N'-tetrakis(methylenephosponic acid); O,O'-bis(2-aminoethyl)ethyleneglycol-N,N,N',N'-tetraacetic acid; N,N-bis(2-hydroxybenzyl)ethylenediamine-N,N-diacetic acid; 1,6-hexamethylenediamine-N,N,N',N'-tetraacetic acid; N-(2-hydroxyethyl)iminodiacetic acid; iminodiacetic acid; 1,2-diaminopropane-N,N,N',N'-tetraacetic acid; nitrilotriacetic acid; nitrilotripropionic acid; the trisodium salt of nitrilotris(methylenephosphoric acid); 7,19,30-trioxa-1,4,10,13,16,22,27,33-octaazabicyclo[11,11,11] pentatriacontane hexahydrobromide; or triethylenetetramine-N,N,N',N",N'",N'"-hexaacetic acid.

Also contemplated are combination products that include one or more modified oncolytic viruses disclosed herein and one or more other antimicrobial or antifungal agents, for example, polyenes such as amphotericin B, amphotericin B lipid complex (ABCD), liposomal amphotericin B (L-AMB), and liposomal nystatin, azoles and triazoles such as voriconazole, fluconazole, ketoconazole, itraconazole, pozaconazole and the like; glucan synthase inhibitors such as caspofungin, micafungin (FK463), and V-echinocandin (LY303366); griseofulvin; allylamines such as terbinafine; flucytosine or other antifungal agents, including those described herein. In addition, it is contemplated that a peptide can be combined with topical antifungal agents such as ciclopirox olamine, haloprogin, tolnaftate, undecylenate, topical nystatin, amorolfine, butenafine, naftifine, terbinafine, and other topical agents. In some instances, a pharmaceutical composition can comprise an additional agent. In some cases, an additional agent can be present in a therapeutically effective amount in a pharmaceutical composition.

Under ordinary conditions of storage and use, the pharmaceutical compositions as described herein can comprise a preservative to prevent the growth of microorganisms. In certain examples, the pharmaceutical compositions as described herein may not comprise a preservative. The pharmaceutical forms suitable for injectable use can include sterile aqueous solutions or dispersions and sterile powders for the extemporaneous preparation of sterile injectable solutions or dispersions. The pharmaceutical compositions can comprise a carrier which is a solvent or a dispersion medium containing, for example, water, ethanol, polyol (e.g., glycerol, propylene glycol, and liquid polyethylene glycol, and the like), and/or vegetable oils, or any combinations thereof. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the liquid dosage form can be suitably buffered if necessary and the liquid diluent rendered isotonic with sufficient saline or glucose. The liquid dosage forms are especially suitable for intravenous, intramuscular, subcutaneous, intratumoral, and intraperitoneal administration. In this connection, sterile aqueous media that can be employed will be known to those of skill in the art in light of the present disclosure. For example, one dosage may be dissolved in 1 mL to 20 mL of isotonic NaCl solution and either added to 100 mL to 1000 mL of a fluid, e.g., sodium-bicarbonate buffered saline, or injected at the proposed site of infusion.

In certain embodiments, sterile injectable solutions can be prepared by incorporating a modified oncolytic virus according to the present disclosure, such as oncolytic vaccinia viruses as described herein or a pharmaceutical composition containing the same, in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. The compositions disclosed herein may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, the pharmaceutical compositions can be administered in a manner compatible with the dosage formulation and in such amount as is therapeutically effective.

In certain embodiments, a pharmaceutical composition of this disclosure can comprise an effective amount of a modified virus, disclosed herein, combined with a pharmaceutically acceptable carrier. "Pharmaceutically acceptable," as used herein, includes any carrier which does not interfere with the effectiveness of the biological activity of the active ingredients and/or that is not toxic to the patient to whom it is administered. Non-limiting examples of suitable pharmaceutical carriers include phosphate buffered saline solutions, water, emulsions, such as oil/water emulsions, various types of wetting agents and sterile solutions. Additional non-limiting examples of pharmaceutically compatible carriers can include gels, bioadsorbable matrix materials, implantation elements containing the modified oncolytic virus or any other suitable vehicle, delivery or dispensing means or material. Such carriers can be formulated by conventional methods and can be administered to the subject at an effective amount.

Methods of Production

The modified oncolytic viruses of this disclosure can be produced by methods known to one of skill in the art. In certain embodiments, the modified oncolytic virus can be propagated in suitable host cells, e.g., HeLa cells, 293 cells, or Vero cells, isolated from host cells and stored in conditions that promote stability and integrity of the virus, such that loss of infectivity over time is minimized. In certain exemplary methods, the modified oncolytic viruses are propagated in host cells using cell stacks, roller bottles, or perfusion bioreactors. In some examples, downstream methods for purification of the modified oncolytic viruses can comprise filtration (e.g., depth filtration, tangential flow filtration, or a combination thereof), ultracentrifugation, or chromatographic capture. The modified oncolytic virus can be stored, e.g., by freezing or drying, such as by lyophilization. In certain embodiments, prior to administration, the stored modified oncolytic virus can be reconstituted (if dried for storage) and diluted in a pharmaceutically acceptable carrier for administration.

Some embodiments provide that the modified oncolytic virus as described herein, exhibit a higher titer in HeLa cells and 293 cells compared to an otherwise identical virus that does not comprise the modifications in the modified oncolytic virus. In certain instances, a higher titer in HeLa cells and 293 cells is seen in modified oncolytic virus.

Combination Therapies

In certain embodiments, the methods of this disclosure comprise administering a modified oncolytic virus as disclosed herein or a pharmaceutical composition containing the same, followed by, and preceded by or in combination with one or more further therapy. Examples of the further therapy can include, but are not limited to, chemotherapy, radiation, oncolytic viral therapy with an additional virus, treatment with immunomodulatory proteins, an anti-cancer agent, or any combinations thereof. The further therapy can be administered concurrently or sequentially with respect to administration of the modified virus, such as oncolytic vaccinia virus. In certain embodiments, the methods of this disclosure can comprise administering a modified oncolytic virus as disclosed herein, followed by, preceded by, or in combination with one or more anti-cancer agents or cancer therapies. Anti-cancer agents can include, but are not limited to, chemotherapeutic agents, radiotherapeutic agents, cytokines, immune checkpoint inhibitors, anti-angiogenic agents, apoptosis-inducing agents, anti-cancer antibodies and/or anti-cyclin-dependent kinase agents. In certain embodiments, the cancer therapies can include chemotherapy, biological therapy, radiotherapy, immunotherapy, hormone therapy, anti-vascular therapy, cryotherapy, toxin therapy and/or surgery or combinations thereof. In certain embodiments, the methods of this disclosure can include administering a modified virus, disclosed herein, followed by, preceded by or in combination with an modified oncolytic virus of this disclosure. Combination of the modified oncolytic vaccinia virus with chemotherapy achieves a synergistic effect which is not seen in modified oncolytic viruses that do not comprise the modifications in the modified oncolytic virus. The synergistic effect of the above combination can be advantageously used to lower the dose of chemotherapy, such as Taxol®. Thus, the treatment method disclosed here, with the modified virus, can reduced toxicities associated with chemotherapy, e.g., patients who respond to chemotherapy but suffer side effects at therapeutic doses. The synergistic effect, can, in certain cases, results in a decrease in tumor growth compared to chemotherapy alone or oncolytic vaccinia virus alone.

Exemplary decrease in tumor growth can be from about 2% to about 50%, such as about 5%, about 10%, about 20%, about 25%, about 35%, about 45% or about 50%.

In certain embodiments, treatment using a modified oncolytic virus can be used alone or in combination with one or immunomodulatory agents. An immunomodulatory agent can include any compound, molecule or substance capable of suppressing antiviral immunity associated with a tumor or cancer. In certain embodiments, the immunomodulatory agent can be capable of suppressing innate immunity or adaptive immunity to the modified virus. Non-limiting examples of immunomodulatory agents include anti-CD33 antibody or variable region thereof, an anti-CD11b antibody or variable region thereof, a COX2 inhibitor, e.g., celecoxib, cytokines, such as IL-12, GM-CSF, IL-2, IFN3 and IFNγ, and chemokines, such as MIP-1, MCP-1 and IL-8. In certain embodiments, the immunomodulatory agent can include immune checkpoint modulators such as, but not limited to, anti-CTLA4, anti-PD-1, and anti-PD-L1 and TLR agonists (e.g., Poly I:C). In some examples, the immunomodulatory agent can include an immune checkpoint inhibitor, such as an antagonist of PD-1 (e.g., an antagonist antibody that binds to PD-1), an antagonist of PD-L1 (e.g., an antagonist antibody that binds to PD-L1), an antagonist of CTLA-4 (e.g., an antagonist antibody that binds to CTLA-4), an antagonist of A2AR (e.g., an antagonist antibody that binds to A2AR), an antagonist of B7-H3 (e.g., an antagonist antibody that binds to B7-H3), an antagonist of B7-H4 (e.g., an antagonist antibody that binds to B7-H4), an antagonist of BTLA (e.g., an antagonist antibody that binds to BTLA), an antagonist of IDO (e.g., an antagonist antibody that binds to IDO), an antagonist of KIR (e.g., an antagonist antibody that binds to KIR), an antagonist of LAG3 (e.g., an antagonist antibody that binds to LAG3), an antagonist of TIM-3 (e.g., an antagonist antibody that binds to TIM3). In some embodiments, the further therapy can comprise administering an immune checkpoint regulator. In one example, the immune checkpoint regulator can be TGN1412. In one example, the immune checkpoint regulator can be NKTR-214. In one example, the immune checkpoint regulator can be MEDI0562. In one example, the immune checkpoint regulator can be MEDI6469. In one example, the immune checkpoint regulator can be MEDI6383. In one example, the immune checkpoint regulator can be JTX-2011. In one example, the immune checkpoint regulator can be Keytruda (pembrolizumab). In one example, the immune checkpoint regulator can be Opdivo (nivolumab). In one example, the immune checkpoint regulator can be Yervoy (ipilimumab). In one example, the immune checkpoint regulator can be tremelimumab. In one example, the immune checkpoint regulator can be Tecentriq (atezolizumab). In one example, the immune checkpoint regulator can be MGA271. In one example, the immune checkpoint regulator can be indoximod. In one example, the immune checkpoint regulator can be Epacadostat. In one example, the immune checkpoint regulator can be lirilumab. In one example, the immune checkpoint regulator can be BMS-986016. In one example, the immune checkpoint regulator can be MPDL3280A. In one example, the immune checkpoint regulator can be avelumab. In one example, the immune checkpoint regulator can be durvalumab. In one example, the immune checkpoint regulator can be MEDI4736. In one example, the immune checkpoint regulator can be MEDI4737. In one example, the immune checkpoint regulator can be TRX518. In one example, the immune checkpoint regulator can be MK-4166. In one example, the immune checkpoint regulator can be urelumab (BMS-663513). In one example, the immune checkpoint regulator can be PF-05082566 (PF-2566)

In certain examples, where the further therapy is radiation exemplary doses can be 5,000 Rads (50 Gy) to 100,000 Rads (1000 Gy), or 50,000 Rads (500 Gy), or other appropriate doses within the recited ranges. Alternatively, the radiation dose can be about 30 to 60 Gy, about 40 to about 50 Gy, about 40 to 48 Gy, or about 44 Gy, or other appropriate doses within the recited ranges, with the dose determined, example, by means of a dosimetry study as described above. "Gy" as used herein can refer to a unit for a specific absorbed dose of radiation equal to 100 Rads. Gy is the abbreviation for "Gray."

In certain examples, where the further therapy is chemotherapy, exemplary chemotherapeutic agents can include without limitation alkylating agents (e.g., nitrogen mustard derivatives, ethylenimines, alkylsulfonates, hydrazines and triazines, nitrosureas, and metal salts), plant alkaloids (e.g., vinca alkaloids, taxanes, podophyllotoxins, and camptothecan analogs), antitumor antibiotics (e.g., anthracyclines, chromomycins, and the like), antimetabolites (e.g., folic acid antagonists, pyrimidine antagonists, purine antagonists, and adenosine deaminase inhibitors), topoisomerase I inhibitors, topoisomerase II inhibitors, and miscellaneous antineoplastics (e.g., ribonucleotide reductase inhibitors, adrenocortical steroid inhibitors, enzymes, antimicrotubule agents, and retinoids). Exemplary chemotherapeutic agents can include, without limitation, anastrozole (Arimidex®), bicalutamide (Casodex®), bleomycin sulfate (Blenoxane®), busulfan (Myleran®), busulfan injection (Busulfex®), capecitabine (Xeloda®), N4-pentoxycarbonyl-5-deoxy-5-fluorocytidine, carboplatin (Paraplatin®), carmustine (BiCNU®), chlorambucil (Leukeran®), cisplatin (Platinol®), cladribine (Leustatin®), cyclophosphamide (Cytoxan® or Neosar®), cytarabine, cytosine arabinoside (Cytosar-U®), cytarabine liposome injection (DepoCyt®), dacarbazine (DTIC-Dome®), dactinomycin (Actinomycin D, Cosmegan), daunorubicin hydrochloride (Cerubidine®), daunorubicin citrate liposome injection (DaunoXome®), dexamethasone, docetaxel (Taxotere®), doxorubicin hydrochloride (Adriamycin®, Rubex®), etoposide (Vepesid®), fludarabine phosphate (Fludara®), 5-fluorouracil (Adrucil®, Efudex®), flutamide (Eulexin®), tezacitibine, Gemcitabine (difluorodeoxycitidine), hydroxyurea (Hydrea®), Idarubicin (Idamycin®), ifosfamide (IFEX®), irinotecan (Camptosar®), L-asparaginase (ELSPAR®), leucovorin calcium, melphalan (Alkeran®), 6-mercaptopurine (Purinethol®), methotrexate (Folex®), mitoxantrone (Novantrone®), mylotarg, paclitaxel (Taxol®), phoenix (Yttrium90/MX-DTPA), pentostatin, polifeprosan 20 with carmustine implant (Gliadel®), tamoxifen citrate (Nolvadex®), teniposide (Vumon®), 6-thioguanine, thiotepa, tirapazamine (Tirazone®), topotecan hydrochloride for injection (Hycamptin®), vinblastine (Velban®), vincristine (Oncovin®), and vinorelbine (Navelbine®), Ibrutinib, idelalisib, and brentuximab vedotin.

Exemplary alkylating agents can include, without limitation, nitrogen mustards, ethylenimine derivatives, alkyl sulfonates, nitrosoureas and triazenes): uracil mustard (Aminouracil Mustard®, Chlorethaminacil®, Demethyldopan®, Desmethyldopan®, Haemanthamine®, Nordopan®, Uracil nitrogen Mustard®, Uracillost®, Uracilmostaza®, Uramustin®, Uramustine®), chlormethine (Mustargen®), cyclophosphamide (Cytoxan®, Neosar®, Clafen®, Endoxan®, Procytox®, Revimmune™), ifosfamide (Mitoxana®), melphalan (Alkeran®), Chlorambucil (Leukeran®), pipobroman (Amedel®, Vercyte®), triethylenemelamine (Hemel®, Hexalen®, Hexastat®), triethylenethiophosphoramine, Temozolomide (Temodar®), thiotepa (Thioplex®), busulfan (Busilvex®, Myleran®), carmustine (BiCNU®), lomustine (CeeNU®), streptozocin (Zanosar®), and Dacarbazine (DTIC-Dome®). Additional exemplary alkylating agents include, without limitation, Oxaliplatin (Eloxatin®); Temozolomide (Temodar® and Temodal®); Dactinomycin (also known as actinomycin-D, Cosmegen®); Melphalan (also known as L-PAM, L-sarcolysin, and phenylalanine mustard, Alkeran®); Altretamine (also known as hexamethylmelamine (HMM), Hexalen®); Carmustine (BiCNU®); Bendamustine (Treanda®); Busulfan (Busulfex® and Myleran®); Carboplatin (Paraplatin®); Lomustine (also known as CCNU, CeeNU®); Cisplatin (also known as CDDP, Platinol® and Platinol®-AQ); Chlorambucil (Leukeran®); Cyclophosphamide (Cytoxan® and Neosar®); Dacarbazine (also known as DTIC, DIC and imidazole carboxamide, DTIC-Dome®); Altretamine (also known as hexamethylmelamine (HMM), Hexalen®); Ifosfamide (Ifex®); Prednumustine; Procarbazine (Matulane®); Mechlorethamine (also known as nitrogen mustard, mustine and mechloroethamine hydrochloride, Mustargen®); Streptozocin (Zanosar®); Thiotepa (also known as thiophosphoamide, TESPA and TSPA, Thioplex®); Cyclophosphamide (Endoxan®, Cytoxan®, Neosar®, Procytox®, Revimmune®); and Bendamustine HCl (Treanda®).

Exemplary anthracyclines can include, without limitation, e.g., doxorubicin (Adriamycin® and Rubex®); bleomycin (Lenoxane®); daunorubicin (dauorubicin hydrochloride, daunomycin, and rubidomycin hydrochloride, Cerubidine®); daunorubicin liposomal (daunorubicin citrate liposome, DaunoXome®); mitoxantrone (DHAD, Novantrone®); epirubicin (Ellence™); idarubicin (Idamycin®, Idamycin PFS®); mitomycin C (Mutamycin®); geldanamycin; herbimycin; ravidomycin; and desacetylravidomycin.

Exemplary vinca alkaloids can include, but are not limited to, vinorelbine tartrate (Navelbine®), Vincristine (Oncovin®), and Vindesine (Eldisine®)); vinblastine (also known as vinblastine sulfate, vincaleukoblastine and VLB, Alkaban-AQ® and Velban®); and vinorelbine (Navelbine®).

Exemplary proteasome inhibitors can, but are not limited to, bortezomib (Velcade®); carfilzomib (PX-171-007, (S)-4-Methyl-N—((S)-1-(((S)-4-methyl-1-((R)-2-methyloxiran-2-yl)-1-oxopentan-2-yl)amino)-1-oxo-3-phenylpropan-2-yl)-2-((S)-2-(2-morpholinoac etamido)-4-phenylbutanamido)-pentanamide); marizomib (NPI-0052); ixazomib citrate (MLN-9708); delanzomib (CEP-18770); and O-Methyl-N-[(2-methyl-5-thiazolyl)carbonyl]-L-seryl-O-methyl-N-[(1S)-2-[(2R)-2-methyl-2-oxiranyl]-2-oxo-1-(phenylmethyl)ethyl]-L-serinamide (ONX-0912).

"In combination with," as used herein, means that the modified virus, such as an oncolytic vaccinia virus as described herein or a pharmaceutical composition comprising the same, and the further therapy, such as a further therapy comprising one or more agents are administered to a subject as part of a treatment regimen or plan. In certain embodiments, being used in combination does not require that the modified oncolytic virus and the one or more agents are physically combined prior to administration or that they be administered over the same time frame. For example, and not by way of limitation, the modified oncolytic virus and the one or more agents can be administered concurrently to the subject being treated, or can be administered at the same time or sequentially in any order or at different points in time.

The further therapy can be administered, in various embodiments, in a liquid dosage form, a solid dosage form, a suppository, an inhalable dosage form, an intranasal dosage form, in a liposomal formulation, a dosage form comprising nanoparticles, a dosage form comprising microparticles, a polymeric dosage form, or any combinations thereof. In certain embodiments, the further therapy is administered over a period of about 1 week to about 2 weeks, about 2 weeks to about 3 weeks, about 3 weeks to about 4 weeks, about 4 weeks to about 5 weeks, about 6 weeks to about 7 weeks, about 7 weeks to about 8 weeks, about 8 weeks to about 9 weeks, about 9 weeks to about 10 weeks, about 10 weeks to about 11 weeks, about 11 weeks to about 12 weeks, about 12 weeks to about 24 weeks, about 24 weeks to about 48 weeks, about 48 weeks or about 52 weeks, or longer. The frequency of administration of the further therapy can be, in certain instances, once daily, twice daily, once every week, once every three weeks, once every four weeks (or once a month), once every 8 weeks (or once every 2 months), once every 12 weeks (or once every 3 months), or once every 24 weeks (once every 6 months). In certain embodiments, a method of treating a subject having a cancer can include administering, to the subject, an effective amount of a modified oncolytic virus, e.g., modified vaccinia virus, of this disclosure. In certain embodiments, the methods of this disclosure can further include administering to the subject an effective amount of one or more agents. For example, and not by way of limitation, the agent can be an anti-cancer agent, an immunomodulatory agent, or any combinations thereof, as described above.

Kits

In embodiments, this disclosure provides for a kit for administering a modified oncolytic virus as described herein. In certain embodiments, a kit of this disclosure can include a modified oncolytic virus or a pharmaceutical composition comprising a modified oncolytic virus as described above. In certain embodiments, a kit of this disclosure can further include one or more components such as instructions for use, devices and additional reagents, and components, such as tubes, containers and syringes for performing the methods disclosed above. In certain embodiments, a kit of this disclosure can further include one or more agents, e.g., at least one of an anti-cancer agent, an immunomodulatory agent, or any combinations thereof, that can be administered in combination with a modified virus.

In certain embodiments, a kit of this disclosure can comprise one or more containers containing a modified virus, disclosed herein. For example, and not by way of limitation, a kit of this disclosure can comprise one or more containers that contain a modified oncolytic virus of this disclosure.

In certain embodiments, a kit of this disclosure can include instructions for use, a device for administering the modified oncolytic virus to a subject, or a device for administering an additional agent or compound to a subject. For example, and not by way of limitation, the instructions can include a description of the modified oncolytic virus and, optionally, other components included in the kit, and methods for administration, including methods for determining the proper state of the subject, the proper dosage amount and the proper administration method for administering the modified virus. Instructions can also include guidance for monitoring the subject over duration of the treatment time.

In certain embodiments, a kit of this disclosure can include a device for administering the modified oncolytic virus to a subject. Any of a variety of devices known in the art for administering medications and pharmaceutical compositions can be included in the kits provided herein. For example, and not by way of limitation, such devices include, a hypodermic needle, an intravenous needle, a catheter, a needle-less injection device, an inhaler and a liquid dispenser, such as an eyedropper. In certain embodiments, a modified oncolytic virus to be delivered systemically, for example, by intravenous injection, an intratumoral injection, an intraperitoneal injection, can be included in a kit with a hypodermic needle and syringe.

EXAMPLES

The examples below further illustrate the described embodiments without limiting the scope of this disclosure.

Example 1: Exemplary Modified Vaccinia Virus Having a Mutation in B5R Gene Shows Enhanced Therapeutic Effects in Murine Tumor Models The aim of this study was to explore the effects of an exemplary modified vaccinia virus according to this disclosure, where an exemplary mutation was introduced to the SCR3 and SCR4 regions of the viral B5R gene and the viral thymidine kinase (TK) gene was deleted (referred to herein as WR.B5RmutTK-), in murine tumor models, in comparison with vaccinia viruses that do not have the exemplary B5R mutation.

In one experiment, the WR.B5RmutTK- virus was compared with a vehicle (buffered saline) control, and another modified vaccinia virus where TK gene was deleted and an exogenous nucleic acid encoding GMCSF was added (referred to herein as WR.TK-GMCSF). A single dose of either one of the three viruses ($1\times10^7$ PFU) was administered to treat BALB/c mice implanted subcutaneously with pre-established RENCA tumors (FIG. 1). Tumor volumes were monitored by caliper measurement as shown in FIG. 1 (n=10-15 per group). It was noted that WR.TK-GMCSF virus administered intratumorally ("IT") at the given dose, as expected, did not delay the tumor volume increase over time, as compared to the control virus administrated intravenously ("IV"). However, the treatment of WR.B5RmutTK- virus at the same dose via either intratumoral or intravenous delivery both led to significant delay in tumor volume growth, demonstrating an enhanced therapeutic effect of the exemplary modified vaccinia virus having the exemplary B5R mutation.

Figure 3A:
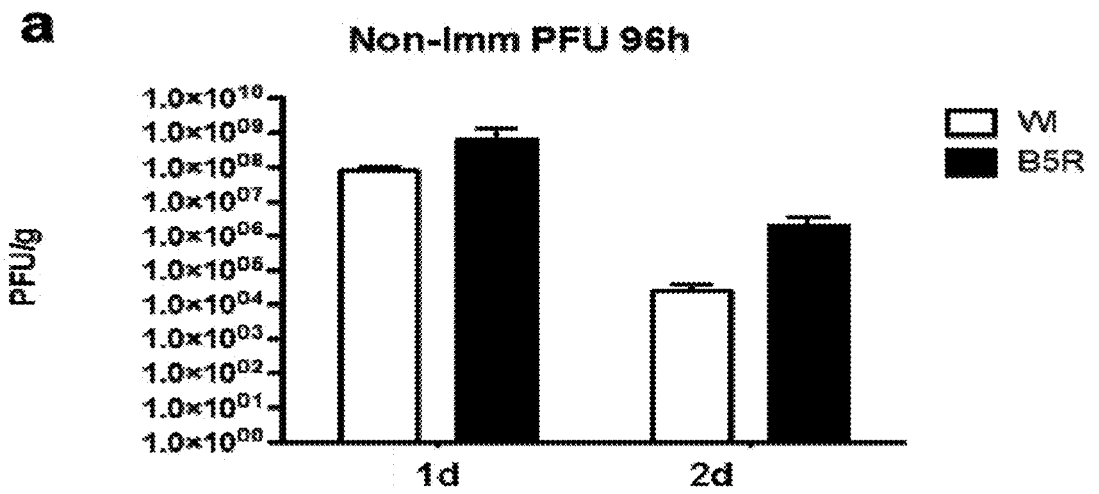
FIGS. 3A-3B show the effect of an exemplary mutation in B5R gene on the replication of an exemplary modified vaccinia virus (WR.B5RmutTK- virus) (referred to as B5R in FIGS. 3A and 3B), in tumors.
Figure 3B:
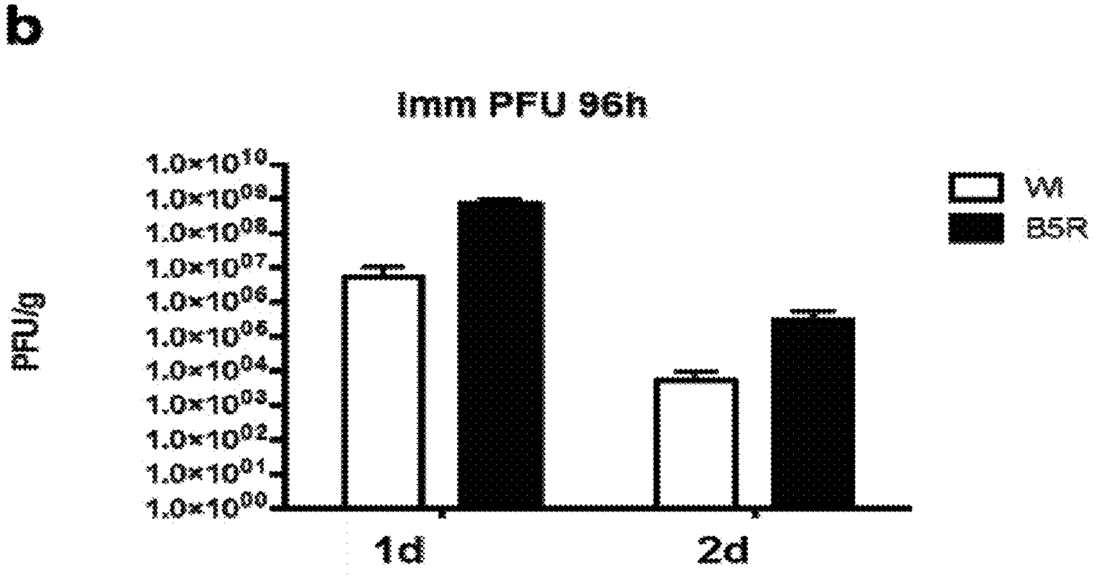

In another experiment, a different mouse tumor model, C57/BL6 mice bearing subcutaneous B16 tumors, was used to test the effects of the exemplary vaccinia virus having the exemplary B5R mutation (FIGS. 2A-2B). The mice were split into two groups, one group received immunization of vaccinia virus through one injection of WR. TK-virus (where TK gene was deleted from the genome) 3 weeks prior to tumor implantation ("Immunized mice") (FIG. 2B), and the other group were not immunized ("Non-immunized mice") (FIG. 2A). WR.B5RmutTK- virus (referred to as B5R in the figure) was examined in comparison with another modified vaccinia virus WR.TK-A34R K151E, where TK was deleted and the viral A34R gene was mutated with an amino acid change, K151 to E (referred to WI in the figure). A single intravenous injection of either virus was given to the mice ($1\times10^8$ PFU/mouse, n=5 per group/timepoint) 96 hours after the tumor implantation, and then the mice were sacrificed 1 day or 2 days after the injection. Tumors were collected for quantification of the number of viral genomes per gram of tumor by Q-PCR. It was observed that WR.B5RmutTK- virus exhibited significantly enhanced accumulation in the tumors in both immunized and non-immunized mice, suggesting the exemplary B5R mutation may promote delivery and spreading of the modified vaccinia virus in tumor. Increased viral replication in tumor were also observed in a plaque assay (FIGS. 3A-3B), which quantified the plaque forming capability of the viruses in the collected tumors, suggesting that the exemplary B5R mutation can promote replication of the modified vaccinia virus in tumor.

Example 2: Exemplary Modified Vaccinia Virus Having an Exemplary Exogenous Nucleic Acid that Encodes Chemokine Receptor Shows Enhanced Therapeutic Effects in Cancer Cell Lines and Murine Tumor Models The aim of this study was to explore the effects of several exemplary modified vaccinia viruses according to this disclosure, in each of which an exemplary exogenous nucleic acid encoding a chemokine receptor was added, in cancer cell lines and murine tumor models, in comparison with vaccinia viruses that do not have the exemplary exogenous nucleic acids.

Figure 4:
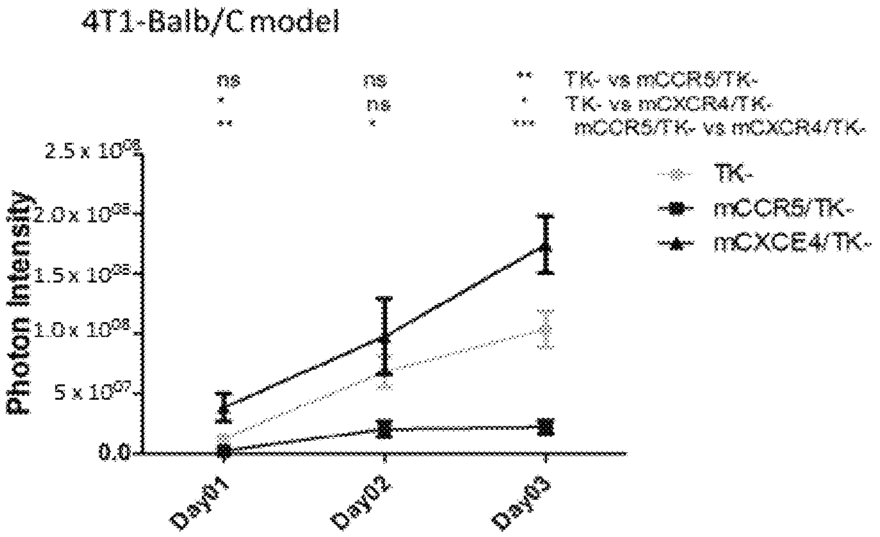
FIG. 4 shows the effect of exemplary modified vaccinia viruses having an exogenous nucleic acid that codes for CXCR4 or CCR5 on viral expression of luciferase in tumors. The graph quantifies the luciferase-mediated photon intensity in the tumors by bioluminescence imaging in mice bearing orthotopic (mammary fat pad) 4T1 tumors. The mice were treated with a single dose of a modified vaccinia virus where TK gene was deleted and an exogenous nucleic acid encoding mouse CCR5 was added (mCCR5/TK- virus), a modified vaccinia virus where TK gene was deleted and an exemplary exogenous nucleic acid encoding mouse CXCR4 was added (mCXCR4/TK- virus), or a TK- virus, where TK gene was deleted. All viruses were engineered to express luciferase.

In one experiment, three different modified vaccinia viruses were tested in mice bearing orthotopic (mammary fat pad) 4T1 tumors subcutaneously. In one vaccinia virus, as termed mCCR5/TK- virus herein, TK gene was deleted from the genome and an exogenous nucleic acid encoding mouse CCR5 was added. In another vaccinia virus, as termed mCXCR4/TK- virus herein, TK gene was deleted and an exogenous nucleic acid encoding mouse CXCR4 was added. In a third vaccinia virus, as termed TK- virus herein, TK gene was deleted. All three viruses were also engineered to express luciferase as a reporter. Each mouse was treated with a single injection of either one of the three viruses at a dose of $1\times10^8$ PFU. Number of viruses in the tumors was quantified by bioluminescence imaging and measurement of the luciferase activity in vivo, every day after the injection for three days (FIG. 4). It was observed that mCXCR4/TK- virus receiving mice showed significantly more photon intensity in the tumors, as compared to mice receiving mCCR5/TK- virus or TK-virus, suggesting expression of CXCR4 may promote viral delivery to the tumor. In contrast, CCR5/TK-showed relatively low photon intensity among the three over all three day measurement, suggesting expression of CCR5 may reduce viral delivery to the tumor.

Figure 5A:
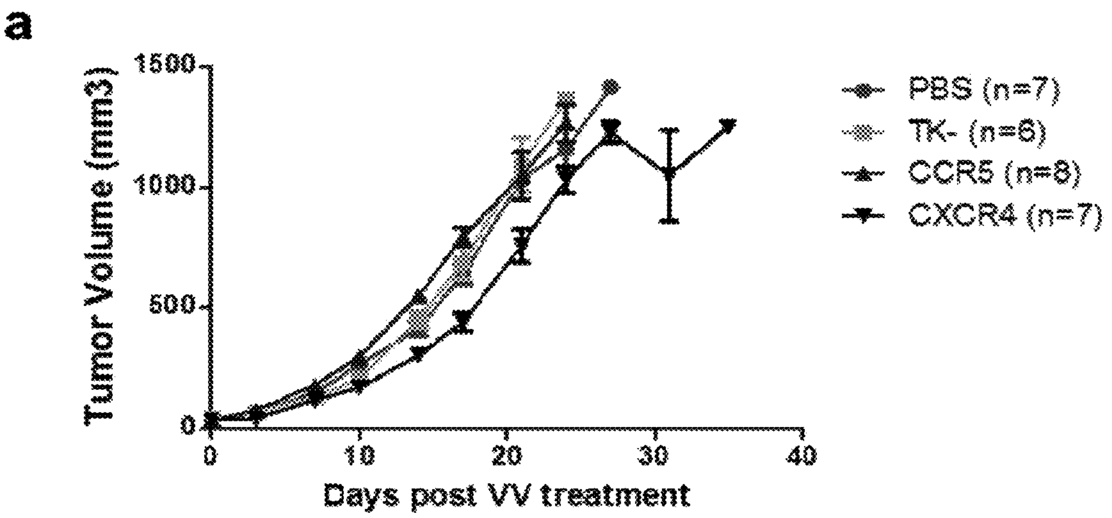
FIGS. 5A-5B show the effects of exemplary modified vaccinia viruses containing an exogenous nucleic acid that codes for CXCR4 or CCR5 on tumor growth and animal survival.
Figure 5B:
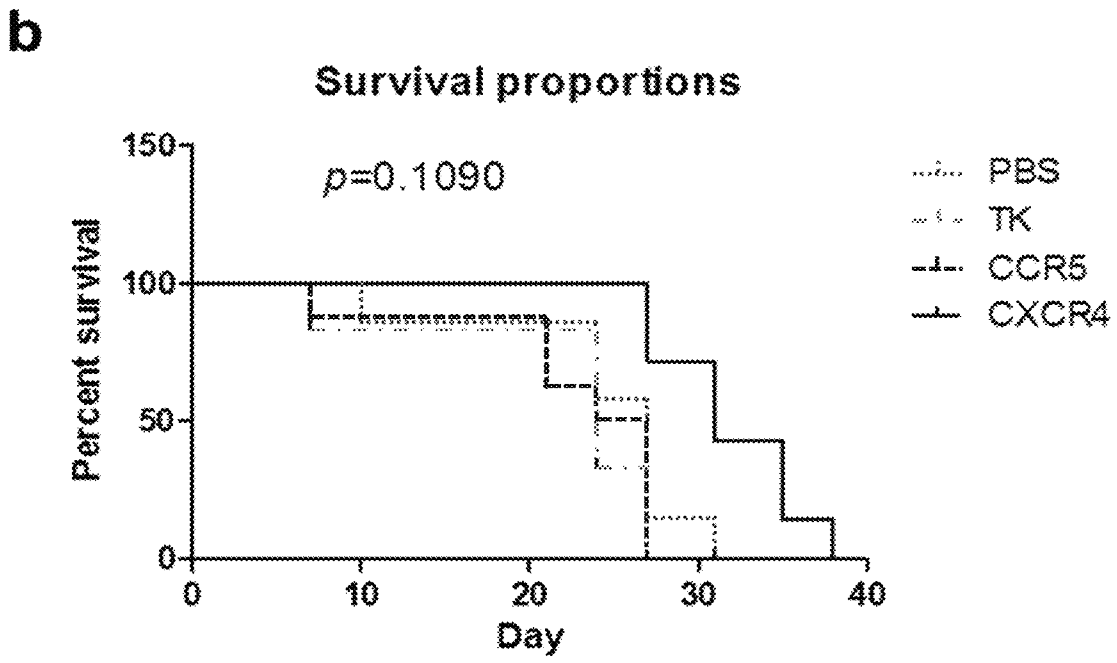

The therapeutic effects of the viruses were also examined. Tumor volume was monitored as described above (FIG. 5A), showing that mCXCR4/TK- virus significantly delayed the tumor volume growth as compared to other two viruses and PBS sham control. Moreover, as shown in FIG. 5B, mouse survival percentage was also significantly improved by the administration of mCXCR4/TK- virus (identified in FIG. 5B as CXCR4).

Figure 6A:
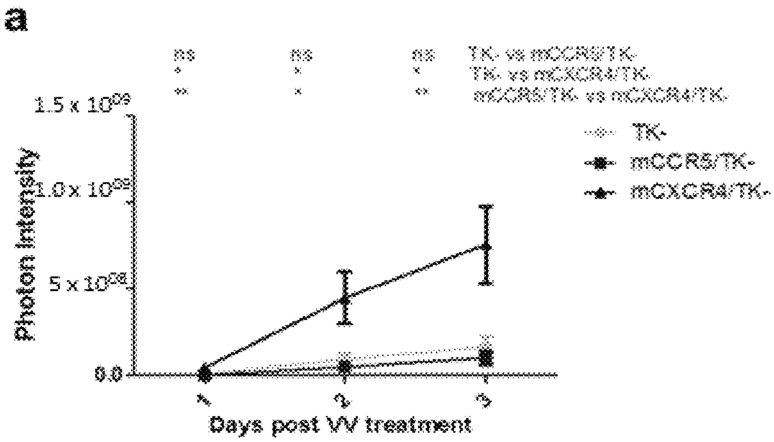
FIGS. 6A-6B show the effects of expression of an exemplary exogenous nucleic acid coding for CXCR4 or CCR5 on viral expression of luciferase in tumors.
Figure 6B:
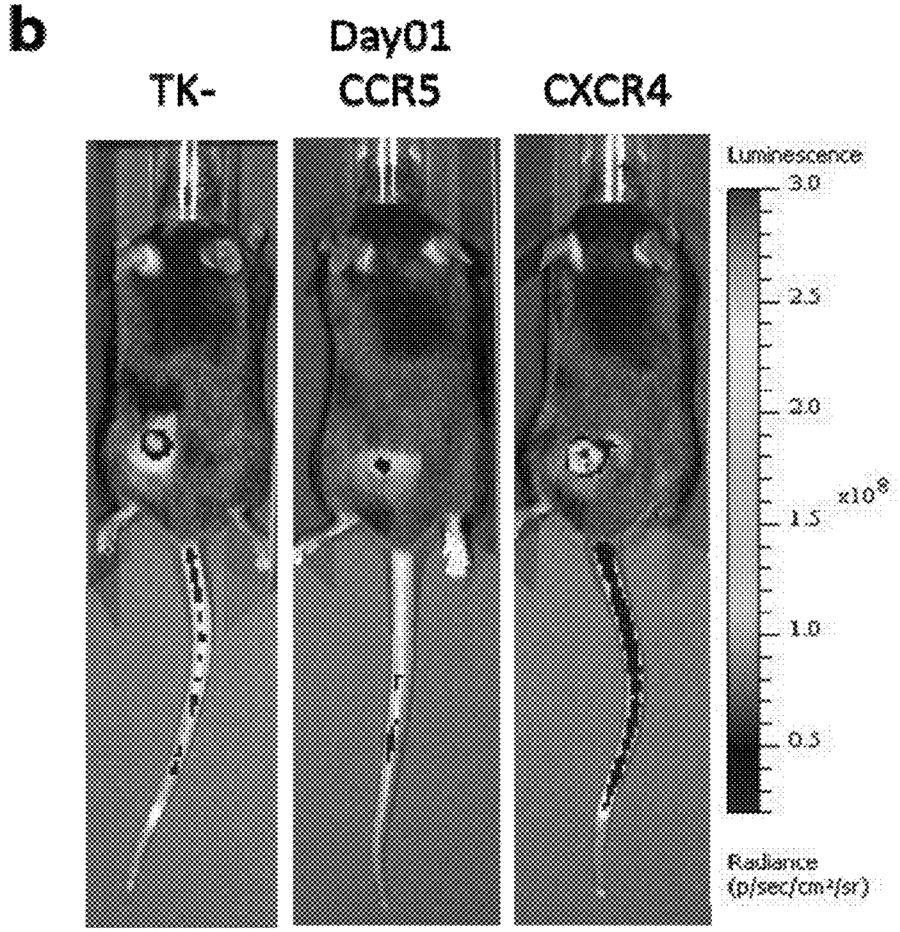
Figure 7:
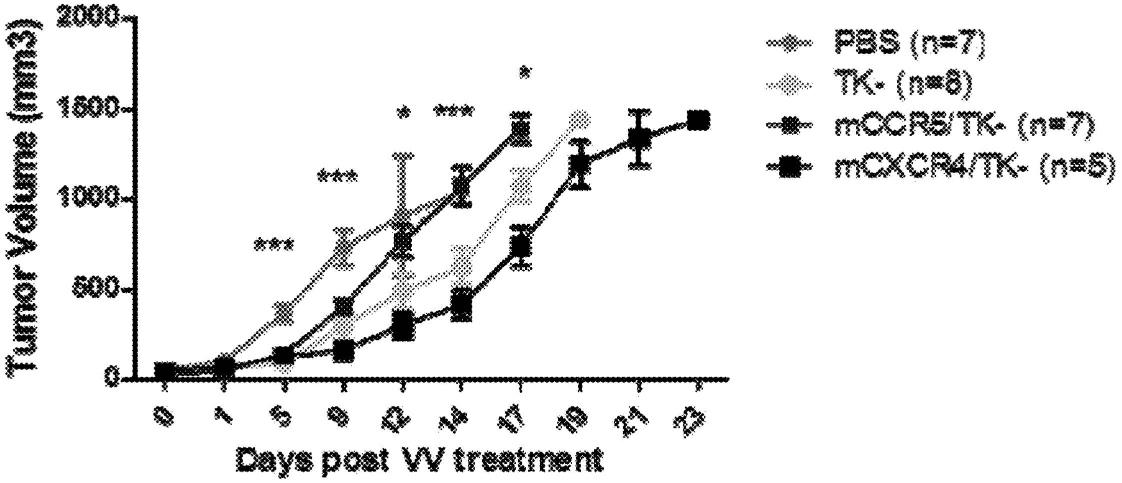
FIG. 7 shows the effects of expression of an exemplary exogenous nucleic acid coding for CXCR4 or CCR5 on tumor growth. The graph quantifies the tumor volume in C57/BL6 mice bearing B16 tumors subcutaneously over the days post vaccinia virus treatment. The mice were treated with a single dose of a modified vaccinia virus where TK gene was deleted and an exogenous nucleic acid encoding mouse CCR5 was added (mCCR5/TK- virus), a modified vaccinia virus where TK gene was deleted and an exemplary exogenous nucleic acid encoding mouse CXCR4 was added (mCXCR4/TK- virus), or a TK-virus, where TK gene was deleted, or PBS.
Figures 8A, 8B:
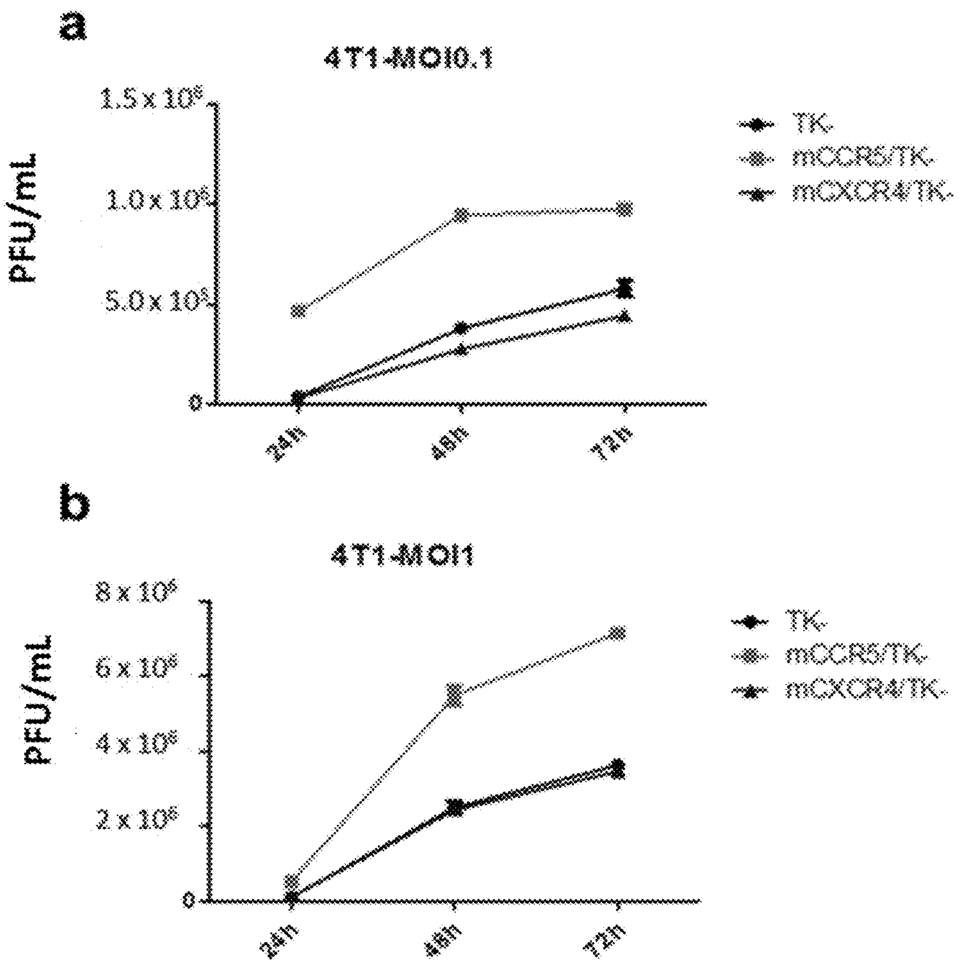
FIGS. 8A-8D show the effects of expression of an exemplary exogenous nucleic acid coding for CCR5 on viral replication in tumors.
Figures 8C, 8D:
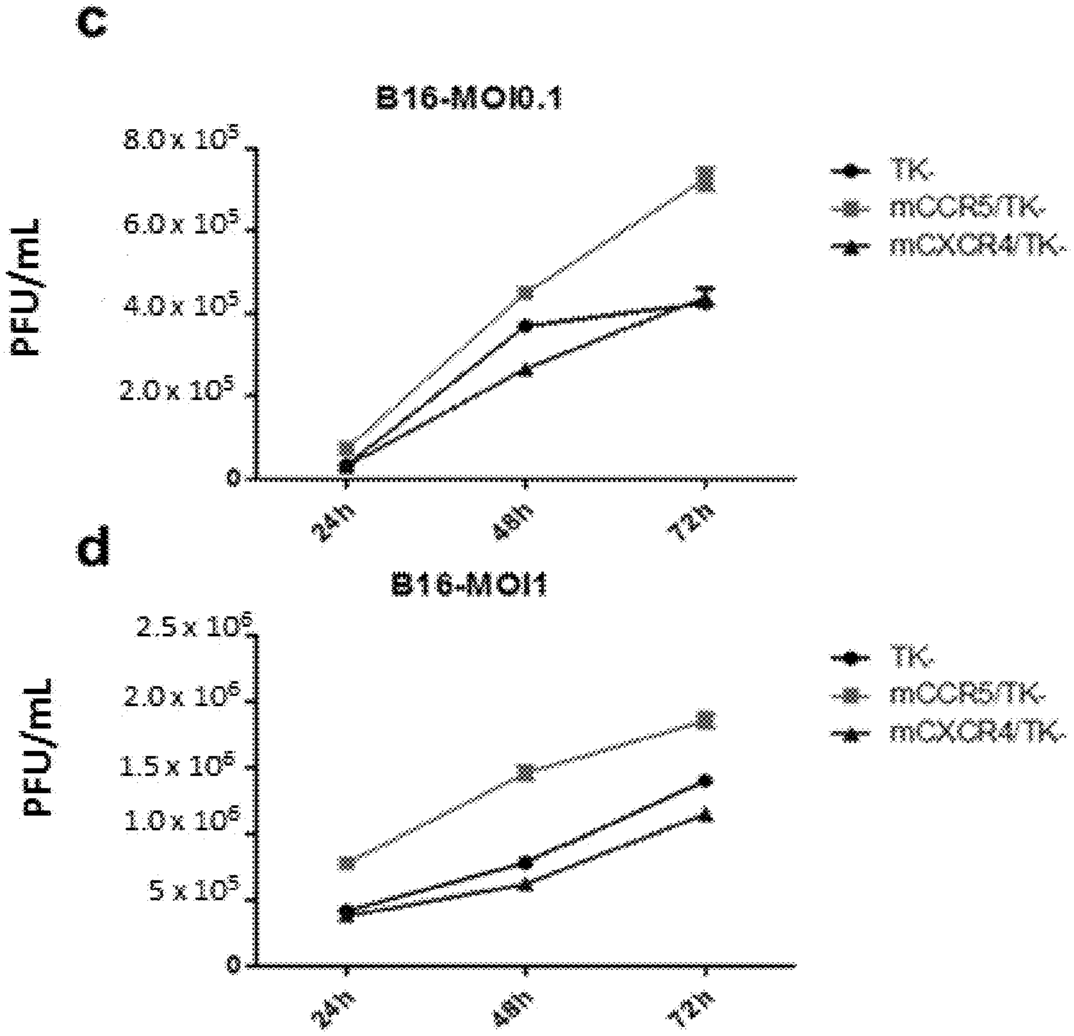

In another experiment, the same three viruses were tested in a different tumor model, C57/BL6 mice bearing B16 tumors subcutaneously. Increased photon intensity was observed in mCXCR4/TK- virus-treated mice, as compared to in mice treated with TK-virus or mCCR5/TK- virus, as can be seen in both the quantification plot in FIG. 6A and the representative photos from the bioluminescence imaging in FIG. 6B. Similarly, mCXCR4/TK- virus administration significantly delayed the tumor volume growth (FIG. 7). These results, as well as the results above, suggest that the addition of the exogenous nucleic acid that encodes CXCR4 to the vaccinia virus resulted in enhanced therapeutic effects against tumor.

Next, viral replication capability for the three viruses in different cancer cell lines in vitro was examined with plaque assays. Plaque-forming was quantified every 24 hours after addition of the viruses to the cell line. As shown in FIGS. 8A-8D, mCCR5/TK- virus, but not mCXCR4/TK- virus, showed increased replication in both cancer cell lines tested (4T1 and B16), at two different multiplicity of infections (MOI 0.1, as in FIGS. 8A and 8C and MOI 1, as in FIGS. 8B and 8D), suggesting that expression of CCR5, but not CXCR4, can promote viral replication in cancer cells. This further can suggest that CXCR4 can display an enhanced effect in vivo, despite not increasing replication in vitro and the enhanced effect of the exemplary modified oncolytic vaccinia virus can be attributed to the delivery, such as, improved systemic delivery.

Figure 10A:
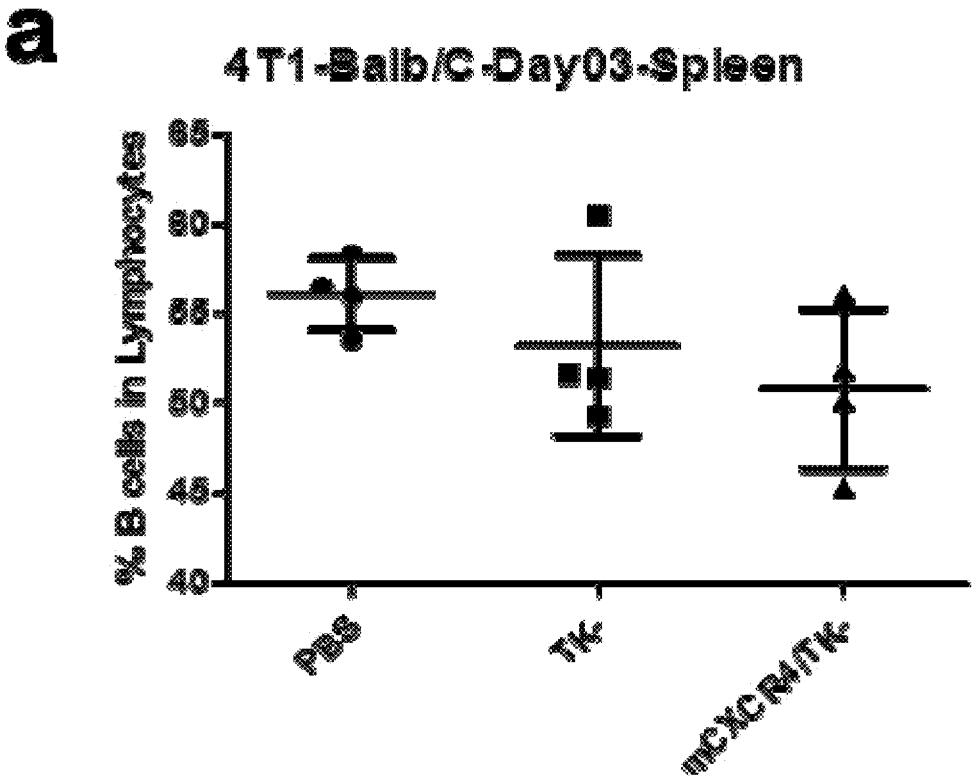
FIGS. 10A-10C show the effects of an exemplary modified vaccinia virus having an exemplary exogenous nucleic acid that codes for CXCR4 on B cell accumulation in tumors.
Figure 10B:
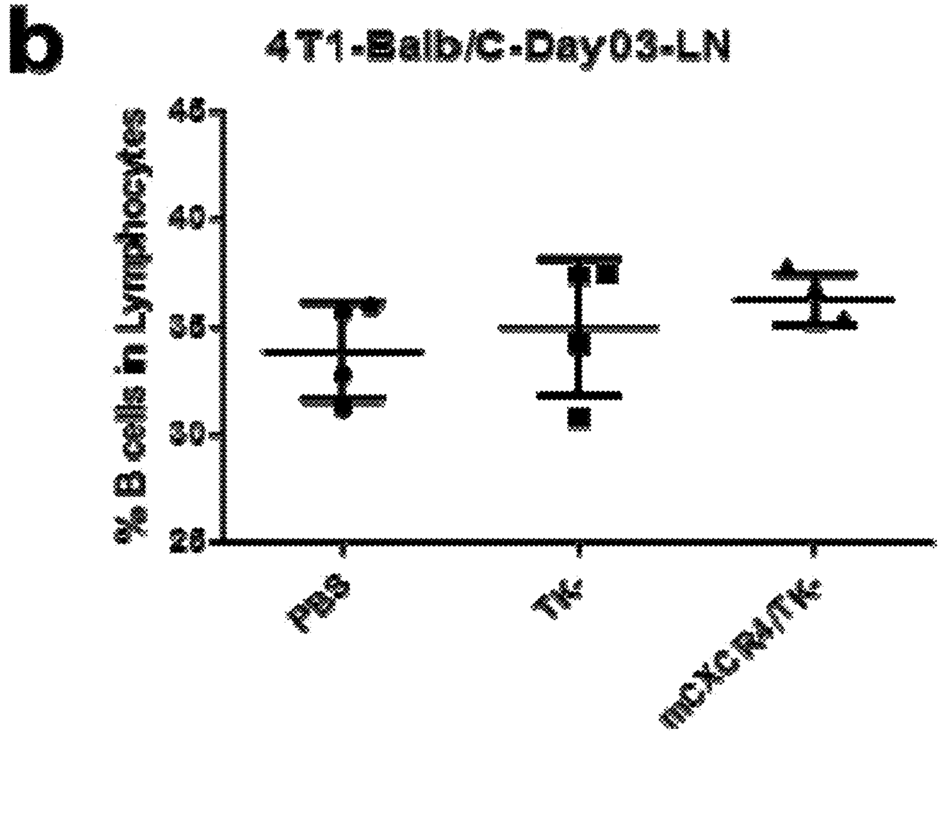
Figure 10C:
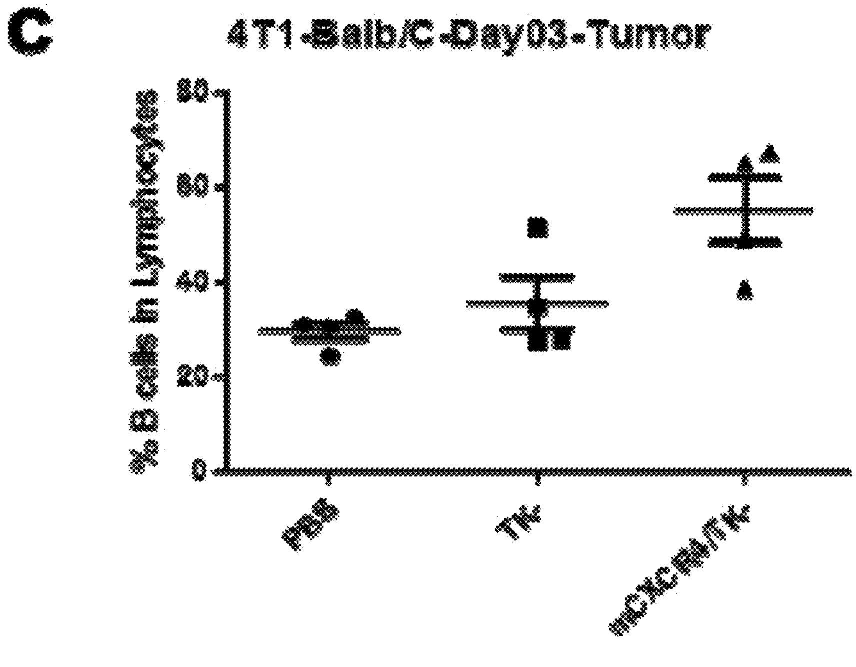

In an effort to start to understand the mechanisms underlying the enhanced therapeutic effects conferred by CXCR4 expression, experiments were conducted using transgenic mice with B-cells depleted (referred to herein as JH). Viruses as described above were administered to Balb/C mice having B-Cells and JH mice without B-cells, both of which had been implanted subcutaneously with pre-established 4T1 tumors. As shown in FIGS. 9A-9C, consistent with the data above, in Balb/C mice, mCXCR4/TK- virus displayed increased accumulation in the tumors as measured by the bioluminescence imaging radiance. However, such an increase was not observed in JH mice, suggesting the enhanced accumulation of mCXCR4/TK- in tumors was at least partially dependent on B cells. On the other hand, flow cytometry experiments showed that mCXCR4/TK- virus administration led to increased entry of B cells into the tumors, but not other organs, like spleen or lymph nodes (LN), in BALB/c mice bearing 4T1 tumor subcutaneously (FIGS. 10A-10C). These data indicate that B cells may serve as a vehicle for vaccinia virus to be delivered to the tumors in vivo.

Figure 11A:
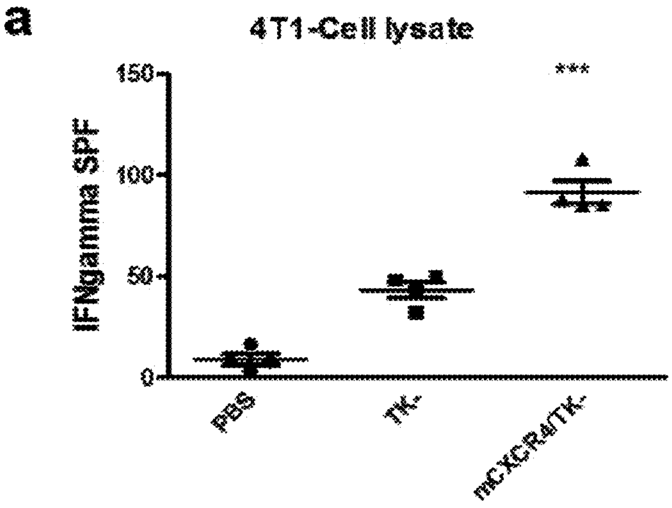
FIGS. 11A-11B show the effects of an exemplary modified vaccinia virus having an exemplary exogenous nucleic acid coding for CXCR4 on T cell activation.
Figure 11B:
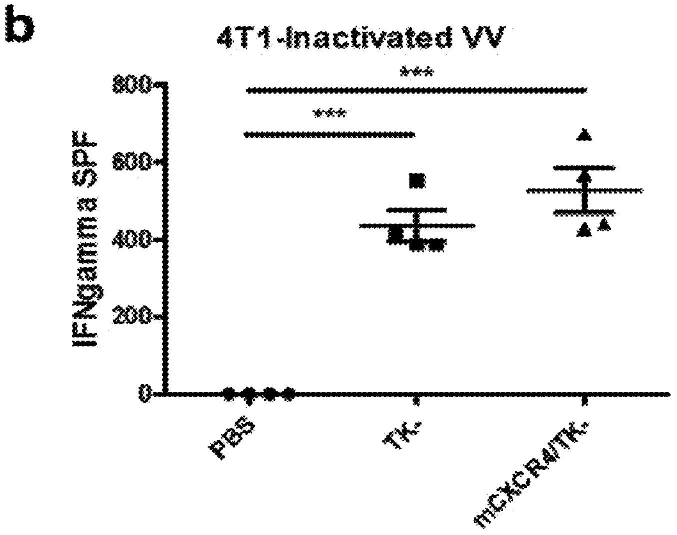

Moreover, enhanced T cell function was also observed in mCXCR4/TK-virus-treated mice. As shown in FIGS. 11A-11B, T cells were collected from the mice that had been implanted with 4T1 tumors subcutaneously and subsequently treated as described above, and their immune activity was examined by ELISpot assays that tested their interferon-γ (IFNgamma) release in response to different immunogens. The tested T cells were recovered from spleens 14 days after the virus injection. T cells from TK-virus-treated mice displayed some immune response to tumor immunogens (4T1-cell lysate), as compared to T cells from PBS-treated mice, whereas T cells from mCXCR4/TK-virus-treated mice displayed enhanced immune response (FIG. 11A). In contrast, CXCR4 expression did not seem to enhance T cell function against the vaccinia virus, as FIG. 11B shows that the interferon-γ release, in response to inactivated vaccinia virus (VV) mixed with tumor cell 4T1 lysate, was not significantly different between T cells from TK- virus-treated mice and mCXCR4/TK- virus-treated mice. These data indicate that CXCR4 expression can result in enhanced immune response against the tumor, thereby contributing, at least partially, to the enhanced therapeutic benefits of the exemplary modified vaccinia virus.

Figure 16:
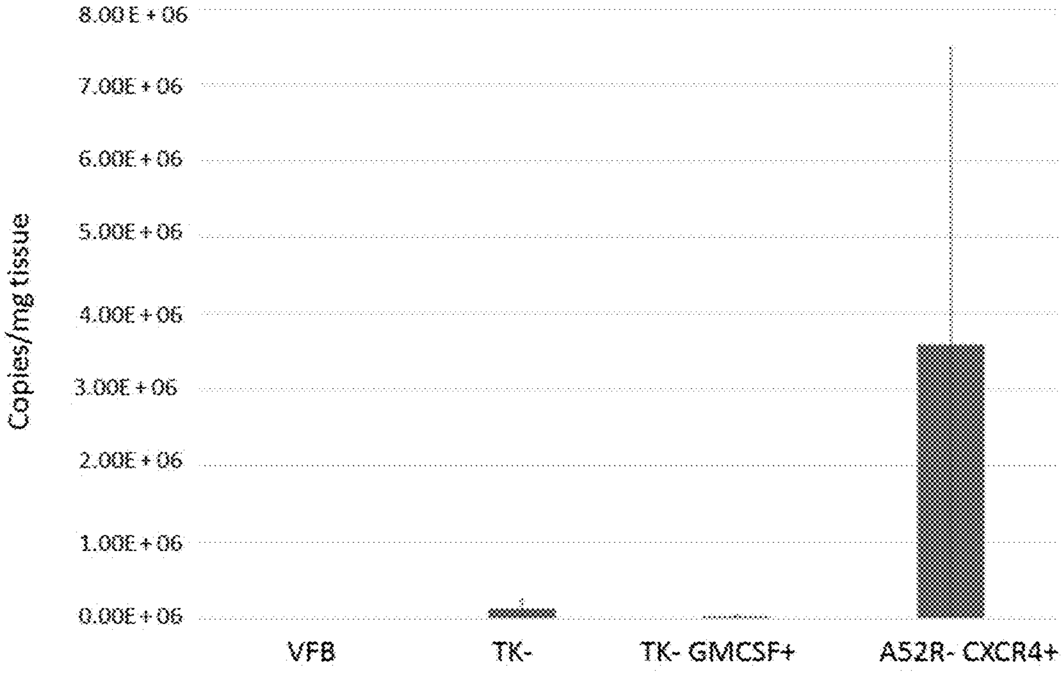
FIG. 16 shows the effect of deletion of A52R and insertion of an exogenous nucleic acid encoding mouse CXCR4 on the delivery of modified vaccinia virus to tumors. BALB/c mice bearing RENCA tumors subcutaneously were treated with a single intravenous injection ($1\times10^7$ PFU) of one of the four modified viruses. Tumors were harvested 24 hours later, and the number of viral genomes per milligram of tissue quantified by qPCR.

Additional experiments were conducted using another exemplary modified vaccinia virus encoding CXCR4. In these experiments, the vaccinia viruses used were as follows: (i) a modified virus with the A52R gene deleted and an exogenous nucleic acid encoding mouse CXCR4 added, termed A52R− CXCR4+; (ii) a modified virus with the TK gene deleted and an exogenous nucleic acid encoding mouse GMCSF added, termed TK-GMCSF+; (iii) a modified virus with the TK gene deleted and no exogenous nucleic acid added, termed TK-, and (iv) a vehicle formulated buffer, termed VFB. In one experiment, BALB/c mice bearing RENCA tumors subcutaneously were treated with a single intravenous injection ($1\times10^7$ PFU) of one of the four modified viruses. Tumors were harvested 24 hours later, and the number of viral genomes per milligram of tissue quantified by qPCR (FIG. 16). Higher numbers of A52R− CXCR4+ genomes were found in the tumors compared to the other modified viruses, supporting the above conclusion that viral CXCR4 expression can enhance viral delivery to tumors.

Figure 17:
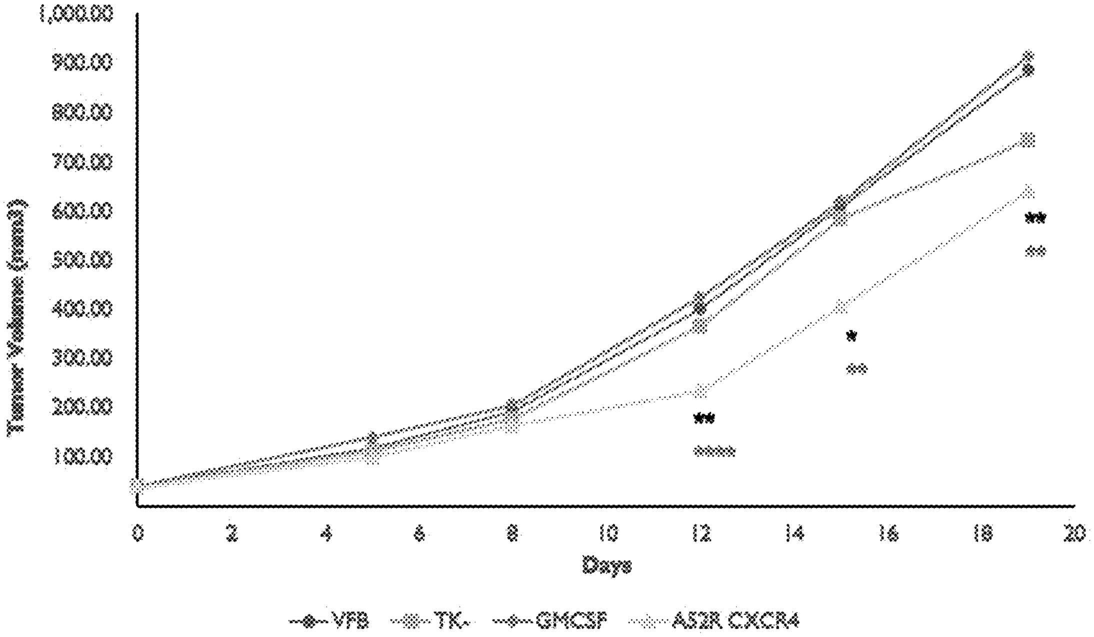
FIG. 17 shows the effect of a modified vaccinia virus having a deletion of A52R and an insertion of an exogenous nucleic acid encoding mouse CXCR4 on tumor growth. BALB/c mice bearing RENCA tumors subcutaneously were treated with intravenous injections ($1\times10^7$ PFU) of one of the same four modified viruses on day 1 and 4, and tumor volume was monitored.
Figure 18A:
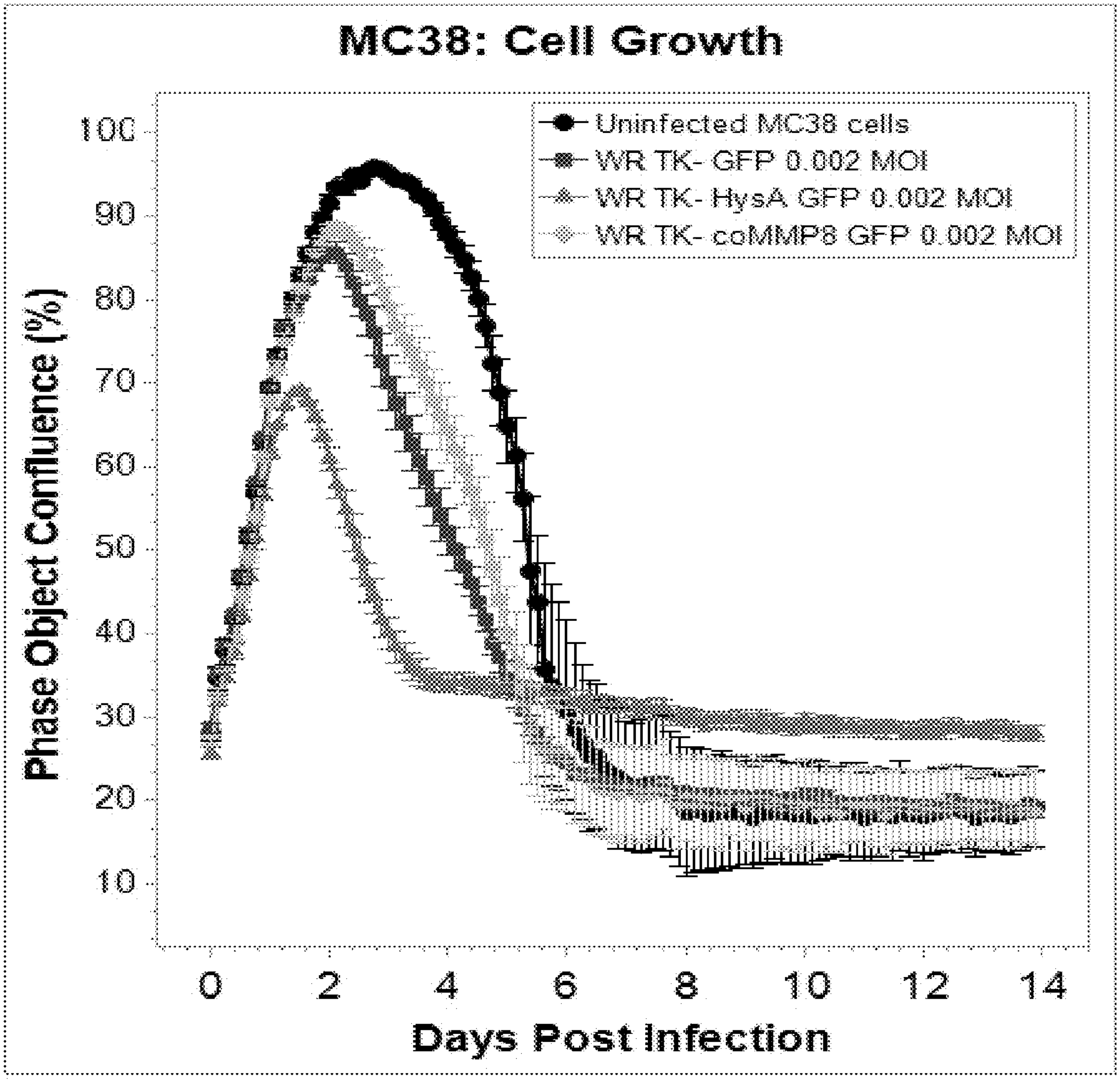
FIGS. 18A-18D show that modified vaccinia viruses having a deletion of TK and an insertion of an exogenous nucleic acid encoding either HysA or MMP8 infect cultures of MC38 cancer cells, replicate, spread, and prevent expansion of the cancer cells. MC38 cells were seeded in a 96-well plate at a density of $5\times10^3$ cells per well. The following day, cells were infected with different GFP-expressing viruses at a MOI of 0.002 and imaged using IncuCyte to measure phase confluence (FIG. 18A), GFP area (FIG. 18B), GFP intensity (FIG. 18C), and virus infectivity (FIG. 18D).
Figure 18B:
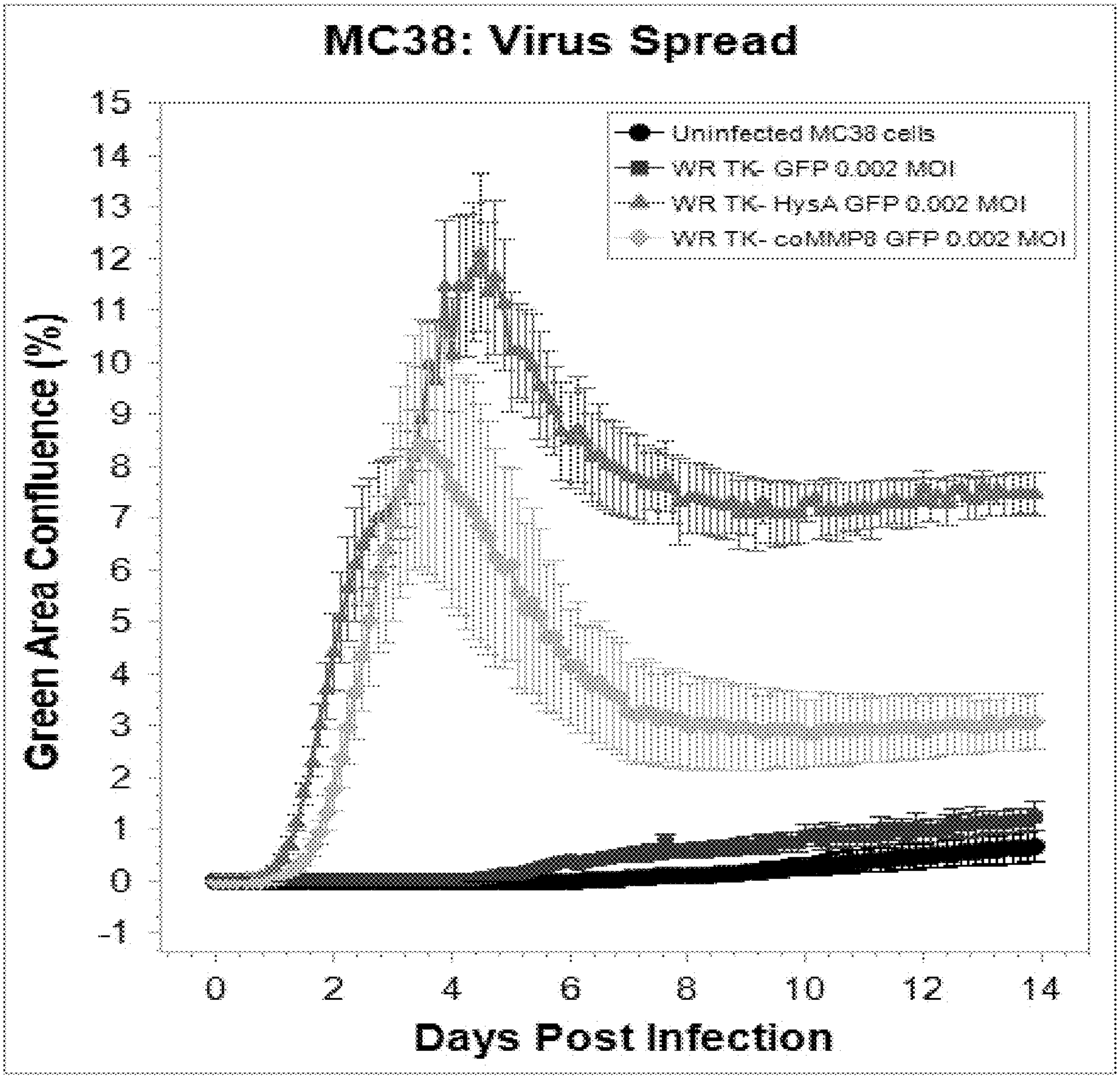
Figure 18C:
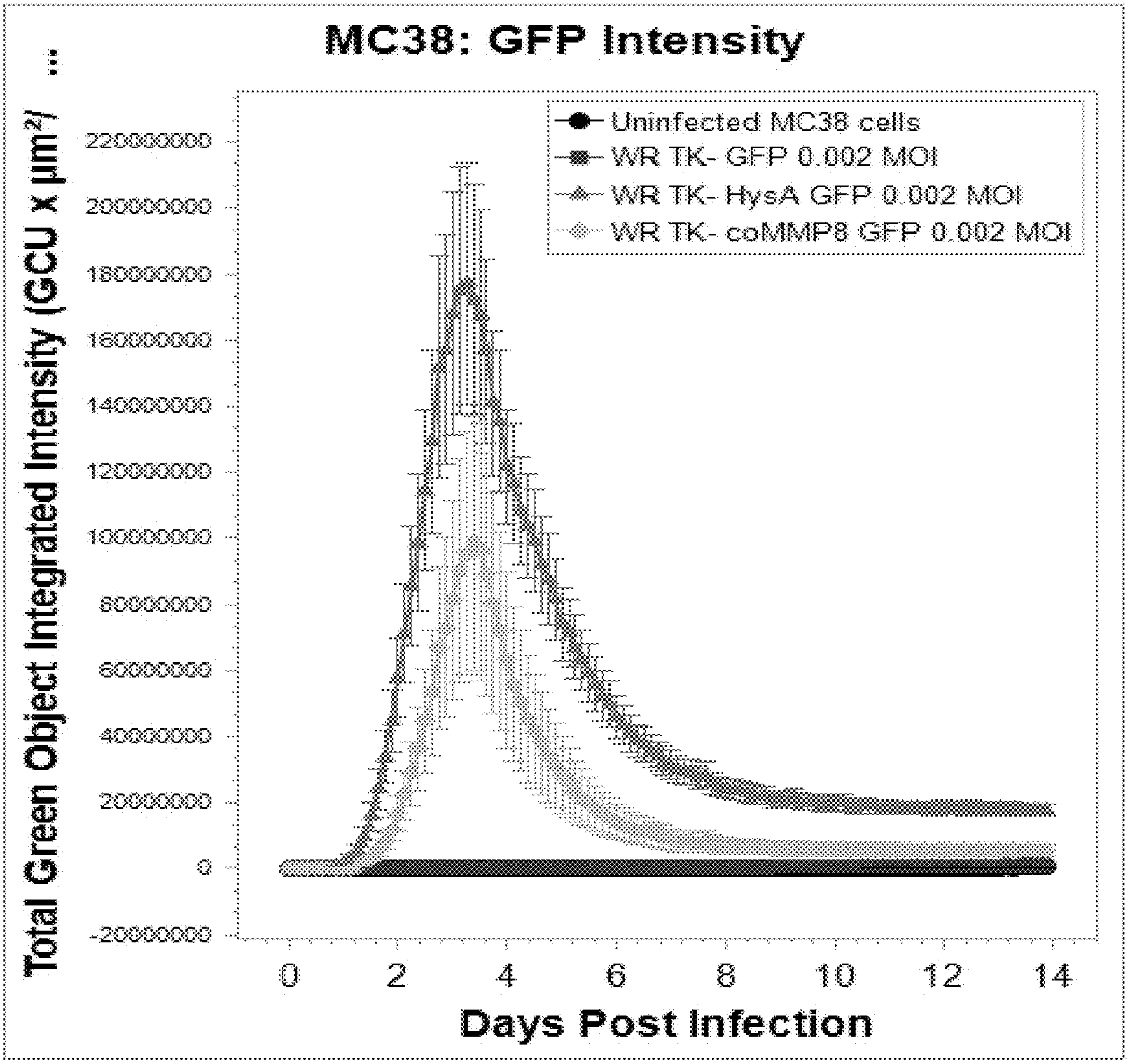
Figure 18D:
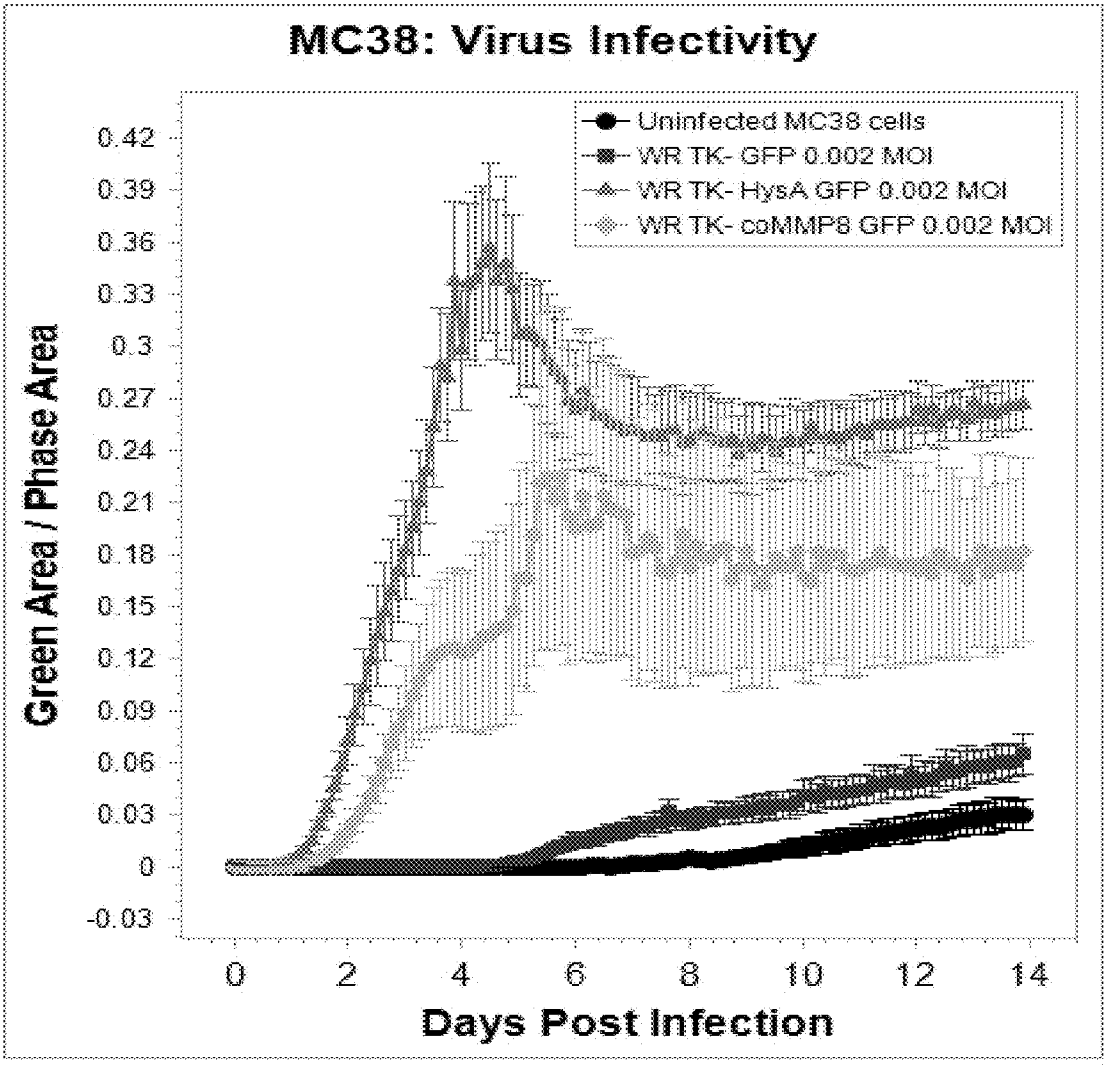
Figure 19A:
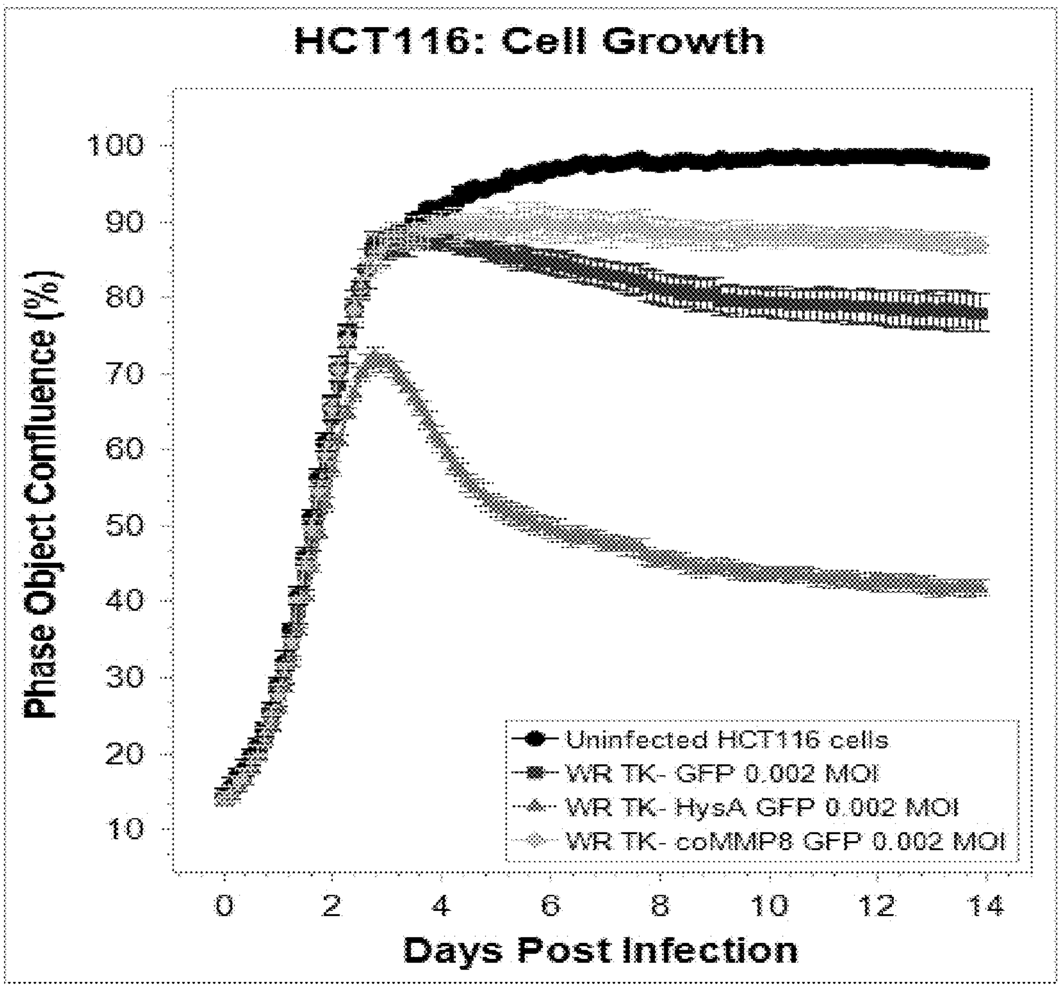
FIGS. 19A-19D show that modified vaccinia viruses having a deletion of TK and an insertion of an exogenous nucleic acid encoding either HysA or MMP8 infect cultures of HCT116 cancer cells, replicate, spread, and prevent expansion of the cancer cells. HCT116 cells were seeded in a 96-well plate at a density of $5\times10^3$ cells per well. The following day, cells were infected with different GFP-expressing viruses at a MOI of 0.002 and imaged using IncuCyte to measure phase confluence (FIG. 19A), GFP area (FIG. 19B), GFP intensity (FIG. 19C), and virus infectivity (FIG. 19D).
Figure 19B:
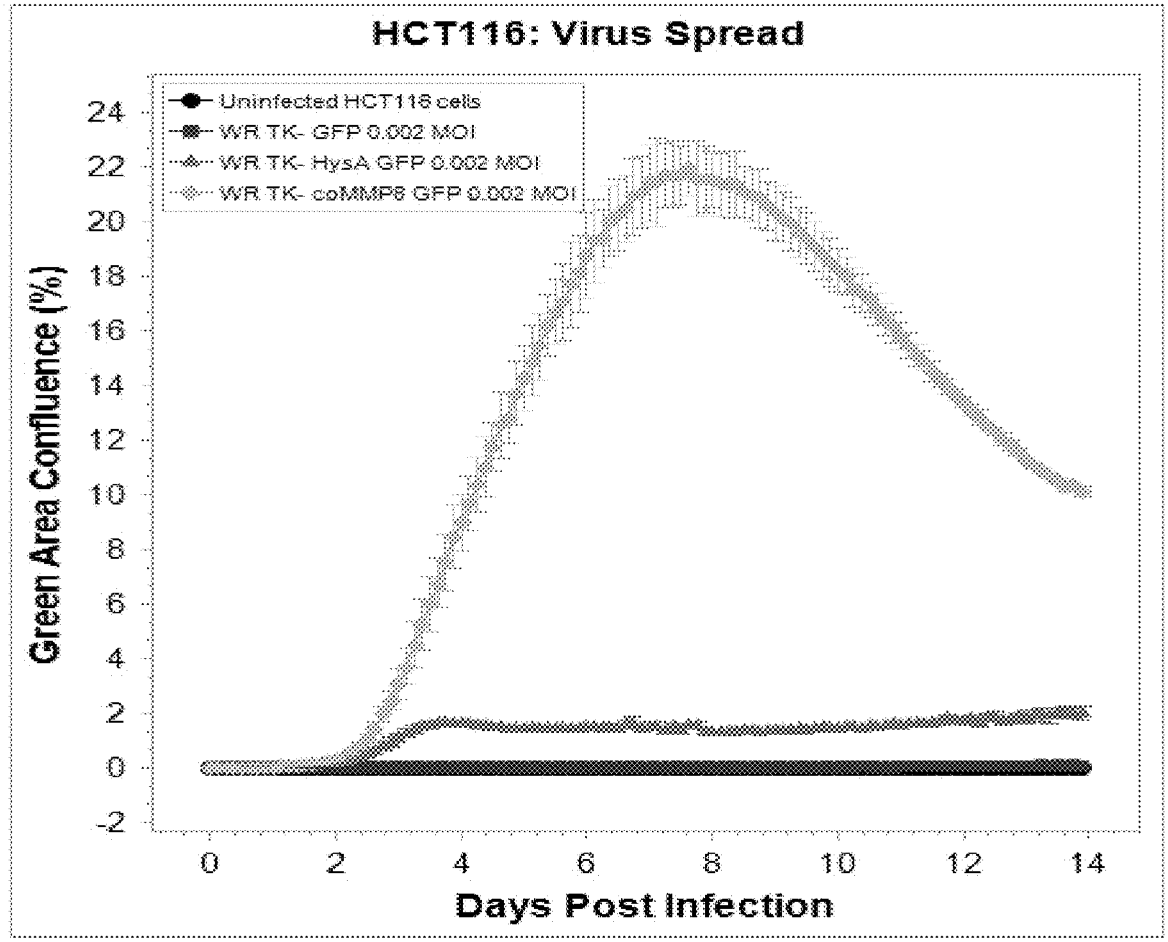
Figure 19C:
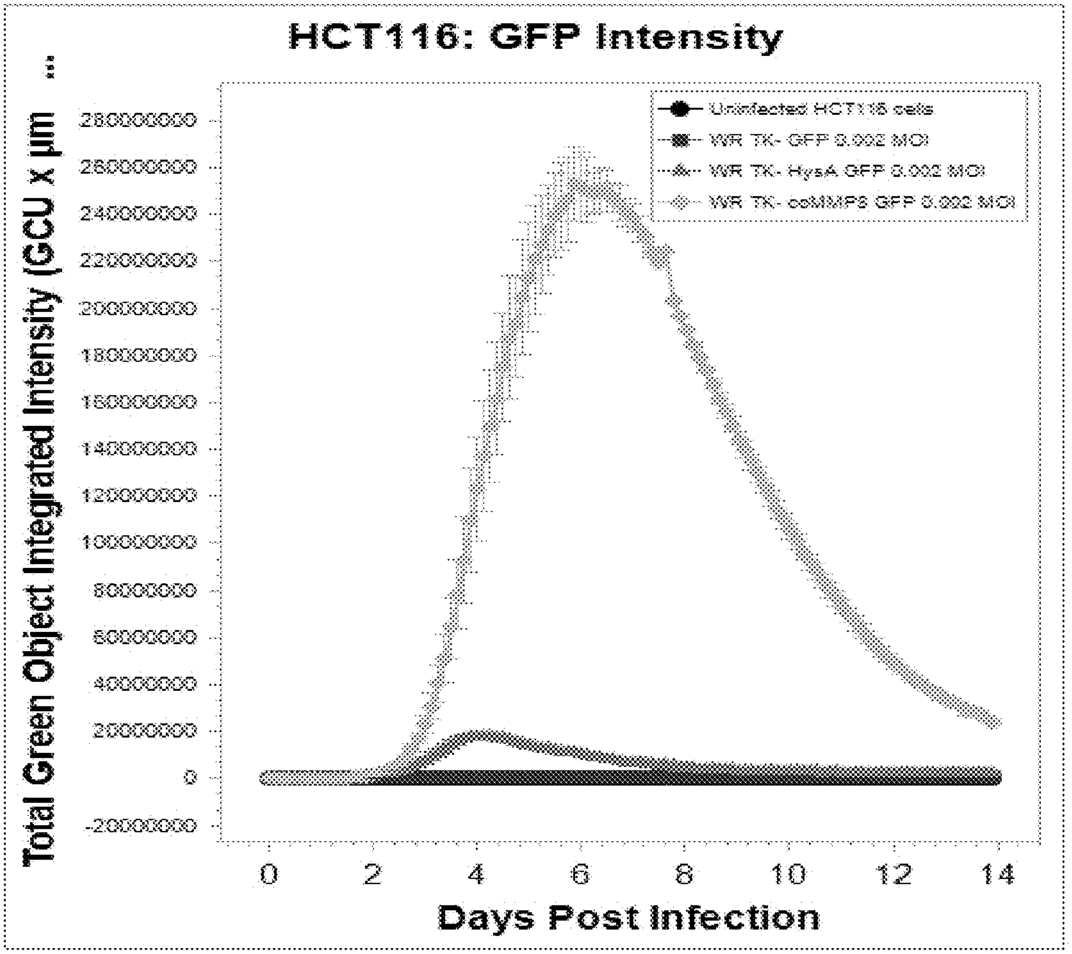
Figure 19D:
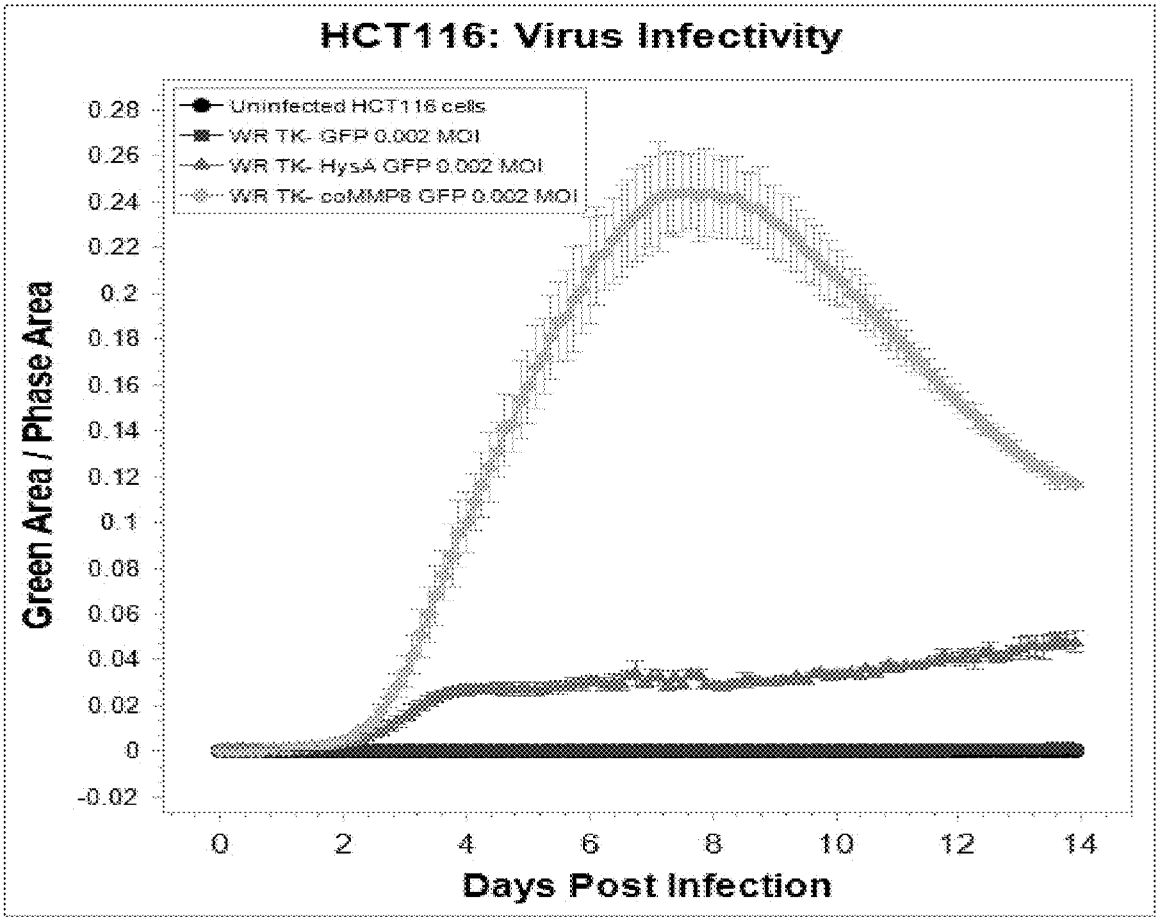

In another experiment, BALB/c mice bearing RENCA tumors subcutaneously were treated with intravenous injections ($1\times10^7$ PFU) of one of the same four modified viruses on day 1 and 4, and tumor volume was monitored as described above. Intravenously-delivered A52R− CXCR4+ virus significantly delayed tumor volume growth (FIG. 17), further supporting the notion that the addition of an exogenous nucleic acid encoding CXCR4 can result in enhanced anti-cancer therapeutic effects.

Example 3: Exemplary Vaccinia Viruses Having Exemplary Exogenous Nucleic Acids that Encode Extracellular Matrix-Degrading Enzymes Show Enhanced Therapeutic Effects in Murine Tumor Models The aim of this study was to explore the effects of exemplary modified vaccinia virus according to this disclosure, where exemplary exogenous nucleic acids encoding extracellular matrix-degrading enzymes (such as hyaluronidases) were added, in murine tumor models, in comparison with vaccinia viruses that do not have an exemplary exogenous nucleic acid.

In one experiment, an exemplary modified vaccinia virus having an exogenous nucleic acid that encodes hyaluronidase PH-20 and having TK gene deleted (referred to herein as WR. TK-PH20) was tested in comparison with a WR.TK-only virus where there was only deletion of TK gene but no addition of PH-20 gene, together with another exemplary vaccinia virus having an exogenous nucleic acid that encodes a MMP8 and having TK gene deleted (referred to herein as WR.TK-mmp8). All three viruses were also engineered to express luciferase as a reporter. A single injection of either virus was given to BALB/c mice bearing RENCA tumors subcutaneously. The subsequent accumulation and spread of the virus was followed through measurement of the viral luciferase activity via bioluminescence imaging. As shown in FIGS. 12A-12B, it was found that WR.TK-Ph20 virus displayed significantly more accumulation in the tumors in vivo as compared to the other two viruses, while WR.TK-mmp8 virus was also relatively high compared to WR.TK-only. These data indicate that expression of PH-20 can enhance viral delivery and spread to the tumors through degradation of ECM and reduction of IFP.

Figure 13A:
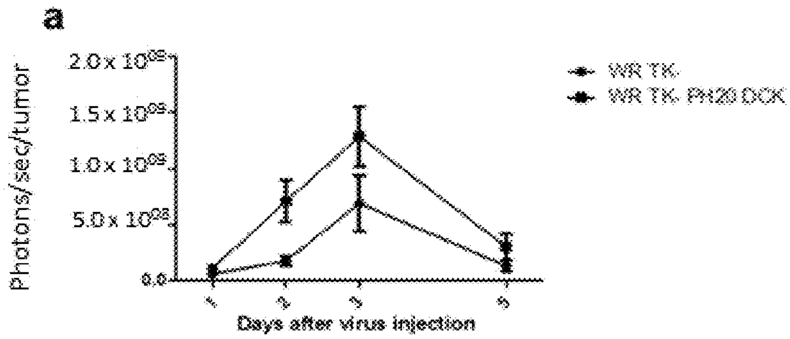
FIGS. 13A-13B show the therapeutic effects of an exemplary modified vaccinia virus having an exemplary exogenous nucleic acid that encodes hyaluronidase PH-20.

Next, the therapeutic effects against tumor were also examined for the viral expression of PH-20. In the first experiment, BALB/c mice subcutaneously implanted with 4T1 tumors were treated intravenously with WR.TK- virus or another exemplary vaccinia virus WR.TK-PH20DCK, where TK gene was deleted, and an exogenous nucleic acid encoding PH20 and an exogenous nucleic acid encoding deoxycytidine kinase (DCK) were both added. Both viruses expressed luciferase, and the viral luciferase expression inside the tumor was measured with bioluminescence imaging. As shown in FIG. 13A, similar as WR.TK-PH20 virus in the RENCA model, WR.TK-PH20DCK virus-injected mice showed significantly higher luciferase activity inside the tumor (n=10), suggesting an enhanced viral accumulation of WR.TK-PH20DCK virus in the tumor as compared to WR.TK- virus.

Figure 13B:
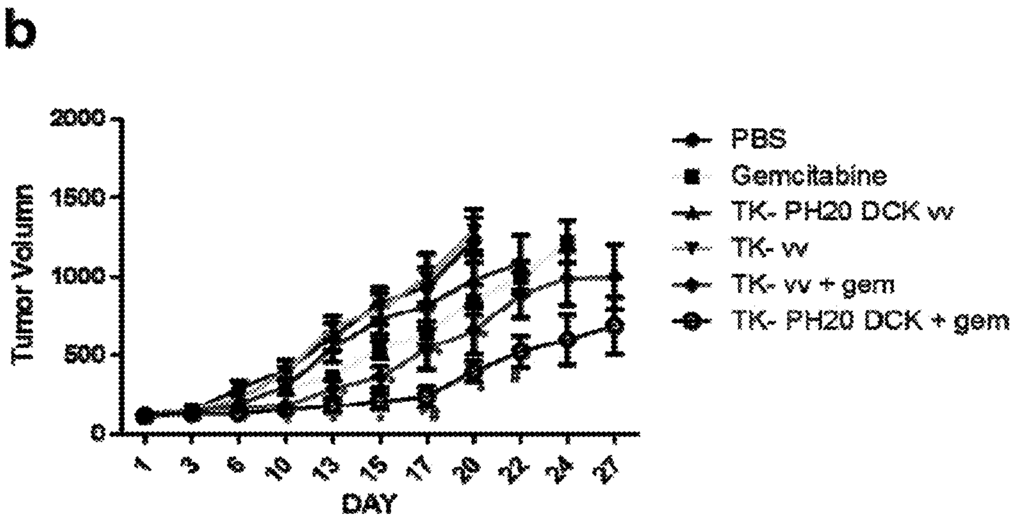
Figure 13C:
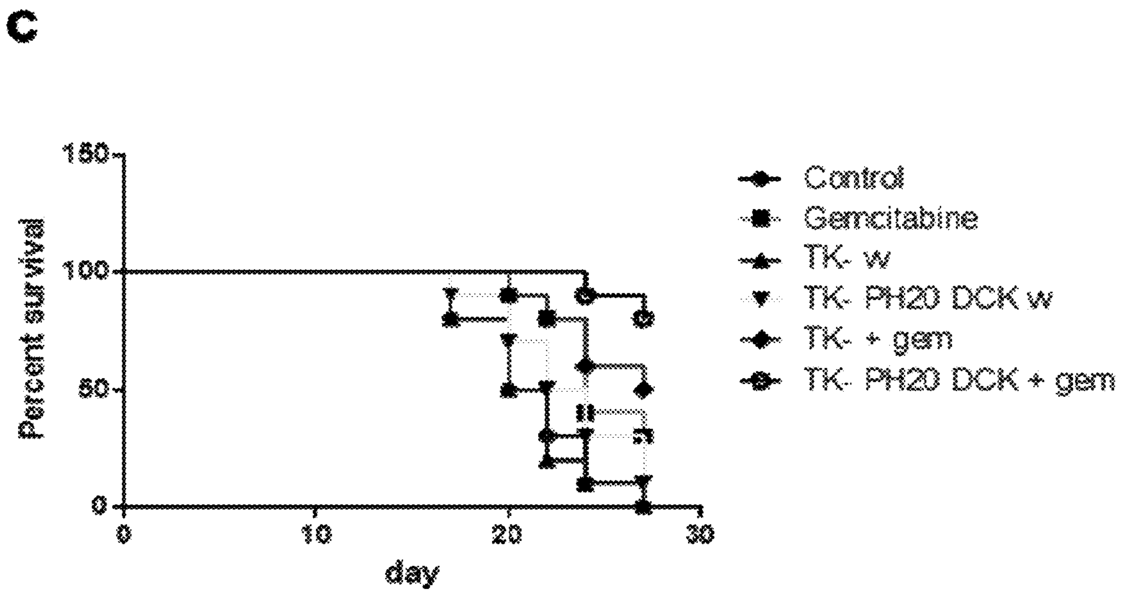
FIG. 13C shows the survival curves for these mice.

In the second experiment, combined therapies were tested on BALB/c mice bearing the 4T1 tumors subcutaneously. Six groups of mice were used. Each group of mice received a single intravenous injection of WR.TK- virus or WR.TK-PH20DCK virus, or control PBS, and then received an intraperitoneal injection of chemotherapeutic drug gemcitabine or water on day3 and day 7 after the virus injection. As shown in FIG. 13B and FIG. 13C, there were a control group receiving water for all three injections, a Gemcitabine group receiving no virus injection but gemcitabine injections, a TK-w group receiving injection of WR.TK- but no gemcitabine, a TK-PH20DCK w group receiving injection of WR.TK-PH20DCK but no gemcitabine, a TK-+gem group receiving injections of both WR.TK- and gemcitabine, and a TK-PH20DCK+gem group receiving injections of both WR.TK-PH20CK and gemcitabine. Continued monitoring of tumor volume (n=10, monitored until more than 4 mice died in the group) and survival curves (*, $P<0.05$ compared with PBS group; #, $P<0.05$ compared with TK-vv+gem group; **, $P<0.05$ compared with TK- group) both showed that the combined treatment of WR.TK-PH20DCK virus and gemcitabine yielded the best result, suggesting that the PH20-mediated reduced interstitial fluid pressure may enhance the chemotherapeutic-delivery, thereby yielding better therapeutic effects.

Figure 14:
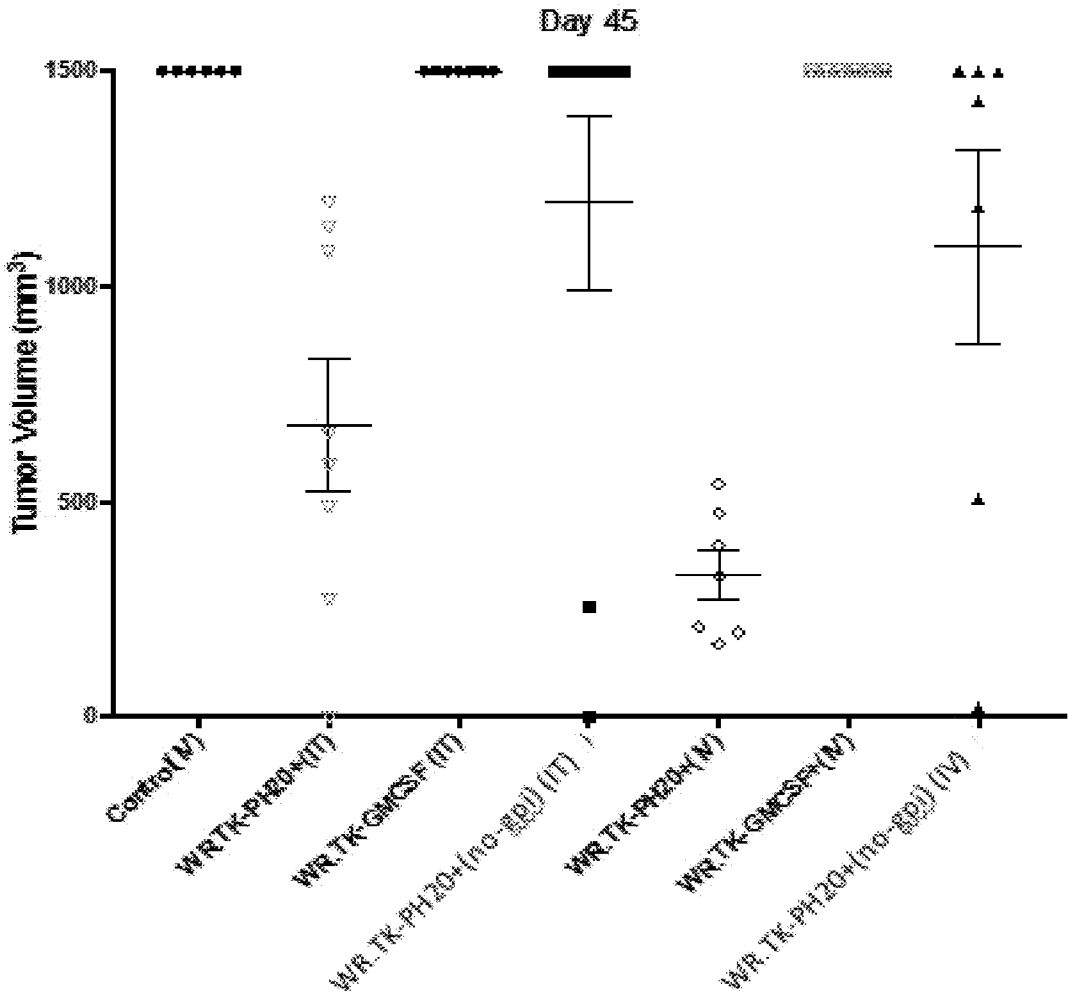
FIG. 14 shows the therapeutic effects 45 days after the viral injection of an exemplary modified vaccinia virus having an exemplary exogenous nucleic acid that encodes, in various combinations or individually, hyaluronidase PH-20, and GMCSF. The graph quantifies the tumor volume in the mice treated with a control sham, a modified vaccinia virus where the TK gene was deleted and which has an exemplary exogenous nucleic acid that codes for PH-20 (WR. TK-PH20 virus), where the PH-20 was with or without a GPI-anchor, a modified vaccinia virus where the TK gene was deleted and which has an exemplary exogenous nucleic acid that codes for GMCSF (WR.TK-GMCSF), either intratumorally (IT) or intravenously (IV), 45 days after the viral injection.

In the third experiment, exemplary vaccinia virus having an exogenous nucleic acid that encodes PH-20 with GPI-anchor and vaccinia virus having an exogenous nucleic acid that encodes PH-20 without GPI-anchor were examined and compared. BALB/c mice bearing RENCA tumors subcutaneously were treated with a single dose of $1\times10^7$ PFU of virus via intratumoral (IT) or intravenous (IV) delivery, and their tumor volumes was measured 45 days after the virus injection. Seven groups of mice were examined at this point (FIG. 14): one control group of mice receiving intravenous injection of no virus but sham control; WR.TK-PH20+(IT) group receiving intratumoral injection of WR.TK-PH20+ virus, where the PH20 expressed by the virus had a GPI-anchor; WR.TK-GMCSF(IT) group receiving intratumoral injection of WR.TK-GMCSF virus, where no PH20 was expressed but GMCSF; WR.TK-PH20+(no-gpi)(IT) group receiving intratumoral injection of WR.TK-PH20+(no-gpi) virus, where PH20 expressed by the virus had no GPI; WR.TK-PH20+(IV) group receiving intravenous injection of WR.TK-PH20+ virus, WR.TK-GMCSF(IV) group receiving intravenous injection of WR.TK-GMCSF virus, and WR.TK-PH20+(no-gpi)(IV) group receiving intravenous injection of WR.TK-PH20+(no-gpi) virus. Remarkably, at the late time such as 45 days after the virus injection, every PH-20-expressing virus-treated animal (IT or IV) was still alive, whereas controls and WR.TK-GMCSF virus-treated mice had all been sacrificed as their tumors had grown larger than 1500 $mm^3$. As shown in FIG. 14, strikingly, the inhibitory effect on tumor growth seemed more enhanced by the presence of the GPI anchor in the WR.TK-PH20+ virus-treated mice as compared to no GPI in the case of WR.TK-PH20+(no-gpi) virus. This is an unexpected result, given that GPI anchors PH-20 to cell membranes, and secretory PH-20 without the GPI anchor that exists more freely in the ECM is believed to be more effective in degrading ECM and reducing IFP.

Additional experiments were performed using exemplary modified vaccinia viruses expressing secreted hyaluronidases to determine how these enzymes affected viral delivery, spread, cell killing, and therapeutic efficacy.

Modified viruses were constructed wherein the TK gene was deleted and an exogenous nucleic acid encoding a hyaluronidase (HysA, lin, or sko) was added; these modified viruses are referred to as TK-HysA, TK-lin, and TK-sko, respectively In an initial experiment, a hyaluronidase activity ELISA was used to determine the activity of the secreted hyaluronidases expressed by the modified viruses described above. HysA showed the most activity, as shown in Table 3.

TABLE 3

| | % protein degraded | |
|---|---|---|
| Virus/control | 24 h | 48 h |
| TK-HysA | 98.55 | 100 |
| TK-lin | 7.29 | 0 |
| TK-sko | 97.96 | 98.45 |
| rv | 0 | 0 |
| WR | 0.69 | 0 |
| No virus | 16.61 | 0 |
| Buffer | 0 | 0 |

In another experiment, cells in culture were infected with one of: the TK-modified virus, the TK- HysA modified virus, or the TK-MMP8 modified virus described above, each of which also expressed GFP. In infected cultures of MC38 cancer cells, the TK-HysA and TK-MMP8 viruses replicated, spread, and prevented cancer cell expansion more so than the TK- virus, suggesting that HysA or MMP8 expression can enhance oncolytic virus replication, spread, and cancer cell killing (FIGS. 18A-18D). In infected cultures of HCT116 cancer cells, the TK-HysA and TK-MMP8 viruses replicated and spread more than the TK-virus, and the TK-HysA virus prevented cancer cell expansion more effectively than the TK-virus, supporting a role for HysA in enhancing oncolytic viral replication, spread, and cancer cell killing (FIGS. 19A-19D).

Figure 20:
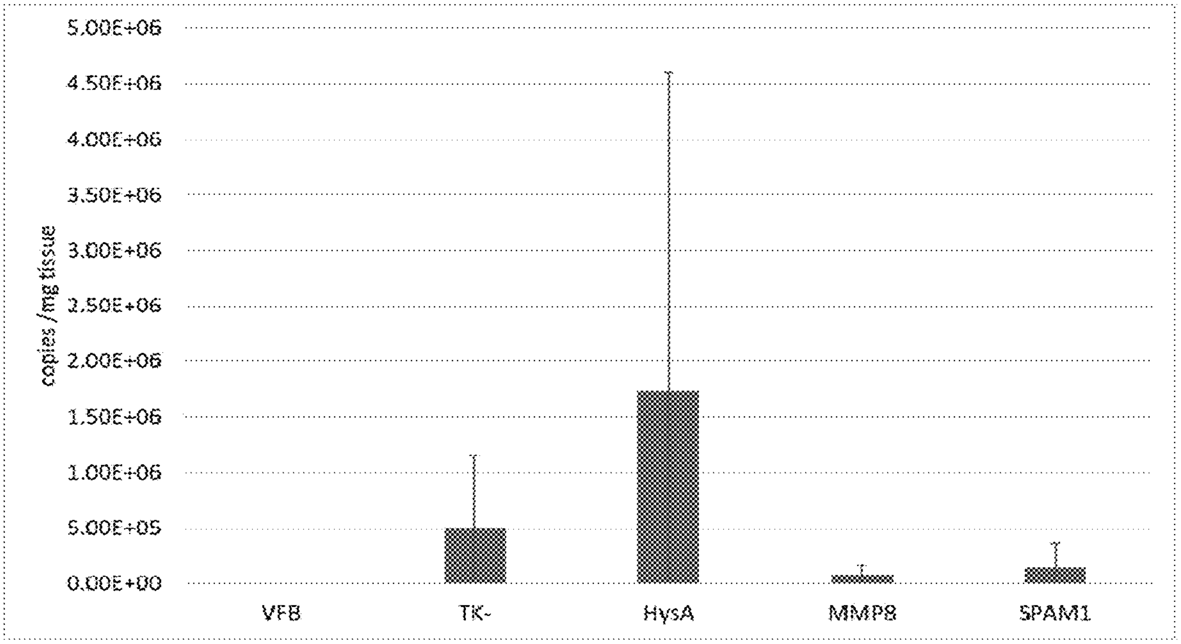
FIG. 20 shows the effect of expression of HysA on delivery of modified vaccinia virus to tumors. The viruses used were: (i) the TK-HysA modified virus (ii) the TK-MMP8 modified virus, (iii) the TK-PH20-expressing modified virus, (iv) the TK- modified virus without an exogenous enzyme added, and (v) vehicle formulated buffer (VFB). BALB/c mice bearing RENCA tumors subcutaneously were treated with a single intravenous injection ($1\times10^7$ PFU) of one of the viruses. Tumors were harvested 24 hours later, and the number of viral genomes per milligram of tissue quantified by qPCR.

Additional experiments were performed using the following viruses: (i) the TK-HysA modified virus (ii) the TK-MMP8 modified virus, (iii) the TK-PH20-expressing modified virus described above (TK-PH20/TK-SPAM1), (iv) the TK- modified virus without an exogenous enzyme added, and (v) a vehicle formulated buffer (VFB). BALB/c mice bearing RENCA tumors subcutaneously were treated with a single intravenous injection ($1\times10^7$ PFU) of one of the five viruses. Tumors were harvested 24 hours later, and the number of viral genomes per milligram of tissue quantified by qPCR (FIG. 20). Higher numbers of TK-HysA genomes were found in the tumors compared to the other viruses, suggesting that HysA expression can result in enhanced delivery of a modified vaccinia virus to tumors.

Figure 21:
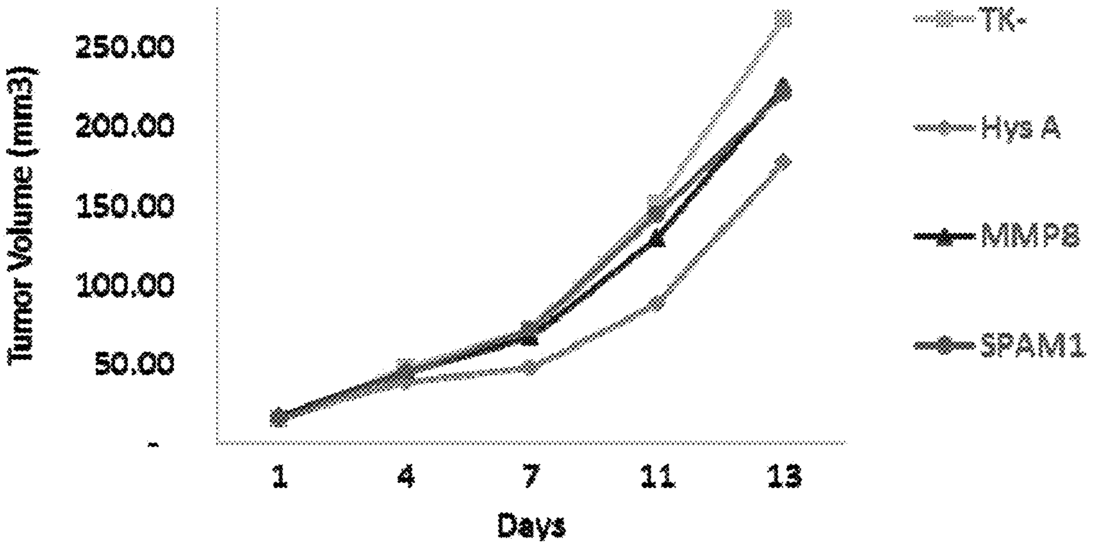
FIG. 21 shows the effect of a modified vaccinia virus having a deletion of TK- and an insertion of an exogenous nucleic acid encoding HysA, MMP8, or PH20 (labeled in FIG. 21 as SPAM1) on tumor growth. BALB/c mice bearing RENCA tumors subcutaneously were treated with one intratumoral injection ($1\times10^7$ PFU) of the TK-HysA, TK-MMP8, TK-PH20, or TK-modified virus, and tumor volume was monitored.
Figure 22A:
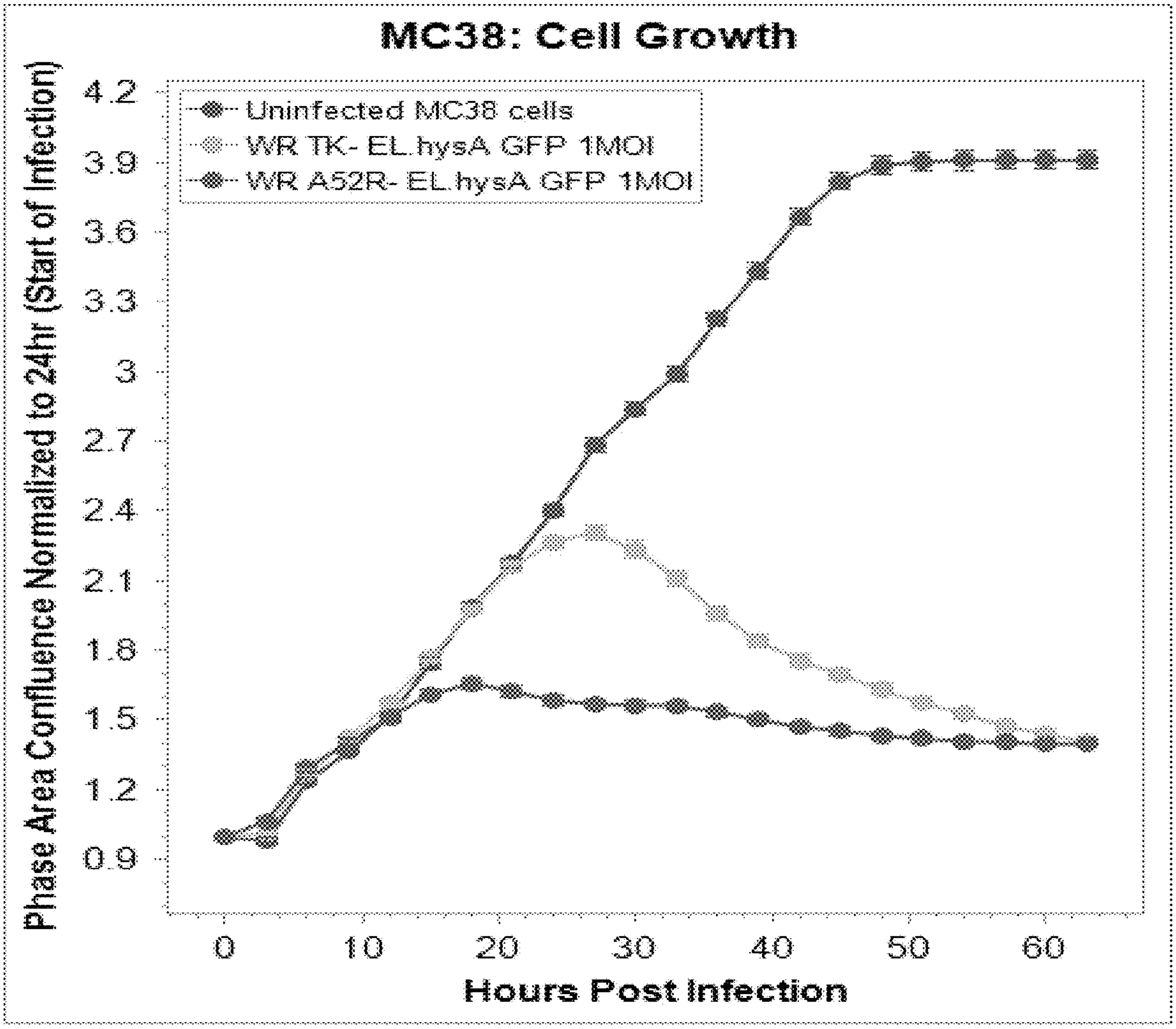
FIGS. 22A-22D shows that modified vaccinia viruses having a deletion of TK or A52R and an insertion of an exogenous nucleic acid encoding HysA infect cultures of MC38 and LLC cancer cells, replicate, spread, and prevent expansion of the cancer cells. LLC or MC38 cells were seeded in a 96-well plate at a density of $5\times10^3$ cells per well. The following day, cells were infected with different GFP-expressing viruses at a MOI of 1 and imaged using IncuCyte to measure phase confluence (FIG. 22A and FIG. 22C) and GFP area (FIG. 22B and FIG. 22D).
Figure 22B:
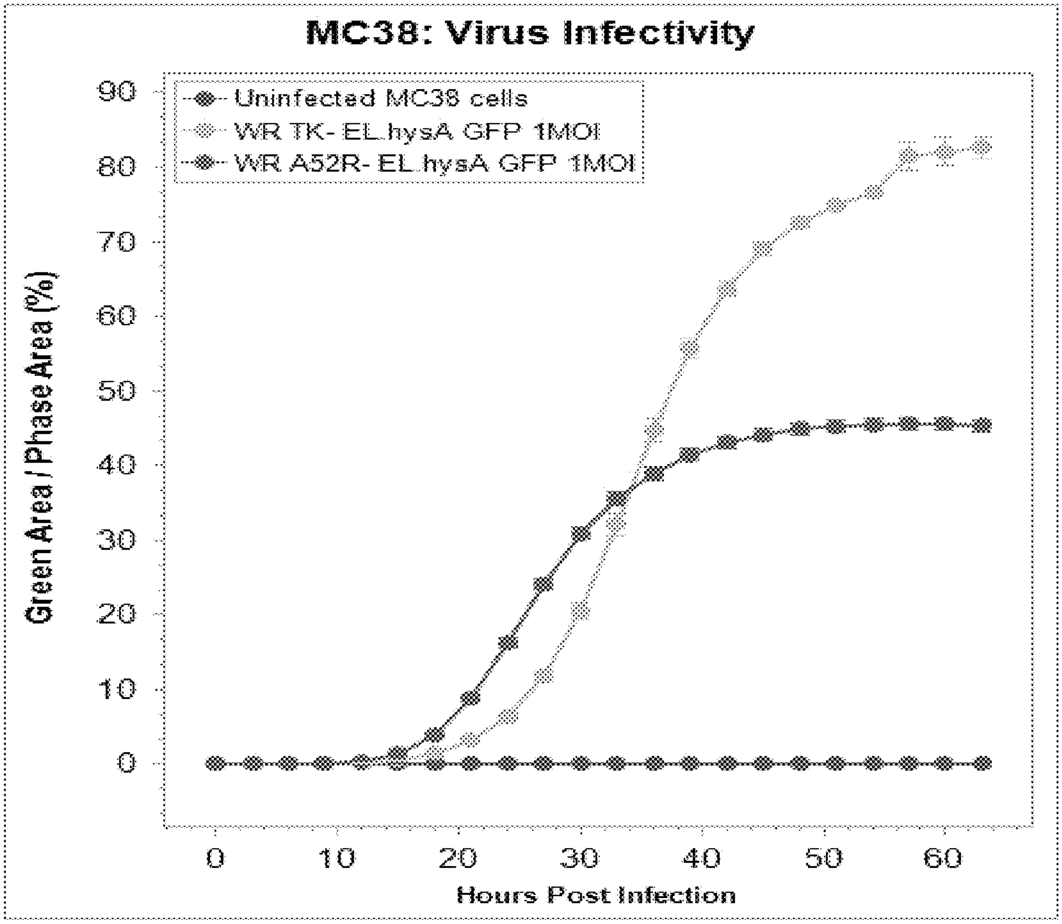
Figure 22C:
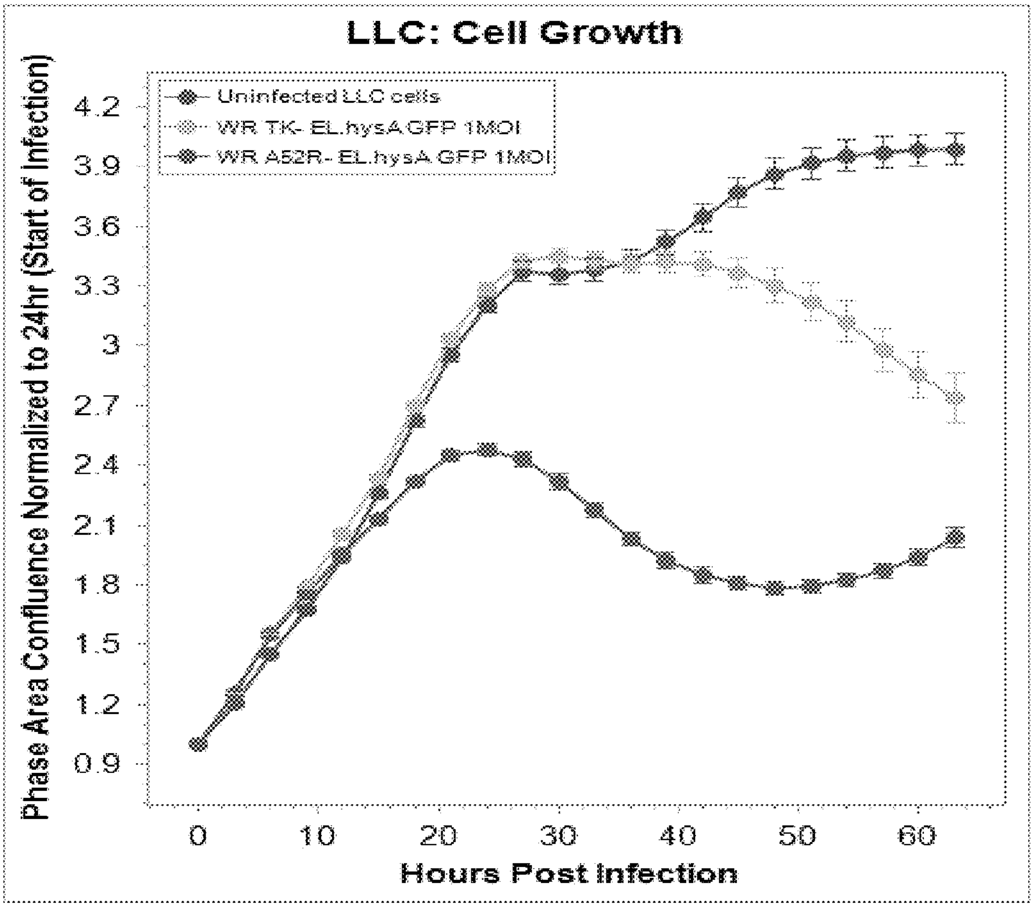
Figure 22D:
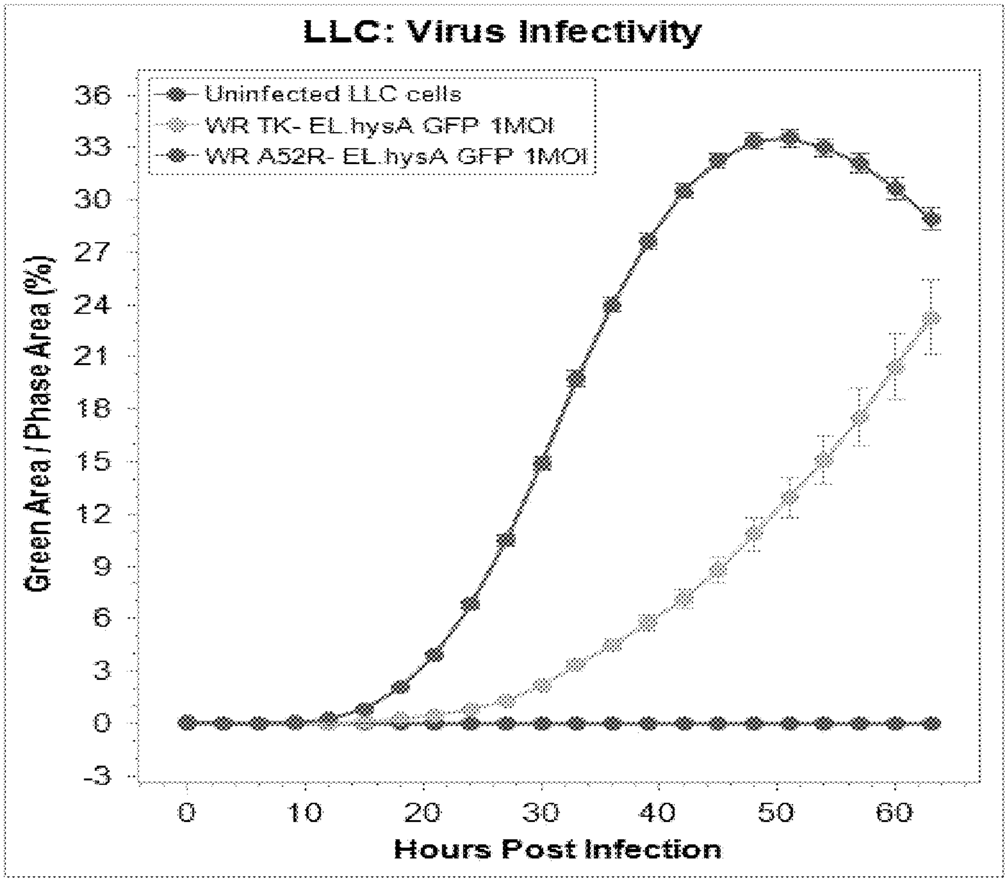

In another experiment, BALB/c mice bearing RENCA tumors subcutaneously were treated with one intratumoral injection ($1\times10^7$ PFU) of the TK-HysA, TK-MMP8, TK-PH20 (labeled in FIG. 21 as SPAM1), or TK- modified virus, and tumor volume was monitored as described above. Intratumorally-delivered TK-HysA, TK-MMP8 and TK-PH20 delayed tumor growth more the TK- virus, suggesting that expression of HysA, MMP8 or PH20 can enhance the anti-tumoral efficacy of oncolytic viruses (FIG. 21).

To further investigate the potential utility of HysA in oncolytic viruses, modified viruses were generated wherein the A52R gene was deleted, and an exogenous nucleic acid encoding HysA inserted to the A52R locus (A52R− HysA) (labeled in FIG. 22A-D as WR. A52R− EL hysA GFP 1MOI). Like the TK- HysA (labeled in FIG. 22A-D as WR. TK- EL hysA GFP 1MOI) modified virus, the A52R-HysA modified virus successfully spread in cultures of LLC or MC38 cancer cells, and limited expansion of the cancer cells (FIGS. 22A-22D). These results further support a role for HysA in enhancing oncolytic viral replication, spread, and cancer cell killing, and demonstrate that modified viruses with A52R deleted can be used as onclytic viruses.

Collectively, these data demonstrate that expression of an extracellular matrix-degrading enzyme such as PH20, HysA, or MMP8 can enhance the replication, spread, cancer killing, and therapeutic efficacy of oncolytic viruses.

Example 4: Exemplary Vaccinia Virus Having an Exemplary Modified VH1 Gene Shows Enhanced Therapeutic Effects in Murine Tumor Models The aim of this study was to explore the effects of an exemplary modified vaccinia virus according to this disclosure, where the vaccinia virus VH1 gene was replaced with a mutated VH1 gene from a different poxvirus, in murine tumor models, in comparison with vaccinia viruses that do not have the exemplary modifications.

Figure 15:
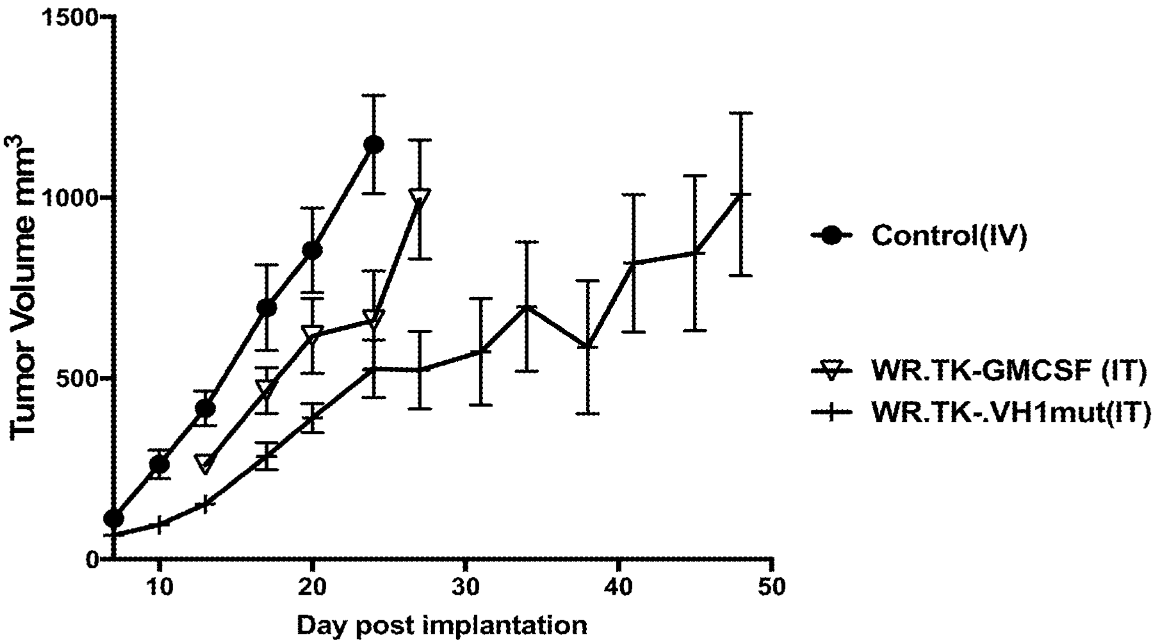
FIG. 15 shows the effects of an exemplary modified vaccinia virus having a modified VH1 gene on tumor growth. The graph quantifies the relative tumor volume in the mice treated with a control sham intravenously (IV), a modified vaccinia virus where the TK gene was deleted and which has an exemplary exogenous nucleic acid that codes for GMCSF (WR.TK-GMCSF) intratumorally (IT), or a modified vaccinia virus where the TK gene was deleted and which has a modified VH1 gene (WR.TK-.VH1mut) intratumorally, over the days after the tumor implantation.

In one experiment, BALB/c mice bearing RENCA tumors subcutaneously were treated with a single intratumoral injection ($10\times10^7$ PFU) of WR.TK-GMCSF virus, WR.TK-VH1mut virus, or sham control. In this case, the WR.TK-VH1mut virus had TK gene deleted and VH1 gene replaced with a VH1 gene from a different species of poxvirus, which was also modified with certain mutations to be more active. The WR.TK-GMCSF virus had TK gene deleted and had an exogenous nucleic acid encoding GMCSF, but had no modification of VH1 gene. Tumor volume growth was monitored as shown in FIG. 15 over the time after the virus injection by caliper measurement. WR.TK-VH1mut virus significantly delayed the tumor growth as compared to both other two groups, suggesting that the exemplary modifications of the viral VH1 gene can result in enhanced therapeutic effects against the tumor.

Example 5: Clinical Study of an Exemplary Modified Vaccinia Virus in Patients with a Metastatic Cancer A Phase 1B/2, open-label, study of an exemplary vaccinia virus (WR.TK-PH20.CXCR4) as disclosed herein is carried out in patients with a metastatic cancer.

Study Design:

The study is an open-label, Phase 1B/2 study evaluating the modified vaccinia virus WR.TK-PH20.CXCR4 in patients with a metastatic cancer. The study has 2 phases: a Dose Escalation/Confirmation Phase (Phase 1b) and an Expansion Phase (Phase 2), with the Expansion Phase utilizing a Simon 2-stage design for each cohort.

The modified vaccinia virus WR.TK-PH20.CXCR4 is a Western Reserve vaccinia virus, comprising a deletion of TK gene, an exogenous nucleic acid coding for PH20 and CXCR4. As implicated in animal studies, the deletion of TK and expression of PH20 and CXCR4 in vaccinia virus can result in greater therapeutic effects against cancer.

Phase 1B (Dose Escalation Phase)

Objectives:

Dose

Determine the dose-limiting toxicities (DLT) and maximum tolerated dose (MTD) or recommended Phase 2 dose (RP2D) of WR.TK-PH20.CXCR4 virus.

Evaluate safety and the tolerability of WR.TK-PH20.CXCR4 virus, as measured by clinical adverse events (AEs) and laboratory parameters.

The starting dose (dose level 1) for WR.TK-PH20.CXCR4 virus is up to $5\times10^9$ PFU by intravenous injection once.

If dose level 1 is not tolerated, dose level −1 for WR.TK-PH20.CXCR4 virus is set at up to $5\times10^7$ PFU once.

Each dose level in the dose escalation phase enrolls between 6 and 12 evaluable patients.

TABLE 1

Dose Escalation Schematic

| Cohort | Number of Subjects | Exemplary WR.TK-PH20.CXCR4 Dose |
|---|---|---|
| −1 | 6-12 | $5X10^9$ PFU |
| 1 | 6-12 | $5X10^8$ PFU |

Safety

Safety is assessed during the study by documentation of AEs, clinical laboratory tests, physical examination, vital sign measurements, electrocardiograms (ECGs), and other relevant procedures.

Any detected cumulative toxicity may require later dose reductions and/or other changes to the dosing schedule, as appropriate, including further refinement of the RP2D.

If the dose of up to $5\times10^9$ PFU exceeds the MTD, then a lower dose is evaluated. Toxicities are assessed by the study Investigator using the United States (US) National Cancer Institute (NCI) Common Terminology Criteria for Adverse Events (CTCAE), version 4.03. The decision regarding whether to proceed to the next dose level is made by the Medical Monitor in consultation with the study Investigators after the majority of the safety assessments for each cohort are completed.

After completion of the Dose Escalation/Confirmation Phase of the study, with identification of the MTD/RP2D, the Phase 2 portion of the study commences.

Phase 2

Phase 2 (Expansion): In the Expansion Phase, WR.TK-PH20.CXCR4 virus is evaluated using the RP2D identified in the Dose Escalation/Confirmation Phase in patients with a metastatic cancer. In the phase 2 component, patients with the metastatic cancer are randomized in a 2:1 ratio to receive WR.TK-PH20.CXCR4 virus (at the RP2D) or placebo. The primary endpoint of this randomized component is progression free survival (PFS) as assessed by iRECIST. Secondary endpoints include durable remission rate (DRR), treatment free interval (TFI), quality of life (QoL), overall response rate (ORR), overall survival (OS), and safety. The sample size in the Phase 2 component is 100-150 patients, which can result in 90% power with a one-sided p=0.1 to detect a PFS benefit with a hazard ratio (HR) of about 0.5. The duration of treatment for the test arm is 6 months, 9 months, 12 months, or 18 months, and that for the control arm is 4-6 months. Accrual is estimated to take 12 months, and the duration of the trial is projected to be 2-3 years.

Example 6: Clinical Study of an Exemplary Modified Vaccinia Virus in Patients with a Cancer A Phase 1B/2, open-label, study of an exemplary vaccinia virus (WR.TK-PH20.CXCR4) as disclosed herein is carried out in patients with a cancer.

Study Design:

The study is an open-label, Phase 1B/2 study evaluating the modified vaccinia virus WR.TK-PH20.CXCR4 in patients with a cancer. The study has 2 phases: a Dose Escalation/Confirmation Phase (Phase 1b) and an Expansion Phase (Phase 2), with the Expansion Phase utilizing a Simon 2-stage design for each cohort.

The modified vaccinia virus WR.TK-PH20.CXCR4 is a Western Reserve vaccinia virus, comprising a deletion of TK gene, an exogenous nucleic acid coding for PH20 and CXCR4. As implicated in animal studies, the deletion of TK and expression of PH20 and CXCR4 in vaccinia virus can result in greater therapeutic effects against cancer.

Phase 1B (Dose Escalation Phase)

Objectives:

Dose

Determine the dose-limiting toxicities (DLT) and maximum tolerated dose (MTD) or recommended Phase 2 dose (RP2D) of WR.TK-PH20.CXCR4 virus.

Evaluate safety and the tolerability of WR.TK-PH20.CXCR4 virus, as measured by clinical adverse events (AEs) and laboratory parameters.

The starting dose (dose level 1) for WR.TK-PH20.CXCR4 virus is up to $5\times10^9$ PFU by intravenous injection once.

If dose level 1 is not tolerated, dose level −1 for WR.TK-PH20.CXCR4 virus is set at up to $5\times10^7$ PFU once.

Each dose level in the dose escalation phase enrolls between 6 and 12 evaluable patients.

TABLE 2

| Dose Escalation Schematic | | |
|---|---|---|
| Cohort | Number of Subjects | WR.TK-PH20.CXCR4 Dose |
| −1 | 6-12 | $5X10^9$ PFU |
| 1 | 6-12 | $5X10^8$ PFU |

Safety

Safety is assessed during the study by documentation of AEs, clinical laboratory tests, physical examination, vital sign measurements, electrocardiograms (ECGs), and other relevant procedures.

Any detected cumulative toxicity may require later dose reductions and/or other changes to the dosing schedule, as appropriate, including further refinement of the RP2D.

If the dose of up to $5\times10^9$ PFU exceeds the MTD, then a lower dose is evaluated. Toxicities are assessed by the study Investigator using the United States (US) National Cancer Institute (NCI) Common Terminology Criteria for Adverse Events (CTCAE), version 4.03. The decision regarding whether to proceed to the next dose level is made by the Medical Monitor in consultation with the study Investigators after the majority of the safety assessments for each cohort are completed.

After completion of the Dose Escalation/Confirmation Phase of the study, with identification of the MTD/RP2D, the Phase 2 portion of the study commences.

Phase 2

Phase 2 (Expansion): In the Expansion Phase, WR.TK-PH20.CXCR4 virus is evaluated using the RP2D identified in the Dose Escalation/Confirmation Phase in patients with a cancer. In the phase 2 component, patients with the cancer are randomized in a 2:1 ratio to receive WR.TK-PH20.CXCR4 virus (at the RP2D) or placebo. The primary endpoint of this randomized component is progression free survival (PFS) as assessed by iRECIST. Secondary endpoints include durable remission rate (DRR), treatment free interval (TFI), quality of life (QoL), overall response rate (ORR), overall survival (OS), and safety. The sample size in the Phase 2 component is 100-150 patients, which can result in 90% power with a one-sided p=0.1 to detect a PFS benefit with a hazard ratio (HR) of about 0.5. The duration of treatment for the test arm is 6 months, 9 months, 12 months, or 18 months, and that for the control arm is 4-6 months. Accrual is estimated to take 12 months, and the duration of the trial is projected to be 2-3 years.

Example 7: Exemplary Vaccinia Viruses with Exemplary Mutations to Promote NK Cell Activity Show Enhanced Therapeutic Effects in Murine Tumor Models In order to test whether oncolytic viruses with mutations designed to promote NK cell activity displayed anti-cancer effects, the following modified viruses were generated: (i) a virus with K7R deleted, and exogenous nucleic acids encoding both IL15 and CCL5 inserted, referred to as K7R− IL15 CCL5, (ii) a virus with TK deleted, and an exogenous nucleic acid encoding LIGHT inserted, referred to as TK-LIGHT, (iii) a virus with TK deleted, and exogenous nucleic acids encoding both ITAC and fractalkine (also known as CX3CL1) inserted, referred to as TK-ITAC fractalkine, (iv) a virus with A52R deleted, and exogenous nucleic acids encoding both IL15 and IL15-Rα inserted, referred to as A52R− IL15/IL15-Rα, and (v) a virus with TK deleted, A52R deleted, and exogenous nucleic acids encoding ITAC, LIGHT, IL15, and IL15Rα inserted, referred to as TK- ITAC LIGHT A52R− IL15/IL15-Ra.

Figure 23:
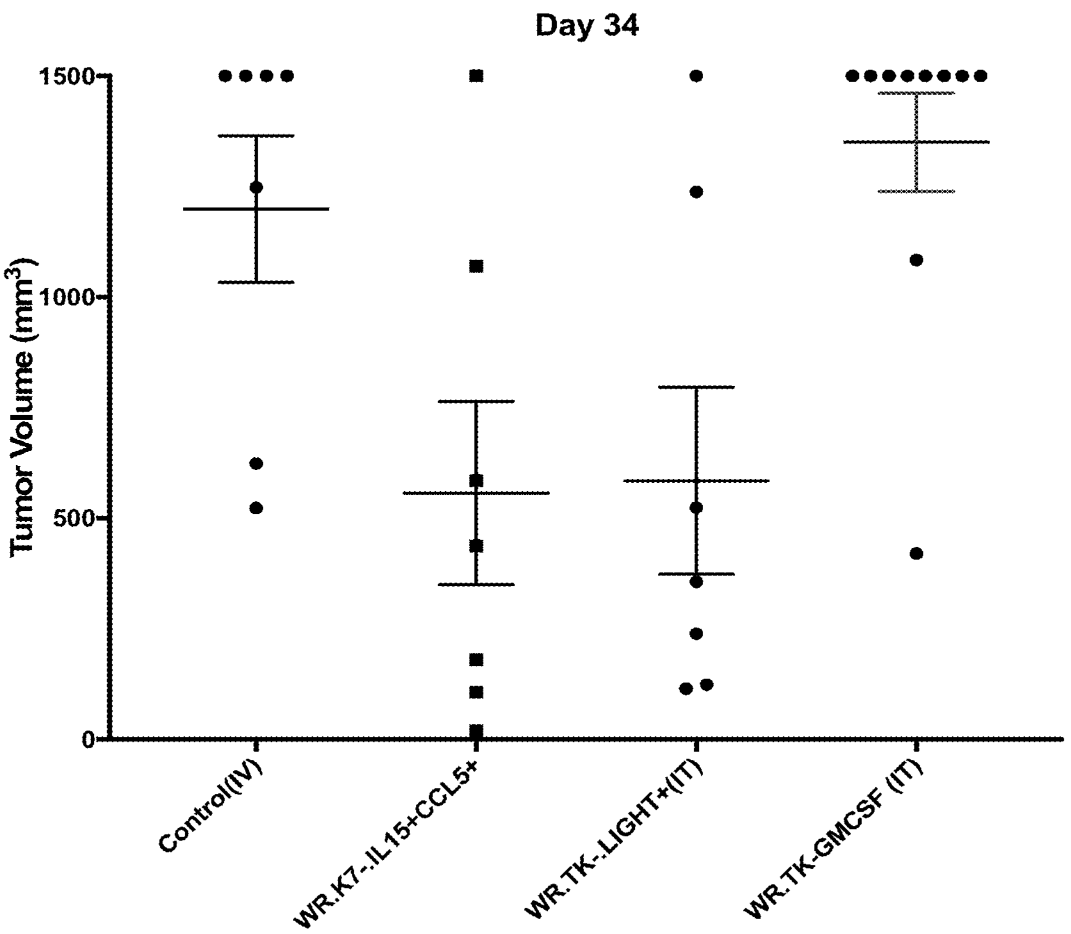
FIG. 23 shows that exemplary vaccinia viruses with exemplary mutations to promote NK cell activity show enhanced therapeutic effects in murine tumor models. BALB/c mice bearing RENCA tumors subcutaneously were treated with a single intratumoral injection ($1\times10^8$PFU) of K7R− IL15+ CCL5+, TK-LIGHT+, or TK-GMCSF+. Tumor volume was quantified on day 34 after treatment.

In one experiment, BALB/c mice bearing RENCA tumors subcutaneously were treated with a single intratumoral injection ($1\times10^8$ PFU) of K7R− IL15+ CCL5+, TK-LIGHT+, or TK-GMCSF+ viruses. Control mice received an intravenous injection of a control buffer. Tumor volume was quantified on day 34 after treatment. Tumor volume was smaller in mice having received the K7R-IL15+ CCL5+ or TK-LIGHT+ modified viruses, suggesting that mutations in oncolytic viruses designed to promote NK cell activity can result in enhanced anti-cancer therapeutic effects (FIG. 23).

Figure 24:
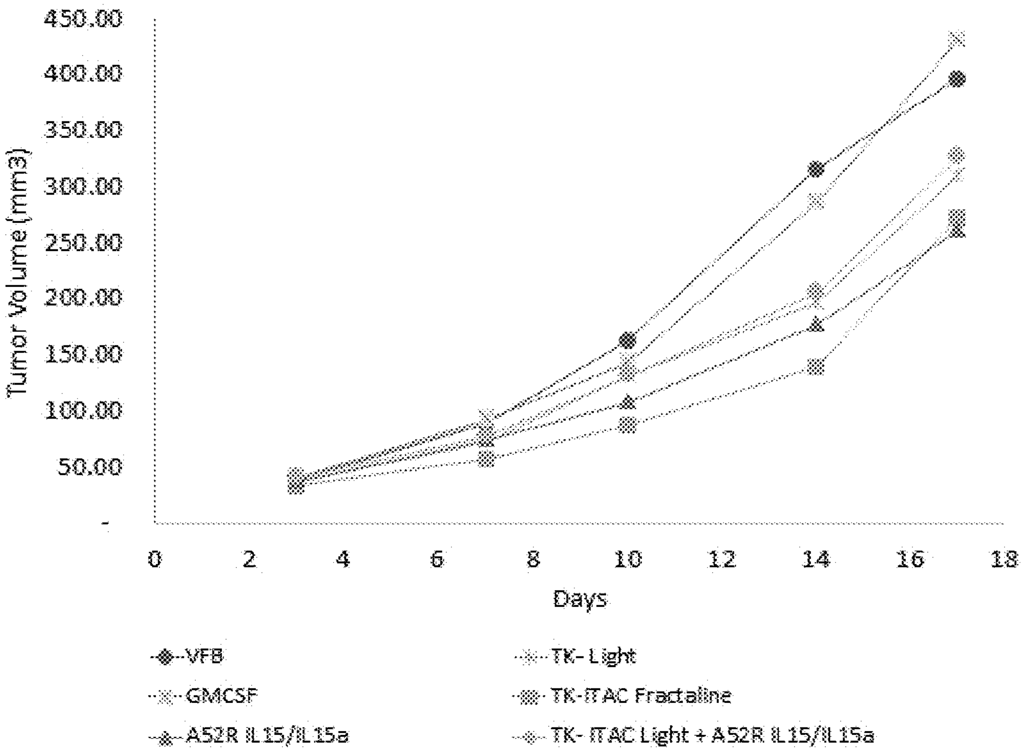
FIG. 24 shows that exemplary vaccinia viruses with exemplary mutations to promote NK cell activity show enhanced therapeutic effects in murine tumor models. In another experiment, BALB/c mice bearing RENCA tumors subcutaneously were treated with a single intratumoral injection ($1\times10^7$ PFU) of TK-LIGHT+, TK-GMCSF+, TK-ITAC+ fractalkine (CX3CL1)+, A52R− IL15+IL15A+, TK-ITAC+ LIGHT+A52R− IL15+IL15A+, or a vehicle formulated buffer, termed VFB, and tumor volume was monitored over time.

In another experiment, BALB/c mice bearing RENCA tumors subcutaneously were treated with a single intratumoral injection ($1\times10^7$ PFU) of TK-LIGHT+, TK-GMCSF+, TK-ITAC+ fractalkine+, A52R− IL15+/IL15R-α+, TK- ITAC+ LIGHT+A52R− IL15+/IL15-Rα, or a vehicle formulated buffer, termed VFB, and tumor volume was monitored over time as described above. Intratumorally-delivered TK-LIGHT+, TK-ITAC+ fractalkine+, A52R− IL15+/IL15-Rα, and TK- ITAC+ LIGHT+A52R− IL15+/IL15-Rα+ delayed tumor growth, suggesting that mutations in oncolytic viruses designed to promote NK cell activity resulted in enhanced therapeutic effects against tumor (FIG. 24).

Figure 25A:
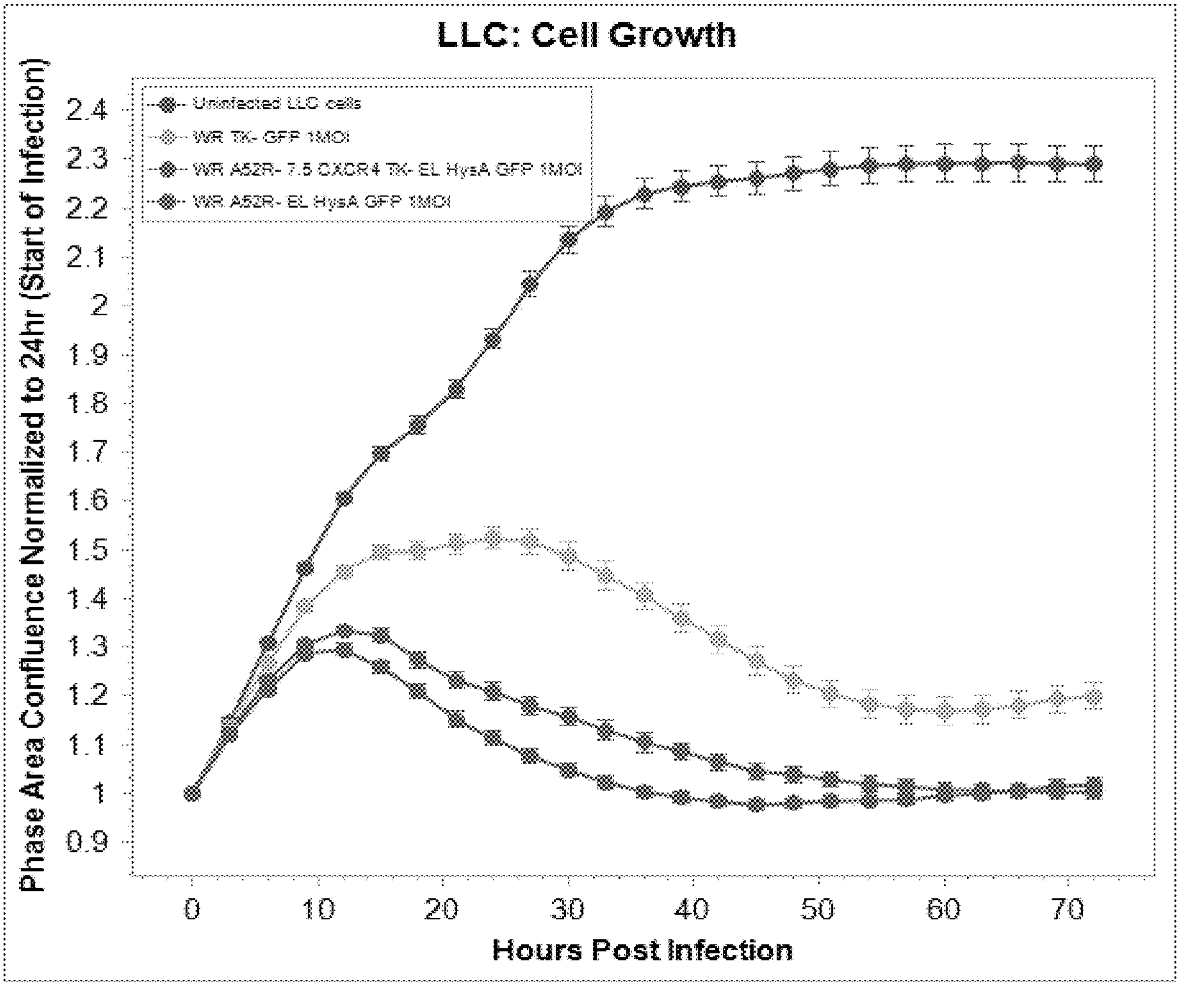
FIGS. 25A-25B shows that an exemplary vaccinia virus with exemplary exogenous nucleic acids encoding a chemokine receptor and an extracellular-matrix-degrading enzyme show spread between and killing of cancer cells. LLC cells were seeded in a 96-well plate at a density of $5\times10^3$ cells per well. The next day, cells were infected with different viruses at a MOI of 1 and imaged using IncuCyte to measure phase confluence (FIG. 25A) and GFP area (FIG. 25B).
Figure 25B:
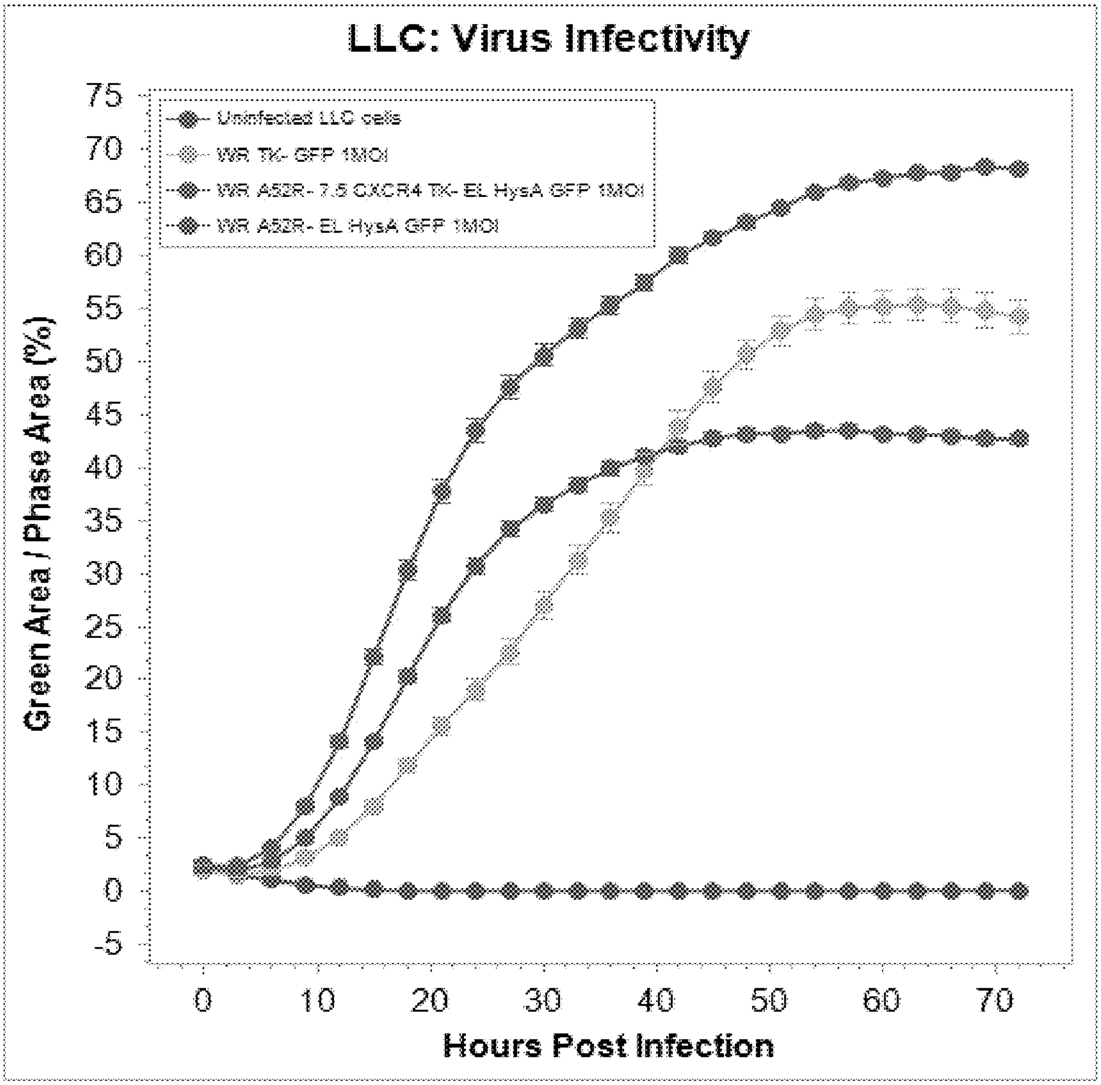

Example 8: Exemplary Vaccinia Virus with Exemplary Exogenous Nucleic Acids Encoding a Chemokine Receptor and an Extracellular Matrix-Degrading Enzyme Shows Spread Between and Killing of Cancer Cells In order to test the feasibility of combining elements of the modified oncolytic viruses disclosed above, a modified virus was developed wherein the A52R gene and TK gene were deleted, and exogenous nucleic acids encoding HysA and CXCR4 were inserted (TK- HysA A52R− CXCR4). LLC cancer cells in culture were infected with the TK- (labeled in FIGS. 25A-25B as WR TK- GFP 1MOI), A52R-HysA (labeled in FIGS. 25A-25B as WR A52R− EL HysA GFP 1MOI), or TK- HysA A52R− CXCR4 (labeled in FIGS. 25A-25B as WR A52R− 7.5 CXCR4 TK- EL HysA) modified viruses, each of which also expressed GFP. The A52R-HysA and TK- HysA A52R− CXCR4 viruses were capable of spreading between cancer cells and reducing cancer cell expansion (FIGS. 25A-25B). These data provide a non-limiting example demonstrating that oncolytic viruses comprising multiple modified elements disclosed herein can be generated, and can have anti-cancer activity, including spread between and killing of cancer cells.

Figure 26A:
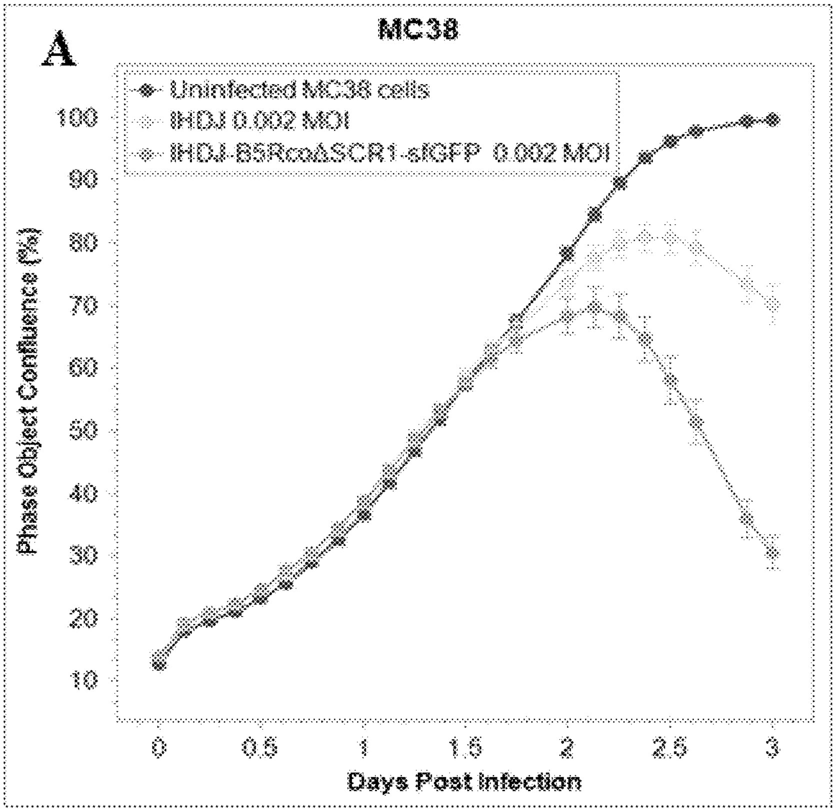
FIGS. 26A-26D show that an exemplary modified high EEV-producing vaccinia virus having an exemplary deletion of SCR1 shows spread between and killing of cancer cells. A modified IHDJ virus was developed wherein the neutralizing antibody binding site on the surface of the EEV (B5R SCR1) was deleted (IHDJ-B5RcoΔSCR1). MC38 or HCT116 cells were seeded in a 96-well plate at a density of $5\times10^3$ cells per well. The following day, cells were infected with different viruses at a MOI of 0.002 and imaged using IncuCyte to measure phase confluence, as shown in FIG. 26A (MC38 cells) and FIG. 26B (HCT116 cells). Results of a plaque assay demonstrating the ability of the IHDJ and IHDJ-B5RcoΔSCR1 viruses to spread between and kill cancer cells is shown in FIG. 26C. Results of a comet tail assay demonstrating the ability of the WR IHDJ and IHDJ-B5RcoΔSCR1 viruses to spread between and kill cancer cells is shown in FIG. 26D.
Figure 26B:
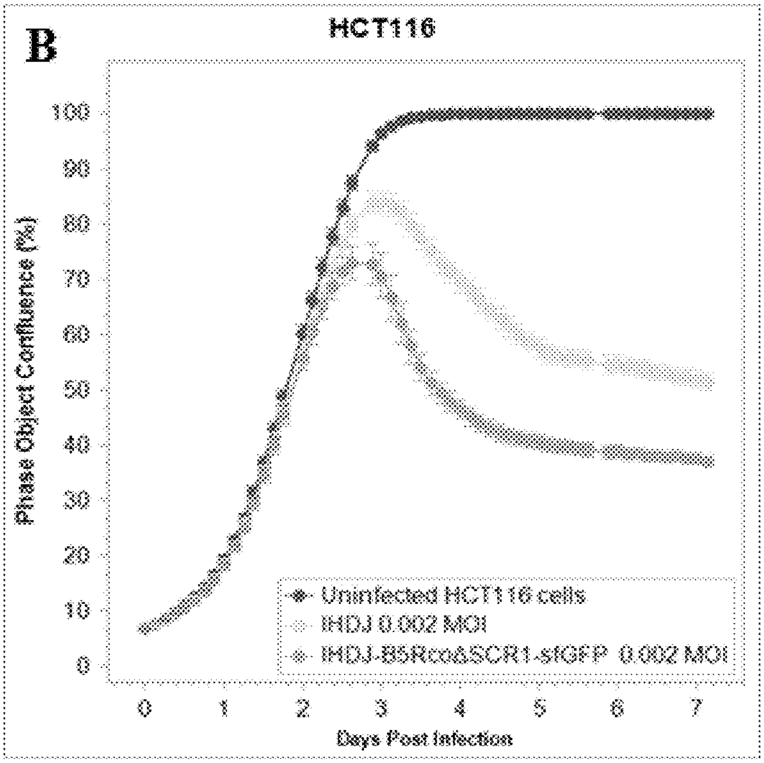
Figure 26C:
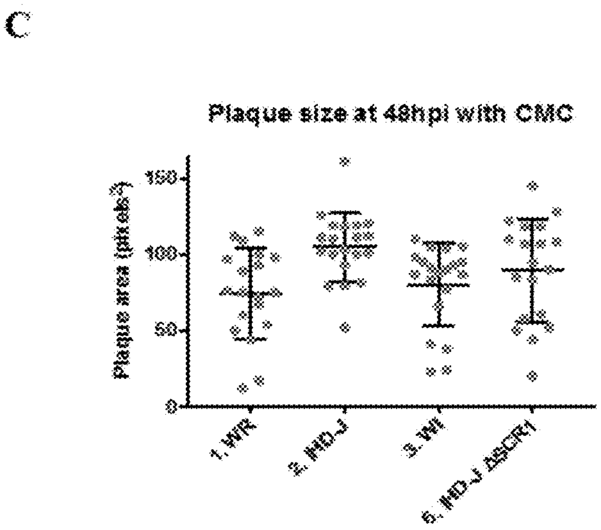
Figure 26D:
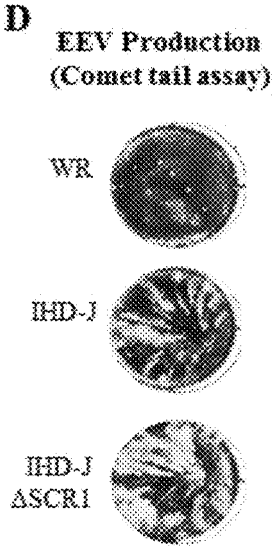

Example 9: An Exemplary Modified High EEV-Expressing Vaccinia Virus Having an Exemplary Deletion of SCR1 Shows Spread Between and Killing of Cancer Cells IHDJ was selected as an exemplary high EEV-producing virus to be evaluated for oncolytic potential. A modified IHDJ virus was developed wherein the neutralizing antibody binding site on the surface of the EEV (B5R SCR1) was deleted (IHDJ-B5RcoΔSCR1). Infection of cultures of MC38 and HCT116 cancer cells demonstrated that the IHDJ and IHDJ-B5RcoΔSCR1 (both expressing GFP) were capable of spreading between cancer cells and reducing cancer cell expansion (FIGS. 26A-26B). A plaque assay further supported the ability of the IHDJ and IHDJ- B5RcoΔSCR1 viruses to spread between and kill cancer cells (FIG. 26C). In another experiment, a comet tail assay was performed, wherein cancer cell monolayers were infected at a low multiplicity of infection and incubated under liquid media. In this assay, spread of the virus results in elongated "comet tail"-shaped plaques. The IHDJ and IHDJ-B5RcoΔSCR1 viruses produced prominent comet tails, consistent with effective EEV production (FIG. 26D). These experiments demonstrate that high EEV-expressing vaccinia viruses, including an exemplary modified virus with the neutralizing antibody binding site on the surface of the EEV deleted, can have anti-cancer activity, including spread between and killing of cancer cells.

Exemplary sequences for the viral backbone genes and viral proteins are provided in Table 4. Further provided are exemplary sequences for proteins expressed by various exogenous nucleic acid sequences that can be inserted into the modified oncolytic viruses described herein. In some cases, the above described viral backbones genes and viral proteins, in the modified oncolytic viruses described herein, can comprise sequences that are about 70%, about 75%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identical to the exemplary sequences of viral backbones genes and viral proteins provided in Table 4. In some cases, the above described proteins expressed from the exogenous nucleic acid sequences in the modified oncolytic viruses described herein, can comprise sequences that are about 70%, about 75%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identical to the exemplary sequences of proteins provided in Table 4.

TABLE 4

| No. | PROTEIN/ NUCLIEC ACID | EXEMPLARY AMINO ACID/NUCLEIC ACID SEQUENCES |
|---|---|---|
| 1 | B5R | >tr\|Q80KX4\|Q80KX4_9POXV B5R OS = Vaccinia virus GN = B5R PE = 4 SV = 1<br>MKTISVVILLCVLPAVVYSICTVPIMNNAKLISTETSENDKOKVIFTCDOGY<br>HSLDPNAVCETDKWKYENPCKKMCIVSDYVSELYDKPLYEVNSTMILSCNGE<br>TKYFRCEEKNGNTSWNDTVICPNAECOPLOLEHGSCOPVKEKYSFGEYITIN<br>CDVGYEVIGASYISCIANSWNVIPSCOOKCDMPSLSNGLISGSTFSIGGVIH<br>LSCKSGFILIGSPSSICIDGKWNPILPTCVRSNKEFDPVDDGPDDETDLSKL<br>SKDVVOYEQEIESLEATYHIIIVALTIMGVIFLISVIVLVCSCDKNNDQYKF<br>HKLLP |
| 2 | F13L | >tr\|Q1M1R8\|Q1M1R8_9POXV EEV phospholipase OS = Vaccinia virus GN = F13L PE = 4 SV = 1<br>MWPFASVPAGAKCRLVETLPENMDFRSDHLTIFECFNEIITLAKKYIYIASF<br>CCNPLSTIRGALIFDKLKEASEKGIKIIVLLDERGKRNLGELOSHCPDINFI<br>TVNIDKKNNVGLLLGCFWVSDDERCYVGNASFIGGSIHTIKTLGVYSDYPPL<br>AIDLRRRFDIFKAFNSAKNSWLNLCSAACCLPVSTAYHIKNPIGGVFFIDSP<br>EHLLGYSRDLDTDVVIDKLRSAKTSIDIEHLAIVPITRVDGNSYYWPDIYNS<br>IIEAAINRGVKIRLLVGNWDKNDVYSMATARSLDALCVONDLSVKVFTIONN<br>TKLLIVDDEYVHITSANFDGTHYONHGFVSFNSIDKOLVSEAKKIFERDWVS<br>SHSKSLKI |
| 3 | A36R | >sp\|P68618\|A36_VACCC Protein A36 OS = Vaccinia virus (strain Copenhagen) GN = A36R PE = 3 SV = 1<br>MMLVPLITVTVVAGTILVCYILYICRKKIRTVYNDNKIIMTKLKKIKSSNSS<br>KSSKSTDSESDWEDHCSAMEQNNDVDNISRNEILDDDSFAGSLIWDNESNVM<br>APSTEHIYDSVAGSTLLINNDRNEQTIYQNTTVVINETETVEVLNEDTKQNP<br>NYSSNPFVNYNKTSICSKSNPFITELNNKFSENNPFRRAHSDDYLNKQEQDH<br>EHDDIESSWSLV |
| 4 | A34R | >sp\|P21057\|A34_VACCC Protein A34 OS = Vaccinia virus (strain Copenhagen) GN = A34R PE = 3 SV = 1<br>MKSLNRQTVSMFKKLSVPAAIMMILSTIISGIGTFLHYKEELMPSACANGWI<br>QYDKHCYLDTNIKMSTDNAVYQCRKLRARLPRPDTRHLRVLFSIFYKDYWVS<br>LKKTNNKWLDINNDKDIDISKLTNFKQLNSTTDAEACYIYKSGKLVKTVCKS<br>TQSVLCVKKFYK |
| 5 | A33R | >tr\|Q71TT1\|Q71TT1 9POXV A33R OS = Vaccinia virus GN = A33R PE = 1 SV = 1<br>MMTPENDEEQTSVFSATVYGDKIQGKNKRKRVIGLCIRISMVISLLSMITMS<br>AFLIVRLNQCMSANEAAITDAAVAVAAASSTHRKVASSTTQYDHKESCNGLY<br>YQGSCYILHSDYQLFSDAKANCTAESSTLPNKSDVLITWLIDYVEDTWGSDG<br>NPITKTTSDYQDSDVSQEVRKYFCVKTMN |
| 6 | B8R | >sp\|P21004\|B8_VACCC Soluble interferon gamma receptor B8 OS = Vaccinia virus (strain Copenhagen) GN = B8R PE = 3 SV = 1<br>MRYIIILAVLFINSIHAKITSYKFESVNFDSKIEWTGDGLYNISLKNYGIKT<br>WQTMYTNVPEGTYDISAFPKNDFVSFWVKFEQGDYKVEEYCTGLCVEVKIGP<br>PTVTLTEYDDHINLYIEHPYATRGSKKIPIYKRGDMCDIYLLYTANFTFGDS<br>EEPVTYDIDDYDCTSTGCSIDFATTEKVCVTAQGATEGFLEKITPWSSEVCL<br>TPKKNVYTCAIRSKEDVPNFKDKMARVIKRKFNKQSQSYLTKFLGSTSNDVT<br>TFLSMLNLTKYS |

TABLE 4-continued

| No. | PROTEIN/ NUCLIEC ACID | EXEMPLARY AMINO ACID/NUCLEIC ACID SEQUENCES |
|---|---|---|
| 7 | B18R | >tr\|Q9DUN2\|Q9DUN2_9POXV Interferon-alpha/beta receptor OS = Vaccinia virus GN = B18R PE = 4 SV = 1 MTMKMMVHIYFVSLSLLLLLFHSYAIDIENEITEFFNKMRDTLPAKDSKWLN PACMFGGTMNDIAALGEPFSAKCPPIEDSLLSHRYKDYVVKWERLEKNRRRQ VSNKRVKHGDLWIANYTSKFSNRRYLCTVTTKNGDCVQGIVRSHIRKPPSCI PKTYELGTHDKYGIDLYCGILYAKHYNNITWYKDNKEINIDDIKYSQTGKKL IIHNPELEDSGRYDCYVHYDDVRIKNDIVVSRCKILTVLPSQDHRFKLKRNC GYASN |
| 8 | SPI-1 | >sp\|P15058\|SPI1_VACCW Serine proteinase inhibitor 1 OS = Vaccinia virus (strain Western Reserve) GN = SPI-1 PE = 2 SV = 1 MDIFKELILKHTDENVLISPVSILSTLSILNHGAAGSTAEQLSKYIENMNEN TPDDNNDMDVDIPYCATLATANKIYGSDSIEFHASFLQKIKDDFQTVNFNNA NQTKELINEWVKTMTNGKINSLLTSPLSINTRMTVVSAVHFKAMWKYPFSKH LTYTDKFYISKNIVTSVDMMVSTENNLQYVHINELFGGFSIIDIPYEGNSSM VIILPDDIEGIYNIEKNITDEKFKKWCGMLSTKSIDLYMPKFKVEMTEPYNL VPILENLGLTNIFGYYADFSKMCNETITVEKFLHTTFIDVNEEYTEASAVTG VFMTNFSMVYRTKVYINHPFMYMIKDNTGRILFIGKYCYPQ |
| 9 | SPI-2 | >sp\|P15059\|SPI2_VACCW Serine proteinase inhibitor 2 OS = Vaccinia virus (strain Western Reserve) GN = SPI-2 PE = 2 SV = 2 MDIFREIASSMKGENVFISPASISSVLTILYYGANGSTAEQLSKYVEKEENM DKVSAQNISFKSINKVYGRYSAVFKDSFLRKIGDKFQTVDFTDCRTIDAINK CVDIFTEGKINPLLDEPLSPDTCLLAISAVYFKAKWLTPFEKEFTSDYPFYV SPTEMVDVSMMSMYGKAFNHASVKESFGNFS11ELPYVGDTSMMVILPDKID GLESIEQNLTDTNFKKWCNSLEATFIDVHIPKFKVTGSYNLVDTLVKSGLTE VFGSTGDYSNMCNSDVSVDAMIHKTYIDVNEEYTEAAAATCALVSDCASTIT NEFCVDHPFIYVIRHVDGKILFVGRYCSPTTNC |
| 10 | B15R | >tr\|L7QJF6\|L7QJF6_9POXV Uncharacterized protein OS = Vaccinia virus GN = B15R PE = 4 SV = 1 MTANFSTHVFSPQHCGCDRLTSIDDVRQCLTEYIYWSSYAYRNRQCAGQLYS ILLSFRDDAESVFIDIRELVKNMPWDDVKDCTEIIRCYIPDEQKTIREISAI IGLCAYAATYWGGEDHPISNSLNALFVMLEMLNYVDYNIIERRMN |
| 11 | B14R (Vaccinia virus Copenhagen strain) | >sp\|P210891B14_VACCC Protein B14 OS = Vaccinia virus (strain Copenhagen) GN = B15R PE = 3 SV = 1 MTANFSTHVFSPQHCGCDRLTSIDDVKQCLTEYIYWSSYAYRNRQCAGQLYS TLLSFRDDAELVFIDIRELVKNMPWDDVKDCTEIIRCYIPDEQKTIREISAI IGLCAYAATYWGGEDHPTSNSLNALFVMLEMLNYVDYNIIFRRMN |
| 12 | VGF | >sp\|P01136\|VGF_VACCW Pro-vaccinia growth factor OS = Vaccinia virus (strain Western Reserve) GN = VGF-1 PE = 1 SV = 1 MSMKYLMLLFAAMIIRSFADSGNAIETTSPEITNATTDIPAIRLCGPEGDGY CLHGDCIHARDIDGMYCRCSHGYTGIRCQHVVLVDYQRSENPNITTSYIPSP GIMLVLVGIIIITCCLLSVYRFIRRIKLPIQDMVVP |
| 13 | E3L | >trIQ866381Q86638 9POXV Double-stranded RNA-binding protein OS = Vaccinia virus GN = E3L PE = 1 SV = 1 MSKIYIDERSNAEIVCEAIKTIGIEGATAAQLTRQLNMEKREVNKALYDLQR SAMVYSSDDIPPRWFMTTEADEADADAMSDVIIDDVSREKSMREDHKSFDDV IPAKKIIDWKGANPVIVINEYCQIIRRDWSFRIESVGPSNSPIFYACVDIDG RVEDKADGKSKRDAKNNAAKLAVDKLLGYVIIRF |
| 14 | K3L | >sp\|P206391K3_VACCC Protein K3 OS = Vaccinia virus (strain Copenhagen) GN = K3L PE = 1 SV = 1 MLAFCYSLPNAGDVIKGRVYEKDYALYIYLFDYPHSEAILAESVKMHMDRYV EYRDKLVGKTVKVKVIRVDYTKGYIDVNYKRMCRHQ |
| 15 | A41L | >sp\|P21064\|A41_VACCC Protein A41 OS = Vaccinia virus (strain Copenhagen) GN = A41L PE = 3 SV = 1 MYSLLFIILMCIPFSFQTVYDDKSVCDSDNKEYMGIEVYVEATLDEPLRQTT CESEIHKYGASVSNGGLNISVDLLNCFLNFHTVGVYTNRDTVYAKFASLDPW TTEPINSMTHDDLVKLTEECIVDIYLKCEVDKIKDFMKTNGNRLKPRDFKTV PPSDVGSMIELQSDYCVNDVTAYVKIYDECGNIKQHSIPTLRDYFTTKNGQP RKILKKKFDNC |
| 16 | K7R | >sp\|P68467\|K7_VACCC Protein K7 OS = Vaccinia virus (strain Copenhagen) GN = K7R PE = 1 SV = 1 MATKLDYEDAVFYFVDDDKICSRDSIIDLIDEYITWRNHVIVFNKDITSCGR LYKELMKFDDVAIRYYGIDKINEIVEAMSEGDHYINFTKVHDQESLFATIGI CAKITEHWGYKKISESRFQSLGNITDLMTDDNINILILFLEKKLN |

TABLE 4-continued

| No. | PROTEIN/ NUCLIEC ACID | EXEMPLARY AMINO ACID/NUCLEIC ACID SEQUENCES |
|---|---|---|
| 17 | N1L | >sp\|P21054\|N1_VACCC Protein N1 OS = Vaccinia virus (strain Copenhagen) GN = N1L PE = 1 SV = 1<br>MRILLIRYILWRNDNDQTYYNDDFKKLMLLDELVDDGDVCILIKNMRMILSD<br>GPLLDRLNQPVNNIEDAKRMIAISAKVARDIGERSEIRWEESETILFRMIET<br>YFDDLMIDLYGEK |
| 18 | A52R | >sp\|Q01220\|A52_VACCW Protein A52 OS = Vaccinia virus (strain Western Reserve) GN = VACWR178 PE = 1 SV = 1<br>MDIKIDISISGDKFTVITRRENEERKKYLPLQKEKTIDVIKPDYLEYDDLLD<br>RDEMFTILEEYFMYRGLLGLRIKYGRLFNEIKKFDNDAEEQFGTIEELKQKL<br>RLNSEEGADNFIDYIKVQKQDIVKLIVYDCISMIGLCACVVDVWRNEKLFSR<br>WKYCLRAIKLFINDHMLDKIKSILQNRLVYVEMS |
| 19 | B5R | >NC_006998.1:168374-169327 Vaccinia virus, complete genome<br>ATGAAAACGATTTCCGTTGTTACGTTGTTATGCGTACTACCTGCTGTTGTTT<br>ATTCAACATGTACTGTACCCACTATGAATAACGCTAAATTAACGTCTACCGA<br>AACATCGTTTAATGATAAACAGAAAGTTACGTTTACATGTGATCAGGGATAT<br>CATTCTTCGGATCCAAATGCTGTCTGCGAAACAGATAAATGGAAATACGAAA<br>ATCCATGCAAAAAAATGTGCACAGTTTCTGATTACATCTCTGAATTATATAA<br>TAAACCGCTATACGAAGTGAATTCCACCATGACACTAAGTTGCAACGGCGAA<br>ACAAAATATTTTCGTTGCGAAGAAAAAAATGGAAATACTTCTTGGAATGATA<br>CTGTTACGTGTCCTAATGCGGAATGTCAACCTCTTCAATTAGAACACGGATC<br>GTGTCAACCAGTTAAAGAAAAATACTCATTTGGGGAATATATGACTATCAAC<br>TGTGATGTTGGATATGAGGTTATTGGTGCTTCGTACATAAGTTGTACAGCTA<br>ATTCTTGGAATGTTATTCCATCATGTCAACAAAAATGTGATATGCCGTCTCT<br>ATCTAATGGATTAATTTCCGGATCTACATTTTCTATCGGTGGCGTTATACAT<br>CTTAGTTGTAAAAGTGGTTTTACACTAACGGGGTCTCCATCATCCACATGTA<br>TCGACGGTAAATGGAATCCCGTACTCCCAATATGTGTACGAACTAACGAAGA<br>ATTTGATCCAGTGGATGATGGTCCCGACGATGAGACAGATTTGAGCAAACTC<br>TCGAAAGACGTTGTACAATATGAACAAGAAATAGAATCGTTAGAAGCAACTT<br>ATCATATAATCATAGTGGCGTTAACAATTATGGGCGTCATATTTTTAATCTC<br>CGTTATAGTATTAGTTTGTTCCTGTGACAAAAATAATGACCAATATAAGTTC<br>CATAAATTGCTACCGTAA |
| 20 | F13L | >NC_006998.1: c41949-40831 Vaccinia virus, complete genome<br>ATGTGGCCATTTGCATCGGTACCTGCGGGAGCAAAATGTAGGCTGGTAGAAA<br>CACTACCAGAAAATATGGATTTTAGATCCGATCATTTAACAACATTTGAATG<br>TTTTAACGAAATTATCACTCTAGCTAAGAAATATATATACATAGCATCTTTT<br>TGTTGTAATCCTCTGAGTACGACTAGGGGAGCGCTTATTTTTGATAAACTAA<br>AAGAGGCATCTGAAAAAGGGATTAAAATAATAGTTTTGCTAGATGAACGAGG<br>GAAAAGAAATCTGGGAGAGCTACAAAGTCACTGCCCGGATATAAATTTTATA<br>ACCGTTAATATAGATAAAAAAAATAATGTGGGACTACTACTCGGTTGTTTTT<br>GGGTGTCAGATGATGAAAGATGTTATGTAGGAAACGCGTCATTTACTGGAGG<br>ATCTATACATACGATTAAAACGTTAGGTGTATATTCTGATTATCCCCCGCTG<br>GCCACAGATCTTCGTAGAAGATTTGATACTTTTAAAGCCTTTAATAGCGCAA<br>AAAATTCATGGTTGAATTTATGCTCTGCGGCTTGTTGTTTGCCAGTTAGCAC<br>TGCGTATCATATTAAGAATCCTATAGGTGGAGTGTTCTTTACTGATTCTCCG<br>GAACACCTATTGGGATATTCTAGAGATCTAGATACCGATGTAGTTATTGATA<br>AACTCAAGTCGGCTAAGACTAGTATAGATATTGAACATTTGGCCATAGTTCC<br>CACTACACGTGTCGACGGTAATAGCTACTATTGGCCCGACATTTACAACTCC<br>ATTATAGAAGCAGCCATTAATAGAGGAGTTAAGATCAGACTTCTAGTTGGTA<br>ATTGGGATAAGAACGACGTATATTCTATGGCAACCGCCAGAAGTCTAGACGC<br>GTTGTGTGTTCAAAATGATCTATCTGTGAAGGTTTTCACTATTCAGAATAAT<br>ACAAAATTGTTGATAGTCGACGACGAATATGTTCATATCACTTCGGCAAATT<br>TCGACGGAACCCATTACCAAAATCACGGATTCGTCAGTTTTAATAGTATAGA<br>TAAACAGCTTGTAAGCGAGGCTAAAAAAATATTTGAGAGAGATTGGGTATCT<br>AGCCACAGTAAATCGTTAAAAATTTAA |
| 21 | A36R | >NC_006998.1:145059-145724 Vaccinia virus, complete genome<br>ATGATGCTGGTACCTCTTATCACGGTGACCGTAGTTGCGGGAACAATATTAG<br>TATGTTATATATTATATATTTGTAGGAAAAAGATACGTACTGTCTATAATGA<br>CAATAAAATTATCATGACAAAATTAAAAAAGATAAAGAGTTCTAATTCCAGC<br>AAATCTAGTAAATCAACTGATAGCGAATCAGACTGGGAGGATCACTGTAGTG<br>CTATGGAACAAAACAATGACGTAGATAATATTTCTAGGAATGAGATATTGGA<br>CGATGATAGCTTCGCTGGTAGTTTAATATGGGATAACGAATCCAATGTCATG<br>GCGCCTAGCACAGAACACATTTACGATAGTGTTGCTGGAAGCACGCTGCTAA<br>TAAATAATGATCGTAATGAACAGACTATTTATCAGAACACTACAGTAGTAAT<br>TAATGAGACGGAGACTGTTGAAGTACTTAATGAAGATACCAAACAGAATCCT<br>AACTATTCATCCAATCCTTTCGTAAATTATAATAAAACCAGTATTTGTAGCA<br>AGTCAAATCCGTTCATTACAGAACTCAACAATAAATTTAGTGAGAATAATCC<br>GTTTAGACGAGCACATAGCGATGATTATCTTAATAAGCAAGAACAAGATCAT<br>GAACACGATGATATAGAATCATCGGTCGTATCATTGGTGTGA |

TABLE 4-continued

| No. | PROTEIN/<br>NUCLIEC ACID | EXEMPLARY AMINO ACID/NUCLEIC ACID SEQUENCES |
|---|---|---|
| 22 | A34R | >NC_006998.1:143912-144418 Vaccinia virus, complete genome<br>ATGAAATCGCTTAATAGACAAACTGTAAGTAGGTTTAAGAAGTTGTCGGTGC<br>CGGCCGCTATAATGATGATACTCTCAACCATTATTAGTGGCATAGGAACATT<br>TCTGCATTACAAAGAAGAACTGATGCCTAGTGCTTGCGCCAATGGATGGATA<br>CAATACGATAAACATTGTTATTTAGATACTAACATTAAAATGTCTACAGATA<br>ATGCGGTTTATCAGTGTCGTAAATTACGAGCCAGATTGCCTAGACCGGATAC<br>TAGACATCTGAGAGTATTGTTTAGTATTTTTTATAAAGATTATTGGGTAAGT<br>TTAAAAAAGACCAATGATAAATGGTTAGATATTAATAATGATAAAGATATAG<br>ATATTAGTAAATTAACAAATTTTAAACAACTAAACAGTACGACGGATGCTGA<br>AGCGTGTTATATATACAAGTCTGGAAAACTGGTTAAAACAGTATGTAAAAGT<br>ACTCAATCTGTACTATGTGTTAAAAAATTCTACAAGTGA |
| 23 | A33R | >NC_006998.1:143331-143888 Vaccinia virus, complete genome<br>ATGATGACACCAGAAAACGACGAAGAGCAGACATCTGTGTTCTCCGCTACTG<br>TTTACGGAGACAAAATTCAAGGAAAGAATAAACGCAAACGCGTGATTGGTCT<br>ATGTATTAGAATATCTATGGTTATTTCACTACTATCTATGATTACCATGTCC<br>GCGTTTCTCATAGTGCGCCTAAATCAATGCATGTCTGCTAACGAGGCTGCTA<br>TTACTGACGCCGCTGTTGCCGTTGCTGCTGCATCATCTACTCATAGAAAGGT<br>TGCGTCTAGCACTACACAATATGATCACAAAGAAAGCTGTAATGGTTTATAT<br>TACCAGGGTTCTTGTTATATATTACATTCAGACTACCAGTTATTCTCGGATG<br>CTAAAGCAAATTGCACTGCGGAATCATCAACACTACCCAATAAATCCGATGT<br>CTTGATTACCTGGCTCATTGATTATGTTGAGGATACATGGGGATCTGATGGT<br>AATCCAATTACAAAAACTACATCCGATTATCAAGATTCTGATGTATCACAAG<br>AAGTTAGAAAGTATTTTTGTGTTAAAACAATGAACTAA |
| 24 | B8R | >NC_006998.1:170571-171389 Vaccinia virus, complete genome<br>ATGAGATATATTATAATTCTCGCAGTTTTGTTCATTAATAGTATACACGCTA<br>AAATAACTAGTTATAAGTTTGAATCCGTCAATTTTGATTCCAAAATTGAATG<br>GACTGGGGATGGTCTATACAATATATCCCTTAAAAATTATGGCATCAAGACG<br>TGGCAAACAATGTATACAAATGTACCAGAAGGAACATACGACATATCCGCAT<br>TTCCAAAGAATGATTTCGTATCTTTCTGGGTTAAATTTGAACAAGGCGATTA<br>TAAAGTGGAAGAGTATTGTACGGGACTATGCGTCGAAGTAAAAATTGGACCA<br>CCGACTGTAACATTGACTGAATACGACGACCATATCAATTTGTACATCGAGC<br>ATCCGTATGCTACTAGAGGTAGCAAAAAGATTCCTATTTACAAACGCGGTGA<br>CATGTGTGATATCTACTTGTTGTATACGGCTAACTTCACATTCGGAGATTCT<br>AAAGAACCAGTACCATATGATATCGATGACTACGATTGCACGTCTACAGGTT<br>GCAGCATAGACTTTGTCACAACAGAAAAAGTGTGCGTGACAGCACAGGGAGC<br>CACAGAAGGGTTTCTCGAAAAAATTACTCCATGGAGTTCGAAAGTATGTCTG<br>ACACCTAAAAAGAGTGTATATACATGCGCAATTAGATCCAAAGAAGATGTTC<br>CCAATTTCAAGGACAAAATGGCCAGAGTTATCAAGAGAAAATTTAATAAACA<br>GTCTCAATCTTATTTAACTAAATTTCTCGGTAGCACATCAAATGATGTTACC<br>ACTTTTCTTAGCATGCTTAACTTGACTAAATATTCATAA |
| 25 | B18R | >NC_006998.1:177306-179030 Vaccinia virus, complete genome<br>ATGAGTCGTCGTCTGATTTATGTTTTAAATATCAACCGCGAATCAACTCATA<br>AAATACAAGAGAATGAAATATATACATATTTTAGTCATTGCAATATAGACCA<br>TACTTCTACAGAACTTGATTTTGTAGTTAAAAACTATGATCTAAACAGACGA<br>CAACCTGTAACTGGGTATACTGCACTACACTGCTATTTGTATAATAATTACT<br>TTACAAACGATGTACTGAAGATATTATTAAATCATGGAGTGGATGTAACGAT<br>GAAAACCAGTAGCGGACGTATGCCTGTTTATATATTGCTTACTAGATGTTGC<br>AATATTTCACATGATGTAGTGATAGATATGATAGACAAAGATAAAAACCACT<br>TATTACATAGAGACTATTCCAACCTATTACTAGAGTATATAAAATCTCGTTA<br>CATGTTATTAAAGGAAGAGGATATCGATGAGAACATAGTATCCACTTTATTA<br>GATAAGGGAATCGATCCTAACTTTAAACAAGACGGATATACAGCGTTACATT<br>ATTATTATTTGTGTCTCGCACACGTTTATAAACCAGGTGAGTGTAGAAAACC<br>GATAACGATAAAAAAGGCCAAGCGAATTATTTCTTTGTTTATACAACATGGA<br>GCTAATCTAAACGCGTTAGATAATTGTGGTAATACACCATTCCATTTGTATC<br>TTAGTATTGAAATGTGTAATAATATTCATATGACTAAAATGCTGTTGACTTT<br>TAATCCGAATTTCGAAATATGTAATAATCATGGATTAACGCCTATACTATGT<br>TATATAACTTCCGACTACATACAACACGATATTCTTGTTATGTTAATACATC<br>ACTATGAAACAAATGTTGGAGAAATGCCGATAGATGAGCGTCGTATAATCGT<br>ATTCGAGTTTATCAAAACATATTCTACACGTCCTGCAGATTCGATAACTTAT<br>TTGATGAATAGGTTTAAAAATATAGATATTTATACCCGCTATGAAGGAAAGA<br>CATTATTACACGTAGCATGTGAATATAATAATACACACGTAATAGATTATCT<br>TATACGTATCAACGGAGATATAAATGCGTTAACCGACAATAACAAACACGCT<br>ACACAACTCATTATAGATAACAAAGAAAATTCCCCATATACCATTAATTGTT<br>TACTGTATATACTTAGATATATTGTAGATAAGAATGTGATAAGATCGTTGGT<br>GGATCAACTTCCATCTCTACCTATCTTCGATATAAAATCATTTGAGAAATTC<br>ATATCCTACTGTATACTTTTAGATGACACATTTTACAATAGACACGTTAGGA<br>ATCGCGATTCTAAAACGTATCGATACGCATTTTCAAAATACATGTCGTTTGA<br>TAAATACGATGGTATAATAACTAAATGTCATAAAGAAACAATATTGCTCAAA<br>CTATCCACTGTTCTAGACACTACACTATATGCAGTTTTAAGATGCCATAATT<br>CGAAAAAGTTAAGAAGATACCTCACCGAGTTAAAAAAATATAATAACGATAA |

TABLE 4-continued

| No. | PROTEIN/<br>NUCLIEC ACID | EXEMPLARY AMINO ACID/NUCLEIC ACID SEQUENCES |
|---|---|---|
| | | GTCCTTTAAAATATATTCTAATATTATGAATGAGAGATACCTTAATGTATAT<br>TATAAAGATATGTACGTGTCAAAGGTATATGATAAACTATTTCCTGTTTTCA<br>CAGATAAAAATTGTCTACTAACATTACTACCTTCAGAAATTATATACGAAAT<br>ATTATACATGCTGACAATTAACGATCTTTATAATATATCGTATCCACCTACC<br>AAAGTATAG |
| 26 | SPI-1 | >M24217.1 Vaccinia virus serine protease inhibitor<br>superfamily gene SPI-1<br>TCACATAATCTATTTAGAGATCGAGTCATGCACGATTATATAAGTAATACAT<br>ATATTGATCTTGAGTGTTTAGATATTATTAGATCGTTGGATGGATTCGATAT<br>CAATGGTTACTTTGAAGGACGTACACCACTTCATTGCGCTATACAACATAAC<br>TTCACTCAGATTGCTAAGTACTTATTAGATCGAGGAGCTGATATAGTCGTAC<br>CCAACACATTGATTATACATCAGTACATACAGTAAATAGCATAGATATGGAG<br>GAGGATACAAATATTTCAAATAAAGTTATAAGGTACAACACTGTCAATAATA<br>TATGGGAAACATTACCTAACTTCTGGACTGGAACTATAAATCCAGGCGTGGT<br>CTCGCATAAAGATGATATATATGTTGTATGCGACATCAAAGATGAAAAAAAT<br>GTTAAAACTTGTATATTTAGATATAACACGAATACGTATAACGGATGGGAAT<br>TGGTCACGACGACAGAAAGCAGATTATCAGCTCTGCATACTATTCTTTATAA<br>CAATACCATAATGATGTTACATTGTTATGAATCGTATATGTTACAAGATACA<br>TTTAATGTGTACACTCGCGAATGGAATCATATGTGTCATCAACATTCGAATA<br>GTTATATCATGTACAATATACTACCCATCTACTAAATATAATAGAATAAAAT<br>AAATGAGTATGATCATTTTAGATAACGATTGATTTTATCATTACCGCTTCAT<br>TCTTATATTCTTTGCTTACGGAACCTATATTTAGAAACATCTACTAACGATT<br>TTTTATGCTTGCATTATTAATGGTATGTAATATGATTGATTGTGTACGCAAT<br>ACCAATTTGTTAAGTATGAATACGGGGTACAAACATAAACTGAAGTTTAACA<br>TTATTTATTTATGATATATATCGTTATTGTTTGGTCTATACCATGGATATCT<br>TTAAAGAACTAATCTTAAAACACACGGATGAAAATGTTTTGATTTCTCCAGT<br>TTCTATTTTATCTACTTTATCTATTCTAAATCATGGAGCAGCTGGTTCTACA<br>GCTGAACAACTATCAAAATATATAGAGAATATGAATGAGAATACACCCGATG<br>ACAATAATGACATGGACGTAGATATTCCGTATTGTGCGACACTAGCTACCGC<br>AAATAAAATATACGGTAGCGATAGTATCGAGTTCCACGCCTCCTTCCTACAA<br>AAAATAAAAGACGATTTTCAAACTGTAAACTTTAATAATGCTAACCAAACAA<br>AGGAACTAATCAACGAATGGGTTAAGACAATGACAAATGGTAAAATTAATTC<br>CTTATTGACTAGTCCGCTATCCATTAATACTCGTATGACAGTTGTTAGCGCC<br>GTCCATTTTAAAGCAATGTGGAAATATCCATTTTCTAAACATCTTACATATA<br>CAGACAAGTTTTATATTTCTAAGAATATAGTTACCAGTGTTGATATGATGGT<br>GAGCACTGAGAATAACTTGCAATATGTACATATTAATGAATTATTCGGAGGA<br>TTCTCTATTATCGATATTCCATACGAGGGAAACTCTAGTATGGTAATTATAC<br>TACCGGACGACATAGAAGGTATATATAACATAGAAAAAAATATAACAGATGA<br>AAAATTTAAAAAATGGTGTGGTATGTTATCTACTAAAAGTATAGACTTGTAT<br>ATGCCAAAGTTTAAAGTGGAAATGACAGAACCGTATAATCTGGTACCGATTT<br>TAGAAAATTTAGGACTTACTAATATATTCGGATATTATGCAGATTTTAGCAA<br>GATGTGTAATGAAACTATCACTGTAGAAAAATTTCTACATACGACGTTTATA<br>GATGTTAATGAGGAGTATACAGAAGCATCGGCCGTTACAGGAGTATTTATGA<br>CTAACTTTTCGATGGTATATCGTACGAAGGTCTACATAAACCATCCATTCAT<br>GTACATGATTAAAGACAACACAGGACGTATACTTTTTATAGGGAAATACTGC<br>TATCCGCAATAAATATAAACAAATAGACTTTTATCACGTTTATCTATGTCTA<br>AATATTACAAATAGTAATAGTATAAACTAAAGCTGATAATACTTAAAAAAAT<br>AATAATATCATTTACAATTAATAGTATAAACTAAAAATTAAACAAATCGTTA<br>TTATAAGTAATATCAAAATGATGATATACGGATTAATAGCGTGTCTTATATT<br>CGTGACTTCATCCATCGCTAGTCCACTTTATATTCCCGTTATTCCACCCATT<br>TCGGAAGATAAATCGTTCAATAGTGTAGAGGTATTAGTTTCCTTGTTTAGAG<br>ATGACCAAAAAGACTATACGGTAACTTCTCAGTTCAATAACTACACTATCGA<br>TACCAAAGACTGGACTATCGGCGTACTATCCACACCTGATGGTTTGGATATA<br>CCATTGACTAATATAACTTATTGGTCACGGTTTACTATAGGTCGTGCATTGT<br>TCAAATCAGAGTCTGAGGATATTTTCCAAAAGAAAATGAGTATTCTAGGTGT<br>TTCTATAGAATGTAAGAAGTCGTCGACATTACTTACTTTTTTGACCGTGCGT<br>AAAATGACTCGAGTATTTAATAAATTTCCAGATATGGCTTATTATCGAGGAG<br>ACTGTTTAAAAGCCGTTTATGTAACAATGACTTATAAAAATACTAAAACTGG<br>AGAGACTGATTACACGTACCTCTCTAATGGGGGGTTGCCTGCATACTATCGT<br>AATGGGGTCGATGGTTGATTATTGATTAGTATATTCCTTATTCTTTTTATTC<br>ACACAAAAAGAACATTTTTATAAACATGAAACCACTGTCTAAATGTAATTAT<br>GATCTTGATTTATAGATGAAGATCAGCCTTTAGAGGATTTTAACCAGTATGT<br>TTAATATGAAAAAAATAAACATAACATATTTTGAGATTAAGCGCTATTGTGC<br>AAGATTATATTAGAATCAAATTAATCTTTCATACGAGAAAAATAACGACATA<br>CGTCGTCAACAAATTAAACTTTTATTTATTAGTTA<br>ACTAGCTTATAGAACTTGCTCATTGTTATGTTTCTAAAACGGG |
| 27 | SPI-2 | >M24218.1 Vaccinia virus serine protease inhibitor<br>superfamily gene SPI-2<br>TCCATGGAAAAACGAAAGTAGTATAAAAGTAATAAAACAAAAAAAAGAATAT<br>AAAAAATTTATAGCTACTTTCTTTGAGGACTGTTTTCCTGAAGGAAATGAAC<br>CTCTGGAATTAGTTAGATATATAGAATTAGTATACACGTTAGATTATTCTCA<br>AACTCCTAATTATGACAGACTACGTAAACTGTTTATACAAGATTGAAATTAT<br>ATTCTTTTTTTTATAGAGTGTGGTAGTGTTACGGATATTTAATATTAGACTA<br>TCTCTATCGCGCTACACGACCAATATCGATTACTATGGATATCTTCAGGGAA<br>ATCGCATCTTCTATGAAAGGAGAGAATGTATTCATTTCTCCAGCGTCAATCT |

TABLE 4-continued

| No. | PROTEIN/ NUCLIEC ACID | EXEMPLARY AMINO ACID/NUCLEIC ACID SEQUENCES |
|---|---|---|
| | | CGTCAGTATTGACAATACTGTATTATGGAGCTAATGGATCCACTGCTGAACA<br>GCTATCAAAATATGTAGAAAAGGAGGAGAACATGGATAAGGTTAGCGCTCAA<br>AATATCTCATTCAAATCCATAAATAAAGTATATGGGCGATATTCTGCCGTGT<br>TTAAAGATTCCTTTTTGAGAAAAATTGGCGATAAGTTTCAAACTGTTGACTT<br>CACTGATTGTCGCACTATAGATGCAATCAACAAGTGTGTAGATATCTTTACT<br>GAGGGGAAAATCAATCCACTATTGGATGAACCATTGTCTCCTGATACCTGTC<br>TCCTAGCAATTAGTGCCGTATACTTTAAAGCAAAATGGTTGACGCCATTCGA<br>AAAGGAATTTACCAGTGATTATCCCTTTTACGTATCTCCGACGGAAATGGTA<br>GATGTAAGTATGATGTCTATGTACGGCAAGGCATTTAATCACGCATCTGTAA<br>AGGAATCATTCGGCAACTTTTCAATCATAGAACTGCCATATGTTGGAGATAC<br>TAGTATGATGGTCATTCTTCCAGACAAGATTGATGGATTAGAATCCATAGAA<br>CAAAATCTAACAGATACAAATTTTAAGAAATGGTGTAACTCTCTGGAAGCTA<br>CGTTTATCGATGTTCACATTCCCAAGTTTAAGGTAACAGGCTCGTATAATCT<br>GGTGGATACTCTAGTAAAGTCAGGACTGACAGAGGTGTTCGGTTCAACTGGA<br>GATTATAGCAATATGTGTAATTCAGATGTGAGTGTCGACGCTATGATCCACA<br>AAACGTATATAGATGTCAATGAAGAGTATACAGAAGCAGCTGCAGCAACTTG<br>TGCACTGGTGTCAGACTGTGCATCAACAATTACAAATGAGTTCTGTGTAGAT<br>CATCCGTTCATCTATGTGATTAGGCATGTTGATGGAAAAATTCTTTTCGTTG<br>GTAGATATTGCTCTCCGACAACTAATTGTTAACCATTTTTTTTAAAAAATAG<br>AAAAAACATGTGGTATTAGTGCAGGTCGTTATTCTTCCAATTGCAATTGGTA<br>AGATGACGGCCAACTTTAGTACCCACGTCTTTTCACCACAGCACTGTGGATG<br>TGACAGACTGACCAGTATT |
| 28 | B15R | >NC_006998.1:174585-175034 Vaccinia virus, complete genome<br>ATGACGGCCAACTTTAGTACCCACGTCTTTTCACCACAGCACTGTGGATGTG<br>ACAGACTGACCAGTATTGATGACGTCAGACAATGTTTGACTGAATATATTTA<br>TTGGTCGTCCTATGCATACCGCAACAGGCAATGCGCTGGACAATTGTATTCC<br>ACACTCCTCTCTTTTAGAGATGATGCGGAATTAGTGTTCATCGACATTCGCG<br>AGCTGGTAAAAAATATGCCGTGGGATGATGTCAAAGATTGTGCAGAAATCAT<br>CCGTTGTTATATACCGGATGAGCAAAAAACCATCAGAGAGATTTCGGCCATC<br>ATCGGACTTTGTGCATATGCTGCTACTTACTGGGGAGGTGAAGACCATCCCA<br>CTAGTAACAGTCTGAACGCATTGTTTGTGATGCTTGAGATGCTCAATTACGT<br>GGATTATAACATCATATTCCGGCGTATGAATTGA |
| 29 | VGF | >S61049.1 VGF = growth factor [vaccinia virus, LIVP, Genomic, 423 nt]<br>ATGTCGATGAAATATCTGATGTTGTTGTTCGCTGCTATGATAATCAGATCAT<br>TCGCCGATAGTGGTAACGCTATCGAAACGACATTGCCAGAAATTACAAACGC<br>TACAACAGATATTCCAGCTATCAGATTATGCGGTCCAGAGGGAGATGGATAT<br>TGTTTACACGGTGACTGTATCCACGCTAGAGATATTGACGGTATGTATTGTA<br>GATGCTCTCATGGTTATACAGGCATTAGATGTCAGCATGTAGTATTAGTAGA<br>CTATCAACGTTCAGAAAACCCAAACACTACAACGTCATATATCCCATCTCCC<br>GGTATTGTGCTTGTATTAGTAGGCATTATTATTATTACGTGTTGTTCATTAT<br>CTGTTTATAGGTTCACTCGACGAACTAAACTACCTATACAAGATATGGTTGT<br>GCCATAA |
| 30 | E3L | >NC_006998.1:c48352-47780 Vaccinia virus, complete genome<br>ATGTCTAAAATCTATATCGACGAGCGTTCTAACGCAGAGATTGTGTGTGAGG<br>CTATTAAAACCATTGGAATCGAAGGAGCTACTGCTGCACAACTAACTAGACA<br>ACTTAATATGGAGAAGCGAGAAGTTAATAAAGCTCTGTACGATCTTCAACGT<br>AGTGCTATGGTGTACAGCTCCGACGATATTCCTCCTCGTTGGTTTATGACAA<br>CGGAGGCGGATAAGCCGGATGCTGATGCTATGGCTGACGTCATAATAGATGA<br>TGTATCCCGCGAAAAATCAATGAGAGAGGATCATAAGTCTTTTGATGATGTT<br>ATTCCGGCTAAAAAAATTATTGATTGGAAAGGTGCTAACCCTGTCACCGTTA<br>TTAATGAGTACTGCCAAATTACTAGGAGAGATTGGTCTTTTCGTATTGAATC<br>AGTGGGGCCTAGTAACTCTCCTACATTTTATGCCTGTGTAGACATCGACGGA<br>AGAGTATTCGATAAGGCAGATGGAAAATCTAAACGAGATGCTAAAAATAATG<br>CAGCTAAATTGGCAGTAGATAAACTTCTTGGTTACGTCATCATTAGATTCTG<br>A |
| 31 | K3L | >NC_006998.1:c27572-27306 Vaccinia virus, complete genome<br>ATGCTTGCATTTTGTTATTCGTTGCCCAATGCGGGTGATGTAATAAAGGGCA<br>GAGTATACGAGAAGGATTATGCTCTATATATTTATCTTTTTGACTATCCTCA<br>CTTTGAAGCTATCTTGGCAGAGAGTGTTAAGATGCATATGGATAGATATGTT<br>GAATATAGGGATAAACTGGTAGGGAAAACTGTAAAAGTTAAAGTGATTAGAG<br>TTGATTATACAAAAGGATATATAGATGTCAATTACAAAAGGATGTGTAGACA<br>TCAATAA |
| 32 | A41L | >NC_006998.1:c150164-149505 Vaccinia virus, complete genome<br>ATGTACTCGTTAGTATTTGTTATTTTGATGTGTATACCATTTAGTTTTCAAA<br>CAGTGTATGATGATAAATCGGTATGCGATTCTGACAATAAAGAATATATGGG<br>AATAGAAGTTTATGTAGAAGCAACGCTAGACGAACCCCTCAGACAAACAACG<br>TGTGAATCCAAAATCCATAAATATGGTGCATCTGTATCAAACGGAGGATTAA |

TABLE 4-continued

| No. | PROTEIN/<br>NUCLIEC ACID | EXEMPLARY AMINO ACID/NUCLEIC ACID SEQUENCES |
|---|---|---|
| | | ATATTTCTGTTGATCTATTAAACTGTTTTCTTAATTTTCATACAGTTGGTGT<br>ATACACTAATCGCGATACCGTATACGCGAAGTTTGCTAGTTTGGATCCATGG<br>ACTACGGAACCTATAAATTCTATGACCCATGACGATCTAGTAAAATTAACAG<br>AAGAATGTATAGTGGACATTTATTTAAAATGTGAAGTGGATAAAACAAAGGA<br>TTTCATGAAAACTAACGGTAATAGATTAAAACCAAGAGACTTTAAAACTGTT<br>CCTCCTTCTAATGTAGGAAGCATGATAGAACTACAGTCTGACTATTGCGTAA<br>ACGATGTGACTACATACGTCAAAATATACGATGAGTGTGGAAACATTAAACA<br>GCATTCCATTCCAACACTAAGAGATTATTTTACCACCAAGAATGGTCAACCA<br>CGTAAAATATTAAAGAAAAAATTTGATAATTGTTAA |
| 33 | K7R | >NC_006998.1:29832-30281 Vaccinia virus, complete<br>genome<br>ATGGCGACTAAATTAGATTATGAGGATGCTGTTTTTTACTTTGTGGATGATG<br>ATAAAATATGTAGTCGCGACTCCATCATCGATCTAATAGATGAATATATTAC<br>GTGGAGAAATCATGTTATAGTGTTTAACAAAGATATTACCAGTTGTGGAAGA<br>CTGTACAAGGAATTGATGAAGTTCGATGATGTCGCTATACGGTACTATGGTA<br>TTGATAAAATTAATGAGATTGTCGAAGCTATGAGCGAAGGAGACCACTACAT<br>CAATTTTACAAAAGTCCATGATCAGGAAAGTTTATTCGCTACCATAGGAATA<br>TGTGCTAAAATCACTGAACATTGGGGATACAAAAAGATTTCAGAATCTAGAT<br>TCCAATCATTGGGAAACATTACAGATCTGATGACCGACGATAATATAAACAT<br>CTTGATACTTTTTCTAGAAAAAAAATTGAATTGA |
| 34 | N1L | >NC_006998.1:c22172-21819 Vaccinia virus, complete<br>genome<br>ATGAGGACTCTACTTATTAGATATATTCTTTGGAGAAATGACAACGATCAAA<br>CCTATTATAATGATGATTTTAAAAAGCTTATGTTGTTGGATGAATTGGTAGA<br>TGACGGCGATGTATGTACATTGATTAAGAACATGAGAATGACGCTGTCCGAC<br>GGTCCATTGCTAGATAGATTGAATCAACCAGTTAATAATATAGAAGACGCTA<br>AGCGAATGATCGCTATTAGTGCCAAAGTGGCTAGAGACATTGGTGAACGTTC<br>AGAAATTAGATGGGAAGAGTCATTCACCATACTCTTTAGGATGATTGAAACA<br>TATTTTGATGATCTAATGATTGATCTATATGGTGAAAAATAA |
| 35 | A52R | >NC_006998.1:158743-159315 Vaccinia virus, complete<br>genome<br>ATGGACATAAAGATAGATATTAGTATTTCTGGTGATAAATTTACGGTGACTA<br>CTAGGAGGGAAAATGAAGAAAGAAAAAAATATCTACCTCTCCAAAAAGAAAA<br>AACTACTGATGTTATCAAACCTGATTATCTTGAGTACGATGACTTGTAGATA<br>GAGATGAGATGTTTACTATTCTAGAGGAATATTTTATGTACAGAGGTCTATT<br>AGGCCTCAGAATAAAATATGGACGACTCTTTAACGAAATTAAAAAATTCGAC<br>AATGATGCGGAAGAACAATTCGGTACTATAGAAGAACTCAAGCAGAAACTTA<br>GATTAAATTCTGAAGAGGGAGCAGATAACTTTATAGATTATATAAAGGTACA<br>AAAACAGGATATCGTCAAACTTACTGTATACGATTGCATATCTATGATAGGA<br>TTGTGTGCATGCGTGGTAGATGTTTGGAGAAATGAGAAACTGTTTTCTAGAT<br>GGAAATATTGTTTACGAGCTATTAAACTGTTTATTAATGATCACATGCTTGA<br>TAAGATAAAATCTATACTGCAGAATAGACTAGTATATGTGGAAATGTCATAG |
| 36 | PH-20 | MGVLKEKHIFFRSFVKSSGVSQIVETFLLIPCCLTLNFRAPPVIPNVPFLWA<br>WNAPSEFCLGKFDEPLDMSLFSFIGSPRINATGQGVTIFYVDRLGYYPYIDS<br>ITGVTVNGGIPQKISLQDHLDKAKKDITFYMPVDNLGMAVIDWEEWRPTWAR<br>NWKPKDVYKNRSIELVQQQNVQLSLTEATEKAKQEFEKAGKDFLVETIKLGK<br>LLRPNHLWGYYLFPDCYNHHYKKPGYNGSCFNVEIKRNDDLSWLWNESTALY<br>PSIYLNTQQSPVAATLYVRNRVREAIRVSKIPDAKSPLPVFAYTRIVFTDQV<br>LKFLSQDELVYTFGETVALGASGIVIWGTLSIMRSMKSCLLLDNYMETILNP<br>YIINVTLAAKMCSQVLCQEQGVCIRKNWNSSDYLHLNPDNFAIQLEKGGKFT<br>VRGKPTLEDLEQFSEKFYCSCYSTLSCKEKADVKDTDAVDVCIADGVCIDAF<br>LKPPMETEEPQIFYNASPSTLSATMFIVSILFLIISSVASL |
| 37 | Hyaluronidase<br>(*Bos*<br>*taurus*) | MRPFSLEVSLHLPWAMAAHLLPVCTLFLNLLSMTQGSRDPVVPNQPFTTIWN<br>ANTEWCMKKHGVDVDISIEDVVTNPGQTERGPNMTIFYSSQLGTYPYYTSAG<br>EPVEGGLPQNASLNAHLARTFQDILAAMPEPRFSGLAVIDWEAWRPRWAFNW<br>DTKDIYRQRSRALVQKQHPDWLAPRVEAAAQDQFEGAAEEWMAGILKLGQAL<br>RPQGLWGFYNFPECYNYDEKSPNYTGRCPLNICAQNDQLGWLWGQSRALYPS<br>IYLPAALEGIKKTQMFVQHRVAEAFRVAAGAGDPKLPVLPYMQLFYDMINHF<br>LPAEELEHSLGESAAQGAAGVVLWVSWLSTSTKESCQAIKEYVDTTLGPSIL<br>NVISGARLCSQVLCSGHGRCARRPSYPKARLILNSTSFSIKPIPGGGPLTLQ<br>GALSLEDRLRMAVEFECRCYRGWRGTRCEQWGMW |
| 38 | Hyaluronidase<br>(*Bos*<br>*taurus*) | MRMLRRHHISFRSFAGSSGTPQAVETFLLLPCCLALDFRAPPLISNTSFLWA<br>WNAPVERCVNRRFQLPPDLRLFSVKGSPQKSATGQFITLFYADRLGYYPHID<br>EKTGKIVEGGIPQLGNLKSHMEKAKNDIAYYIPNDSVGLAVIDWENWRPTWA<br>RNWKPKDVYRDESVELVLQKNPQLSEPEASKIAKVDFETAGKSFMQETLKLG<br>KLLRPNHLWGYYLFPDCYNHNHNQPTYNGNCPDVEKRRNDDLEWLWKESTAL<br>FPSVYLNIRLKSTQNAALYVRNRVQEAIRLSKIASVESPLPVFVYARPVFID<br>GSSTYLSQGDLVNSVGEIVSLGASGIIMWGSLNLSLSMQSCMNLGTYLNITL<br>NPYIINVILAAKMCSQVLCHNEGVCIRKHWNSSDYLHLNPMNFAIQTGEGGK |

TABLE 4-continued

| No. | PROTEIN/ NUCLIEC ACID | EXEMPLARY AMINO ACID/NUCLEIC ACID SEQUENCES |
|---|---|---|
| | | YTVPGIVTLEDLQKFSDIFYCSCYANIHCKKRVDIKNVHSVNVCMAEDICID SPVKLQPSDHSSSQEASTTIFSSISPSITTATVSPCIPEKHSPECLKVRCSE VIPNVTQKACQSVKLKNISYQSPIQNIKNQTTY |
| 39 | Hyaluronidase (*Bos taurus*) | MGMERRHHISFRSFAGSSGTPQAVETFLLLPCCLALDFRAPPLISNTSFLWA WNAPVERCVNRRFQLPPDLRLFSVKGSPQKSATGQFITLFYADRLGYYPHID EKTGKIVEGGIPQLGNLKSHLEKAKNDIAYYIPNDSVGLAVIDWENWRPTWA RNWKPKDVYRDESVELVLQKNPQLSEPEASKIAKVDFETAGKSFMQETLKLG KLLRPNHLWGYYLFPDCYNHNHNQPTYNGNCPDVEKRRNDDLEWLWKESTAL FPSVYLNIRLKSTQNAALYVRNRVQEAIRLSKIASVESPLPVFVYARPVFID GSSTYLSQGDLVNSVGEIVSLGASGIIMWGSLNLSLSVQSCMNLGTYLNITL NPYIINVILAAKMCSQVLCHDGGVCIRKHWNSSDYLHLNPMNFAIQTGEGGK YTVPGILTLEDLQKFSDIFYCSCYSNLSCKKRVDIKNVHSVDVCMAEDVCID AFLKPP |
| 40 | Hyaluronidase (*Vespula vulgaris*) | SERPKRVFNIYWNVPIFMCHQYDLYFDEVINFNIKRNSKDDFQGDKIAIFYD PGEFPALLSLKDGKYKKRNGGVPQEGNITIHLQKFIENLDKIYPNRNFSGIG VIDFERWRPIFRQNWGNMKIHKNFSIDLVRNEHPIWNKKMIELEASKRFEKY ARFFMEETLKLAKKTRKQADWGYYGYPYCFNMSPNNLVPECDVTAMHENDKM SWLFNNQNVLLPSVYVRQELTPDQRIGLVQGRVKEAVRISNNLKHSPKVLSY WWYVYQDETNTFLTETDVKKTFQEIVINGGDGIIIWGSSSDVNSLSKCKRLQ DYLLTVLGPIAINVTEAVN |
| 41 | Hyaluronidase (*Vespula vulgaris*) | DRTIWPKKGFSIYWNIPTHFCHNFGVYFKELKQFNIKYNSMNNFRGETISLF YDPGNFPSMVLLKNGTYEIRNEGVPQKGNLTIHLEQFTKELDEIYPKKIAGG IGVIHFHNWRPIFRRNVDNLKINKDISIDLVRKEHPKWDKSMIEKEASNRFE TSAKIFMEKTLKLAKEIRKKTEWGYHGYPHCLSGSTDKPSFDCDALSMSEND KMSWLENNQNVLLPSIYLKNVLKPDEKIHLVQERLKEAIRISKNEKHLPKVL PYWWYTYQDKESIFLTEADVKNIFKEILINGADGIIIWGVSYELTDRKRCEK LKEYLMKILGPIAFKVIKAVKENTPLNE |
| 42 | Hyaluronidase (*Apis mellifera*) | MSRPLVITEGMMIGVLLMLAPINALLLGFVQSTPDNNKTVREFNVYWNVPIF MCHKYGLRFEEVSEKYGILQNWMDKERGEEIAILYDPGMFPALLKDPNGNVV ARNGGVPQLGNLIKHLQVFRDHLINQIPDKSFPGVGVIDFESWRPIFRQNWA SLQPYKKLSVEVVRREHPFWDDQRVEQEAKRRFEKYGQLFMEETLKAAKRMR PAANWGYYAYPYCYNLTPNQPSAQCEATTMQENDKMSWLFESEDVLLPSVYL RWNLTSGERVGLVGGRVKEALRIARQMITSRKKVLPYYWYKYQDRRDIDLSR ADLEATLRKITDLGADGFIIWGSSDDINTKAKCLQFREYLNNELGPAVKRIA LNNNANDRLTVDVSVDQV |
| 43 | Hyaluronidasese *Dolichovespula maculata* | SERPKRVFNIYWNVPIFMCHQYGLYFDEVINFNIKHNSKDDFQGDKISIFYD PGEFPALLPLKEGNYKIRNGGVPQEGNITIHLQRFIENLDKTYPNRNFNGIG VIDFERWRPIFRQNWGNMMIHKKFSIDLVRNEHPFWDKKMIELEASKRFEKY ARLFMEETLKLAKKTRKQADWGYYGYPYCFNMSPNNLVPDCDATAMLENDKM SWLFNNQNVLLPSVYIRHELTPDQRVGLVQGRVKEAVRISNNLKHSPKVLSY WWYVYQDDINTFLTETDVKKTFQEIAINGGDGIIIWGSSSDVNSLSKCKRLR EYLLTVLGPITVNVTETVN |
| 44 | Hyaluronidase *Polistes annularis* | YVSLSPDSVFNIITDDISHQILSRSNCERSKRPKRVFSIYWNVPTFMCHQYG MNFDEVTDFNIKHNSKDNFRGETISIYYDPGKFPALMPLKNGNYEERNGGVP QRGNITIHLQQFNEDLDKMTPDKNFGGIGVIDFERWKPIFRQNWGNTEIHKK YSIELVRKEHPKWSESMIEAEATKKFEKYARYFMEETLKLAKKTRKRAKWGY YGFPYCYNVTPNNPGPDCDAKATIENDRLSWMYNNQEILFPSVYVRHEQKPE ERVYLVQGRIKEAVRISNNLEHSPSVLAYWWYVYQDKMDIYLSETDVEKTFQ EIVTNGGDGIIIWGSSSDVNSLSKCKRLREYLLNTLGPFAVNVTETVNGRSS LNF |
| 45 | Hyaluronidase *Mus musculus* | MRAGLGPIITLALVLEVAWAGELKPTAPPIFTGRPFVVAWNVPTQECAPRHK VPLDLRAFDVKATPNEGFENQNITTFYYDRLGLYPRFDAAGTSVHGGVPQNG SLCAHLPMLKESVERYIQTQEPGGLAVIDWEEWRPVWVRNWQEKDVYRQSSR QLVASRHPDWPSDRVMKQAQYEFEFAARQFMLNTLRYVKAVRPQHLWGFYLF PDCYNHDYVQNWESYTGRCPDVEVARNDQLAWLWAESTALFPSVYLDETLAS SVHSRNFVSFRVREALRVAHTHHANHALPVYVFTRPTYTRGLTGLSQVDLIS TIGESAALGSAGVIFWGDSEDASSMETCQYLKNYLTQLLVPYIVNVSWATQY CSWTQCHGHGRCVRRNPSANTFLHLNASSFRLVPGHTPSEPQLRPEGQLSEA DLNYLQKHERCQCYLGWGGEQCQRNYKGAAGNASRAWAGSHLTSLLGLVAVA LTWTL |
| 46 | Hyaluronidase *Mus musculus* | MRAGLGPIITLALVLEVAWAGELKPTAPPIFTGRPFVVAWNVPTQECAPRHK VPLDLRAFDVKATPNEGFENQNITTFYYDRLGLYPRFDAAGTSVHGGVPQNG SLCAHLPMLKESVERYIQTQEPGGLAVIDWEEWRPVWVRNWQEKDVYRQSSR QLVASRHPDWPSDRVMKQAQYEFEFAARQFMLNTLRYVKAVRPQHLWGFYLF PDCYNHDYVQNWESYTGRCPDVEVARNDQLAWLWAESTALFPSVYLDETLAS |

TABLE 4-continued

| No. | PROTEIN/ NUCLIEC ACID | EXEMPLARY AMINO ACID/NUCLEIC ACID SEQUENCES |
|---|---|---|
| | | SVHSRNFVSFRVREALRVAHTHHANHALPVYVFTRPTYTRGLTGLSQVDLIS<br>TIGESAALGSAGVIFWGDSEDASSMETCQYLKNYLTQLLVPYIVNVSWATQY<br>CSWTQCHGHGRCVRRNPSANTFLHLNASSFRLVPGHTPSEPQLRPEGQLSEA<br>DLNYLQKHERCQCYLGWGGEQCQRNYKGAAGNASRAWAGSHLTSLLGLVAVA<br>LTWTL |
| 47 | Hyaluronidase *Mus musculus* | MIMHLGLMMVVGLTLCLMHGQALLQVPEHPFSVVWNVPSARCKAHFGVHLPL<br>DALGIVANHGQHFHGQNISIFYKNQFGLYPYFGPRGTAHNGGIPQAVSLDHH<br>LARAAHQILHSLGSSFAGLAVLDWEEWYPLWAGNWGPHRQVYLAASWVWTQQ<br>MFPGLDPQEQLHKAHTSFEQAARALMEYTLQLGRTLRPSGLWGFYRYPACGN<br>GWHKMASNYTGHCHAAITTQNTQLRWLWAASSALFPSIYLPPRLPLAYRQAF<br>VRHRLEEAFRVALLEHSHPLPVLAYSRLTHRSSGRFLSLDDLMQTIGVSAAL<br>GTAGVVLWGDLSFSSSEEKCWRLHDYLVGTLGPYVINVTKADMACSHQRCHG<br>HGRCARKDPGQMEAFLHLQPDDSLGAWNSFRCHCYSGWAGPTCLEPKP |
| 48 | Hyaluronidase *Rattus norvegicus* | MGELQFKWLFWRSFAESGGTFQTVLIFLFIPYSLTVDYRATPVLSDTTFVWV<br>WNVPTEACVENVTEPIDLSFFSLIGSPRKTAIGQPVTLFYVDRLGNYPHIDA<br>QQTEHHGGIPQKGDLTTHLVKAKEDVERYIPTDKLGLAIIDWEEWRPTWMRN<br>WTPKDIYRNKSIELVQQADPAINITEATVRAKAQFEGAAKEEMEGTLKLGKH<br>IRPKHLWGFYLFPDCYNNKFQVDNYDGQCPDVEKKRNDDLDWLWKESTGLYP<br>SVYLKKDLKSSRKATLYVRYRVLESIRVSKVSDESNPVPIFVYIRLVFTDHV<br>SEYLLEDDLVNTIGEIVAQGTSGIIIWDAMSLAQRSAGCPILRQYMKTTLNP<br>YIVNVTLAAKMCSQTLCKEKGMCSRKTESSDAYLHLDPSSFSINVTEAGKYE<br>VLGKPEVKDLEYFSEHFKCSCFSKMTCEETSDMRSIQDVNVCMGDNVCIKAT<br>LGPNSAFHLLPGKGLLLMTTLAHILHHLPHDIFVFPWKMLVSTP |
| 49 | Hyaluronidase *Sus scrofa* | MAAHLLPICTLFLNLLSVAQGSRDPVVLNRPFTTIWNANTQWCLKRHGVDVD<br>VSVFEVVVNPGQTERGPNMTIFYSSQLGTYPYYTSAGEPVEGGLPQNASLDV<br>HLNRTFKDILAAMPESNFSGLAVIDWEAWRPRWAFNWDAKDIYRQRSRALVQ<br>KQHPDWPAPWVEAAAQDQFQEAAQTWMAGTLKLGQTLRPHGLWGFYGFPDCY<br>NYDEQSSNYTGQCPPGVSAQNDQLGWLWGQSRALYPSIYLPSALEGTNKTQL<br>YVQHRVNEAFRVAAAAGDPNLPVLPYAQIFHDMTNRLLSREELEHSLGESAA<br>QGAAGVVLWVSWENTRTKESCQSIKEYVDTTLGPFILNVTSGALLCSQAVCS<br>GHGRCVRRPSHTEALPILNPSSFSIKPTPGGGPLTLQGALSLKDRVQMAEEF<br>QCRCYPGWRGTWCEQQGTR |
| 50 | Hyaluronidase *Sus scrofa* | MTMQLGLALVLGVAMCLGCGQPLLRAPERPFCVLWNVPSARCKARFGVHLPL<br>EALGITANHGQRFHGQNITIFYKSQLGLYPYFGPRGTAHNGGIPQAVSLDHH<br>LARAAYQIHRSLRPGFTGLAVLDWEEWCPLWAGNWGRRQAYQAASCAWAQRV<br>YPNLDPQEQLCKARAGFEEAARALMEDTLRLGRMLRPHGLWGFYHYPACGNG<br>WHGTASNYTGHCHAAALARNTQLYWLWAASSALFPSIYLPPGLPPAYHQAFV<br>RYRLEEAFRVALVGHPHPLPVLAYARLTHRNSGRFLSQDELVQTIGVSAALG<br>ASGVVLWGDLSFSSSEEECWHLRGYLVGTLGPYVINVTRAAMACSHQRCHGH<br>GRCAWQDPGQLKVFLHLHPGGSPGAWESFSCRCYWGWAGPTCQEPRPELGPE<br>EAT |
| 51 | Hyaluronidase *Rattus norvegicus* | MKPFSPEVSPDPCPATAAHLLRTYTLFLTLLELAQGCRGSMVSNRPFITVWN<br>ADTHWCLKDHGVDVDVSVFDVVANKEQNFQGPNMTIFYREELGTYPYYTPTG<br>EPVFGGLPQNASLVTHLAHAFQDIKAAMPEPDFSGLAVIDWEAWRPRWAFNW<br>DSKDIYQQRSMELVRAEHPDWPETLVEAEAQGQFQEAAEAWMAGTLQLGQVL<br>RPRGLWGYYGFPDCYNYDFLSPNYTGQCSLSIHDQNDQLGWLWNQSYALYPS<br>IYLPAALMGTGKSQMYVRYRVQEAFRLALVSRDPHVPIMPYVQIFYEKTDYL<br>LPLEELEHSLGESAAQGAAGAVLWISSEKTSTKESCQAIKAYMDSTLGPFIL<br>NVTSAALLCSEALCSGRGRCVRHPSYPEALLTLSPASFSIEPTHDGRPLSLK<br>GTLSLKDRAQMAMKFKCRCYRGWSGEWCKKQDM |
| 52 | Hyaluronidase *Rattus norvegicus* | MRAGLGPIITLALVLEVAWASELKPTAPPIFTGRPFVVAWNVPTQECAPRHK<br>VPLDLRAFDVEATPNEGFFNQNITTFYYDRLGLYPRFDAAGMSVHGGVPQNG<br>SLCAHLPMLKEAVERYIQTQEPAGLAVIDWEEWRPVWVRNWQEKDVYRQSSR<br>QLVASRHPDWPSDRIVKQAQYEFEFAARQFMLNTLRYVKAVRPQHLWGFYLF<br>PDCYNHDYVQNWDSYTGRCPDVEVAQNDQLAWLWAENTALFPSVYLDKTLAS<br>SKHSRNFVSFRVQEALRVAHTHHANHALPVYVFTRPTYTRRLTELNQMDLIS<br>TIGESAALGSAGVIFWGDSVYASSMENCQNLKKYLTQTLVPYIVNVSWATQY<br>CSWTQCHGHGRCVRRNPSASTFLHLSPSSFRLVPGRTPSEPQLRPEGELSED<br>DLSYLQMHFRCHCYLGWGGEQCQWNHKRAAGDASRAWAGAHLASLLGLVAMT<br>LTWTL |
| 53 | Hyaluronidase *Rattus norvegicus* | MITQLGLTLVVGLTLCLVHVQALLQVPEFPFSVLWNVPSARCKTRFGVHLPL<br>DALGIIANHGQRFHGQNITIFYKNQFGLYPYFGPRGTAHNGGIPQAVSLDHH<br>LAQAAHQILHNLGSSFAGLAVLDWEEWYPLWAGNWGTHRQVYQAASWAWAQQ<br>MFPDLNPQEQLHKAQTGFEQAARALMEHTLRLGQMLRPHGLWGFYRYPVCGN<br>GWHNMASNYTGHCHPAIITRNTQLRWLWAASSALFPSIYLPPRLPPAYHQTF<br>VRHRLEEAFRVALTGHAHPLPVLAYVRLTHRSSGRFLSLDDLMQTIGVSAAL<br>GAAGVVLWGDLSVSSSEEECWRLHDYLVGTLGPYVINVTKAATACSHQRCHG<br>HGRCSWKDPGQMEAFLHLQPDDNLGAWKSFRCRCYLGWSGPTCLEPKP |

TABLE 4-continued

| No. | PROTEIN/ NUCLIEC ACID | EXEMPLARY AMINO ACID/NUCLEIC ACID SEQUENCES |
|---|---|---|
| 54 | Hyaluronidase *Cavia porcellus* | MGAFTFKHSFFGSFVECSGVLQTVFIFLLIPCCLADKRAPPLIPNVPLLWVW NAPTEFCIGGTNQPLDMSFFSIVGTPRKNITGQSITLYYVDRLGYYPYIDPH TGAIVHGGLPQLMNLQQHLRKSRQDILFYMPTDSVGLAVIDWEEWRPTWTRN WRPKDIYRNKSIELVKSQHPQYNHSYAVAVAKRDFERTGKAFMLETLKLGKS LRPSSLWGYYLFPDCYNTHFTKPNYDGHCPPIELQRNNDLQWLWNDSTALYP SVYLTSRVRSSQNGALYVRNRVHESIRVSKLMDDKNPLPIYVYIRLVFTDQT TTFLELDDLVHSVGEIVPLGVSGIIIWGSLSLTRSLVSCIGLENYMKGTLLP YLINVTLAAKMCGQVLCKNQGICTRKDWNTNTYLHLNATNFDIELQQNGKFV VHGKPSLEDLQEFSKNFHCSCYTNVACKDRLDVHNVRSVNVCTANNICIDAV LNFPSLDDDDEPPITDDTSQNQDSISDITSSAPPSSHILPKDLSWCLFLLSI FSQHWKYLL |
| 55 | Hyaluronidase *Oryctolagus cuniculus* | MGVLKFKHIFFGSAVELSGVFQIVFIFLLIPCCLTANFRAPPVIPNVPFLWA WNAPTEFCLGKSGEPLDMSLFSLFGSPRKNKTGQGITIFYVDRLGYYPYIDP HTGAIVHGRIPQLGPLQQHLTKLRQEILYYMPKDNVGLAVIDWEEWLPTWLR NWKPKDIYRIKSIELVKSQHPQYNHSYATEKAKRDFEKAGKDFMEETLKLGR LLRPNHLWGYYLFPDCYNHHYDKPNLYKGSCFDIEKKRNDDLSWLWKESTAL FPSVYLTSRARSATALSKLYVVRNRVHEAIRVSKIPDDKSPLPNEVYTRLVF TDQIFQFLSHHDLVYTIGEIVALGASGIVVWGSQSLARSMKSCLHLDNYMKT ILNPYLINVTLAAKMCNQVLCQEQGVCTRKNWNPNDYLHLNPGNFAIQLGSN GTYKVDGKPTLTDLEQFSKNFQCSCYTNLNCKERTDMNNVRTVNVCAVENVC IDTNVGPQAVTYAPKEKKDVAHILSNTTSINSSTTMSLPFPRKHVSGCLLVL CMYSQYLNICYRLVAIGIQHGYYLK |
| 56 | Hyaluronidase *Ovis arias* | MWTGLGPAVTLALVLVVAWATELKPTAPPIFTGRPFVVAWDVPTQDCGPRHK MPLDPKDMKAFDVQASPNEGFVNQNITIFYRDRLGMYPHENSVGRSVHGGVP QNGSLWVHLEMLKGHVEHYIRTQEPAGLAVIDWEDWRPVWVRNWQDKDVYRR LSRQLVASHHPDWPPERIVKEAQYEFEFAARQFMLETLRFVKAFRPRHLWGF YLFPDCYNHDYVQNWETYTGRCPDVEVSRNDQLSWLWAESTALFPSVYLEET LASSTHGRNEVSFRVQEALRVADVHHANHALPVYVETRPTYSRGLTGLSEMD LISTIGESAALGAAGVILWGDAGFTTSNETCRRLKDYLTRSLVPYVVNVSWA AQYCSWAQCHGHGRCVRRDPNAHTFLHLSASSFRLVPSHAPDEPRLRPEGEL SWADRNHLQTHERCQCYLGWGGEQCQWDRRRAAGGASGAWAGSHLTGLLAVA VLAFTWTS |
| 57 | Hyaluronidase *Ovis arias* | LYVRNRVREAIRLSKIASVESPLPVEVYHRPVETDGSSTYLSQGDLVNSVGE IVALGASGIIMWGSLNLSLTMQSCMNLGNYLNTTLNPYIINVTLAAKMCSQV LCQEQGVCIR |
| 58 | Hyaluronidase *Ovis arias* | LDFPAPPLISNTSFLWAWNAPAERCVKIFKLPPDLRLFSVKGSPQKSATGQF ITLFYADRLGYYPHIDEKTGNTVYGGIPQLGNLKNHLEKAKKDIAYYIPNDS VGLAVIDWENWRPTWARNWKPKDVYRDESVELVLQKNPQLSFPEASKIAKVD FETAGKSFMQETLKLGKLLRPNHLWGYYLFPDCYNHNYNQPTYNGNCSDLEK RRNDDLDWLWKESTALFPSVYLNIKLKSTPKAAFYVRNRVQEAIRLSKIASV ESPLPVEVYHRPVETDGSSTYLSQGDLVNSVGEIVALGASGIIMWGSLNLSL TMQSCMNLGNYNTTLNPYIINVTLAAKMCSQVLCHDEGVCTRKQWNSSDYLH LNPIMNFAIQTGKGGKYTVPGKVTLEDLQTFSDKFYCSCYANINCKKRVDIK NVHSVNVCMAEDICIEGPVKLQPSDHSSSQNEASTTTVSSISPSTTATTVVS PCTPEKQSPECLKVRCLEATANVTQTGCQGVKWKNTSSQSQSSIQNIKNQTT |
| 59 | Hyaluronidase *Ovis arias* | DFRAPPLISNTSFLWAWNAPAERCIKIFKLPPDLRLFSVKGSPQKSATGQFI TLFYADRLGYYPHIDEKTGNTVYGGIPQLGNLKNHLEKAKKDIAYYIPNDSV GLAVIDWENWRPTWARNWKPKDVYRDESVELVLQKNPQLSFPEASKIAKVDF ETAGKSFMQETLKLGKLLRPNHLWGYYLFPDCYNHNYNQPTYNGNCSDLEKR RNDDLDWLWKESTALFPSVYLNIKLKSTPKAAFYVRNRVQEAIRLSKIASVE SPLPVEVYHRPVETDGSSTYLSQGDLVNSVGEIVALGASGIIMWGSLNLSLT MQSCMNLGNYLNTTLNPYIINVTLAAKMCSQVLCHDEGVCTRKQWNSSDYLH LNPMNFAIQTGKGGKYTVPGKVTLEDLQTFSDKFYCSCYANINCKKRVDIKN VHSVNVCMAEDICIEGPVKLQPSDHSSSQNEASTTTVSSISPSTTATTVSPC TPEKQSPECLKVRCLEAIANVTQTGCQGVKWKNTSSQSSIQNIKNQTTY |
| 60 | Hyaluronidase *Pan troglodytes* | MGVLKEKHIFFRSFVKSSGVSQIVETFLLIPCCLTLNFRAPPVIPNVPFLWA WNAPSEFCLGKFDEPLDMSLFSFIGSPRINVTGQDVTIFYVDRLGYYPYIDS ITGVTVNGGIPQKISLQDHLDKAKKDITFYMPVDNLGMAVIDWEEWRPTWAR NWKPKDVYKNRSIELVQQQNVQLSLTEATEKAKQEFEKAGKDFLVETIKLGK LLRPNHLWGYYLFPDCYNHHYKKPGYNGSCFNVEIKRNDDLSWLWNESTALY PSIYLNTQQSPVAATLYVRNRVQEAIRVSKIPDAKSPLPVFVYTRIVFTDQV LKFLSQDELVYTFGETVALGASGIVIWGTLSIMRSMKSCLLLDNYMETILNP YIINVTLAAKMCSQVLCQEQGVCIRKNWNSSDYLHLNPDNFAIQLEKGGKFT VRGKPTLEDLEQFSEKFYCSCYSTLSCKEKADVKDTDAVDVCIADGVCIDAF LKPPMETEESQIFYNASPSTLSATMFIDLCDLYLVPTSYLIL |
| 61 | Hyaluronidase *Pan troglodytes* | MGVLKEKHIFFRSFVKSSGVSQIVETFLLIPCCLTLNFRAPPIIPNVPFLWA WNAPSEFCLGKFNEPLDMSLFTLMGSPRINITGQGVTIFYVDRLGYYPYIDL TTGVTVHGGIPQKVSLQDHLDKSKQDILFYMPVDNLGMAVIDWEEWRPTWAR NWKPKDVYKNRSIELVQQQNVQLSLPQATDKAKQEFEKAGKDFMLETIKLGR |

TABLE 4-continued

| No. | PROTEIN/ NUCLIEC ACID | EXEMPLARY AMINO ACID/NUCLEIC ACID SEQUENCES |
|---|---|---|
| | | SLRPNHLWGYYLFPDCYNHHYRKPGYNGSCFDVEIKRNDDLSWLWNESTALY PSIYLNTQQSVVVATLYVRNRVREAIRVSKIPDAKNPLPVFVYARLVFTDQV LKELSREELVSTLGETVALGASGIVIWGSLSITRSMKSCLLLDTYMETILNP YIINVTLAAKMCSQVLCQEQGVCIRKDWNSSDYLHLNPDNFDIRLEKGGKFT VHGKPTVEDLEEFSEKFYCSCYTNLSCKEKADVKDTDAVDVCIADGVCIDAS LKPPVETEGSPPIFYNTSSSTVSTTMFIWRLEVWDQGISRIGFF |
| 62 | Hyaluronidase *Pongo pygmaeus* | MTTRLGPALVLGVALCLGCGQPLPQVPERPFSVLWNVPSAHCKSRFGVHLPL NALGIIANRGQHFHGQNMTIFYKNQLGLYPYFGPKGTAHNGGIPQALPLDRH LALAAYQIHHSLRPGFAGPAVLDWEEWCPLWAGNWGRRRAYQAASWAWAQQV FPDLDPQEQLYKAYTGFEQAARALMEDTLRVAQALRPHGLWGFYHYPACGNG WHSMASNYTGRCHAATLARNTQLHWLWAASSALFPSIYLPPRLPPAHHQAFV RHRLEEAFRVALVGHLPVLAYVRLTHRRSGRFLSQDDLVQTIGVSAALGAAG VVLWGDLSLSSSEEECWHLHDYLVDTLGPYGINVTRAAMACSHQRCHGHGRC ARRDPGQMEAFLHLWPDGSLGDWKSFSCHCYWGWAGPTCQEPRLGPKEAV |
| 63 | Hyaluronidase *Macaca fascicularis* | MGVLKEKHIFFRSFVKSSGVSQIVETFLLIPCCLTLNFRAPPIIPNVPFLWA WNAPSEFCLGKFNEPLDMSLFTLMGSPRINVTGQGVTIFYVDRLGYYPYIDL TTGVTVHGGIPQKVSLQDHLDKSKQDILFYMPVDNLGMAVIDWEEWRPTWAR NWKPKDVYKNRSIELVQQQNVQLSLPQATDKAKQEFEKAGKDFMLETIKLGR SLRPNHLWGYYLFPDCYNHHYRKPGYNGSCFDVEIKRNDDLSWLWNESTALY PSIYLNTQQSVVVATLYVRNRVREAIRVSKIPDAKNPLPVFVYARLVFTDQV LKELSREELVSTLGETVALGASGIVIWGSLSITRSMKSCLLLDTYMETILNP YIINVTLAAKMCSQVLCQEQGVCIRKDWNSSDYLHLNPDNFDIRLEKGGKFT VHGKPTVEDLEEFSEKFYCSCYTNLSCKEKADVKDTDAVDVCIADGVCIDAS LKPPVETEGSPPIFYNTSSSTVSTTMFIVNILFLIISSVASL |
| 64 | Hyaluronidase *Mus musculus* | MGELRREKHLFWGSFVESGGTFQTVLIFLLIPCSLTVDYRAAPILSNTTFLWI WNVPTERCVGNVNDPIDLSFFSLIGSPRKTATGQPVTLFYVDRLGLYPHIDA NQAEHYGGIPQRGDYQAHLRKAKTDIEHYIPDDKLGLAIIDWEEWRPTWLRN WKPKDNYRNKSIELVQSTNPGLSITEATQKAIQQFEEAGRKFMEGTLHLGKF LRPNQLWGYYLFPDCYNNKFQDPKYDGQCPAVEKKRNDNLKWLWKASTGLYP SVYLKKDLKSNRQATLYVRYRVVEAIRVSKVGNASDPVPIFVYIRLVFTDRT SEYLLEDDLVNTIGEIVALGTSGIIIWDAMSLAQRAAGCPILHKYMQTTLNP YIVNVTLAAKMCSQTLCNEKGMCSRRKESSDVYLHLNPSHFDIMLTETGKYE VLGNPRVGDLEYFSEHFKCSCFSRMTCKETSDVKNVQDVNVCVGDNVCIKAK VEPNPAFYLLPGKSLLFMTTLGHVLYHLPQDIFVFPRKTLVSTP |
| 65 | Hyaluronidase *Arthrobacter* sp. | MTREFSRRTALKGAALSGLLLAMVHGPAHAAATANATLTPADFAGLRQRWVD QITGRKVLVAGDNDFVTALAALDKKARTAIDLLERSAGRLTVFSDLSLAKDT DLVTTHTRLATMATAWATPGSEHFADAGLLAAIRAGLADANSLCYNASKEEQ GNWWSWEIGTPKALADTMVLLHAELTAAERAAYCAAIDHFVPDPWQQFPPKR GKITSVGANRVDLCQAVTIRSLVDEDAEKLTHAVAGLSEVWQYVSAGNGEFT DGSFIQHSTTPYTGSYGVVLLTGLSKLFALLGGTGAEVSDPSRDILEKTVEG SFAPFMVAGAMADSVRGRSISRESNTGFDLGASTIESILLLARAVDPVTARR WRSLCLAWINQNRKAPILADAGVGRTALVKELLAMGLTETDLPGGHYLFPAM DRTMHHSQGWTLSTAMASSRIAWYECGNGENNRGYHTGSGMTYVYDGDLGQY DDAFWATANHCRLPGITVDTSSLPDKVEGEWGAATPANEWTGSTAYGDVAAV GQHLIGPGGTGLTARKSWFVSKDVIVCLGADIRTGSGSRIETVVDHRNLHAG ENAMGTAAGTVAATPGHPEVLTVDRWVHLEGFGGYVVLDAAPLQVLREQREG SWSEVNVKGSAARQTRNYATLYFDHGHEPEAASYAYLVAPGASASMTSSLSG QSFHTVLRNDEVAQAVKFKKEKTTAATFWRPGTVGDLALSGPACVVVKEVGD RLSIAVSDPTQNASTLTLRLKTKRFFRIIEGQGASLSHGADGFTVLEVDIAN HAGRTKQIELSAE |
| 66 | Hyaluronidase *Bdellovibrio bacteriovorus* | MTKFFFLLTLISATAFAQSEPDWTAGVPVPPGGRSNIYSWNDFDFQATLNKG KIHAQVYPVTVTGMLPPYEPVRRLIEEKNSNPLRKWIQSLMKGLSGFRSFED VLKNLGLHKYPLENERGVYAVPYPNEIRPDTLMGFGLIERNGAEGFTFSCAA CHSSNLFGKTVLGMTNRFPRANEFFIKAKKVMPLMDPHIFQAYTRATDAETA LLVESKERLKSVALKQPIALGLDTSLAQVSLSLNRRAKDGYANYSDKAARSP RADAYLDNKPADSKPAVWWNVKYKNRWLSDGSVLSGNPIFTNLIWNEIGRGA DLHELEQWLADNDHIIKELTTAVFASEAPHITDFYPAEKIDLGRAKAGEQIE KNTCAKCHGHYEKAWNLPQALVLSAAERLKTVEVRYKEKTPVVNVGTDPFRR QGMKSLEQLNDLEISKKNGIVIKAQEGYVPPPLVGIWARWPYMHNNSIPNLC VLLTPAKKRPSIYYSGEALNKDTDYDFSCGGYPIGDKTPKAWKTREHLYDTR NPGMGNMGHDEGIFIKDGKEILSAEDKYNLIQFLQTL |
| 67 | Hyaluronidase *Propionibacterium acnes* | MEGTPSRRTFLTASALSAMALAASPTVTDAIAAPGPDSWSALCERWIDIITG RRAARTSDPRARAIIAKTDRKVAEILTDLVSGSSRQTVLISADLRKEQSPFI TKTARAIESMACAWATPGSSYHKDPEILSACIEGLRDFCRLRYNPSQDEYGN WWDWEDGASRAVADVMCILHDVLPPEVMSAAAAGIDHFIPDPWFQQPASVKP TANPVQPVVSTGANRMDLTRAVMCRSIATGDEKRLRHAVDGLPDAWRVTTEG DGFRADGGFIQHSHIPYTGGYGDVLFSGLAMLFPLVSGMRFDIVESARKAFH DQVERGFIPVMYNGQILDDVRGRSISRINESAAMHGISTARAMLMMADALPT HRAEQWRGIVHGWMARNTEDHLSEPSTLVDISLFDAAAKARPVPESSTPSYF ASMDRLVHRTADWLITVSNCSDRIAWYEYGNGENEWASRTSQGMRYLLLPGD MGQYEDGYWATVDYSAPTGTTVDSTPLKRAVGASWAAKTPTNEWSGGLASGS |

TABLE 4-continued

| No. | PROTEIN/ NUCLIEC ACID | EXEMPLARY AMINO ACID/NUCLEIC ACID SEQUENCES |
|---|---|---|
| | | WSAAASHITSQDSALKARRLWVGLKDAMVELTTDVTTDASRAITVVEHRKVA SSSTKLLVDGNRVSSATSFQNPRWAHLDGVGGYVFATDTDLSADVATRKGTW IDVNPSRKVKGADEVIERAYASLHVTHHDRPVAWALLPTASRSHTMALATRP GVEPFTVLRNDATVQAVRSAGALLTKDPTVVTTLAFWKPATCGGVAVNRPAL VQTRESANQMEVVIVEPTQKRGSLTVTIEGSWKVKTADSHVDVSCENAAGTL HVDTAGLGGQSVRVTLARQVTQTPSGGGRHDRA |
| 68 | Hyaluronidase *Streptococcus agalactiae* | MEIKKKYRIMLYSALILGTILVNNSYQAKAEELTKTTSTSQIRDTQTNNIEV LQTESTTVKETSTTTTQQDLSNPTASTATATATHSTMKQVVDNQTQNKELVK NGDFNQTNPVSGSWSHTSAREWSAWIDKENTADKSPIIQRTEQGQVSLSSDK GFRGAVTQKVNIDPTKKYEVKFDIETSNKAGQAFLRIMEKKDNNTRLWLSEM TSGTTNKHTLTKIYNPKLNVSEVTLELYYEKGTGSATFDNISMKAKGPKDSE HPQPVTTQIEESVNTALNKNYVFNKADYQYTLTNPSLGKIVGGILYPNATGS TTVKISDKSGKIIKEVPLSVTASTEDKFTKLLDKWNDVTIGNHVYDTNDSNM QKINQKLDETNAKNIKTIKLDSNHTFLWKDLDNLNNSAQLTATYRRLEDLAK QITNPHSTIYKNEKAIRTVKESLAWLHQNFYNVNKDIEGSANWWDFEIGVPR SITATLALMNNYFTDAEIKTYTDPIEHFVPDAGYFRKTLDNPFKALGGNLVD MGRVKIIEGLLRKDNTIIEKTSHSLKNLFTTATKAEGFYADGSYIDHTNVAY TGAYGNVLIDGLTQLLPIIQETDYKISNQELDMVYKWINQSFLPLIVKGELM DMSRGRSISREAASSHAAAVEVLRGFLRLANMSNEERNLDLKSTIKTIITSN KFYNVFNNLKSYSDIANMNKMLNDSTVATKPLKSNLSTFNSMDRLAYYNAEK DFGFALSLHSKRTLNYEGMNDENTRGWYTGDGMFYLYNSDQSHYSNHFWPTV NPYKMAGTTEKDAKREDTTKEFMSKHSKDAKEKTGQVTGTSDEVGSVKLNDH FALAAMDFTNWDRTLTAQKGWVILNDKIVFLGSNIKNTNGIGNVSTTIDQRK DDSKTPYTTYVNGKTIDLKQASSQQFTDTKSVFLESKEPGRNIGYIFFKNST IDIERKEQTGTWNSINRTSKNTSIVSNPFITISQKHDNKGDSYGYMMVPNID RTSFDKLANSKEVELLENSSKQQVIYDKNSQTWAVIKHDNQESLINNQFKMN KAGLYLVQKVGNDYQNVYYQPQTMTKTDQLAI |
| 69 | Hyaluronidasese *Streptococcus agalactiae* 18RS21 | MEIKKKHRIMLYSALILGTILVNNSYQAKAEELTKTTSTSQIRDTQTNNIEV LQTESTTVKETSTTTTQQDLSNPTASTATATATHSTMKQVVDNQTQNKELVK NGDFNQTNPVSGSWSHTSAREWSAWIDKENTADKSPIIQRTEQGQVSLSSDK GFRGAVTQKVNIDPTKKYEVKFDIETSNKAGQAFLRIMEKKDNNTRLWLSEM TSGTTNKHTLTKIYNPKLNVSEVTLELYYEKGTGSATFDNISMKAKGPKDSE HPQPVTTQIEESVNTALNKNYVFNKADYQYTLTNPSLGKIVGGILYPNATGS TTVKISDKSGKIIKEVPLSVTASTEDKFTKLLDKWNDVTIGNHVYDTNDSNM QKINQKLDETNAKNIKTIKLDSNHTFLWKDLDNLNNSAQLTATYRRLEDLAK QITNPHSTIYKNEKAIRTVKESLAWLHQNFYNVNKDIEGSANWWDFEIGVPR SITATLALMNNYFTDAEIKTYTDPIEHFVPDAGYFRKTLDNPFKALGGNLVD MGRVKIIEGLLRKDNTIIEKTSHSLKNLFTTATKAEGFYADGSYIDHTNVAY TGAYGNVLIDGLTQLLPIIQETDYKISNQELDMVYKWINQSFLPLIVKGELM DMSRGRSISREAASSHAAAVEVLRGFLRLANMSNEERNLDLISTIKTIITSN KFYNVFNNLKSYSDIANMNKMLNDSTVATKPLKSNLSTFNSMDRLAYYNAEK DFGFALSLHSKRTLNYEGMNDENTRGWYTGDGMFYLYNSDQSHYSNHFWPTV NPYKMAGTTEKDAKREDTTKEFMSKHSKDAKEKTGQVTGTSDEVGSVKLNDH FALAAMDFTNWDRTLTAQKGWVILNDKIVFLGSNIKNTNGIGNVSTTIDQRK DDSKTPYTTYVNGKTIDLKQASSQQFTDTKSVFLESKEPGRNIGYIFFKNST IDIERKEQTGTWNSINRTSKNTSIVSNPFITISQKHDNKGDSYGYMMVPNID RTSFDKLANSKEVELLENSSKQQVIYDKNSQTWAVIKHDNQESLINNQFKMN KAGLYLVQKVGNDYQNVYYQPQTMTKTDQLAI |
| 70 | Hyaluronidase *Streptococcus agalactiae* serogroup III | MKQVVDNQTQNKELVKNGDFNQTNPVSGSWSHTSAREWSAWIDKENTADKSP IIQRTEQGQVSLSSDKGERGAVTQKVNIDPTKKYEVKFDIETSNKAGQAFLR IMEKKDNNTRLWLSEMTSGTTNKHTLTKIYNPKLNVSEVTLELYYEKGTGSA TEDNISMKAKGPKDSEHPQPVTTQIEESVNTALNKNYVENKADYQYTLTNPS LGKIVGGILYPNATGSTTVKISDKSGKIIKEVPLSVTASTEDKFTKLLDKWN DVTIGNHVYDTNDSNMQKINQKLDETNAKNIKTIKLDSNHTFLWKDLDNLNN SAQLTATYRRLEDLAKQITNPHSTIYKNEKAIRTVKESLAWLHQNFYNVNKD IEGSANWWDFEIGVPRSITATLALMNNYFTDAEIKTYTDPIEHFVPDAGYFR KTLDNPFKALGGNLVDMGRVKIIEGLLRKDNTIIEKTSHSLKNLETTATKAE GFYADGSYIDHTNVAYTGAYGNVLIDGLTQLLPIIQETDYKISNQELDMVYK WINQSFLPLIVKGELMDMSRGRSISREAASSHAAAVEVLRGFLRLANMSNEE RNLDLKSTIKTIITSNKFYNVFNNLKSYSDIANMNKMLNDSTVATKPLKSNL STFNSMDRLAYYNAEKDFGFALSLHSKRTLNYEGMNDENTRDWYTGDGMFYL YNSDQSHYSNHEWPTVNPYKMAGTTEKDAKREDTTKEEMSKHSKDAKEKTGQ VTGTSDEVGSVKLNDHFALAAMDFTNWDRTLTAQKGWVILNDKIVFLGSNIK NTNGIGNVSTTIDQRKDDSKTPYTTYVNGKTIDLKQASSQQFTDTKSVFLES KEPGRNIGYIFFKNSTIDIERKEQTGTWNSINRTSKNTSIVSNPFITISQKH DNKGDSYGYMMVPNIDRTSFDKLANSKEVELLENSSKQQVIYDKNSQTWAVI KHDNQESLINNQFKMNKAGLYLVQKVGNDYQNVYYQPQTMTKTDQLAI |
| 71 | Hyaluronidase *Staphylococcus aureus* (strain COL) | MTYRIKKWQKLSTITLLMAGVITLNGGEFRSVDKHQIAVADTNVQTPDYEKL RNTWLDVNYGYDKYDENNPDMKKKFDATEKEATNLLKEMKTESGRKYLWSGA ETLETNSSHMTRTYRNIEKIAEAMRNPKTTLNTDENKKKVKDALEWLHKNAY GKEPDKKVKELSENFTKTTGKNTNLNWWDYEIGTPKSLTNTLILLNDQFSNE EKKKFTAPIKTFAPDSDKILSSVGKAELAKGGNLVDISKVKLLECIIEEDKD MMKKSIDSFNKVFTYVQDSATGKERNGFYKDGSYIDHQDVPYTGAYGVVLLE |

TABLE 4-continued

| No. | PROTEIN/ NUCLIEC ACID | EXEMPLARY AMINO ACID/NUCLEIC ACID SEQUENCES |
| --- | --- | --- |
| | | GISQMMPMIKETPFNDKTQNDTTLKSWIDDGEMPLIYKGEMMDLSRGRAISR<br>ENETSHSASATVMKSLLRLSDAMDDSTKAKYKKIVKSSVESDSSYKQNDYLN<br>SYSDIDKMKSLMTDNSISKNGLTQQLKIYNDMDRVTYHNKDLDFAFGLSMTS<br>KNVARYESINGENLKGWHTGAGMSYLYNSDVKHYHDNFWVTADMKRLSGTTT<br>LDNEILKDTDDKKSSKTFVGGTKVDDQHASIGMDFENQDKTLTAKKSYFILN<br>DKIVFLGTGIKSTDSSKNPVTTIENRKANGYTLYTDDKQTTNSDNQENNSVF<br>LESTDTKKNIGYHFLNKPKITVKKESHTGKWKEINKSQKDTQKTDEYYEVTQ<br>KHSNSDNKYGYVLYPGLSKDVFKTKKDEVTVVKQEDDFHVVKDNESVWAGVN<br>YSNSTQTEDINNTKVEVKAKGMFILKKKDDNTYECSFYNPESTNSASDIESK<br>ISMTGYSITNKNTSTSNESGVHFELTK |
| 72 | Hyaluronidase *Streptococcus agalactiae* serotype Ia | MEIKKKHRIMLYSALILGTILVNNSYQAKAEEFTKTTSTSQIRDTQTNNVEV<br>PQTESTTVKGTSTTTQQDLSNSTASTATATATHSTMKQVVDNQTQNKELVK<br>NGDFKEKIIDKKIDKKSQWTNLYGAKDWNTYIDQTKSVNKSPIIQRTEQGQV<br>SLSSDKGFRGAVTQKVNIDPTKKYEVKFDIETSNKVGQAFLRIMKKKDKNTR<br>LWLSEMTSGTTNKHTLTKIYNPKLNVSEVTLELYYEKGTGSVTEDNISMKAK<br>GPKDSEHPQPVTTQIEESVNTALNKNYVENKADYQYTLTNPSLGKIVGGILY<br>PSATGSTTVKISDKSGKIIKEVPLSVTASTEDNFTKLLDKWNDVTIGNHVYD<br>TNDSNMQKLNQKLDETNAKNIKDIKLDSNRTFLWEDLKGLNNSAQLTATYRR<br>LEDLAKQITNPHSTIYKNEKAIRTVKESLAWLHQNFYNVNKDIEGSANWWDF<br>EIGVPRSITATLALMNNYFTDAEIKTYTDPIEHFVPDAGYFRKTLVNPFKAL<br>GGNLVDMGRVKIIEGLLRKDNTIIKKTSHSLKNLETTATKAEGFYADGSYID<br>HTNVAYTGAYGNVLIDGLTQLLPIIQETDYKISNQELDMVYKWINQSFLPLI<br>VKGELMDMSRGRSISREAASSHAAAVEVLRGFLRLANMSNEERNLDLKSTIK<br>TIITSNKFYNVFNNLKSYSDIANMNKLLNDSTVATKPLKSNLSTFNSMDRLA<br>YYNAEKDFGFALSLHSKRTLNYEGMNDENTRGWYTGDGMFYLYNSDQSHYSN<br>HFWPTVNPYKMAGTTEKDTGREDTIKKLMNRYDKTNKNSKVMTGQVTGTSDE<br>VGSVKLNDHFALAAMDFTNWDRTLTAQKGWVILNDKIVFLGSNIKNTNGVGN<br>VSTTIDQRKDDSKTPYTTYVNGKTVDLKQASSQQFTDTKSVFLESKEPGRNI<br>GYIFFKNSTIDIERKEQTGTWNSINRTSKNTSIVSNPFITISQKHDNKGDSY<br>GYMMVPNIDRTSFDKLANSKEVELLENSSKQQVIYDKNSQTWAVIKHDNQES<br>LINNQFKMNKAGLYLVQKVGNDYQNVYYQPQTMTKTDQLAI |
| 73 | Hyaluronidase *Staphylococcus aureus* (strain MRSA252) | MTYRMKKWQKLSTITLLMAGVITLNGGEFRSIDKHQIAVADTNVQTTDYEKL<br>RNIWLDVNYGYDKYDENNPDMKKKFEATENEAEKLLKEMKTESDRKYLWESS<br>KDLDTKSADMTRTYRNIEKISEAMKHKNTKLKTDENKTKVKDALEWLHKNAY<br>GKEPDKKVADLTSNEKNKTSRNTNLNWWDYEIGTPRALTNTLILLQEDFTDE<br>EKKKYTAPIKTFAPDSDKILSSVGKSEPAKGGNLVDISKVKLLESIIEEDKD<br>MMKKSIDSFNTVFTYAQNSATGKERNGFYKDGSYIDHQDVPYTGAYGVVLLE<br>GISQMMPMIKETPFNDSNQNDTTLKSWIDDGEMPLIYKGEMMDLSRGRAISR<br>ENETSHSASATVMKSLLRLSDTMDKSTKAKYKKIVKTSVESDSSYKQTDYLS<br>SYSD |
| 74 | Hyaluronidase *Staphylococcus aureus* (strain MRSA252) | MTNKMKKWQKLSTITLLMTGVIALNNGEFRNVDKHQIAVADTNVQTPDYEKL<br>KKTWLDVNYGYDQYDENNQDMKKKFDAKEKEAKKLLDDMKTDTNRTYLWSGA<br>ENLETNSSHMTKTYRNIEKIAESMQHKNTVLKTVENKLKIKEALDWMHKNVY<br>GKNPSQKVEDLTKNRKGQTTPKNNSLNWWDYEIGTPRALTNTLLLMDDMLTK<br>DEMKNYSKPISTYAPSSDKILSSVGESEDAKGGNLVDISKVKLLESVIEEDV<br>DMLKKSIDSFNKVFTYVQDSATGKGRNGFYKDGSYIDHQDVPYTGAYGVVLL<br>EGISQMMPMIKESPFKTTQDNATLSNWIDEGFMPLIYKGEMMDLSRGRAISR<br>ENETSHTASATVMKSLLRLNDTMDDSTKTRYKQIVKTSVNSDSSYNQNNYLN<br>SYSDIAKMKKLMNDSTISKNDLTQQLKIYNDMDRVTYHNKDLDFAFGLSMTS<br>KNIARYENINGENLKGWHTGAGMSYLYNSDVKHYRDNFWATADMTCLPGTTT<br>LNDMPSTNTKNDKSFVGGTKLNNKYASIGMDFENQDKTLTAKKSYFILNDKI<br>VFLGTGIKSTDSSKNPVTSVENRKANGYKLFKDDIEITTSDVNAQETHSVFL<br>ESNDTKKNIGYHFLDKPKITVKKESHTGKWSEINKSQKKDDKKDEYYEVTQT<br>HNTSDSKYAYVLYPGLSKSDFKSKNNNVSIVKQDEDFHVIKDNDGVFAGVNY<br>SDNTKSFDINGITVELKEKGMFVIKKKDDKAYKCSFYNPETTNTASNIESKI<br>FIKGYTITNKSVINSNDAGVNFELTK |
| 75 | Hyaluronidase *Staphylococcus aureus* (strain MSSA476) | MTYRIKKWQKLSTITLLMAGVITLNGGEFRSIDKYQIAVADTNVQTPDYEKL<br>RNTWLDVNYGYDKYDEKNDAMKKKFEATENEAKKLLSEMKTESDRKYLWENS<br>KDLDTKSADMTRTYRNIEKIAEAMKHKDTKLKIDENKKKVKDALEWLHKNAY<br>GKEPDKKVADLTSNEKNKTSRNTNLNWWDYEIGTPRALTNTLILLNDQFSND<br>EKKKYTAPIKTFAPESDKILSSVGQPEQAKGGNLVDIAKVKLLESIIEEDKD<br>ITKNSIDAFNKVFTYVQSNATGKERNGFYKDGSYIDHQDVPYTGAYGVVLLE<br>GISQMMPMIKETPFNDKTQNDTTLKSWIDDGEMPLIYKGEMMDLSRGRAISR<br>ENETSHTASATVMKSLLRLSDAMDDSTKAKYKQIVKTSVKSDSSYGQNDTLS<br>SYSDISKMKSLMEDSTISTNGLTQQLKIYNDMDRVTYHNKDLDFAFGLSMTS<br>KNVARYESINGENLKGWHTGAGMSYLYNSDVKHYRDNFWATADMKRLAGTTT<br>LENEEPKGTDVKKSSKTFVGGTKFDDQHASIGMDFENQDKTLTAKKSYFILN<br>DKIVFLGTGIKSTDSSKNPVTTIENRKANGYTLYTDDKQTTASDNQGTNSVF<br>LESTNKPKNNIGYHFLNESKITVKKESHTGKWSDINKSQKQDSKTNQYYEVT<br>QKHSNTDSKYAYVLYPGLSKDDFNTKKDKVTVVKQDDDFHVVKDNESVWAGV<br>NYSDSTQTFIINNTKVEVKAKGMFILKKKDDKTYECSFYNPESTNTASDIES<br>KISMTGYSITNKNTSTSNESGVRFELQQTLNKDDN |

TABLE 4-continued

| No. | PROTEIN/ NUCLIEC ACID | EXEMPLARY AMINO ACID/NUCLEIC ACID SEQUENCES |
|---|---|---|
| 76 | Hyaluronidase *Staphylococcus aureus* (strain NCTC 8325) | MTYRIKKWQKLSTITLLMAGVITLNGGEFRSVDKHQIAVADTNVQTPDYEKL<br>RNTWLDVNYGYDKYDENNPDMKKKFDATEKEATNLLKEMKTESGRKYLWSGA<br>ETLETNSSHMTRTYRNIEKIAEAMRNPKTTLNTDENKKKVKDALEWLHKNAY<br>GKEPDKKVKELSENFTKTTGKNTNLNWWDYEIGTPKSLTNTLILLNDQFSNE<br>EKKKFTAPIKTFAPDSDKILSSVGKAELAKGGNLVDISKVKLLECIIEEDKD<br>MMKKSIDSFNKVFTYVQDSATGKERNGFYKDGSYIDHQDVPYTGAYGVVLLE<br>GISQMMPMIKETPFNDKTQNDTTLKSWIDDGEMPLIYKGEMMDLSRGRAISR<br>ENETSHSASATVMKSLLRLSDAMDDSTKAKYKKIVKSSVESDSSYKQNDYLN<br>SYSDIDKMKSLMTDNSISKNGLTQQLKIYNDMDRVTYHNKDLDFAFGLSMTS<br>KNVARYESINGENLKGWHTGAGMSYLYNSDVKHYHDNFWVTADMKRLSGTTT<br>LDNEILKDTDDKKSSKTFVGGTKVDDQHASIGMDFENQDKTLTAKKSYFILN<br>DKIVFLGTGIKSTDSSKNPVTTIENRKANGYTLYTDDKQTTNSDNQENNSVF<br>LESTDTKKNIGYHFLNKPKITVKKESHTGKWKEINKSQKDTQKTDEYYEVTQ<br>KHSNSDNKYGYVLYPGLSKDVFKTKKDEVTVVKQEDDFHVVKDNESVWAGVN<br>YSNSTQTEDINNTKVEVKAKGMFILKKKDDNTYECSFYNPESTNSASDIESK<br>ISMTGYSITNKNTSTSNESGVHFELTK |
| 77 | Hyaluronidase *Staphylococcus aureus* (strain bovine RF122) | MTYRMKKWQKLSTITLLMAGGITENDSEFRSVDKHQIAVADTNVQTPNYEKL<br>KNTWLDVNYGYDKYDESNPDMKKKFEATEKEARKLLSEMKTESDRKYLWENS<br>KDLDTKSADMTRTYRNIEKIAEAMKHPKTTLKNDENKKKVKDALEWLHKNAY<br>GKEPGKKVADLKTNESKSAPQKNTNLNWWDYEIGTPRALTNTLILLKEDFTD<br>EEKKKYTAPIKTFAPKSDEILSSVGKAEPAKGGNLVDISKVKLLESIIEEDK<br>DMMKNSIDSFNKVFTYVQDSATDKERNGFYKDGSYIDHKDVPYTGAYGVVLL<br>EGISQMMPMIKETPFNDKTQNNTTLTSWIDDGEMPLIYKGEMMDLSRGRAIS<br>RENETSHSASATVMKSLLRLSDAMDESTKAKYKQIVKNSVKSDSSYGQNDTL<br>SSYSDIDKMKSLMTDSTISTNGLTQQLKIYNAMDRVTYHNKDLDFAFGLSMT<br>SKNVARYENINGENLKGWHTGAGMSYLYNSDVRHYRDNFWATADMKRLADTT<br>TLENEEPKGTDVKKSSKTFVGGTKFDDQHASIGMDFENQDKTLTAKKSYFIL<br>NDKIVFLGTGIKTTDSSKNPVTTIENRKAHGYTLYTDDKQTTNSNNQETNSV<br>FLESTNSTQNNIGYHFLNKSKITVKKESHTGKWSDINKSQKDTQKTDEYYEV<br>TQKHSNTDDKYAYVLYPGITKDNFKSKASQVTVVKQDDDFHVVKDNESVWAG<br>VNYSDSTQTEDINGTKVEVKAKGMFILKKKDDNTYECSFYNPESTNSASDIE<br>SKISMTGYSITNKNTSNTNESGVRFELTK |
| 78 | Hyaluronidase *Staphylococcus aureus* (strain bovine RF122) | MTYKMKKWQKLSTITLLMAGVITLNNGEFRNVDKHQIAVADTNVQTPDYEKL<br>KKTWLDVNYGNDQYDENNQDMKKKFDAKENEAKKLLEDMKTDTNRTYLWSGA<br>ENLETNSSHMTKTYRNIEKIAEAMRHKNTSLKTDENKLKIKDAIKWLHHNVY<br>GKDPDKKVADLTTNRKEKDSSKKNNSLNWWDYEIGTPRALTNTLLLMDNMLT<br>KDEMKNYSKPISIYSPSSYKILSSVGESEDAKGGNLVDIAKVKFLESVIEED<br>VDMMKKSIDSENKVETYVQDSATGKARNGFYKDGSYIDHQDVPYTGAYGVVL<br>LEGISQMMPMIKESPFKHTQDKATLSNWIDEGEMPLIYKGEMMDLSRGRAIS<br>RENETSHTASATVMKSLLRLSDTMDESTKTKYKQIVKTSVKSDSSYDSNDTL<br>NSYSDIDKMKKLMNDSTISKNDLTQQLKIYNDMDRVTYHNKELDFAFGLSMT<br>SKNIARYENINGENLKGWHTGAGMSYLYNSDVKHYRDNFWATADMTRLPGTT<br>TLNDMPSTNTKNDKSFVGGTKLNNKYASIGMDFENQDKTLTAKKSYFILNDK<br>IVFIGTGIKSTDSSKNPVTSVENRKANGYKLFKGDIEITTSDVNAQETHSVF<br>LESNDTKKNIGYHFLDKPKITVKKESHTGKWSEINKSQKTDDKKDEYYEVTQ<br>THNTSDSKYAYVLYPGLSKSDFKSKNNNVSIVKQDEDFHVIKDNDGVFAGVN<br>YSDSTKSFDINGTIVELKEKGMFVIKKKDDNTYECSFYNPTSTNSTSNKESK<br>ISVTGYTITNQSVSNEKESDIHFELTK |
| 79 | Hyaluronidase *Staphylococcus aureus* (strain USA300) | MTYRIKKWQKLSTITLLMAGVITLNGGEFRSVDKHQIAVADTNVQTPDYEKL<br>RNTWLDVNYGYDKYDENNPDMKKKFDATEKEATNLLKEMKTESGRKYLWSGA<br>ETLETNSSHMTRTYRNIEKIAEAMRNPKTTLNTDENKKKVKDALEWLHKNAY<br>GKEPDKKVKELSENFTKTTGKNTNLNWWDYEIGTPKSLTNTLILLNDQFSNE<br>EKKKFTAPIKTFAPDSDKILSSVGKAELAKGGNLVDISKVKLLECIIEEDKD<br>MMKKSIDSFNKVFTYVQDSATGKERNGFYKDGSYIDHQDVPYTGAYGVVLLE<br>GISQMMPMIKETPFNDKTQNDTTLKSWIDDGEMPLIYKGEMMDLSRGRAISR<br>ENETSHSASATVMKSLLRLSDAMDDSTKAKYKKIVKSSVESDSSYKQNDYLN<br>SYSDIDKMKSLMTDNSISKNGLTQQLKIYNDMDRVTYHNKDLDFAFGLSMTS<br>KNVARYESINGENLKGWHTGAGMSYLYNSDVKHYHDNFWVTADMKRLSGTTT<br>LDNEILKDTDDKKSSKTFVGGTKVDDQHASIGMDFENQDKTLTAKKSYFILN<br>DKIVFLGTGIKSTDSSKNPVTTIENRKANGYTLYTDDKQTTNSDNQENNSVF<br>LESTDTKKNIGYHFLNKPKITVKKESHTGKWKEINKSQKDTQKTDEYYEVTQ<br>KHSNSDNKYGYVLYPGLSKDVFKTKKDEVTVVKQEDDFHVVKDNESVWAGVN<br>YSNSTQTEDINNTKVEVKAKGMFILKKKDDNTYECSFYNPESTNSASDIESK<br>ISMTGYSITNKNTSTSNESGVHFELTK |
| 80 | Hyaluronidase *Streptococcus pneumoniae* | MQTKTKKLIVSLSSLVLSGFLLNHYMTIGAEETTTNTIQQSQKEVQYQQRDT<br>KNLVENGDFGQTEDGSSPWTGSKAQGWSAWVDQKNSADASTRVIEAKDGAIT<br>ISSHEKLRAALHRMVPIEAKKKYKLRFKIKTDNKIGIAKVRIIEESGKDKRL<br>WNSATTSGTKDWQTIEADYSPTLDVDKIKLELFYETGTGTVSFKDIELVEVA<br>DQLSEDSQTDKQLEEKIDLPIGKKHVFSLADYTYKVENPDVASVKNGILEPL<br>KEGTTNVIVSKDGKEVKKIPLKILASVKDAYTDRLDDWNGIIAGNQYYDSKN<br>EQMAKLNQELEGKVADSLSSISSQADRTYLWEKFSNYKTSANLTATYRKLEE<br>MAKQVTNPSSRYYQDETVVRTVRDSMEWMHKHVYNSEKSIVGNWWDYEIGTP<br>RAINNTLSLMKEYFSDEEIKKYTDVIEKEVPDPEHERKTTDNPFKALGGNLV |

TABLE 4-continued

| No. | PROTEIN/ NUCLIEC ACID | EXEMPLARY AMINO ACID/NUCLEIC ACID SEQUENCES |
|---|---|---|
| | | DMGRVKVIAGLLRKDDQEISSTIRSIEQVFKLVDQGEGFYQDGSYIDHTNVA YTGAYGNVLIDGLSQLLPVIQKTKNPIDKDKMQTMYHWIDKSFAPLLVNGEL MDMSRGRSISRANSEGHVAAVEVLRGIHRIADMSEGETKQCLQSLVKTIVQS DSYYDVFKNLKTYKDISLMQSLLSDAGVASVPRPSYLSAFNKMDKTAMYNAE KGFGEGLSLESSRTLNYEHMNKENKRGWYTSDGMFYLYNGDLSHYSDGYWPT VNPYKMPGTTETDAKRADSDTGKVLPSAFVGTSKLDDANATATMDFTNWNQT LTAHKSWFMLKDKIAFLGSNIQNTSTDTAATTIDQRKLESGNPYKVYVNDKE ASLTEQEKDYPETQSVFLESEDSKKNIGYFFEKKSSISMSKALQKGAWKDIN EGQSDKEVENEFLTISQAHKQNRDSYGYMLIPNVDRATENQMIKELESSLIE NNETLQSVYDAKQGVWGIVKYDDSVSTISNQFQVLKRGVYTIRKEGDEYKIA YYNPETQESAPDQEVFKKLEQAAQPQVQNSKEKEKSEEEKNHSDQKNLPQTG EGQSILASLGFLLLGAFYLFRRGKNN |
| 81 | Hyaluronidase *Streptococcus pneumoniae* R6 | MILQYVYWSVYMQTKTKKLIVSLSSLVLSGFLLNHYMTVGAEETTTNTIQQS QKEVQYQQRDTKNLVENGDFGQTEDGSSPWTGSKAQGWSAWVDQKNSSADAS TRVIEAKDGAITISSPEKLRAAVHRMVPIEAKKKYKLRFKIKTDNKVGIAKV RIIEESGKDKRLWNSATTSGTKDWQTIEADYSPTLDVDKIKLELFYETGTGT VSFKDIELVEVADQPSEDSQTDKQLEEKIDLPIGKKHVFSLADYTYKVENPD VASVKNGILEPLKEGTTNVIVSKDGKEVKKIPLKILASVKDTYTDRLDDWNG IIAGNQYYDSKNEQMAKLNQELEGKVADSLSSISSQADRIYLWEKFSNYKTS ANLTATYRKLEEMAKQVTNPSSRYYQDETVVRTVRDSMEWMHKHVYNSEKSI VGNWWDYEIGTPRAINNTLSLMKEYFSDEEIKKYTDVIEKEVPDPEHERKTT DNPFKALGGNLVDMGRVKVIAGLLRKDDQEISSTIRSIEQVFKLVDQGEGFY QDGSYIDHTNVAYTGAYGNVLIDGLSQLLPVIQKTKNPIDKDKMQTMYHWID KSFAPLLVNGELMDMSRGRSISRANSEGHVAAVEVLRGIHRIADMSEGETKQ RLQSLVKTIVQSDSYYDVFKNLKTYKDISLMQSLLSDAGVASVPRTSYLSAF NKMDKTAMYNAEKGFGEGLSLESSRTLNYEHMNKENKRGWYTSDGMFYLYNG DLSHYSDGYWPTVNPYKMPGTTETDAKRADSDTGKVLPSAFVGTSKLDDANA TATMDFTNWNQTLTAHKSWFMLKDKIAFLGSNIQNTSTDTAATTIDQRKLES SNPYKVYVNDKEASLTEQEKDYPETQSVFLESSDSKKNIGYFFEKKSSISMS KALQKGAWKDINEGQSDKEVENEFLTISQAHKQNGDSYGYMLIPNVDRATFN QMIKELESSLIENNETLQSVYDAKQGVWGIVKYDDSVSTISNQFQVLKRGVY TIRKEGDEYKIAYYNPETQESAPDQEVFKKLEQAAQPQVQNSKEKEKSEEEK NHSDQKNLPQTGEGQSILASLGFLLLGAFYLFRRGKNN |
| 82 | Hyaluronidase *Streptococcus pneumoniae* serotype 2 (strain D39/N) | MQTKTKKLIVSLSSLVLSGFLLNHYMTVGAEETTTNTIQQSQKEVQYQQRDT KNLVENGDFGQTEDGSSPWTGSKAQGWSAWVDQKNSSADASTRVIEAKDGAI TISSPEKLRAAVHRMVPIEAKKKYKLRFKIKTDNKVGIAKVRIIEESGKDKR LWNSATTSGTKDWQTIEADYSPTLDVDKIKLELFYETGTGTVSFKDIELVEV ADQPSEDSQTDKQLEEKIDLPIGKKHVFSLADYTYKVENPDVASVKNGILEP LKEGTTNVIVSKDGKEVKKIPLKILASVKDTYTDRLDDWNGIIAGNQYYDSK NEQMAKLNQELEGKVADSLSSISSQADRIYLWEKFSNYKTSANLTATYRKLE EMAKQVTNPSSRYYQDETVVRTVRDSMEWMHKHVYNSEKSIVGNWWDYEIGT PRAINNTLSLMKEYFSDEEIKKYTDVIEKFVPDPEHERKTTDNPFKALGGNL VDMGRVKVIAGLLRKDDQEISSTIRSIEQVFKLVDQGEGFYQDGSYIDHTNV AYTGAYGNVLIDGLSQLLPVIQKTKNPIDKDKMQTMYHWIDKSFAPLLVNGE LMDMSRGRSISRANSEGHVAAVEVLRGIHRIADMSEGETKQRLQSLVKTIVQ SDSYYDVFKNLKTYKDISLMQSLLSDAGVASVPRTSYLSAFNKMDKTAMYNA EKGFGFGLSLFSSRTLNYEHMNKENKRGWYTSDGMFYLYNGDLSHYSDGYWP TVNPYKMPGTTETDAKRADSDTGKVLPSAFVGTSKLDDANATATMDFTNWNQ TLTAHKSWFMLKDKIAFLGSNIQNTSTDTAATTIDQRKLESSNPYKVYVNDK EASLTEQEKDYPETQSVFLESSDSKKNIGYFFEKKSSISMSKALQKGAWKDI NEGQSDKEVENEFLTISQAHKQNGDSYGYMLIPNVDRATFNQMIKELESSLI ENNETLQSVYDAKQGVWGIVKYDDSVSTISNQFQVLKRGVYTIRKEGDEYKI AYYNPETQESAPDQEVFKKLEQAAQPQVQNSKEKEKSEEEKNHSDQKNLPQT GEGQSILASLGFLLLGAFYLFRRGKNN |
| 83 | Hyaluronidase *Streptococcus pyogenes* serotype Ng | MNTYFCTHHKQLLLYSNLELSFAMMGQGTAIYADTLTSNSEPNNTYFQTQTL TTTDSEKKVVQPQQKDYYTELLDQWNSIIAGNDAYDKTNPDMVTFHNKAEKD AQNIIKSYQGPDHENRTYLWEHAKDYSASANITKTYRNIEKIAKQITNPESC YYQDSKAIAIVKDGMAFMYEHAYNLDRENHQTTGKENKENWWVYEIGTPRAI NNTLSLMYPYFTQEEILKYTAPIEKFVPDPTRFRVRAANFSPFEANSGNLID MGRVKLISGILRKDDLEISDTIKAIEKVFTLVDEGNGFYQDGSLIDHVVTNA QSPLYKKGIAYTGAYGNVLIDGLSQLIPIIQKTKSPIKADKMATIYHWINHS FFPIIVRGEMMDMTRGRSISRFNAQSHVAGIEALRAILRIADMSEEPHRLAL KTRIKTLVTQGNAFYNVYDNLKTYHDIKLMKELLSDTSVPVQKLDSYVASFN SMDKLALYNNKHDFAFGLSMFSNRTQNYEAMNNENLHGWFTSDGMFYLYNND LGHYSENYWATVNPYRLPGTTETEQKPLEGTPENIKTNYQQVGMTGLSDDAF VASKKLNNTSALAAMTFTNWNKSLTLNKGWFILGNKIIFVGSNIKNQSSHKA YTTIEQRKENQKYPYCSYVNNQPVDLNNQLVDETNTKSIFLESDDPAQNIGY YFFKPTTLSISKALQTGKWQNIKADDKSPEAIKEVSNTFITIMQNHTQDGDR YAYMMLPNMTRQEFETYISKLDIDLLENNDKLAAVYDHDSQQMHVIHYGKKA TMESNHNLSHQGFYSEPHPVRQNQQ |

TABLE 4-continued

| No. | PROTEIN/ NUCLIEC ACID | EXEMPLARY AMINO ACID/NUCLEIC ACID SEQUENCES |
|---|---|---|
| 84 | Hyaluronidase *Streptococcus pyogenes* serotype M2 (strain MGAS10) | MVYFYLVNQSTFIISFLYWRNVSVNTYFCTHHKQLLLYSNLELSFAMIGQGT AIYADTLTSNSEPNNTYFQTQTLTTTDSEKKVVQPQQKDYYTELLDQWNSII AGNDAYDKTNPDMVTEHNKAEKDAQNIIKSYQGPDHENRTYLWEHAKDYSAS TNITKTYRNIEKIAKQITNPESCYYQDSKAIAIVKDGMAFMYEHAYNLNREN HQTTGKENKENWWVYEIGTPRAINNTLSLMYPYFTQEEILKYTAPIEKFVPD PTRFRVRAANFSPFEANSGNLIDMGRVKLISGILRKDDLEISDTIKAIEKVF TLVDEGNGFYQDGSLIDHVVTNTQSPLYKKGIAYTGAYGNVLIDGLSQLIPI IQKTKSPIEADKMATIYHWINHSFFPIIVRGEMMDMTRGRSISRFNAQSHVA GIEALRAILRIADMSEEPHRLELKTRIKTLVTQGNAFYNVYDNLKTYHDIKL MKELLSDTSVPVQKLDSYVASFNSMDKLALYNNKHDFAFGLSMFSNRTQNYE AMNNENLHGWFTSDGMFYLYNNDLGHYSENYWATVNPYRLPGTTETEQKPLE GTPENIKTNYQQVGMTSLSDDAFVASKKLNNTSALAAMTFTNWNKSLTLNKG WFILGNKIIFVGSNIKNQSSHKAYTTIEQRKENQKHPYCSYVNNQPVDLNNQ LVDFTNTKSIFLESDDPAQNIGYYFFKPRTLSISKALQTGKWQNIKADDKSP EAIKEVSNTFITIMQNHTQEGDRYAYMMLPNMTRQEFETYISKLDIDLLENN |
| 85 | Hyaluronidase *Streptococcus pyogenes* serotype M4 (strain MGAS10) | MNTYFCTHHKQLLLYSNLELSFAMMGQGTAIYADTLTSNSKPNNTYFQTQTL TTTDSEKKVVQPQQKDYYTELLDQWNSIIAGNDAYDKTNPDMVTFHNKAEKD AQNIIKSYQEPDHENRTYLWEHAKDYSASANITKTYRNIEKIAKQITNPESC YYQDSKAIAIVKDGMAFMYEHAYNLDRENHQTTGKENKENWWDYEIGTPRAI NNTLSLMYPYFTQEEILKYTAPIEKEVPDPTRERVRAANFPPFEANSGNLID MGRVKLISGILRKDDLEISDTIKAIEKVFTLVDEGNGFYQDGSLIDHVVTNA QSPLYKKGIAYTGAYGNVLIDGLSQLIPIIQKTKSPIEADKMATIYHWINHS FFPIIVRGEMMDMTRGRSISRFNAQSHVAGIEALRAILRIADMSEEPHRLAL KTRIKTLVTQGNVFYNVYDNLKTYHDIKLMKELLSDTSVPVQKLDSYVASFN SMDKLALYNNKHDFAFGLSMFSNRTQNYEAMNNENLHGWFTSDGMFYLYNND LGHYSENYWATVNPYRLPGTTETEQKPLEGTPENIKTNYQQVGMTSLSDDAF VASKKLNNTSALAAMTFTNWNKSLTLNKGWFILGNKIIFVGSNIKNQSSHKA YTTIEQRKENQKHPYCSYVNNQPVDLNNQLVDFTNTKSIFLESDDPAQNIGY YFFKPTTLSISKALQTGKWQNIKADDKSPEAIKEVSNTFITIMQNHTQDGDR YAYMMLPNMTRQEFETYISKLDIDLLENNDKLAAVYDHDSQQMHVIHYEKKA TTFSNHNLSHQGFYSFPHPVKQNQQQKLAHQGIAAKNNALNSHKIPHKRQRR LPRTGYQSSSLEFLGGALVASFNHITKPFRKKDLRI |
| 86 | Hyaluronidase *Streptococcus pyogenes* serotype M6 | MVYFYLVDQFTFIISFLYWRNLSVNTYFCTHHKQLLLYSNLFLSFAMMGQGT AIYADTLTSNSEPNNTYFQTQTLTTTDSEKKVVQPQQKDYYTELLDQWNSII AGNDAYDKTNPDMVTFHNKAEKDAQNIIKSYQGPDHENRTYLWEHAKDYSAS TNITKTYRNIEKIAKQITNPESCYYQDSKAIAIVKDGMAFMYEHAYNLDREN HQTTGKENKENWWVYEIGTPRAINNTLSLMYPYFTQEEILKYTAPIEKEVPD PTRERVRAANFSPFEANSGNLIDMGRVKLISGILRKDDLEISDTIKAIEKVF TLVDEGNGFYQDGSLIDHVVTNAQSPLYKKGIAYTGAYGNVLIDGLSQLIPI IQKTKSPIEADKMATIYHWINHSFFPIIVRGEMMDMTRGRSISRFNAQSHVA GIEALRAILRIADMSEEPHRLALKTRIKTLVTQGNAFYNVYDNLKTYHDIKL MKELLSDTFVPVQKLDSYVASFNSMDKLALYNNKHDFAFGLSMFSNRTQNYE AMNNENLHGWFTSDGMFYLYNNDLGHYSENYWATVNPYRLPGTTETEQKPLE GTPENIKTDYQQVGMTSLSDDAFVASKKLNNTSALAAMTFTNWNKSLTLNKG WFILGNKIIFVGSNIKNQSSHKAYTTIEQRKENQKHPYCSYVNNQPVDLNNQ LVDFTNTKSIFLESDDPAQNIGYYFFKPTTLSISKALQTGKWQNIKADDKSP EAIKEVSNTFITIMQNHTQDGDRYAYMMLPNMTRQEFETYISKLDIDLLENN DKLAAVYDHDSQQMHVIHYEKKATMESNHNLSHQGFYSEPHPVKQNQQ |
| 87 | Hyaluronidase *Streptococcus pyogenes* serotype M12 (strain MGAS2) | MVYFYLVNQSTFIISFLYWRNLSVNTYFCTHHKQLLLYSNLFLSFAMMGQGT AIYADTLTSNSEPNNTYFQTQTLTTTDSEKKVVQPQQKDYYTELLDQWNSII AGNDAYDKTNPDMVTFHNKAEKDAQNIIKSYQGPDHENRTYLGNMQRIIPLL LISRKLTAILKKISKMKSLMEDSTISTNGLTQQLKIYNDMDRVTYHNKGLDF AFGLSMTSKNVARYESINGENLKGWHTGAGMSYLYNSDVKHYRDNFWATADM KRLAGTTTLDNEEPKSTDVKKSSKTFVGGTKFDDQHASIGMDFENQDKTLTA KKSYFILNDKIVFLGTGIKSTDSSKNPVTTIENRKANDYKLYKDDTQTTNSD NQETNSLFLESTNSTQNNIGYHFLNESKITVKKESHTGKWSDINKSQKDIQK TDEYYEVTQKHSNTDSKYAYVLYPGLSKDVFKSKASKVTVVKQEDDFHVVKD NESVWAGINYSDSAKTFEINNTKVEVKAKGMFILTKKDDNTYECSFYNPEST NSVSDIESKISMTGYSIINKNTSTSNESGVRFELTK |
| 88 | Hyaluronidase *Streptococcus pyogenes* serotype M12 (strain MGAS2) | MAFMYEHAYNLNRENHQTTGKENKENWWVYEIGTPRAINNTLSLMYPYFTQE EILKYTAPIEKEVPDPTRERVRAANFSPFEASSGNLIDMGRVKLISGILRKD DLEISDTIKAIEKVFTLVDEGNGFYQDGSLIDHVVTNAQSPLYKKGLAYTGA YGNVLIDGLSQLIPIIQKTKSPIEADKMATIYHWINHSFFPIIVRGEMMDMT RGRSISRFNAQSHVAGIEALRAILRIADMSEEPHRLALKTRIKTLVTQGNAF YNVYDNLKTYHDIKLMKELLSDTSVPVQKLDSYVASFNSMDKLALYNNKHDF AFGLSMESNRTQNYEAMNNENLHGWFTSDGMFYLYNNDLGHYSENYWATVNP YRLPGTTETEQKPLEGTPENIKTNYQQVGMTSLSDDAFVASKKLNNTSALAA MTFTNWNKSLTLNKGWFILGNKIIFVGSNIKNQSSHKAYTTIEQRKENQKHP YCSYVNNQPVDLNNQLVDFTNTKSIFLESDDPAQNIGYYFFKPTTLSISKAL QTGKWQNIKADDKSPEAIKEVSNTFITIMQNHTQDGDRYAYMMLPNMTRQEF ETYISKLDIDLLENNDKLAAVYDHDSQQMHVIHYEKKATMFSNHNLSHQGFY SFPHPVKQNQQ |

TABLE 4-continued

| No. | PROTEIN/ NUCLIEC ACID | EXEMPLARY AMINO ACID/NUCLEIC ACID SEQUENCES |
|---|---|---|
| 89 | Hyaluronidase *Streptococcus pyogenes* serotype M12 (strain MGAS9) | MVYFYLVNQSTFIISFLYWRNLSVNTYFCTHHKQLLLYSNLELSFAMMGQGT<br>AIYADTLTSNSEPNNTYFQTQTLTTTDSEKKVVQPQQKDYYTELLDQWNSII<br>AGNDAYVKTNPDMVTFHNKAEKDAQNIIKSYQGPDHENRTYLWEHAKDYSAS<br>TNITKTYRNIEKIAKQITNPESCYYQDSKAIAIVKDGMAFMYEHAYNLNREN<br>HQTTGKENKENWWVYEIGTPRAINNTLSLMYPYFTQEEILKYTAPIEKEVPD<br>PTRERVRAANFSPFEASSGNLIDMGRVKLISGILRKDDLEISDTIKAIEKVF<br>TLVDEGNGFYQDGSLIDHVVTNAQSPLYKKGIAYTGAYGNVLIDGLSQLIPI<br>IQKTKSPIEADKMATIYHWINHSFFPIIVRGEMMDMTRGRSISRFNAQSHVA<br>GIEALRAILRIADMSEEPHRLALKTRIKTLVTQGNAFYNVYDNLKTYHDIKL<br>MKELLSDTSVPVQKLDSYVASFNSMDKLALYNNKHDFAFGLSMESNRTQNYE<br>AMNNENLHGWFTSDGMFYLYNNDLGHYSENYWATVNPYRLPGTTETEQKPLE<br>GTPENIKTNYQQVGMTSLSDDAFVASKKLNNTSALAAMTFTNWNKSLTLNKG<br>WFILGNKIIFVGSNIKNQSSHKAYTTIEQRKENQKHPYCSYVNNQPVDLNNQ<br>LVDFTNTKSIFLESDDPAQNIGYYFFKPTTLSISKALQTGKWQNIKADDKSP<br>EAIKEVSNTFITIMQNHTQDGDRYAYMMLPNMTRQEFETYISKLDIDLLENN<br>DKLAAVYDHDSQQMHVIHYEKKATMESNHNLSHQGFYSEPHPVKQNQQ |
| 90 | Hyaluronidase *Streptococcus pyogenes* serotype M28 | MVYFYLVNQFTFIISFLYRRNLSVNTYFCTHHKQLLLYSNLELSFAMMGQGT<br>AIYADTLTSNSEPNNTYFQTQMLTTTDSEKKVVQPQQKDYYTELLDQWNSII<br>AGNDAYDKTNPDMVTFHNKAEKDAQNIIKSYQGPDHENRTYLWEHAKDYSAS<br>ANITKTYRNIEKIAKQITNPESCYYQDSKAIAIVKDGMAFMYEHAYNLDREN<br>HQTTGKENKENWWVYEIGTPRAINNTLSLMYPYFTQEEILKYTAPIEKEVPD<br>PTRERVRAANFSPFEANSGNLIDMGRVKLISGILRKDDLEISDTIKAIEKVF<br>TLVDEGNGFYQDGSLIDHVVTNAQSPLYKKGIAYTGAYGNVLIDGLSQLIPI<br>IQKTKSSIEADKMATIYHWINHSFFPIIVRGEMMDMTRGRSISRFNAQSHVA<br>GIEALRAILRIADMSEEPHRLALKTRIKTLVTQGNAFYNVYDNLKTYHDIKL<br>MKELLSDTSVPVQKLDSYVASFNSMDKLALYNNKHDFAFGLSMESNRTQNYE<br>AMNNENLHGWFTSDGMFYLYNNDLGHYSENYWATVNPYRLPGTTETEQKPLE<br>GTPENIKTNYQQVGMTSLSDDAFVASKKLNNTSALAAMTFTNWNKSLTLNKG<br>WFILGNKIIFVGSNIKNQSSHKAYTTIEQRKENQKHPYHAYVNNQPVDLNNQ<br>LVDFTNTKSIFLESDDSAQNIGYYFFKPTTLSISKALQTGKWQNIKADDKSP<br>EAIKEVSNTFITIMQNHTQDGDRYAYMMLPNMTRQEFETYISKLDIDLLENN<br>DKLAAVYDHDSQQMHVIHYEKKATMESNHNLSHQGFYSEPHPVKQNQQ |
| 91 | Hyaluronidase *Streptococcus suis* | MGFFISQSKQHYGIRKYKVGVCSALIALSILGTRVAANQLPSTETASPQSSQ<br>LVETTPETTEAVNLTTEAVMTSEVSSEVSPVTSTETQPSSTAAETLASPQAV<br>QATKEEEKNLVANGEFASTTAASGNWADPAATNWETWIPANVKKENGQVRID<br>EGRLHISSTASYRVAVHQTVDVDPNKRYLFSYNVETKDLKGSGVRVRLRSLT<br>AEGKDLSPQEFAYTPYKNGSQAEHIEQILTVSPETRKLKVELFFENSVGQAW<br>LDNISLVEYVEKTPETPEPSLELVQPETGQISLASNKVYLPVRPDLTYRIAD<br>AAVAIVEKNMIRPLAAGKTQVDVYDKDTKLSSFELTVTEHQATVFDTLRNNW<br>EDISLANKRYQSNDTQMKAFLGRLDAGVASSLKKWVEPTNQGKTIFNDIDFS<br>KSSHLTTVYRRLEQMAQVVENPDSAYYHDRSLIDLVRKGMNWLYTNVYNENK<br>SIDGNWWDYEIGTPRAVVNTLIYMHPYFSQEEILTYTKPISKFVPDPTTISV<br>KH |
| 92 | Hyaluronidase *Streptococcus suis* | MGFFISQSKQHYGIRKYKVGVCSALIALSILGTRVAANQLPSTETASPQSSQ<br>LVETTPETTEAVMTSEVSSEVSPVTSTETQPSSTTAETLASPQAVQATKEEK<br>NLVANGEFISTTAPSGNWKELAATNWETWIPANVKKENGQVRIDEGRLHISS<br>TASYRVAVHQTVDVDPNKRYLFSYDVETKDLKGSGVRVRLRSLTAEGKDLSP<br>QEFAYTPYKNGSQAEHIEQILTVSPETRKLKVELFFENSVGQAWLDNISLVE<br>YVEKTPETPEQSPELVQPETGQISLASNKVYLPVRPDLTYRIADAAVATVEK<br>NMIRPLAAGKTQVDVYDKDTKLSSFELIVTEHQATVFDTLRNNWEDISLANK<br>RYQSNDAQMKAFLGRLDAGVASSLEKWVEPTEQSKTIFNDIDFSKSSHLTTV<br>YRRLEQMAQVVENPDSAYYHDRSLIDLVRKGMNWLYANVYNENKSIDGNWWD<br>YEIGTSRAVVNTLIYMHPYFSQEEILTYTKPISKFVPDPTTIRKTLTNPVPA<br>VGGNQTDLSKVAILEGALREDADRVRAGAQGLTTIMKFVDKGEGFYRDGSFI<br>DHTNVAYTGAYGNVLIEGFSQLLPVIQPTEFALKEEQTNILYEWIEKAFMPI<br>LVRGELMDMTRGRSISRATGESHVQAMEILRSLVRIAESAQPEQKTKLLSFV<br>KAQLTSDTFYDSYRSLKSYKDIDLVNKLLADNQIPAEVDKDYIAAFNNMDKF<br>VYRSAQEGFTFALSMYSSRTQNYEDMNNENRKGWYTADGMVYLYNDDLSHYS<br>NHYWATVDPYRLPGTTTTKDKREDGSGEVTLASDEVGASQLGNRLATIAMDF<br>NNWNNSLTARKAWIVLGNKIVFLGTDIQHQSAQGAETTIENRKLLTGEKYSY<br>YINGQPVDLSKEVVTDKTQSFYMTNGKDNQSIGYVFLNQLPTHAKLDQRTGK<br>WSDINYNQSKEEVSNSFVSLWHEHAQTSSNYAYVLVPNQSMEKVNQAAASVK<br>LLHQDRDLQVVYDQEQNVWGVVKYTDTAYKLTDDITLTDAGLYTIQKVEGGY<br>RIAFYNPSTRTVKNGIELTKAGSSLTVEMEPTAAYPSTVWKVTMPEGSDKQT<br>GSVEKTEKEEKQLKENQPSSEVKQVVHHAAEKTKPSKPRLPQTGEEASLGLG<br>FLGLLTLGAVVDFKCRRSHS |
| 93 | Hyaluronidase (*Streptococcus suis*) | MGFFISQSKQHYGIRKYKVGVCSALIALSILGTRVAANQLPSTETASPQSSQ<br>LVETTPETTEAVMTSEVSSEVSPVTSTETQPSSTTAETLASPQAVQATKEEK<br>NLVANGEFISTTAPSGNWKELAATNWETWIPANVKKENGQVRIDEGRLHISS<br>TASYRVAVHQTVDVDPNKRYLFSYDVETKDLKGSGVRVRLRSLTAEGKDLSP<br>QEFAYTPYKNGSQAEHIEQILTVSPETRKLKVELFFENSVGQAWLDNISLVE<br>YVEKTPETPEQSPELVQPETGQISLASNKVYLPVRPDLTYRIADAAVATVEK |

TABLE 4-continued

| No. | PROTEIN/ NUCLIEC ACID | EXEMPLARY AMINO ACID/NUCLEIC ACID SEQUENCES |
|---|---|---|
| | | NMIRPLAAGKTQVDVYDKDTKLSSFELIVTEHQATVFDTLRNNWEDISLANK RYQSNDAQMKAFLGRLDAGVASSLEKWVEPTEQSKTIFNDIDFSKSSHLTTV YRRLEQMAQVVENPDSAYYHDRSLIDLVRKGMNWLYTNVYNENKSIDGNWWD YEIGTPRAVVNTLIYMHPYFSQEEILTYTKPISKFVPDPTTIRKTLTNPVPA VGGNQTDLSKVAILEGALREDADRVRAGAQGLTTIMKFVDKGEGFYRDGSFI DHTNVAYTGAYGNVLIEGFSQLLPVIQPTEFALKEEQTNILYEWIEKAFMPI LVRGELMDMTRGRSISRATGESHVQAMEILRSLVRIAESAQPEQKTKLLSFV KAQLTSDTFYDSYRSLKSYKDIDLVNKLLADNQIPAEVDKDYIAAFNNMDKF VYRSAQEGFTFALSMYSSRTQNYEDMNNENRKGWYTADGMVYLYNDDLSHYS NHYWATVDPYRLPGTTTTKDKREDGSGEVTLASDEVGASQLGNRLATIAMDF NNWNNSLTARKAWIVLGNKIVFLGTDIQHQSAQGAETTIENRKLLTGEKYSY YINGQPVDLSKEVVTDKTQSFYMTNGKDNQSIGYVFLNQLPTHAKLDQRTGK WSDINYNQSKEEVSNSFVSLWHEHAQTSSNYAYVLVPNQSMEKVNQAAASVK LLHQDRDLQVVYDQEQNVWGVVKYTDTAYKLTDDITLTDAGLYTIQKVEGGY RIAFYNPSTRTVKNGIELTKAGSSLTVEMEPTAAYPSTVWKVTMPEGSDKQT GSVEKTEKEEKQLKENQPSSEVKQVVHHAAEKTKPSKPRLPQTGEEASLGLG FLGLLTLGAVVDFKCRRSHS |
| 94 | Hyaluronidase *Vibrio fischeri* (strain ATCC 700601/ ES114) | MYMIKKHRLNTIALSMLFLFTGNAYAAKNTQTPQYLPSDFEQVRENWAENYL GDPAITFDQTLKNMVTSTNSSAQKHWDSMTPQPNASGIWDDLPLIDKDTTLG PNIRNSYQRLFTMAKAYRLRDGNLENNQLMLNDIMTAMNYINQNFYFVNQLE YGNWWQWELAIPKDIHNILVLLFDDIKDNYQTIITNHLNATRYFTPDPTHLG VSPGAAESTNPNYRESTGGNRTDNAQVVLIRGMLENNSEEISQATAALPAVI EYVSEGDGYYTDGSFLQHSDIAYNGTYGNVLLGGLGIQMNAVAGSPWSMDNQ TISNVYNIINQSYEPLLYKGAMMDMVNGRSISRSAEQNHDVGLNIVNSMLFY TNGPDSDKNKQLSSLIKTQITDDTYQNFFDKIYYVSTYQAAQHIVNDPTVSL KDPLIGNESYPSMDRIVHRRTDWAFALAMHSYRIGNYECMNGENLKGWFTGD GMIYLYNDQLDHYTGYWPTVNASRMPGTTVDSQIMADCSGERVGGNVNTNMQ WVGSTSLNNYGIAGMQFYNWSDTLSAYKSWFMEDNEVVMLGSNIKDQSNANN ITTIENRKRLAETKLFIDGTEQAALPYQGAPATFSIRNKTLANSDLSYVMLT PKTISISQNDVDGNWSDIGNSKGDVSDSYLQATLTQVDQADYQYALLPNQNN DTVQNYAQHPDVTVLRQDEQAHAVQENTLNIIAANNWKNNPVNITDTITLNS MMGEMIKEESSNTFTVAVSEPIQTIDSVNFTFDKQGIVIKEDIENRVVLNGT TLTINTSGLQGQSYSFQVTIQD |
| 95 | Hyaluronidase (*Hiduro nipponia*) | >sp\|X4Y2L4\|LHYAL_HIRNI Hyaluronoglucuronidase OS = *Hirudo nipponia* PE = 1 SV = 1 MKEIAVTIDDKNVIASVSESFHGVAFDASLFSPKGLWSFVDITSPKLFKLLE GLSPGYFRVGGTFANWLFFDLDENNKWKDYWAFKDKTPETATITRRWLFRKQ NNLKKETFDDLVKLTKGSKMRLLFDLNAEVRTGYEIGKKMTSTWDSSEAEKL FKYCVSKGYGDNIDWELGNEPDHTSAHNLTEKQVGEDFKALHKVLEKYPTLN KGSLVGPDVGWMGVSYVKGLADGAGDHVTAFTLHQYYFDGNTSDVSTYLDAT YFKKLQQLFDKVKDVLKNSPHKDKPLWLGETSSGYNSGTKDVSDRYVSGFLT LDKLGLSAANNVKVVIRQTIYNGYYGLLDKNTLEPNPDYWLMHVHNSLVGNT VEKVDVSDPTNKARVYAQCTKTNSKHTQSRYYKGSLTIFALNVGDEDVTLKI DQYSGKKIYSYILTPEGGQLTSQKVLLNGKELKLVSDQLPELNADESKTSFT LSPKTFGFFVVSDANVEACKK |
| 96 | Hyaluronidase (*Staphylococcus aureus*) | >WP_070029084.1 hyaluronate lyase [*Staphylococcus aureus*] MTYRMKKWQKLSTITLLMAGAITLNGGEFRSIDKHQIAVADTNVQTPDYEKL RNTWLNVNYGYDQYDEKNDAMKKKEDATEKEAEKLLSSMKTESGRTYLWDSA KDLDNKSADMTRTYRNIEKIAEAMKHKDTKLNTPDNKNKVKDALEWLHKNAY GKEPVKKLEELKTNESKSAPQKNTNLNWWDYEIGTPRALTNTLILLKEDFTD EEKKKYTAPIKTFAPKSDEILSSVGKAEPAKGGNLVDISKVKLLESIIEEDA TMMKESIEAFNKVETYVQSNATGKERNGFYKDGSYIDHQDVPYTGAYGVVLL EGISQMMPMIKETPFKDSNQNDTTLKSWIDEGEMPLIYKGEMMDLSRGRAIS RENETSHSTSATVMKSLLRLSDAMDESTKAKYKQIVKTSVKSDSSYKQNDYL SSYSDISKMKSLIEDSTISTNGLTQQLKIYNDMNRVTYHNKDLDFAFGLSMT SKNVAHYESINGENLKGWHTGAGMSYLYNSDVKHYRDNFWATADMKRLAGTT TLDNEEPKENKNSDKTFVGGTKFDDQHASIGMDFENQDKTLTAKKSYFILND KIVFLGTGIKSTDSSKNPVTTIENRKSNGYTLFTDDKQTTASNINDQETNSV FLESTDTKKNIGYHFLNESKITVKKESHTGKWSDINKSQKSDDKTDEYYEVT QKHSNTDDKYAYVLYPGLSKDNEKSKASQVTIVKQDDDFHIVKDNESVWAGV NYSNSTQTEDINNTKVEVKAKGMFILKNKDDNTYECSFYNPESTNTASDIES KISMTGYSITNKNTSTSNESGVRFELQQTLNKDDN |
| 97 | Hyaluronidase (*Loxosceles intermedia*) | >sp\|R4J7Z9IHYAL LOXIN Hyaluronidasese OS = *Loxosceles intermedia* PE = 2 SV = 1 MQTILVLTTFLSAWFLAVGFDVFWNVPSQQCKKYGMKFVPLLEQYSILVNKE DNFKGDKITIFYESQLGLYPHIGANDESENGGIPQLGDLKAHLEKSAVDIRR DILDKSATGLRIIDWEAWRPIWEFNWSSLRKYQDKMKKVVRQFNPTAHESTV AKLAHNEWENSSKSWMLSTLQLGKQLRPNSVWCYYLFPDCYNYDGNSVQEFQ CSEAIRKGNDRLKWLWEESTAVCPSIYIKEGQLTNYTLQKRIWFTNGRLQEA LRVAQPKARTYPYINYSIKPGMMVPEVEFWRLIAQIASLGMDGAVIWGSSAS VGSKNHCAQLMKYIADVLGPATLRIKENVARCSKQACSGRGRCTWPKDTSVI AWKFLVEKEDYDFYLGDIECKCVEGYEGRYCEQKTK |

TABLE 4-continued

| No. | PROTEIN/ NUCLIEC ACID | EXEMPLARY AMINO ACID/NUCLEIC ACID SEQUENCES |
|---|---|---|
| 99 | Hyaluronidase (*Streptomyces koganeiensis*) | >AKQ62598.1 hyaluronidase [*Streptomyces koganeiensis*] MPVARRLFLGSFTAGAVTVATAAATGTASAAGENGATTTFDGPVAAERFSAD TTLEAAFLKTTSETNHAATIYQAGTSGDGAALNVISDNPGTSAMYLSGTETA RGTLKITHRGYADGSDKDAAALSLDLRVAGTAAQGIYVTATNGPTKGNLIAL RNNTGLDDEVVKGTGRIGVGIDRAATPRAQVHIVQRGDALAALLVEGSVRIG NAATVPTSVDSSGGGALYASGGALLWRGSNGTVTTIAPA |
| 100 | Hyaluronidase (*Mycobacterium tuberculosis*) | >WP_055373619.1 hypothetical protein [*Mycobacterium tuberculosis*] MTESRPVFAVVISAGLSAIPMVGGPLQTVFDAIEERTRHRAETTTREICESV GGADTVLSRIDKNPELEPLLSQATEAATRTSMEAKRRLLAQAAAAALEDDQK VEPASLIVATLSQLEPVHIHALVRLAKAAKSSPDQDEIQRREVMRAASKVEP VPVLAALIQTGVAIATTTVWHGNGTGTPAEESGHILIHDVSDFGHRLLAYLR AADAGAELLILPSGGSAPTGDHPTPHPSTSR |
| 101 | Hyaluronidase (*Hiduro nipponia*) | MDWTWILFLVAAATRVHSGRKEIAVTIDDKNVIASVSESFHGVAFDASLFSP KGLWSFVDITSPKLFKLLEGLSPGYFRVGGTFANWLFFDLDENNKWKDYWAF KDKTPETATITRRWLFRKQNNLKKETFDDLVKLTKGSKMRLLFDLNAEVRTG YEIGKKMTSTWDSSEAEKLFKYCVSKGYGDNIDWELGNEPDHTSAHNLTEKQ VGEDFKALHKVLEKYPTLNKGSLVGPDVGWMGVSYVKGLADGAGDHVTAFTL HQYYFDGNTSDVSTYLDATYFKKLQQLFDKVKDVLKNSPHKDKPLWLGETSS GYNSGTKDVSDRYVSGFLTLDKLGLSAANNVKVVIRQTIYNGYYGLLDKNTL EPNPDYWMHVHNSLVGNTVEKVDVSDPTNKARVYAQCTKTNSKHTQSRYYKG SLTIFALNVGDEDVTLKIDQYSGKKIYSYILTPEGGQLTSQKVLLNGKELKL VSDQLPELNADESKTSFTLSPKTFGFFVVSDANVEACKK |
| 102 | Hyaluronidase (*Staphylococcus aureus*) | MDWTWILFLVAAATRVHSGRDTNVQTPDYEKLRNTWLNVNYGYDQYDEKNDA MKKKFDATEKEAEKLLSSMKTESGRTYLWDSAKDLDNKSADMTRTYRNIEKI AEAMKHKDTKLNTPDNKNKVKDALEWLHKNAYGKEPVKKLEELKTNFSKSAP QKNTNLNWWDYEIGTPRALTNTLILLKEDFTDEEKKKYTAPIKTFAPKSDEI LSSVGKAEPAKGGNLVDISKVKLLESIIEEDATMMKESIEAFNKVETYVQSN ATGKERNGFYKDGSYIDHQDVPYTGAYGVVLLEGISQMMPMIKETPFKDSNQ NDTTLKSWIDEGEMPLIYKGEMMDLSRGRAISRENETSHSTSATVMKSLLRL SDAMDESTKAKYKQIVKTSVKSDSSYKQNDYLSSYSDISMKSLIEDSTISTN GLTQQLKIYNDMNRVTYHNKDLDFAFGLSMTSKNVAHYESINGENLKGWHTG AGMSYLYNSDVKHYRDNFWATADMKRLAGTTTLDNEEPKENKNSDKTFVGGT KFDDQHASIGMDFENQDKTLTAKKSYFILNDKIVFLGTGIKSTDSSKNPVTT IENRKSNGYTLFTDDKQTTASNINDQETNSVFLESTDTKKNIGYHFLNESKI TVKKESHTGKWSDINKSQKSDDKTDEYYEVTQKHSNTDDKYAYVLYPGLSKD NEKSKASQVTIVKQDDDFHIVKDNESVWAGVNYSNSTQTEDINNTKVEVKAK GMFILKNKDDNTYECSFYNPESTNTASDIESKISMTGYSITNKNTSTSNESG VHFELTK |
| 103 | Hyaluronidase (*Loxosceles intermedia*) | MDWTWILFLVAAATRVHSGRDVFWNVPSQQCKKYGMKFVPLLEQYSILVNKE DNFKGDKITIFYESQLGLYPHIGANDESENGGIPQLGDLKAHLEKSAVDIRR DILDKSATGLRIIDWEAWRPIWEFNWSSLRKYQDKMKKVVRQFNPTAHESTV AKLAHNEWENSSKSWMLSTLQLGKQLRPNSVWCYYLFPDCYNYDGNSVQEFQ CSEAIRKGNDRLKWLWEESTAVCPSIYIKEGQLTNYTLQKRIWFTNGRLQEA LRVAQPKARTYPYINYSIKPGMMVPEVEFWRLIAQIASLGMDGAVIWGSSAS VGSKNHCAQLMKYIADVLGPATLRIKENVARCSKQACSGRGRCTWPKDTSVI AWKFLVEKEDYDFYLGDIECKCVEGYEGRYCEQKTK |
| 104 | Hyaluronidase (*Streptomyces koganeiensis*) | MDWTWILFLVAAATRVHSGRATGTASAAGENGATTTEDGPVAAERFSADTTL EAAFLKTTSETNHAATIYQAGTSGDGAALNVISDNPGTSAMYLSGTETARGT LKITHRGYADGSDKDAAALSLDLRVAGTAAQGIYVTATNGPTKGNLIALRNN TGLDDEVVKGTGRIGVGIDRAATPRAQVHIVQRGDALAALLVEGSVRIGNAA TVPTSVDSSGGGALYASGGALLWRGSNGTVTTIAPA |
| 105 | Hyaluronidase (*Mycobacterium tuberculosis*) | MDWTWILFLVAAATRVHSGRGSAIEERTRHRAETTTREICESVGGADTVLSR IDKNPELEPLLSQATEAATRTSMEAKRRLLAQAAAAALEDDQKVEPASLIVA TLSQLEPVHIHALVRLAKAAKSSPDQDEIQRREVMRAASKVEPVPVLAALIQ TGVAIATTTVWHGNGTGTPAEESGHILIHDVSDFGHRLLAYLRAADAGAELL ILPSGGSAPTGDHPTPHPSTSR |
| 106 | HYAL1 | MAAHLLPICALFLTLLDMAQGFRGPLLPNRPFTTVWNANTQWCLERHGVDVD VSVFDVVANPGQTFRGPDMTIFYSSQLGTYPYYTPTGEPVFGGLPQNASLIA HLARTFQDILAAIPAPDFSGLAVIDWEAWRPRWAFNWDTKDIYRQRSRALVQ AQHPDWPAPQVEAVAQDQFQGAARAWMAGTLQLGRALRPRGLWGFYGFPDCY NYDFLSPNYTGQCPSGIRAQNDQLGWLWGQSRALYPSIYMPAVLEGTGKSQM YVQHRVAEAFRVAVAAGDPNLPVLPYVQIFYDTTNHFLPLDELEHSLGESAA QGAAGVVLWVSWENTRTKESCQAIKEYMDTTLGPFILNVTSGALLCSQALCS GHGRCVRRTSHPKALLLLNPASFSIQLTPGGGPLSLRGALSLEDQAQMAVEF KCRCYPGWQAPWCERKSMW |

TABLE 4-continued

| No. | PROTEIN/ NUCLIEC ACID | EXEMPLARY AMINO ACID/NUCLEIC ACID SEQUENCES |
|---|---|---|
| 107 | HYAL2 | MRAGPGPTVTLALVLAVAWAMELKPTAPPIFTGRPFVVAWDVPTQDCGPRLK VPLDLNAFDVQASPNEGFVNQNITIFYRDRLGLYPRFDSAGRSVHGGVPQNV SLWAHRKMLQKRVEHYIRTQESAGLAVIDWEDWRPVWVRNWQDKDVYRRLSR QLVASRHPDWPPDRIVKQAQYEFEFAAQQFMLETLRYVKAVRPRHLWGFYLF PDCYNHDYVQNWESYTGRCPDVEVARNDQLAWLWAESTALFPSVYLDETLAS SRHGRNFVSFRVQEALRVARTHHANHALPVYVFTRPTYSRRLTGLSEMDLIS TIGESAALGAAGVILWGDAGYTTSTETCQYLKDYLTRLLVPYVVNVSWATQY CSRAQCHGHGRCVRRNPSASTFLHLSTNSFRLVPGHAPGEPQLRPVGELSWA DIDHLQTHFRCQCYLGWSGEQCQWDHRQAAGGASEAWAGSHLTSLLALAALA FTWTL |
| 108 | HYAL3 | MTTQLGPALVLGVALCLGCGQPLPQVPERPFSVLWNVPSAHCEARFGVHLPL NALGIIANRGQHFHGQNMTIFYKNQLGLYPYFGPRGTAHNGGIPQALPLDRH LALAAYQIHHSLRPGFAGPAVLDWEEWCPLWAGNWGRRRAYQAASWAWAQQV FPDLDPQEQLYKAYTGFEQAARALMEDTLRVAQALRPHGLWGFYHYPACGNG WHSMASNYTGRCHAATLARNTQLHWLWAASSALFPSIYLPPRLPPAHHQAFV RHRLEEAFRVALVGHRHPLPVLAYVRLTHRRSGRFLSQDDLVQSIGVSAALG AAGVVLWGDLSLSSSEEECWHLHDYLVDTLGPYVINVTRAAMACSHQRCHGH GRCARRDPGQMEAFLHLWPDGSLGDWKSFSCHCYWGWAGPTCQEPRPGPKEA V |
| 109 | HYAL4 | MKVLSEGQLKLCVVQPVHLTSWLLIFFILKSISCLKPARLPIYQRKPFIAAW NAPTDQCLIKYNLRLNLKMFPVIGSPLAKARGQNVTIFYVNRLGYYPWYTSQ GVPINGGLPQNISLQVHLEKADQDINYYIPAEDFSGLAVIDWEYWRPQWARN WNSKDVYRQKSRKLISDMGKNVSATDIEYLAKVTFEESAKAFMKETIKLGIK SRPKGLWGYYLYPDCHNYNVYAPNYSGSCPEDEVLRNNELSWLWNSSAALYP SIGVWKSLGDSENILRFSKFRVHESMRISTMTSHDYALPVFVYTRLGYRDEP LFFLSKQDLVSTIGESAALGAAGIVIWGDMNLTASKANCTKVKQFVSSDLGS YIANVTRAAEVCSLHLCRNNGRCIRKMWNAPSYLHLNPASYHIEASEDGEFT VKGKASDTDLAVMADTFSCHCYQGYEGADCREIKTADGCSGVSPSPGSLMTL CLLLLASYRSIQL |
| 110 | CXCR4 | >sp\|P250251CXCR2 HUMAN C—X—C chemokine receptor type 2 OS = *Homo sapiens* GN = CXCR2 PE = 1 SV = 2 MEDFNMESDSFEDFWKGEDLSNYSYSSTLPPFLLDAAPCEPESLEINKYFVV IIYALVFLLSLLGNSLVMLVILYSRVGRSVTDVYLLNLALADLLFALTLPIW AASKVNGWIFGTFLCKVVSLLKEVNFYSGILLLACISVDRYLAIVHATRTLT QKRYLVKFICLSIWGLSLLLALPVLLFRRTVYSSNVSPACYEDMGNNTANWR MLLRILPQSFGFIVPLLIMLFCYGFTLRTLFKAHMGQKHRAMRVIFAVVLIF LLCWLPYNLVLLADTLMRTQVIQETCERRNHIDRALDATEILGILHSCLNPL IYAFIGQKFRHGLLKILAIHGLISKDSLPKDSRPSFVGSSSGHTSTTL |
| 111 | CCR2 | >sp\|P41597\|CCR2_HUMAN C-C chemokine receptor type 2 OS = *Homo sapiens* GN = CCR2 PE = 1 SV = 1 MLSTSRSRFIRNINESGEEVTIFFDYDYGAPCHKFDVKQIGAQLLPPLYSLV FIFGFVGNMLVVLILINCKKLKCLIDIYLLNLAISDLLFLITLPLWAHSAAN EWVFGNAMCKLFTGLYHIGYFGGIFFIILLTIDRYLAIVHAVFALKARTVIF GVVISVITWLVAVFASVPGIIFTKCQKEDSVYVCGPYFPRGWNNFHTIMRNI LGLVLPLLIMVICYSGILKILLRCRNEKKRHRAVRVIFTIMIVYFLFWIPYN IVILLNIFQEFFGLSNCESTSQLDQATQVIETLGMTHCCINPIIYAFVGEKF RSLFHIALGCRIAPLQKPVCGGPGVRPGKNVKVITQGLLDGRGKGKSIGRAP EASLQDKEGA |
| 112 | CCL5 | >sp\|P13501\|CCL5 HUMAN C-C motif chemokine 5 OS = *Homo sapiens* GN = CCL5 PE = 1 SV = 3 MKVSAAALAVILIATALCAPASASPYSSDTTPCCFAYIARPLPRAHIKEYFY TSGKCSNPAVVFVTRKNRQVCANPEKKWVREYINSLEMS |
| 113 | CCR5 | >sp\|P51681\|CCR5 HUMAN C-C chemokine receptor type 5 OS = *Homo sapiens* GN = CCR5 PE = 1 SV = 1 MDYQVSSPIYDINYYTSEPCQKINVKQIAARLLPPLYSLVFIFGFVGNMLVI LILINCKRLKSMIDIYLLNLAISDLFFLLTVPFWAHYAAAQWDFGNIMCQLL TGLYFIGFFSGIFFIILLTIDRYLAVVHAVFALKARTVIFGVVISVITWVVA VFASLPGIIFIRSQKEGLHYTCSSHFPYSQYQFWKNFQTLKIVILGLVLPLL VMVICYSGILKILLRCRNEKKRHRAVRLIFTIMIVYFLFWAPYNIVLLLNTF QEFFGLNNCSSSNRLDQAMQVIETLGMTHCCINPIIYAFVGEKFRNYLLVFF QKHIAKRFCKCCSIFQQEAPERASSVYTRSTGEQEISVGL |
| 114 | HMGB1 | >sp\|P09429\|HMGB1_HUMAN High mobility group protein B1 OS = *Homo sapiens* GN = HMGB1 PE = 1 SV = 3 MGKGDPKKPRGKMSSYAFFVQTCREEHKKKHPDASVNFSEFSKKCSERWKTM SAKEKGKFEDMAKADKARYEREMKTYIPPKGETKKKFKDPNAPKRPPSAFFL FCSEYRPKIKGEHPGLSIGDVAKKLGEMWNNTAADDKQPYEKKAAKLKEKYE KDIAAYRAKGKPDAAKKGVVKAEKSKKKKEEEEDEEDEEDEEEEEDEEDEDE EEDDDDE |

TABLE 4-continued

| No. | PROTEIN/ NUCLIEC ACID | EXEMPLARY AMINO ACID/NUCLEIC ACID SEQUENCES |
|---|---|---|
| 115 | PIAS3 | >sp\|Q9Y6X2\|PIAS3 HUMAN E3 SUMO-protein ligase PIAS3 OS = *Homo sapiens* GN = PIAS3 PE = 1 SV = 2 MAELGELKHMVMSFRVSELQVLLGFAGRNKSGRKHELLAKALHLLKSSCAPS VQMKIKELYRRRFPRKTLGPSDLSLLSLPPGISPVGSPGPLAPIPPILLAPG ILLGPKREVDMHPPLPQPVHPDVIMKPLPFYEVYGELIRPTTLASTSSQRFE EAHFTFALTPQQVQQILTSREVLPGAKCDYTIQVQLRFCLCETSCPQEDYFP PNLFVKVNGKLCPLPGYLPPIKNGAEPKRPSRPINITPLARLSATVPNTIVV NWSSEFGRNYSLSVYLVRQLTAGILLQKLRAKGIRNPDHSRALIKEKLTADP DSEVATTSLRVSLMCPLGKMRLIVPCRALICAHLQSFDAALYLQMNEKKPIW TCPVCDKKAPYESLIIDGLFMEILSSCSDCDEIQFMEDGSWCPMKPKKEASE VCPPPGYGLDGLQYSPVQGGDPSENKKKVEVIDLTIESSSDEEDLPPIKKHC SVISAAIPALPGSKGVLTSGHQPSSVLRSPAMGILGGDFLSSLPLHEYPPAF PLGADIQGLDLFSFLQTESQHYGPSVITSLDEQDALGHFFQYRGIPSHFLGP LAPTLGSSHCSATPAPPPGRVSSIVAPGGALREGHGGPLPSGPSLIGCRSDI ISLD |
| 116 | IL15 | >sp\|P40933\|IL15_HUMAN Interleukin-15 OS = *Homo sapiens* GN = IL15 PE = 1 SV = 1 MRISKPHLRSISIQCYLCLLLNSHFLTEAGIHVFILGCFSAGLPKTEANWVN VISDLKKIEDLIQSMHIDATLYTESDVHPSCKVTAMKCFLLELQVISLESGD ASIHDTVENLIILANNSLSSNGNVIESGCKECEELEEKNIKEFLQSFVHIVQ MFINTS |
| 117 | HysA | >sp\|Q59801\|HYSA STAA8 Hyaluronate lyase OS = *Staphylococcus aureus* (strain NCTC 8325) OX = 93061 GN = hysA PE = 3 SV = 1 MTYRIKKWQKLSTITLLMAGVITLNGGEFRSVDKHQIAVADTNVQTPDYEKL RNTWLDVNYGYDKYDENNPDMKKKEDATEKEATNLLKEMKTESGRKYLWSGA ETLETNSSHMTRTYRNIEKIAEAMRNPKTTLNTDENKKKVKDALEWLHKNAY GKEPDKKVKELSENFTKTTGKNTNLNWWDYEIGTPKSLTNTLILLNDQFSNE EKKKFTAPIKTFAPDSDKILSSVGKAELAKGGNLVDISKVKLLECIIEEDKD MMKKSIDSENKVETYVQDSATGKERNGFYKDGSYIDHQDVPYTGAYGVVLLE GISQMMPMIKETPENDKTQNDTTLKSWIDDGEMPLIYKGEMMDLSRGRAISR ENETSHSASATVMKSLLRLSDAMDDSTKAKYKKIVKSSVESDSSYKQNDYLN SYSDIDKMKSLMTDNSISKNGLTQQLKIYNDMDRVTYHNKDLDFAFGLSMTS KNVARYESINGENLKGWHTGAGMSYLYNSDVKHYHDNFWVTADMKRLSGTTT LDNEILKDTDDKKSSKTFVGGTKVDDQHASIGMDFENQDKTLTAKKSYFILN DKIVFLGTGIKSTDSSKNPVTTIENRKANGYTLYTDDKQTTNSDNQENNSVF LESTDTKKNIGYHFLNKPKITVKKESHTGKWKEINKSQKDTQKTDEYYEVTQ KHSNSDNKYGYVLYPGLSKDVFKTKKDEVTVVKQEDDFHVVKDNESVWAGVN YSNSTQTEDINNTKVEVKAKGMFILKKKDDNTYECSFYNPESTNSASDIESK ISMTGYSITNKNTSTSNESGVHFELTK |
| 118 | SPAM1 (*Sus scrofa*) | >tr\|Q8MI021Q8MI02_PIG Hyaluronidasese OS = *Sus scrofa* OX = 9823 GN = SPAM-1 PE = 1 SV = 1 MGVQRLQHISFRSFFVPSGAPQVVETFLLIPCCLALDFRASPIIPNTTFLWV WNAPTESCAKKEYMPPDLSLFSFVTSPRASVTGQFLTLFYANRLGYYPHVDE NTGKNVNGGIPQLGSLQRHLDKAEKDILHYMQIDKVGLSVIDWENWRPTWER NWKEKAIYRRQSIELVQQKNIKLTPAAATKLAKREFEKAGKTFMQETLKLGK LLRPNHLWGYYLFPDCYNHNYHKPGYNGSCLDIEKRRNDALDWLWKESTALF PSIYLNTRLKPSQVALFVRNRVQEAIRVSKVANAQSPLPVFVYTRPVFSGAS SRYLSQDDLVNTIGETVALGASGIVMWGSLNLSLTMQSCMNLGSYLKTTLNP YLINVTLAAKMCSQVLCQEQGVCTRKHWNSSDYLHLNPANFAIRTGKGNKYI VHGKPTLEDLKEFSKNEYCSCFANFHCKERADIENIHAINVCITEDVCVEAF LNSEPELPDEVQQDNQPPCGGSGRC |
| 119 | LIGHT | >sp\|043557\|TNF14_HUMAN Tumor necrosis factor ligand superfamily member 14 OS = *Homo sapiens* OX = 9606 GN = TNFSF14 PE = 1 SV = 2 MEESVVRPSVFVVDGQTDIPFTRLGRSHRRQSCSVARVGLGLLLLLMGAGLA VQGWFLLQLHWRLGEMVTRLPDGPAGSWEQLIQERRSHEVNPAAHLTGANSS LTGSGGPLLWETQLGLAFLRGLSYHDGALVVTKAGYYYTYSKVQLGGVGCPL GLASTITHGLYKRTPRYPEELELLVSQQSPCGRATSSSRVWWDSSFLGGVVH LEAGEKVVVRVLDERLVRLRDGTRSYFGAFMV |
| 120 | ITAC | >sp1014625ICXL11 HUMAN C—X—C motif chemokine 11 OS = *Homo sapiens* OX = 9606 GN = CXCL11 PE = 1 SV = 1 MSVKGMAIALAVILCATVVQGFPMFKRGRCLCIGPGVKAVKVADIEKASIMY PSNNCDKIEVIITLKENKGQRCLNPKSKQARLIIKKVERKNF |
| 121 | fractalkine | >sp\|P78423\|X3CL1_HUMAN Fractalkine OS = *Homo sapiens* OX = 9606 GN = CX3CL1 PE = 1 SV = 1 MAPISLSWLLRLATFCHLTVLLAGQHHGVTKCNITCSKMTSKIPVALLIHYQ QNQASCGKRAIILETRQHRLFCADPKEQWVKDAMQHLDRQAAALTRNGGTFE KQIGEVKPRTTPAAGGMDESVVLEPEATGESSSLEPTPSSQEAQRALGTSPE LPTGVTGSSGTRLPPTPKAQDGGPVGTELFRVPPVSTAATWQSSAPHQPGPS |

TABLE 4-continued

| No. | PROTEIN/ NUCLIEC ACID | EXEMPLARY AMINO ACID/NUCLEIC ACID SEQUENCES |
|---|---|---|
| | | LWAEAKTSEAPSTQDPSTQASTASSPAPEENAPSEGQRVWGQGQSPRPENSL EREEMGPVPAETDAFQDWGPGSMAHVSVVPVSSEGTPSREPVASGSWTPKAE EPIHATMDPQRLGVLITPVPDAQAATRRQAVGLLAFLGLLFCLGVAMFTYQS LQGCPRKMAGEMAEGLRYIPRSCGSNSYVLVPV |
| 122 | HysA | MDWTWILFLVAAATRVHSGRDTNVQTPDYEKLRNTWLNVNYGYDQYDEKNDA MKKKFDATEKEAEKLLSSMKTESGRTYLWDSAKDLDNKSADMTRTYRNIEKI AEAMKHKDTKLNTPDNKNKVKDALEWLHKNAYGKEPVKKLEELKTNESKSAP QKNTNLNWWDYEIGTPRALTNTLILLKEDFTDEEKKKYTAPIKTFAPKSDEI LSSVGKAEPAKGGNLVDISKVKLLESIIEEDATMMKESIEAFNKVETYVOSN ATGKERNGFYKDGSYIDHODVPYTGAYGVVLLEGISOMMPMIKETPFKDSNQ NDTTLKSWIDEGEMPLIYKGEMMDLSRGRAISRENETSHSTSATVMKSLLRL SDAMDESTKAKYKOIVKTSVKSDSSYKONDYLSSYSDISKMKSLIEDSTIST NGLTQQLKIYNDMNRVTYHNKDLDFAFGLSMTSKNVAHYESINGENLKGWHT GAGMSYLYNSDVKHYRDNFWATADMKRLAGTTTLDNEEPKENKNSDKTFVGG TKFDDOHASIGMDFENODKTLTAKKSYFILNDKIVFLGTGIKSTDSSKNPVT TIENRKSNGYTLFTDDKOTTASNINDOETNSVFLESTDTKKNIGYHFLNESK ITVKKESHTGKWSDINKSOKSDDKTDEYYEVTOKHSNTDDKYAYVLYPGLSK DNEKSKASQVTIVKODDDFHIVKDNESVWAGVNYSNSTOTEDINNTKVEVKA KGMFILKNKDDNTYECSFYNPESTNTASDIESKISMTGYSITNKNTSTSNES GVHFELTK |
| 123 | HysA(Q59801) | >sp\|Q59801\|HYSA_STAA8 Hyaluronate lyase OS = *Staphylococcus aureus* (strain NCTC 8325) OX = 93061 GN = hysA PE = 3 SV = 1 MTYRIKKWOKLSTITLLMAGVITLNGGEFRSVDKHOIAVADTNVOTPDYEKL RNTWLDVNYGYDKYDENNPDMKKKEDATEKEATNLLKEMKTESGRKYLWSGA ETLETNSSHMTRTYRNIEKIAEAMRNPKTTLNTDENKKKVKDALEWLHKNAY GKEPDKKVKELSENFTKTTGKNTNLNWWDYEIGTPKSLTNTLILLNDQFSNE EKKKFTAPIKTFAPDSDKILSSVGKAELAKGGNLVDISKVKLLECIIEEDKD MMKKSIDSFNKVFTYVQDSATGKERNGFYKDGSYIDHQDVPYTGAYGVVLLE GISQMMPMIKETPFNDKTONDTTLKSWIDDGFMPLIYKGEMMDLSRGRAISR ENETSHSASATVMKSLLRLSDAMDDSTKAKYKKIVKSSVESDSSYKONDYLN SYSDIDKMKSLMTDNSISKNGLTOOLKIYNDMDRVTYHNKDLDFAFGLSMTS KNVARYESINGENLKGWHTGAGMSYLYNSDVKHYHDNFWVTADMKRLSGTTT LDNEILKDTDDKKSSKTFVGGTKVDDOHASIGMDFENODKTLTAKKSYFILN DKIVFLGTGIKSTDSSKNPVTTIENRKANGYTLYTDDKQTTNSDNOENNSVF LESTDTKKNIGYHFLNKPKITVKKESHTGKWKEINKSOKDTOKTDEYYEVTQ KHSNSDNKYGYVLYPGLSKDVEKTKKDEVTVVKQEDDFHVVKDNESVWAGVN YSNSTQTEDINNTKVEVKAKGMFILKKKDDNTYECSFYNPESTNSASDIESK ISMTGYSITNKNTSTSNESGVHFELTK |
| 124 | lin | MDWTWILFLVAAATRVHSGRDVFWNVPSQQCKKYGMKFVPLLEQYSILVNKE DNFKGDKITIFYESQLGLYPHIGANDESENGGIPQLGDLKAHLEKSAVDIRR DILDKSATGLRIIDWEAWRPIWEFNWSSLRKYQDKMKKVVRQFNPTAHESTV AKLAHNEWENSSKSWMLSTLQLGKQLRPNSVWCYYLFPDCYNYDGNSVQEFQ CSEAIRKGNDRLKWLWEESTAVCPSIYIKEGQLTNYTLQKRIWFTNGRLQEA LRVAQPKARTYPYINYSIKPGMMVPEVEFWRLIAQIASLGMDGAVIWGSSAS VGSKNHCAQLMKYIADVLGPATLRIKENVARCSKQACSGRGRCTWPKDTSVI AWKFLVEKEDYDFYLGDIECKCVEGYEGRYCEQKTK |
| 125 | rv | MDWTWILFLVAAATRVHSGRGSAIEERTRHRAETTTREICESVGGADTVLSR IDKNPELEPLLSOATEAATRTSMEAKRRLLAQAAAAALEDDQKVEPASLIVA TLSOLEPVHIHALVRLAKAAKSSPDODEIORREVMRAASKVEPVPVLAALIQ TGVAIATTTVWHGNGTGTPAEESGHILIHDVSDFGHRLLAYLRAADAGAELL ILPSGGSAPTGDHPTPHPSTSR |
| 126 | sko | MDWTWILFLVAAATRVHSGRATGTASAAGENGATTTEDGPVAAERFSADTTL EAAFLKTTSETNHAATIYQAGTSGDGAALNVISDNPGTSAMYLSGTETARGT LKITHRGYADGSDKDAAALSLDLRVAGTAAQGIYVTATNGPTKGNLIALRNN TGLDDEVVKGTGRIGVGIDRAATPRAQVHIVORGDALAALLVEGSVRIGNAA TVPTSVDSSGGGALYASGGALLWRGSNGTVTTIAPA |
| 127 | UniProtKB - R4J7Z9 (HYAL_LOXIN) | >sp\|R4J7Z9\|HYAL_LOXIN Hyaluronidasese OS = *Loxosceles intermedia* OX = 58218 PE = 2 SV = 1 MQTILVLTTFLSAWFLAVGFDVFWNVPSQQCKKYGMKFVPLLEQYSILVNKE DNFKGDKITIFYESQLGLYPHIGANDESENGGIPQLGDLKAHLEKSAVDIRR DILDKSATGLRIIDWEAWRPIWEFNWSSLRKYQDKMKKVVRQFNPTAHESTV AKLAHNEWENSSKSWMLSTLQLGKQLRPNSVWCYYLFPDCYNYDGNSVQEFQ CSEAIRKGNDRLKWLWEESTAVCPSIYIKEGQLTNYTLQKRIWFTNGRLQEA LRVAQPKARTYPYINYSIKPGMMVPEVEFWRLIAQIASLGMDGAVIWGSSAS VGSKNHCAQLMKYIADVLGPATLRIKENVARCSKQACSGRGRCTWPKDTSVI AWKFLVEKEDYDFYLGDIECKCVEGYEGRYCEQKTK |

TABLE 4-continued

| No. | PROTEIN/ NUCLIEC ACID | EXEMPLARY AMINO ACID/NUCLEIC ACID SEQUENCES |
|---|---|---|
| 128 | UniProtKB - P95202 (P95202_MYCTU) | >tr\|P95202\|P95202_MYCTU Possible secreted protein OS = *Mycobacterium tuberculosis* (strain ATCC 25618/ H37Rv) OX = 83332 GN = Rv0394c PE = 1 SV = 1<br>MTEPRPVFAVVISAGLSAIPMVGGPLQTVFDAIEERTRHRAETTTREICESV<br>GGADTVLSRIDKNPELEPLLSQATEAATRTSMEAKRRLLAQAAAAALEDDQK<br>VEPASLIVATLSQLEPVHIHALVRLAKAAKSSPDQDEIQRREVMRAASKVEP<br>VPVLAALIQTGVAIATTTVWHGNGTGTPAEESGHILIHDVSDFGHRLLAYLR<br>AADAGAELLILPSGGSAPTGDHPTPHPSTSR |
| 129 | UniProtKB - A0A0U2E2J7 (A0A0U2E2J7_9ACTN) | >tr\|A0A0U2E2J7\|A0A0U2E2J7_9ACTN Hyaluronidasese OS = *Streptomyces koganeiensis* OX = 1684313 PE = 1 SV = 1<br>MPVARRLFLGSFTAGAVTVATAAATGTASAAGENGATTTFDGPVAAERFSAD<br>TTLEAAFLKTTSETNHAATIYQAGTSGDGAALNVISDNPGTSAMYLSGTETA<br>RGTLKITHRGYADGSDKDAAALSLDLRVAGTAAQGIYVTATNGPTKGNLIAL<br>RNNTGLDDEVVKGTGRIGVGIDRAATPRAQVHIVQRGDALAALLVEGSVRIG<br>NAATVPTSVDSSGGGALYASGGALLWRGSNGT<br>VTTIAPA |
| 130 | PH-20 (truncated) | MGVLKEKHIFFRSFVKSSGVSQIVETFLLIPCCLTLNFRAPPVIPNVPFLWA<br>WNAPSEFCLGKFDEPLDMSLFSFIGSPRINATGQGVTIFYVDRLGYYPYIDS<br>ITGVTVNGGIPQKISLQDHLDKAKKDITFYMPVDNLGMAVIDWEEWRPTWAR<br>NWKPKDVYKNRSIELVQQQNVQLSLTEATEKAKQEFEKAGKDFLVETIKLGK<br>LLRPNHLWGYYLFPDCYNHHYKKPGYNGSCFNVEIKRNDDLSWLWNESTALY<br>PSIYLNTQQSPVAATLYVRNRVREAIRVSKIPDAKSPLPVFAYTRIVETDQV<br>LKFLSQDELVYTFGETVALGASGIVIWGTLSIMRSMKSCLLLDNYMETILNP<br>YIINVTLAAKMCSQVLCQEQGVCIRKNWNSSDYLHLNPDNFAIQLEKGGKFT<br>VRGKPTLEDLEQFSEKFYCSCYSTLSCKEKADVKDTDAVDVCIADGVCIDAF<br>LKPPMETEEPQIFYNASPSTL |

What is claimed is:

1. An oncolytic virus, wherein the oncolytic virus comprises:

an oncolytic virus genome, wherein the oncolytic virus genome comprises a modification;

an exogenous nucleic acid that codes for a protein or a functional variant thereof, that enhances degradation of an extracellular matrix (ECM) of a tumor, wherein the protein or the functional variant thereof is a membrane-anchored protein, and wherein the membrane-anchored protein comprises a membrane-anchored hyaluronidase; and an exogenous nucleic acid that codes for a chemokine receptor or a functional variant thereof, wherein the exogenous nucleic acid that codes for the chemokine receptor or the functional variant thereof is inserted into the oncolytic virus genome, and wherein the chemokine receptor or the functional variant thereof: (i) comprises a transmembrane spanning structure for membrane association, and (ii) selectively binds to a chemokine ligand and induces cellular chemotaxis towards the chemokine ligand.

2. The oncolytic virus of claim 1, wherein the membrane-anchored hyaluronidase is PH-20.

3. The oncolytic virus of claim 2, wherein the protein or the functional variant thereof comprises a glycosylphosphatidylinositol signal sequence.

4. The oncolytic virus of claim 1, wherein the modification comprises a mutation or a deletion or a partial deletion of a viral gene selected from the group consisting of: F13L, A36R, A34R, B5R, A33R, B8R, B18R, SPI-1, SPI-2, B15R, VGF, E3L, K3L, A41L, K7R, NIL, and any combinations thereof.

5. The oncolytic virus of claim 1, wherein the modification comprises a mutation or a deletion or a partial deletion of an A52R gene.

6. The oncolytic virus of claim 1, wherein the modification comprises a mutation or a deletion or a partial deletion of a thymidine kinase gene.

7. The oncolytic virus of claim 1, wherein the oncolytic virus comprises a poxvirus, an adeno associated virus, an adenovirus, a reovirus, a lentivirus, a herpes simplex virus, a vesicular stomatitis virus, a mengovirus, or a myxoma virus.

8. The oncolytic virus of claim 7, wherein the oncolytic virus is the poxvirus.

9. The oncolytic virus of claim 8, wherein the poxvirus is a vaccinia virus.

10. The oncolytic virus of claim 1, wherein oncolytic virus is part of a pharmaceutical composition.

11. The oncolytic virus of claim 10, wherein the pharmaceutical composition is in a liquid dosage form.

12. The oncolytic virus of claim 10, wherein the membrane-anchored hyaluronidase is PH-20.

13. The oncolytic virus of claim 1, wherein the chemokine receptor comprises a CXC receptor, a CC receptor, a CX3C receptor, or a XC receptor.

14. The oncolytic virus of claim 13, wherein the chemokine receptor comprises the CXC receptor, and wherein the CXC receptor comprises CXCR4.

15. The oncolytic virus of claim 13, wherein the chemokine receptor comprises the CC receptor, and wherein the CC receptor comprises CCR2.

16. The oncolytic virus of claim 1, wherein the chemokine receptor comprises CXCR1, CXCR2, CXCR3, CXCR4, CXCR5, CXCR6, CXCR7, CCR1, CCR2, CCR3, CCR4, CCR5, CCR6, CCR7, CX3CR1, or XCR1.

17. The oncolytic virus of claim 1, wherein the exogenous nucleic acid that codes for the protein or the functional variant thereof is inserted into the oncolytic virus genome.

18. The oncolytic virus of claim 1, wherein the transmembrane spanning structure for membrane association comprises a seven-transmembrane spanning structure.

* * * * *

SEQUENCE LISTING

<160> NUMBER OF SEQ ID NOS: 131

<210> SEQ ID NO 1
<211> LENGTH: 317
<212> TYPE: PRT
<213> ORGANISM: Vaccinia virus

<400> SEQUENCE: 1

Met Lys Thr Ile Ser Val Val Thr Leu Leu Cys Val Leu Pro Ala Val
1 5 10 15

Val Tyr Ser Thr Cys Thr Val Pro Thr Met Asn Asn Ala Lys Leu Thr
20 25 30

Ser Thr Glu Thr Ser Phe Asn Asp Lys Gln Lys Val Thr Phe Thr Cys
35 40 45

Asp Gln Gly Tyr His Ser Leu Asp Pro Asn Ala Val Cys Glu Thr Asp
50 55 60

Lys Trp Lys Tyr Glu Asn Pro Cys Lys Lys Met Cys Thr Val Ser Asp
65 70 75 80

Tyr Val Ser Glu Leu Tyr Asp Lys Pro Leu Tyr Glu Val Asn Ser Thr
85 90 95

Met Thr Leu Ser Cys Asn Gly Glu Thr Lys Tyr Phe Arg Cys Glu Glu
100 105 110

Lys Asn Gly Asn Thr Ser Trp Asn Asp Thr Val Thr Cys Pro Asn Ala
115 120 125

Glu Cys Gln Pro Leu Gln Leu Glu His Gly Ser Cys Gln Pro Val Lys
130 135 140

Glu Lys Tyr Ser Phe Gly Glu Tyr Ile Thr Ile Asn Cys Asp Val Gly
145 150 155 160

-continued

```
Tyr Glu Val Ile Gly Ala Ser Tyr Ile Ser Cys Thr Ala Asn Ser Trp
                165                 170                 175

Asn Val Ile Pro Ser Cys Gln Gln Lys Cys Asp Met Pro Ser Leu Ser
            180                 185                 190

Asn Gly Leu Ile Ser Gly Ser Thr Phe Ser Ile Gly Gly Val Ile His
        195                 200                 205

Leu Ser Cys Lys Ser Gly Phe Ile Leu Thr Gly Ser Pro Ser Ser Thr
    210                 215                 220

Cys Ile Asp Gly Lys Trp Asn Pro Ile Leu Pro Thr Cys Val Arg Ser
225                 230                 235                 240

Asn Lys Glu Phe Asp Pro Val Asp Asp Gly Pro Asp Asp Glu Thr Asp
                245                 250                 255

Leu Ser Lys Leu Ser Lys Asp Val Val Gln Tyr Glu Gln Glu Ile Glu
            260                 265                 270

Ser Leu Glu Ala Thr Tyr His Ile Ile Ile Val Ala Leu Thr Ile Met
        275                 280                 285

Gly Val Ile Phe Leu Ile Ser Val Ile Val Leu Val Cys Ser Cys Asp
    290                 295                 300

Lys Asn Asn Asp Gln Tyr Lys Phe His Lys Leu Leu Pro
305                 310                 315


<210> SEQ ID NO 2
<211> LENGTH: 372
<212> TYPE: PRT
<213> ORGANISM: Vaccinia virus

<400> SEQUENCE: 2

Met Trp Pro Phe Ala Ser Val Pro Ala Gly Ala Lys Cys Arg Leu Val
1               5                   10                  15

Glu Thr Leu Pro Glu Asn Met Asp Phe Arg Ser Asp His Leu Thr Thr
            20                  25                  30

Phe Glu Cys Phe Asn Glu Ile Ile Thr Leu Ala Lys Lys Tyr Ile Tyr
        35                  40                  45

Ile Ala Ser Phe Cys Cys Asn Pro Leu Ser Thr Thr Arg Gly Ala Leu
    50                  55                  60

Ile Phe Asp Lys Leu Lys Glu Ala Ser Glu Lys Gly Ile Lys Ile Ile
65                  70                  75                  80

Val Leu Leu Asp Glu Arg Gly Lys Arg Asn Leu Gly Glu Leu Gln Ser
                85                  90                  95

His Cys Pro Asp Ile Asn Phe Ile Thr Val Asn Ile Asp Lys Lys Asn
            100                 105                 110

Asn Val Gly Leu Leu Leu Gly Cys Phe Trp Val Ser Asp Asp Glu Arg
        115                 120                 125

Cys Tyr Val Gly Asn Ala Ser Phe Thr Gly Gly Ser Ile His Thr Ile
    130                 135                 140

Lys Thr Leu Gly Val Tyr Ser Asp Tyr Pro Pro Leu Ala Thr Asp Leu
145                 150                 155                 160

Arg Arg Arg Phe Asp Thr Phe Lys Ala Phe Asn Ser Ala Lys Asn Ser
                165                 170                 175

Trp Leu Asn Leu Cys Ser Ala Ala Cys Cys Leu Pro Val Ser Thr Ala
            180                 185                 190

Tyr His Ile Lys Asn Pro Ile Gly Gly Val Phe Phe Thr Asp Ser Pro
        195                 200                 205

Glu His Leu Leu Gly Tyr Ser Arg Asp Leu Asp Thr Asp Val Val Ile
    210                 215                 220
```

```
Asp Lys Leu Arg Ser Ala Lys Thr Ser Ile Asp Ile Glu His Leu Ala
225                 230                 235                 240

Ile Val Pro Thr Thr Arg Val Asp Gly Asn Ser Tyr Tyr Trp Pro Asp
                245                 250                 255

Ile Tyr Asn Ser Ile Ile Glu Ala Ala Ile Asn Arg Gly Val Lys Ile
            260                 265                 270

Arg Leu Leu Val Gly Asn Trp Asp Lys Asn Asp Val Tyr Ser Met Ala
        275                 280                 285

Thr Ala Arg Ser Leu Asp Ala Leu Cys Val Gln Asn Asp Leu Ser Val
    290                 295                 300

Lys Val Phe Thr Ile Gln Asn Asn Thr Lys Leu Leu Ile Val Asp Asp
305                 310                 315                 320

Glu Tyr Val His Ile Thr Ser Ala Asn Phe Asp Gly Thr His Tyr Gln
                325                 330                 335

Asn His Gly Phe Val Ser Phe Asn Ser Ile Asp Lys Gln Leu Val Ser
            340                 345                 350

Glu Ala Lys Lys Ile Phe Glu Arg Asp Trp Val Ser Ser His Ser Lys
        355                 360                 365

Ser Leu Lys Ile
    370


<210> SEQ ID NO 3
<211> LENGTH: 221
<212> TYPE: PRT
<213> ORGANISM: Vaccinia virus

<400> SEQUENCE: 3

Met Met Leu Val Pro Leu Ile Thr Val Thr Val Val Ala Gly Thr Ile
1               5                   10                  15

Leu Val Cys Tyr Ile Leu Tyr Ile Cys Arg Lys Lys Ile Arg Thr Val
            20                  25                  30

Tyr Asn Asp Asn Lys Ile Ile Met Thr Lys Leu Lys Lys Ile Lys Ser
        35                  40                  45

Ser Asn Ser Ser Lys Ser Ser Lys Ser Thr Asp Ser Glu Ser Asp Trp
    50                  55                  60

Glu Asp His Cys Ser Ala Met Glu Gln Asn Asn Asp Val Asp Asn Ile
65                  70                  75                  80

Ser Arg Asn Glu Ile Leu Asp Asp Asp Ser Phe Ala Gly Ser Leu Ile
                85                  90                  95

Trp Asp Asn Glu Ser Asn Val Met Ala Pro Ser Thr Glu His Ile Tyr
            100                 105                 110

Asp Ser Val Ala Gly Ser Thr Leu Leu Ile Asn Asn Asp Arg Asn Glu
        115                 120                 125

Gln Thr Ile Tyr Gln Asn Thr Thr Val Val Ile Asn Glu Thr Glu Thr
    130                 135                 140

Val Glu Val Leu Asn Glu Asp Thr Lys Gln Asn Pro Asn Tyr Ser Ser
145                 150                 155                 160

Asn Pro Phe Val Asn Tyr Asn Lys Thr Ser Ile Cys Ser Lys Ser Asn
                165                 170                 175

Pro Phe Ile Thr Glu Leu Asn Asn Lys Phe Ser Glu Asn Asn Pro Phe
            180                 185                 190

Arg Arg Ala His Ser Asp Asp Tyr Leu Asn Lys Gln Glu Gln Asp His
        195                 200                 205

Glu His Asp Asp Ile Glu Ser Ser Val Val Ser Leu Val
```

```
    210                 215                 220


<210> SEQ ID NO 4
<211> LENGTH: 168
<212> TYPE: PRT
<213> ORGANISM: Vaccinia virus

<400> SEQUENCE: 4

Met Lys Ser Leu Asn Arg Gln Thr Val Ser Met Phe Lys Lys Leu Ser
1               5                   10                  15

Val Pro Ala Ala Ile Met Met Ile Leu Ser Thr Ile Ile Ser Gly Ile
            20                  25                  30

Gly Thr Phe Leu His Tyr Lys Glu Glu Leu Met Pro Ser Ala Cys Ala
        35                  40                  45

Asn Gly Trp Ile Gln Tyr Asp Lys His Cys Tyr Leu Asp Thr Asn Ile
    50                  55                  60

Lys Met Ser Thr Asp Asn Ala Val Tyr Gln Cys Arg Lys Leu Arg Ala
65                  70                  75                  80

Arg Leu Pro Arg Pro Asp Thr Arg His Leu Arg Val Leu Phe Ser Ile
                85                  90                  95

Phe Tyr Lys Asp Tyr Trp Val Ser Leu Lys Lys Thr Asn Asn Lys Trp
            100                 105                 110

Leu Asp Ile Asn Asn Asp Lys Asp Ile Asp Ile Ser Lys Leu Thr Asn
        115                 120                 125

Phe Lys Gln Leu Asn Ser Thr Thr Asp Ala Glu Ala Cys Tyr Ile Tyr
    130                 135                 140

Lys Ser Gly Lys Leu Val Lys Thr Val Cys Lys Ser Thr Gln Ser Val
145                 150                 155                 160

Leu Cys Val Lys Lys Phe Tyr Lys
                165


<210> SEQ ID NO 5
<211> LENGTH: 185
<212> TYPE: PRT
<213> ORGANISM: Vaccinia virus

<400> SEQUENCE: 5

Met Met Thr Pro Glu Asn Asp Glu Glu Gln Thr Ser Val Phe Ser Ala
1               5                   10                  15

Thr Val Tyr Gly Asp Lys Ile Gln Gly Lys Asn Lys Arg Lys Arg Val
            20                  25                  30

Ile Gly Leu Cys Ile Arg Ile Ser Met Val Ile Ser Leu Leu Ser Met
        35                  40                  45

Ile Thr Met Ser Ala Phe Leu Ile Val Arg Leu Asn Gln Cys Met Ser
    50                  55                  60

Ala Asn Glu Ala Ala Ile Thr Asp Ala Ala Val Ala Val Ala Ala Ala
65                  70                  75                  80

Ser Ser Thr His Arg Lys Val Ala Ser Ser Thr Thr Gln Tyr Asp His
                85                  90                  95

Lys Glu Ser Cys Asn Gly Leu Tyr Tyr Gln Gly Ser Cys Tyr Ile Leu
            100                 105                 110

His Ser Asp Tyr Gln Leu Phe Ser Asp Ala Lys Ala Asn Cys Thr Ala
        115                 120                 125

Glu Ser Ser Thr Leu Pro Asn Lys Ser Asp Val Leu Ile Thr Trp Leu
    130                 135                 140

Ile Asp Tyr Val Glu Asp Thr Trp Gly Ser Asp Gly Asn Pro Ile Thr
```

-continued

```
145                 150                 155                 160

Lys Thr Thr Ser Asp Tyr Gln Asp Ser Asp Val Ser Gln Glu Val Arg
                165                 170                 175

Lys Tyr Phe Cys Val Lys Thr Met Asn
            180                 185


<210> SEQ ID NO 6
<211> LENGTH: 272
<212> TYPE: PRT
<213> ORGANISM: Vaccinia virus

<400> SEQUENCE: 6

Met Arg Tyr Ile Ile Ile Leu Ala Val Leu Phe Ile Asn Ser Ile His
1               5                   10                  15

Ala Lys Ile Thr Ser Tyr Lys Phe Glu Ser Val Asn Phe Asp Ser Lys
            20                  25                  30

Ile Glu Trp Thr Gly Asp Gly Leu Tyr Asn Ile Ser Leu Lys Asn Tyr
        35                  40                  45

Gly Ile Lys Thr Trp Gln Thr Met Tyr Thr Asn Val Pro Glu Gly Thr
    50                  55                  60

Tyr Asp Ile Ser Ala Phe Pro Lys Asn Asp Phe Val Ser Phe Trp Val
65                  70                  75                  80

Lys Phe Glu Gln Gly Asp Tyr Lys Val Glu Glu Tyr Cys Thr Gly Leu
                85                  90                  95

Cys Val Glu Val Lys Ile Gly Pro Pro Thr Val Thr Leu Thr Glu Tyr
            100                 105                 110

Asp Asp His Ile Asn Leu Tyr Ile Glu His Pro Tyr Ala Thr Arg Gly
        115                 120                 125

Ser Lys Lys Ile Pro Ile Tyr Lys Arg Gly Asp Met Cys Asp Ile Tyr
    130                 135                 140

Leu Leu Tyr Thr Ala Asn Phe Thr Phe Gly Asp Ser Glu Glu Pro Val
145                 150                 155                 160

Thr Tyr Asp Ile Asp Asp Tyr Asp Cys Thr Ser Thr Gly Cys Ser Ile
                165                 170                 175

Asp Phe Ala Thr Thr Glu Lys Val Cys Val Thr Ala Gln Gly Ala Thr
            180                 185                 190

Glu Gly Phe Leu Glu Lys Ile Thr Pro Trp Ser Ser Glu Val Cys Leu
        195                 200                 205

Thr Pro Lys Lys Asn Val Tyr Thr Cys Ala Ile Arg Ser Lys Glu Asp
    210                 215                 220

Val Pro Asn Phe Lys Asp Lys Met Ala Arg Val Ile Lys Arg Lys Phe
225                 230                 235                 240

Asn Lys Gln Ser Gln Ser Tyr Leu Thr Lys Phe Leu Gly Ser Thr Ser
                245                 250                 255

Asn Asp Val Thr Thr Phe Leu Ser Met Leu Asn Leu Thr Lys Tyr Ser
            260                 265                 270


<210> SEQ ID NO 7
<211> LENGTH: 265
<212> TYPE: PRT
<213> ORGANISM: Vaccinia virus

<400> SEQUENCE: 7

Met Thr Met Lys Met Met Val His Ile Tyr Phe Val Ser Leu Ser Leu
1               5                   10                  15

Leu Leu Leu Leu Phe His Ser Tyr Ala Ile Asp Ile Glu Asn Glu Ile
```

```
            20                  25                  30

Thr Glu Phe Phe Asn Lys Met Arg Asp Thr Leu Pro Ala Lys Asp Ser
        35                  40                  45

Lys Trp Leu Asn Pro Ala Cys Met Phe Gly Gly Thr Met Asn Asp Ile
    50                  55                  60

Ala Ala Leu Gly Glu Pro Phe Ser Ala Lys Cys Pro Pro Ile Glu Asp
65                  70                  75                  80

Ser Leu Leu Ser His Arg Tyr Lys Asp Tyr Val Val Lys Trp Glu Arg
                85                  90                  95

Leu Glu Lys Asn Arg Arg Arg Gln Val Ser Asn Lys Arg Val Lys His
            100                 105                 110

Gly Asp Leu Trp Ile Ala Asn Tyr Thr Ser Lys Phe Ser Asn Arg Arg
        115                 120                 125

Tyr Leu Cys Thr Val Thr Thr Lys Asn Gly Asp Cys Val Gln Gly Ile
    130                 135                 140

Val Arg Ser His Ile Arg Lys Pro Pro Ser Cys Ile Pro Lys Thr Tyr
145                 150                 155                 160

Glu Leu Gly Thr His Asp Lys Tyr Gly Ile Asp Leu Tyr Cys Gly Ile
                165                 170                 175

Leu Tyr Ala Lys His Tyr Asn Asn Ile Thr Trp Tyr Lys Asp Asn Lys
            180                 185                 190

Glu Ile Asn Ile Asp Asp Ile Lys Tyr Ser Gln Thr Gly Lys Lys Leu
        195                 200                 205

Ile Ile His Asn Pro Glu Leu Glu Asp Ser Gly Arg Tyr Asp Cys Tyr
    210                 215                 220

Val His Tyr Asp Asp Val Arg Ile Lys Asn Asp Ile Val Val Ser Arg
225                 230                 235                 240

Cys Lys Ile Leu Thr Val Leu Pro Ser Gln Asp His Arg Phe Lys Leu
                245                 250                 255

Lys Arg Asn Cys Gly Tyr Ala Ser Asn
            260                 265
```

<210> SEQ ID NO 8
<211> LENGTH: 353
<212> TYPE: PRT
<213> ORGANISM: Vaccinia virus

<400> SEQUENCE: 8

```
Met Asp Ile Phe Lys Glu Leu Ile Leu Lys His Thr Asp Glu Asn Val
1               5                   10                  15

Leu Ile Ser Pro Val Ser Ile Leu Ser Thr Leu Ser Ile Leu Asn His
            20                  25                  30

Gly Ala Ala Gly Ser Thr Ala Glu Gln Leu Ser Lys Tyr Ile Glu Asn
        35                  40                  45

Met Asn Glu Asn Thr Pro Asp Asp Asn Asn Asp Met Asp Val Asp Ile
    50                  55                  60

Pro Tyr Cys Ala Thr Leu Ala Thr Ala Asn Lys Ile Tyr Gly Ser Asp
65                  70                  75                  80

Ser Ile Glu Phe His Ala Ser Phe Leu Gln Lys Ile Lys Asp Asp Phe
                85                  90                  95

Gln Thr Val Asn Phe Asn Asn Ala Asn Gln Thr Lys Glu Leu Ile Asn
            100                 105                 110

Glu Trp Val Lys Thr Met Thr Asn Gly Lys Ile Asn Ser Leu Leu Thr
        115                 120                 125
```

```
Ser Pro Leu Ser Ile Asn Thr Arg Met Thr Val Val Ser Ala Val His
    130                 135                 140

Phe Lys Ala Met Trp Lys Tyr Pro Phe Ser Lys His Leu Thr Tyr Thr
145                 150                 155                 160

Asp Lys Phe Tyr Ile Ser Lys Asn Ile Val Thr Ser Val Asp Met Met
                165                 170                 175

Val Ser Thr Glu Asn Asn Leu Gln Tyr Val His Ile Asn Glu Leu Phe
            180                 185                 190

Gly Gly Phe Ser Ile Ile Asp Ile Pro Tyr Glu Gly Asn Ser Ser Met
        195                 200                 205

Val Ile Ile Leu Pro Asp Asp Ile Glu Gly Ile Tyr Asn Ile Glu Lys
    210                 215                 220

Asn Ile Thr Asp Glu Lys Phe Lys Lys Trp Cys Gly Met Leu Ser Thr
225                 230                 235                 240

Lys Ser Ile Asp Leu Tyr Met Pro Lys Phe Lys Val Glu Met Thr Glu
                245                 250                 255

Pro Tyr Asn Leu Val Pro Ile Leu Glu Asn Leu Gly Leu Thr Asn Ile
            260                 265                 270

Phe Gly Tyr Tyr Ala Asp Phe Ser Lys Met Cys Asn Glu Thr Ile Thr
        275                 280                 285

Val Glu Lys Phe Leu His Thr Thr Phe Ile Asp Val Asn Glu Glu Tyr
    290                 295                 300

Thr Glu Ala Ser Ala Val Thr Gly Val Phe Met Thr Asn Phe Ser Met
305                 310                 315                 320

Val Tyr Arg Thr Lys Val Tyr Ile Asn His Pro Phe Met Tyr Met Ile
                325                 330                 335

Lys Asp Asn Thr Gly Arg Ile Leu Phe Ile Gly Lys Tyr Cys Tyr Pro
            340                 345                 350

Gln


<210> SEQ ID NO 9
<211> LENGTH: 345
<212> TYPE: PRT
<213> ORGANISM: Vaccinia virus

<400> SEQUENCE: 9

Met Asp Ile Phe Arg Glu Ile Ala Ser Ser Met Lys Gly Glu Asn Val
1               5                   10                  15

Phe Ile Ser Pro Ala Ser Ile Ser Ser Val Leu Thr Ile Leu Tyr Tyr
            20                  25                  30

Gly Ala Asn Gly Ser Thr Ala Glu Gln Leu Ser Lys Tyr Val Glu Lys
        35                  40                  45

Glu Glu Asn Met Asp Lys Val Ser Ala Gln Asn Ile Ser Phe Lys Ser
    50                  55                  60

Ile Asn Lys Val Tyr Gly Arg Tyr Ser Ala Val Phe Lys Asp Ser Phe
65                  70                  75                  80

Leu Arg Lys Ile Gly Asp Lys Phe Gln Thr Val Asp Phe Thr Asp Cys
                85                  90                  95

Arg Thr Ile Asp Ala Ile Asn Lys Cys Val Asp Ile Phe Thr Glu Gly
            100                 105                 110

Lys Ile Asn Pro Leu Leu Asp Glu Pro Leu Ser Pro Asp Thr Cys Leu
        115                 120                 125

Leu Ala Ile Ser Ala Val Tyr Phe Lys Ala Lys Trp Leu Thr Pro Phe
    130                 135                 140
```

```
Glu Lys Glu Phe Thr Ser Asp Tyr Pro Phe Tyr Val Ser Pro Thr Glu
145                 150                 155                 160

Met Val Asp Val Ser Met Met Ser Met Tyr Gly Lys Ala Phe Asn His
                165                 170                 175

Ala Ser Val Lys Glu Ser Phe Gly Asn Phe Ser Ile Ile Glu Leu Pro
            180                 185                 190

Tyr Val Gly Asp Thr Ser Met Met Val Ile Leu Pro Asp Lys Ile Asp
        195                 200                 205

Gly Leu Glu Ser Ile Glu Gln Asn Leu Thr Asp Thr Asn Phe Lys Lys
    210                 215                 220

Trp Cys Asn Ser Leu Glu Ala Thr Phe Ile Asp Val His Ile Pro Lys
225                 230                 235                 240

Phe Lys Val Thr Gly Ser Tyr Asn Leu Val Asp Thr Leu Val Lys Ser
                245                 250                 255

Gly Leu Thr Glu Val Phe Gly Ser Thr Gly Asp Tyr Ser Asn Met Cys
            260                 265                 270

Asn Ser Asp Val Ser Val Asp Ala Met Ile His Lys Thr Tyr Ile Asp
        275                 280                 285

Val Asn Glu Glu Tyr Thr Glu Ala Ala Ala Ala Thr Cys Ala Leu Val
    290                 295                 300

Ser Asp Cys Ala Ser Thr Ile Thr Asn Glu Phe Cys Val Asp His Pro
305                 310                 315                 320

Phe Ile Tyr Val Ile Arg His Val Asp Gly Lys Ile Leu Phe Val Gly
                325                 330                 335

Arg Tyr Cys Ser Pro Thr Thr Asn Cys
            340                 345


<210> SEQ ID NO 10
<211> LENGTH: 149
<212> TYPE: PRT
<213> ORGANISM: Vaccinia virus

<400> SEQUENCE: 10

Met Thr Ala Asn Phe Ser Thr His Val Phe Ser Pro Gln His Cys Gly
1               5                   10                  15

Cys Asp Arg Leu Thr Ser Ile Asp Asp Val Arg Gln Cys Leu Thr Glu
            20                  25                  30

Tyr Ile Tyr Trp Ser Ser Tyr Ala Tyr Arg Asn Arg Gln Cys Ala Gly
        35                  40                  45

Gln Leu Tyr Ser Thr Leu Leu Ser Phe Arg Asp Asp Ala Glu Ser Val
    50                  55                  60

Phe Ile Asp Ile Arg Glu Leu Val Lys Asn Met Pro Trp Asp Asp Val
65                  70                  75                  80

Lys Asp Cys Thr Glu Ile Ile Arg Cys Tyr Ile Pro Asp Glu Gln Lys
                85                  90                  95

Thr Ile Arg Glu Ile Ser Ala Ile Ile Gly Leu Cys Ala Tyr Ala Ala
            100                 105                 110

Thr Tyr Trp Gly Gly Glu Asp His Pro Thr Ser Asn Ser Leu Asn Ala
        115                 120                 125

Leu Phe Val Met Leu Glu Met Leu Asn Tyr Val Asp Tyr Asn Ile Ile
    130                 135                 140

Phe Arg Arg Met Asn
145


<210> SEQ ID NO 11
```

```
<211> LENGTH: 149
<212> TYPE: PRT
<213> ORGANISM: Vaccinia virus

<400> SEQUENCE: 11

Met Thr Ala Asn Phe Ser Thr His Val Phe Ser Pro Gln His Cys Gly
1               5                   10                  15

Cys Asp Arg Leu Thr Ser Ile Asp Asp Val Lys Gln Cys Leu Thr Glu
            20                  25                  30

Tyr Ile Tyr Trp Ser Ser Tyr Ala Tyr Arg Asn Arg Gln Cys Ala Gly
        35                  40                  45

Gln Leu Tyr Ser Thr Leu Leu Ser Phe Arg Asp Asp Ala Glu Leu Val
    50                  55                  60

Phe Ile Asp Ile Arg Glu Leu Val Lys Asn Met Pro Trp Asp Asp Val
65                  70                  75                  80

Lys Asp Cys Thr Glu Ile Ile Arg Cys Tyr Ile Pro Asp Glu Gln Lys
                85                  90                  95

Thr Ile Arg Glu Ile Ser Ala Ile Ile Gly Leu Cys Ala Tyr Ala Ala
            100                 105                 110

Thr Tyr Trp Gly Gly Glu Asp His Pro Thr Ser Asn Ser Leu Asn Ala
        115                 120                 125

Leu Phe Val Met Leu Glu Met Leu Asn Tyr Val Asp Tyr Asn Ile Ile
    130                 135                 140

Phe Arg Arg Met Asn
145


<210> SEQ ID NO 12
<211> LENGTH: 140
<212> TYPE: PRT
<213> ORGANISM: Vaccinia virus

<400> SEQUENCE: 12

Met Ser Met Lys Tyr Leu Met Leu Leu Phe Ala Ala Met Ile Ile Arg
1               5                   10                  15

Ser Phe Ala Asp Ser Gly Asn Ala Ile Glu Thr Thr Ser Pro Glu Ile
            20                  25                  30

Thr Asn Ala Thr Thr Asp Ile Pro Ala Ile Arg Leu Cys Gly Pro Glu
        35                  40                  45

Gly Asp Gly Tyr Cys Leu His Gly Asp Cys Ile His Ala Arg Asp Ile
    50                  55                  60

Asp Gly Met Tyr Cys Arg Cys Ser His Gly Tyr Thr Gly Ile Arg Cys
65                  70                  75                  80

Gln His Val Val Leu Val Asp Tyr Gln Arg Ser Glu Asn Pro Asn Thr
                85                  90                  95

Thr Thr Ser Tyr Ile Pro Ser Pro Gly Ile Met Leu Val Leu Val Gly
            100                 105                 110

Ile Ile Ile Ile Thr Cys Cys Leu Leu Ser Val Tyr Arg Phe Thr Arg
        115                 120                 125

Arg Thr Lys Leu Pro Ile Gln Asp Met Val Val Pro
    130                 135                 140


<210> SEQ ID NO 13
<211> LENGTH: 190
<212> TYPE: PRT
<213> ORGANISM: Vaccinia virus

<400> SEQUENCE: 13
```

-continued

Met Ser Lys Ile Tyr Ile Asp Glu Arg Ser Asn Ala Glu Ile Val Cys
1 5 10 15

Glu Ala Ile Lys Thr Ile Gly Ile Glu Gly Ala Thr Ala Ala Gln Leu
20 25 30

Thr Arg Gln Leu Asn Met Glu Lys Arg Glu Val Asn Lys Ala Leu Tyr
35 40 45

Asp Leu Gln Arg Ser Ala Met Val Tyr Ser Ser Asp Asp Ile Pro Pro
50 55 60

Arg Trp Phe Met Thr Thr Glu Ala Asp Glu Ala Asp Ala Asp Ala Met
65 70 75 80

Ser Asp Val Ile Ile Asp Asp Val Ser Arg Glu Lys Ser Met Arg Glu
85 90 95

Asp His Lys Ser Phe Asp Asp Val Ile Pro Ala Lys Lys Ile Ile Asp
100 105 110

Trp Lys Gly Ala Asn Pro Val Thr Val Ile Asn Glu Tyr Cys Gln Ile
115 120 125

Thr Arg Arg Asp Trp Ser Phe Arg Ile Glu Ser Val Gly Pro Ser Asn
130 135 140

Ser Pro Thr Phe Tyr Ala Cys Val Asp Ile Asp Gly Arg Val Phe Asp
145 150 155 160

Lys Ala Asp Gly Lys Ser Lys Arg Asp Ala Lys Asn Asn Ala Ala Lys
165 170 175

Leu Ala Val Asp Lys Leu Leu Gly Tyr Val Ile Ile Arg Phe
180 185 190

<210> SEQ ID NO 14
<211> LENGTH: 88
<212> TYPE: PRT
<213> ORGANISM: Vaccinia virus

<400> SEQUENCE: 14

Met Leu Ala Phe Cys Tyr Ser Leu Pro Asn Ala Gly Asp Val Ile Lys
1 5 10 15

Gly Arg Val Tyr Glu Lys Asp Tyr Ala Leu Tyr Ile Tyr Leu Phe Asp
20 25 30

Tyr Pro His Ser Glu Ala Ile Leu Ala Glu Ser Val Lys Met His Met
35 40 45

Asp Arg Tyr Val Glu Tyr Arg Asp Lys Leu Val Gly Lys Thr Val Lys
50 55 60

Val Lys Val Ile Arg Val Asp Tyr Thr Lys Gly Tyr Ile Asp Val Asn
65 70 75 80

Tyr Lys Arg Met Cys Arg His Gln
85

<210> SEQ ID NO 15
<211> LENGTH: 219
<212> TYPE: PRT
<213> ORGANISM: Vaccinia virus

<400> SEQUENCE: 15

Met Tyr Ser Leu Leu Phe Ile Ile Leu Met Cys Ile Pro Phe Ser Phe
1 5 10 15

Gln Thr Val Tyr Asp Asp Lys Ser Val Cys Asp Ser Asp Asn Lys Glu
20 25 30

Tyr Met Gly Ile Glu Val Tyr Val Glu Ala Thr Leu Asp Glu Pro Leu
35 40 45

-continued

```
Arg Gln Thr Thr Cys Glu Ser Glu Ile His Lys Tyr Gly Ala Ser Val
    50                  55                  60

Ser Asn Gly Gly Leu Asn Ile Ser Val Asp Leu Leu Asn Cys Phe Leu
65                  70                  75                  80

Asn Phe His Thr Val Gly Val Tyr Thr Asn Arg Asp Thr Val Tyr Ala
                85                  90                  95

Lys Phe Ala Ser Leu Asp Pro Trp Thr Thr Glu Pro Ile Asn Ser Met
            100                 105                 110

Thr His Asp Asp Leu Val Lys Leu Thr Glu Glu Cys Ile Val Asp Ile
        115                 120                 125

Tyr Leu Lys Cys Glu Val Asp Lys Thr Lys Asp Phe Met Lys Thr Asn
    130                 135                 140

Gly Asn Arg Leu Lys Pro Arg Asp Phe Lys Thr Val Pro Pro Ser Asp
145                 150                 155                 160

Val Gly Ser Met Ile Glu Leu Gln Ser Asp Tyr Cys Val Asn Asp Val
                165                 170                 175

Thr Ala Tyr Val Lys Ile Tyr Asp Glu Cys Gly Asn Ile Lys Gln His
            180                 185                 190

Ser Ile Pro Thr Leu Arg Asp Tyr Phe Thr Thr Lys Asn Gly Gln Pro
        195                 200                 205

Arg Lys Ile Leu Lys Lys Lys Phe Asp Asn Cys
    210                 215
```

<210> SEQ ID NO 16
<211> LENGTH: 149
<212> TYPE: PRT
<213> ORGANISM: Vaccinia virus

<400> SEQUENCE: 16

```
Met Ala Thr Lys Leu Asp Tyr Glu Asp Ala Val Phe Tyr Phe Val Asp
1               5                   10                  15

Asp Asp Lys Ile Cys Ser Arg Asp Ser Ile Ile Asp Leu Ile Asp Glu
            20                  25                  30

Tyr Ile Thr Trp Arg Asn His Val Ile Val Phe Asn Lys Asp Ile Thr
        35                  40                  45

Ser Cys Gly Arg Leu Tyr Lys Glu Leu Met Lys Phe Asp Asp Val Ala
    50                  55                  60

Ile Arg Tyr Tyr Gly Ile Asp Lys Ile Asn Glu Ile Val Glu Ala Met
65                  70                  75                  80

Ser Glu Gly Asp His Tyr Ile Asn Phe Thr Lys Val His Asp Gln Glu
                85                  90                  95

Ser Leu Phe Ala Thr Ile Gly Ile Cys Ala Lys Ile Thr Glu His Trp
            100                 105                 110

Gly Tyr Lys Lys Ile Ser Glu Ser Arg Phe Gln Ser Leu Gly Asn Ile
        115                 120                 125

Thr Asp Leu Met Thr Asp Asp Asn Ile Asn Ile Leu Ile Leu Phe Leu
    130                 135                 140

Glu Lys Lys Leu Asn
145
```

<210> SEQ ID NO 17
<211> LENGTH: 117
<212> TYPE: PRT
<213> ORGANISM: Vaccinia virus

<400> SEQUENCE: 17

```
Met Arg Thr Leu Leu Ile Arg Tyr Ile Leu Trp Arg Asn Asp Asn Asp
1               5                   10                  15

Gln Thr Tyr Tyr Asn Asp Asp Phe Lys Lys Leu Met Leu Leu Asp Glu
            20                  25                  30

Leu Val Asp Asp Gly Asp Val Cys Thr Leu Ile Lys Asn Met Arg Met
        35                  40                  45

Thr Leu Ser Asp Gly Pro Leu Leu Asp Arg Leu Asn Gln Pro Val Asn
    50                  55                  60

Asn Ile Glu Asp Ala Lys Arg Met Ile Ala Ile Ser Ala Lys Val Ala
65                  70                  75                  80

Arg Asp Ile Gly Glu Arg Ser Glu Ile Arg Trp Glu Glu Ser Phe Thr
                85                  90                  95

Ile Leu Phe Arg Met Ile Glu Thr Tyr Phe Asp Asp Leu Met Ile Asp
            100                 105                 110

Leu Tyr Gly Glu Lys
        115


<210> SEQ ID NO 18
<211> LENGTH: 190
<212> TYPE: PRT
<213> ORGANISM: Vaccinia virus

<400> SEQUENCE: 18

Met Asp Ile Lys Ile Asp Ile Ser Ile Ser Gly Asp Lys Phe Thr Val
1               5                   10                  15

Thr Thr Arg Arg Glu Asn Glu Glu Arg Lys Lys Tyr Leu Pro Leu Gln
            20                  25                  30

Lys Glu Lys Thr Thr Asp Val Ile Lys Pro Asp Tyr Leu Glu Tyr Asp
        35                  40                  45

Asp Leu Leu Asp Arg Asp Glu Met Phe Thr Ile Leu Glu Glu Tyr Phe
    50                  55                  60

Met Tyr Arg Gly Leu Leu Gly Leu Arg Ile Lys Tyr Gly Arg Leu Phe
65                  70                  75                  80

Asn Glu Ile Lys Lys Phe Asp Asn Asp Ala Glu Glu Gln Phe Gly Thr
                85                  90                  95

Ile Glu Glu Leu Lys Gln Lys Leu Arg Leu Asn Ser Glu Glu Gly Ala
            100                 105                 110

Asp Asn Phe Ile Asp Tyr Ile Lys Val Gln Lys Gln Asp Ile Val Lys
        115                 120                 125

Leu Thr Val Tyr Asp Cys Ile Ser Met Ile Gly Leu Cys Ala Cys Val
    130                 135                 140

Val Asp Val Trp Arg Asn Glu Lys Leu Phe Ser Arg Trp Lys Tyr Cys
145                 150                 155                 160

Leu Arg Ala Ile Lys Leu Phe Ile Asn Asp His Met Leu Asp Lys Ile
                165                 170                 175

Lys Ser Ile Leu Gln Asn Arg Leu Val Tyr Val Glu Met Ser
            180                 185                 190


<210> SEQ ID NO 19
<211> LENGTH: 954
<212> TYPE: DNA
<213> ORGANISM: Vaccinia virus

<400> SEQUENCE: 19

atgaaaacga tttccgttgt tacgttgtta tgcgtactac ctgctgttgt ttattcaaca      60

tgtactgtac ccactatgaa taacgctaaa ttaacgtcta ccgaaacatc gtttaatgat     120
```

aaacagaaag ttacgtttac atgtgatcag ggatatcatt cttcggatcc aaatgctgtc 180
tgcgaaacag ataaatggaa atacgaaaat ccatgcaaaa aaatgtgcac agtttctgat 240
tacatctctg aattatataa taaaccgcta tacgaagtga attccaccat gacactaagt 300
tgcaacggcg aaacaaaata ttttcgttgc gaagaaaaaa atggaaatac ttcttggaat 360
gatactgtta cgtgtcctaa tgcggaatgt caacctcttc aattagaaca cggatcgtgt 420
caaccagtta aagaaaaata ctcatttggg gaatatatga ctatcaactg tgatgttgga 480
tatgaggtta ttggtgcttc gtacataagt tgtacagcta attcttggaa tgttattcca 540
tcatgtcaac aaaaatgtga tatgccgtct ctatctaatg gattaatttc cggatctaca 600
ttttctatcg gtggcgttat acatcttagt tgtaaaagtg gttttacact aacggggtct 660
ccatcatcca catgtatcga cggtaaatgg aatcccgtac tcccaatatg tgtacgaact 720
aacgaagaat ttgatccagt ggatgatggt cccgacgatg agacagattt gagcaaactc 780
tcgaaagacg ttgtacaata tgaacaagaa atagaatcgt tagaagcaac ttatcatata 840
atcatagtgg cgttaacaat tatgggcgtc atatttttaa tctccgttat agtattagtt 900
tgttcctgtg acaaaaataa tgaccaatat aagttccata aattgctacc gtaa 954

<210> SEQ ID NO 20
<211> LENGTH: 1119
<212> TYPE: DNA
<213> ORGANISM: Vaccinia virus

<400> SEQUENCE: 20
atgtggccat ttgcatcggt acctgcggga gcaaaatgta ggctggtaga aacactacca 60
gaaaatatgg attttagatc cgatcattta acaacatttg aatgttttaa cgaaattatc 120
actctagcta agaaatatat atacatagca tctttttgtt gtaatcctct gagtacgact 180
aggggagcgc ttatttttga taaactaaaa gaggcatctg aaaaagggat taaaataata 240
gttttgctag atgaacgagg gaaaagaaat ctgggagagc tacaaagtca ctgcccggat 300
ataaatttta taaccgttaa tatagataaa aaaaataatg tgggactact actcggttgt 360
ttttgggtgt cagatgatga aagatgttat gtaggaaacg cgtcatttac tggaggatct 420
atacatacga ttaaaacgtt aggtgtatat tctgattatc ccccgctggc cacagatctt 480
cgtagaagat ttgatacttt taaagccttt aatagcgcaa aaaattcatg gttgaattta 540
tgctctgcgg cttgttgttt gccagttagc actgcgtatc atattaagaa tcctataggt 600
ggagtgttct ttactgattc tccggaacac ctattgggat attctagaga tctagatacc 660
gatgtagtta ttgataaact caagtcggct aagactagta tagatattga acatttggcc 720
atagttccca ctacacgtgt cgacggtaat agctactatt ggcccgacat ttacaactcc 780
attatagaag cagccattaa tagaggagtt aagatcagac ttctagttgg taattgggat 840
aagaacgacg tatattctat ggcaaccgcc agaagtctag acgcgttgtg tgttcaaaat 900
gatctatctg tgaaggtttt cactattcag aataatacaa aattgttgat agtcgacgac 960
gaatatgttc atatcacttc ggcaaatttc gacggaaccc attaccaaaa tcacggattc 1020
gtcagtttta atagtataga taaacagctt gtaagcgagg ctaaaaaaat atttgagaga 1080
gattgggtat ctagccacag taaatcgtta aaaatttaa 1119

<210> SEQ ID NO 21
<211> LENGTH: 666
<212> TYPE: DNA

<213> ORGANISM: Vaccinia virus

<400> SEQUENCE: 21
atgatgctgg tacctcttat cacggtgacc gtagttgcgg gaacaatatt agtatgttat 60
atattatata tttgtaggaa aaagatacgt actgtctata atgacaataa aattatcatg 120
acaaaattaa aaaagataaa gagttctaat tccagcaaat ctagtaaatc aactgatagc 180
gaatcagact gggaggatca ctgtagtgct atggaacaaa acaatgacgt agataatatt 240
tctaggaatg agatattgga cgatgatagc ttcgctggta gtttaatatg ggataacgaa 300
tccaatgtca tggcgcctag cacagaacac atttacgata gtgttgctgg aagcacgctg 360
ctaataaata atgatcgtaa tgaacagact atttatcaga acactacagt agtaattaat 420
gagacggaga ctgttgaagt acttaatgaa gataccaaac agaatcctaa ctattcatcc 480
aatcctttcg taaattataa taaaaccagt atttgtagca agtcaaatcc gttcattaca 540
gaactcaaca ataaatttag tgagaataat ccgtttagac gagcacatag cgatgattat 600
cttaataagc aagaacaaga tcatgaacac gatgatatag aatcatcggt cgtatcattg 660
gtgtga 666

<210> SEQ ID NO 22
<211> LENGTH: 507
<212> TYPE: DNA
<213> ORGANISM: Vaccinia virus

<400> SEQUENCE: 22
atgaaatcgc ttaatagaca aactgtaagt aggtttaaga agttgtcggt gccggccgct 60
ataatgatga tactctcaac cattattagt ggcataggaa catttctgca ttacaaagaa 120
gaactgatgc ctagtgcttg cgccaatgga tggatacaat acgataaaca ttgttattta 180
gatactaaca ttaaaatgtc tacagataat gcggtttatc agtgtcgtaa attacgagcc 240
agattgccta gaccggatac tagacatctg agagtattgt ttagtatttt ttataaagat 300
tattgggtaa gtttaaaaaa gaccaatgat aaatggttag atattaataa tgataaagat 360
atagatatta gtaaattaac aaattttaaa caactaaaca gtacgacgga tgctgaagcg 420
tgttatatat acaagtctgg aaaactggtt aaaacagtat gtaaaagtac tcaatctgta 480
ctatgtgtta aaaaattcta caagtga 507

<210> SEQ ID NO 23
<211> LENGTH: 558
<212> TYPE: DNA
<213> ORGANISM: Vaccinia virus

<400> SEQUENCE: 23
atgatgacac cagaaaacga cgaagagcag acatctgtgt tctccgctac tgtttacgga 60
gacaaaattc aaggaaagaa taaacgcaaa cgcgtgattg gtctatgtat tagaatatct 120
atggttattt cactactatc tatgattacc atgtccgcgt ttctcatagt gcgcctaaat 180
caatgcatgt ctgctaacga ggctgctatt actgacgccg ctgttgccgt tgctgctgca 240
tcatctactc atagaaaggt tgcgtctagc actacacaat atgatcacaa agaaagctgt 300
aatggtttat attaccaggg ttcttgttat atattacatt cagactacca gttattctcg 360
gatgctaaag caaattgcac tgcggaatca tcaacactac ccaataaatc cgatgtcttg 420
attacctggc tcattgatta tgttgaggat acatggggat ctgatggtaa tccaattaca 480
aaaactacat ccgattatca agattctgat gtatcacaag aagttagaaa gtatttttgt 540
gttaaaacaa tgaactaa 558

<210> SEQ ID NO 24
<211> LENGTH: 819
<212> TYPE: DNA
<213> ORGANISM: Vaccinia virus

<400> SEQUENCE: 24
atgagatata ttataattct cgcagttttg ttcattaata gtatacacgc taaaataact 60
agttataagt ttgaatccgt caattttgat tccaaaattg aatggactgg ggatggtcta 120
tacaatatat cccttaaaaa ttatggcatc aagacgtggc aaacaatgta tacaaatgta 180
ccagaaggaa catacgacat atccgcattt ccaaagaatg atttcgtatc tttctgggtt 240
aaatttgaac aaggcgatta taaagtggaa gagtattgta cgggactatg cgtcgaagta 300
aaaattggac caccgactgt aacattgact gaatacgacg accatatcaa tttgtacatc 360
gagcatccgt atgctactag aggtagcaaa aagattccta tttacaaacg cggtgacatg 420
tgtgatatct acttgttgta tacggctaac ttcacattcg gagattctaa agaaccagta 480
ccatatgata tcgatgacta cgattgcacg tctacaggtt gcagcataga ctttgtcaca 540
acagaaaaag tgtgcgtgac agcacaggga gccacagaag ggtttctcga aaaaattact 600
ccatggagtt cgaaagtatg tctgacacct aaaaagagtg tatatacatg cgcaattaga 660
tccaaagaag atgttcccaa tttcaaggac aaaatggcca gagttatcaa gagaaaattt 720
aataaacagt ctcaatctta tttaactaaa tttctcggta gcacatcaaa tgatgttacc 780
acttttctta gcatgcttaa cttgactaaa tattcataa 819

<210> SEQ ID NO 25
<211> LENGTH: 1725
<212> TYPE: DNA
<213> ORGANISM: Vaccinia virus

<400> SEQUENCE: 25
atgagtcgtc gtctgattta tgttttaaat atcaaccgcg aatcaactca taaaatacaa 60
gagaatgaaa tatatacata ttttagtcat tgcaatatag accatacttc tacagaactt 120
gattttgtag ttaaaaacta tgatctaaac agacgacaac ctgtaactgg gtatactgca 180
ctacactgct atttgtataa taattacttt acaaacgatg tactgaagat attattaaat 240
catggagtgg atgtaacgat gaaaaccagt agcggacgta tgcctgttta tatattgctt 300
actagatgtt gcaatatttc acatgatgta gtgatagata tgatagacaa agataaaaac 360
cacttattac atagagacta ttccaaccta ttactagagt atataaaatc tcgttacatg 420
ttattaaagg aagaggatat cgatgagaac atagtatcca ctttattaga taagggaatc 480
gatcctaact ttaaacaaga cggatataca gcgttacatt attattattt gtgtctcgca 540
cacgtttata aaccaggtga gtgtagaaaa ccgataacga taaaaaaggc caagcgaatt 600
atttctttgt ttatacaaca tggagctaat ctaaacgcgt tagataattg tggtaataca 660
ccattccatt tgtatcttag tattgaaatg tgtaataata ttcatatgac taaaatgctg 720
ttgactttta atccgaattt cgaaatatgt aataatcatg gattaacgcc tatactatgt 780
tatataactt ccgactacat acaacacgat attcttgtta tgttaataca tcactatgaa 840
acaaatgttg gagaaatgcc gatagatgag cgtcgtataa tcgtattcga gtttatcaaa 900
acatattcta cacgtcctgc agattcgata acttatttga tgaataggtt taaaaatata 960

-continued

```
gatatttata cccgctatga aggaaagaca ttattacacg tagcatgtga atataataat   1020
acacacgtaa tagattatct tatacgtatc aacggagata taaatgcgtt aaccgacaat   1080
aacaaacacg ctacacaact cattatagat aacaaagaaa attccccata taccattaat   1140
tgtttactgt atatacttag atatattgta gataagaatg tgataagatc gttggtggat   1200
caacttccat ctctacctat cttcgatata aaatcatttg agaaattcat atcctactgt   1260
atacttttag atgacacatt ttacaataga cacgttagga atcgcgattc taaaacgtat   1320
cgatacgcat tttcaaaata catgtcgttt gataaatacg atggtataat aactaaatgt   1380
cataaagaaa caatattgct caaactatcc actgttctag acactacact atatgcagtt   1440
ttaagatgcc ataattcgaa aaagttaaga agatacctca ccgagttaaa aaaatataat   1500
aacgataagt cctttaaaat atattctaat attatgaatg agagatacct taatgtatat   1560
tataaagata tgtacgtgtc aaaggtatat gataaactat ttcctgtttt cacagataaa   1620
aattgtctac taacattact accttcagaa attatatacg aaatattata catgctgaca   1680
attaacgatc tttataatat atcgtatcca cctaccaaag tatag                   1725
```

<210> SEQ ID NO 26
<211> LENGTH: 3043
<212> TYPE: DNA
<213> ORGANISM: Vaccinia virus

<400> SEQUENCE: 26

```
tcacataatc tatttagaga tcgagtcatg cacgattata taagtaatac atatattgat     60
cttgagtgtt tagatattat tagatcgttg gatggattcg atatcaatgg ttactttgaa    120
ggacgtacac cacttcattg cgctatacaa cataacttca ctcagattgc taagtactta    180
ttagatcgag gagctgatat agtcgtaccc aacacattga ttatacatca gtacatacag    240
taaatagcat agatatggag gaggatacaa atatttcaaa taaagttata aggtacaaca    300
ctgtcaataa tatatgggaa acattaccta acttctggac tggaactata aatccaggcg    360
tggtctcgca taaagatgat atatatgttg tatgcgacat caaagatgaa aaaaatgtta    420
aaacttgtat atttagatat aacacgaata cgtataacgg atgggaattg gtcacgacga    480
cagaaagcag attatcagct ctgcatacta ttctttataa caataccata atgatgttac    540
attgttatga atcgtatatg ttacaagata catttaatgt gtacactcgc gaatggaatc    600
atatgtgtca tcaacattcg aatagttata tcatgtacaa tatactaccc atctactaaa    660
tataatagaa taaaataaat gagtatgatc attttagata acgattgatt ttatcattac    720
cgcttcattc ttatattctt tgcttacgga acctatattt agaaacatct actaacgatt    780
ttttatgctt gcattattaa tggtatgtaa tatgattgat tgtgtacgca ataccaattt    840
gttaagtatg aatacggggt acaaacataa actgaagttt aacattattt atttatgata    900
tatatcgtta ttgtttggtc tataccatgg atatctttaa agaactaatc ttaaaacaca    960
cggatgaaaa tgttttgatt tctccagttt ctattttatc tactttatct attctaaatc   1020
atggagcagc tggttctaca gctgaacaac tatcaaaata tatagagaat atgaatgaga   1080
atacacccga tgacaataat gacatggacg tagatattcc gtattgtgcg acactagcta   1140
ccgcaaataa aatatacggt agcgatagta tcgagttcca cgcctccttc ctacaaaaaa   1200
taaaagacga ttttcaaact gtaaacttta ataatgctaa ccaaacaaag gaactaatca   1260
acgaatgggt taagacaatg acaaatggta aaattaattc cttattgact agtccgctat   1320
ccattaatac tcgtatgaca gttgttagcg ccgtccattt taaagcaatg tggaaatatc   1380
```

cattttctaa acatcttaca tatacagaca agttttatat ttctaagaat atagttacca 1440
gtgttgatat gatggtgagc actgagaata acttgcaata tgtacatatt aatgaattat 1500
tcggaggatt ctctattatc gatattccat acgagggaaa ctctagtatg gtaattatac 1560
taccggacga catagaaggt atatataaca tagaaaaaaa tataacagat gaaaaattta 1620
aaaaatggtg tggtatgtta tctactaaaa gtatagactt gtatatgcca aagtttaaag 1680
tggaaatgac agaaccgtat aatctggtac cgattttaga aaatttagga cttactaata 1740
tattcggata ttatgcagat tttagcaaga tgtgtaatga aactatcact gtagaaaaat 1800
ttctacatac gacgtttata gatgttaatg aggagtatac agaagcatcg gccgttacag 1860
gagtatttat gactaacttt tcgatggtat atcgtacgaa ggtctacata aaccatccat 1920
tcatgtacat gattaaagac aacacaggac gtatactttt tatagggaaa tactgctatc 1980
cgcaataaat ataaacaaat agacttttat cacgtttatc tatgtctaaa tattacaaat 2040
agtaatagta taaactaaag ctgataatac ttaaaaaaat aataatatca tttacaatta 2100
atagtataaa ctaaaaatta aacaaatcgt tattataagt aatatcaaaa tgatgatata 2160
cggattaata gcgtgtctta tattcgtgac ttcatccatc gctagtccac tttatattcc 2220
cgttattcca cccatttcgg aagataaatc gttcaatagt gtagaggtat tagtttcctt 2280
gtttagagat gaccaaaaag actatacggt aacttctcag ttcaataact acactatcga 2340
taccaaagac tggactatcg gcgtactatc cacacctgat ggtttggata taccattgac 2400
taatataact tattggtcac ggtttactat aggtcgtgca ttgttcaaat cagagtctga 2460
ggatattttc caaaagaaaa tgagtattct aggtgtttct atagaatgta agaagtcgtc 2520
gacattactt actttttga ccgtgcgtaa aatgactcga gtatttaata aatttccaga 2580
tatggcttat tatcgaggag actgtttaaa agccgtttat gtaacaatga cttataaaaa 2640
tactaaaact ggagagactg attacacgta cctctctaat ggggggttgc ctgcatacta 2700
tcgtaatggg gtcgatggtt gattattgat tagtatattc cttattcttt ttattcacac 2760
aaaaagaaca tttttataaa catgaaacca ctgtctaaat gtaattatga tcttgattta 2820
tagatgaaga tcagccttta gaggatttta accagtatgt ttaatatgaa aaaaataaac 2880
ataacatatt ttgagattaa gcgctattgt gcaagattat attagaatca aattaatctt 2940
tcatacgaga aaaataacga catacgtcgt caacaaatta aactttttat ttattagtta 3000
actagcttat agaacttgct cattgttatg tttctaaaac ggg 3043

<210> SEQ ID NO 27
<211> LENGTH: 1475
<212> TYPE: DNA
<213> ORGANISM: Vaccinia virus

<400> SEQUENCE: 27
tccatggaaa aacgaaagta gtataaaagt aataaaacaa aaaaaagaat ataaaaaatt 60
tatagctact ttctttgagg actgttttcc tgaaggaaat gaacctctgg aattagttag 120
atatatagaa ttagtataca cgttagatta ttctcaaact cctaattatg acagactacg 180
taaactgttt atacaagatt gaaattatat tcttttttt atagagtgtg gtagtgttac 240
ggatatttaa tattagacta tctctatcgc gctacacgac caatatcgat tactatggat 300
atcttcaggg aaatcgcatc ttctatgaaa ggagagaatg tattcatttc tccagcgtca 360
atctcgtcag tattgacaat actgtattat ggagctaatg gatccactgc tgaacagcta 420

```
tcaaaatatg tagaaaagga ggagaacatg gataaggtta gcgctcaaaa tatctcattc    480

aaatccataa ataaagtata tgggcgatat tctgccgtgt ttaaagattc ctttttgaga    540

aaaattggcg ataagtttca aactgttgac ttcactgatt gtcgcactat agatgcaatc    600

aacaagtgtg tagatatctt tactgagggg aaaatcaatc cactattgga tgaaccattg    660

tctcctgata cctgtctcct agcaattagt gccgtatact ttaaagcaaa atggttgacg    720

ccattcgaaa aggaatttac cagtgattat cccttttacg tatctccgac ggaaatggta    780

gatgtaagta tgatgtctat gtacggcaag gcatttaatc acgcatctgt aaaggaatca    840

ttcggcaact tttcaatcat agaactgcca tatgttggag atactagtat gatggtcatt    900

cttccagaca agattgatgg attagaatcc atagaacaaa atctaacaga tacaaatttt    960

aagaaatggt gtaactctct ggaagctacg tttatcgatg ttcacattcc caagtttaag   1020

gtaacaggct cgtataatct ggtggatact ctagtaaagt caggactgac agaggtgttc   1080

ggttcaactg gagattatag caatatgtgt aattcagatg tgagtgtcga cgctatgatc   1140

cacaaaacgt atatagatgt caatgaagag tatacagaag cagctgcagc aacttgtgca   1200

ctggtgtcag actgtgcatc aacaattaca aatgagttct gtgtagatca tccgttcatc   1260

tatgtgatta ggcatgttga tggaaaaatt cttttcgttg gtagatattg ctctccgaca   1320

actaattgtt aaccattttt tttaaaaaat agaaaaaaca tgtggtatta gtgcaggtcg   1380

ttattcttcc aattgcaatt ggtaagatga cggccaactt tagtacccac gtcttttcac   1440

cacagcactg tggatgtgac agactgacca gtatt                              1475
```

<210> SEQ ID NO 28
<211> LENGTH: 450
<212> TYPE: DNA
<213> ORGANISM: Vaccinia virus

<400> SEQUENCE: 28

```
atgacggcca actttagtac ccacgtcttt tcaccacagc actgtggatg tgacagactg     60

accagtattg atgacgtcag acaatgtttg actgaatata tttattggtc gtcctatgca    120

taccgcaaca ggcaatgcgc tggacaattg tattccacac tcctctcttt tagagatgat    180

gcggaattag tgttcatcga cattcgcgag ctggtaaaaa atatgccgtg ggatgatgtc    240

aaagattgtg cagaaatcat ccgttgttat ataccggatg agcaaaaaac catcagagag    300

atttcggcca tcatcggact ttgtgcatat gctgctactt actggggagg tgaagaccat    360

cccactagta acagtctgaa cgcattgttt gtgatgcttg agatgctcaa ttacgtggat    420

tataacatca tattccggcg tatgaattga                                     450
```

<210> SEQ ID NO 29
<211> LENGTH: 423
<212> TYPE: DNA
<213> ORGANISM: Vaccinia virus

<400> SEQUENCE: 29

```
atgtcgatga aatatctgat gttgttgttc gctgctatga taatcagatc attcgccgat     60

agtggtaacg ctatcgaaac gacattgcca gaaattacaa acgctacaac agatattcca    120

gctatcagat tatgcggtcc agagggagat ggatattgtt tacacggtga ctgtatccac    180

gctagagata ttgacggtat gtattgtaga tgctctcatg gttatacagg cattagatgt    240

cagcatgtag tattagtaga ctatcaacgt tcagaaaacc caaacactac aacgtcatat    300

atcccatctc ccggtattgt gcttgtatta gtaggcatta ttattattac gtgttgttca    360
```

-continued ttatctgttt ataggttcac tcgacgaact aaactaccta tacaagatat ggttgtgcca 420
taa 423

<210> SEQ ID NO 30
<211> LENGTH: 573
<212> TYPE: DNA
<213> ORGANISM: Vaccinia virus

<400> SEQUENCE: 30
atgtctaaaa tctatatcga cgagcgttct aacgcagaga ttgtgtgtga ggctattaaa 60
accattggaa tcgaaggagc tactgctgca caactaacta gacaacttaa tatggagaag 120
cgagaagtta ataaagctct gtacgatctt caacgtagtg ctatggtgta cagctccgac 180
gatattcctc ctcgttggtt tatgacaacg gaggcggata agccggatgc tgatgctatg 240
gctgacgtca taatagatga tgtatcccgc gaaaaatcaa tgagagagga tcataagtct 300
tttgatgatg ttattccggc taaaaaaatt attgattgga aaggtgctaa ccctgtcacc 360
gttattaatg agtactgcca aattactagg agagattggt cttttcgtat tgaatcagtg 420
gggcctagta actctcctac attttatgcc tgtgtagaca tcgacggaag agtattcgat 480
aaggcagatg gaaaatctaa acgagatgct aaaaataatg cagctaaatt ggcagtagat 540
aaacttcttg gttacgtcat cattagattc tga 573

<210> SEQ ID NO 31
<211> LENGTH: 267
<212> TYPE: DNA
<213> ORGANISM: Vaccinia virus

<400> SEQUENCE: 31
atgcttgcat tttgttattc gttgcccaat gcgggtgatg taataaaggg cagagtatac 60
gagaaggatt atgctctata tatttatctt tttgactatc ctcactttga agctatcttg 120
gcagagagtg ttaagatgca tatggataga tatgttgaat atagggataa actggtaggg 180
aaaactgtaa aagttaaagt gattagagtt gattatacaa aaggatatat agatgtcaat 240
tacaaaagga tgtgtagaca tcaataa 267

<210> SEQ ID NO 32
<211> LENGTH: 660
<212> TYPE: DNA
<213> ORGANISM: Vaccinia virus

<400> SEQUENCE: 32
atgtactcgt tagtatttgt tattttgatg tgtataccat ttagttttca aacagtgtat 60
gatgataaat cggtatgcga ttctgacaat aaagaatata tgggaataga agtttatgta 120
gaagcaacgc tagacgaacc cctcagacaa acaacgtgtg aatccaaaat ccataaatat 180
ggtgcatctg tatcaaacgg aggattaaat atttctgttg atctattaaa ctgttttctt 240
aattttcata cagttggtgt atacactaat cgcgataccg tatacgcgaa gtttgctagt 300
ttggatccat ggactacgga acctataaat tctatgaccc atgacgatct agtaaaatta 360
acagaagaat gtatagtgga catttattta aaatgtgaag tggataaaac aaaggatttc 420
atgaaaacta acggtaatag attaaaacca agagacttta aaactgttcc tccttctaat 480
gtaggaagca tgatagaact acagtctgac tattgcgtaa acgatgtgac tacatacgtc 540
aaaatatacg atgagtgtgg aaacattaaa cagcattcca ttccaacact aagagattat 600
tttaccacca agaatggtca accacgtaaa atattaaaga aaaaatttga taattgttaa 660

<210> SEQ ID NO 33
<211> LENGTH: 450
<212> TYPE: DNA
<213> ORGANISM: Vaccinia virus

<400> SEQUENCE: 33
atggcgacta aattagatta tgaggatgct gtttttttact ttgtggatga tgataaaata 60
tgtagtcgcg actccatcat cgatctaata gatgaatata ttacgtggag aaatcatgtt 120
atagtgttta acaaagatat taccagttgt ggaagactgt acaaggaatt gatgaagttc 180
gatgatgtcg ctatacggta ctatggtatt gataaaatta atgagattgt cgaagctatg 240
agcgaaggag accactacat caattttaca aaagtccatg atcaggaaag tttattcgct 300
accataggaa tatgtgctaa aatcactgaa cattggggat acaaaaagat ttcagaatct 360
agattccaat cattgggaaa cattacagat ctgatgaccg acgataatat aaacatcttg 420
atactttttc tagaaaaaaa attgaattga 450

<210> SEQ ID NO 34
<211> LENGTH: 354
<212> TYPE: DNA
<213> ORGANISM: Vaccinia virus

<400> SEQUENCE: 34
atgaggactc tacttattag atatattctt tggagaaatg acaacgatca aacctattat 60
aatgatgatt ttaaaaagct tatgttgttg gatgaattgg tagatgacgg cgatgtatgt 120
acattgatta agaacatgag aatgacgctg tccgacggtc cattgctaga tagattgaat 180
caaccagtta ataatataga agacgctaag cgaatgatcg ctattagtgc caaagtggct 240
agagacattg gtgaacgttc agaaattaga tgggaagagt cattcaccat actctttagg 300
atgattgaaa catattttga tgatctaatg attgatctat atggtgaaaa ataa 354

<210> SEQ ID NO 35
<211> LENGTH: 572
<212> TYPE: DNA
<213> ORGANISM: Vaccinia virus

<400> SEQUENCE: 35
atggacataa agatagatat tagtatttct ggtgataaat ttacggtgac tactaggagg 60
gaaaatgaag aaagaaaaaa atatctacct ctccaaaaag aaaaaactac tgatgttatc 120
aaacctgatt atcttgagta cgatgacttg tagatagaga tgagatgttt actattctag 180
aggaatattt tatgtacaga ggtctattag gcctcagaat aaaatatgga cgactcttta 240
acgaaattaa aaaattcgac aatgatgcgg aagaacaatt cggtactata gaagaactca 300
agcagaaact tagattaaat tctgaagagg gagcagataa ctttatagat tatataaagg 360
tacaaaaaca ggatatcgtc aaacttactg tatacgattg catatctatg ataggattgt 420
gtgcatgcgt ggtagatgtt tggagaaatg agaaactgtt ttctagatgg aaatattgtt 480
tacgagctat taaactgttt attaatgatc acatgcttga taagataaaa tctatactgc 540
agaatagact agtatatgtg gaaatgtcat ag 572

<210> SEQ ID NO 36
<211> LENGTH: 509
<212> TYPE: PRT
<213> ORGANISM: Homo sapiens

<400> SEQUENCE: 36

Met Gly Val Leu Lys Phe Lys His Ile Phe Phe Arg Ser Phe Val Lys
1               5                   10                  15

Ser Ser Gly Val Ser Gln Ile Val Phe Thr Phe Leu Leu Ile Pro Cys
            20                  25                  30

Cys Leu Thr Leu Asn Phe Arg Ala Pro Pro Val Ile Pro Asn Val Pro
        35                  40                  45

Phe Leu Trp Ala Trp Asn Ala Pro Ser Glu Phe Cys Leu Gly Lys Phe
    50                  55                  60

Asp Glu Pro Leu Asp Met Ser Leu Phe Ser Phe Ile Gly Ser Pro Arg
65                  70                  75                  80

Ile Asn Ala Thr Gly Gln Gly Val Thr Ile Phe Tyr Val Asp Arg Leu
                85                  90                  95

Gly Tyr Tyr Pro Tyr Ile Asp Ser Ile Thr Gly Val Thr Val Asn Gly
            100                 105                 110

Gly Ile Pro Gln Lys Ile Ser Leu Gln Asp His Leu Asp Lys Ala Lys
        115                 120                 125

Lys Asp Ile Thr Phe Tyr Met Pro Val Asp Asn Leu Gly Met Ala Val
    130                 135                 140

Ile Asp Trp Glu Glu Trp Arg Pro Thr Trp Ala Arg Asn Trp Lys Pro
145                 150                 155                 160

Lys Asp Val Tyr Lys Asn Arg Ser Ile Glu Leu Val Gln Gln Gln Asn
                165                 170                 175

Val Gln Leu Ser Leu Thr Glu Ala Thr Glu Lys Ala Lys Gln Glu Phe
            180                 185                 190

Glu Lys Ala Gly Lys Asp Phe Leu Val Glu Thr Ile Lys Leu Gly Lys
        195                 200                 205

Leu Leu Arg Pro Asn His Leu Trp Gly Tyr Tyr Leu Phe Pro Asp Cys
    210                 215                 220

Tyr Asn His His Tyr Lys Lys Pro Gly Tyr Asn Gly Ser Cys Phe Asn
225                 230                 235                 240

Val Glu Ile Lys Arg Asn Asp Asp Leu Ser Trp Leu Trp Asn Glu Ser
                245                 250                 255

Thr Ala Leu Tyr Pro Ser Ile Tyr Leu Asn Thr Gln Gln Ser Pro Val
            260                 265                 270

Ala Ala Thr Leu Tyr Val Arg Asn Arg Val Arg Glu Ala Ile Arg Val
        275                 280                 285

Ser Lys Ile Pro Asp Ala Lys Ser Pro Leu Pro Val Phe Ala Tyr Thr
    290                 295                 300

Arg Ile Val Phe Thr Asp Gln Val Leu Lys Phe Leu Ser Gln Asp Glu
305                 310                 315                 320

Leu Val Tyr Thr Phe Gly Glu Thr Val Ala Leu Gly Ala Ser Gly Ile
                325                 330                 335

Val Ile Trp Gly Thr Leu Ser Ile Met Arg Ser Met Lys Ser Cys Leu
            340                 345                 350

Leu Leu Asp Asn Tyr Met Glu Thr Ile Leu Asn Pro Tyr Ile Ile Asn
        355                 360                 365

Val Thr Leu Ala Ala Lys Met Cys Ser Gln Val Leu Cys Gln Glu Gln
    370                 375                 380

Gly Val Cys Ile Arg Lys Asn Trp Asn Ser Ser Asp Tyr Leu His Leu
385                 390                 395                 400

Asn Pro Asp Asn Phe Ala Ile Gln Leu Glu Lys Gly Gly Lys Phe Thr

-continued

```
                405                 410                 415

Val Arg Gly Lys Pro Thr Leu Glu Asp Leu Glu Gln Phe Ser Glu Lys
            420                 425                 430

Phe Tyr Cys Ser Cys Tyr Ser Thr Leu Ser Cys Lys Glu Lys Ala Asp
        435                 440                 445

Val Lys Asp Thr Asp Ala Val Asp Val Cys Ile Ala Asp Gly Val Cys
    450                 455                 460

Ile Asp Ala Phe Leu Lys Pro Pro Met Glu Thr Glu Glu Pro Gln Ile
465                 470                 475                 480

Phe Tyr Asn Ala Ser Pro Ser Thr Leu Ser Ala Thr Met Phe Ile Val
                485                 490                 495

Ser Ile Leu Phe Leu Ile Ile Ser Ser Val Ala Ser Leu
            500                 505


<210> SEQ ID NO 37
<211> LENGTH: 450
<212> TYPE: PRT
<213> ORGANISM: Bos taurus

<400> SEQUENCE: 37

Met Arg Pro Phe Ser Leu Glu Val Ser Leu His Leu Pro Trp Ala Met
1               5                   10                  15

Ala Ala His Leu Leu Pro Val Cys Thr Leu Phe Leu Asn Leu Leu Ser
            20                  25                  30

Met Thr Gln Gly Ser Arg Asp Pro Val Val Pro Asn Gln Pro Phe Thr
        35                  40                  45

Thr Ile Trp Asn Ala Asn Thr Glu Trp Cys Met Lys Lys His Gly Val
    50                  55                  60

Asp Val Asp Ile Ser Ile Phe Asp Val Val Thr Asn Pro Gly Gln Thr
65                  70                  75                  80

Phe Arg Gly Pro Asn Met Thr Ile Phe Tyr Ser Ser Gln Leu Gly Thr
                85                  90                  95

Tyr Pro Tyr Tyr Thr Ser Ala Gly Glu Pro Val Phe Gly Gly Leu Pro
            100                 105                 110

Gln Asn Ala Ser Leu Asn Ala His Leu Ala Arg Thr Phe Gln Asp Ile
        115                 120                 125

Leu Ala Ala Met Pro Glu Pro Arg Phe Ser Gly Leu Ala Val Ile Asp
    130                 135                 140

Trp Glu Ala Trp Arg Pro Arg Trp Ala Phe Asn Trp Asp Thr Lys Asp
145                 150                 155                 160

Ile Tyr Arg Gln Arg Ser Arg Ala Leu Val Gln Lys Gln His Pro Asp
                165                 170                 175

Trp Leu Ala Pro Arg Val Glu Ala Ala Ala Gln Asp Gln Phe Glu Gly
            180                 185                 190

Ala Ala Glu Glu Trp Met Ala Gly Thr Leu Lys Leu Gly Gln Ala Leu
        195                 200                 205

Arg Pro Gln Gly Leu Trp Gly Phe Tyr Asn Phe Pro Glu Cys Tyr Asn
    210                 215                 220

Tyr Asp Phe Lys Ser Pro Asn Tyr Thr Gly Arg Cys Pro Leu Asn Ile
225                 230                 235                 240

Cys Ala Gln Asn Asp Gln Leu Gly Trp Leu Trp Gly Gln Ser Arg Ala
                245                 250                 255

Leu Tyr Pro Ser Ile Tyr Leu Pro Ala Ala Leu Glu Gly Thr Lys Lys
            260                 265                 270
```

```
Thr Gln Met Phe Val Gln His Arg Val Ala Glu Ala Phe Arg Val Ala
        275                 280                 285

Ala Gly Ala Gly Asp Pro Lys Leu Pro Val Leu Pro Tyr Met Gln Leu
    290                 295                 300

Phe Tyr Asp Met Thr Asn His Phe Leu Pro Ala Glu Glu Leu Glu His
305                 310                 315                 320

Ser Leu Gly Glu Ser Ala Ala Gln Gly Ala Ala Gly Val Val Leu Trp
                325                 330                 335

Val Ser Trp Leu Ser Thr Ser Thr Lys Glu Ser Cys Gln Ala Ile Lys
            340                 345                 350

Glu Tyr Val Asp Thr Thr Leu Gly Pro Ser Ile Leu Asn Val Thr Ser
        355                 360                 365

Gly Ala Arg Leu Cys Ser Gln Val Leu Cys Ser Gly His Gly Arg Cys
    370                 375                 380

Ala Arg Arg Pro Ser Tyr Pro Lys Ala Arg Leu Ile Leu Asn Ser Thr
385                 390                 395                 400

Ser Phe Ser Ile Lys Pro Thr Pro Gly Gly Gly Pro Leu Thr Leu Gln
                405                 410                 415

Gly Ala Leu Ser Leu Glu Asp Arg Leu Arg Met Ala Val Glu Phe Glu
            420                 425                 430

Cys Arg Cys Tyr Arg Gly Trp Arg Gly Thr Arg Cys Glu Gln Trp Gly
        435                 440                 445

Met Trp
    450


<210> SEQ ID NO 38
<211> LENGTH: 553
<212> TYPE: PRT
<213> ORGANISM: Bos taurus

<400> SEQUENCE: 38

Met Arg Met Leu Arg Arg His His Ile Ser Phe Arg Ser Phe Ala Gly
1               5                   10                  15

Ser Ser Gly Thr Pro Gln Ala Val Phe Thr Phe Leu Leu Leu Pro Cys
            20                  25                  30

Cys Leu Ala Leu Asp Phe Arg Ala Pro Pro Leu Ile Ser Asn Thr Ser
        35                  40                  45

Phe Leu Trp Ala Trp Asn Ala Pro Val Glu Arg Cys Val Asn Arg Arg
    50                  55                  60

Phe Gln Leu Pro Pro Asp Leu Arg Leu Phe Ser Val Lys Gly Ser Pro
65                  70                  75                  80

Gln Lys Ser Ala Thr Gly Gln Phe Ile Thr Leu Phe Tyr Ala Asp Arg
                85                  90                  95

Leu Gly Tyr Tyr Pro His Ile Asp Glu Lys Thr Gly Lys Thr Val Phe
            100                 105                 110

Gly Gly Ile Pro Gln Leu Gly Asn Leu Lys Ser His Met Glu Lys Ala
        115                 120                 125

Lys Asn Asp Ile Ala Tyr Tyr Ile Pro Asn Asp Ser Val Gly Leu Ala
    130                 135                 140

Val Ile Asp Trp Glu Asn Trp Arg Pro Thr Trp Ala Arg Asn Trp Lys
145                 150                 155                 160

Pro Lys Asp Val Tyr Arg Asp Glu Ser Val Glu Leu Val Leu Gln Lys
                165                 170                 175

Asn Pro Gln Leu Ser Phe Pro Glu Ala Ser Lys Ile Ala Lys Val Asp
            180                 185                 190
```

```
Phe Glu Thr Ala Gly Lys Ser Phe Met Gln Glu Thr Leu Lys Leu Gly
        195                 200                 205

Lys Leu Leu Arg Pro Asn His Leu Trp Gly Tyr Tyr Leu Phe Pro Asp
    210                 215                 220

Cys Tyr Asn His Asn His Asn Gln Pro Thr Tyr Asn Gly Asn Cys Pro
225                 230                 235                 240

Asp Val Glu Lys Arg Arg Asn Asp Asp Leu Glu Trp Leu Trp Lys Glu
                245                 250                 255

Ser Thr Ala Leu Phe Pro Ser Val Tyr Leu Asn Ile Arg Leu Lys Ser
            260                 265                 270

Thr Gln Asn Ala Ala Leu Tyr Val Arg Asn Arg Val Gln Glu Ala Ile
        275                 280                 285

Arg Leu Ser Lys Ile Ala Ser Val Glu Ser Pro Leu Pro Val Phe Val
    290                 295                 300

Tyr Ala Arg Pro Val Phe Thr Asp Gly Ser Ser Thr Tyr Leu Ser Gln
305                 310                 315                 320

Gly Asp Leu Val Asn Ser Val Gly Glu Ile Val Ser Leu Gly Ala Ser
                325                 330                 335

Gly Ile Ile Met Trp Gly Ser Leu Asn Leu Ser Leu Ser Met Gln Ser
            340                 345                 350

Cys Met Asn Leu Gly Thr Tyr Leu Asn Thr Thr Leu Asn Pro Tyr Ile
        355                 360                 365

Ile Asn Val Thr Leu Ala Ala Lys Met Cys Ser Gln Val Leu Cys His
    370                 375                 380

Asn Glu Gly Val Cys Thr Arg Lys His Trp Asn Ser Ser Asp Tyr Leu
385                 390                 395                 400

His Leu Asn Pro Met Asn Phe Ala Ile Gln Thr Gly Glu Gly Gly Lys
                405                 410                 415

Tyr Thr Val Pro Gly Thr Val Thr Leu Glu Asp Leu Gln Lys Phe Ser
            420                 425                 430

Asp Thr Phe Tyr Cys Ser Cys Tyr Ala Asn Ile His Cys Lys Lys Arg
        435                 440                 445

Val Asp Ile Lys Asn Val His Ser Val Asn Val Cys Met Ala Glu Asp
    450                 455                 460

Ile Cys Ile Asp Ser Pro Val Lys Leu Gln Pro Ser Asp His Ser Ser
465                 470                 475                 480

Ser Gln Glu Ala Ser Thr Thr Thr Phe Ser Ser Ile Ser Pro Ser Thr
                485                 490                 495

Thr Thr Ala Thr Val Ser Pro Cys Thr Pro Glu Lys His Ser Pro Glu
            500                 505                 510

Cys Leu Lys Val Arg Cys Ser Glu Val Ile Pro Asn Val Thr Gln Lys
        515                 520                 525

Ala Cys Gln Ser Val Lys Leu Lys Asn Ile Ser Tyr Gln Ser Pro Ile
    530                 535                 540

Gln Asn Ile Lys Asn Gln Thr Thr Tyr
545                 550
```

<210> SEQ ID NO 39
<211> LENGTH: 474
<212> TYPE: PRT
<213> ORGANISM: Bos taurus

<400> SEQUENCE: 39

```
Met Gly Met Phe Arg Arg His His Ile Ser Phe Arg Ser Phe Ala Gly
```

-continued

```
1               5                   10                  15

Ser Ser Gly Thr Pro Gln Ala Val Phe Thr Phe Leu Leu Leu Pro Cys
            20                  25                  30

Cys Leu Ala Leu Asp Phe Arg Ala Pro Pro Leu Ile Ser Asn Thr Ser
        35                  40                  45

Phe Leu Trp Ala Trp Asn Ala Pro Val Glu Arg Cys Val Asn Arg Arg
    50                  55                  60

Phe Gln Leu Pro Pro Asp Leu Arg Leu Phe Ser Val Lys Gly Ser Pro
65                  70                  75                  80

Gln Lys Ser Ala Thr Gly Gln Phe Ile Thr Leu Phe Tyr Ala Asp Arg
                85                  90                  95

Leu Gly Tyr Tyr Pro His Ile Asp Glu Lys Thr Gly Lys Thr Val Phe
            100                 105                 110

Gly Gly Ile Pro Gln Leu Gly Asn Leu Lys Ser His Leu Glu Lys Ala
        115                 120                 125

Lys Asn Asp Ile Ala Tyr Tyr Ile Pro Asn Asp Ser Val Gly Leu Ala
    130                 135                 140

Val Ile Asp Trp Glu Asn Trp Arg Pro Thr Trp Ala Arg Asn Trp Lys
145                 150                 155                 160

Pro Lys Asp Val Tyr Arg Asp Glu Ser Val Glu Leu Val Leu Gln Lys
                165                 170                 175

Asn Pro Gln Leu Ser Phe Pro Glu Ala Ser Lys Ile Ala Lys Val Asp
            180                 185                 190

Phe Glu Thr Ala Gly Lys Ser Phe Met Gln Glu Thr Leu Lys Leu Gly
        195                 200                 205

Lys Leu Leu Arg Pro Asn His Leu Trp Gly Tyr Tyr Leu Phe Pro Asp
    210                 215                 220

Cys Tyr Asn His Asn His Asn Gln Pro Thr Tyr Asn Gly Asn Cys Pro
225                 230                 235                 240

Asp Val Glu Lys Arg Arg Asn Asp Asp Leu Glu Trp Leu Trp Lys Glu
                245                 250                 255

Ser Thr Ala Leu Phe Pro Ser Val Tyr Leu Asn Ile Arg Leu Lys Ser
            260                 265                 270

Thr Gln Asn Ala Ala Leu Tyr Val Arg Asn Arg Val Gln Glu Ala Ile
        275                 280                 285

Arg Leu Ser Lys Ile Ala Ser Val Glu Ser Pro Leu Pro Val Phe Val
    290                 295                 300

Tyr Ala Arg Pro Val Phe Thr Asp Gly Ser Ser Thr Tyr Leu Ser Gln
305                 310                 315                 320

Gly Asp Leu Val Asn Ser Val Gly Glu Ile Val Ser Leu Gly Ala Ser
                325                 330                 335

Gly Ile Ile Met Trp Gly Ser Leu Asn Leu Ser Leu Ser Val Gln Ser
            340                 345                 350

Cys Met Asn Leu Gly Thr Tyr Leu Asn Thr Thr Leu Asn Pro Tyr Ile
        355                 360                 365

Ile Asn Val Thr Leu Ala Ala Lys Met Cys Ser Gln Val Leu Cys His
    370                 375                 380

Asp Gly Gly Val Cys Thr Arg Lys His Trp Asn Ser Ser Asp Tyr Leu
385                 390                 395                 400

His Leu Asn Pro Met Asn Phe Ala Ile Gln Thr Gly Glu Gly Gly Lys
                405                 410                 415

Tyr Thr Val Pro Gly Thr Leu Thr Leu Glu Asp Leu Gln Lys Phe Ser
            420                 425                 430
```

```
Asp Thr Phe Tyr Cys Ser Cys Tyr Ser Asn Leu Ser Cys Lys Lys Arg
        435                 440                 445

Val Asp Ile Lys Asn Val His Ser Val Asp Val Cys Met Ala Glu Asp
    450                 455                 460

Val Cys Ile Asp Ala Phe Leu Lys Pro Pro
465                 470


<210> SEQ ID NO 40
<211> LENGTH: 331
<212> TYPE: PRT
<213> ORGANISM: Vespula vulgaris

<400> SEQUENCE: 40

Ser Glu Arg Pro Lys Arg Val Phe Asn Ile Tyr Trp Asn Val Pro Thr
1               5                   10                  15

Phe Met Cys His Gln Tyr Asp Leu Tyr Phe Asp Glu Val Thr Asn Phe
            20                  25                  30

Asn Ile Lys Arg Asn Ser Lys Asp Asp Phe Gln Gly Asp Lys Ile Ala
        35                  40                  45

Ile Phe Tyr Asp Pro Gly Glu Phe Pro Ala Leu Leu Ser Leu Lys Asp
    50                  55                  60

Gly Lys Tyr Lys Lys Arg Asn Gly Gly Val Pro Gln Glu Gly Asn Ile
65                  70                  75                  80

Thr Ile His Leu Gln Lys Phe Ile Glu Asn Leu Asp Lys Ile Tyr Pro
                85                  90                  95

Asn Arg Asn Phe Ser Gly Ile Gly Val Ile Asp Phe Glu Arg Trp Arg
            100                 105                 110

Pro Ile Phe Arg Gln Asn Trp Gly Asn Met Lys Ile His Lys Asn Phe
        115                 120                 125

Ser Ile Asp Leu Val Arg Asn Glu His Pro Thr Trp Asn Lys Lys Met
    130                 135                 140

Ile Glu Leu Glu Ala Ser Lys Arg Phe Glu Lys Tyr Ala Arg Phe Phe
145                 150                 155                 160

Met Glu Glu Thr Leu Lys Leu Ala Lys Lys Thr Arg Lys Gln Ala Asp
                165                 170                 175

Trp Gly Tyr Tyr Gly Tyr Pro Tyr Cys Phe Asn Met Ser Pro Asn Asn
            180                 185                 190

Leu Val Pro Glu Cys Asp Val Thr Ala Met His Glu Asn Asp Lys Met
        195                 200                 205

Ser Trp Leu Phe Asn Asn Gln Asn Val Leu Leu Pro Ser Val Tyr Val
    210                 215                 220

Arg Gln Glu Leu Thr Pro Asp Gln Arg Ile Gly Leu Val Gln Gly Arg
225                 230                 235                 240

Val Lys Glu Ala Val Arg Ile Ser Asn Asn Leu Lys His Ser Pro Lys
                245                 250                 255

Val Leu Ser Tyr Trp Trp Tyr Val Tyr Gln Asp Glu Thr Asn Thr Phe
            260                 265                 270

Leu Thr Glu Thr Asp Val Lys Lys Thr Phe Gln Glu Ile Val Ile Asn
        275                 280                 285

Gly Gly Asp Gly Ile Ile Ile Trp Gly Ser Ser Ser Asp Val Asn Ser
    290                 295                 300

Leu Ser Lys Cys Lys Arg Leu Gln Asp Tyr Leu Leu Thr Val Leu Gly
305                 310                 315                 320

Pro Ile Ala Ile Asn Val Thr Glu Ala Val Asn
```

325 330

<210> SEQ ID NO 41
<211> LENGTH: 340
<212> TYPE: PRT
<213> ORGANISM: Vespula vulgaris

<400> SEQUENCE: 41

Asp Arg Thr Ile Trp Pro Lys Lys Gly Phe Ser Ile Tyr Trp Asn Ile
1 5 10 15

Pro Thr His Phe Cys His Asn Phe Gly Val Tyr Phe Lys Glu Leu Lys
20 25 30

Gln Phe Asn Ile Lys Tyr Asn Ser Met Asn Asn Phe Arg Gly Glu Thr
35 40 45

Ile Ser Leu Phe Tyr Asp Pro Gly Asn Phe Pro Ser Met Val Leu Leu
50 55 60

Lys Asn Gly Thr Tyr Glu Ile Arg Asn Glu Gly Val Pro Gln Lys Gly
65 70 75 80

Asn Leu Thr Ile His Leu Glu Gln Phe Thr Lys Glu Leu Asp Glu Ile
85 90 95

Tyr Pro Lys Lys Ile Ala Gly Gly Ile Gly Val Ile His Phe His Asn
100 105 110

Trp Arg Pro Ile Phe Arg Arg Asn Val Asp Asn Leu Lys Ile Asn Lys
115 120 125

Asp Ile Ser Ile Asp Leu Val Arg Lys Glu His Pro Lys Trp Asp Lys
130 135 140

Ser Met Ile Glu Lys Glu Ala Ser Asn Arg Phe Glu Thr Ser Ala Lys
145 150 155 160

Ile Phe Met Glu Lys Thr Leu Lys Leu Ala Lys Glu Ile Arg Lys Lys
165 170 175

Thr Glu Trp Gly Tyr His Gly Tyr Pro His Cys Leu Ser Gly Ser Thr
180 185 190

Asp Lys Pro Ser Phe Asp Cys Asp Ala Leu Ser Met Ser Glu Asn Asp
195 200 205

Lys Met Ser Trp Leu Phe Asn Asn Gln Asn Val Leu Leu Pro Ser Ile
210 215 220

Tyr Leu Lys Asn Val Leu Lys Pro Asp Glu Lys Ile His Leu Val Gln
225 230 235 240

Glu Arg Leu Lys Glu Ala Ile Arg Ile Ser Lys Asn Phe Lys His Leu
245 250 255

Pro Lys Val Leu Pro Tyr Trp Trp Tyr Thr Tyr Gln Asp Lys Glu Ser
260 265 270

Ile Phe Leu Thr Glu Ala Asp Val Lys Asn Thr Phe Lys Glu Ile Leu
275 280 285

Thr Asn Gly Ala Asp Gly Ile Ile Ile Trp Gly Val Ser Tyr Glu Leu
290 295 300

Thr Asp Arg Lys Arg Cys Glu Lys Leu Lys Glu Tyr Leu Met Lys Ile
305 310 315 320

Leu Gly Pro Ile Ala Phe Lys Val Thr Lys Ala Val Lys Glu Asn Thr
325 330 335

Pro Leu Asn Phe
340

<210> SEQ ID NO 42
<211> LENGTH: 382

<212> TYPE: PRT
<213> ORGANISM: Apis mellifera

<400> SEQUENCE: 42

```
Met Ser Arg Pro Leu Val Ile Thr Glu Gly Met Met Ile Gly Val Leu
1               5                   10                  15

Leu Met Leu Ala Pro Ile Asn Ala Leu Leu Leu Gly Phe Val Gln Ser
            20                  25                  30

Thr Pro Asp Asn Asn Lys Thr Val Arg Glu Phe Asn Val Tyr Trp Asn
        35                  40                  45

Val Pro Thr Phe Met Cys His Lys Tyr Gly Leu Arg Phe Glu Glu Val
    50                  55                  60

Ser Glu Lys Tyr Gly Ile Leu Gln Asn Trp Met Asp Lys Phe Arg Gly
65                  70                  75                  80

Glu Glu Ile Ala Ile Leu Tyr Asp Pro Gly Met Phe Pro Ala Leu Leu
                85                  90                  95

Lys Asp Pro Asn Gly Asn Val Val Ala Arg Asn Gly Gly Val Pro Gln
            100                 105                 110

Leu Gly Asn Leu Thr Lys His Leu Gln Val Phe Arg Asp His Leu Ile
        115                 120                 125

Asn Gln Ile Pro Asp Lys Ser Phe Pro Gly Val Gly Val Ile Asp Phe
    130                 135                 140

Glu Ser Trp Arg Pro Ile Phe Arg Gln Asn Trp Ala Ser Leu Gln Pro
145                 150                 155                 160

Tyr Lys Lys Leu Ser Val Glu Val Val Arg Arg Glu His Pro Phe Trp
                165                 170                 175

Asp Asp Gln Arg Val Glu Gln Glu Ala Lys Arg Arg Phe Glu Lys Tyr
            180                 185                 190

Gly Gln Leu Phe Met Glu Glu Thr Leu Lys Ala Ala Lys Arg Met Arg
        195                 200                 205

Pro Ala Ala Asn Trp Gly Tyr Tyr Ala Tyr Pro Tyr Cys Tyr Asn Leu
    210                 215                 220

Thr Pro Asn Gln Pro Ser Ala Gln Cys Glu Ala Thr Thr Met Gln Glu
225                 230                 235                 240

Asn Asp Lys Met Ser Trp Leu Phe Glu Ser Glu Asp Val Leu Leu Pro
                245                 250                 255

Ser Val Tyr Leu Arg Trp Asn Leu Thr Ser Gly Glu Arg Val Gly Leu
            260                 265                 270

Val Gly Gly Arg Val Lys Glu Ala Leu Arg Ile Ala Arg Gln Met Thr
        275                 280                 285

Thr Ser Arg Lys Lys Val Leu Pro Tyr Tyr Trp Tyr Lys Tyr Gln Asp
    290                 295                 300

Arg Arg Asp Thr Asp Leu Ser Arg Ala Asp Leu Glu Ala Thr Leu Arg
305                 310                 315                 320

Lys Ile Thr Asp Leu Gly Ala Asp Gly Phe Ile Ile Trp Gly Ser Ser
                325                 330                 335

Asp Asp Ile Asn Thr Lys Ala Lys Cys Leu Gln Phe Arg Glu Tyr Leu
            340                 345                 350

Asn Asn Glu Leu Gly Pro Ala Val Lys Arg Ile Ala Leu Asn Asn Asn
        355                 360                 365

Ala Asn Asp Arg Leu Thr Val Asp Val Ser Val Asp Gln Val
    370                 375                 380
```

<210> SEQ ID NO 43

<211> LENGTH: 331
<212> TYPE: PRT
<213> ORGANISM: Dolichovespula maculata

<400> SEQUENCE: 43

Ser Glu Arg Pro Lys Arg Val Phe Asn Ile Tyr Trp Asn Val Pro Thr
1 5 10 15

Phe Met Cys His Gln Tyr Gly Leu Tyr Phe Asp Glu Val Thr Asn Phe
20 25 30

Asn Ile Lys His Asn Ser Lys Asp Asp Phe Gln Gly Asp Lys Ile Ser
35 40 45

Ile Phe Tyr Asp Pro Gly Glu Phe Pro Ala Leu Leu Pro Leu Lys Glu
50 55 60

Gly Asn Tyr Lys Ile Arg Asn Gly Gly Val Pro Gln Glu Gly Asn Ile
65 70 75 80

Thr Ile His Leu Gln Arg Phe Ile Glu Asn Leu Asp Lys Thr Tyr Pro
85 90 95

Asn Arg Asn Phe Asn Gly Ile Gly Val Ile Asp Phe Glu Arg Trp Arg
100 105 110

Pro Ile Phe Arg Gln Asn Trp Gly Asn Met Met Ile His Lys Lys Phe
115 120 125

Ser Ile Asp Leu Val Arg Asn Glu His Pro Phe Trp Asp Lys Lys Met
130 135 140

Ile Glu Leu Glu Ala Ser Lys Arg Phe Glu Lys Tyr Ala Arg Leu Phe
145 150 155 160

Met Glu Glu Thr Leu Lys Leu Ala Lys Lys Thr Arg Lys Gln Ala Asp
165 170 175

Trp Gly Tyr Tyr Gly Tyr Pro Tyr Cys Phe Asn Met Ser Pro Asn Asn
180 185 190

Leu Val Pro Asp Cys Asp Ala Thr Ala Met Leu Glu Asn Asp Lys Met
195 200 205

Ser Trp Leu Phe Asn Asn Gln Asn Val Leu Leu Pro Ser Val Tyr Ile
210 215 220

Arg His Glu Leu Thr Pro Asp Gln Arg Val Gly Leu Val Gln Gly Arg
225 230 235 240

Val Lys Glu Ala Val Arg Ile Ser Asn Asn Leu Lys His Ser Pro Lys
245 250 255

Val Leu Ser Tyr Trp Trp Tyr Val Tyr Gln Asp Asp Thr Asn Thr Phe
260 265 270

Leu Thr Glu Thr Asp Val Lys Lys Thr Phe Gln Glu Ile Ala Ile Asn
275 280 285

Gly Gly Asp Gly Ile Ile Ile Trp Gly Ser Ser Ser Asp Val Asn Ser
290 295 300

Leu Ser Lys Cys Lys Arg Leu Arg Glu Tyr Leu Leu Thr Val Leu Gly
305 310 315 320

Pro Ile Thr Val Asn Val Thr Glu Thr Val Asn
325 330

<210> SEQ ID NO 44
<211> LENGTH: 367
<212> TYPE: PRT
<213> ORGANISM: Polistes annularis

<400> SEQUENCE: 44

Tyr Val Ser Leu Ser Pro Asp Ser Val Phe Asn Ile Ile Thr Asp Asp
1 5 10 15

```
Ile Ser His Gln Ile Leu Ser Arg Ser Asn Cys Glu Arg Ser Lys Arg
            20                  25                  30

Pro Lys Arg Val Phe Ser Ile Tyr Trp Asn Val Pro Thr Phe Met Cys
        35                  40                  45

His Gln Tyr Gly Met Asn Phe Asp Glu Val Thr Asp Phe Asn Ile Lys
    50                  55                  60

His Asn Ser Lys Asp Asn Phe Arg Gly Glu Thr Ile Ser Ile Tyr Tyr
65                  70                  75                  80

Asp Pro Gly Lys Phe Pro Ala Leu Met Pro Leu Lys Asn Gly Asn Tyr
                85                  90                  95

Glu Glu Arg Asn Gly Gly Val Pro Gln Arg Gly Asn Ile Thr Ile His
            100                 105                 110

Leu Gln Gln Phe Asn Glu Asp Leu Asp Lys Met Thr Pro Asp Lys Asn
        115                 120                 125

Phe Gly Gly Ile Gly Val Ile Asp Phe Glu Arg Trp Lys Pro Ile Phe
    130                 135                 140

Arg Gln Asn Trp Gly Asn Thr Glu Ile His Lys Lys Tyr Ser Ile Glu
145                 150                 155                 160

Leu Val Arg Lys Glu His Pro Lys Trp Ser Glu Ser Met Ile Glu Ala
                165                 170                 175

Glu Ala Thr Lys Lys Phe Glu Lys Tyr Ala Arg Tyr Phe Met Glu Glu
            180                 185                 190

Thr Leu Lys Leu Ala Lys Lys Thr Arg Lys Arg Ala Lys Trp Gly Tyr
        195                 200                 205

Tyr Gly Phe Pro Tyr Cys Tyr Asn Val Thr Pro Asn Asn Pro Gly Pro
    210                 215                 220

Asp Cys Asp Ala Lys Ala Thr Ile Glu Asn Asp Arg Leu Ser Trp Met
225                 230                 235                 240

Tyr Asn Asn Gln Glu Ile Leu Phe Pro Ser Val Tyr Val Arg His Glu
                245                 250                 255

Gln Lys Pro Glu Glu Arg Val Tyr Leu Val Gln Gly Arg Ile Lys Glu
            260                 265                 270

Ala Val Arg Ile Ser Asn Asn Leu Glu His Ser Pro Ser Val Leu Ala
        275                 280                 285

Tyr Trp Trp Tyr Val Tyr Gln Asp Lys Met Asp Ile Tyr Leu Ser Glu
    290                 295                 300

Thr Asp Val Glu Lys Thr Phe Gln Glu Ile Val Thr Asn Gly Gly Asp
305                 310                 315                 320

Gly Ile Ile Ile Trp Gly Ser Ser Ser Asp Val Asn Ser Leu Ser Lys
                325                 330                 335

Cys Lys Arg Leu Arg Glu Tyr Leu Leu Asn Thr Leu Gly Pro Phe Ala
            340                 345                 350

Val Asn Val Thr Glu Thr Val Asn Gly Arg Ser Ser Leu Asn Phe
        355                 360                 365


<210> SEQ ID NO 45
<211> LENGTH: 473
<212> TYPE: PRT
<213> ORGANISM: Mus musculus

<400> SEQUENCE: 45

Met Arg Ala Gly Leu Gly Pro Ile Ile Thr Leu Ala Leu Val Leu Glu
1               5                   10                  15

Val Ala Trp Ala Gly Glu Leu Lys Pro Thr Ala Pro Pro Ile Phe Thr
```

-continued

```
            20                  25                  30

Gly Arg Pro Phe Val Val Ala Trp Asn Val Pro Thr Gln Glu Cys Ala
        35                  40                  45

Pro Arg His Lys Val Pro Leu Asp Leu Arg Ala Phe Asp Val Lys Ala
    50                  55                  60

Thr Pro Asn Glu Gly Phe Phe Asn Gln Asn Ile Thr Thr Phe Tyr Tyr
65                  70                  75                  80

Asp Arg Leu Gly Leu Tyr Pro Arg Phe Asp Ala Ala Gly Thr Ser Val
                85                  90                  95

His Gly Gly Val Pro Gln Asn Gly Ser Leu Cys Ala His Leu Pro Met
            100                 105                 110

Leu Lys Glu Ser Val Glu Arg Tyr Ile Gln Thr Gln Glu Pro Gly Gly
        115                 120                 125

Leu Ala Val Ile Asp Trp Glu Glu Trp Arg Pro Val Trp Val Arg Asn
    130                 135                 140

Trp Gln Glu Lys Asp Val Tyr Arg Gln Ser Ser Arg Gln Leu Val Ala
145                 150                 155                 160

Ser Arg His Pro Asp Trp Pro Ser Asp Arg Val Met Lys Gln Ala Gln
                165                 170                 175

Tyr Glu Phe Glu Phe Ala Ala Arg Gln Phe Met Leu Asn Thr Leu Arg
            180                 185                 190

Tyr Val Lys Ala Val Arg Pro Gln His Leu Trp Gly Phe Tyr Leu Phe
        195                 200                 205

Pro Asp Cys Tyr Asn His Asp Tyr Val Gln Asn Trp Glu Ser Tyr Thr
    210                 215                 220

Gly Arg Cys Pro Asp Val Glu Val Ala Arg Asn Asp Gln Leu Ala Trp
225                 230                 235                 240

Leu Trp Ala Glu Ser Thr Ala Leu Phe Pro Ser Val Tyr Leu Asp Glu
                245                 250                 255

Thr Leu Ala Ser Ser Val His Ser Arg Asn Phe Val Ser Phe Arg Val
            260                 265                 270

Arg Glu Ala Leu Arg Val Ala His Thr His His Ala Asn His Ala Leu
        275                 280                 285

Pro Val Tyr Val Phe Thr Arg Pro Thr Tyr Thr Arg Gly Leu Thr Gly
    290                 295                 300

Leu Ser Gln Val Asp Leu Ile Ser Thr Ile Gly Glu Ser Ala Ala Leu
305                 310                 315                 320

Gly Ser Ala Gly Val Ile Phe Trp Gly Asp Ser Glu Asp Ala Ser Ser
                325                 330                 335

Met Glu Thr Cys Gln Tyr Leu Lys Asn Tyr Leu Thr Gln Leu Leu Val
            340                 345                 350

Pro Tyr Ile Val Asn Val Ser Trp Ala Thr Gln Tyr Cys Ser Trp Thr
        355                 360                 365

Gln Cys His Gly His Gly Arg Cys Val Arg Arg Asn Pro Ser Ala Asn
    370                 375                 380

Thr Phe Leu His Leu Asn Ala Ser Ser Phe Arg Leu Val Pro Gly His
385                 390                 395                 400

Thr Pro Ser Glu Pro Gln Leu Arg Pro Glu Gly Gln Leu Ser Glu Ala
                405                 410                 415

Asp Leu Asn Tyr Leu Gln Lys His Phe Arg Cys Gln Cys Tyr Leu Gly
            420                 425                 430

Trp Gly Gly Glu Gln Cys Gln Arg Asn Tyr Lys Gly Ala Ala Gly Asn
        435                 440                 445
```

```
Ala Ser Arg Ala Trp Ala Gly Ser His Leu Thr Ser Leu Leu Gly Leu
    450                 455                 460

Val Ala Val Ala Leu Thr Trp Thr Leu
465                 470


<210> SEQ ID NO 46
<211> LENGTH: 473
<212> TYPE: PRT
<213> ORGANISM: Mus musculus

<400> SEQUENCE: 46

Met Arg Ala Gly Leu Gly Pro Ile Ile Thr Leu Ala Leu Val Leu Glu
1               5                   10                  15

Val Ala Trp Ala Gly Glu Leu Lys Pro Thr Ala Pro Pro Ile Phe Thr
            20                  25                  30

Gly Arg Pro Phe Val Val Ala Trp Asn Val Pro Thr Gln Glu Cys Ala
        35                  40                  45

Pro Arg His Lys Val Pro Leu Asp Leu Arg Ala Phe Asp Val Lys Ala
    50                  55                  60

Thr Pro Asn Glu Gly Phe Phe Asn Gln Asn Ile Thr Thr Phe Tyr Tyr
65                  70                  75                  80

Asp Arg Leu Gly Leu Tyr Pro Arg Phe Asp Ala Ala Gly Thr Ser Val
                85                  90                  95

His Gly Gly Val Pro Gln Asn Gly Ser Leu Cys Ala His Leu Pro Met
            100                 105                 110

Leu Lys Glu Ser Val Glu Arg Tyr Ile Gln Thr Gln Glu Pro Gly Gly
        115                 120                 125

Leu Ala Val Ile Asp Trp Glu Glu Trp Arg Pro Val Trp Val Arg Asn
    130                 135                 140

Trp Gln Glu Lys Asp Val Tyr Arg Gln Ser Ser Arg Gln Leu Val Ala
145                 150                 155                 160

Ser Arg His Pro Asp Trp Pro Ser Asp Arg Val Met Lys Gln Ala Gln
                165                 170                 175

Tyr Glu Phe Glu Phe Ala Ala Arg Gln Phe Met Leu Asn Thr Leu Arg
            180                 185                 190

Tyr Val Lys Ala Val Arg Pro Gln His Leu Trp Gly Phe Tyr Leu Phe
        195                 200                 205

Pro Asp Cys Tyr Asn His Asp Tyr Val Gln Asn Trp Glu Ser Tyr Thr
    210                 215                 220

Gly Arg Cys Pro Asp Val Glu Val Ala Arg Asn Asp Gln Leu Ala Trp
225                 230                 235                 240

Leu Trp Ala Glu Ser Thr Ala Leu Phe Pro Ser Val Tyr Leu Asp Glu
                245                 250                 255

Thr Leu Ala Ser Ser Val His Ser Arg Asn Phe Val Ser Phe Arg Val
            260                 265                 270

Arg Glu Ala Leu Arg Val Ala His Thr His His Ala Asn His Ala Leu
        275                 280                 285

Pro Val Tyr Val Phe Thr Arg Pro Thr Tyr Thr Arg Gly Leu Thr Gly
    290                 295                 300

Leu Ser Gln Val Asp Leu Ile Ser Thr Ile Gly Glu Ser Ala Ala Leu
305                 310                 315                 320

Gly Ser Ala Gly Val Ile Phe Trp Gly Asp Ser Glu Asp Ala Ser Ser
                325                 330                 335

Met Glu Thr Cys Gln Tyr Leu Lys Asn Tyr Leu Thr Gln Leu Leu Val
```

```
            340                 345                 350

Pro Tyr Ile Val Asn Val Ser Trp Ala Thr Gln Tyr Cys Ser Trp Thr
        355                 360                 365

Gln Cys His Gly His Gly Arg Cys Val Arg Arg Asn Pro Ser Ala Asn
    370                 375                 380

Thr Phe Leu His Leu Asn Ala Ser Ser Phe Arg Leu Val Pro Gly His
385                 390                 395                 400

Thr Pro Ser Glu Pro Gln Leu Arg Pro Glu Gly Gln Leu Ser Glu Ala
                405                 410                 415

Asp Leu Asn Tyr Leu Gln Lys His Phe Arg Cys Gln Cys Tyr Leu Gly
            420                 425                 430

Trp Gly Gly Glu Gln Cys Gln Arg Asn Tyr Lys Gly Ala Ala Gly Asn
        435                 440                 445

Ala Ser Arg Ala Trp Ala Gly Ser His Leu Thr Ser Leu Leu Gly Leu
    450                 455                 460

Val Ala Val Ala Leu Thr Trp Thr Leu
465                 470


<210> SEQ ID NO 47
<211> LENGTH: 412
<212> TYPE: PRT
<213> ORGANISM: Mus musculus

<400> SEQUENCE: 47

Met Ile Met His Leu Gly Leu Met Met Val Val Gly Leu Thr Leu Cys
1               5                   10                  15

Leu Met His Gly Gln Ala Leu Leu Gln Val Pro Glu His Pro Phe Ser
            20                  25                  30

Val Val Trp Asn Val Pro Ser Ala Arg Cys Lys Ala His Phe Gly Val
        35                  40                  45

His Leu Pro Leu Asp Ala Leu Gly Ile Val Ala Asn His Gly Gln His
    50                  55                  60

Phe His Gly Gln Asn Ile Ser Ile Phe Tyr Lys Asn Gln Phe Gly Leu
65                  70                  75                  80

Tyr Pro Tyr Phe Gly Pro Arg Gly Thr Ala His Asn Gly Gly Ile Pro
                85                  90                  95

Gln Ala Val Ser Leu Asp His His Leu Ala Arg Ala Ala His Gln Ile
            100                 105                 110

Leu His Ser Leu Gly Ser Ser Phe Ala Gly Leu Ala Val Leu Asp Trp
        115                 120                 125

Glu Glu Trp Tyr Pro Leu Trp Ala Gly Asn Trp Gly Pro His Arg Gln
    130                 135                 140

Val Tyr Leu Ala Ala Ser Trp Val Trp Thr Gln Gln Met Phe Pro Gly
145                 150                 155                 160

Leu Asp Pro Gln Glu Gln Leu His Lys Ala His Thr Ser Phe Glu Gln
                165                 170                 175

Ala Ala Arg Ala Leu Met Glu Tyr Thr Leu Gln Leu Gly Arg Thr Leu
            180                 185                 190

Arg Pro Ser Gly Leu Trp Gly Phe Tyr Arg Tyr Pro Ala Cys Gly Asn
        195                 200                 205

Gly Trp His Lys Met Ala Ser Asn Tyr Thr Gly His Cys His Ala Ala
    210                 215                 220

Ile Thr Thr Gln Asn Thr Gln Leu Arg Trp Leu Trp Ala Ala Ser Ser
225                 230                 235                 240
```

```
Ala Leu Phe Pro Ser Ile Tyr Leu Pro Pro Arg Leu Pro Leu Ala Tyr
                245                 250                 255

Arg Gln Ala Phe Val Arg His Arg Leu Glu Glu Ala Phe Arg Val Ala
            260                 265                 270

Leu Leu Glu His Ser His Pro Leu Pro Val Leu Ala Tyr Ser Arg Leu
        275                 280                 285

Thr His Arg Ser Ser Gly Arg Phe Leu Ser Leu Asp Asp Leu Met Gln
    290                 295                 300

Thr Ile Gly Val Ser Ala Ala Leu Gly Thr Ala Gly Val Val Leu Trp
305                 310                 315                 320

Gly Asp Leu Ser Phe Ser Ser Ser Glu Glu Lys Cys Trp Arg Leu His
                325                 330                 335

Asp Tyr Leu Val Gly Thr Leu Gly Pro Tyr Val Ile Asn Val Thr Lys
            340                 345                 350

Ala Asp Met Ala Cys Ser His Gln Arg Cys His Gly His Gly Arg Cys
        355                 360                 365

Ala Arg Lys Asp Pro Gly Gln Met Glu Ala Phe Leu His Leu Gln Pro
    370                 375                 380

Asp Asp Ser Leu Gly Ala Trp Asn Ser Phe Arg Cys His Cys Tyr Ser
385                 390                 395                 400

Gly Trp Ala Gly Pro Thr Cys Leu Glu Pro Lys Pro
                405                 410


<210> SEQ ID NO 48
<211> LENGTH: 512
<212> TYPE: PRT
<213> ORGANISM: Rattus norvegicus

<400> SEQUENCE: 48

Met Gly Glu Leu Gln Phe Lys Trp Leu Phe Trp Arg Ser Phe Ala Glu
1               5                   10                  15

Ser Gly Gly Thr Phe Gln Thr Val Leu Ile Phe Leu Phe Ile Pro Tyr
            20                  25                  30

Ser Leu Thr Val Asp Tyr Arg Ala Thr Pro Val Leu Ser Asp Thr Thr
        35                  40                  45

Phe Val Trp Val Trp Asn Val Pro Thr Glu Ala Cys Val Glu Asn Val
    50                  55                  60

Thr Glu Pro Ile Asp Leu Ser Phe Phe Ser Leu Ile Gly Ser Pro Arg
65                  70                  75                  80

Lys Thr Ala Ile Gly Gln Pro Val Thr Leu Phe Tyr Val Asp Arg Leu
                85                  90                  95

Gly Asn Tyr Pro His Ile Asp Ala Gln Gln Thr Glu His His Gly Gly
            100                 105                 110

Ile Pro Gln Lys Gly Asp Leu Thr Thr His Leu Val Lys Ala Lys Glu
        115                 120                 125

Asp Val Glu Arg Tyr Ile Pro Thr Asp Lys Leu Gly Leu Ala Ile Ile
    130                 135                 140

Asp Trp Glu Glu Trp Arg Pro Thr Trp Met Arg Asn Trp Thr Pro Lys
145                 150                 155                 160

Asp Ile Tyr Arg Asn Lys Ser Ile Glu Leu Val Gln Ala Ala Asp Pro
                165                 170                 175

Ala Ile Asn Ile Thr Glu Ala Thr Val Arg Ala Lys Ala Gln Phe Glu
            180                 185                 190

Gly Ala Ala Lys Glu Phe Met Glu Gly Thr Leu Lys Leu Gly Lys His
        195                 200                 205
```

```
Ile Arg Pro Lys His Leu Trp Gly Phe Tyr Leu Phe Pro Asp Cys Tyr
    210                 215                 220

Asn Asn Lys Phe Gln Val Asp Asn Tyr Asp Gly Gln Cys Pro Asp Val
225                 230                 235                 240

Glu Lys Lys Arg Asn Asp Asp Leu Asp Trp Leu Trp Lys Glu Ser Thr
                245                 250                 255

Gly Leu Tyr Pro Ser Val Tyr Leu Lys Lys Asp Leu Lys Ser Ser Arg
            260                 265                 270

Lys Ala Thr Leu Tyr Val Arg Tyr Arg Val Leu Glu Ser Ile Arg Val
        275                 280                 285

Ser Lys Val Ser Asp Glu Ser Asn Pro Val Pro Ile Phe Val Tyr Ile
    290                 295                 300

Arg Leu Val Phe Thr Asp His Val Ser Glu Tyr Leu Leu Glu Asp Asp
305                 310                 315                 320

Leu Val Asn Thr Ile Gly Glu Ile Val Ala Gln Gly Thr Ser Gly Ile
                325                 330                 335

Ile Ile Trp Asp Ala Met Ser Leu Ala Gln Arg Ser Ala Gly Cys Pro
            340                 345                 350

Ile Leu Arg Gln Tyr Met Lys Thr Thr Leu Asn Pro Tyr Ile Val Asn
        355                 360                 365

Val Thr Leu Ala Ala Lys Met Cys Ser Gln Thr Leu Cys Lys Glu Lys
    370                 375                 380

Gly Met Cys Ser Arg Lys Thr Glu Ser Ser Asp Ala Tyr Leu His Leu
385                 390                 395                 400

Asp Pro Ser Ser Phe Ser Ile Asn Val Thr Glu Ala Gly Lys Tyr Glu
                405                 410                 415

Val Leu Gly Lys Pro Glu Val Lys Asp Leu Glu Tyr Phe Ser Glu His
            420                 425                 430

Phe Lys Cys Ser Cys Phe Ser Lys Met Thr Cys Glu Glu Thr Ser Asp
        435                 440                 445

Met Arg Ser Ile Gln Asp Val Asn Val Cys Met Gly Asp Asn Val Cys
    450                 455                 460

Ile Lys Ala Thr Leu Gly Pro Asn Ser Ala Phe His Leu Leu Pro Gly
465                 470                 475                 480

Lys Gly Leu Leu Leu Met Thr Thr Leu Ala His Ile Leu His His Leu
                485                 490                 495

Pro His Asp Ile Phe Val Phe Pro Trp Lys Met Leu Val Ser Thr Pro
            500                 505                 510
```

<210> SEQ ID NO 49
<211> LENGTH: 435
<212> TYPE: PRT
<213> ORGANISM: Sus scrofa

<400> SEQUENCE: 49

```
Met Ala Ala His Leu Leu Pro Ile Cys Thr Leu Phe Leu Asn Leu Leu
1               5                   10                  15

Ser Val Ala Gln Gly Ser Arg Asp Pro Val Val Leu Asn Arg Pro Phe
            20                  25                  30

Thr Thr Ile Trp Asn Ala Asn Thr Gln Trp Cys Leu Lys Arg His Gly
        35                  40                  45

Val Asp Val Asp Val Ser Val Phe Glu Val Val Val Asn Pro Gly Gln
    50                  55                  60

Thr Phe Arg Gly Pro Asn Met Thr Ile Phe Tyr Ser Ser Gln Leu Gly
```

-continued

```
65                  70                  75                  80

Thr Tyr Pro Tyr Tyr Thr Ser Ala Gly Glu Pro Val Phe Gly Gly Leu
                85                  90                  95

Pro Gln Asn Ala Ser Leu Asp Val His Leu Asn Arg Thr Phe Lys Asp
            100                 105                 110

Ile Leu Ala Ala Met Pro Glu Ser Asn Phe Ser Gly Leu Ala Val Ile
        115                 120                 125

Asp Trp Glu Ala Trp Arg Pro Arg Trp Ala Phe Asn Trp Asp Ala Lys
    130                 135                 140

Asp Ile Tyr Arg Gln Arg Ser Arg Ala Leu Val Gln Lys Gln His Pro
145                 150                 155                 160

Asp Trp Pro Ala Pro Trp Val Glu Ala Ala Ala Gln Asp Gln Phe Gln
                165                 170                 175

Glu Ala Ala Gln Thr Trp Met Ala Gly Thr Leu Lys Leu Gly Gln Thr
            180                 185                 190

Leu Arg Pro His Gly Leu Trp Gly Phe Tyr Gly Phe Pro Asp Cys Tyr
        195                 200                 205

Asn Tyr Asp Phe Gln Ser Ser Asn Tyr Thr Gly Gln Cys Pro Pro Gly
    210                 215                 220

Val Ser Ala Gln Asn Asp Gln Leu Gly Trp Leu Trp Gly Gln Ser Arg
225                 230                 235                 240

Ala Leu Tyr Pro Ser Ile Tyr Leu Pro Ser Ala Leu Glu Gly Thr Asn
                245                 250                 255

Lys Thr Gln Leu Tyr Val Gln His Arg Val Asn Glu Ala Phe Arg Val
            260                 265                 270

Ala Ala Ala Ala Gly Asp Pro Asn Leu Pro Val Leu Pro Tyr Ala Gln
        275                 280                 285

Ile Phe His Asp Met Thr Asn Arg Leu Leu Ser Arg Glu Glu Leu Glu
    290                 295                 300

His Ser Leu Gly Glu Ser Ala Ala Gln Gly Ala Ala Gly Val Val Leu
305                 310                 315                 320

Trp Val Ser Trp Glu Asn Thr Arg Thr Lys Glu Ser Cys Gln Ser Ile
                325                 330                 335

Lys Glu Tyr Val Asp Thr Thr Leu Gly Pro Phe Ile Leu Asn Val Thr
            340                 345                 350

Ser Gly Ala Leu Leu Cys Ser Gln Ala Val Cys Ser Gly His Gly Arg
        355                 360                 365

Cys Val Arg Arg Pro Ser His Thr Glu Ala Leu Pro Ile Leu Asn Pro
    370                 375                 380

Ser Ser Phe Ser Ile Lys Pro Thr Pro Gly Gly Gly Pro Leu Thr Leu
385                 390                 395                 400

Gln Gly Ala Leu Ser Leu Lys Asp Arg Val Gln Met Ala Glu Glu Phe
                405                 410                 415

Gln Cys Arg Cys Tyr Pro Gly Trp Arg Gly Thr Trp Cys Glu Gln Gln
            420                 425                 430

Gly Thr Arg
        435
```

<210> SEQ ID NO 50
<211> LENGTH: 419
<212> TYPE: PRT
<213> ORGANISM: Sus scrofa

<400> SEQUENCE: 50

-continued

```
Met Thr Met Gln Leu Gly Leu Ala Leu Val Leu Gly Val Ala Met Cys
1               5                   10                  15

Leu Gly Cys Gly Gln Pro Leu Leu Arg Ala Pro Glu Arg Pro Phe Cys
            20                  25                  30

Val Leu Trp Asn Val Pro Ser Ala Arg Cys Lys Ala Arg Phe Gly Val
        35                  40                  45

His Leu Pro Leu Glu Ala Leu Gly Ile Thr Ala Asn His Gly Gln Arg
    50                  55                  60

Phe His Gly Gln Asn Ile Thr Ile Phe Tyr Lys Ser Gln Leu Gly Leu
65                  70                  75                  80

Tyr Pro Tyr Phe Gly Pro Arg Gly Thr Ala His Asn Gly Gly Ile Pro
                85                  90                  95

Gln Ala Val Ser Leu Asp His His Leu Ala Arg Ala Ala Tyr Gln Ile
            100                 105                 110

His Arg Ser Leu Arg Pro Gly Phe Thr Gly Leu Ala Val Leu Asp Trp
        115                 120                 125

Glu Glu Trp Cys Pro Leu Trp Ala Gly Asn Trp Gly Arg Arg Gln Ala
    130                 135                 140

Tyr Gln Ala Ala Ser Cys Ala Trp Ala Gln Arg Val Tyr Pro Asn Leu
145                 150                 155                 160

Asp Pro Gln Glu Gln Leu Cys Lys Ala Arg Ala Gly Phe Glu Glu Ala
                165                 170                 175

Ala Arg Ala Leu Met Glu Asp Thr Leu Arg Leu Gly Arg Met Leu Arg
            180                 185                 190

Pro His Gly Leu Trp Gly Phe Tyr His Tyr Pro Ala Cys Gly Asn Gly
        195                 200                 205

Trp His Gly Thr Ala Ser Asn Tyr Thr Gly His Cys His Ala Ala Ala
    210                 215                 220

Leu Ala Arg Asn Thr Gln Leu Tyr Trp Leu Trp Ala Ala Ser Ser Ala
225                 230                 235                 240

Leu Phe Pro Ser Ile Tyr Leu Pro Pro Gly Leu Pro Pro Ala Tyr His
                245                 250                 255

Gln Ala Phe Val Arg Tyr Arg Leu Glu Glu Ala Phe Arg Val Ala Leu
            260                 265                 270

Val Gly His Pro His Pro Leu Pro Val Leu Ala Tyr Ala Arg Leu Thr
        275                 280                 285

His Arg Asn Ser Gly Arg Phe Leu Ser Gln Asp Glu Leu Val Gln Thr
    290                 295                 300

Ile Gly Val Ser Ala Ala Leu Gly Ala Ser Gly Val Val Leu Trp Gly
305                 310                 315                 320

Asp Leu Ser Phe Ser Ser Ser Glu Glu Glu Cys Trp His Leu Arg Gly
                325                 330                 335

Tyr Leu Val Gly Thr Leu Gly Pro Tyr Val Ile Asn Val Thr Arg Ala
            340                 345                 350

Ala Met Ala Cys Ser His Gln Arg Cys His Gly His Gly Arg Cys Ala
        355                 360                 365

Trp Gln Asp Pro Gly Gln Leu Lys Val Phe Leu His Leu His Pro Gly
    370                 375                 380

Gly Ser Pro Gly Ala Trp Glu Ser Phe Ser Cys Arg Cys Tyr Trp Gly
385                 390                 395                 400

Trp Ala Gly Pro Thr Cys Gln Glu Pro Arg Pro Glu Leu Gly Pro Glu
                405                 410                 415

Glu Ala Thr
```

<210> SEQ ID NO 51
<211> LENGTH: 449
<212> TYPE: PRT
<213> ORGANISM: Rattus norvegicus

<400> SEQUENCE: 51

```
Met Lys Pro Phe Ser Pro Glu Val Ser Pro Asp Pro Cys Pro Ala Thr
1               5                   10                  15

Ala Ala His Leu Leu Arg Thr Tyr Thr Leu Phe Leu Thr Leu Leu Glu
            20                  25                  30

Leu Ala Gln Gly Cys Arg Gly Ser Met Val Ser Asn Arg Pro Phe Ile
        35                  40                  45

Thr Val Trp Asn Ala Asp Thr His Trp Cys Leu Lys Asp His Gly Val
    50                  55                  60

Asp Val Asp Val Ser Val Phe Asp Val Val Ala Asn Lys Glu Gln Asn
65                  70                  75                  80

Phe Gln Gly Pro Asn Met Thr Ile Phe Tyr Arg Glu Glu Leu Gly Thr
                85                  90                  95

Tyr Pro Tyr Tyr Thr Pro Thr Gly Glu Pro Val Phe Gly Gly Leu Pro
            100                 105                 110

Gln Asn Ala Ser Leu Val Thr His Leu Ala His Ala Phe Gln Asp Ile
        115                 120                 125

Lys Ala Ala Met Pro Glu Pro Asp Phe Ser Gly Leu Ala Val Ile Asp
    130                 135                 140

Trp Glu Ala Trp Arg Pro Arg Trp Ala Phe Asn Trp Asp Ser Lys Asp
145                 150                 155                 160

Ile Tyr Gln Gln Arg Ser Met Glu Leu Val Arg Ala Glu His Pro Asp
                165                 170                 175

Trp Pro Glu Thr Leu Val Glu Ala Glu Ala Gln Gly Gln Phe Gln Glu
            180                 185                 190

Ala Ala Glu Ala Trp Met Ala Gly Thr Leu Gln Leu Gly Gln Val Leu
        195                 200                 205

Arg Pro Arg Gly Leu Trp Gly Tyr Tyr Gly Phe Pro Asp Cys Tyr Asn
    210                 215                 220

Tyr Asp Phe Leu Ser Pro Asn Tyr Thr Gly Gln Cys Ser Leu Ser Ile
225                 230                 235                 240

His Asp Gln Asn Asp Gln Leu Gly Trp Leu Trp Asn Gln Ser Tyr Ala
                245                 250                 255

Leu Tyr Pro Ser Ile Tyr Leu Pro Ala Ala Leu Met Gly Thr Gly Lys
            260                 265                 270

Ser Gln Met Tyr Val Arg Tyr Arg Val Gln Glu Ala Phe Arg Leu Ala
        275                 280                 285

Leu Val Ser Arg Asp Pro His Val Pro Ile Met Pro Tyr Val Gln Ile
    290                 295                 300

Phe Tyr Glu Lys Thr Asp Tyr Leu Leu Pro Leu Glu Glu Leu Glu His
305                 310                 315                 320

Ser Leu Gly Glu Ser Ala Ala Gln Gly Ala Ala Gly Ala Val Leu Trp
                325                 330                 335

Ile Ser Ser Glu Lys Thr Ser Thr Lys Glu Ser Cys Gln Ala Ile Lys
            340                 345                 350

Ala Tyr Met Asp Ser Thr Leu Gly Pro Phe Ile Leu Asn Val Thr Ser
        355                 360                 365

Ala Ala Leu Leu Cys Ser Glu Ala Leu Cys Ser Gly Arg Gly Arg Cys
```

```
    370                 375                 380

Val Arg His Pro Ser Tyr Pro Glu Ala Leu Leu Thr Leu Ser Pro Ala
385                 390                 395                 400

Ser Phe Ser Ile Glu Pro Thr His Asp Gly Arg Pro Leu Ser Leu Lys
                405                 410                 415

Gly Thr Leu Ser Leu Lys Asp Arg Ala Gln Met Ala Met Lys Phe Lys
            420                 425                 430

Cys Arg Cys Tyr Arg Gly Trp Ser Gly Glu Trp Cys Lys Lys Gln Asp
        435                 440                 445

Met


<210> SEQ ID NO 52
<211> LENGTH: 473
<212> TYPE: PRT
<213> ORGANISM: Rattus norvegicus

<400> SEQUENCE: 52

Met Arg Ala Gly Leu Gly Pro Ile Ile Thr Leu Ala Leu Val Leu Glu
1               5                   10                  15

Val Ala Trp Ala Ser Glu Leu Lys Pro Thr Ala Pro Pro Ile Phe Thr
            20                  25                  30

Gly Arg Pro Phe Val Val Ala Trp Asn Val Pro Thr Gln Glu Cys Ala
        35                  40                  45

Pro Arg His Lys Val Pro Leu Asp Leu Arg Ala Phe Asp Val Glu Ala
    50                  55                  60

Thr Pro Asn Glu Gly Phe Phe Asn Gln Asn Ile Thr Thr Phe Tyr Tyr
65                  70                  75                  80

Asp Arg Leu Gly Leu Tyr Pro Arg Phe Asp Ala Ala Gly Met Ser Val
                85                  90                  95

His Gly Gly Val Pro Gln Asn Gly Ser Leu Cys Ala His Leu Pro Met
            100                 105                 110

Leu Lys Glu Ala Val Glu Arg Tyr Ile Gln Thr Gln Glu Pro Ala Gly
        115                 120                 125

Leu Ala Val Ile Asp Trp Glu Glu Trp Arg Pro Val Trp Val Arg Asn
    130                 135                 140

Trp Gln Glu Lys Asp Val Tyr Arg Gln Ser Ser Arg Gln Leu Val Ala
145                 150                 155                 160

Ser Arg His Pro Asp Trp Pro Ser Asp Arg Ile Val Lys Gln Ala Gln
                165                 170                 175

Tyr Glu Phe Glu Phe Ala Ala Arg Gln Phe Met Leu Asn Thr Leu Arg
            180                 185                 190

Tyr Val Lys Ala Val Arg Pro Gln His Leu Trp Gly Phe Tyr Leu Phe
        195                 200                 205

Pro Asp Cys Tyr Asn His Asp Tyr Val Gln Asn Trp Asp Ser Tyr Thr
    210                 215                 220

Gly Arg Cys Pro Asp Val Glu Val Ala Gln Asn Asp Gln Leu Ala Trp
225                 230                 235                 240

Leu Trp Ala Glu Asn Thr Ala Leu Phe Pro Ser Val Tyr Leu Asp Lys
                245                 250                 255

Thr Leu Ala Ser Ser Lys His Ser Arg Asn Phe Val Ser Phe Arg Val
            260                 265                 270

Gln Glu Ala Leu Arg Val Ala His Thr His His Ala Asn His Ala Leu
        275                 280                 285

Pro Val Tyr Val Phe Thr Arg Pro Thr Tyr Thr Arg Arg Leu Thr Glu
```

```
    290                 295                 300

Leu Asn Gln Met Asp Leu Ile Ser Thr Ile Gly Glu Ser Ala Ala Leu
305                 310                 315                 320

Gly Ser Ala Gly Val Ile Phe Trp Gly Asp Ser Val Tyr Ala Ser Ser
                325                 330                 335

Met Glu Asn Cys Gln Asn Leu Lys Lys Tyr Leu Thr Gln Thr Leu Val
            340                 345                 350

Pro Tyr Ile Val Asn Val Ser Trp Ala Thr Gln Tyr Cys Ser Trp Thr
        355                 360                 365

Gln Cys His Gly His Gly Arg Cys Val Arg Arg Asn Pro Ser Ala Ser
    370                 375                 380

Thr Phe Leu His Leu Ser Pro Ser Ser Phe Arg Leu Val Pro Gly Arg
385                 390                 395                 400

Thr Pro Ser Glu Pro Gln Leu Arg Pro Glu Gly Glu Leu Ser Glu Asp
                405                 410                 415

Asp Leu Ser Tyr Leu Gln Met His Phe Arg Cys His Cys Tyr Leu Gly
            420                 425                 430

Trp Gly Gly Glu Gln Cys Gln Trp Asn His Lys Arg Ala Ala Gly Asp
        435                 440                 445

Ala Ser Arg Ala Trp Ala Gly Ala His Leu Ala Ser Leu Leu Gly Leu
    450                 455                 460

Val Ala Met Thr Leu Thr Trp Thr Leu
465                 470


<210> SEQ ID NO 53
<211> LENGTH: 412
<212> TYPE: PRT
<213> ORGANISM: Rattus norvegicus

<400> SEQUENCE: 53

Met Ile Thr Gln Leu Gly Leu Thr Leu Val Val Gly Leu Thr Leu Cys
1               5                   10                  15

Leu Val His Val Gln Ala Leu Leu Gln Val Pro Glu Phe Pro Phe Ser
            20                  25                  30

Val Leu Trp Asn Val Pro Ser Ala Arg Cys Lys Thr Arg Phe Gly Val
        35                  40                  45

His Leu Pro Leu Asp Ala Leu Gly Ile Ile Ala Asn His Gly Gln Arg
    50                  55                  60

Phe His Gly Gln Asn Ile Thr Ile Phe Tyr Lys Asn Gln Phe Gly Leu
65                  70                  75                  80

Tyr Pro Tyr Phe Gly Pro Arg Gly Thr Ala His Asn Gly Gly Ile Pro
                85                  90                  95

Gln Ala Val Ser Leu Asp His His Leu Ala Gln Ala Ala His Gln Ile
            100                 105                 110

Leu His Asn Leu Gly Ser Ser Phe Ala Gly Leu Ala Val Leu Asp Trp
        115                 120                 125

Glu Glu Trp Tyr Pro Leu Trp Ala Gly Asn Trp Gly Thr His Arg Gln
    130                 135                 140

Val Tyr Gln Ala Ala Ser Trp Ala Trp Ala Gln Gln Met Phe Pro Asp
145                 150                 155                 160

Leu Asn Pro Gln Glu Gln Leu His Lys Ala Gln Thr Gly Phe Glu Gln
                165                 170                 175

Ala Ala Arg Ala Leu Met Glu His Thr Leu Arg Leu Gly Gln Met Leu
            180                 185                 190
```

```
Arg Pro His Gly Leu Trp Gly Phe Tyr Arg Tyr Pro Val Cys Gly Asn
        195                 200                 205

Gly Trp His Asn Met Ala Ser Asn Tyr Thr Gly His Cys His Pro Ala
    210                 215                 220

Ile Ile Thr Arg Asn Thr Gln Leu Arg Trp Leu Trp Ala Ala Ser Ser
225                 230                 235                 240

Ala Leu Phe Pro Ser Ile Tyr Leu Pro Pro Arg Leu Pro Pro Ala Tyr
                245                 250                 255

His Gln Thr Phe Val Arg His Arg Leu Glu Glu Ala Phe Arg Val Ala
            260                 265                 270

Leu Thr Gly His Ala His Pro Leu Pro Val Leu Ala Tyr Val Arg Leu
        275                 280                 285

Thr His Arg Ser Ser Gly Arg Phe Leu Ser Leu Asp Asp Leu Met Gln
    290                 295                 300

Thr Ile Gly Val Ser Ala Ala Leu Gly Ala Ala Gly Val Val Leu Trp
305                 310                 315                 320

Gly Asp Leu Ser Val Ser Ser Ser Glu Glu Glu Cys Trp Arg Leu His
                325                 330                 335

Asp Tyr Leu Val Gly Thr Leu Gly Pro Tyr Val Ile Asn Val Thr Lys
            340                 345                 350

Ala Ala Thr Ala Cys Ser His Gln Arg Cys His Gly His Gly Arg Cys
        355                 360                 365

Ser Trp Lys Asp Pro Gly Gln Met Glu Ala Phe Leu His Leu Gln Pro
    370                 375                 380

Asp Asp Asn Leu Gly Ala Trp Lys Ser Phe Arg Cys Arg Cys Tyr Leu
385                 390                 395                 400

Gly Trp Ser Gly Pro Thr Cys Leu Glu Pro Lys Pro
                405                 410


<210> SEQ ID NO 54
<211> LENGTH: 529
<212> TYPE: PRT
<213> ORGANISM: Cavia porcellus

<400> SEQUENCE: 54

Met Gly Ala Phe Thr Phe Lys His Ser Phe Phe Gly Ser Phe Val Glu
1               5                   10                  15

Cys Ser Gly Val Leu Gln Thr Val Phe Ile Phe Leu Leu Ile Pro Cys
            20                  25                  30

Cys Leu Ala Asp Lys Arg Ala Pro Pro Leu Ile Pro Asn Val Pro Leu
        35                  40                  45

Leu Trp Val Trp Asn Ala Pro Thr Glu Phe Cys Ile Gly Gly Thr Asn
    50                  55                  60

Gln Pro Leu Asp Met Ser Phe Phe Ser Ile Val Gly Thr Pro Arg Lys
65                  70                  75                  80

Asn Ile Thr Gly Gln Ser Ile Thr Leu Tyr Tyr Val Asp Arg Leu Gly
                85                  90                  95

Tyr Tyr Pro Tyr Ile Asp Pro His Thr Gly Ala Ile Val His Gly Gly
            100                 105                 110

Leu Pro Gln Leu Met Asn Leu Gln Gln His Leu Arg Lys Ser Arg Gln
        115                 120                 125

Asp Ile Leu Phe Tyr Met Pro Thr Asp Ser Val Gly Leu Ala Val Ile
    130                 135                 140

Asp Trp Glu Glu Trp Arg Pro Thr Trp Thr Arg Asn Trp Arg Pro Lys
145                 150                 155                 160
```

-continued

```
Asp Ile Tyr Arg Asn Lys Ser Ile Glu Leu Val Lys Ser Gln His Pro
                165                 170                 175

Gln Tyr Asn His Ser Tyr Ala Val Ala Val Ala Lys Arg Asp Phe Glu
            180                 185                 190

Arg Thr Gly Lys Ala Phe Met Leu Glu Thr Leu Lys Leu Gly Lys Ser
        195                 200                 205

Leu Arg Pro Ser Ser Leu Trp Gly Tyr Tyr Leu Phe Pro Asp Cys Tyr
    210                 215                 220

Asn Thr His Phe Thr Lys Pro Asn Tyr Asp Gly His Cys Pro Pro Ile
225                 230                 235                 240

Glu Leu Gln Arg Asn Asn Asp Leu Gln Trp Leu Trp Asn Asp Ser Thr
                245                 250                 255

Ala Leu Tyr Pro Ser Val Tyr Leu Thr Ser Arg Val Arg Ser Ser Gln
            260                 265                 270

Asn Gly Ala Leu Tyr Val Arg Asn Arg Val His Glu Ser Ile Arg Val
        275                 280                 285

Ser Lys Leu Met Asp Asp Lys Asn Pro Leu Pro Ile Tyr Val Tyr Ile
    290                 295                 300

Arg Leu Val Phe Thr Asp Gln Thr Thr Thr Phe Leu Glu Leu Asp Asp
305                 310                 315                 320

Leu Val His Ser Val Gly Glu Ile Val Pro Leu Gly Val Ser Gly Ile
                325                 330                 335

Ile Ile Trp Gly Ser Leu Ser Leu Thr Arg Ser Leu Val Ser Cys Ile
            340                 345                 350

Gly Leu Glu Asn Tyr Met Lys Gly Thr Leu Leu Pro Tyr Leu Ile Asn
        355                 360                 365

Val Thr Leu Ala Ala Lys Met Cys Gly Gln Val Leu Cys Lys Asn Gln
    370                 375                 380

Gly Ile Cys Thr Arg Lys Asp Trp Asn Thr Asn Thr Tyr Leu His Leu
385                 390                 395                 400

Asn Ala Thr Asn Phe Asp Ile Glu Leu Gln Gln Asn Gly Lys Phe Val
                405                 410                 415

Val His Gly Lys Pro Ser Leu Glu Asp Leu Gln Glu Phe Ser Lys Asn
            420                 425                 430

Phe His Cys Ser Cys Tyr Thr Asn Val Ala Cys Lys Asp Arg Leu Asp
        435                 440                 445

Val His Asn Val Arg Ser Val Asn Val Cys Thr Ala Asn Asn Ile Cys
    450                 455                 460

Ile Asp Ala Val Leu Asn Phe Pro Ser Leu Asp Asp Asp Asp Glu Pro
465                 470                 475                 480

Pro Ile Thr Asp Asp Thr Ser Gln Asn Gln Asp Ser Ile Ser Asp Ile
                485                 490                 495

Thr Ser Ser Ala Pro Pro Ser Ser His Ile Leu Pro Lys Asp Leu Ser
            500                 505                 510

Trp Cys Leu Phe Leu Leu Ser Ile Phe Ser Gln His Trp Lys Tyr Leu
        515                 520                 525

Leu
```

<210> SEQ ID NO 55
<211> LENGTH: 545
<212> TYPE: PRT
<213> ORGANISM: Oryctolagus cuniculus

<400> SEQUENCE: 55

-continued

```
Met Gly Val Leu Lys Phe Lys His Ile Phe Phe Gly Ser Ala Val Glu
1               5                   10                  15

Leu Ser Gly Val Phe Gln Ile Val Phe Ile Phe Leu Leu Ile Pro Cys
            20                  25                  30

Cys Leu Thr Ala Asn Phe Arg Ala Pro Pro Val Ile Pro Asn Val Pro
        35                  40                  45

Phe Leu Trp Ala Trp Asn Ala Pro Thr Glu Phe Cys Leu Gly Lys Ser
    50                  55                  60

Gly Glu Pro Leu Asp Met Ser Leu Phe Ser Leu Phe Gly Ser Pro Arg
65                  70                  75                  80

Lys Asn Lys Thr Gly Gln Gly Ile Thr Ile Phe Tyr Val Asp Arg Leu
                85                  90                  95

Gly Tyr Tyr Pro Tyr Ile Asp Pro His Thr Gly Ala Ile Val His Gly
            100                 105                 110

Arg Ile Pro Gln Leu Gly Pro Leu Gln Gln His Leu Thr Lys Leu Arg
        115                 120                 125

Gln Glu Ile Leu Tyr Tyr Met Pro Lys Asp Asn Val Gly Leu Ala Val
    130                 135                 140

Ile Asp Trp Glu Glu Trp Leu Pro Thr Trp Leu Arg Asn Trp Lys Pro
145                 150                 155                 160

Lys Asp Ile Tyr Arg Ile Lys Ser Ile Glu Leu Val Lys Ser Gln His
                165                 170                 175

Pro Gln Tyr Asn His Ser Tyr Ala Thr Glu Lys Ala Lys Arg Asp Phe
            180                 185                 190

Glu Lys Ala Gly Lys Asp Phe Met Glu Glu Thr Leu Lys Leu Gly Arg
        195                 200                 205

Leu Leu Arg Pro Asn His Leu Trp Gly Tyr Tyr Leu Phe Pro Asp Cys
    210                 215                 220

Tyr Asn His His Tyr Asp Lys Pro Asn Leu Tyr Lys Gly Ser Cys Phe
225                 230                 235                 240

Asp Ile Glu Lys Lys Arg Asn Asp Asp Leu Ser Trp Leu Trp Lys Glu
                245                 250                 255

Ser Thr Ala Leu Phe Pro Ser Val Tyr Leu Thr Ser Arg Ala Arg Ser
            260                 265                 270

Ala Thr Ala Leu Ser Lys Leu Tyr Val Val Arg Asn Arg Val His Glu
        275                 280                 285

Ala Ile Arg Val Ser Lys Ile Pro Asp Asp Lys Ser Pro Leu Pro Asn
    290                 295                 300

Phe Val Tyr Thr Arg Leu Val Phe Thr Asp Gln Ile Phe Gln Phe Leu
305                 310                 315                 320

Ser His His Asp Leu Val Tyr Thr Ile Gly Glu Ile Val Ala Leu Gly
                325                 330                 335

Ala Ser Gly Ile Val Val Trp Gly Ser Gln Ser Leu Ala Arg Ser Met
            340                 345                 350

Lys Ser Cys Leu His Leu Asp Asn Tyr Met Lys Thr Ile Leu Asn Pro
        355                 360                 365

Tyr Leu Ile Asn Val Thr Leu Ala Ala Lys Met Cys Asn Gln Val Leu
    370                 375                 380

Cys Gln Glu Gln Gly Val Cys Thr Arg Lys Asn Trp Asn Pro Asn Asp
385                 390                 395                 400

Tyr Leu His Leu Asn Pro Gly Asn Phe Ala Ile Gln Leu Gly Ser Asn
                405                 410                 415
```

```
Gly Thr Tyr Lys Val Asp Gly Lys Pro Thr Leu Thr Asp Leu Glu Gln
            420                 425                 430

Phe Ser Lys Asn Phe Gln Cys Ser Cys Tyr Thr Asn Leu Asn Cys Lys
        435                 440                 445

Glu Arg Thr Asp Met Asn Asn Val Arg Thr Val Asn Val Cys Ala Val
    450                 455                 460

Glu Asn Val Cys Ile Asp Thr Asn Val Gly Pro Gln Ala Val Thr Tyr
465                 470                 475                 480

Ala Pro Lys Glu Lys Lys Asp Val Ala His Ile Leu Ser Asn Thr Thr
                485                 490                 495

Ser Ile Asn Ser Ser Thr Thr Met Ser Leu Pro Phe Pro Arg Lys His
            500                 505                 510

Val Ser Gly Cys Leu Leu Val Leu Cys Met Tyr Ser Gln Tyr Leu Asn
        515                 520                 525

Ile Cys Tyr Arg Leu Val Ala Ile Gly Ile Gln His Gly Tyr Tyr Leu
    530                 535                 540

Lys
545


<210> SEQ ID NO 56
<211> LENGTH: 476
<212> TYPE: PRT
<213> ORGANISM: Ovis aries

<400> SEQUENCE: 56

Met Trp Thr Gly Leu Gly Pro Ala Val Thr Leu Ala Leu Val Leu Val
1               5                   10                  15

Val Ala Trp Ala Thr Glu Leu Lys Pro Thr Ala Pro Pro Ile Phe Thr
            20                  25                  30

Gly Arg Pro Phe Val Val Ala Trp Asp Val Pro Thr Gln Asp Cys Gly
        35                  40                  45

Pro Arg His Lys Met Pro Leu Asp Pro Lys Asp Met Lys Ala Phe Asp
    50                  55                  60

Val Gln Ala Ser Pro Asn Glu Gly Phe Val Asn Gln Asn Ile Thr Ile
65                  70                  75                  80

Phe Tyr Arg Asp Arg Leu Gly Met Tyr Pro His Phe Asn Ser Val Gly
                85                  90                  95

Arg Ser Val His Gly Gly Val Pro Gln Asn Gly Ser Leu Trp Val His
            100                 105                 110

Leu Glu Met Leu Lys Gly His Val Glu His Tyr Ile Arg Thr Gln Glu
        115                 120                 125

Pro Ala Gly Leu Ala Val Ile Asp Trp Glu Asp Trp Arg Pro Val Trp
    130                 135                 140

Val Arg Asn Trp Gln Asp Lys Asp Val Tyr Arg Arg Leu Ser Arg Gln
145                 150                 155                 160

Leu Val Ala Ser His His Pro Asp Trp Pro Pro Glu Arg Ile Val Lys
                165                 170                 175

Glu Ala Gln Tyr Glu Phe Glu Phe Ala Ala Arg Gln Phe Met Leu Glu
            180                 185                 190

Thr Leu Arg Phe Val Lys Ala Phe Arg Pro Arg His Leu Trp Gly Phe
        195                 200                 205

Tyr Leu Phe Pro Asp Cys Tyr Asn His Asp Tyr Val Gln Asn Trp Glu
    210                 215                 220

Thr Tyr Thr Gly Arg Cys Pro Asp Val Glu Val Ser Arg Asn Asp Gln
225                 230                 235                 240
```

```
Leu Ser Trp Leu Trp Ala Glu Ser Thr Ala Leu Phe Pro Ser Val Tyr
                245                 250                 255

Leu Glu Glu Thr Leu Ala Ser Ser Thr His Gly Arg Asn Phe Val Ser
            260                 265                 270

Phe Arg Val Gln Glu Ala Leu Arg Val Ala Asp Val His His Ala Asn
        275                 280                 285

His Ala Leu Pro Val Tyr Val Phe Thr Arg Pro Thr Tyr Ser Arg Gly
    290                 295                 300

Leu Thr Gly Leu Ser Glu Met Asp Leu Ile Ser Thr Ile Gly Glu Ser
305                 310                 315                 320

Ala Ala Leu Gly Ala Ala Gly Val Ile Leu Trp Gly Asp Ala Gly Phe
                325                 330                 335

Thr Thr Ser Asn Glu Thr Cys Arg Arg Leu Lys Asp Tyr Leu Thr Arg
            340                 345                 350

Ser Leu Val Pro Tyr Val Val Asn Val Ser Trp Ala Ala Gln Tyr Cys
        355                 360                 365

Ser Trp Ala Gln Cys His Gly His Gly Arg Cys Val Arg Arg Asp Pro
    370                 375                 380

Asn Ala His Thr Phe Leu His Leu Ser Ala Ser Ser Phe Arg Leu Val
385                 390                 395                 400

Pro Ser His Ala Pro Asp Glu Pro Arg Leu Arg Pro Glu Gly Glu Leu
                405                 410                 415

Ser Trp Ala Asp Arg Asn His Leu Gln Thr His Phe Arg Cys Gln Cys
            420                 425                 430

Tyr Leu Gly Trp Gly Gly Glu Gln Cys Gln Trp Asp Arg Arg Arg Ala
        435                 440                 445

Ala Gly Gly Ala Ser Gly Ala Trp Ala Gly Ser His Leu Thr Gly Leu
    450                 455                 460

Leu Ala Val Ala Val Leu Ala Phe Thr Trp Thr Ser
465                 470                 475


<210> SEQ ID NO 57
<211> LENGTH: 114
<212> TYPE: PRT
<213> ORGANISM: Ovis aries

<400> SEQUENCE: 57

Leu Tyr Val Arg Asn Arg Val Arg Glu Ala Ile Arg Leu Ser Lys Ile
1               5                   10                  15

Ala Ser Val Glu Ser Pro Leu Pro Val Phe Val Tyr His Arg Pro Val
            20                  25                  30

Phe Thr Asp Gly Ser Ser Thr Tyr Leu Ser Gln Gly Asp Leu Val Asn
        35                  40                  45

Ser Val Gly Glu Ile Val Ala Leu Gly Ala Ser Gly Ile Ile Met Trp
    50                  55                  60

Gly Ser Leu Asn Leu Ser Leu Thr Met Gln Ser Cys Met Asn Leu Gly
65                  70                  75                  80

Asn Tyr Leu Asn Thr Thr Leu Asn Pro Tyr Ile Ile Asn Val Thr Leu
                85                  90                  95

Ala Ala Lys Met Cys Ser Gln Val Leu Cys Gln Glu Gln Gly Val Cys
            100                 105                 110

Ile Arg


<210> SEQ ID NO 58
```

<211> LENGTH: 520
<212> TYPE: PRT
<213> ORGANISM: Ovis aries

<400> SEQUENCE: 58

Leu Asp Phe Pro Ala Pro Pro Leu Ile Ser Asn Thr Ser Phe Leu Trp
1 5 10 15

Ala Trp Asn Ala Pro Ala Glu Arg Cys Val Lys Ile Phe Lys Leu Pro
20 25 30

Pro Asp Leu Arg Leu Phe Ser Val Lys Gly Ser Pro Gln Lys Ser Ala
35 40 45

Thr Gly Gln Phe Ile Thr Leu Phe Tyr Ala Asp Arg Leu Gly Tyr Tyr
50 55 60

Pro His Ile Asp Glu Lys Thr Gly Asn Thr Val Tyr Gly Gly Ile Pro
65 70 75 80

Gln Leu Gly Asn Leu Lys Asn His Leu Glu Lys Ala Lys Lys Asp Ile
85 90 95

Ala Tyr Tyr Ile Pro Asn Asp Ser Val Gly Leu Ala Val Ile Asp Trp
100 105 110

Glu Asn Trp Arg Pro Thr Trp Ala Arg Asn Trp Lys Pro Lys Asp Val
115 120 125

Tyr Arg Asp Glu Ser Val Glu Leu Val Leu Gln Lys Asn Pro Gln Leu
130 135 140

Ser Phe Pro Glu Ala Ser Lys Ile Ala Lys Val Asp Phe Glu Thr Ala
145 150 155 160

Gly Lys Ser Phe Met Gln Glu Thr Leu Lys Leu Gly Lys Leu Leu Arg
165 170 175

Pro Asn His Leu Trp Gly Tyr Tyr Leu Phe Pro Asp Cys Tyr Asn His
180 185 190

Asn Tyr Asn Gln Pro Thr Tyr Asn Gly Asn Cys Ser Asp Leu Glu Lys
195 200 205

Arg Arg Asn Asp Asp Leu Asp Trp Leu Trp Lys Glu Ser Thr Ala Leu
210 215 220

Phe Pro Ser Val Tyr Leu Asn Ile Lys Leu Lys Ser Thr Pro Lys Ala
225 230 235 240

Ala Phe Tyr Val Arg Asn Arg Val Gln Glu Ala Ile Arg Leu Ser Lys
245 250 255

Ile Ala Ser Val Glu Ser Pro Leu Pro Val Phe Val Tyr His Arg Pro
260 265 270

Val Phe Thr Asp Gly Ser Ser Thr Tyr Leu Ser Gln Gly Asp Leu Val
275 280 285

Asn Ser Val Gly Glu Ile Val Ala Leu Gly Ala Ser Gly Ile Ile Met
290 295 300

Trp Gly Ser Leu Asn Leu Ser Leu Thr Met Gln Ser Cys Met Asn Leu
305 310 315 320

Gly Asn Tyr Asn Thr Thr Leu Asn Pro Tyr Ile Ile Asn Val Thr Leu
325 330 335

Ala Ala Lys Met Cys Ser Gln Val Leu Cys His Asp Glu Gly Val Cys
340 345 350

Thr Arg Lys Gln Trp Asn Ser Ser Asp Tyr Leu His Leu Asn Pro Ile
355 360 365

Met Asn Phe Ala Ile Gln Thr Gly Lys Gly Gly Lys Tyr Thr Val Pro
370 375 380

Gly Lys Val Thr Leu Glu Asp Leu Gln Thr Phe Ser Asp Lys Phe Tyr

```
385                 390                 395                 400

Cys Ser Cys Tyr Ala Asn Ile Asn Cys Lys Lys Arg Val Asp Ile Lys
                405                 410                 415

Asn Val His Ser Val Asn Val Cys Met Ala Glu Asp Ile Cys Ile Glu
            420                 425                 430

Gly Pro Val Lys Leu Gln Pro Ser Asp His Ser Ser Ser Gln Asn Glu
        435                 440                 445

Ala Ser Thr Thr Thr Val Ser Ser Ile Ser Pro Ser Thr Thr Ala Thr
    450                 455                 460

Thr Val Val Ser Pro Cys Thr Pro Glu Lys Gln Ser Pro Glu Cys Leu
465                 470                 475                 480

Lys Val Arg Cys Leu Glu Ala Ile Ala Asn Val Thr Gln Thr Gly Cys
                485                 490                 495

Gln Gly Val Lys Trp Lys Asn Thr Ser Ser Gln Ser Gln Ser Ser Ile
            500                 505                 510

Gln Asn Ile Lys Asn Gln Thr Thr
        515                 520


<210> SEQ ID NO 59
<211> LENGTH: 517
<212> TYPE: PRT
<213> ORGANISM: Ovis aries

<400> SEQUENCE: 59

Asp Phe Arg Ala Pro Pro Leu Ile Ser Asn Thr Ser Phe Leu Trp Ala
1               5                   10                  15

Trp Asn Ala Pro Ala Glu Arg Cys Ile Lys Ile Phe Lys Leu Pro Pro
            20                  25                  30

Asp Leu Arg Leu Phe Ser Val Lys Gly Ser Pro Gln Lys Ser Ala Thr
        35                  40                  45

Gly Gln Phe Ile Thr Leu Phe Tyr Ala Asp Arg Leu Gly Tyr Tyr Pro
    50                  55                  60

His Ile Asp Glu Lys Thr Gly Asn Thr Val Tyr Gly Gly Ile Pro Gln
65                  70                  75                  80

Leu Gly Asn Leu Lys Asn His Leu Glu Lys Ala Lys Lys Asp Ile Ala
                85                  90                  95

Tyr Tyr Ile Pro Asn Asp Ser Val Gly Leu Ala Val Ile Asp Trp Glu
            100                 105                 110

Asn Trp Arg Pro Thr Trp Ala Arg Asn Trp Lys Pro Lys Asp Val Tyr
        115                 120                 125

Arg Asp Glu Ser Val Glu Leu Val Leu Gln Lys Asn Pro Gln Leu Ser
    130                 135                 140

Phe Pro Glu Ala Ser Lys Ile Ala Lys Val Asp Phe Glu Thr Ala Gly
145                 150                 155                 160

Lys Ser Phe Met Gln Glu Thr Leu Lys Leu Gly Lys Leu Leu Arg Pro
                165                 170                 175

Asn His Leu Trp Gly Tyr Tyr Leu Phe Pro Asp Cys Tyr Asn His Asn
            180                 185                 190

Tyr Asn Gln Pro Thr Tyr Asn Gly Asn Cys Ser Asp Leu Glu Lys Arg
        195                 200                 205

Arg Asn Asp Asp Leu Asp Trp Leu Trp Lys Glu Ser Thr Ala Leu Phe
    210                 215                 220

Pro Ser Val Tyr Leu Asn Ile Lys Leu Lys Ser Thr Pro Lys Ala Ala
225                 230                 235                 240
```

```
Phe Tyr Val Arg Asn Arg Val Gln Glu Ala Ile Arg Leu Ser Lys Ile
                245                 250                 255

Ala Ser Val Glu Ser Pro Leu Pro Val Phe Val Tyr His Arg Pro Val
            260                 265                 270

Phe Thr Asp Gly Ser Ser Thr Tyr Leu Ser Gln Gly Asp Leu Val Asn
        275                 280                 285

Ser Val Gly Glu Ile Val Ala Leu Gly Ala Ser Gly Ile Ile Met Trp
    290                 295                 300

Gly Ser Leu Asn Leu Ser Leu Thr Met Gln Ser Cys Met Asn Leu Gly
305                 310                 315                 320

Asn Tyr Leu Asn Thr Thr Leu Asn Pro Tyr Ile Ile Asn Val Thr Leu
                325                 330                 335

Ala Ala Lys Met Cys Ser Gln Val Leu Cys His Asp Glu Gly Val Cys
            340                 345                 350

Thr Arg Lys Gln Trp Asn Ser Ser Asp Tyr Leu His Leu Asn Pro Met
        355                 360                 365

Asn Phe Ala Ile Gln Thr Gly Lys Gly Gly Lys Tyr Thr Val Pro Gly
    370                 375                 380

Lys Val Thr Leu Glu Asp Leu Gln Thr Phe Ser Asp Lys Phe Tyr Cys
385                 390                 395                 400

Ser Cys Tyr Ala Asn Ile Asn Cys Lys Lys Arg Val Asp Ile Lys Asn
                405                 410                 415

Val His Ser Val Asn Val Cys Met Ala Glu Asp Ile Cys Ile Glu Gly
            420                 425                 430

Pro Val Lys Leu Gln Pro Ser Asp His Ser Ser Ser Gln Asn Glu Ala
        435                 440                 445

Ser Thr Thr Thr Val Ser Ser Ile Ser Pro Ser Thr Thr Ala Thr Thr
    450                 455                 460

Val Ser Pro Cys Thr Pro Glu Lys Gln Ser Pro Glu Cys Leu Lys Val
465                 470                 475                 480

Arg Cys Leu Glu Ala Ile Ala Asn Val Thr Gln Thr Gly Cys Gln Gly
                485                 490                 495

Val Lys Trp Lys Asn Thr Ser Ser Gln Ser Ser Ile Gln Asn Ile Lys
            500                 505                 510

Asn Gln Thr Thr Tyr
        515


<210> SEQ ID NO 60
<211> LENGTH: 510
<212> TYPE: PRT
<213> ORGANISM: Pan troglodytes

<400> SEQUENCE: 60

Met Gly Val Leu Lys Phe Lys His Ile Phe Phe Arg Ser Phe Val Lys
1               5                   10                  15

Ser Ser Gly Val Ser Gln Ile Val Phe Thr Phe Leu Leu Ile Pro Cys
            20                  25                  30

Cys Leu Thr Leu Asn Phe Arg Ala Pro Pro Val Ile Pro Asn Val Pro
        35                  40                  45

Phe Leu Trp Ala Trp Asn Ala Pro Ser Glu Phe Cys Leu Gly Lys Phe
    50                  55                  60

Asp Glu Pro Leu Asp Met Ser Leu Phe Ser Phe Ile Gly Ser Pro Arg
65                  70                  75                  80

Ile Asn Val Thr Gly Gln Asp Val Thr Ile Phe Tyr Val Asp Arg Leu
                85                  90                  95
```

```
Gly Tyr Tyr Pro Tyr Ile Asp Ser Ile Thr Gly Val Thr Val Asn Gly
            100                 105                 110

Gly Ile Pro Gln Lys Ile Ser Leu Gln Asp His Leu Asp Lys Ala Lys
        115                 120                 125

Lys Asp Ile Thr Phe Tyr Met Pro Val Asp Asn Leu Gly Met Ala Val
    130                 135                 140

Ile Asp Trp Glu Glu Trp Arg Pro Thr Trp Ala Arg Asn Trp Lys Pro
145                 150                 155                 160

Lys Asp Val Tyr Lys Asn Arg Ser Ile Glu Leu Val Gln Gln Gln Asn
                165                 170                 175

Val Gln Leu Ser Leu Thr Glu Ala Thr Glu Lys Ala Lys Gln Glu Phe
            180                 185                 190

Glu Lys Ala Gly Lys Asp Phe Leu Val Glu Thr Ile Lys Leu Gly Lys
        195                 200                 205

Leu Leu Arg Pro Asn His Leu Trp Gly Tyr Tyr Leu Phe Pro Asp Cys
    210                 215                 220

Tyr Asn His His Tyr Lys Lys Pro Gly Tyr Asn Gly Ser Cys Phe Asn
225                 230                 235                 240

Val Glu Ile Lys Arg Asn Asp Asp Leu Ser Trp Leu Trp Asn Glu Ser
                245                 250                 255

Thr Ala Leu Tyr Pro Ser Ile Tyr Leu Asn Thr Gln Gln Ser Pro Val
            260                 265                 270

Ala Ala Thr Leu Tyr Val Arg Asn Arg Val Gln Glu Ala Ile Arg Val
        275                 280                 285

Ser Lys Ile Pro Asp Ala Lys Ser Pro Leu Pro Val Phe Val Tyr Thr
    290                 295                 300

Arg Ile Val Phe Thr Asp Gln Val Leu Lys Phe Leu Ser Gln Asp Glu
305                 310                 315                 320

Leu Val Tyr Thr Phe Gly Glu Thr Val Ala Leu Gly Ala Ser Gly Ile
                325                 330                 335

Val Ile Trp Gly Thr Leu Ser Ile Met Arg Ser Met Lys Ser Cys Leu
            340                 345                 350

Leu Leu Asp Asn Tyr Met Glu Thr Ile Leu Asn Pro Tyr Ile Ile Asn
        355                 360                 365

Val Thr Leu Ala Ala Lys Met Cys Ser Gln Val Leu Cys Gln Glu Gln
    370                 375                 380

Gly Val Cys Ile Arg Lys Asn Trp Asn Ser Ser Asp Tyr Leu His Leu
385                 390                 395                 400

Asn Pro Asp Asn Phe Ala Ile Gln Leu Glu Lys Gly Gly Lys Phe Thr
                405                 410                 415

Val Arg Gly Lys Pro Thr Leu Glu Asp Leu Glu Gln Phe Ser Glu Lys
            420                 425                 430

Phe Tyr Cys Ser Cys Tyr Ser Thr Leu Ser Cys Lys Glu Lys Ala Asp
        435                 440                 445

Val Lys Asp Thr Asp Ala Val Asp Val Cys Ile Ala Asp Gly Val Cys
    450                 455                 460

Ile Asp Ala Phe Leu Lys Pro Pro Met Glu Thr Glu Glu Ser Gln Ile
465                 470                 475                 480

Phe Tyr Asn Ala Ser Pro Ser Thr Leu Ser Ala Thr Met Phe Ile Asp
                485                 490                 495

Leu Cys Asp Leu Tyr Leu Val Pro Thr Ser Tyr Leu Ile Leu
            500                 505                 510
```

<210> SEQ ID NO 61
<211> LENGTH: 512
<212> TYPE: PRT
<213> ORGANISM: Pan troglodytes

<400> SEQUENCE: 61

```
Met Gly Val Leu Lys Phe Lys His Ile Phe Phe Arg Ser Phe Val Lys
1               5                   10                  15

Ser Ser Gly Val Ser Gln Ile Val Phe Thr Phe Leu Leu Ile Pro Cys
            20                  25                  30

Cys Leu Thr Leu Asn Phe Arg Ala Pro Pro Ile Ile Pro Asn Val Pro
        35                  40                  45

Phe Leu Trp Ala Trp Asn Ala Pro Ser Glu Phe Cys Leu Gly Lys Phe
    50                  55                  60

Asn Glu Pro Leu Asp Met Ser Leu Phe Thr Leu Met Gly Ser Pro Arg
65                  70                  75                  80

Ile Asn Ile Thr Gly Gln Gly Val Thr Ile Phe Tyr Val Asp Arg Leu
                85                  90                  95

Gly Tyr Tyr Pro Tyr Ile Asp Leu Thr Thr Gly Val Thr Val His Gly
            100                 105                 110

Gly Ile Pro Gln Lys Val Ser Leu Gln Asp His Leu Asp Lys Ser Lys
        115                 120                 125

Gln Asp Ile Leu Phe Tyr Met Pro Val Asp Asn Leu Gly Met Ala Val
    130                 135                 140

Ile Asp Trp Glu Glu Trp Arg Pro Thr Trp Ala Arg Asn Trp Lys Pro
145                 150                 155                 160

Lys Asp Val Tyr Lys Asn Arg Ser Ile Glu Leu Val Gln Gln Gln Asn
                165                 170                 175

Val Gln Leu Ser Leu Pro Gln Ala Thr Asp Lys Ala Lys Gln Glu Phe
            180                 185                 190

Glu Lys Ala Gly Lys Asp Phe Met Leu Glu Thr Ile Lys Leu Gly Arg
        195                 200                 205

Ser Leu Arg Pro Asn His Leu Trp Gly Tyr Tyr Leu Phe Pro Asp Cys
    210                 215                 220

Tyr Asn His His Tyr Arg Lys Pro Gly Tyr Asn Gly Ser Cys Phe Asp
225                 230                 235                 240

Val Glu Ile Lys Arg Asn Asp Asp Leu Ser Trp Leu Trp Asn Glu Ser
                245                 250                 255

Thr Ala Leu Tyr Pro Ser Ile Tyr Leu Asn Thr Gln Gln Ser Val Val
            260                 265                 270

Val Ala Thr Leu Tyr Val Arg Asn Arg Val Arg Glu Ala Ile Arg Val
        275                 280                 285

Ser Lys Ile Pro Asp Ala Lys Asn Pro Leu Pro Val Phe Val Tyr Ala
    290                 295                 300

Arg Leu Val Phe Thr Asp Gln Val Leu Lys Phe Leu Ser Arg Glu Glu
305                 310                 315                 320

Leu Val Ser Thr Leu Gly Glu Thr Val Ala Leu Gly Ala Ser Gly Ile
                325                 330                 335

Val Ile Trp Gly Ser Leu Ser Ile Thr Arg Ser Met Lys Ser Cys Leu
            340                 345                 350

Leu Leu Asp Thr Tyr Met Glu Thr Ile Leu Asn Pro Tyr Ile Ile Asn
        355                 360                 365

Val Thr Leu Ala Ala Lys Met Cys Ser Gln Val Leu Cys Gln Glu Gln
    370                 375                 380
```

```
Gly Val Cys Ile Arg Lys Asp Trp Asn Ser Ser Asp Tyr Leu His Leu
385                 390                 395                 400

Asn Pro Asp Asn Phe Asp Ile Arg Leu Glu Lys Gly Gly Lys Phe Thr
                405                 410                 415

Val His Gly Lys Pro Thr Val Glu Asp Leu Glu Glu Phe Ser Glu Lys
            420                 425                 430

Phe Tyr Cys Ser Cys Tyr Thr Asn Leu Ser Cys Lys Glu Lys Ala Asp
        435                 440                 445

Val Lys Asp Thr Asp Ala Val Asp Val Cys Ile Ala Asp Gly Val Cys
    450                 455                 460

Ile Asp Ala Ser Leu Lys Pro Pro Val Glu Thr Glu Gly Ser Pro Pro
465                 470                 475                 480

Ile Phe Tyr Asn Thr Ser Ser Ser Thr Val Ser Thr Thr Met Phe Ile
                485                 490                 495

Trp Arg Leu Glu Val Trp Asp Gln Gly Ile Ser Arg Ile Gly Phe Phe
            500                 505                 510


<210> SEQ ID NO 62
<211> LENGTH: 414
<212> TYPE: PRT
<213> ORGANISM: Pongo pygmaeus

<400> SEQUENCE: 62

Met Thr Thr Arg Leu Gly Pro Ala Leu Val Leu Gly Val Ala Leu Cys
1               5                   10                  15

Leu Gly Cys Gly Gln Pro Leu Pro Gln Val Pro Glu Arg Pro Phe Ser
            20                  25                  30

Val Leu Trp Asn Val Pro Ser Ala His Cys Lys Ser Arg Phe Gly Val
        35                  40                  45

His Leu Pro Leu Asn Ala Leu Gly Ile Ile Ala Asn Arg Gly Gln His
    50                  55                  60

Phe His Gly Gln Asn Met Thr Ile Phe Tyr Lys Asn Gln Leu Gly Leu
65                  70                  75                  80

Tyr Pro Tyr Phe Gly Pro Lys Gly Thr Ala His Asn Gly Gly Ile Pro
                85                  90                  95

Gln Ala Leu Pro Leu Asp Arg His Leu Ala Leu Ala Ala Tyr Gln Ile
            100                 105                 110

His His Ser Leu Arg Pro Gly Phe Ala Gly Pro Ala Val Leu Asp Trp
        115                 120                 125

Glu Glu Trp Cys Pro Leu Trp Ala Gly Asn Trp Gly Arg Arg Arg Ala
    130                 135                 140

Tyr Gln Ala Ala Ser Trp Ala Trp Ala Gln Gln Val Phe Pro Asp Leu
145                 150                 155                 160

Asp Pro Gln Glu Gln Leu Tyr Lys Ala Tyr Thr Gly Phe Glu Gln Ala
                165                 170                 175

Ala Arg Ala Leu Met Glu Asp Thr Leu Arg Val Ala Gln Ala Leu Arg
            180                 185                 190

Pro His Gly Leu Trp Gly Phe Tyr His Tyr Pro Ala Cys Gly Asn Gly
        195                 200                 205

Trp His Ser Met Ala Ser Asn Tyr Thr Gly Arg Cys His Ala Ala Thr
    210                 215                 220

Leu Ala Arg Asn Thr Gln Leu His Trp Leu Trp Ala Ala Ser Ser Ala
225                 230                 235                 240

Leu Phe Pro Ser Ile Tyr Leu Pro Pro Arg Leu Pro Pro Ala His His
```

-continued

```
                245                 250                 255

Gln Ala Phe Val Arg His Arg Leu Glu Glu Ala Phe Arg Val Ala Leu
            260                 265                 270

Val Gly His Leu Pro Val Leu Ala Tyr Val Arg Leu Thr His Arg Arg
        275                 280                 285

Ser Gly Arg Phe Leu Ser Gln Asp Asp Leu Val Gln Thr Ile Gly Val
    290                 295                 300

Ser Ala Ala Leu Gly Ala Ala Gly Val Val Leu Trp Gly Asp Leu Ser
305                 310                 315                 320

Leu Ser Ser Ser Glu Glu Glu Cys Trp His Leu His Asp Tyr Leu Val
                325                 330                 335

Asp Thr Leu Gly Pro Tyr Gly Ile Asn Val Thr Arg Ala Ala Met Ala
            340                 345                 350

Cys Ser His Gln Arg Cys His Gly His Gly Arg Cys Ala Arg Arg Asp
        355                 360                 365

Pro Gly Gln Met Glu Ala Phe Leu His Leu Trp Pro Asp Gly Ser Leu
    370                 375                 380

Gly Asp Trp Lys Ser Phe Ser Cys His Cys Tyr Trp Gly Trp Ala Gly
385                 390                 395                 400

Pro Thr Cys Gln Glu Pro Arg Leu Gly Pro Lys Glu Ala Val
                405                 410


<210> SEQ ID NO 63
<211> LENGTH: 510
<212> TYPE: PRT
<213> ORGANISM: Macaca fascicularis

<400> SEQUENCE: 63

Met Gly Val Leu Lys Phe Lys His Ile Phe Phe Arg Ser Phe Val Lys
1               5                   10                  15

Ser Ser Gly Val Ser Gln Ile Val Phe Thr Phe Leu Leu Ile Pro Cys
            20                  25                  30

Cys Leu Thr Leu Asn Phe Arg Ala Pro Pro Ile Ile Pro Asn Val Pro
        35                  40                  45

Phe Leu Trp Ala Trp Asn Ala Pro Ser Glu Phe Cys Leu Gly Lys Phe
    50                  55                  60

Asn Glu Pro Leu Asp Met Ser Leu Phe Thr Leu Met Gly Ser Pro Arg
65                  70                  75                  80

Ile Asn Val Thr Gly Gln Gly Val Thr Ile Phe Tyr Val Asp Arg Leu
                85                  90                  95

Gly Tyr Tyr Pro Tyr Ile Asp Leu Thr Thr Gly Val Thr Val His Gly
            100                 105                 110

Gly Ile Pro Gln Lys Val Ser Leu Gln Asp His Leu Asp Lys Ser Lys
        115                 120                 125

Gln Asp Ile Leu Phe Tyr Met Pro Val Asp Asn Leu Gly Met Ala Val
    130                 135                 140

Ile Asp Trp Glu Glu Trp Arg Pro Thr Trp Ala Arg Asn Trp Lys Pro
145                 150                 155                 160

Lys Asp Val Tyr Lys Asn Arg Ser Ile Glu Leu Val Gln Gln Gln Asn
                165                 170                 175

Val Gln Leu Ser Leu Pro Gln Ala Thr Asp Lys Ala Lys Gln Glu Phe
            180                 185                 190

Glu Lys Ala Gly Lys Asp Phe Met Leu Glu Thr Ile Lys Leu Gly Arg
        195                 200                 205
```

```
Ser Leu Arg Pro Asn His Leu Trp Gly Tyr Tyr Leu Phe Pro Asp Cys
    210                 215                 220

Tyr Asn His His Tyr Arg Lys Pro Gly Tyr Asn Gly Ser Cys Phe Asp
225                 230                 235                 240

Val Glu Ile Lys Arg Asn Asp Asp Leu Ser Trp Leu Trp Asn Glu Ser
                245                 250                 255

Thr Ala Leu Tyr Pro Ser Ile Tyr Leu Asn Thr Gln Gln Ser Val Val
            260                 265                 270

Val Ala Thr Leu Tyr Val Arg Asn Arg Val Arg Glu Ala Ile Arg Val
        275                 280                 285

Ser Lys Ile Pro Asp Ala Lys Asn Pro Leu Pro Val Phe Val Tyr Ala
    290                 295                 300

Arg Leu Val Phe Thr Asp Gln Val Leu Lys Phe Leu Ser Arg Glu Glu
305                 310                 315                 320

Leu Val Ser Thr Leu Gly Glu Thr Val Ala Leu Gly Ala Ser Gly Ile
                325                 330                 335

Val Ile Trp Gly Ser Leu Ser Ile Thr Arg Ser Met Lys Ser Cys Leu
            340                 345                 350

Leu Leu Asp Thr Tyr Met Glu Thr Ile Leu Asn Pro Tyr Ile Ile Asn
        355                 360                 365

Val Thr Leu Ala Ala Lys Met Cys Ser Gln Val Leu Cys Gln Glu Gln
    370                 375                 380

Gly Val Cys Ile Arg Lys Asp Trp Asn Ser Ser Asp Tyr Leu His Leu
385                 390                 395                 400

Asn Pro Asp Asn Phe Asp Ile Arg Leu Glu Lys Gly Gly Lys Phe Thr
                405                 410                 415

Val His Gly Lys Pro Thr Val Glu Asp Leu Glu Glu Phe Ser Glu Lys
            420                 425                 430

Phe Tyr Cys Ser Cys Tyr Thr Asn Leu Ser Cys Lys Glu Lys Ala Asp
        435                 440                 445

Val Lys Asp Thr Asp Ala Val Asp Val Cys Ile Ala Asp Gly Val Cys
    450                 455                 460

Ile Asp Ala Ser Leu Lys Pro Pro Val Glu Thr Glu Gly Ser Pro Pro
465                 470                 475                 480

Ile Phe Tyr Asn Thr Ser Ser Ser Thr Val Ser Thr Thr Met Phe Ile
                485                 490                 495

Val Asn Ile Leu Phe Leu Ile Ile Ser Ser Val Ala Ser Leu
            500                 505                 510


<210> SEQ ID NO 64
<211> LENGTH: 512
<212> TYPE: PRT
<213> ORGANISM: Mus musculus

<400> SEQUENCE: 64

Met Gly Glu Leu Arg Phe Lys His Leu Phe Trp Gly Ser Phe Val Glu
1               5                   10                  15

Ser Gly Gly Thr Phe Gln Thr Val Leu Ile Phe Leu Leu Ile Pro Cys
            20                  25                  30

Ser Leu Thr Val Asp Tyr Arg Ala Ala Pro Ile Leu Ser Asn Thr Thr
        35                  40                  45

Phe Leu Trp Ile Trp Asn Val Pro Thr Glu Arg Cys Val Gly Asn Val
    50                  55                  60

Asn Asp Pro Ile Asp Leu Ser Phe Phe Ser Leu Ile Gly Ser Pro Arg
65                  70                  75                  80
```

```
Lys Thr Ala Thr Gly Gln Pro Val Thr Leu Phe Tyr Val Asp Arg Leu
                85                  90                  95

Gly Leu Tyr Pro His Ile Asp Ala Asn Gln Ala Glu His Tyr Gly Gly
            100                 105                 110

Ile Pro Gln Arg Gly Asp Tyr Gln Ala His Leu Arg Lys Ala Lys Thr
        115                 120                 125

Asp Ile Glu His Tyr Ile Pro Asp Asp Lys Leu Gly Leu Ala Ile Ile
    130                 135                 140

Asp Trp Glu Glu Trp Arg Pro Thr Trp Leu Arg Asn Trp Lys Pro Lys
145                 150                 155                 160

Asp Asn Tyr Arg Asn Lys Ser Ile Glu Leu Val Gln Ser Thr Asn Pro
                165                 170                 175

Gly Leu Ser Ile Thr Glu Ala Thr Gln Lys Ala Ile Gln Gln Phe Glu
            180                 185                 190

Glu Ala Gly Arg Lys Phe Met Glu Gly Thr Leu His Leu Gly Lys Phe
        195                 200                 205

Leu Arg Pro Asn Gln Leu Trp Gly Tyr Tyr Leu Phe Pro Asp Cys Tyr
    210                 215                 220

Asn Asn Lys Phe Gln Asp Pro Lys Tyr Asp Gly Gln Cys Pro Ala Val
225                 230                 235                 240

Glu Lys Lys Arg Asn Asp Asn Leu Lys Trp Leu Trp Lys Ala Ser Thr
                245                 250                 255

Gly Leu Tyr Pro Ser Val Tyr Leu Lys Lys Asp Leu Lys Ser Asn Arg
            260                 265                 270

Gln Ala Thr Leu Tyr Val Arg Tyr Arg Val Val Glu Ala Ile Arg Val
        275                 280                 285

Ser Lys Val Gly Asn Ala Ser Asp Pro Val Pro Ile Phe Val Tyr Ile
    290                 295                 300

Arg Leu Val Phe Thr Asp Arg Thr Ser Glu Tyr Leu Leu Glu Asp Asp
305                 310                 315                 320

Leu Val Asn Thr Ile Gly Glu Ile Val Ala Leu Gly Thr Ser Gly Ile
                325                 330                 335

Ile Ile Trp Asp Ala Met Ser Leu Ala Gln Arg Ala Ala Gly Cys Pro
            340                 345                 350

Ile Leu His Lys Tyr Met Gln Thr Thr Leu Asn Pro Tyr Ile Val Asn
        355                 360                 365

Val Thr Leu Ala Ala Lys Met Cys Ser Gln Thr Leu Cys Asn Glu Lys
    370                 375                 380

Gly Met Cys Ser Arg Arg Lys Glu Ser Ser Asp Val Tyr Leu His Leu
385                 390                 395                 400

Asn Pro Ser His Phe Asp Ile Met Leu Thr Glu Thr Gly Lys Tyr Glu
                405                 410                 415

Val Leu Gly Asn Pro Arg Val Gly Asp Leu Glu Tyr Phe Ser Glu His
            420                 425                 430

Phe Lys Cys Ser Cys Phe Ser Arg Met Thr Cys Lys Glu Thr Ser Asp
        435                 440                 445

Val Lys Asn Val Gln Asp Val Asn Val Cys Val Gly Asp Asn Val Cys
    450                 455                 460

Ile Lys Ala Lys Val Glu Pro Asn Pro Ala Phe Tyr Leu Leu Pro Gly
465                 470                 475                 480

Lys Ser Leu Leu Phe Met Thr Thr Leu Gly His Val Leu Tyr His Leu
                485                 490                 495
```

-continued

Pro Gln Asp Ile Phe Val Phe Pro Arg Lys Thr Leu Val Ser Thr Pro
500 505 510

<210> SEQ ID NO 65
<211> LENGTH: 793
<212> TYPE: PRT
<213> ORGANISM: Arthrobacter sp.

<400> SEQUENCE: 65

Met Thr Arg Glu Phe Ser Arg Arg Thr Ala Leu Lys Gly Ala Ala Leu
1 5 10 15

Ser Gly Leu Leu Leu Ala Met Val His Gly Pro Ala His Ala Ala Ala
20 25 30

Thr Ala Asn Ala Thr Leu Thr Pro Ala Asp Phe Ala Gly Leu Arg Gln
35 40 45

Arg Trp Val Asp Gln Ile Thr Gly Arg Lys Val Leu Val Ala Gly Asp
50 55 60

Asn Asp Phe Val Thr Ala Leu Ala Ala Leu Asp Lys Lys Ala Arg Thr
65 70 75 80

Ala Ile Asp Leu Leu Glu Arg Ser Ala Gly Arg Leu Thr Val Phe Ser
85 90 95

Asp Leu Ser Leu Ala Lys Asp Thr Asp Leu Val Thr Thr His Thr Arg
100 105 110

Leu Ala Thr Met Ala Thr Ala Trp Ala Thr Pro Gly Ser Glu His Phe
115 120 125

Ala Asp Ala Gly Leu Leu Ala Ala Ile Arg Ala Gly Leu Ala Asp Ala
130 135 140

Asn Ser Leu Cys Tyr Asn Ala Ser Lys Glu Glu Gln Gly Asn Trp Trp
145 150 155 160

Ser Trp Glu Ile Gly Thr Pro Lys Ala Leu Ala Asp Thr Met Val Leu
165 170 175

Leu His Ala Glu Leu Thr Ala Ala Glu Arg Ala Ala Tyr Cys Ala Ala
180 185 190

Ile Asp His Phe Val Pro Asp Pro Trp Gln Gln Phe Pro Pro Lys Arg
195 200 205

Gly Lys Ile Thr Ser Val Gly Ala Asn Arg Val Asp Leu Cys Gln Ala
210 215 220

Val Thr Ile Arg Ser Leu Val Asp Glu Asp Ala Glu Lys Leu Thr His
225 230 235 240

Ala Val Ala Gly Leu Ser Glu Val Trp Gln Tyr Val Ser Ala Gly Asn
245 250 255

Gly Phe Phe Thr Asp Gly Ser Phe Ile Gln His Ser Thr Thr Pro Tyr
260 265 270

Thr Gly Ser Tyr Gly Val Val Leu Leu Thr Gly Leu Ser Lys Leu Phe
275 280 285

Ala Leu Leu Gly Gly Thr Gly Ala Glu Val Ser Asp Pro Ser Arg Asp
290 295 300

Ile Leu Phe Lys Thr Val Glu Gly Ser Phe Ala Pro Phe Met Val Ala
305 310 315 320

Gly Ala Met Ala Asp Ser Val Arg Gly Arg Ser Ile Ser Arg Glu Ser
325 330 335

Asn Thr Gly Phe Asp Leu Gly Ala Ser Thr Ile Glu Ser Ile Leu Leu
340 345 350

Leu Ala Arg Ala Val Asp Pro Val Thr Ala Arg Arg Trp Arg Ser Leu
355 360 365

-continued

```
Cys Leu Ala Trp Ile Asn Gln Asn Arg Lys Ala Pro Ile Leu Ala Asp
    370                 375                 380

Ala Gly Val Gly Arg Thr Ala Leu Val Lys Glu Leu Leu Ala Met Gly
385                 390                 395                 400

Leu Thr Glu Thr Asp Leu Pro Gly Gly His Tyr Leu Phe Pro Ala Met
                405                 410                 415

Asp Arg Thr Met His His Ser Gln Gly Trp Thr Leu Ser Thr Ala Met
            420                 425                 430

Ala Ser Ser Arg Ile Ala Trp Tyr Glu Cys Gly Asn Gly Glu Asn Asn
        435                 440                 445

Arg Gly Tyr His Thr Gly Ser Gly Met Thr Tyr Val Tyr Asp Gly Asp
    450                 455                 460

Leu Gly Gln Tyr Asp Asp Ala Phe Trp Ala Thr Ala Asn His Cys Arg
465                 470                 475                 480

Leu Pro Gly Ile Thr Val Asp Thr Ser Ser Leu Pro Asp Lys Val Glu
                485                 490                 495

Gly Glu Trp Gly Ala Ala Thr Pro Ala Asn Glu Trp Thr Gly Ser Thr
            500                 505                 510

Ala Tyr Gly Asp Val Ala Ala Val Gly Gln His Leu Ile Gly Pro Gly
        515                 520                 525

Gly Thr Gly Leu Thr Ala Arg Lys Ser Trp Phe Val Ser Lys Asp Val
    530                 535                 540

Ile Val Cys Leu Gly Ala Asp Ile Arg Thr Gly Ser Gly Ser Arg Ile
545                 550                 555                 560

Glu Thr Val Val Asp His Arg Asn Leu His Ala Gly Phe Asn Ala Met
                565                 570                 575

Gly Thr Ala Ala Gly Thr Val Ala Ala Thr Pro Gly His Pro Glu Val
            580                 585                 590

Leu Thr Val Asp Arg Trp Val His Leu Glu Gly Phe Gly Gly Tyr Val
        595                 600                 605

Val Leu Asp Ala Ala Pro Leu Gln Val Leu Arg Glu Gln Arg Glu Gly
    610                 615                 620

Ser Trp Ser Glu Val Asn Val Lys Gly Ser Ala Ala Arg Gln Thr Arg
625                 630                 635                 640

Asn Tyr Ala Thr Leu Tyr Phe Asp His Gly His Glu Pro Glu Ala Ala
                645                 650                 655

Ser Tyr Ala Tyr Leu Val Ala Pro Gly Ala Ser Ala Ser Met Thr Ser
            660                 665                 670

Ser Leu Ser Gly Gln Ser Phe His Thr Val Leu Arg Asn Asp Glu Val
        675                 680                 685

Ala Gln Ala Val Lys Phe Lys Lys Glu Lys Thr Thr Ala Ala Thr Phe
    690                 695                 700

Trp Arg Pro Gly Thr Val Gly Asp Leu Ala Leu Ser Gly Pro Ala Cys
705                 710                 715                 720

Val Val Val Lys Glu Val Gly Asp Arg Leu Ser Ile Ala Val Ser Asp
                725                 730                 735

Pro Thr Gln Asn Ala Ser Thr Leu Thr Leu Arg Leu Lys Thr Lys Arg
            740                 745                 750

Phe Phe Arg Ile Ile Glu Gly Gln Gly Ala Ser Leu Ser His Gly Ala
        755                 760                 765

Asp Gly Phe Thr Val Leu Glu Val Asp Ile Ala Asn His Ala Gly Arg
    770                 775                 780
```

```
Thr Lys Gln Ile Glu Leu Ser Ala Glu
785                 790


<210> SEQ ID NO 66
<211> LENGTH: 557
<212> TYPE: PRT
<213> ORGANISM: Bdellovibrio bacteriovorus

<400> SEQUENCE: 66

Met Thr Lys Phe Phe Phe Leu Leu Thr Leu Ile Ser Ala Thr Ala Phe
1               5                   10                  15

Ala Gln Ser Glu Pro Asp Trp Thr Ala Gly Val Pro Val Pro Pro Gly
            20                  25                  30

Gly Arg Ser Asn Ile Tyr Ser Trp Asn Asp Phe Asp Phe Gln Ala Thr
        35                  40                  45

Leu Asn Lys Gly Lys Ile His Ala Gln Val Tyr Pro Val Thr Val Thr
    50                  55                  60

Gly Met Leu Pro Pro Tyr Glu Pro Val Arg Arg Leu Ile Glu Glu Lys
65                  70                  75                  80

Asn Ser Asn Pro Leu Arg Lys Trp Ile Gln Ser Leu Met Lys Gly Leu
                85                  90                  95

Ser Gly Phe Arg Ser Phe Glu Asp Val Leu Lys Asn Leu Gly Leu His
            100                 105                 110

Lys Tyr Pro Leu Glu Asn Glu Arg Gly Val Tyr Ala Val Pro Tyr Pro
        115                 120                 125

Asn Glu Ile Arg Pro Asp Thr Leu Met Gly Phe Gly Leu Ile Glu Arg
    130                 135                 140

Asn Gly Ala Glu Gly Phe Thr Phe Ser Cys Ala Ala Cys His Ser Ser
145                 150                 155                 160

Asn Leu Phe Gly Lys Thr Val Leu Gly Met Thr Asn Arg Phe Pro Arg
                165                 170                 175

Ala Asn Glu Phe Phe Ile Lys Ala Lys Lys Val Met Pro Leu Met Asp
            180                 185                 190

Pro His Ile Phe Gln Ala Tyr Thr Arg Ala Thr Asp Ala Glu Thr Ala
        195                 200                 205

Leu Leu Val Glu Ser Lys Glu Arg Leu Lys Ser Val Ala Leu Lys Gln
    210                 215                 220

Pro Ile Ala Leu Gly Leu Asp Thr Ser Leu Ala Gln Val Ser Leu Ser
225                 230                 235                 240

Leu Asn Arg Arg Ala Lys Asp Gly Tyr Ala Asn Tyr Ser Asp Lys Ala
                245                 250                 255

Ala Arg Ser Pro Arg Ala Asp Ala Tyr Leu Asp Asn Lys Pro Ala Asp
            260                 265                 270

Ser Lys Pro Ala Val Trp Trp Asn Val Lys Tyr Lys Asn Arg Trp Leu
        275                 280                 285

Ser Asp Gly Ser Val Leu Ser Gly Asn Pro Ile Phe Thr Asn Leu Ile
    290                 295                 300

Trp Asn Glu Ile Gly Arg Gly Ala Asp Leu His Glu Leu Glu Gln Trp
305                 310                 315                 320

Leu Ala Asp Asn Asp His Ile Ile Lys Glu Leu Thr Thr Ala Val Phe
                325                 330                 335

Ala Ser Glu Ala Pro His Ile Thr Asp Phe Tyr Pro Ala Glu Lys Ile
            340                 345                 350

Asp Leu Gly Arg Ala Lys Ala Gly Glu Gln Ile Phe Lys Asn Thr Cys
        355                 360                 365
```

```
Ala Lys Cys His Gly His Tyr Glu Lys Ala Trp Asn Leu Pro Gln Ala
    370                 375                 380

Leu Val Leu Ser Ala Ala Glu Arg Leu Lys Thr Val Glu Val Arg Tyr
385                 390                 395                 400

Lys Glu Lys Thr Pro Val Val Asn Val Gly Thr Asp Pro Phe Arg Arg
                405                 410                 415

Gln Gly Met Lys Ser Leu Glu Gln Leu Asn Asp Leu Glu Ile Ser Lys
            420                 425                 430

Lys Asn Gly Ile Val Ile Lys Ala Gln Glu Gly Tyr Val Pro Pro Pro
        435                 440                 445

Leu Val Gly Ile Trp Ala Arg Trp Pro Tyr Met His Asn Asn Ser Ile
    450                 455                 460

Pro Asn Leu Cys Val Leu Leu Thr Pro Ala Lys Lys Arg Pro Ser Ile
465                 470                 475                 480

Tyr Tyr Ser Gly Glu Ala Leu Asn Lys Asp Thr Asp Tyr Asp Phe Ser
                485                 490                 495

Cys Gly Gly Tyr Pro Ile Gly Asp Lys Thr Pro Lys Ala Trp Lys Thr
            500                 505                 510

Arg Glu His Leu Tyr Asp Thr Arg Asn Pro Gly Met Gly Asn Met Gly
        515                 520                 525

His Asp Glu Gly Ile Phe Ile Lys Asp Gly Lys Glu Ile Leu Ser Ala
    530                 535                 540

Glu Asp Lys Tyr Asn Leu Ile Gln Phe Leu Gln Thr Leu
545                 550                 555


<210> SEQ ID NO 67
<211> LENGTH: 813
<212> TYPE: PRT
<213> ORGANISM: Propionibacterium acnes

<400> SEQUENCE: 67

Met Phe Gly Thr Pro Ser Arg Arg Thr Phe Leu Thr Ala Ser Ala Leu
1               5                   10                  15

Ser Ala Met Ala Leu Ala Ala Ser Pro Thr Val Thr Asp Ala Ile Ala
            20                  25                  30

Ala Pro Gly Pro Asp Ser Trp Ser Ala Leu Cys Glu Arg Trp Ile Asp
        35                  40                  45

Ile Ile Thr Gly Arg Arg Ala Ala Arg Thr Ser Asp Pro Arg Ala Arg
    50                  55                  60

Ala Ile Ile Ala Lys Thr Asp Arg Lys Val Ala Glu Ile Leu Thr Asp
65                  70                  75                  80

Leu Val Ser Gly Ser Ser Arg Gln Thr Val Leu Ile Ser Ala Asp Leu
                85                  90                  95

Arg Lys Glu Gln Ser Pro Phe Ile Thr Lys Thr Ala Arg Ala Ile Glu
            100                 105                 110

Ser Met Ala Cys Ala Trp Ala Thr Pro Gly Ser Ser Tyr His Lys Asp
        115                 120                 125

Pro Glu Ile Leu Ser Ala Cys Ile Glu Gly Leu Arg Asp Phe Cys Arg
    130                 135                 140

Leu Arg Tyr Asn Pro Ser Gln Asp Glu Tyr Gly Asn Trp Trp Asp Trp
145                 150                 155                 160

Glu Asp Gly Ala Ser Arg Ala Val Ala Asp Val Met Cys Ile Leu His
                165                 170                 175

Asp Val Leu Pro Pro Glu Val Met Ser Ala Ala Ala Ala Gly Ile Asp
```

-continued

```
            180                 185                 190

His Phe Ile Pro Asp Pro Trp Phe Gln Gln Pro Ala Ser Val Lys Pro
        195                 200                 205

Thr Ala Asn Pro Val Gln Pro Val Val Ser Thr Gly Ala Asn Arg Met
    210                 215                 220

Asp Leu Thr Arg Ala Val Met Cys Arg Ser Ile Ala Thr Gly Asp Glu
225                 230                 235                 240

Lys Arg Leu Arg His Ala Val Asp Gly Leu Pro Asp Ala Trp Arg Val
                245                 250                 255

Thr Thr Glu Gly Asp Gly Phe Arg Ala Asp Gly Gly Phe Ile Gln His
            260                 265                 270

Ser His Ile Pro Tyr Thr Gly Gly Tyr Gly Asp Val Leu Phe Ser Gly
        275                 280                 285

Leu Ala Met Leu Phe Pro Leu Val Ser Gly Met Arg Phe Asp Ile Val
    290                 295                 300

Glu Ser Ala Arg Lys Ala Phe His Asp Gln Val Glu Arg Gly Phe Ile
305                 310                 315                 320

Pro Val Met Tyr Asn Gly Gln Ile Leu Asp Asp Val Arg Gly Arg Ser
                325                 330                 335

Ile Ser Arg Ile Asn Glu Ser Ala Ala Met His Gly Ile Ser Ile Ala
            340                 345                 350

Arg Ala Met Leu Met Met Ala Asp Ala Leu Pro Thr His Arg Ala Glu
        355                 360                 365

Gln Trp Arg Gly Ile Val His Gly Trp Met Ala Arg Asn Thr Phe Asp
    370                 375                 380

His Leu Ser Glu Pro Ser Thr Leu Val Asp Ile Ser Leu Phe Asp Ala
385                 390                 395                 400

Ala Ala Lys Ala Arg Pro Val Pro Glu Ser Ser Thr Pro Ser Tyr Phe
                405                 410                 415

Ala Ser Met Asp Arg Leu Val His Arg Thr Ala Asp Trp Leu Ile Thr
            420                 425                 430

Val Ser Asn Cys Ser Asp Arg Ile Ala Trp Tyr Glu Tyr Gly Asn Gly
        435                 440                 445

Glu Asn Glu Trp Ala Ser Arg Thr Ser Gln Gly Met Arg Tyr Leu Leu
    450                 455                 460

Leu Pro Gly Asp Met Gly Gln Tyr Glu Asp Gly Tyr Trp Ala Thr Val
465                 470                 475                 480

Asp Tyr Ser Ala Pro Thr Gly Thr Thr Val Asp Ser Thr Pro Leu Lys
                485                 490                 495

Arg Ala Val Gly Ala Ser Trp Ala Ala Lys Thr Pro Thr Asn Glu Trp
            500                 505                 510

Ser Gly Gly Leu Ala Ser Gly Ser Trp Ser Ala Ala Ala Ser His Ile
        515                 520                 525

Thr Ser Gln Asp Ser Ala Leu Lys Ala Arg Arg Leu Trp Val Gly Leu
    530                 535                 540

Lys Asp Ala Met Val Glu Leu Thr Thr Asp Val Thr Thr Asp Ala Ser
545                 550                 555                 560

Arg Ala Ile Thr Val Val Glu His Arg Lys Val Ala Ser Ser Ser Thr
                565                 570                 575

Lys Leu Leu Val Asp Gly Asn Arg Val Ser Ser Ala Thr Ser Phe Gln
            580                 585                 590

Asn Pro Arg Trp Ala His Leu Asp Gly Val Gly Gly Tyr Val Phe Ala
        595                 600                 605
```

Thr Asp Thr Asp Leu Ser Ala Asp Val Ala Thr Arg Lys Gly Thr Trp
610 615 620

Ile Asp Val Asn Pro Ser Arg Lys Val Lys Gly Ala Asp Glu Val Ile
625 630 635 640

Glu Arg Ala Tyr Ala Ser Leu His Val Thr His His Asp Arg Pro Val
645 650 655

Ala Trp Ala Leu Leu Pro Thr Ala Ser Arg Ser His Thr Met Ala Leu
660 665 670

Ala Thr Arg Pro Gly Val Glu Pro Phe Thr Val Leu Arg Asn Asp Ala
675 680 685

Thr Val Gln Ala Val Arg Ser Ala Gly Ala Leu Leu Thr Lys Asp Pro
690 695 700

Thr Val Val Thr Thr Leu Ala Phe Trp Lys Pro Ala Thr Cys Gly Gly
705 710 715 720

Val Ala Val Asn Arg Pro Ala Leu Val Gln Thr Arg Glu Ser Ala Asn
725 730 735

Gln Met Glu Val Val Ile Val Glu Pro Thr Gln Lys Arg Gly Ser Leu
740 745 750

Thr Val Thr Ile Glu Gly Ser Trp Lys Val Lys Thr Ala Asp Ser His
755 760 765

Val Asp Val Ser Cys Glu Asn Ala Ala Gly Thr Leu His Val Asp Thr
770 775 780

Ala Gly Leu Gly Gly Gln Ser Val Arg Val Thr Leu Ala Arg Gln Val
785 790 795 800

Thr Gln Thr Pro Ser Gly Gly Gly Arg His Asp Arg Ala
805 810

<210> SEQ ID NO 68
<211> LENGTH: 1072
<212> TYPE: PRT
<213> ORGANISM: Streptococcus agalactiae

<400> SEQUENCE: 68

Met Glu Ile Lys Lys Lys Tyr Arg Ile Met Leu Tyr Ser Ala Leu Ile
1 5 10 15

Leu Gly Thr Ile Leu Val Asn Asn Ser Tyr Gln Ala Lys Ala Glu Glu
20 25 30

Leu Thr Lys Thr Thr Ser Thr Ser Gln Ile Arg Asp Thr Gln Thr Asn
35 40 45

Asn Ile Glu Val Leu Gln Thr Glu Ser Thr Thr Val Lys Glu Thr Ser
50 55 60

Thr Thr Thr Thr Gln Gln Asp Leu Ser Asn Pro Thr Ala Ser Thr Ala
65 70 75 80

Thr Ala Thr Ala Thr His Ser Thr Met Lys Gln Val Val Asp Asn Gln
85 90 95

Thr Gln Asn Lys Glu Leu Val Lys Asn Gly Asp Phe Asn Gln Thr Asn
100 105 110

Pro Val Ser Gly Ser Trp Ser His Thr Ser Ala Arg Glu Trp Ser Ala
115 120 125

Trp Ile Asp Lys Glu Asn Thr Ala Asp Lys Ser Pro Ile Ile Gln Arg
130 135 140

Thr Glu Gln Gly Gln Val Ser Leu Ser Ser Asp Lys Gly Phe Arg Gly
145 150 155 160

Ala Val Thr Gln Lys Val Asn Ile Asp Pro Thr Lys Lys Tyr Glu Val

-continued

```
                165                 170                 175

Lys Phe Asp Ile Glu Thr Ser Asn Lys Ala Gly Gln Ala Phe Leu Arg
            180                 185                 190

Ile Met Glu Lys Lys Asp Asn Asn Thr Arg Leu Trp Leu Ser Glu Met
        195                 200                 205

Thr Ser Gly Thr Thr Asn Lys His Thr Leu Thr Lys Ile Tyr Asn Pro
    210                 215                 220

Lys Leu Asn Val Ser Glu Val Thr Leu Glu Leu Tyr Tyr Glu Lys Gly
225                 230                 235                 240

Thr Gly Ser Ala Thr Phe Asp Asn Ile Ser Met Lys Ala Lys Gly Pro
                245                 250                 255

Lys Asp Ser Glu His Pro Gln Pro Val Thr Thr Gln Ile Glu Glu Ser
            260                 265                 270

Val Asn Thr Ala Leu Asn Lys Asn Tyr Val Phe Asn Lys Ala Asp Tyr
        275                 280                 285

Gln Tyr Thr Leu Thr Asn Pro Ser Leu Gly Lys Ile Val Gly Gly Ile
    290                 295                 300

Leu Tyr Pro Asn Ala Thr Gly Ser Thr Thr Val Lys Ile Ser Asp Lys
305                 310                 315                 320

Ser Gly Lys Ile Ile Lys Glu Val Pro Leu Ser Val Thr Ala Ser Thr
                325                 330                 335

Glu Asp Lys Phe Thr Lys Leu Leu Asp Lys Trp Asn Asp Val Thr Ile
            340                 345                 350

Gly Asn His Val Tyr Asp Thr Asn Asp Ser Asn Met Gln Lys Ile Asn
        355                 360                 365

Gln Lys Leu Asp Glu Thr Asn Ala Lys Asn Ile Lys Thr Ile Lys Leu
    370                 375                 380

Asp Ser Asn His Thr Phe Leu Trp Lys Asp Leu Asp Asn Leu Asn Asn
385                 390                 395                 400

Ser Ala Gln Leu Thr Ala Thr Tyr Arg Arg Leu Glu Asp Leu Ala Lys
                405                 410                 415

Gln Ile Thr Asn Pro His Ser Thr Ile Tyr Lys Asn Glu Lys Ala Ile
            420                 425                 430

Arg Thr Val Lys Glu Ser Leu Ala Trp Leu His Gln Asn Phe Tyr Asn
        435                 440                 445

Val Asn Lys Asp Ile Glu Gly Ser Ala Asn Trp Trp Asp Phe Glu Ile
    450                 455                 460

Gly Val Pro Arg Ser Ile Thr Ala Thr Leu Ala Leu Met Asn Asn Tyr
465                 470                 475                 480

Phe Thr Asp Ala Glu Ile Lys Thr Tyr Thr Asp Pro Ile Glu His Phe
                485                 490                 495

Val Pro Asp Ala Gly Tyr Phe Arg Lys Thr Leu Asp Asn Pro Phe Lys
            500                 505                 510

Ala Leu Gly Gly Asn Leu Val Asp Met Gly Arg Val Lys Ile Ile Glu
        515                 520                 525

Gly Leu Leu Arg Lys Asp Asn Thr Ile Ile Glu Lys Thr Ser His Ser
    530                 535                 540

Leu Lys Asn Leu Phe Thr Thr Ala Thr Lys Ala Glu Gly Phe Tyr Ala
545                 550                 555                 560

Asp Gly Ser Tyr Ile Asp His Thr Asn Val Ala Tyr Thr Gly Ala Tyr
                565                 570                 575

Gly Asn Val Leu Ile Asp Gly Leu Thr Gln Leu Leu Pro Ile Ile Gln
            580                 585                 590
```

```
Glu Thr Asp Tyr Lys Ile Ser Asn Gln Glu Leu Asp Met Val Tyr Lys
        595                 600                 605

Trp Ile Asn Gln Ser Phe Leu Pro Leu Ile Val Lys Gly Glu Leu Met
    610                 615                 620

Asp Met Ser Arg Gly Arg Ser Ile Ser Arg Glu Ala Ala Ser Ser His
625                 630                 635                 640

Ala Ala Ala Val Glu Val Leu Arg Gly Phe Leu Arg Leu Ala Asn Met
                645                 650                 655

Ser Asn Glu Glu Arg Asn Leu Asp Leu Lys Ser Thr Ile Lys Thr Ile
            660                 665                 670

Ile Thr Ser Asn Lys Phe Tyr Asn Val Phe Asn Asn Leu Lys Ser Tyr
        675                 680                 685

Ser Asp Ile Ala Asn Met Asn Lys Met Leu Asn Asp Ser Thr Val Ala
    690                 695                 700

Thr Lys Pro Leu Lys Ser Asn Leu Ser Thr Phe Asn Ser Met Asp Arg
705                 710                 715                 720

Leu Ala Tyr Tyr Asn Ala Glu Lys Asp Phe Gly Phe Ala Leu Ser Leu
                725                 730                 735

His Ser Lys Arg Thr Leu Asn Tyr Glu Gly Met Asn Asp Glu Asn Thr
            740                 745                 750

Arg Gly Trp Tyr Thr Gly Asp Gly Met Phe Tyr Leu Tyr Asn Ser Asp
        755                 760                 765

Gln Ser His Tyr Ser Asn His Phe Trp Pro Thr Val Asn Pro Tyr Lys
    770                 775                 780

Met Ala Gly Thr Thr Glu Lys Asp Ala Lys Arg Glu Asp Thr Thr Lys
785                 790                 795                 800

Glu Phe Met Ser Lys His Ser Lys Asp Ala Lys Glu Lys Thr Gly Gln
                805                 810                 815

Val Thr Gly Thr Ser Asp Phe Val Gly Ser Val Lys Leu Asn Asp His
            820                 825                 830

Phe Ala Leu Ala Ala Met Asp Phe Thr Asn Trp Asp Arg Thr Leu Thr
        835                 840                 845

Ala Gln Lys Gly Trp Val Ile Leu Asn Asp Lys Ile Val Phe Leu Gly
    850                 855                 860

Ser Asn Ile Lys Asn Thr Asn Gly Ile Gly Asn Val Ser Thr Thr Ile
865                 870                 875                 880

Asp Gln Arg Lys Asp Asp Ser Lys Thr Pro Tyr Thr Thr Tyr Val Asn
                885                 890                 895

Gly Lys Thr Ile Asp Leu Lys Gln Ala Ser Ser Gln Gln Phe Thr Asp
            900                 905                 910

Thr Lys Ser Val Phe Leu Glu Ser Lys Glu Pro Gly Arg Asn Ile Gly
        915                 920                 925

Tyr Ile Phe Phe Lys Asn Ser Thr Ile Asp Ile Glu Arg Lys Glu Gln
    930                 935                 940

Thr Gly Thr Trp Asn Ser Ile Asn Arg Thr Ser Lys Asn Thr Ser Ile
945                 950                 955                 960

Val Ser Asn Pro Phe Ile Thr Ile Ser Gln Lys His Asp Asn Lys Gly
                965                 970                 975

Asp Ser Tyr Gly Tyr Met Met Val Pro Asn Ile Asp Arg Thr Ser Phe
            980                 985                 990

Asp Lys Leu Ala Asn Ser Lys Glu  Val Glu Leu Leu Glu  Asn Ser Ser
        995                 1000                1005
```

```
Lys Gln  Gln Val Ile Tyr Asp  Lys Asn Ser Gln Thr  Trp Ala Val
    1010                 1015                 1020

Ile Lys  His Asp Asn Gln Glu  Ser Leu Ile Asn Asn  Gln Phe Lys
    1025                 1030                 1035

Met Asn  Lys Ala Gly Leu Tyr  Leu Val Gln Lys Val  Gly Asn Asp
    1040                 1045                 1050

Tyr Gln  Asn Val Tyr Tyr Gln  Pro Gln Thr Met Thr  Lys Thr Asp
    1055                 1060                 1065

Gln Leu  Ala Ile
    1070


<210> SEQ ID NO 69
<211> LENGTH: 1072
<212> TYPE: PRT
<213> ORGANISM: Streptococcus agalactiae

<400> SEQUENCE: 69

Met Glu Ile Lys Lys Lys His Arg Ile Met Leu Tyr Ser Ala Leu Ile
1               5                   10                  15

Leu Gly Thr Ile Leu Val Asn Asn Ser Tyr Gln Ala Lys Ala Glu Glu
            20                  25                  30

Leu Thr Lys Thr Thr Ser Thr Ser Gln Ile Arg Asp Thr Gln Thr Asn
        35                  40                  45

Asn Ile Glu Val Leu Gln Thr Glu Ser Thr Thr Val Lys Glu Thr Ser
    50                  55                  60

Thr Thr Thr Thr Gln Gln Asp Leu Ser Asn Pro Thr Ala Ser Thr Ala
65                  70                  75                  80

Thr Ala Thr Ala Thr His Ser Thr Met Lys Gln Val Val Asp Asn Gln
                85                  90                  95

Thr Gln Asn Lys Glu Leu Val Lys Asn Gly Asp Phe Asn Gln Thr Asn
            100                 105                 110

Pro Val Ser Gly Ser Trp Ser His Thr Ser Ala Arg Glu Trp Ser Ala
        115                 120                 125

Trp Ile Asp Lys Glu Asn Thr Ala Asp Lys Ser Pro Ile Ile Gln Arg
    130                 135                 140

Thr Glu Gln Gly Gln Val Ser Leu Ser Ser Asp Lys Gly Phe Arg Gly
145                 150                 155                 160

Ala Val Thr Gln Lys Val Asn Ile Asp Pro Thr Lys Lys Tyr Glu Val
                165                 170                 175

Lys Phe Asp Ile Glu Thr Ser Asn Lys Ala Gly Gln Ala Phe Leu Arg
            180                 185                 190

Ile Met Glu Lys Lys Asp Asn Asn Thr Arg Leu Trp Leu Ser Glu Met
        195                 200                 205

Thr Ser Gly Thr Thr Asn Lys His Thr Leu Thr Lys Ile Tyr Asn Pro
    210                 215                 220

Lys Leu Asn Val Ser Glu Val Thr Leu Glu Leu Tyr Tyr Glu Lys Gly
225                 230                 235                 240

Thr Gly Ser Ala Thr Phe Asp Asn Ile Ser Met Lys Ala Lys Gly Pro
                245                 250                 255

Lys Asp Ser Glu His Pro Gln Pro Val Thr Thr Gln Ile Glu Glu Ser
            260                 265                 270

Val Asn Thr Ala Leu Asn Lys Asn Tyr Val Phe Asn Lys Ala Asp Tyr
        275                 280                 285

Gln Tyr Thr Leu Thr Asn Pro Ser Leu Gly Lys Ile Val Gly Gly Ile
    290                 295                 300
```

-continued

```
Leu Tyr Pro Asn Ala Thr Gly Ser Thr Thr Val Lys Ile Ser Asp Lys
305                 310                 315                 320

Ser Gly Lys Ile Ile Lys Glu Val Pro Leu Ser Val Thr Ala Ser Thr
                325                 330                 335

Glu Asp Lys Phe Thr Lys Leu Leu Asp Lys Trp Asn Asp Val Thr Ile
            340                 345                 350

Gly Asn His Val Tyr Asp Thr Asn Asp Ser Asn Met Gln Lys Ile Asn
        355                 360                 365

Gln Lys Leu Asp Glu Thr Asn Ala Lys Asn Ile Lys Thr Ile Lys Leu
    370                 375                 380

Asp Ser Asn His Thr Phe Leu Trp Lys Asp Leu Asp Asn Leu Asn Asn
385                 390                 395                 400

Ser Ala Gln Leu Thr Ala Thr Tyr Arg Arg Leu Glu Asp Leu Ala Lys
                405                 410                 415

Gln Ile Thr Asn Pro His Ser Thr Ile Tyr Lys Asn Glu Lys Ala Ile
            420                 425                 430

Arg Thr Val Lys Glu Ser Leu Ala Trp Leu His Gln Asn Phe Tyr Asn
        435                 440                 445

Val Asn Lys Asp Ile Glu Gly Ser Ala Asn Trp Trp Asp Phe Glu Ile
    450                 455                 460

Gly Val Pro Arg Ser Ile Thr Ala Thr Leu Ala Leu Met Asn Asn Tyr
465                 470                 475                 480

Phe Thr Asp Ala Glu Ile Lys Thr Tyr Thr Asp Pro Ile Glu His Phe
                485                 490                 495

Val Pro Asp Ala Gly Tyr Phe Arg Lys Thr Leu Asp Asn Pro Phe Lys
            500                 505                 510

Ala Leu Gly Gly Asn Leu Val Asp Met Gly Arg Val Lys Ile Ile Glu
        515                 520                 525

Gly Leu Leu Arg Lys Asp Asn Thr Ile Ile Glu Lys Thr Ser His Ser
    530                 535                 540

Leu Lys Asn Leu Phe Thr Thr Ala Thr Lys Ala Glu Gly Phe Tyr Ala
545                 550                 555                 560

Asp Gly Ser Tyr Ile Asp His Thr Asn Val Ala Tyr Thr Gly Ala Tyr
                565                 570                 575

Gly Asn Val Leu Ile Asp Gly Leu Thr Gln Leu Leu Pro Ile Ile Gln
            580                 585                 590

Glu Thr Asp Tyr Lys Ile Ser Asn Gln Glu Leu Asp Met Val Tyr Lys
        595                 600                 605

Trp Ile Asn Gln Ser Phe Leu Pro Leu Ile Val Lys Gly Glu Leu Met
    610                 615                 620

Asp Met Ser Arg Gly Arg Ser Ile Ser Arg Glu Ala Ala Ser Ser His
625                 630                 635                 640

Ala Ala Ala Val Glu Val Leu Arg Gly Phe Leu Arg Leu Ala Asn Met
                645                 650                 655

Ser Asn Glu Glu Arg Asn Leu Asp Leu Ile Ser Thr Ile Lys Thr Ile
            660                 665                 670

Ile Thr Ser Asn Lys Phe Tyr Asn Val Phe Asn Asn Leu Lys Ser Tyr
        675                 680                 685

Ser Asp Ile Ala Asn Met Asn Lys Met Leu Asn Asp Ser Thr Val Ala
    690                 695                 700

Thr Lys Pro Leu Lys Ser Asn Leu Ser Thr Phe Asn Ser Met Asp Arg
705                 710                 715                 720
```

-continued

```
Leu Ala Tyr Tyr Asn Ala Glu Lys Asp Phe Gly Phe Ala Leu Ser Leu
            725                 730                 735

His Ser Lys Arg Thr Leu Asn Tyr Glu Gly Met Asn Asp Glu Asn Thr
            740                 745                 750

Arg Gly Trp Tyr Thr Gly Asp Gly Met Phe Tyr Leu Tyr Asn Ser Asp
        755                 760                 765

Gln Ser His Tyr Ser Asn His Phe Trp Pro Thr Val Asn Pro Tyr Lys
    770                 775                 780

Met Ala Gly Thr Thr Glu Lys Asp Ala Lys Arg Glu Asp Thr Thr Lys
785                 790                 795                 800

Glu Phe Met Ser Lys His Ser Lys Asp Ala Lys Glu Lys Thr Gly Gln
            805                 810                 815

Val Thr Gly Thr Ser Asp Phe Val Gly Ser Val Lys Leu Asn Asp His
            820                 825                 830

Phe Ala Leu Ala Ala Met Asp Phe Thr Asn Trp Asp Arg Thr Leu Thr
        835                 840                 845

Ala Gln Lys Gly Trp Val Ile Leu Asn Asp Lys Ile Val Phe Leu Gly
    850                 855                 860

Ser Asn Ile Lys Asn Thr Asn Gly Ile Gly Asn Val Ser Thr Thr Ile
865                 870                 875                 880

Asp Gln Arg Lys Asp Asp Ser Lys Thr Pro Tyr Thr Thr Tyr Val Asn
            885                 890                 895

Gly Lys Thr Ile Asp Leu Lys Gln Ala Ser Ser Gln Gln Phe Thr Asp
            900                 905                 910

Thr Lys Ser Val Phe Leu Glu Ser Lys Glu Pro Gly Arg Asn Ile Gly
        915                 920                 925

Tyr Ile Phe Phe Lys Asn Ser Thr Ile Asp Ile Glu Arg Lys Glu Gln
    930                 935                 940

Thr Gly Thr Trp Asn Ser Ile Asn Arg Thr Ser Lys Asn Thr Ser Ile
945                 950                 955                 960

Val Ser Asn Pro Phe Ile Thr Ile Ser Gln Lys His Asp Asn Lys Gly
            965                 970                 975

Asp Ser Tyr Gly Tyr Met Met Val Pro Asn Ile Asp Arg Thr Ser Phe
            980                 985                 990

Asp Lys Leu Ala Asn Ser Lys Glu  Val Glu Leu Leu Glu  Asn Ser Ser
        995                 1000                1005

Lys Gln  Gln Val Ile Tyr Asp  Lys Asn Ser Gln Thr  Trp Ala Val
    1010                1015                1020

Ile Lys  His Asp Asn Gln Glu  Ser Leu Ile Asn Asn  Gln Phe Lys
    1025                1030                1035

Met Asn  Lys Ala Gly Leu Tyr  Leu Val Gln Lys Val  Gly Asn Asp
    1040                1045                1050

Tyr Gln  Asn Val Tyr Tyr Gln  Pro Gln Thr Met Thr  Lys Thr Asp
    1055                1060                1065

Gln Leu  Ala Ile
    1070


<210> SEQ ID NO 70
<211> LENGTH: 984
<212> TYPE: PRT
<213> ORGANISM: Streptococcus agalactiae

<400> SEQUENCE: 70

Met Lys Gln Val Val Asp Asn Gln Thr Gln Asn Lys Glu Leu Val Lys
1               5                   10                  15
```

-continued

```
Asn Gly Asp Phe Asn Gln Thr Asn Pro Val Ser Gly Ser Trp Ser His
            20                  25                  30

Thr Ser Ala Arg Glu Trp Ser Ala Trp Ile Asp Lys Glu Asn Thr Ala
        35                  40                  45

Asp Lys Ser Pro Ile Ile Gln Arg Thr Glu Gln Gly Gln Val Ser Leu
    50                  55                  60

Ser Ser Asp Lys Gly Phe Arg Gly Ala Val Thr Gln Lys Val Asn Ile
65                  70                  75                  80

Asp Pro Thr Lys Lys Tyr Glu Val Lys Phe Asp Ile Glu Thr Ser Asn
                85                  90                  95

Lys Ala Gly Gln Ala Phe Leu Arg Ile Met Glu Lys Lys Asp Asn Asn
            100                 105                 110

Thr Arg Leu Trp Leu Ser Glu Met Thr Ser Gly Thr Thr Asn Lys His
        115                 120                 125

Thr Leu Thr Lys Ile Tyr Asn Pro Lys Leu Asn Val Ser Glu Val Thr
    130                 135                 140

Leu Glu Leu Tyr Tyr Glu Lys Gly Thr Gly Ser Ala Thr Phe Asp Asn
145                 150                 155                 160

Ile Ser Met Lys Ala Lys Gly Pro Lys Asp Ser Glu His Pro Gln Pro
                165                 170                 175

Val Thr Thr Gln Ile Glu Glu Ser Val Asn Thr Ala Leu Asn Lys Asn
            180                 185                 190

Tyr Val Phe Asn Lys Ala Asp Tyr Gln Tyr Thr Leu Thr Asn Pro Ser
        195                 200                 205

Leu Gly Lys Ile Val Gly Gly Ile Leu Tyr Pro Asn Ala Thr Gly Ser
    210                 215                 220

Thr Thr Val Lys Ile Ser Asp Lys Ser Gly Lys Ile Ile Lys Glu Val
225                 230                 235                 240

Pro Leu Ser Val Thr Ala Ser Thr Glu Asp Lys Phe Thr Lys Leu Leu
                245                 250                 255

Asp Lys Trp Asn Asp Val Thr Ile Gly Asn His Val Tyr Asp Thr Asn
            260                 265                 270

Asp Ser Asn Met Gln Lys Ile Asn Gln Lys Leu Asp Glu Thr Asn Ala
        275                 280                 285

Lys Asn Ile Lys Thr Ile Lys Leu Asp Ser Asn His Thr Phe Leu Trp
    290                 295                 300

Lys Asp Leu Asp Asn Leu Asn Asn Ser Ala Gln Leu Thr Ala Thr Tyr
305                 310                 315                 320

Arg Arg Leu Glu Asp Leu Ala Lys Gln Ile Thr Asn Pro His Ser Thr
                325                 330                 335

Ile Tyr Lys Asn Glu Lys Ala Ile Arg Thr Val Lys Glu Ser Leu Ala
            340                 345                 350

Trp Leu His Gln Asn Phe Tyr Asn Val Asn Lys Asp Ile Glu Gly Ser
        355                 360                 365

Ala Asn Trp Trp Asp Phe Glu Ile Gly Val Pro Arg Ser Ile Thr Ala
    370                 375                 380

Thr Leu Ala Leu Met Asn Asn Tyr Phe Thr Asp Ala Glu Ile Lys Thr
385                 390                 395                 400

Tyr Thr Asp Pro Ile Glu His Phe Val Pro Asp Ala Gly Tyr Phe Arg
                405                 410                 415

Lys Thr Leu Asp Asn Pro Phe Lys Ala Leu Gly Gly Asn Leu Val Asp
            420                 425                 430
```

```
Met Gly Arg Val Lys Ile Ile Glu Gly Leu Leu Arg Lys Asp Asn Thr
        435                 440                 445

Ile Ile Glu Lys Thr Ser His Ser Leu Lys Asn Leu Phe Thr Thr Ala
    450                 455                 460

Thr Lys Ala Glu Gly Phe Tyr Ala Asp Gly Ser Tyr Ile Asp His Thr
465                 470                 475                 480

Asn Val Ala Tyr Thr Gly Ala Tyr Gly Asn Val Leu Ile Asp Gly Leu
                485                 490                 495

Thr Gln Leu Leu Pro Ile Ile Gln Glu Thr Asp Tyr Lys Ile Ser Asn
            500                 505                 510

Gln Glu Leu Asp Met Val Tyr Lys Trp Ile Asn Gln Ser Phe Leu Pro
        515                 520                 525

Leu Ile Val Lys Gly Glu Leu Met Asp Met Ser Arg Gly Arg Ser Ile
    530                 535                 540

Ser Arg Glu Ala Ala Ser Ser His Ala Ala Ala Val Glu Val Leu Arg
545                 550                 555                 560

Gly Phe Leu Arg Leu Ala Asn Met Ser Asn Glu Glu Arg Asn Leu Asp
                565                 570                 575

Leu Lys Ser Thr Ile Lys Thr Ile Ile Thr Ser Asn Lys Phe Tyr Asn
            580                 585                 590

Val Phe Asn Asn Leu Lys Ser Tyr Ser Asp Ile Ala Asn Met Asn Lys
        595                 600                 605

Met Leu Asn Asp Ser Thr Val Ala Thr Lys Pro Leu Lys Ser Asn Leu
    610                 615                 620

Ser Thr Phe Asn Ser Met Asp Arg Leu Ala Tyr Tyr Asn Ala Glu Lys
625                 630                 635                 640

Asp Phe Gly Phe Ala Leu Ser Leu His Ser Lys Arg Thr Leu Asn Tyr
                645                 650                 655

Glu Gly Met Asn Asp Glu Asn Thr Arg Asp Trp Tyr Thr Gly Asp Gly
            660                 665                 670

Met Phe Tyr Leu Tyr Asn Ser Asp Gln Ser His Tyr Ser Asn His Phe
        675                 680                 685

Trp Pro Thr Val Asn Pro Tyr Lys Met Ala Gly Thr Thr Glu Lys Asp
    690                 695                 700

Ala Lys Arg Glu Asp Thr Thr Lys Glu Phe Met Ser Lys His Ser Lys
705                 710                 715                 720

Asp Ala Lys Glu Lys Thr Gly Gln Val Thr Gly Thr Ser Asp Phe Val
                725                 730                 735

Gly Ser Val Lys Leu Asn Asp His Phe Ala Leu Ala Ala Met Asp Phe
            740                 745                 750

Thr Asn Trp Asp Arg Thr Leu Thr Ala Gln Lys Gly Trp Val Ile Leu
        755                 760                 765

Asn Asp Lys Ile Val Phe Leu Gly Ser Asn Ile Lys Asn Thr Asn Gly
    770                 775                 780

Ile Gly Asn Val Ser Thr Thr Ile Asp Gln Arg Lys Asp Asp Ser Lys
785                 790                 795                 800

Thr Pro Tyr Thr Thr Tyr Val Asn Gly Lys Thr Ile Asp Leu Lys Gln
                805                 810                 815

Ala Ser Ser Gln Gln Phe Thr Asp Thr Lys Ser Val Phe Leu Glu Ser
            820                 825                 830

Lys Glu Pro Gly Arg Asn Ile Gly Tyr Ile Phe Phe Lys Asn Ser Thr
        835                 840                 845

Ile Asp Ile Glu Arg Lys Glu Gln Thr Gly Thr Trp Asn Ser Ile Asn
```

```
    850                 855                 860

Arg Thr Ser Lys Asn Thr Ser Ile Val Ser Asn Pro Phe Ile Thr Ile
865                 870                 875                 880

Ser Gln Lys His Asp Asn Lys Gly Asp Ser Tyr Gly Tyr Met Met Val
                885                 890                 895

Pro Asn Ile Asp Arg Thr Ser Phe Asp Lys Leu Ala Asn Ser Lys Glu
            900                 905                 910

Val Glu Leu Leu Glu Asn Ser Ser Lys Gln Gln Val Ile Tyr Asp Lys
        915                 920                 925

Asn Ser Gln Thr Trp Ala Val Ile Lys His Asp Asn Gln Glu Ser Leu
    930                 935                 940

Ile Asn Asn Gln Phe Lys Met Asn Lys Ala Gly Leu Tyr Leu Val Gln
945                 950                 955                 960

Lys Val Gly Asn Asp Tyr Gln Asn Val Tyr Tyr Gln Pro Gln Thr Met
                965                 970                 975

Thr Lys Thr Asp Gln Leu Ala Ile
            980


<210> SEQ ID NO 71
<211> LENGTH: 807
<212> TYPE: PRT
<213> ORGANISM: Staphylococcus aureus

<400> SEQUENCE: 71

Met Thr Tyr Arg Ile Lys Lys Trp Gln Lys Leu Ser Thr Ile Thr Leu
1               5                   10                  15

Leu Met Ala Gly Val Ile Thr Leu Asn Gly Gly Glu Phe Arg Ser Val
            20                  25                  30

Asp Lys His Gln Ile Ala Val Ala Asp Thr Asn Val Gln Thr Pro Asp
        35                  40                  45

Tyr Glu Lys Leu Arg Asn Thr Trp Leu Asp Val Asn Tyr Gly Tyr Asp
    50                  55                  60

Lys Tyr Asp Glu Asn Asn Pro Asp Met Lys Lys Lys Phe Asp Ala Thr
65                  70                  75                  80

Glu Lys Glu Ala Thr Asn Leu Leu Lys Glu Met Lys Thr Glu Ser Gly
                85                  90                  95

Arg Lys Tyr Leu Trp Ser Gly Ala Glu Thr Leu Glu Thr Asn Ser Ser
            100                 105                 110

His Met Thr Arg Thr Tyr Arg Asn Ile Glu Lys Ile Ala Glu Ala Met
        115                 120                 125

Arg Asn Pro Lys Thr Thr Leu Asn Thr Asp Glu Asn Lys Lys Lys Val
    130                 135                 140

Lys Asp Ala Leu Glu Trp Leu His Lys Asn Ala Tyr Gly Lys Glu Pro
145                 150                 155                 160

Asp Lys Lys Val Lys Glu Leu Ser Glu Asn Phe Thr Lys Thr Thr Gly
                165                 170                 175

Lys Asn Thr Asn Leu Asn Trp Trp Asp Tyr Glu Ile Gly Thr Pro Lys
            180                 185                 190

Ser Leu Thr Asn Thr Leu Ile Leu Leu Asn Asp Gln Phe Ser Asn Glu
        195                 200                 205

Glu Lys Lys Lys Phe Thr Ala Pro Ile Lys Thr Phe Ala Pro Asp Ser
    210                 215                 220

Asp Lys Ile Leu Ser Ser Val Gly Lys Ala Glu Leu Ala Lys Gly Gly
225                 230                 235                 240
```

-continued

```
Asn Leu Val Asp Ile Ser Lys Val Lys Leu Leu Glu Cys Ile Ile Glu
                245                 250                 255

Glu Asp Lys Asp Met Met Lys Lys Ser Ile Asp Ser Phe Asn Lys Val
            260                 265                 270

Phe Thr Tyr Val Gln Asp Ser Ala Thr Gly Lys Glu Arg Asn Gly Phe
        275                 280                 285

Tyr Lys Asp Gly Ser Tyr Ile Asp His Gln Asp Val Pro Tyr Thr Gly
    290                 295                 300

Ala Tyr Gly Val Val Leu Leu Glu Gly Ile Ser Gln Met Met Pro Met
305                 310                 315                 320

Ile Lys Glu Thr Pro Phe Asn Asp Lys Thr Gln Asn Asp Thr Thr Leu
                325                 330                 335

Lys Ser Trp Ile Asp Asp Gly Phe Met Pro Leu Ile Tyr Lys Gly Glu
            340                 345                 350

Met Met Asp Leu Ser Arg Gly Arg Ala Ile Ser Arg Glu Asn Glu Thr
        355                 360                 365

Ser His Ser Ala Ser Ala Thr Val Met Lys Ser Leu Leu Arg Leu Ser
    370                 375                 380

Asp Ala Met Asp Asp Ser Thr Lys Ala Lys Tyr Lys Lys Ile Val Lys
385                 390                 395                 400

Ser Ser Val Glu Ser Asp Ser Ser Tyr Lys Gln Asn Asp Tyr Leu Asn
                405                 410                 415

Ser Tyr Ser Asp Ile Asp Lys Met Lys Ser Leu Met Thr Asp Asn Ser
            420                 425                 430

Ile Ser Lys Asn Gly Leu Thr Gln Gln Leu Lys Ile Tyr Asn Asp Met
        435                 440                 445

Asp Arg Val Thr Tyr His Asn Lys Asp Leu Asp Phe Ala Phe Gly Leu
    450                 455                 460

Ser Met Thr Ser Lys Asn Val Ala Arg Tyr Glu Ser Ile Asn Gly Glu
465                 470                 475                 480

Asn Leu Lys Gly Trp His Thr Gly Ala Gly Met Ser Tyr Leu Tyr Asn
                485                 490                 495

Ser Asp Val Lys His Tyr His Asp Asn Phe Trp Val Thr Ala Asp Met
            500                 505                 510

Lys Arg Leu Ser Gly Thr Thr Thr Leu Asp Asn Glu Ile Leu Lys Asp
        515                 520                 525

Thr Asp Asp Lys Lys Ser Ser Lys Thr Phe Val Gly Gly Thr Lys Val
    530                 535                 540

Asp Asp Gln His Ala Ser Ile Gly Met Asp Phe Glu Asn Gln Asp Lys
545                 550                 555                 560

Thr Leu Thr Ala Lys Lys Ser Tyr Phe Ile Leu Asn Asp Lys Ile Val
                565                 570                 575

Phe Leu Gly Thr Gly Ile Lys Ser Thr Asp Ser Ser Lys Asn Pro Val
            580                 585                 590

Thr Thr Ile Glu Asn Arg Lys Ala Asn Gly Tyr Thr Leu Tyr Thr Asp
        595                 600                 605

Asp Lys Gln Thr Thr Asn Ser Asp Asn Gln Glu Asn Asn Ser Val Phe
    610                 615                 620

Leu Glu Ser Thr Asp Thr Lys Lys Asn Ile Gly Tyr His Phe Leu Asn
625                 630                 635                 640

Lys Pro Lys Ile Thr Val Lys Lys Glu Ser His Thr Gly Lys Trp Lys
                645                 650                 655

Glu Ile Asn Lys Ser Gln Lys Asp Thr Gln Lys Thr Asp Glu Tyr Tyr
```

```
            660                 665                 670

Glu Val Thr Gln Lys His Ser Asn Ser Asp Asn Lys Tyr Gly Tyr Val
        675                 680                 685

Leu Tyr Pro Gly Leu Ser Lys Asp Val Phe Lys Thr Lys Lys Asp Glu
    690                 695                 700

Val Thr Val Val Lys Gln Glu Asp Asp Phe His Val Val Lys Asp Asn
705                 710                 715                 720

Glu Ser Val Trp Ala Gly Val Asn Tyr Ser Asn Ser Thr Gln Thr Phe
                725                 730                 735

Asp Ile Asn Asn Thr Lys Val Glu Val Lys Ala Lys Gly Met Phe Ile
            740                 745                 750

Leu Lys Lys Lys Asp Asp Asn Thr Tyr Glu Cys Ser Phe Tyr Asn Pro
        755                 760                 765

Glu Ser Thr Asn Ser Ala Ser Asp Ile Glu Ser Lys Ile Ser Met Thr
    770                 775                 780

Gly Tyr Ser Ile Thr Asn Lys Asn Thr Ser Thr Ser Asn Glu Ser Gly
785                 790                 795                 800

Val His Phe Glu Leu Thr Lys
                805


<210> SEQ ID NO 72
<211> LENGTH: 1081
<212> TYPE: PRT
<213> ORGANISM: Streptococcus agalactiae

<400> SEQUENCE: 72

Met Glu Ile Lys Lys Lys His Arg Ile Met Leu Tyr Ser Ala Leu Ile
1               5                   10                  15

Leu Gly Thr Ile Leu Val Asn Asn Ser Tyr Gln Ala Lys Ala Glu Glu
            20                  25                  30

Phe Thr Lys Thr Thr Ser Thr Ser Gln Ile Arg Asp Thr Gln Thr Asn
        35                  40                  45

Asn Val Glu Val Pro Gln Thr Glu Ser Thr Thr Val Lys Gly Thr Ser
    50                  55                  60

Thr Thr Thr Thr Gln Gln Asp Leu Ser Asn Ser Thr Ala Ser Thr Ala
65                  70                  75                  80

Thr Ala Thr Ala Thr His Ser Thr Met Lys Gln Val Val Asp Asn Gln
                85                  90                  95

Thr Gln Asn Lys Glu Leu Val Lys Asn Gly Asp Phe Lys Glu Lys Ile
            100                 105                 110

Ile Asp Lys Lys Ile Asp Lys Lys Ser Gln Trp Thr Asn Leu Tyr Gly
        115                 120                 125

Ala Lys Asp Trp Asn Thr Tyr Ile Asp Gln Thr Lys Ser Val Asn Lys
    130                 135                 140

Ser Pro Ile Ile Gln Arg Thr Glu Gln Gly Gln Val Ser Leu Ser Ser
145                 150                 155                 160

Asp Lys Gly Phe Arg Gly Ala Val Thr Gln Lys Val Asn Ile Asp Pro
                165                 170                 175

Thr Lys Lys Tyr Glu Val Lys Phe Asp Ile Glu Thr Ser Asn Lys Val
            180                 185                 190

Gly Gln Ala Phe Leu Arg Ile Met Lys Lys Lys Asp Lys Asn Thr Arg
        195                 200                 205

Leu Trp Leu Ser Glu Met Thr Ser Gly Thr Thr Asn Lys His Thr Leu
    210                 215                 220
```

-continued

```
Thr Lys Ile Tyr Asn Pro Lys Leu Asn Val Ser Glu Val Thr Leu Glu
225                 230                 235                 240

Leu Tyr Tyr Glu Lys Gly Thr Gly Ser Val Thr Phe Asp Asn Ile Ser
                245                 250                 255

Met Lys Ala Lys Gly Pro Lys Asp Ser Glu His Pro Gln Pro Val Thr
            260                 265                 270

Thr Gln Ile Glu Glu Ser Val Asn Thr Ala Leu Asn Lys Asn Tyr Val
        275                 280                 285

Phe Asn Lys Ala Asp Tyr Gln Tyr Thr Leu Thr Asn Pro Ser Leu Gly
    290                 295                 300

Lys Ile Val Gly Gly Ile Leu Tyr Pro Ser Ala Thr Gly Ser Thr Thr
305                 310                 315                 320

Val Lys Ile Ser Asp Lys Ser Gly Lys Ile Ile Lys Glu Val Pro Leu
                325                 330                 335

Ser Val Thr Ala Ser Thr Glu Asp Asn Phe Thr Lys Leu Leu Asp Lys
            340                 345                 350

Trp Asn Asp Val Thr Ile Gly Asn His Val Tyr Asp Thr Asn Asp Ser
        355                 360                 365

Asn Met Gln Lys Leu Asn Gln Lys Leu Asp Glu Thr Asn Ala Lys Asn
    370                 375                 380

Ile Lys Asp Ile Lys Leu Asp Ser Asn Arg Thr Phe Leu Trp Glu Asp
385                 390                 395                 400

Leu Lys Gly Leu Asn Asn Ser Ala Gln Leu Thr Ala Thr Tyr Arg Arg
                405                 410                 415

Leu Glu Asp Leu Ala Lys Gln Ile Thr Asn Pro His Ser Thr Ile Tyr
            420                 425                 430

Lys Asn Glu Lys Ala Ile Arg Thr Val Lys Glu Ser Leu Ala Trp Leu
        435                 440                 445

His Gln Asn Phe Tyr Asn Val Asn Lys Asp Ile Glu Gly Ser Ala Asn
    450                 455                 460

Trp Trp Asp Phe Glu Ile Gly Val Pro Arg Ser Ile Thr Ala Thr Leu
465                 470                 475                 480

Ala Leu Met Asn Asn Tyr Phe Thr Asp Ala Glu Ile Lys Thr Tyr Thr
                485                 490                 495

Asp Pro Ile Glu His Phe Val Pro Asp Ala Gly Tyr Phe Arg Lys Thr
            500                 505                 510

Leu Val Asn Pro Phe Lys Ala Leu Gly Gly Asn Leu Val Asp Met Gly
        515                 520                 525

Arg Val Lys Ile Ile Glu Gly Leu Leu Arg Lys Asp Asn Thr Ile Ile
    530                 535                 540

Lys Lys Thr Ser His Ser Leu Lys Asn Leu Phe Thr Thr Ala Thr Lys
545                 550                 555                 560

Ala Glu Gly Phe Tyr Ala Asp Gly Ser Tyr Ile Asp His Thr Asn Val
                565                 570                 575

Ala Tyr Thr Gly Ala Tyr Gly Asn Val Leu Ile Asp Gly Leu Thr Gln
            580                 585                 590

Leu Leu Pro Ile Ile Gln Glu Thr Asp Tyr Lys Ile Ser Asn Gln Glu
        595                 600                 605

Leu Asp Met Val Tyr Lys Trp Ile Asn Gln Ser Phe Leu Pro Leu Ile
    610                 615                 620

Val Lys Gly Glu Leu Met Asp Met Ser Arg Gly Arg Ser Ile Ser Arg
625                 630                 635                 640

Glu Ala Ala Ser Ser His Ala Ala Ala Val Glu Val Leu Arg Gly Phe
```

-continued

```
                645                 650                 655

Leu Arg Leu Ala Asn Met Ser Asn Glu Glu Arg Asn Leu Asp Leu Lys
            660                 665                 670

Ser Thr Ile Lys Thr Ile Ile Thr Ser Asn Lys Phe Tyr Asn Val Phe
        675                 680                 685

Asn Asn Leu Lys Ser Tyr Ser Asp Ile Ala Asn Met Asn Lys Leu Leu
    690                 695                 700

Asn Asp Ser Thr Val Ala Thr Lys Pro Leu Lys Ser Asn Leu Ser Thr
705                 710                 715                 720

Phe Asn Ser Met Asp Arg Leu Ala Tyr Tyr Asn Ala Glu Lys Asp Phe
                725                 730                 735

Gly Phe Ala Leu Ser Leu His Ser Lys Arg Thr Leu Asn Tyr Glu Gly
            740                 745                 750

Met Asn Asp Glu Asn Thr Arg Gly Trp Tyr Thr Gly Asp Gly Met Phe
        755                 760                 765

Tyr Leu Tyr Asn Ser Asp Gln Ser His Tyr Ser Asn His Phe Trp Pro
    770                 775                 780

Thr Val Asn Pro Tyr Lys Met Ala Gly Thr Thr Glu Lys Asp Thr Gly
785                 790                 795                 800

Arg Glu Asp Thr Ile Lys Lys Leu Met Asn Arg Tyr Asp Lys Thr Asn
                805                 810                 815

Lys Asn Ser Lys Val Met Thr Gly Gln Val Thr Gly Thr Ser Asp Phe
            820                 825                 830

Val Gly Ser Val Lys Leu Asn Asp His Phe Ala Leu Ala Ala Met Asp
        835                 840                 845

Phe Thr Asn Trp Asp Arg Thr Leu Thr Ala Gln Lys Gly Trp Val Ile
    850                 855                 860

Leu Asn Asp Lys Ile Val Phe Leu Gly Ser Asn Ile Lys Asn Thr Asn
865                 870                 875                 880

Gly Val Gly Asn Val Ser Thr Thr Ile Asp Gln Arg Lys Asp Asp Ser
                885                 890                 895

Lys Thr Pro Tyr Thr Thr Tyr Val Asn Gly Lys Thr Val Asp Leu Lys
            900                 905                 910

Gln Ala Ser Ser Gln Gln Phe Thr Asp Thr Lys Ser Val Phe Leu Glu
        915                 920                 925

Ser Lys Glu Pro Gly Arg Asn Ile Gly Tyr Ile Phe Phe Lys Asn Ser
    930                 935                 940

Thr Ile Asp Ile Glu Arg Lys Glu Gln Thr Gly Thr Trp Asn Ser Ile
945                 950                 955                 960

Asn Arg Thr Ser Lys Asn Thr Ser Ile Val Ser Asn Pro Phe Ile Thr
                965                 970                 975

Ile Ser Gln Lys His Asp Asn Lys Gly Asp Ser Tyr Gly Tyr Met Met
            980                 985                 990

Val Pro Asn Ile Asp Arg Thr Ser  Phe Asp Lys Leu Ala  Asn Ser Lys
        995                 1000                1005

Glu Val  Glu Leu Leu Glu Asn  Ser Ser Lys Gln Gln  Val Ile Tyr
    1010                1015                1020

Asp Lys  Asn Ser Gln Thr Trp  Ala Val Ile Lys His  Asp Asn Gln
    1025                1030                1035

Glu Ser  Leu Ile Asn Asn Gln  Phe Lys Met Asn Lys  Ala Gly Leu
    1040                1045                1050

Tyr Leu  Val Gln Lys Val Gly  Asn Asp Tyr Gln Asn  Val Tyr Tyr
    1055                1060                1065
```

```
Gln Pro  Gln Thr Met Thr Lys  Thr Asp Gln Leu Ala  Ile
    1070                 1075                 1080


<210> SEQ ID NO 73
<211> LENGTH: 420
<212> TYPE: PRT
<213> ORGANISM: Staphylococcus aureus

<400> SEQUENCE: 73

Met Thr Tyr Arg Met Lys Lys Trp Gln Lys Leu Ser Thr Ile Thr Leu
1               5                   10                  15

Leu Met Ala Gly Val Ile Thr Leu Asn Gly Gly Glu Phe Arg Ser Ile
            20                  25                  30

Asp Lys His Gln Ile Ala Val Ala Asp Thr Asn Val Gln Thr Thr Asp
        35                  40                  45

Tyr Glu Lys Leu Arg Asn Ile Trp Leu Asp Val Asn Tyr Gly Tyr Asp
    50                  55                  60

Lys Tyr Asp Glu Asn Asn Pro Asp Met Lys Lys Lys Phe Glu Ala Thr
65                  70                  75                  80

Glu Asn Glu Ala Glu Lys Leu Leu Lys Glu Met Lys Thr Glu Ser Asp
                85                  90                  95

Arg Lys Tyr Leu Trp Glu Ser Ser Lys Asp Leu Asp Thr Lys Ser Ala
            100                 105                 110

Asp Met Thr Arg Thr Tyr Arg Asn Ile Glu Lys Ile Ser Glu Ala Met
        115                 120                 125

Lys His Lys Asn Thr Lys Leu Lys Thr Asp Glu Asn Lys Thr Lys Val
    130                 135                 140

Lys Asp Ala Leu Glu Trp Leu His Lys Asn Ala Tyr Gly Lys Glu Pro
145                 150                 155                 160

Asp Lys Lys Val Ala Asp Leu Thr Ser Asn Phe Lys Asn Lys Thr Ser
                165                 170                 175

Arg Asn Thr Asn Leu Asn Trp Trp Asp Tyr Glu Ile Gly Thr Pro Arg
            180                 185                 190

Ala Leu Thr Asn Thr Leu Ile Leu Leu Gln Glu Asp Phe Thr Asp Glu
        195                 200                 205

Glu Lys Lys Lys Tyr Thr Ala Pro Ile Lys Thr Phe Ala Pro Asp Ser
    210                 215                 220

Asp Lys Ile Leu Ser Ser Val Gly Lys Ser Glu Pro Ala Lys Gly Gly
225                 230                 235                 240

Asn Leu Val Asp Ile Ser Lys Val Lys Leu Leu Glu Ser Ile Ile Glu
                245                 250                 255

Glu Asp Lys Asp Met Met Lys Lys Ser Ile Asp Ser Phe Asn Thr Val
            260                 265                 270

Phe Thr Tyr Ala Gln Asn Ser Ala Thr Gly Lys Glu Arg Asn Gly Phe
        275                 280                 285

Tyr Lys Asp Gly Ser Tyr Ile Asp His Gln Asp Val Pro Tyr Thr Gly
    290                 295                 300

Ala Tyr Gly Val Val Leu Leu Glu Gly Ile Ser Gln Met Met Pro Met
305                 310                 315                 320

Ile Lys Glu Thr Pro Phe Asn Asp Ser Asn Gln Asn Asp Thr Thr Leu
                325                 330                 335

Lys Ser Trp Ile Asp Asp Gly Phe Met Pro Leu Ile Tyr Lys Gly Glu
            340                 345                 350

Met Met Asp Leu Ser Arg Gly Arg Ala Ile Ser Arg Glu Asn Glu Thr
```

```
        355                 360                 365

Ser His Ser Ala Ser Ala Thr Val Met Lys Ser Leu Leu Arg Leu Ser
    370                 375                 380

Asp Thr Met Asp Lys Ser Thr Lys Ala Lys Tyr Lys Lys Ile Val Lys
385                 390                 395                 400

Thr Ser Val Glu Ser Asp Ser Ser Tyr Lys Gln Thr Asp Tyr Leu Ser
                405                 410                 415

Ser Tyr Ser Asp
            420


<210> SEQ ID NO 74
<211> LENGTH: 806
<212> TYPE: PRT
<213> ORGANISM: Staphylococcus aureus

<400> SEQUENCE: 74

Met Thr Asn Lys Met Lys Lys Trp Gln Lys Leu Ser Thr Ile Thr Leu
1               5                   10                  15

Leu Met Thr Gly Val Ile Ala Leu Asn Asn Gly Glu Phe Arg Asn Val
            20                  25                  30

Asp Lys His Gln Ile Ala Val Ala Asp Thr Asn Val Gln Thr Pro Asp
        35                  40                  45

Tyr Glu Lys Leu Lys Lys Thr Trp Leu Asp Val Asn Tyr Gly Tyr Asp
    50                  55                  60

Gln Tyr Asp Glu Asn Asn Gln Asp Met Lys Lys Lys Phe Asp Ala Lys
65                  70                  75                  80

Glu Lys Glu Ala Lys Lys Leu Leu Asp Asp Met Lys Thr Asp Thr Asn
                85                  90                  95

Arg Thr Tyr Leu Trp Ser Gly Ala Glu Asn Leu Glu Thr Asn Ser Ser
            100                 105                 110

His Met Thr Lys Thr Tyr Arg Asn Ile Glu Lys Ile Ala Glu Ser Met
        115                 120                 125

Gln His Lys Asn Thr Val Leu Lys Thr Val Glu Asn Lys Leu Lys Ile
    130                 135                 140

Lys Glu Ala Leu Asp Trp Met His Lys Asn Val Tyr Gly Lys Asn Pro
145                 150                 155                 160

Ser Gln Lys Val Glu Asp Leu Thr Lys Asn Arg Lys Gly Gln Thr Thr
                165                 170                 175

Pro Lys Asn Asn Ser Leu Asn Trp Trp Asp Tyr Glu Ile Gly Thr Pro
            180                 185                 190

Arg Ala Leu Thr Asn Thr Leu Leu Leu Met Asp Asp Met Leu Thr Lys
        195                 200                 205

Asp Glu Met Lys Asn Tyr Ser Lys Pro Ile Ser Thr Tyr Ala Pro Ser
    210                 215                 220

Ser Asp Lys Ile Leu Ser Ser Val Gly Glu Ser Glu Asp Ala Lys Gly
225                 230                 235                 240

Gly Asn Leu Val Asp Ile Ser Lys Val Lys Leu Leu Glu Ser Val Ile
                245                 250                 255

Glu Glu Asp Val Asp Met Leu Lys Lys Ser Ile Asp Ser Phe Asn Lys
            260                 265                 270

Val Phe Thr Tyr Val Gln Asp Ser Ala Thr Gly Lys Gly Arg Asn Gly
        275                 280                 285

Phe Tyr Lys Asp Gly Ser Tyr Ile Asp His Gln Asp Val Pro Tyr Thr
    290                 295                 300
```

-continued

```
Gly Ala Tyr Gly Val Val Leu Leu Glu Gly Ile Ser Gln Met Met Pro
305                 310                 315                 320

Met Ile Lys Glu Ser Pro Phe Lys Thr Thr Gln Asp Asn Ala Thr Leu
                325                 330                 335

Ser Asn Trp Ile Asp Glu Gly Phe Met Pro Leu Ile Tyr Lys Gly Glu
            340                 345                 350

Met Met Asp Leu Ser Arg Gly Arg Ala Ile Ser Arg Glu Asn Glu Thr
        355                 360                 365

Ser His Thr Ala Ser Ala Thr Val Met Lys Ser Leu Leu Arg Leu Asn
    370                 375                 380

Asp Thr Met Asp Asp Ser Thr Lys Thr Arg Tyr Lys Gln Ile Val Lys
385                 390                 395                 400

Thr Ser Val Asn Ser Asp Ser Ser Tyr Asn Gln Asn Asn Tyr Leu Asn
                405                 410                 415

Ser Tyr Ser Asp Ile Ala Lys Met Lys Lys Leu Met Asn Asp Ser Thr
            420                 425                 430

Ile Ser Lys Asn Asp Leu Thr Gln Gln Leu Lys Ile Tyr Asn Asp Met
        435                 440                 445

Asp Arg Val Thr Tyr His Asn Lys Asp Leu Asp Phe Ala Phe Gly Leu
    450                 455                 460

Ser Met Thr Ser Lys Asn Ile Ala Arg Tyr Glu Asn Ile Asn Gly Glu
465                 470                 475                 480

Asn Leu Lys Gly Trp His Thr Gly Ala Gly Met Ser Tyr Leu Tyr Asn
                485                 490                 495

Ser Asp Val Lys His Tyr Arg Asp Asn Phe Trp Ala Thr Ala Asp Met
            500                 505                 510

Thr Cys Leu Pro Gly Thr Thr Thr Leu Asn Asp Met Pro Ser Thr Asn
        515                 520                 525

Thr Lys Asn Asp Lys Ser Phe Val Gly Gly Thr Lys Leu Asn Asn Lys
    530                 535                 540

Tyr Ala Ser Ile Gly Met Asp Phe Glu Asn Gln Asp Lys Thr Leu Thr
545                 550                 555                 560

Ala Lys Lys Ser Tyr Phe Ile Leu Asn Asp Lys Ile Val Phe Leu Gly
                565                 570                 575

Thr Gly Ile Lys Ser Thr Asp Ser Ser Lys Asn Pro Val Thr Ser Val
            580                 585                 590

Glu Asn Arg Lys Ala Asn Gly Tyr Lys Leu Phe Lys Asp Asp Ile Glu
        595                 600                 605

Ile Thr Thr Ser Asp Val Asn Ala Gln Glu Thr His Ser Val Phe Leu
    610                 615                 620

Glu Ser Asn Asp Thr Lys Lys Asn Ile Gly Tyr His Phe Leu Asp Lys
625                 630                 635                 640

Pro Lys Ile Thr Val Lys Lys Glu Ser His Thr Gly Lys Trp Ser Glu
                645                 650                 655

Ile Asn Lys Ser Gln Lys Lys Asp Asp Lys Lys Asp Glu Tyr Tyr Glu
            660                 665                 670

Val Thr Gln Thr His Asn Thr Ser Asp Ser Lys Tyr Ala Tyr Val Leu
        675                 680                 685

Tyr Pro Gly Leu Ser Lys Ser Asp Phe Lys Ser Lys Asn Asn Asn Val
    690                 695                 700

Ser Ile Val Lys Gln Asp Glu Asp Phe His Val Ile Lys Asp Asn Asp
705                 710                 715                 720

Gly Val Phe Ala Gly Val Asn Tyr Ser Asp Asn Thr Lys Ser Phe Asp
```

```
                725                 730                 735

Ile Asn Gly Ile Thr Val Glu Leu Lys Glu Lys Gly Met Phe Val Ile
            740                 745                 750

Lys Lys Lys Asp Asp Lys Ala Tyr Lys Cys Ser Phe Tyr Asn Pro Glu
        755                 760                 765

Thr Thr Asn Thr Ala Ser Asn Ile Glu Ser Lys Ile Phe Ile Lys Gly
    770                 775                 780

Tyr Thr Ile Thr Asn Lys Ser Val Ile Asn Ser Asn Asp Ala Gly Val
785                 790                 795                 800

Asn Phe Glu Leu Thr Lys
                805


<210> SEQ ID NO 75
<211> LENGTH: 815
<212> TYPE: PRT
<213> ORGANISM: Staphylococcus aureus

<400> SEQUENCE: 75

Met Thr Tyr Arg Ile Lys Lys Trp Gln Lys Leu Ser Thr Ile Thr Leu
1               5                   10                  15

Leu Met Ala Gly Val Ile Thr Leu Asn Gly Gly Glu Phe Arg Ser Ile
            20                  25                  30

Asp Lys Tyr Gln Ile Ala Val Ala Asp Thr Asn Val Gln Thr Pro Asp
        35                  40                  45

Tyr Glu Lys Leu Arg Asn Thr Trp Leu Asp Val Asn Tyr Gly Tyr Asp
    50                  55                  60

Lys Tyr Asp Glu Lys Asn Asp Ala Met Lys Lys Lys Phe Glu Ala Thr
65                  70                  75                  80

Glu Asn Glu Ala Lys Lys Leu Leu Ser Glu Met Lys Thr Glu Ser Asp
                85                  90                  95

Arg Lys Tyr Leu Trp Glu Asn Ser Lys Asp Leu Asp Thr Lys Ser Ala
            100                 105                 110

Asp Met Thr Arg Thr Tyr Arg Asn Ile Glu Lys Ile Ala Glu Ala Met
        115                 120                 125

Lys His Lys Asp Thr Lys Leu Lys Ile Asp Glu Asn Lys Lys Lys Val
    130                 135                 140

Lys Asp Ala Leu Glu Trp Leu His Lys Asn Ala Tyr Gly Lys Glu Pro
145                 150                 155                 160

Asp Lys Lys Val Ala Asp Leu Thr Ser Asn Phe Lys Asn Lys Thr Ser
                165                 170                 175

Arg Asn Thr Asn Leu Asn Trp Trp Asp Tyr Glu Ile Gly Thr Pro Arg
            180                 185                 190

Ala Leu Thr Asn Thr Leu Ile Leu Leu Asn Asp Gln Phe Ser Asn Asp
        195                 200                 205

Glu Lys Lys Lys Tyr Thr Ala Pro Ile Lys Thr Phe Ala Pro Glu Ser
    210                 215                 220

Asp Lys Ile Leu Ser Ser Val Gly Gln Pro Glu Gln Ala Lys Gly Gly
225                 230                 235                 240

Asn Leu Val Asp Ile Ala Lys Val Lys Leu Leu Glu Ser Ile Ile Glu
                245                 250                 255

Glu Asp Lys Asp Ile Thr Lys Asn Ser Ile Asp Ala Phe Asn Lys Val
            260                 265                 270

Phe Thr Tyr Val Gln Ser Asn Ala Thr Gly Lys Glu Arg Asn Gly Phe
        275                 280                 285
```

-continued

```
Tyr Lys Asp Gly Ser Tyr Ile Asp His Gln Asp Val Pro Tyr Thr Gly
    290                 295                 300

Ala Tyr Gly Val Val Leu Leu Glu Gly Ile Ser Gln Met Met Pro Met
305                 310                 315                 320

Ile Lys Glu Thr Pro Phe Asn Asp Lys Thr Gln Asn Asp Thr Thr Leu
                325                 330                 335

Lys Ser Trp Ile Asp Asp Gly Phe Met Pro Leu Ile Tyr Lys Gly Glu
            340                 345                 350

Met Met Asp Leu Ser Arg Gly Arg Ala Ile Ser Arg Glu Asn Glu Thr
        355                 360                 365

Ser His Thr Ala Ser Ala Thr Val Met Lys Ser Leu Leu Arg Leu Ser
    370                 375                 380

Asp Ala Met Asp Asp Ser Thr Lys Ala Lys Tyr Lys Gln Ile Val Lys
385                 390                 395                 400

Thr Ser Val Lys Ser Asp Ser Ser Tyr Gly Gln Asn Asp Thr Leu Ser
                405                 410                 415

Ser Tyr Ser Asp Ile Ser Lys Met Lys Ser Leu Met Glu Asp Ser Thr
            420                 425                 430

Ile Ser Thr Asn Gly Leu Thr Gln Gln Leu Lys Ile Tyr Asn Asp Met
        435                 440                 445

Asp Arg Val Thr Tyr His Asn Lys Asp Leu Asp Phe Ala Phe Gly Leu
    450                 455                 460

Ser Met Thr Ser Lys Asn Val Ala Arg Tyr Glu Ser Ile Asn Gly Glu
465                 470                 475                 480

Asn Leu Lys Gly Trp His Thr Gly Ala Gly Met Ser Tyr Leu Tyr Asn
                485                 490                 495

Ser Asp Val Lys His Tyr Arg Asp Asn Phe Trp Ala Thr Ala Asp Met
            500                 505                 510

Lys Arg Leu Ala Gly Thr Thr Thr Leu Glu Asn Glu Glu Pro Lys Gly
        515                 520                 525

Thr Asp Val Lys Lys Ser Ser Lys Thr Phe Val Gly Gly Thr Lys Phe
    530                 535                 540

Asp Asp Gln His Ala Ser Ile Gly Met Asp Phe Glu Asn Gln Asp Lys
545                 550                 555                 560

Thr Leu Thr Ala Lys Lys Ser Tyr Phe Ile Leu Asn Asp Lys Ile Val
                565                 570                 575

Phe Leu Gly Thr Gly Ile Lys Ser Thr Asp Ser Ser Lys Asn Pro Val
            580                 585                 590

Thr Thr Ile Glu Asn Arg Lys Ala Asn Gly Tyr Thr Leu Tyr Thr Asp
        595                 600                 605

Asp Lys Gln Thr Thr Ala Ser Asp Asn Gln Gly Thr Asn Ser Val Phe
    610                 615                 620

Leu Glu Ser Thr Asn Lys Pro Lys Asn Asn Ile Gly Tyr His Phe Leu
625                 630                 635                 640

Asn Glu Ser Lys Ile Thr Val Lys Lys Glu Ser His Thr Gly Lys Trp
                645                 650                 655

Ser Asp Ile Asn Lys Ser Gln Lys Gln Asp Ser Lys Thr Asn Gln Tyr
            660                 665                 670

Tyr Glu Val Thr Gln Lys His Ser Asn Thr Asp Ser Lys Tyr Ala Tyr
        675                 680                 685

Val Leu Tyr Pro Gly Leu Ser Lys Asp Asp Phe Asn Thr Lys Lys Asp
    690                 695                 700

Lys Val Thr Val Val Lys Gln Asp Asp Asp Phe His Val Val Lys Asp
```

```
705                 710                 715                 720

Asn Glu Ser Val Trp Ala Gly Val Asn Tyr Ser Asp Ser Thr Gln Thr
                725                 730                 735

Phe Ile Ile Asn Asn Thr Lys Val Glu Val Lys Ala Lys Gly Met Phe
            740                 745                 750

Ile Leu Lys Lys Lys Asp Asp Lys Thr Tyr Glu Cys Ser Phe Tyr Asn
        755                 760                 765

Pro Glu Ser Thr Asn Thr Ala Ser Asp Ile Glu Ser Lys Ile Ser Met
    770                 775                 780

Thr Gly Tyr Ser Ile Thr Asn Lys Asn Thr Ser Thr Ser Asn Glu Ser
785                 790                 795                 800

Gly Val Arg Phe Glu Leu Gln Gln Thr Leu Asn Lys Asp Asp Asn
                805                 810                 815


<210> SEQ ID NO 76
<211> LENGTH: 807
<212> TYPE: PRT
<213> ORGANISM: Staphylococcus aureus

<400> SEQUENCE: 76

Met Thr Tyr Arg Ile Lys Lys Trp Gln Lys Leu Ser Thr Ile Thr Leu
1               5                   10                  15

Leu Met Ala Gly Val Ile Thr Leu Asn Gly Gly Glu Phe Arg Ser Val
            20                  25                  30

Asp Lys His Gln Ile Ala Val Ala Asp Thr Asn Val Gln Thr Pro Asp
        35                  40                  45

Tyr Glu Lys Leu Arg Asn Thr Trp Leu Asp Val Asn Tyr Gly Tyr Asp
    50                  55                  60

Lys Tyr Asp Glu Asn Asn Pro Asp Met Lys Lys Lys Phe Asp Ala Thr
65                  70                  75                  80

Glu Lys Glu Ala Thr Asn Leu Leu Lys Glu Met Lys Thr Glu Ser Gly
                85                  90                  95

Arg Lys Tyr Leu Trp Ser Gly Ala Glu Thr Leu Glu Thr Asn Ser Ser
            100                 105                 110

His Met Thr Arg Thr Tyr Arg Asn Ile Glu Lys Ile Ala Glu Ala Met
        115                 120                 125

Arg Asn Pro Lys Thr Thr Leu Asn Thr Asp Glu Asn Lys Lys Lys Val
    130                 135                 140

Lys Asp Ala Leu Glu Trp Leu His Lys Asn Ala Tyr Gly Lys Glu Pro
145                 150                 155                 160

Asp Lys Lys Val Lys Glu Leu Ser Glu Asn Phe Thr Lys Thr Thr Gly
                165                 170                 175

Lys Asn Thr Asn Leu Asn Trp Trp Asp Tyr Glu Ile Gly Thr Pro Lys
            180                 185                 190

Ser Leu Thr Asn Thr Leu Ile Leu Leu Asn Asp Gln Phe Ser Asn Glu
        195                 200                 205

Glu Lys Lys Lys Phe Thr Ala Pro Ile Lys Thr Phe Ala Pro Asp Ser
    210                 215                 220

Asp Lys Ile Leu Ser Ser Val Gly Lys Ala Glu Leu Ala Lys Gly Gly
225                 230                 235                 240

Asn Leu Val Asp Ile Ser Lys Val Lys Leu Leu Glu Cys Ile Ile Glu
                245                 250                 255

Glu Asp Lys Asp Met Met Lys Lys Ser Ile Asp Ser Phe Asn Lys Val
            260                 265                 270
```

```
Phe Thr Tyr Val Gln Asp Ser Ala Thr Gly Lys Glu Arg Asn Gly Phe
        275                 280                 285

Tyr Lys Asp Gly Ser Tyr Ile Asp His Gln Asp Val Pro Tyr Thr Gly
    290                 295                 300

Ala Tyr Gly Val Val Leu Leu Glu Gly Ile Ser Gln Met Met Pro Met
305                 310                 315                 320

Ile Lys Glu Thr Pro Phe Asn Asp Lys Thr Gln Asn Asp Thr Thr Leu
                325                 330                 335

Lys Ser Trp Ile Asp Asp Gly Phe Met Pro Leu Ile Tyr Lys Gly Glu
            340                 345                 350

Met Met Asp Leu Ser Arg Gly Arg Ala Ile Ser Arg Glu Asn Glu Thr
        355                 360                 365

Ser His Ser Ala Ser Ala Thr Val Met Lys Ser Leu Leu Arg Leu Ser
    370                 375                 380

Asp Ala Met Asp Asp Ser Thr Lys Ala Lys Tyr Lys Lys Ile Val Lys
385                 390                 395                 400

Ser Ser Val Glu Ser Asp Ser Ser Tyr Lys Gln Asn Asp Tyr Leu Asn
                405                 410                 415

Ser Tyr Ser Asp Ile Asp Lys Met Lys Ser Leu Met Thr Asp Asn Ser
            420                 425                 430

Ile Ser Lys Asn Gly Leu Thr Gln Gln Leu Lys Ile Tyr Asn Asp Met
        435                 440                 445

Asp Arg Val Thr Tyr His Asn Lys Asp Leu Asp Phe Ala Phe Gly Leu
    450                 455                 460

Ser Met Thr Ser Lys Asn Val Ala Arg Tyr Glu Ser Ile Asn Gly Glu
465                 470                 475                 480

Asn Leu Lys Gly Trp His Thr Gly Ala Gly Met Ser Tyr Leu Tyr Asn
                485                 490                 495

Ser Asp Val Lys His Tyr His Asp Asn Phe Trp Val Thr Ala Asp Met
            500                 505                 510

Lys Arg Leu Ser Gly Thr Thr Thr Leu Asp Asn Glu Ile Leu Lys Asp
        515                 520                 525

Thr Asp Asp Lys Lys Ser Ser Lys Thr Phe Val Gly Gly Thr Lys Val
    530                 535                 540

Asp Asp Gln His Ala Ser Ile Gly Met Asp Phe Glu Asn Gln Asp Lys
545                 550                 555                 560

Thr Leu Thr Ala Lys Lys Ser Tyr Phe Ile Leu Asn Asp Lys Ile Val
                565                 570                 575

Phe Leu Gly Thr Gly Ile Lys Ser Thr Asp Ser Ser Lys Asn Pro Val
            580                 585                 590

Thr Thr Ile Glu Asn Arg Lys Ala Asn Gly Tyr Thr Leu Tyr Thr Asp
        595                 600                 605

Asp Lys Gln Thr Thr Asn Ser Asp Asn Gln Glu Asn Asn Ser Val Phe
    610                 615                 620

Leu Glu Ser Thr Asp Thr Lys Lys Asn Ile Gly Tyr His Phe Leu Asn
625                 630                 635                 640

Lys Pro Lys Ile Thr Val Lys Lys Glu Ser His Thr Gly Lys Trp Lys
                645                 650                 655

Glu Ile Asn Lys Ser Gln Lys Asp Thr Gln Lys Thr Asp Glu Tyr Tyr
            660                 665                 670

Glu Val Thr Gln Lys His Ser Asn Ser Asp Asn Lys Tyr Gly Tyr Val
        675                 680                 685

Leu Tyr Pro Gly Leu Ser Lys Asp Val Phe Lys Thr Lys Lys Asp Glu
```

```
    690                 695                 700

Val Thr Val Val Lys Gln Glu Asp Asp Phe His Val Val Lys Asp Asn
705                 710                 715                 720

Glu Ser Val Trp Ala Gly Val Asn Tyr Ser Asn Ser Thr Gln Thr Phe
                725                 730                 735

Asp Ile Asn Asn Thr Lys Val Glu Val Lys Ala Lys Gly Met Phe Ile
            740                 745                 750

Leu Lys Lys Lys Asp Asp Asn Thr Tyr Glu Cys Ser Phe Tyr Asn Pro
        755                 760                 765

Glu Ser Thr Asn Ser Ala Ser Asp Ile Glu Ser Lys Ile Ser Met Thr
    770                 775                 780

Gly Tyr Ser Ile Thr Asn Lys Asn Thr Ser Thr Ser Asn Glu Ser Gly
785                 790                 795                 800

Val His Phe Glu Leu Thr Lys
                805


<210> SEQ ID NO 77
<211> LENGTH: 809
<212> TYPE: PRT
<213> ORGANISM: Staphylococcus aureus

<400> SEQUENCE: 77

Met Thr Tyr Arg Met Lys Lys Trp Gln Lys Leu Ser Thr Ile Thr Leu
1               5                   10                  15

Leu Met Ala Gly Gly Ile Thr Phe Asn Asp Ser Glu Phe Arg Ser Val
            20                  25                  30

Asp Lys His Gln Ile Ala Val Ala Asp Thr Asn Val Gln Thr Pro Asn
        35                  40                  45

Tyr Glu Lys Leu Lys Asn Thr Trp Leu Asp Val Asn Tyr Gly Tyr Asp
    50                  55                  60

Lys Tyr Asp Glu Ser Asn Pro Asp Met Lys Lys Lys Phe Glu Ala Thr
65                  70                  75                  80

Glu Lys Glu Ala Arg Lys Leu Leu Ser Glu Met Lys Thr Glu Ser Asp
                85                  90                  95

Arg Lys Tyr Leu Trp Glu Asn Ser Lys Asp Leu Asp Thr Lys Ser Ala
            100                 105                 110

Asp Met Thr Arg Thr Tyr Arg Asn Ile Glu Lys Ile Ala Glu Ala Met
        115                 120                 125

Lys His Pro Lys Thr Thr Leu Lys Asn Asp Glu Asn Lys Lys Lys Val
    130                 135                 140

Lys Asp Ala Leu Glu Trp Leu His Lys Asn Ala Tyr Gly Lys Glu Pro
145                 150                 155                 160

Gly Lys Lys Val Ala Asp Leu Lys Thr Asn Phe Ser Lys Ser Ala Pro
                165                 170                 175

Gln Lys Asn Thr Asn Leu Asn Trp Trp Asp Tyr Glu Ile Gly Thr Pro
            180                 185                 190

Arg Ala Leu Thr Asn Thr Leu Ile Leu Leu Lys Glu Asp Phe Thr Asp
        195                 200                 205

Glu Glu Lys Lys Lys Tyr Thr Ala Pro Ile Lys Thr Phe Ala Pro Lys
    210                 215                 220

Ser Asp Glu Ile Leu Ser Ser Val Gly Lys Ala Glu Pro Ala Lys Gly
225                 230                 235                 240

Gly Asn Leu Val Asp Ile Ser Lys Val Lys Leu Leu Glu Ser Ile Ile
                245                 250                 255
```

-continued

```
Glu Glu Asp Lys Asp Met Met Lys Asn Ser Ile Asp Ser Phe Asn Lys
            260                 265                 270

Val Phe Thr Tyr Val Gln Asp Ser Ala Thr Asp Lys Glu Arg Asn Gly
        275                 280                 285

Phe Tyr Lys Asp Gly Ser Tyr Ile Asp His Lys Asp Val Pro Tyr Thr
    290                 295                 300

Gly Ala Tyr Gly Val Val Leu Leu Glu Gly Ile Ser Gln Met Met Pro
305                 310                 315                 320

Met Ile Lys Glu Thr Pro Phe Asn Asp Lys Thr Gln Asn Asn Thr Thr
                325                 330                 335

Leu Thr Ser Trp Ile Asp Asp Gly Phe Met Pro Leu Ile Tyr Lys Gly
            340                 345                 350

Glu Met Met Asp Leu Ser Arg Gly Arg Ala Ile Ser Arg Glu Asn Glu
        355                 360                 365

Thr Ser His Ser Ala Ser Ala Thr Val Met Lys Ser Leu Leu Arg Leu
    370                 375                 380

Ser Asp Ala Met Asp Glu Ser Thr Lys Ala Lys Tyr Lys Gln Ile Val
385                 390                 395                 400

Lys Asn Ser Val Lys Ser Asp Ser Ser Tyr Gly Gln Asn Asp Thr Leu
                405                 410                 415

Ser Ser Tyr Ser Asp Ile Asp Lys Met Lys Ser Leu Met Thr Asp Ser
            420                 425                 430

Thr Ile Ser Thr Asn Gly Leu Thr Gln Gln Leu Lys Ile Tyr Asn Ala
        435                 440                 445

Met Asp Arg Val Thr Tyr His Asn Lys Asp Leu Asp Phe Ala Phe Gly
    450                 455                 460

Leu Ser Met Thr Ser Lys Asn Val Ala Arg Tyr Glu Asn Ile Asn Gly
465                 470                 475                 480

Glu Asn Leu Lys Gly Trp His Thr Gly Ala Gly Met Ser Tyr Leu Tyr
                485                 490                 495

Asn Ser Asp Val Arg His Tyr Arg Asp Asn Phe Trp Ala Thr Ala Asp
            500                 505                 510

Met Lys Arg Leu Ala Asp Thr Thr Thr Leu Glu Asn Glu Glu Pro Lys
        515                 520                 525

Gly Thr Asp Val Lys Lys Ser Ser Lys Thr Phe Val Gly Gly Thr Lys
    530                 535                 540

Phe Asp Asp Gln His Ala Ser Ile Gly Met Asp Phe Glu Asn Gln Asp
545                 550                 555                 560

Lys Thr Leu Thr Ala Lys Lys Ser Tyr Phe Ile Leu Asn Asp Lys Ile
                565                 570                 575

Val Phe Leu Gly Thr Gly Ile Lys Thr Thr Asp Ser Ser Lys Asn Pro
            580                 585                 590

Val Thr Thr Ile Glu Asn Arg Lys Ala His Gly Tyr Thr Leu Tyr Thr
        595                 600                 605

Asp Asp Lys Gln Thr Thr Asn Ser Asn Asn Gln Glu Thr Asn Ser Val
    610                 615                 620

Phe Leu Glu Ser Thr Asn Ser Thr Gln Asn Asn Ile Gly Tyr His Phe
625                 630                 635                 640

Leu Asn Lys Ser Lys Ile Thr Val Lys Lys Glu Ser His Thr Gly Lys
                645                 650                 655

Trp Ser Asp Ile Asn Lys Ser Gln Lys Asp Thr Gln Lys Thr Asp Glu
            660                 665                 670

Tyr Tyr Glu Val Thr Gln Lys His Ser Asn Thr Asp Asp Lys Tyr Ala
```

```
        675                 680                 685

Tyr Val Leu Tyr Pro Gly Ile Thr Lys Asp Asn Phe Lys Ser Lys Ala
    690                 695                 700

Ser Gln Val Thr Val Val Lys Gln Asp Asp Asp Phe His Val Val Lys
705                 710                 715                 720

Asp Asn Glu Ser Val Trp Ala Gly Val Asn Tyr Ser Asp Ser Thr Gln
                725                 730                 735

Thr Phe Asp Ile Asn Gly Thr Lys Val Glu Val Lys Ala Lys Gly Met
            740                 745                 750

Phe Ile Leu Lys Lys Lys Asp Asp Asn Thr Tyr Glu Cys Ser Phe Tyr
        755                 760                 765

Asn Pro Glu Ser Thr Asn Ser Ala Ser Asp Ile Glu Ser Lys Ile Ser
    770                 775                 780

Met Thr Gly Tyr Ser Ile Thr Asn Lys Asn Thr Ser Asn Thr Asn Glu
785                 790                 795                 800

Ser Gly Val Arg Phe Glu Leu Thr Lys
                805


<210> SEQ ID NO 78
<211> LENGTH: 807
<212> TYPE: PRT
<213> ORGANISM: Staphylococcus aureus

<400> SEQUENCE: 78

Met Thr Tyr Lys Met Lys Lys Trp Gln Lys Leu Ser Thr Ile Thr Leu
1               5                   10                  15

Leu Met Ala Gly Val Ile Thr Leu Asn Asn Gly Glu Phe Arg Asn Val
            20                  25                  30

Asp Lys His Gln Ile Ala Val Ala Asp Thr Asn Val Gln Thr Pro Asp
        35                  40                  45

Tyr Glu Lys Leu Lys Lys Thr Trp Leu Asp Val Asn Tyr Gly Asn Asp
    50                  55                  60

Gln Tyr Asp Glu Asn Asn Gln Asp Met Lys Lys Lys Phe Asp Ala Lys
65                  70                  75                  80

Glu Asn Glu Ala Lys Lys Leu Leu Glu Asp Met Lys Thr Asp Thr Asn
                85                  90                  95

Arg Thr Tyr Leu Trp Ser Gly Ala Glu Asn Leu Glu Thr Asn Ser Ser
            100                 105                 110

His Met Thr Lys Thr Tyr Arg Asn Ile Glu Lys Ile Ala Glu Ala Met
        115                 120                 125

Arg His Lys Asn Thr Ser Leu Lys Thr Asp Glu Asn Lys Leu Lys Ile
    130                 135                 140

Lys Asp Ala Ile Lys Trp Leu His His Asn Val Tyr Gly Lys Asp Pro
145                 150                 155                 160

Asp Lys Lys Val Ala Asp Leu Thr Thr Asn Arg Lys Glu Lys Asp Ser
                165                 170                 175

Ser Lys Lys Asn Asn Ser Leu Asn Trp Trp Asp Tyr Glu Ile Gly Thr
            180                 185                 190

Pro Arg Ala Leu Thr Asn Thr Leu Leu Leu Met Asp Asn Met Leu Thr
        195                 200                 205

Lys Asp Glu Met Lys Asn Tyr Ser Lys Pro Ile Ser Ile Tyr Ser Pro
    210                 215                 220

Ser Ser Tyr Lys Ile Leu Ser Ser Val Gly Glu Ser Glu Asp Ala Lys
225                 230                 235                 240
```

```
Gly Gly Asn Leu Val Asp Ile Ala Lys Val Lys Phe Leu Glu Ser Val
                245                 250                 255

Ile Glu Glu Asp Val Asp Met Met Lys Lys Ser Ile Asp Ser Phe Asn
            260                 265                 270

Lys Val Phe Thr Tyr Val Gln Asp Ser Ala Thr Gly Lys Ala Arg Asn
        275                 280                 285

Gly Phe Tyr Lys Asp Gly Ser Tyr Ile Asp His Gln Asp Val Pro Tyr
    290                 295                 300

Thr Gly Ala Tyr Gly Val Val Leu Leu Glu Gly Ile Ser Gln Met Met
305                 310                 315                 320

Pro Met Ile Lys Glu Ser Pro Phe Lys His Thr Gln Asp Lys Ala Thr
                325                 330                 335

Leu Ser Asn Trp Ile Asp Glu Gly Phe Met Pro Leu Ile Tyr Lys Gly
            340                 345                 350

Glu Met Met Asp Leu Ser Arg Gly Arg Ala Ile Ser Arg Glu Asn Glu
        355                 360                 365

Thr Ser His Thr Ala Ser Ala Thr Val Met Lys Ser Leu Leu Arg Leu
    370                 375                 380

Ser Asp Thr Met Asp Glu Ser Thr Lys Thr Lys Tyr Lys Gln Ile Val
385                 390                 395                 400

Lys Thr Ser Val Lys Ser Asp Ser Ser Tyr Asp Ser Asn Asp Thr Leu
                405                 410                 415

Asn Ser Tyr Ser Asp Ile Asp Lys Met Lys Lys Leu Met Asn Asp Ser
            420                 425                 430

Thr Ile Ser Lys Asn Asp Leu Thr Gln Gln Leu Lys Ile Tyr Asn Asp
        435                 440                 445

Met Asp Arg Val Thr Tyr His Asn Lys Glu Leu Asp Phe Ala Phe Gly
    450                 455                 460

Leu Ser Met Thr Ser Lys Asn Ile Ala Arg Tyr Glu Asn Ile Asn Gly
465                 470                 475                 480

Glu Asn Leu Lys Gly Trp His Thr Gly Ala Gly Met Ser Tyr Leu Tyr
                485                 490                 495

Asn Ser Asp Val Lys His Tyr Arg Asp Asn Phe Trp Ala Thr Ala Asp
            500                 505                 510

Met Thr Arg Leu Pro Gly Thr Thr Thr Leu Asn Asp Met Pro Ser Thr
        515                 520                 525

Asn Thr Lys Asn Asp Lys Ser Phe Val Gly Gly Thr Lys Leu Asn Asn
    530                 535                 540

Lys Tyr Ala Ser Ile Gly Met Asp Phe Glu Asn Gln Asp Lys Thr Leu
545                 550                 555                 560

Thr Ala Lys Lys Ser Tyr Phe Ile Leu Asn Asp Lys Ile Val Phe Ile
                565                 570                 575

Gly Thr Gly Ile Lys Ser Thr Asp Ser Ser Lys Asn Pro Val Thr Ser
            580                 585                 590

Val Glu Asn Arg Lys Ala Asn Gly Tyr Lys Leu Phe Lys Gly Asp Ile
        595                 600                 605

Glu Ile Thr Thr Ser Asp Val Asn Ala Gln Glu Thr His Ser Val Phe
    610                 615                 620

Leu Glu Ser Asn Asp Thr Lys Lys Asn Ile Gly Tyr His Phe Leu Asp
625                 630                 635                 640

Lys Pro Lys Ile Thr Val Lys Lys Glu Ser His Thr Gly Lys Trp Ser
                645                 650                 655

Glu Ile Asn Lys Ser Gln Lys Thr Asp Asp Lys Lys Asp Glu Tyr Tyr
```

```
            660                 665                 670

Glu Val Thr Gln Thr His Asn Thr Ser Asp Ser Lys Tyr Ala Tyr Val
        675                 680                 685

Leu Tyr Pro Gly Leu Ser Lys Ser Asp Phe Lys Ser Lys Asn Asn Asn
    690                 695                 700

Val Ser Ile Val Lys Gln Asp Glu Asp Phe His Val Ile Lys Asp Asn
705                 710                 715                 720

Asp Gly Val Phe Ala Gly Val Asn Tyr Ser Asp Ser Thr Lys Ser Phe
                725                 730                 735

Asp Ile Asn Gly Thr Ile Val Glu Leu Lys Glu Lys Gly Met Phe Val
            740                 745                 750

Ile Lys Lys Lys Asp Asp Asn Thr Tyr Glu Cys Ser Phe Tyr Asn Pro
        755                 760                 765

Thr Ser Thr Asn Ser Thr Ser Asn Lys Glu Ser Lys Ile Ser Val Thr
    770                 775                 780

Gly Tyr Thr Ile Thr Asn Gln Ser Val Ser Asn Phe Lys Glu Ser Asp
785                 790                 795                 800

Ile His Phe Glu Leu Thr Lys
                805


<210> SEQ ID NO 79
<211> LENGTH: 807
<212> TYPE: PRT
<213> ORGANISM: Staphylococcus aureus

<400> SEQUENCE: 79

Met Thr Tyr Arg Ile Lys Lys Trp Gln Lys Leu Ser Thr Ile Thr Leu
1               5                   10                  15

Leu Met Ala Gly Val Ile Thr Leu Asn Gly Gly Glu Phe Arg Ser Val
            20                  25                  30

Asp Lys His Gln Ile Ala Val Ala Asp Thr Asn Val Gln Thr Pro Asp
        35                  40                  45

Tyr Glu Lys Leu Arg Asn Thr Trp Leu Asp Val Asn Tyr Gly Tyr Asp
    50                  55                  60

Lys Tyr Asp Glu Asn Asn Pro Asp Met Lys Lys Lys Phe Asp Ala Thr
65                  70                  75                  80

Glu Lys Glu Ala Thr Asn Leu Leu Lys Glu Met Lys Thr Glu Ser Gly
                85                  90                  95

Arg Lys Tyr Leu Trp Ser Gly Ala Glu Thr Leu Glu Thr Asn Ser Ser
            100                 105                 110

His Met Thr Arg Thr Tyr Arg Asn Ile Glu Lys Ile Ala Glu Ala Met
        115                 120                 125

Arg Asn Pro Lys Thr Thr Leu Asn Thr Asp Glu Asn Lys Lys Lys Val
    130                 135                 140

Lys Asp Ala Leu Glu Trp Leu His Lys Asn Ala Tyr Gly Lys Glu Pro
145                 150                 155                 160

Asp Lys Lys Val Lys Glu Leu Ser Glu Asn Phe Thr Lys Thr Thr Gly
                165                 170                 175

Lys Asn Thr Asn Leu Asn Trp Trp Asp Tyr Glu Ile Gly Thr Pro Lys
            180                 185                 190

Ser Leu Thr Asn Thr Leu Ile Leu Leu Asn Asp Gln Phe Ser Asn Glu
        195                 200                 205

Glu Lys Lys Lys Phe Thr Ala Pro Ile Lys Thr Phe Ala Pro Asp Ser
    210                 215                 220
```

```
Asp Lys Ile Leu Ser Ser Val Gly Lys Ala Glu Leu Ala Lys Gly Gly
225                 230                 235                 240

Asn Leu Val Asp Ile Ser Lys Val Lys Leu Leu Glu Cys Ile Ile Glu
                245                 250                 255

Glu Asp Lys Asp Met Met Lys Lys Ser Ile Asp Ser Phe Asn Lys Val
            260                 265                 270

Phe Thr Tyr Val Gln Asp Ser Ala Thr Gly Lys Glu Arg Asn Gly Phe
        275                 280                 285

Tyr Lys Asp Gly Ser Tyr Ile Asp His Gln Asp Val Pro Tyr Thr Gly
    290                 295                 300

Ala Tyr Gly Val Val Leu Leu Glu Gly Ile Ser Gln Met Met Pro Met
305                 310                 315                 320

Ile Lys Glu Thr Pro Phe Asn Asp Lys Thr Gln Asn Asp Thr Thr Leu
                325                 330                 335

Lys Ser Trp Ile Asp Asp Gly Phe Met Pro Leu Ile Tyr Lys Gly Glu
            340                 345                 350

Met Met Asp Leu Ser Arg Gly Arg Ala Ile Ser Arg Glu Asn Glu Thr
        355                 360                 365

Ser His Ser Ala Ser Ala Thr Val Met Lys Ser Leu Leu Arg Leu Ser
    370                 375                 380

Asp Ala Met Asp Asp Ser Thr Lys Ala Lys Tyr Lys Lys Ile Val Lys
385                 390                 395                 400

Ser Ser Val Glu Ser Asp Ser Ser Tyr Lys Gln Asn Asp Tyr Leu Asn
                405                 410                 415

Ser Tyr Ser Asp Ile Asp Lys Met Lys Ser Leu Met Thr Asp Asn Ser
            420                 425                 430

Ile Ser Lys Asn Gly Leu Thr Gln Gln Leu Lys Ile Tyr Asn Asp Met
        435                 440                 445

Asp Arg Val Thr Tyr His Asn Lys Asp Leu Asp Phe Ala Phe Gly Leu
    450                 455                 460

Ser Met Thr Ser Lys Asn Val Ala Arg Tyr Glu Ser Ile Asn Gly Glu
465                 470                 475                 480

Asn Leu Lys Gly Trp His Thr Gly Ala Gly Met Ser Tyr Leu Tyr Asn
                485                 490                 495

Ser Asp Val Lys His Tyr His Asp Asn Phe Trp Val Thr Ala Asp Met
            500                 505                 510

Lys Arg Leu Ser Gly Thr Thr Thr Leu Asp Asn Glu Ile Leu Lys Asp
        515                 520                 525

Thr Asp Asp Lys Lys Ser Ser Lys Thr Phe Val Gly Gly Thr Lys Val
    530                 535                 540

Asp Asp Gln His Ala Ser Ile Gly Met Asp Phe Glu Asn Gln Asp Lys
545                 550                 555                 560

Thr Leu Thr Ala Lys Lys Ser Tyr Phe Ile Leu Asn Asp Lys Ile Val
                565                 570                 575

Phe Leu Gly Thr Gly Ile Lys Ser Thr Asp Ser Ser Lys Asn Pro Val
            580                 585                 590

Thr Thr Ile Glu Asn Arg Lys Ala Asn Gly Tyr Thr Leu Tyr Thr Asp
        595                 600                 605

Asp Lys Gln Thr Thr Asn Ser Asp Asn Gln Glu Asn Asn Ser Val Phe
    610                 615                 620

Leu Glu Ser Thr Asp Thr Lys Lys Asn Ile Gly Tyr His Phe Leu Asn
625                 630                 635                 640

Lys Pro Lys Ile Thr Val Lys Lys Glu Ser His Thr Gly Lys Trp Lys
```

```
                645                 650                 655

Glu Ile Asn Lys Ser Gln Lys Asp Thr Gln Lys Thr Asp Glu Tyr Tyr
            660                 665                 670

Glu Val Thr Gln Lys His Ser Asn Ser Asp Asn Lys Tyr Gly Tyr Val
        675                 680                 685

Leu Tyr Pro Gly Leu Ser Lys Asp Val Phe Lys Thr Lys Lys Asp Glu
    690                 695                 700

Val Thr Val Val Lys Gln Glu Asp Asp Phe His Val Val Lys Asp Asn
705                 710                 715                 720

Glu Ser Val Trp Ala Gly Val Asn Tyr Ser Asn Ser Thr Gln Thr Phe
                725                 730                 735

Asp Ile Asn Asn Thr Lys Val Glu Val Lys Ala Lys Gly Met Phe Ile
            740                 745                 750

Leu Lys Lys Lys Asp Asp Asn Thr Tyr Glu Cys Ser Phe Tyr Asn Pro
        755                 760                 765

Glu Ser Thr Asn Ser Ala Ser Asp Ile Glu Ser Lys Ile Ser Met Thr
    770                 775                 780

Gly Tyr Ser Ile Thr Asn Lys Asn Thr Ser Thr Ser Asn Glu Ser Gly
785                 790                 795                 800

Val His Phe Glu Leu Thr Lys
                805


<210> SEQ ID NO 80
<211> LENGTH: 1066
<212> TYPE: PRT
<213> ORGANISM: Streptococcus pneumoniae

<400> SEQUENCE: 80

Met Gln Thr Lys Thr Lys Lys Leu Ile Val Ser Leu Ser Ser Leu Val
1               5                   10                  15

Leu Ser Gly Phe Leu Leu Asn His Tyr Met Thr Ile Gly Ala Glu Glu
            20                  25                  30

Thr Thr Thr Asn Thr Ile Gln Gln Ser Gln Lys Glu Val Gln Tyr Gln
        35                  40                  45

Gln Arg Asp Thr Lys Asn Leu Val Glu Asn Gly Asp Phe Gly Gln Thr
    50                  55                  60

Glu Asp Gly Ser Ser Pro Trp Thr Gly Ser Lys Ala Gln Gly Trp Ser
65                  70                  75                  80

Ala Trp Val Asp Gln Lys Asn Ser Ala Asp Ala Ser Thr Arg Val Ile
                85                  90                  95

Glu Ala Lys Asp Gly Ala Ile Thr Ile Ser Ser His Glu Lys Leu Arg
            100                 105                 110

Ala Ala Leu His Arg Met Val Pro Ile Glu Ala Lys Lys Lys Tyr Lys
        115                 120                 125

Leu Arg Phe Lys Ile Lys Thr Asp Asn Lys Ile Gly Ile Ala Lys Val
    130                 135                 140

Arg Ile Ile Glu Glu Ser Gly Lys Asp Lys Arg Leu Trp Asn Ser Ala
145                 150                 155                 160

Thr Thr Ser Gly Thr Lys Asp Trp Gln Thr Ile Glu Ala Asp Tyr Ser
                165                 170                 175

Pro Thr Leu Asp Val Asp Lys Ile Lys Leu Glu Leu Phe Tyr Glu Thr
            180                 185                 190

Gly Thr Gly Thr Val Ser Phe Lys Asp Ile Glu Leu Val Glu Val Ala
        195                 200                 205
```

```
Asp Gln Leu Ser Glu Asp Ser Gln Thr Asp Lys Gln Leu Glu Glu Lys
    210                 215                 220

Ile Asp Leu Pro Ile Gly Lys Lys His Val Phe Ser Leu Ala Asp Tyr
225                 230                 235                 240

Thr Tyr Lys Val Glu Asn Pro Asp Val Ala Ser Val Lys Asn Gly Ile
                245                 250                 255

Leu Glu Pro Leu Lys Glu Gly Thr Thr Asn Val Ile Val Ser Lys Asp
            260                 265                 270

Gly Lys Glu Val Lys Lys Ile Pro Leu Lys Ile Leu Ala Ser Val Lys
        275                 280                 285

Asp Ala Tyr Thr Asp Arg Leu Asp Asp Trp Asn Gly Ile Ile Ala Gly
    290                 295                 300

Asn Gln Tyr Tyr Asp Ser Lys Asn Glu Gln Met Ala Lys Leu Asn Gln
305                 310                 315                 320

Glu Leu Glu Gly Lys Val Ala Asp Ser Leu Ser Ser Ile Ser Ser Gln
                325                 330                 335

Ala Asp Arg Thr Tyr Leu Trp Glu Lys Phe Ser Asn Tyr Lys Thr Ser
            340                 345                 350

Ala Asn Leu Thr Ala Thr Tyr Arg Lys Leu Glu Glu Met Ala Lys Gln
        355                 360                 365

Val Thr Asn Pro Ser Ser Arg Tyr Tyr Gln Asp Glu Thr Val Val Arg
    370                 375                 380

Thr Val Arg Asp Ser Met Glu Trp Met His Lys His Val Tyr Asn Ser
385                 390                 395                 400

Glu Lys Ser Ile Val Gly Asn Trp Trp Asp Tyr Glu Ile Gly Thr Pro
                405                 410                 415

Arg Ala Ile Asn Asn Thr Leu Ser Leu Met Lys Glu Tyr Phe Ser Asp
            420                 425                 430

Glu Glu Ile Lys Lys Tyr Thr Asp Val Ile Glu Lys Phe Val Pro Asp
        435                 440                 445

Pro Glu His Phe Arg Lys Thr Thr Asp Asn Pro Phe Lys Ala Leu Gly
    450                 455                 460

Gly Asn Leu Val Asp Met Gly Arg Val Lys Val Ile Ala Gly Leu Leu
465                 470                 475                 480

Arg Lys Asp Asp Gln Glu Ile Ser Ser Thr Ile Arg Ser Ile Glu Gln
                485                 490                 495

Val Phe Lys Leu Val Asp Gln Gly Glu Gly Phe Tyr Gln Asp Gly Ser
            500                 505                 510

Tyr Ile Asp His Thr Asn Val Ala Tyr Thr Gly Ala Tyr Gly Asn Val
        515                 520                 525

Leu Ile Asp Gly Leu Ser Gln Leu Leu Pro Val Ile Gln Lys Thr Lys
    530                 535                 540

Asn Pro Ile Asp Lys Asp Lys Met Gln Thr Met Tyr His Trp Ile Asp
545                 550                 555                 560

Lys Ser Phe Ala Pro Leu Leu Val Asn Gly Glu Leu Met Asp Met Ser
                565                 570                 575

Arg Gly Arg Ser Ile Ser Arg Ala Asn Ser Glu Gly His Val Ala Ala
            580                 585                 590

Val Glu Val Leu Arg Gly Ile His Arg Ile Ala Asp Met Ser Glu Gly
        595                 600                 605

Glu Thr Lys Gln Cys Leu Gln Ser Leu Val Lys Thr Ile Val Gln Ser
    610                 615                 620

Asp Ser Tyr Tyr Asp Val Phe Lys Asn Leu Lys Thr Tyr Lys Asp Ile
```

```
625                 630                 635                 640

Ser Leu Met Gln Ser Leu Leu Ser Asp Ala Gly Val Ala Ser Val Pro
                645                 650                 655

Arg Pro Ser Tyr Leu Ser Ala Phe Asn Lys Met Asp Lys Thr Ala Met
            660                 665                 670

Tyr Asn Ala Glu Lys Gly Phe Gly Phe Gly Leu Ser Leu Phe Ser Ser
        675                 680                 685

Arg Thr Leu Asn Tyr Glu His Met Asn Lys Glu Asn Lys Arg Gly Trp
    690                 695                 700

Tyr Thr Ser Asp Gly Met Phe Tyr Leu Tyr Asn Gly Asp Leu Ser His
705                 710                 715                 720

Tyr Ser Asp Gly Tyr Trp Pro Thr Val Asn Pro Tyr Lys Met Pro Gly
                725                 730                 735

Thr Thr Glu Thr Asp Ala Lys Arg Ala Asp Ser Asp Thr Gly Lys Val
            740                 745                 750

Leu Pro Ser Ala Phe Val Gly Thr Ser Lys Leu Asp Asp Ala Asn Ala
        755                 760                 765

Thr Ala Thr Met Asp Phe Thr Asn Trp Asn Gln Thr Leu Thr Ala His
    770                 775                 780

Lys Ser Trp Phe Met Leu Lys Asp Lys Ile Ala Phe Leu Gly Ser Asn
785                 790                 795                 800

Ile Gln Asn Thr Ser Thr Asp Thr Ala Ala Thr Thr Ile Asp Gln Arg
                805                 810                 815

Lys Leu Glu Ser Gly Asn Pro Tyr Lys Val Tyr Val Asn Asp Lys Glu
            820                 825                 830

Ala Ser Leu Thr Glu Gln Glu Lys Asp Tyr Pro Glu Thr Gln Ser Val
        835                 840                 845

Phe Leu Glu Ser Phe Asp Ser Lys Lys Asn Ile Gly Tyr Phe Phe Phe
    850                 855                 860

Lys Lys Ser Ser Ile Ser Met Ser Lys Ala Leu Gln Lys Gly Ala Trp
865                 870                 875                 880

Lys Asp Ile Asn Glu Gly Gln Ser Asp Lys Glu Val Glu Asn Glu Phe
                885                 890                 895

Leu Thr Ile Ser Gln Ala His Lys Gln Asn Arg Asp Ser Tyr Gly Tyr
            900                 905                 910

Met Leu Ile Pro Asn Val Asp Arg Ala Thr Phe Asn Gln Met Ile Lys
        915                 920                 925

Glu Leu Glu Ser Ser Leu Ile Glu Asn Asn Glu Thr Leu Gln Ser Val
    930                 935                 940

Tyr Asp Ala Lys Gln Gly Val Trp Gly Ile Val Lys Tyr Asp Asp Ser
945                 950                 955                 960

Val Ser Thr Ile Ser Asn Gln Phe Gln Val Leu Lys Arg Gly Val Tyr
                965                 970                 975

Thr Ile Arg Lys Glu Gly Asp Glu Tyr Lys Ile Ala Tyr Tyr Asn Pro
            980                 985                 990

Glu Thr Gln Glu Ser Ala Pro Asp  Gln Glu Val Phe Lys  Lys Leu Glu
        995                 1000                 1005

Gln Ala  Ala Gln Pro Gln Val  Gln Asn Ser Lys Glu  Lys Glu Lys
    1010                 1015                 1020

Ser Glu  Glu Glu Lys Asn His  Ser Asp Gln Lys Asn  Leu Pro Gln
    1025                 1030                 1035

Thr Gly  Glu Gly Gln Ser Ile  Leu Ala Ser Leu Gly  Phe Leu Leu
    1040                 1045                 1050
```

```
Leu Gly  Ala Phe Tyr Leu Phe  Arg Arg Gly Lys Asn  Asn
    1055                1060                1065


<210> SEQ ID NO 81
<211> LENGTH: 1078
<212> TYPE: PRT
<213> ORGANISM: Streptococcus pneumoniae

<400> SEQUENCE: 81

Met Ile Leu Gln Tyr Val Tyr Trp Ser Val Tyr Met Gln Thr Lys Thr
1               5                   10                  15

Lys Lys Leu Ile Val Ser Leu Ser Ser Leu Val Leu Ser Gly Phe Leu
            20                  25                  30

Leu Asn His Tyr Met Thr Val Gly Ala Glu Glu Thr Thr Thr Asn Thr
        35                  40                  45

Ile Gln Gln Ser Gln Lys Glu Val Gln Tyr Gln Gln Arg Asp Thr Lys
    50                  55                  60

Asn Leu Val Glu Asn Gly Asp Phe Gly Gln Thr Glu Asp Gly Ser Ser
65                  70                  75                  80

Pro Trp Thr Gly Ser Lys Ala Gln Gly Trp Ser Ala Trp Val Asp Gln
                85                  90                  95

Lys Asn Ser Ser Ala Asp Ala Ser Thr Arg Val Ile Glu Ala Lys Asp
            100                 105                 110

Gly Ala Ile Thr Ile Ser Ser Pro Glu Lys Leu Arg Ala Ala Val His
        115                 120                 125

Arg Met Val Pro Ile Glu Ala Lys Lys Lys Tyr Lys Leu Arg Phe Lys
    130                 135                 140

Ile Lys Thr Asp Asn Lys Val Gly Ile Ala Lys Val Arg Ile Ile Glu
145                 150                 155                 160

Glu Ser Gly Lys Asp Lys Arg Leu Trp Asn Ser Ala Thr Thr Ser Gly
                165                 170                 175

Thr Lys Asp Trp Gln Thr Ile Glu Ala Asp Tyr Ser Pro Thr Leu Asp
            180                 185                 190

Val Asp Lys Ile Lys Leu Glu Leu Phe Tyr Glu Thr Gly Thr Gly Thr
        195                 200                 205

Val Ser Phe Lys Asp Ile Glu Leu Val Glu Val Ala Asp Gln Pro Ser
    210                 215                 220

Glu Asp Ser Gln Thr Asp Lys Gln Leu Glu Glu Lys Ile Asp Leu Pro
225                 230                 235                 240

Ile Gly Lys Lys His Val Phe Ser Leu Ala Asp Tyr Thr Tyr Lys Val
                245                 250                 255

Glu Asn Pro Asp Val Ala Ser Val Lys Asn Gly Ile Leu Glu Pro Leu
            260                 265                 270

Lys Glu Gly Thr Thr Asn Val Ile Val Ser Lys Asp Gly Lys Glu Val
        275                 280                 285

Lys Lys Ile Pro Leu Lys Ile Leu Ala Ser Val Lys Asp Thr Tyr Thr
    290                 295                 300

Asp Arg Leu Asp Asp Trp Asn Gly Ile Ile Ala Gly Asn Gln Tyr Tyr
305                 310                 315                 320

Asp Ser Lys Asn Glu Gln Met Ala Lys Leu Asn Gln Glu Leu Glu Gly
                325                 330                 335

Lys Val Ala Asp Ser Leu Ser Ser Ile Ser Ser Gln Ala Asp Arg Ile
            340                 345                 350

Tyr Leu Trp Glu Lys Phe Ser Asn Tyr Lys Thr Ser Ala Asn Leu Thr
```

-continued

```
        355                 360                 365

Ala Thr Tyr Arg Lys Leu Glu Glu Met Ala Lys Gln Val Thr Asn Pro
    370                 375                 380

Ser Ser Arg Tyr Tyr Gln Asp Glu Thr Val Val Arg Thr Val Arg Asp
385                 390                 395                 400

Ser Met Glu Trp Met His Lys His Val Tyr Asn Ser Glu Lys Ser Ile
                405                 410                 415

Val Gly Asn Trp Trp Asp Tyr Glu Ile Gly Thr Pro Arg Ala Ile Asn
            420                 425                 430

Asn Thr Leu Ser Leu Met Lys Glu Tyr Phe Ser Asp Glu Glu Ile Lys
        435                 440                 445

Lys Tyr Thr Asp Val Ile Glu Lys Phe Val Pro Asp Pro Glu His Phe
    450                 455                 460

Arg Lys Thr Thr Asp Asn Pro Phe Lys Ala Leu Gly Gly Asn Leu Val
465                 470                 475                 480

Asp Met Gly Arg Val Lys Val Ile Ala Gly Leu Leu Arg Lys Asp Asp
                485                 490                 495

Gln Glu Ile Ser Ser Thr Ile Arg Ser Ile Glu Gln Val Phe Lys Leu
            500                 505                 510

Val Asp Gln Gly Glu Gly Phe Tyr Gln Asp Gly Ser Tyr Ile Asp His
        515                 520                 525

Thr Asn Val Ala Tyr Thr Gly Ala Tyr Gly Asn Val Leu Ile Asp Gly
    530                 535                 540

Leu Ser Gln Leu Leu Pro Val Ile Gln Lys Thr Lys Asn Pro Ile Asp
545                 550                 555                 560

Lys Asp Lys Met Gln Thr Met Tyr His Trp Ile Asp Lys Ser Phe Ala
                565                 570                 575

Pro Leu Leu Val Asn Gly Glu Leu Met Asp Met Ser Arg Gly Arg Ser
            580                 585                 590

Ile Ser Arg Ala Asn Ser Glu Gly His Val Ala Ala Val Glu Val Leu
        595                 600                 605

Arg Gly Ile His Arg Ile Ala Asp Met Ser Glu Gly Glu Thr Lys Gln
    610                 615                 620

Arg Leu Gln Ser Leu Val Lys Thr Ile Val Gln Ser Asp Ser Tyr Tyr
625                 630                 635                 640

Asp Val Phe Lys Asn Leu Lys Thr Tyr Lys Asp Ile Ser Leu Met Gln
                645                 650                 655

Ser Leu Leu Ser Asp Ala Gly Val Ala Ser Val Pro Arg Thr Ser Tyr
            660                 665                 670

Leu Ser Ala Phe Asn Lys Met Asp Lys Thr Ala Met Tyr Asn Ala Glu
        675                 680                 685

Lys Gly Phe Gly Phe Gly Leu Ser Leu Phe Ser Ser Arg Thr Leu Asn
    690                 695                 700

Tyr Glu His Met Asn Lys Glu Asn Lys Arg Gly Trp Tyr Thr Ser Asp
705                 710                 715                 720

Gly Met Phe Tyr Leu Tyr Asn Gly Asp Leu Ser His Tyr Ser Asp Gly
                725                 730                 735

Tyr Trp Pro Thr Val Asn Pro Tyr Lys Met Pro Gly Thr Thr Glu Thr
            740                 745                 750

Asp Ala Lys Arg Ala Asp Ser Asp Thr Gly Lys Val Leu Pro Ser Ala
        755                 760                 765

Phe Val Gly Thr Ser Lys Leu Asp Asp Ala Asn Ala Thr Ala Thr Met
    770                 775                 780
```

```
Asp Phe Thr Asn Trp Asn Gln Thr Leu Thr Ala His Lys Ser Trp Phe
785                 790                 795                 800

Met Leu Lys Asp Lys Ile Ala Phe Leu Gly Ser Asn Ile Gln Asn Thr
                805                 810                 815

Ser Thr Asp Thr Ala Ala Thr Thr Ile Asp Gln Arg Lys Leu Glu Ser
            820                 825                 830

Ser Asn Pro Tyr Lys Val Tyr Val Asn Asp Lys Glu Ala Ser Leu Thr
        835                 840                 845

Glu Gln Glu Lys Asp Tyr Pro Glu Thr Gln Ser Val Phe Leu Glu Ser
    850                 855                 860

Ser Asp Ser Lys Lys Asn Ile Gly Tyr Phe Phe Phe Lys Lys Ser Ser
865                 870                 875                 880

Ile Ser Met Ser Lys Ala Leu Gln Lys Gly Ala Trp Lys Asp Ile Asn
                885                 890                 895

Glu Gly Gln Ser Asp Lys Glu Val Glu Asn Glu Phe Leu Thr Ile Ser
            900                 905                 910

Gln Ala His Lys Gln Asn Gly Asp Ser Tyr Gly Tyr Met Leu Ile Pro
        915                 920                 925

Asn Val Asp Arg Ala Thr Phe Asn Gln Met Ile Lys Glu Leu Glu Ser
    930                 935                 940

Ser Leu Ile Glu Asn Asn Glu Thr Leu Gln Ser Val Tyr Asp Ala Lys
945                 950                 955                 960

Gln Gly Val Trp Gly Ile Val Lys Tyr Asp Asp Ser Val Ser Thr Ile
                965                 970                 975

Ser Asn Gln Phe Gln Val Leu Lys Arg Gly Val Tyr Thr Ile Arg Lys
            980                 985                 990

Glu Gly Asp Glu Tyr Lys Ile Ala  Tyr Tyr Asn Pro Glu  Thr Gln Glu
        995                 1000                1005

Ser Ala  Pro Asp Gln Glu Val  Phe Lys Lys Leu Glu  Gln Ala Ala
    1010                1015                1020

Gln Pro  Gln Val Gln Asn Ser  Lys Glu Lys Glu Lys  Ser Glu Glu
    1025                1030                1035

Glu Lys  Asn His Ser Asp Gln  Lys Asn Leu Pro Gln  Thr Gly Glu
    1040                1045                1050

Gly Gln  Ser Ile Leu Ala Ser  Leu Gly Phe Leu Leu  Leu Gly Ala
    1055                1060                1065

Phe Tyr  Leu Phe Arg Arg Gly  Lys Asn Asn
    1070                1075
```

<210> SEQ ID NO 82
<211> LENGTH: 1067
<212> TYPE: PRT
<213> ORGANISM: Streptococcus pneumoniae

<400> SEQUENCE: 82

```
Met Gln Thr Lys Thr Lys Lys Leu Ile Val Ser Leu Ser Ser Leu Val
1               5                   10                  15

Leu Ser Gly Phe Leu Leu Asn His Tyr Met Thr Val Gly Ala Glu Glu
            20                  25                  30

Thr Thr Thr Asn Thr Ile Gln Gln Ser Gln Lys Glu Val Gln Tyr Gln
        35                  40                  45

Gln Arg Asp Thr Lys Asn Leu Val Glu Asn Gly Asp Phe Gly Gln Thr
    50                  55                  60

Glu Asp Gly Ser Ser Pro Trp Thr Gly Ser Lys Ala Gln Gly Trp Ser
```

-continued

```
65                  70                  75                  80

Ala Trp Val Asp Gln Lys Asn Ser Ser Ala Asp Ala Ser Thr Arg Val
                85                  90                  95

Ile Glu Ala Lys Asp Gly Ala Ile Thr Ile Ser Ser Pro Glu Lys Leu
            100                 105                 110

Arg Ala Ala Val His Arg Met Val Pro Ile Glu Ala Lys Lys Lys Tyr
        115                 120                 125

Lys Leu Arg Phe Lys Ile Lys Thr Asp Asn Lys Val Gly Ile Ala Lys
    130                 135                 140

Val Arg Ile Ile Glu Glu Ser Gly Lys Asp Lys Arg Leu Trp Asn Ser
145                 150                 155                 160

Ala Thr Thr Ser Gly Thr Lys Asp Trp Gln Thr Ile Glu Ala Asp Tyr
                165                 170                 175

Ser Pro Thr Leu Asp Val Asp Lys Ile Lys Leu Glu Leu Phe Tyr Glu
            180                 185                 190

Thr Gly Thr Gly Thr Val Ser Phe Lys Asp Ile Glu Leu Val Glu Val
        195                 200                 205

Ala Asp Gln Pro Ser Glu Asp Ser Gln Thr Asp Lys Gln Leu Glu Glu
    210                 215                 220

Lys Ile Asp Leu Pro Ile Gly Lys Lys His Val Phe Ser Leu Ala Asp
225                 230                 235                 240

Tyr Thr Tyr Lys Val Glu Asn Pro Asp Val Ala Ser Val Lys Asn Gly
                245                 250                 255

Ile Leu Glu Pro Leu Lys Glu Gly Thr Thr Asn Val Ile Val Ser Lys
            260                 265                 270

Asp Gly Lys Glu Val Lys Lys Ile Pro Leu Lys Ile Leu Ala Ser Val
        275                 280                 285

Lys Asp Thr Tyr Thr Asp Arg Leu Asp Asp Trp Asn Gly Ile Ile Ala
    290                 295                 300

Gly Asn Gln Tyr Tyr Asp Ser Lys Asn Glu Gln Met Ala Lys Leu Asn
305                 310                 315                 320

Gln Glu Leu Glu Gly Lys Val Ala Asp Ser Leu Ser Ser Ile Ser Ser
                325                 330                 335

Gln Ala Asp Arg Ile Tyr Leu Trp Glu Lys Phe Ser Asn Tyr Lys Thr
            340                 345                 350

Ser Ala Asn Leu Thr Ala Thr Tyr Arg Lys Leu Glu Glu Met Ala Lys
        355                 360                 365

Gln Val Thr Asn Pro Ser Ser Arg Tyr Tyr Gln Asp Glu Thr Val Val
    370                 375                 380

Arg Thr Val Arg Asp Ser Met Glu Trp Met His Lys His Val Tyr Asn
385                 390                 395                 400

Ser Glu Lys Ser Ile Val Gly Asn Trp Trp Asp Tyr Glu Ile Gly Thr
                405                 410                 415

Pro Arg Ala Ile Asn Asn Thr Leu Ser Leu Met Lys Glu Tyr Phe Ser
            420                 425                 430

Asp Glu Glu Ile Lys Lys Tyr Thr Asp Val Ile Glu Lys Phe Val Pro
        435                 440                 445

Asp Pro Glu His Phe Arg Lys Thr Thr Asp Asn Pro Phe Lys Ala Leu
    450                 455                 460

Gly Gly Asn Leu Val Asp Met Gly Arg Val Lys Val Ile Ala Gly Leu
465                 470                 475                 480

Leu Arg Lys Asp Asp Gln Glu Ile Ser Ser Thr Ile Arg Ser Ile Glu
                485                 490                 495
```

```
Gln Val Phe Lys Leu Val Asp Gln Gly Glu Gly Phe Tyr Gln Asp Gly
            500                 505                 510

Ser Tyr Ile Asp His Thr Asn Val Ala Tyr Thr Gly Ala Tyr Gly Asn
        515                 520                 525

Val Leu Ile Asp Gly Leu Ser Gln Leu Leu Pro Val Ile Gln Lys Thr
    530                 535                 540

Lys Asn Pro Ile Asp Lys Asp Lys Met Gln Thr Met Tyr His Trp Ile
545                 550                 555                 560

Asp Lys Ser Phe Ala Pro Leu Leu Val Asn Gly Glu Leu Met Asp Met
                565                 570                 575

Ser Arg Gly Arg Ser Ile Ser Arg Ala Asn Ser Glu Gly His Val Ala
            580                 585                 590

Ala Val Glu Val Leu Arg Gly Ile His Arg Ile Ala Asp Met Ser Glu
        595                 600                 605

Gly Glu Thr Lys Gln Arg Leu Gln Ser Leu Val Lys Thr Ile Val Gln
    610                 615                 620

Ser Asp Ser Tyr Tyr Asp Val Phe Lys Asn Leu Lys Thr Tyr Lys Asp
625                 630                 635                 640

Ile Ser Leu Met Gln Ser Leu Leu Ser Asp Ala Gly Val Ala Ser Val
                645                 650                 655

Pro Arg Thr Ser Tyr Leu Ser Ala Phe Asn Lys Met Asp Lys Thr Ala
            660                 665                 670

Met Tyr Asn Ala Glu Lys Gly Phe Gly Phe Gly Leu Ser Leu Phe Ser
        675                 680                 685

Ser Arg Thr Leu Asn Tyr Glu His Met Asn Lys Glu Asn Lys Arg Gly
    690                 695                 700

Trp Tyr Thr Ser Asp Gly Met Phe Tyr Leu Tyr Asn Gly Asp Leu Ser
705                 710                 715                 720

His Tyr Ser Asp Gly Tyr Trp Pro Thr Val Asn Pro Tyr Lys Met Pro
                725                 730                 735

Gly Thr Thr Glu Thr Asp Ala Lys Arg Ala Asp Ser Asp Thr Gly Lys
            740                 745                 750

Val Leu Pro Ser Ala Phe Val Gly Thr Ser Lys Leu Asp Asp Ala Asn
        755                 760                 765

Ala Thr Ala Thr Met Asp Phe Thr Asn Trp Asn Gln Thr Leu Thr Ala
    770                 775                 780

His Lys Ser Trp Phe Met Leu Lys Asp Lys Ile Ala Phe Leu Gly Ser
785                 790                 795                 800

Asn Ile Gln Asn Thr Ser Thr Asp Thr Ala Ala Thr Thr Ile Asp Gln
                805                 810                 815

Arg Lys Leu Glu Ser Ser Asn Pro Tyr Lys Val Tyr Val Asn Asp Lys
            820                 825                 830

Glu Ala Ser Leu Thr Glu Gln Glu Lys Asp Tyr Pro Glu Thr Gln Ser
        835                 840                 845

Val Phe Leu Glu Ser Ser Asp Ser Lys Lys Asn Ile Gly Tyr Phe Phe
    850                 855                 860

Phe Lys Lys Ser Ser Ile Ser Met Ser Lys Ala Leu Gln Lys Gly Ala
865                 870                 875                 880

Trp Lys Asp Ile Asn Glu Gly Gln Ser Asp Lys Glu Val Glu Asn Glu
                885                 890                 895

Phe Leu Thr Ile Ser Gln Ala His Lys Gln Asn Gly Asp Ser Tyr Gly
            900                 905                 910
```

```
Tyr Met Leu Ile Pro Asn Val Asp Arg Ala Thr Phe Asn Gln Met Ile
        915                 920                 925

Lys Glu Leu Glu Ser Ser Leu Ile Glu Asn Asn Glu Thr Leu Gln Ser
    930                 935                 940

Val Tyr Asp Ala Lys Gln Gly Val Trp Gly Ile Val Lys Tyr Asp Asp
945                 950                 955                 960

Ser Val Ser Thr Ile Ser Asn Gln Phe Gln Val Leu Lys Arg Gly Val
                965                 970                 975

Tyr Thr Ile Arg Lys Glu Gly Asp Glu Tyr Lys Ile Ala Tyr Tyr Asn
            980                 985                 990

Pro Glu Thr Gln Glu Ser Ala Pro  Asp Gln Glu Val Phe  Lys Lys Leu
        995                 1000                1005

Glu Gln  Ala Ala Gln Pro Gln  Val Gln Asn Ser Lys  Glu Lys Glu
    1010                1015                1020

Lys Ser  Glu Glu Glu Lys Asn  His Ser Asp Gln Lys  Asn Leu Pro
    1025                1030                1035

Gln Thr  Gly Glu Gly Gln Ser  Ile Leu Ala Ser Leu  Gly Phe Leu
    1040                1045                1050

Leu Leu  Gly Ala Phe Tyr Leu  Phe Arg Arg Gly Lys  Asn Asn
    1055                1060                1065


<210> SEQ ID NO 83
<211> LENGTH: 805
<212> TYPE: PRT
<213> ORGANISM: Streptococcus pyogenes

<400> SEQUENCE: 83

Met Asn Thr Tyr Phe Cys Thr His His Lys Gln Leu Leu Leu Tyr Ser
1               5                   10                  15

Asn Leu Phe Leu Ser Phe Ala Met Met Gly Gln Gly Thr Ala Ile Tyr
            20                  25                  30

Ala Asp Thr Leu Thr Ser Asn Ser Glu Pro Asn Asn Thr Tyr Phe Gln
        35                  40                  45

Thr Gln Thr Leu Thr Thr Thr Asp Ser Glu Lys Lys Val Val Gln Pro
    50                  55                  60

Gln Gln Lys Asp Tyr Tyr Thr Glu Leu Leu Asp Gln Trp Asn Ser Ile
65                  70                  75                  80

Ile Ala Gly Asn Asp Ala Tyr Asp Lys Thr Asn Pro Asp Met Val Thr
                85                  90                  95

Phe His Asn Lys Ala Glu Lys Asp Ala Gln Asn Ile Ile Lys Ser Tyr
            100                 105                 110

Gln Gly Pro Asp His Glu Asn Arg Thr Tyr Leu Trp Glu His Ala Lys
        115                 120                 125

Asp Tyr Ser Ala Ser Ala Asn Ile Thr Lys Thr Tyr Arg Asn Ile Glu
    130                 135                 140

Lys Ile Ala Lys Gln Ile Thr Asn Pro Glu Ser Cys Tyr Tyr Gln Asp
145                 150                 155                 160

Ser Lys Ala Ile Ala Ile Val Lys Asp Gly Met Ala Phe Met Tyr Glu
                165                 170                 175

His Ala Tyr Asn Leu Asp Arg Glu Asn His Gln Thr Thr Gly Lys Glu
            180                 185                 190

Asn Lys Glu Asn Trp Trp Val Tyr Glu Ile Gly Thr Pro Arg Ala Ile
        195                 200                 205

Asn Asn Thr Leu Ser Leu Met Tyr Pro Tyr Phe Thr Gln Glu Glu Ile
    210                 215                 220
```

-continued

```
Leu Lys Tyr Thr Ala Pro Ile Glu Lys Phe Val Pro Asp Pro Thr Arg
225                 230                 235                 240

Phe Arg Val Arg Ala Ala Asn Phe Ser Pro Phe Glu Ala Asn Ser Gly
                245                 250                 255

Asn Leu Ile Asp Met Gly Arg Val Lys Leu Ile Ser Gly Ile Leu Arg
            260                 265                 270

Lys Asp Asp Leu Glu Ile Ser Asp Thr Ile Lys Ala Ile Glu Lys Val
        275                 280                 285

Phe Thr Leu Val Asp Glu Gly Asn Gly Phe Tyr Gln Asp Gly Ser Leu
    290                 295                 300

Ile Asp His Val Val Thr Asn Ala Gln Ser Pro Leu Tyr Lys Lys Gly
305                 310                 315                 320

Ile Ala Tyr Thr Gly Ala Tyr Gly Asn Val Leu Ile Asp Gly Leu Ser
                325                 330                 335

Gln Leu Ile Pro Ile Ile Gln Lys Thr Lys Ser Pro Ile Lys Ala Asp
            340                 345                 350

Lys Met Ala Thr Ile Tyr His Trp Ile Asn His Ser Phe Phe Pro Ile
        355                 360                 365

Ile Val Arg Gly Glu Met Met Asp Met Thr Arg Gly Arg Ser Ile Ser
    370                 375                 380

Arg Phe Asn Ala Gln Ser His Val Ala Gly Ile Glu Ala Leu Arg Ala
385                 390                 395                 400

Ile Leu Arg Ile Ala Asp Met Ser Glu Glu Pro His Arg Leu Ala Leu
                405                 410                 415

Lys Thr Arg Ile Lys Thr Leu Val Thr Gln Gly Asn Ala Phe Tyr Asn
            420                 425                 430

Val Tyr Asp Asn Leu Lys Thr Tyr His Asp Ile Lys Leu Met Lys Glu
        435                 440                 445

Leu Leu Ser Asp Thr Ser Val Pro Val Gln Lys Leu Asp Ser Tyr Val
    450                 455                 460

Ala Ser Phe Asn Ser Met Asp Lys Leu Ala Leu Tyr Asn Asn Lys His
465                 470                 475                 480

Asp Phe Ala Phe Gly Leu Ser Met Phe Ser Asn Arg Thr Gln Asn Tyr
                485                 490                 495

Glu Ala Met Asn Asn Glu Asn Leu His Gly Trp Phe Thr Ser Asp Gly
            500                 505                 510

Met Phe Tyr Leu Tyr Asn Asn Asp Leu Gly His Tyr Ser Glu Asn Tyr
        515                 520                 525

Trp Ala Thr Val Asn Pro Tyr Arg Leu Pro Gly Thr Thr Glu Thr Glu
    530                 535                 540

Gln Lys Pro Leu Glu Gly Thr Pro Glu Asn Ile Lys Thr Asn Tyr Gln
545                 550                 555                 560

Gln Val Gly Met Thr Gly Leu Ser Asp Asp Ala Phe Val Ala Ser Lys
                565                 570                 575

Lys Leu Asn Asn Thr Ser Ala Leu Ala Ala Met Thr Phe Thr Asn Trp
            580                 585                 590

Asn Lys Ser Leu Thr Leu Asn Lys Gly Trp Phe Ile Leu Gly Asn Lys
        595                 600                 605

Ile Ile Phe Val Gly Ser Asn Ile Lys Asn Gln Ser Ser His Lys Ala
    610                 615                 620

Tyr Thr Thr Ile Glu Gln Arg Lys Glu Asn Gln Lys Tyr Pro Tyr Cys
625                 630                 635                 640
```

Ser Tyr Val Asn Asn Gln Pro Val Asp Leu Asn Asn Gln Leu Val Asp
645 650 655

Phe Thr Asn Thr Lys Ser Ile Phe Leu Glu Ser Asp Asp Pro Ala Gln
660 665 670

Asn Ile Gly Tyr Tyr Phe Phe Lys Pro Thr Thr Leu Ser Ile Ser Lys
675 680 685

Ala Leu Gln Thr Gly Lys Trp Gln Asn Ile Lys Ala Asp Asp Lys Ser
690 695 700

Pro Glu Ala Ile Lys Glu Val Ser Asn Thr Phe Ile Thr Ile Met Gln
705 710 715 720

Asn His Thr Gln Asp Gly Asp Arg Tyr Ala Tyr Met Met Leu Pro Asn
725 730 735

Met Thr Arg Gln Glu Phe Glu Thr Tyr Ile Ser Lys Leu Asp Ile Asp
740 745 750

Leu Leu Glu Asn Asn Asp Lys Leu Ala Ala Val Tyr Asp His Asp Ser
755 760 765

Gln Gln Met His Val Ile His Tyr Gly Lys Lys Ala Thr Met Phe Ser
770 775 780

Asn His Asn Leu Ser His Gln Gly Phe Tyr Ser Phe Pro His Pro Val
785 790 795 800

Arg Gln Asn Gln Gln
805

<210> SEQ ID NO 84
<211> LENGTH: 780
<212> TYPE: PRT
<213> ORGANISM: Streptococcus pyogenes

<400> SEQUENCE: 84

Met Val Tyr Phe Tyr Leu Val Asn Gln Ser Thr Phe Ile Ile Ser Phe
1 5 10 15

Leu Tyr Trp Arg Asn Val Ser Val Asn Thr Tyr Phe Cys Thr His His
20 25 30

Lys Gln Leu Leu Leu Tyr Ser Asn Leu Phe Leu Ser Phe Ala Met Ile
35 40 45

Gly Gln Gly Thr Ala Ile Tyr Ala Asp Thr Leu Thr Ser Asn Ser Glu
50 55 60

Pro Asn Asn Thr Tyr Phe Gln Thr Gln Thr Leu Thr Thr Thr Asp Ser
65 70 75 80

Glu Lys Lys Val Val Gln Pro Gln Gln Lys Asp Tyr Tyr Thr Glu Leu
85 90 95

Leu Asp Gln Trp Asn Ser Ile Ile Ala Gly Asn Asp Ala Tyr Asp Lys
100 105 110

Thr Asn Pro Asp Met Val Thr Phe His Asn Lys Ala Glu Lys Asp Ala
115 120 125

Gln Asn Ile Ile Lys Ser Tyr Gln Gly Pro Asp His Glu Asn Arg Thr
130 135 140

Tyr Leu Trp Glu His Ala Lys Asp Tyr Ser Ala Ser Thr Asn Ile Thr
145 150 155 160

Lys Thr Tyr Arg Asn Ile Glu Lys Ile Ala Lys Gln Ile Thr Asn Pro
165 170 175

Glu Ser Cys Tyr Tyr Gln Asp Ser Lys Ala Ile Ala Ile Val Lys Asp
180 185 190

Gly Met Ala Phe Met Tyr Glu His Ala Tyr Asn Leu Asn Arg Glu Asn
195 200 205

-continued

```
His Gln Thr Thr Gly Lys Glu Asn Lys Glu Asn Trp Trp Val Tyr Glu
    210                 215                 220

Ile Gly Thr Pro Arg Ala Ile Asn Asn Thr Leu Ser Leu Met Tyr Pro
225                 230                 235                 240

Tyr Phe Thr Gln Glu Glu Ile Leu Lys Tyr Thr Ala Pro Ile Glu Lys
                245                 250                 255

Phe Val Pro Asp Pro Thr Arg Phe Arg Val Arg Ala Ala Asn Phe Ser
            260                 265                 270

Pro Phe Glu Ala Asn Ser Gly Asn Leu Ile Asp Met Gly Arg Val Lys
        275                 280                 285

Leu Ile Ser Gly Ile Leu Arg Lys Asp Asp Leu Glu Ile Ser Asp Thr
    290                 295                 300

Ile Lys Ala Ile Glu Lys Val Phe Thr Leu Val Asp Glu Gly Asn Gly
305                 310                 315                 320

Phe Tyr Gln Asp Gly Ser Leu Ile Asp His Val Val Thr Asn Thr Gln
                325                 330                 335

Ser Pro Leu Tyr Lys Lys Gly Ile Ala Tyr Thr Gly Ala Tyr Gly Asn
            340                 345                 350

Val Leu Ile Asp Gly Leu Ser Gln Leu Ile Pro Ile Ile Gln Lys Thr
        355                 360                 365

Lys Ser Pro Ile Glu Ala Asp Lys Met Ala Thr Ile Tyr His Trp Ile
    370                 375                 380

Asn His Ser Phe Phe Pro Ile Ile Val Arg Gly Glu Met Met Asp Met
385                 390                 395                 400

Thr Arg Gly Arg Ser Ile Ser Arg Phe Asn Ala Gln Ser His Val Ala
                405                 410                 415

Gly Ile Glu Ala Leu Arg Ala Ile Leu Arg Ile Ala Asp Met Ser Glu
            420                 425                 430

Glu Pro His Arg Leu Glu Leu Lys Thr Arg Ile Lys Thr Leu Val Thr
        435                 440                 445

Gln Gly Asn Ala Phe Tyr Asn Val Tyr Asp Asn Leu Lys Thr Tyr His
    450                 455                 460

Asp Ile Lys Leu Met Lys Glu Leu Leu Ser Asp Thr Ser Val Pro Val
465                 470                 475                 480

Gln Lys Leu Asp Ser Tyr Val Ala Ser Phe Asn Ser Met Asp Lys Leu
                485                 490                 495

Ala Leu Tyr Asn Asn Lys His Asp Phe Ala Phe Gly Leu Ser Met Phe
            500                 505                 510

Ser Asn Arg Thr Gln Asn Tyr Glu Ala Met Asn Asn Glu Asn Leu His
        515                 520                 525

Gly Trp Phe Thr Ser Asp Gly Met Phe Tyr Leu Tyr Asn Asn Asp Leu
    530                 535                 540

Gly His Tyr Ser Glu Asn Tyr Trp Ala Thr Val Asn Pro Tyr Arg Leu
545                 550                 555                 560

Pro Gly Thr Thr Glu Thr Glu Gln Lys Pro Leu Glu Gly Thr Pro Glu
                565                 570                 575

Asn Ile Lys Thr Asn Tyr Gln Gln Val Gly Met Thr Ser Leu Ser Asp
            580                 585                 590

Asp Ala Phe Val Ala Ser Lys Lys Leu Asn Asn Thr Ser Ala Leu Ala
        595                 600                 605

Ala Met Thr Phe Thr Asn Trp Asn Lys Ser Leu Thr Leu Asn Lys Gly
    610                 615                 620
```

Trp Phe Ile Leu Gly Asn Lys Ile Ile Phe Val Gly Ser Asn Ile Lys
625 630 635 640

Asn Gln Ser Ser His Lys Ala Tyr Thr Thr Ile Glu Gln Arg Lys Glu
645 650 655

Asn Gln Lys His Pro Tyr Cys Ser Tyr Val Asn Asn Gln Pro Val Asp
660 665 670

Leu Asn Asn Gln Leu Val Asp Phe Thr Asn Thr Lys Ser Ile Phe Leu
675 680 685

Glu Ser Asp Asp Pro Ala Gln Asn Ile Gly Tyr Tyr Phe Phe Lys Pro
690 695 700

Arg Thr Leu Ser Ile Ser Lys Ala Leu Gln Thr Gly Lys Trp Gln Asn
705 710 715 720

Ile Lys Ala Asp Asp Lys Ser Pro Glu Ala Ile Lys Glu Val Ser Asn
725 730 735

Thr Phe Ile Thr Ile Met Gln Asn His Thr Gln Glu Gly Asp Arg Tyr
740 745 750

Ala Tyr Met Met Leu Pro Asn Met Thr Arg Gln Glu Phe Glu Thr Tyr
755 760 765

Ile Ser Lys Leu Asp Ile Asp Leu Leu Glu Asn Asn
770 775 780

<210> SEQ ID NO 85
<211> LENGTH: 868
<212> TYPE: PRT
<213> ORGANISM: Streptococcus pyogenes

<400> SEQUENCE: 85

Met Asn Thr Tyr Phe Cys Thr His His Lys Gln Leu Leu Leu Tyr Ser
1 5 10 15

Asn Leu Phe Leu Ser Phe Ala Met Met Gly Gln Gly Thr Ala Ile Tyr
20 25 30

Ala Asp Thr Leu Thr Ser Asn Ser Lys Pro Asn Asn Thr Tyr Phe Gln
35 40 45

Thr Gln Thr Leu Thr Thr Thr Asp Ser Glu Lys Lys Val Val Gln Pro
50 55 60

Gln Gln Lys Asp Tyr Tyr Thr Glu Leu Leu Asp Gln Trp Asn Ser Ile
65 70 75 80

Ile Ala Gly Asn Asp Ala Tyr Asp Lys Thr Asn Pro Asp Met Val Thr
85 90 95

Phe His Asn Lys Ala Glu Lys Asp Ala Gln Asn Ile Ile Lys Ser Tyr
100 105 110

Gln Glu Pro Asp His Glu Asn Arg Thr Tyr Leu Trp Glu His Ala Lys
115 120 125

Asp Tyr Ser Ala Ser Ala Asn Ile Thr Lys Thr Tyr Arg Asn Ile Glu
130 135 140

Lys Ile Ala Lys Gln Ile Thr Asn Pro Glu Ser Cys Tyr Tyr Gln Asp
145 150 155 160

Ser Lys Ala Ile Ala Ile Val Lys Asp Gly Met Ala Phe Met Tyr Glu
165 170 175

His Ala Tyr Asn Leu Asp Arg Glu Asn His Gln Thr Thr Gly Lys Glu
180 185 190

Asn Lys Glu Asn Trp Trp Asp Tyr Glu Ile Gly Thr Pro Arg Ala Ile
195 200 205

Asn Asn Thr Leu Ser Leu Met Tyr Pro Tyr Phe Thr Gln Glu Glu Ile
210 215 220

-continued

```
Leu Lys Tyr Thr Ala Pro Ile Glu Lys Phe Val Pro Asp Pro Thr Arg
225                 230                 235                 240

Phe Arg Val Arg Ala Ala Asn Phe Pro Pro Phe Glu Ala Asn Ser Gly
                245                 250                 255

Asn Leu Ile Asp Met Gly Arg Val Lys Leu Ile Ser Gly Ile Leu Arg
            260                 265                 270

Lys Asp Asp Leu Glu Ile Ser Asp Thr Ile Lys Ala Ile Glu Lys Val
        275                 280                 285

Phe Thr Leu Val Asp Glu Gly Asn Gly Phe Tyr Gln Asp Gly Ser Leu
    290                 295                 300

Ile Asp His Val Val Thr Asn Ala Gln Ser Pro Leu Tyr Lys Lys Gly
305                 310                 315                 320

Ile Ala Tyr Thr Gly Ala Tyr Gly Asn Val Leu Ile Asp Gly Leu Ser
                325                 330                 335

Gln Leu Ile Pro Ile Ile Gln Lys Thr Lys Ser Pro Ile Glu Ala Asp
            340                 345                 350

Lys Met Ala Thr Ile Tyr His Trp Ile Asn His Ser Phe Phe Pro Ile
        355                 360                 365

Ile Val Arg Gly Glu Met Met Asp Met Thr Arg Gly Arg Ser Ile Ser
    370                 375                 380

Arg Phe Asn Ala Gln Ser His Val Ala Gly Ile Glu Ala Leu Arg Ala
385                 390                 395                 400

Ile Leu Arg Ile Ala Asp Met Ser Glu Glu Pro His Arg Leu Ala Leu
                405                 410                 415

Lys Thr Arg Ile Lys Thr Leu Val Thr Gln Gly Asn Val Phe Tyr Asn
            420                 425                 430

Val Tyr Asp Asn Leu Lys Thr Tyr His Asp Ile Lys Leu Met Lys Glu
        435                 440                 445

Leu Leu Ser Asp Thr Ser Val Pro Val Gln Lys Leu Asp Ser Tyr Val
    450                 455                 460

Ala Ser Phe Asn Ser Met Asp Lys Leu Ala Leu Tyr Asn Asn Lys His
465                 470                 475                 480

Asp Phe Ala Phe Gly Leu Ser Met Phe Ser Asn Arg Thr Gln Asn Tyr
                485                 490                 495

Glu Ala Met Asn Asn Glu Asn Leu His Gly Trp Phe Thr Ser Asp Gly
            500                 505                 510

Met Phe Tyr Leu Tyr Asn Asn Asp Leu Gly His Tyr Ser Glu Asn Tyr
        515                 520                 525

Trp Ala Thr Val Asn Pro Tyr Arg Leu Pro Gly Thr Thr Glu Thr Glu
    530                 535                 540

Gln Lys Pro Leu Glu Gly Thr Pro Glu Asn Ile Lys Thr Asn Tyr Gln
545                 550                 555                 560

Gln Val Gly Met Thr Ser Leu Ser Asp Asp Ala Phe Val Ala Ser Lys
                565                 570                 575

Lys Leu Asn Asn Thr Ser Ala Leu Ala Ala Met Thr Phe Thr Asn Trp
            580                 585                 590

Asn Lys Ser Leu Thr Leu Asn Lys Gly Trp Phe Ile Leu Gly Asn Lys
        595                 600                 605

Ile Ile Phe Val Gly Ser Asn Ile Lys Asn Gln Ser Ser His Lys Ala
    610                 615                 620

Tyr Thr Thr Ile Glu Gln Arg Lys Glu Asn Gln Lys His Pro Tyr Cys
625                 630                 635                 640
```

```
Ser Tyr Val Asn Asn Gln Pro Val Asp Leu Asn Asn Gln Leu Val Asp
                645                 650                 655

Phe Thr Asn Thr Lys Ser Ile Phe Leu Glu Ser Asp Asp Pro Ala Gln
            660                 665                 670

Asn Ile Gly Tyr Tyr Phe Phe Lys Pro Thr Thr Leu Ser Ile Ser Lys
        675                 680                 685

Ala Leu Gln Thr Gly Lys Trp Gln Asn Ile Lys Ala Asp Asp Lys Ser
    690                 695                 700

Pro Glu Ala Ile Lys Glu Val Ser Asn Thr Phe Ile Thr Ile Met Gln
705                 710                 715                 720

Asn His Thr Gln Asp Gly Asp Arg Tyr Ala Tyr Met Met Leu Pro Asn
                725                 730                 735

Met Thr Arg Gln Glu Phe Glu Thr Tyr Ile Ser Lys Leu Asp Ile Asp
            740                 745                 750

Leu Leu Glu Asn Asn Asp Lys Leu Ala Ala Val Tyr Asp His Asp Ser
        755                 760                 765

Gln Gln Met His Val Ile His Tyr Glu Lys Lys Ala Thr Thr Phe Ser
    770                 775                 780

Asn His Asn Leu Ser His Gln Gly Phe Tyr Ser Phe Pro His Pro Val
785                 790                 795                 800

Lys Gln Asn Gln Gln Gln Lys Leu Ala His Gln Gly Ile Ala Ala Lys
                805                 810                 815

Asn Asn Ala Leu Asn Ser His Lys Ile Pro His Lys Arg Gln Arg Arg
            820                 825                 830

Leu Pro Arg Thr Gly Tyr Gln Ser Ser Ser Leu Glu Phe Leu Gly Gly
        835                 840                 845

Ala Leu Val Ala Ser Phe Asn His Ile Thr Lys Pro Phe Arg Lys Lys
    850                 855                 860

Asp Leu Arg Ile
865


<210> SEQ ID NO 86
<211> LENGTH: 828
<212> TYPE: PRT
<213> ORGANISM: Streptococcus pyogenes

<400> SEQUENCE: 86

Met Val Tyr Phe Tyr Leu Val Asp Gln Phe Thr Phe Ile Ile Ser Phe
1               5                   10                  15

Leu Tyr Trp Arg Asn Leu Ser Val Asn Thr Tyr Phe Cys Thr His His
            20                  25                  30

Lys Gln Leu Leu Leu Tyr Ser Asn Leu Phe Leu Ser Phe Ala Met Met
        35                  40                  45

Gly Gln Gly Thr Ala Ile Tyr Ala Asp Thr Leu Thr Ser Asn Ser Glu
    50                  55                  60

Pro Asn Asn Thr Tyr Phe Gln Thr Gln Thr Leu Thr Thr Thr Asp Ser
65                  70                  75                  80

Glu Lys Lys Val Val Gln Pro Gln Gln Lys Asp Tyr Tyr Thr Glu Leu
                85                  90                  95

Leu Asp Gln Trp Asn Ser Ile Ile Ala Gly Asn Asp Ala Tyr Asp Lys
            100                 105                 110

Thr Asn Pro Asp Met Val Thr Phe His Asn Lys Ala Glu Lys Asp Ala
        115                 120                 125

Gln Asn Ile Ile Lys Ser Tyr Gln Gly Pro Asp His Glu Asn Arg Thr
    130                 135                 140
```

```
Tyr Leu Trp Glu His Ala Lys Asp Tyr Ser Ala Ser Thr Asn Ile Thr
145                 150                 155                 160

Lys Thr Tyr Arg Asn Ile Glu Lys Ile Ala Lys Gln Ile Thr Asn Pro
                165                 170                 175

Glu Ser Cys Tyr Tyr Gln Asp Ser Lys Ala Ile Ala Ile Val Lys Asp
            180                 185                 190

Gly Met Ala Phe Met Tyr Glu His Ala Tyr Asn Leu Asp Arg Glu Asn
        195                 200                 205

His Gln Thr Thr Gly Lys Glu Asn Lys Glu Asn Trp Trp Val Tyr Glu
    210                 215                 220

Ile Gly Thr Pro Arg Ala Ile Asn Asn Thr Leu Ser Leu Met Tyr Pro
225                 230                 235                 240

Tyr Phe Thr Gln Glu Glu Ile Leu Lys Tyr Thr Ala Pro Ile Glu Lys
                245                 250                 255

Phe Val Pro Asp Pro Thr Arg Phe Arg Val Arg Ala Ala Asn Phe Ser
            260                 265                 270

Pro Phe Glu Ala Asn Ser Gly Asn Leu Ile Asp Met Gly Arg Val Lys
        275                 280                 285

Leu Ile Ser Gly Ile Leu Arg Lys Asp Asp Leu Glu Ile Ser Asp Thr
    290                 295                 300

Ile Lys Ala Ile Glu Lys Val Phe Thr Leu Val Asp Glu Gly Asn Gly
305                 310                 315                 320

Phe Tyr Gln Asp Gly Ser Leu Ile Asp His Val Val Thr Asn Ala Gln
                325                 330                 335

Ser Pro Leu Tyr Lys Lys Gly Ile Ala Tyr Thr Gly Ala Tyr Gly Asn
            340                 345                 350

Val Leu Ile Asp Gly Leu Ser Gln Leu Ile Pro Ile Ile Gln Lys Thr
        355                 360                 365

Lys Ser Pro Ile Glu Ala Asp Lys Met Ala Thr Ile Tyr His Trp Ile
    370                 375                 380

Asn His Ser Phe Phe Pro Ile Ile Val Arg Gly Glu Met Met Asp Met
385                 390                 395                 400

Thr Arg Gly Arg Ser Ile Ser Arg Phe Asn Ala Gln Ser His Val Ala
                405                 410                 415

Gly Ile Glu Ala Leu Arg Ala Ile Leu Arg Ile Ala Asp Met Ser Glu
            420                 425                 430

Glu Pro His Arg Leu Ala Leu Lys Thr Arg Ile Lys Thr Leu Val Thr
        435                 440                 445

Gln Gly Asn Ala Phe Tyr Asn Val Tyr Asp Asn Leu Lys Thr Tyr His
    450                 455                 460

Asp Ile Lys Leu Met Lys Glu Leu Leu Ser Asp Thr Phe Val Pro Val
465                 470                 475                 480

Gln Lys Leu Asp Ser Tyr Val Ala Ser Phe Asn Ser Met Asp Lys Leu
                485                 490                 495

Ala Leu Tyr Asn Asn Lys His Asp Phe Ala Phe Gly Leu Ser Met Phe
            500                 505                 510

Ser Asn Arg Thr Gln Asn Tyr Glu Ala Met Asn Asn Glu Asn Leu His
        515                 520                 525

Gly Trp Phe Thr Ser Asp Gly Met Phe Tyr Leu Tyr Asn Asn Asp Leu
    530                 535                 540

Gly His Tyr Ser Glu Asn Tyr Trp Ala Thr Val Asn Pro Tyr Arg Leu
545                 550                 555                 560
```

```
Pro Gly Thr Thr Glu Thr Glu Gln Lys Pro Leu Glu Gly Thr Pro Glu
                565                 570                 575

Asn Ile Lys Thr Asp Tyr Gln Gln Val Gly Met Thr Ser Leu Ser Asp
            580                 585                 590

Asp Ala Phe Val Ala Ser Lys Lys Leu Asn Asn Thr Ser Ala Leu Ala
        595                 600                 605

Ala Met Thr Phe Thr Asn Trp Asn Lys Ser Leu Thr Leu Asn Lys Gly
    610                 615                 620

Trp Phe Ile Leu Gly Asn Lys Ile Ile Phe Val Gly Ser Asn Ile Lys
625                 630                 635                 640

Asn Gln Ser Ser His Lys Ala Tyr Thr Thr Ile Glu Gln Arg Lys Glu
                645                 650                 655

Asn Gln Lys His Pro Tyr Cys Ser Tyr Val Asn Asn Gln Pro Val Asp
            660                 665                 670

Leu Asn Asn Gln Leu Val Asp Phe Thr Asn Thr Lys Ser Ile Phe Leu
        675                 680                 685

Glu Ser Asp Asp Pro Ala Gln Asn Ile Gly Tyr Tyr Phe Phe Lys Pro
    690                 695                 700

Thr Thr Leu Ser Ile Ser Lys Ala Leu Gln Thr Gly Lys Trp Gln Asn
705                 710                 715                 720

Ile Lys Ala Asp Asp Lys Ser Pro Glu Ala Ile Lys Glu Val Ser Asn
                725                 730                 735

Thr Phe Ile Thr Ile Met Gln Asn His Thr Gln Asp Gly Asp Arg Tyr
            740                 745                 750

Ala Tyr Met Met Leu Pro Asn Met Thr Arg Gln Glu Phe Glu Thr Tyr
        755                 760                 765

Ile Ser Lys Leu Asp Ile Asp Leu Leu Glu Asn Asn Asp Lys Leu Ala
    770                 775                 780

Ala Val Tyr Asp His Asp Ser Gln Gln Met His Val Ile His Tyr Glu
785                 790                 795                 800

Lys Lys Ala Thr Met Phe Ser Asn His Asn Leu Ser His Gln Gly Phe
                805                 810                 815

Tyr Ser Phe Pro His Pro Val Lys Gln Asn Gln Gln
            820                 825
```

```
<210> SEQ ID NO 87
<211> LENGTH: 556
<212> TYPE: PRT
<213> ORGANISM: Streptococcus pyogenes

<400> SEQUENCE: 87

Met Val Tyr Phe Tyr Leu Val Asn Gln Ser Thr Phe Ile Ile Ser Phe
1               5                   10                  15

Leu Tyr Trp Arg Asn Leu Ser Val Asn Thr Tyr Phe Cys Thr His His
            20                  25                  30

Lys Gln Leu Leu Leu Tyr Ser Asn Leu Phe Leu Ser Phe Ala Met Met
        35                  40                  45

Gly Gln Gly Thr Ala Ile Tyr Ala Asp Thr Leu Thr Ser Asn Ser Glu
    50                  55                  60

Pro Asn Asn Thr Tyr Phe Gln Thr Gln Thr Leu Thr Thr Thr Asp Ser
65                  70                  75                  80

Glu Lys Lys Val Val Gln Pro Gln Gln Lys Asp Tyr Tyr Thr Glu Leu
                85                  90                  95

Leu Asp Gln Trp Asn Ser Ile Ile Ala Gly Asn Asp Ala Tyr Asp Lys
            100                 105                 110
```

```
Thr Asn Pro Asp Met Val Thr Phe His Asn Lys Ala Glu Lys Asp Ala
        115                 120                 125

Gln Asn Ile Ile Lys Ser Tyr Gln Gly Pro Asp His Glu Asn Arg Thr
    130                 135                 140

Tyr Leu Gly Asn Met Gln Arg Ile Ile Pro Leu Leu Leu Ile Ser Arg
145                 150                 155                 160

Lys Leu Thr Ala Ile Leu Lys Lys Ile Ser Lys Met Lys Ser Leu Met
                165                 170                 175

Glu Asp Ser Thr Ile Ser Thr Asn Gly Leu Thr Gln Gln Leu Lys Ile
            180                 185                 190

Tyr Asn Asp Met Asp Arg Val Thr Tyr His Asn Lys Gly Leu Asp Phe
        195                 200                 205

Ala Phe Gly Leu Ser Met Thr Ser Lys Asn Val Ala Arg Tyr Glu Ser
    210                 215                 220

Ile Asn Gly Glu Asn Leu Lys Gly Trp His Thr Gly Ala Gly Met Ser
225                 230                 235                 240

Tyr Leu Tyr Asn Ser Asp Val Lys His Tyr Arg Asp Asn Phe Trp Ala
                245                 250                 255

Thr Ala Asp Met Lys Arg Leu Ala Gly Thr Thr Thr Leu Asp Asn Glu
            260                 265                 270

Glu Pro Lys Ser Thr Asp Val Lys Lys Ser Ser Lys Thr Phe Val Gly
        275                 280                 285

Gly Thr Lys Phe Asp Asp Gln His Ala Ser Ile Gly Met Asp Phe Glu
    290                 295                 300

Asn Gln Asp Lys Thr Leu Thr Ala Lys Lys Ser Tyr Phe Ile Leu Asn
305                 310                 315                 320

Asp Lys Ile Val Phe Leu Gly Thr Gly Ile Lys Ser Thr Asp Ser Ser
                325                 330                 335

Lys Asn Pro Val Thr Thr Ile Glu Asn Arg Lys Ala Asn Asp Tyr Lys
            340                 345                 350

Leu Tyr Lys Asp Asp Thr Gln Thr Thr Asn Ser Asp Asn Gln Glu Thr
        355                 360                 365

Asn Ser Leu Phe Leu Glu Ser Thr Asn Ser Thr Gln Asn Asn Ile Gly
    370                 375                 380

Tyr His Phe Leu Asn Glu Ser Lys Ile Thr Val Lys Lys Glu Ser His
385                 390                 395                 400

Thr Gly Lys Trp Ser Asp Ile Asn Lys Ser Gln Lys Asp Ile Gln Lys
                405                 410                 415

Thr Asp Glu Tyr Tyr Glu Val Thr Gln Lys His Ser Asn Thr Asp Ser
            420                 425                 430

Lys Tyr Ala Tyr Val Leu Tyr Pro Gly Leu Ser Lys Asp Val Phe Lys
        435                 440                 445

Ser Lys Ala Ser Lys Val Thr Val Val Lys Gln Glu Asp Asp Phe His
    450                 455                 460

Val Val Lys Asp Asn Glu Ser Val Trp Ala Gly Ile Asn Tyr Ser Asp
465                 470                 475                 480

Ser Ala Lys Thr Phe Glu Ile Asn Asn Thr Lys Val Glu Val Lys Ala
                485                 490                 495

Lys Gly Met Phe Ile Leu Thr Lys Lys Asp Asp Asn Thr Tyr Glu Cys
            500                 505                 510

Ser Phe Tyr Asn Pro Glu Ser Thr Asn Ser Val Ser Asp Ile Glu Ser
        515                 520                 525
```

```
Lys Ile Ser Met Thr Gly Tyr Ser Ile Ile Asn Lys Asn Thr Ser Thr
    530                 535                 540

Ser Asn Glu Ser Gly Val Arg Phe Glu Leu Thr Lys
545                 550                 555


<210> SEQ ID NO 88
<211> LENGTH: 635
<212> TYPE: PRT
<213> ORGANISM: Streptococcus pyogenes

<400> SEQUENCE: 88

Met Ala Phe Met Tyr Glu His Ala Tyr Asn Leu Asn Arg Glu Asn His
1               5                   10                  15

Gln Thr Thr Gly Lys Glu Asn Lys Glu Asn Trp Trp Val Tyr Glu Ile
            20                  25                  30

Gly Thr Pro Arg Ala Ile Asn Asn Thr Leu Ser Leu Met Tyr Pro Tyr
        35                  40                  45

Phe Thr Gln Glu Glu Ile Leu Lys Tyr Thr Ala Pro Ile Glu Lys Phe
    50                  55                  60

Val Pro Asp Pro Thr Arg Phe Arg Val Arg Ala Ala Asn Phe Ser Pro
65                  70                  75                  80

Phe Glu Ala Ser Ser Gly Asn Leu Ile Asp Met Gly Arg Val Lys Leu
                85                  90                  95

Ile Ser Gly Ile Leu Arg Lys Asp Asp Leu Glu Ile Ser Asp Thr Ile
            100                 105                 110

Lys Ala Ile Glu Lys Val Phe Thr Leu Val Asp Glu Gly Asn Gly Phe
        115                 120                 125

Tyr Gln Asp Gly Ser Leu Ile Asp His Val Val Thr Asn Ala Gln Ser
    130                 135                 140

Pro Leu Tyr Lys Lys Gly Ile Ala Tyr Thr Gly Ala Tyr Gly Asn Val
145                 150                 155                 160

Leu Ile Asp Gly Leu Ser Gln Leu Ile Pro Ile Ile Gln Lys Thr Lys
                165                 170                 175

Ser Pro Ile Glu Ala Asp Lys Met Ala Thr Ile Tyr His Trp Ile Asn
            180                 185                 190

His Ser Phe Phe Pro Ile Ile Val Arg Gly Glu Met Met Asp Met Thr
        195                 200                 205

Arg Gly Arg Ser Ile Ser Arg Phe Asn Ala Gln Ser His Val Ala Gly
    210                 215                 220

Ile Glu Ala Leu Arg Ala Ile Leu Arg Ile Ala Asp Met Ser Glu Glu
225                 230                 235                 240

Pro His Arg Leu Ala Leu Lys Thr Arg Ile Lys Thr Leu Val Thr Gln
                245                 250                 255

Gly Asn Ala Phe Tyr Asn Val Tyr Asp Asn Leu Lys Thr Tyr His Asp
            260                 265                 270

Ile Lys Leu Met Lys Glu Leu Leu Ser Asp Thr Ser Val Pro Val Gln
        275                 280                 285

Lys Leu Asp Ser Tyr Val Ala Ser Phe Asn Ser Met Asp Lys Leu Ala
    290                 295                 300

Leu Tyr Asn Asn Lys His Asp Phe Ala Phe Gly Leu Ser Met Phe Ser
305                 310                 315                 320

Asn Arg Thr Gln Asn Tyr Glu Ala Met Asn Asn Glu Asn Leu His Gly
                325                 330                 335

Trp Phe Thr Ser Asp Gly Met Phe Tyr Leu Tyr Asn Asn Asp Leu Gly
            340                 345                 350
```

```
His Tyr Ser Glu Asn Tyr Trp Ala Thr Val Asn Pro Tyr Arg Leu Pro
        355                 360                 365

Gly Thr Thr Glu Thr Glu Gln Lys Pro Leu Glu Gly Thr Pro Glu Asn
    370                 375                 380

Ile Lys Thr Asn Tyr Gln Gln Val Gly Met Thr Ser Leu Ser Asp Asp
385                 390                 395                 400

Ala Phe Val Ala Ser Lys Lys Leu Asn Asn Thr Ser Ala Leu Ala Ala
                405                 410                 415

Met Thr Phe Thr Asn Trp Asn Lys Ser Leu Thr Leu Asn Lys Gly Trp
            420                 425                 430

Phe Ile Leu Gly Asn Lys Ile Ile Phe Val Gly Ser Asn Ile Lys Asn
        435                 440                 445

Gln Ser Ser His Lys Ala Tyr Thr Thr Ile Glu Gln Arg Lys Glu Asn
    450                 455                 460

Gln Lys His Pro Tyr Cys Ser Tyr Val Asn Asn Gln Pro Val Asp Leu
465                 470                 475                 480

Asn Asn Gln Leu Val Asp Phe Thr Asn Thr Lys Ser Ile Phe Leu Glu
                485                 490                 495

Ser Asp Asp Pro Ala Gln Asn Ile Gly Tyr Tyr Phe Phe Lys Pro Thr
            500                 505                 510

Thr Leu Ser Ile Ser Lys Ala Leu Gln Thr Gly Lys Trp Gln Asn Ile
        515                 520                 525

Lys Ala Asp Asp Lys Ser Pro Glu Ala Ile Lys Glu Val Ser Asn Thr
    530                 535                 540

Phe Ile Thr Ile Met Gln Asn His Thr Gln Asp Gly Asp Arg Tyr Ala
545                 550                 555                 560

Tyr Met Met Leu Pro Asn Met Thr Arg Gln Glu Phe Glu Thr Tyr Ile
                565                 570                 575

Ser Lys Leu Asp Ile Asp Leu Leu Glu Asn Asn Asp Lys Leu Ala Ala
            580                 585                 590

Val Tyr Asp His Asp Ser Gln Gln Met His Val Ile His Tyr Glu Lys
        595                 600                 605

Lys Ala Thr Met Phe Ser Asn His Asn Leu Ser His Gln Gly Phe Tyr
    610                 615                 620

Ser Phe Pro His Pro Val Lys Gln Asn Gln Gln
625                 630                 635


<210> SEQ ID NO 89
<211> LENGTH: 828
<212> TYPE: PRT
<213> ORGANISM: Streptococcus pyogenes

<400> SEQUENCE: 89

Met Val Tyr Phe Tyr Leu Val Asn Gln Ser Thr Phe Ile Ile Ser Phe
1               5                   10                  15

Leu Tyr Trp Arg Asn Leu Ser Val Asn Thr Tyr Phe Cys Thr His His
            20                  25                  30

Lys Gln Leu Leu Leu Tyr Ser Asn Leu Phe Leu Ser Phe Ala Met Met
        35                  40                  45

Gly Gln Gly Thr Ala Ile Tyr Ala Asp Thr Leu Thr Ser Asn Ser Glu
    50                  55                  60

Pro Asn Asn Thr Tyr Phe Gln Thr Gln Thr Leu Thr Thr Thr Asp Ser
65                  70                  75                  80

Glu Lys Lys Val Val Gln Pro Gln Gln Lys Asp Tyr Tyr Thr Glu Leu
```

-continued

```
                85                  90                  95

Leu Asp Gln Trp Asn Ser Ile Ile Ala Gly Asn Asp Ala Tyr Val Lys
            100                 105                 110

Thr Asn Pro Asp Met Val Thr Phe His Asn Lys Ala Glu Lys Asp Ala
        115                 120                 125

Gln Asn Ile Ile Lys Ser Tyr Gln Gly Pro Asp His Glu Asn Arg Thr
    130                 135                 140

Tyr Leu Trp Glu His Ala Lys Asp Tyr Ser Ala Ser Thr Asn Ile Thr
145                 150                 155                 160

Lys Thr Tyr Arg Asn Ile Glu Lys Ile Ala Lys Gln Ile Thr Asn Pro
                165                 170                 175

Glu Ser Cys Tyr Tyr Gln Asp Ser Lys Ala Ile Ala Ile Val Lys Asp
            180                 185                 190

Gly Met Ala Phe Met Tyr Glu His Ala Tyr Asn Leu Asn Arg Glu Asn
        195                 200                 205

His Gln Thr Thr Gly Lys Glu Asn Lys Glu Asn Trp Trp Val Tyr Glu
    210                 215                 220

Ile Gly Thr Pro Arg Ala Ile Asn Asn Thr Leu Ser Leu Met Tyr Pro
225                 230                 235                 240

Tyr Phe Thr Gln Glu Glu Ile Leu Lys Tyr Thr Ala Pro Ile Glu Lys
                245                 250                 255

Phe Val Pro Asp Pro Thr Arg Phe Arg Val Arg Ala Ala Asn Phe Ser
            260                 265                 270

Pro Phe Glu Ala Ser Ser Gly Asn Leu Ile Asp Met Gly Arg Val Lys
        275                 280                 285

Leu Ile Ser Gly Ile Leu Arg Lys Asp Asp Leu Glu Ile Ser Asp Thr
    290                 295                 300

Ile Lys Ala Ile Glu Lys Val Phe Thr Leu Val Asp Glu Gly Asn Gly
305                 310                 315                 320

Phe Tyr Gln Asp Gly Ser Leu Ile Asp His Val Val Thr Asn Ala Gln
                325                 330                 335

Ser Pro Leu Tyr Lys Lys Gly Ile Ala Tyr Thr Gly Ala Tyr Gly Asn
            340                 345                 350

Val Leu Ile Asp Gly Leu Ser Gln Leu Ile Pro Ile Ile Gln Lys Thr
        355                 360                 365

Lys Ser Pro Ile Glu Ala Asp Lys Met Ala Thr Ile Tyr His Trp Ile
    370                 375                 380

Asn His Ser Phe Phe Pro Ile Ile Val Arg Gly Glu Met Met Asp Met
385                 390                 395                 400

Thr Arg Gly Arg Ser Ile Ser Arg Phe Asn Ala Gln Ser His Val Ala
                405                 410                 415

Gly Ile Glu Ala Leu Arg Ala Ile Leu Arg Ile Ala Asp Met Ser Glu
            420                 425                 430

Glu Pro His Arg Leu Ala Leu Lys Thr Arg Ile Lys Thr Leu Val Thr
        435                 440                 445

Gln Gly Asn Ala Phe Tyr Asn Val Tyr Asp Asn Leu Lys Thr Tyr His
    450                 455                 460

Asp Ile Lys Leu Met Lys Glu Leu Leu Ser Asp Thr Ser Val Pro Val
465                 470                 475                 480

Gln Lys Leu Asp Ser Tyr Val Ala Ser Phe Asn Ser Met Asp Lys Leu
                485                 490                 495

Ala Leu Tyr Asn Asn Lys His Asp Phe Ala Phe Gly Leu Ser Met Phe
            500                 505                 510
```

Ser Asn Arg Thr Gln Asn Tyr Glu Ala Met Asn Asn Glu Asn Leu His
515 520 525

Gly Trp Phe Thr Ser Asp Gly Met Phe Tyr Leu Tyr Asn Asn Asp Leu
530 535 540

Gly His Tyr Ser Glu Asn Tyr Trp Ala Thr Val Asn Pro Tyr Arg Leu
545 550 555 560

Pro Gly Thr Thr Glu Thr Glu Gln Lys Pro Leu Glu Gly Thr Pro Glu
565 570 575

Asn Ile Lys Thr Asn Tyr Gln Gln Val Gly Met Thr Ser Leu Ser Asp
580 585 590

Asp Ala Phe Val Ala Ser Lys Lys Leu Asn Asn Thr Ser Ala Leu Ala
595 600 605

Ala Met Thr Phe Thr Asn Trp Asn Lys Ser Leu Thr Leu Asn Lys Gly
610 615 620

Trp Phe Ile Leu Gly Asn Lys Ile Ile Phe Val Gly Ser Asn Ile Lys
625 630 635 640

Asn Gln Ser Ser His Lys Ala Tyr Thr Thr Ile Glu Gln Arg Lys Glu
645 650 655

Asn Gln Lys His Pro Tyr Cys Ser Tyr Val Asn Asn Gln Pro Val Asp
660 665 670

Leu Asn Asn Gln Leu Val Asp Phe Thr Asn Thr Lys Ser Ile Phe Leu
675 680 685

Glu Ser Asp Asp Pro Ala Gln Asn Ile Gly Tyr Tyr Phe Phe Lys Pro
690 695 700

Thr Thr Leu Ser Ile Ser Lys Ala Leu Gln Thr Gly Lys Trp Gln Asn
705 710 715 720

Ile Lys Ala Asp Asp Lys Ser Pro Glu Ala Ile Lys Glu Val Ser Asn
725 730 735

Thr Phe Ile Thr Ile Met Gln Asn His Thr Gln Asp Gly Asp Arg Tyr
740 745 750

Ala Tyr Met Met Leu Pro Asn Met Thr Arg Gln Glu Phe Glu Thr Tyr
755 760 765

Ile Ser Lys Leu Asp Ile Asp Leu Leu Glu Asn Asn Asp Lys Leu Ala
770 775 780

Ala Val Tyr Asp His Asp Ser Gln Gln Met His Val Ile His Tyr Glu
785 790 795 800

Lys Lys Ala Thr Met Phe Ser Asn His Asn Leu Ser His Gln Gly Phe
805 810 815

Tyr Ser Phe Pro His Pro Val Lys Gln Asn Gln Gln
820 825

<210> SEQ ID NO 90
<211> LENGTH: 828
<212> TYPE: PRT
<213> ORGANISM: Streptococcus pyogenes

<400> SEQUENCE: 90

Met Val Tyr Phe Tyr Leu Val Asn Gln Phe Thr Phe Ile Ile Ser Phe
1 5 10 15

Leu Tyr Arg Arg Asn Leu Ser Val Asn Thr Tyr Phe Cys Thr His His
20 25 30

Lys Gln Leu Leu Leu Tyr Ser Asn Leu Phe Leu Ser Phe Ala Met Met
35 40 45

Gly Gln Gly Thr Ala Ile Tyr Ala Asp Thr Leu Thr Ser Asn Ser Glu

-continued

```
    50                  55                  60

Pro Asn Asn Thr Tyr Phe Gln Thr Gln Met Leu Thr Thr Thr Asp Ser
65                  70                  75                  80

Glu Lys Lys Val Val Gln Pro Gln Gln Lys Asp Tyr Tyr Thr Glu Leu
                85                  90                  95

Leu Asp Gln Trp Asn Ser Ile Ile Ala Gly Asn Asp Ala Tyr Asp Lys
            100                 105                 110

Thr Asn Pro Asp Met Val Thr Phe His Asn Lys Ala Glu Lys Asp Ala
        115                 120                 125

Gln Asn Ile Ile Lys Ser Tyr Gln Gly Pro Asp His Glu Asn Arg Thr
    130                 135                 140

Tyr Leu Trp Glu His Ala Lys Asp Tyr Ser Ala Ser Ala Asn Ile Thr
145                 150                 155                 160

Lys Thr Tyr Arg Asn Ile Glu Lys Ile Ala Lys Gln Ile Thr Asn Pro
                165                 170                 175

Glu Ser Cys Tyr Tyr Gln Asp Ser Lys Ala Ile Ala Ile Val Lys Asp
            180                 185                 190

Gly Met Ala Phe Met Tyr Glu His Ala Tyr Asn Leu Asp Arg Glu Asn
        195                 200                 205

His Gln Thr Thr Gly Lys Glu Asn Lys Glu Asn Trp Trp Val Tyr Glu
    210                 215                 220

Ile Gly Thr Pro Arg Ala Ile Asn Asn Thr Leu Ser Leu Met Tyr Pro
225                 230                 235                 240

Tyr Phe Thr Gln Glu Glu Ile Leu Lys Tyr Thr Ala Pro Ile Glu Lys
                245                 250                 255

Phe Val Pro Asp Pro Thr Arg Phe Arg Val Arg Ala Ala Asn Phe Ser
            260                 265                 270

Pro Phe Glu Ala Asn Ser Gly Asn Leu Ile Asp Met Gly Arg Val Lys
        275                 280                 285

Leu Ile Ser Gly Ile Leu Arg Lys Asp Asp Leu Glu Ile Ser Asp Thr
    290                 295                 300

Ile Lys Ala Ile Glu Lys Val Phe Thr Leu Val Asp Glu Gly Asn Gly
305                 310                 315                 320

Phe Tyr Gln Asp Gly Ser Leu Ile Asp His Val Val Thr Asn Ala Gln
                325                 330                 335

Ser Pro Leu Tyr Lys Lys Gly Ile Ala Tyr Thr Gly Ala Tyr Gly Asn
            340                 345                 350

Val Leu Ile Asp Gly Leu Ser Gln Leu Ile Pro Ile Ile Gln Lys Thr
        355                 360                 365

Lys Ser Ser Ile Glu Ala Asp Lys Met Ala Thr Ile Tyr His Trp Ile
    370                 375                 380

Asn His Ser Phe Phe Pro Ile Ile Val Arg Gly Glu Met Met Asp Met
385                 390                 395                 400

Thr Arg Gly Arg Ser Ile Ser Arg Phe Asn Ala Gln Ser His Val Ala
                405                 410                 415

Gly Ile Glu Ala Leu Arg Ala Ile Leu Arg Ile Ala Asp Met Ser Glu
            420                 425                 430

Glu Pro His Arg Leu Ala Leu Lys Thr Arg Ile Lys Thr Leu Val Thr
        435                 440                 445

Gln Gly Asn Ala Phe Tyr Asn Val Tyr Asp Asn Leu Lys Thr Tyr His
    450                 455                 460

Asp Ile Lys Leu Met Lys Glu Leu Leu Ser Asp Thr Ser Val Pro Val
465                 470                 475                 480
```

Gln Lys Leu Asp Ser Tyr Val Ala Ser Phe Asn Ser Met Asp Lys Leu
485 490 495

Ala Leu Tyr Asn Asn Lys His Asp Phe Ala Phe Gly Leu Ser Met Phe
500 505 510

Ser Asn Arg Thr Gln Asn Tyr Glu Ala Met Asn Asn Glu Asn Leu His
515 520 525

Gly Trp Phe Thr Ser Asp Gly Met Phe Tyr Leu Tyr Asn Asn Asp Leu
530 535 540

Gly His Tyr Ser Glu Asn Tyr Trp Ala Thr Val Asn Pro Tyr Arg Leu
545 550 555 560

Pro Gly Thr Thr Glu Thr Glu Gln Lys Pro Leu Glu Gly Thr Pro Glu
565 570 575

Asn Ile Lys Thr Asn Tyr Gln Gln Val Gly Met Thr Ser Leu Ser Asp
580 585 590

Asp Ala Phe Val Ala Ser Lys Lys Leu Asn Asn Thr Ser Ala Leu Ala
595 600 605

Ala Met Thr Phe Thr Asn Trp Asn Lys Ser Leu Thr Leu Asn Lys Gly
610 615 620

Trp Phe Ile Leu Gly Asn Lys Ile Ile Phe Val Gly Ser Asn Ile Lys
625 630 635 640

Asn Gln Ser Ser His Lys Ala Tyr Thr Thr Ile Glu Gln Arg Lys Glu
645 650 655

Asn Gln Lys His Pro Tyr His Ala Tyr Val Asn Asn Gln Pro Val Asp
660 665 670

Leu Asn Asn Gln Leu Val Asp Phe Thr Asn Thr Lys Ser Ile Phe Leu
675 680 685

Glu Ser Asp Asp Ser Ala Gln Asn Ile Gly Tyr Tyr Phe Phe Lys Pro
690 695 700

Thr Thr Leu Ser Ile Ser Lys Ala Leu Gln Thr Gly Lys Trp Gln Asn
705 710 715 720

Ile Lys Ala Asp Asp Lys Ser Pro Glu Ala Ile Lys Glu Val Ser Asn
725 730 735

Thr Phe Ile Thr Ile Met Gln Asn His Thr Gln Asp Gly Asp Arg Tyr
740 745 750

Ala Tyr Met Met Leu Pro Asn Met Thr Arg Gln Glu Phe Glu Thr Tyr
755 760 765

Ile Ser Lys Leu Asp Ile Asp Leu Leu Glu Asn Asn Asp Lys Leu Ala
770 775 780

Ala Val Tyr Asp His Asp Ser Gln Gln Met His Val Ile His Tyr Glu
785 790 795 800

Lys Lys Ala Thr Met Phe Ser Asn His Asn Leu Ser His Gln Gly Phe
805 810 815

Tyr Ser Phe Pro His Pro Val Lys Gln Asn Gln Gln
820 825

<210> SEQ ID NO 91
<211> LENGTH: 522
<212> TYPE: PRT
<213> ORGANISM: Streptococcus suis

<400> SEQUENCE: 91

Met Gly Phe Phe Ile Ser Gln Ser Lys Gln His Tyr Gly Ile Arg Lys
1 5 10 15

Tyr Lys Val Gly Val Cys Ser Ala Leu Ile Ala Leu Ser Ile Leu Gly

```
            20                  25                  30

Thr Arg Val Ala Ala Asn Gln Leu Pro Ser Thr Glu Thr Ala Ser Pro
        35                  40                  45

Gln Ser Ser Gln Leu Val Glu Thr Thr Pro Glu Thr Thr Glu Ala Val
    50                  55                  60

Asn Leu Thr Thr Glu Ala Val Met Thr Ser Glu Val Ser Ser Glu Val
65                  70                  75                  80

Ser Pro Val Thr Ser Thr Glu Thr Gln Pro Ser Ser Thr Ala Ala Glu
                85                  90                  95

Thr Leu Ala Ser Pro Gln Ala Val Gln Ala Thr Lys Glu Glu Glu Lys
            100                 105                 110

Asn Leu Val Ala Asn Gly Glu Phe Ala Ser Thr Thr Ala Ala Ser Gly
        115                 120                 125

Asn Trp Ala Asp Pro Ala Ala Thr Asn Trp Glu Thr Trp Ile Pro Ala
    130                 135                 140

Asn Val Lys Lys Glu Asn Gly Gln Val Arg Ile Asp Glu Gly Arg Leu
145                 150                 155                 160

His Ile Ser Ser Thr Ala Ser Tyr Arg Val Ala Val His Gln Thr Val
                165                 170                 175

Asp Val Asp Pro Asn Lys Arg Tyr Leu Phe Ser Tyr Asn Val Glu Thr
            180                 185                 190

Lys Asp Leu Lys Gly Ser Gly Val Arg Val Arg Leu Arg Ser Leu Thr
        195                 200                 205

Ala Glu Gly Lys Asp Leu Ser Pro Gln Glu Phe Ala Tyr Thr Pro Tyr
    210                 215                 220

Lys Asn Gly Ser Gln Ala Glu His Ile Glu Gln Ile Leu Thr Val Ser
225                 230                 235                 240

Pro Glu Thr Arg Lys Leu Lys Val Glu Leu Phe Phe Glu Asn Ser Val
                245                 250                 255

Gly Gln Ala Trp Leu Asp Asn Ile Ser Leu Val Glu Tyr Val Glu Lys
            260                 265                 270

Thr Pro Glu Thr Pro Glu Pro Ser Leu Glu Leu Val Gln Pro Glu Thr
        275                 280                 285

Gly Gln Ile Ser Leu Ala Ser Asn Lys Val Tyr Leu Pro Val Arg Pro
    290                 295                 300

Asp Leu Thr Tyr Arg Ile Ala Asp Ala Ala Val Ala Ile Val Glu Lys
305                 310                 315                 320

Asn Met Ile Arg Pro Leu Ala Ala Gly Lys Thr Gln Val Asp Val Tyr
                325                 330                 335

Asp Lys Asp Thr Lys Leu Ser Ser Phe Glu Leu Thr Val Thr Glu His
            340                 345                 350

Gln Ala Thr Val Phe Asp Thr Leu Arg Asn Asn Trp Glu Asp Ile Ser
        355                 360                 365

Leu Ala Asn Lys Arg Tyr Gln Ser Asn Asp Thr Gln Met Lys Ala Phe
    370                 375                 380

Leu Gly Arg Leu Asp Ala Gly Val Ala Ser Ser Leu Lys Lys Trp Val
385                 390                 395                 400

Glu Pro Thr Asn Gln Gly Lys Thr Ile Phe Asn Asp Ile Asp Phe Ser
                405                 410                 415

Lys Ser Ser His Leu Thr Thr Val Tyr Arg Arg Leu Glu Gln Met Ala
            420                 425                 430

Gln Val Val Glu Asn Pro Asp Ser Ala Tyr Tyr His Asp Arg Ser Leu
        435                 440                 445
```

```
Ile Asp Leu Val Arg Lys Gly Met Asn Trp Leu Tyr Thr Asn Val Tyr
    450                 455                 460

Asn Glu Asn Lys Ser Ile Asp Gly Asn Trp Trp Asp Tyr Glu Ile Gly
465                 470                 475                 480

Thr Pro Arg Ala Val Val Asn Thr Leu Ile Tyr Met His Pro Tyr Phe
                485                 490                 495

Ser Gln Glu Glu Ile Leu Thr Tyr Thr Lys Pro Ile Ser Lys Phe Val
            500                 505                 510

Pro Asp Pro Thr Thr Ile Ser Val Lys His
        515                 520


<210> SEQ ID NO 92
<211> LENGTH: 1164
<212> TYPE: PRT
<213> ORGANISM: Streptococcus suis

<400> SEQUENCE: 92

Met Gly Phe Phe Ile Ser Gln Ser Lys Gln His Tyr Gly Ile Arg Lys
1               5                   10                  15

Tyr Lys Val Gly Val Cys Ser Ala Leu Ile Ala Leu Ser Ile Leu Gly
            20                  25                  30

Thr Arg Val Ala Ala Asn Gln Leu Pro Ser Thr Glu Thr Ala Ser Pro
        35                  40                  45

Gln Ser Ser Gln Leu Val Glu Thr Thr Pro Glu Thr Thr Glu Ala Val
    50                  55                  60

Met Thr Ser Glu Val Ser Ser Glu Val Ser Pro Val Thr Ser Thr Glu
65                  70                  75                  80

Thr Gln Pro Ser Ser Thr Thr Ala Glu Thr Leu Ala Ser Pro Gln Ala
                85                  90                  95

Val Gln Ala Thr Lys Glu Glu Lys Asn Leu Val Ala Asn Gly Glu Phe
            100                 105                 110

Ile Ser Thr Thr Ala Pro Ser Gly Asn Trp Lys Glu Leu Ala Ala Thr
        115                 120                 125

Asn Trp Glu Thr Trp Ile Pro Ala Asn Val Lys Lys Glu Asn Gly Gln
    130                 135                 140

Val Arg Ile Asp Glu Gly Arg Leu His Ile Ser Ser Thr Ala Ser Tyr
145                 150                 155                 160

Arg Val Ala Val His Gln Thr Val Asp Val Asp Pro Asn Lys Arg Tyr
                165                 170                 175

Leu Phe Ser Tyr Asp Val Glu Thr Lys Asp Leu Lys Gly Ser Gly Val
            180                 185                 190

Arg Val Arg Leu Arg Ser Leu Thr Ala Glu Gly Lys Asp Leu Ser Pro
        195                 200                 205

Gln Glu Phe Ala Tyr Thr Pro Tyr Lys Asn Gly Ser Gln Ala Glu His
    210                 215                 220

Ile Glu Gln Ile Leu Thr Val Ser Pro Glu Thr Arg Lys Leu Lys Val
225                 230                 235                 240

Glu Leu Phe Phe Glu Asn Ser Val Gly Gln Ala Trp Leu Asp Asn Ile
                245                 250                 255

Ser Leu Val Glu Tyr Val Glu Lys Thr Pro Glu Thr Pro Glu Gln Ser
            260                 265                 270

Pro Glu Leu Val Gln Pro Glu Thr Gly Gln Ile Ser Leu Ala Ser Asn
        275                 280                 285

Lys Val Tyr Leu Pro Val Arg Pro Asp Leu Thr Tyr Arg Ile Ala Asp
```

-continued

```
    290                 295                 300

Ala Ala Val Ala Thr Val Glu Lys Asn Met Ile Arg Pro Leu Ala Ala
305                 310                 315                 320

Gly Lys Thr Gln Val Asp Val Tyr Asp Lys Asp Thr Lys Leu Ser Ser
                325                 330                 335

Phe Glu Leu Ile Val Thr Glu His Gln Ala Thr Val Phe Asp Thr Leu
            340                 345                 350

Arg Asn Asn Trp Glu Asp Ile Ser Leu Ala Asn Lys Arg Tyr Gln Ser
        355                 360                 365

Asn Asp Ala Gln Met Lys Ala Phe Leu Gly Arg Leu Asp Ala Gly Val
    370                 375                 380

Ala Ser Ser Leu Glu Lys Trp Val Glu Pro Thr Glu Gln Ser Lys Thr
385                 390                 395                 400

Ile Phe Asn Asp Ile Asp Phe Ser Lys Ser Ser His Leu Thr Thr Val
                405                 410                 415

Tyr Arg Arg Leu Glu Gln Met Ala Gln Val Val Glu Asn Pro Asp Ser
            420                 425                 430

Ala Tyr Tyr His Asp Arg Ser Leu Ile Asp Leu Val Arg Lys Gly Met
        435                 440                 445

Asn Trp Leu Tyr Ala Asn Val Tyr Asn Glu Asn Lys Ser Ile Asp Gly
    450                 455                 460

Asn Trp Trp Asp Tyr Glu Ile Gly Thr Ser Arg Ala Val Val Asn Thr
465                 470                 475                 480

Leu Ile Tyr Met His Pro Tyr Phe Ser Gln Glu Glu Ile Leu Thr Tyr
                485                 490                 495

Thr Lys Pro Ile Ser Lys Phe Val Pro Asp Pro Thr Thr Ile Arg Lys
            500                 505                 510

Thr Leu Thr Asn Pro Val Pro Ala Val Gly Gly Asn Gln Thr Asp Leu
        515                 520                 525

Ser Lys Val Ala Ile Leu Glu Gly Ala Leu Arg Glu Asp Ala Asp Arg
    530                 535                 540

Val Arg Ala Gly Ala Gln Gly Leu Thr Thr Ile Met Lys Phe Val Asp
545                 550                 555                 560

Lys Gly Glu Gly Phe Tyr Arg Asp Gly Ser Phe Ile Asp His Thr Asn
                565                 570                 575

Val Ala Tyr Thr Gly Ala Tyr Gly Asn Val Leu Ile Glu Gly Phe Ser
            580                 585                 590

Gln Leu Leu Pro Val Ile Gln Pro Thr Glu Phe Ala Leu Lys Glu Glu
        595                 600                 605

Gln Thr Asn Ile Leu Tyr Glu Trp Ile Glu Lys Ala Phe Met Pro Ile
    610                 615                 620

Leu Val Arg Gly Glu Leu Met Asp Met Thr Arg Gly Arg Ser Ile Ser
625                 630                 635                 640

Arg Ala Thr Gly Glu Ser His Val Gln Ala Met Glu Ile Leu Arg Ser
                645                 650                 655

Leu Val Arg Ile Ala Glu Ser Ala Gln Pro Glu Gln Lys Thr Lys Leu
            660                 665                 670

Leu Ser Phe Val Lys Ala Gln Leu Thr Ser Asp Thr Phe Tyr Asp Ser
        675                 680                 685

Tyr Arg Ser Leu Lys Ser Tyr Lys Asp Ile Asp Leu Val Asn Lys Leu
    690                 695                 700

Leu Ala Asp Asn Gln Ile Pro Ala Glu Val Asp Lys Asp Tyr Ile Ala
705                 710                 715                 720
```

-continued

```
Ala Phe Asn Asn Met Asp Lys Phe Val Tyr Arg Ser Ala Gln Glu Gly
                725                 730                 735

Phe Thr Phe Ala Leu Ser Met Tyr Ser Ser Arg Thr Gln Asn Tyr Glu
            740                 745                 750

Asp Met Asn Asn Glu Asn Arg Lys Gly Trp Tyr Thr Ala Asp Gly Met
        755                 760                 765

Val Tyr Leu Tyr Asn Asp Asp Leu Ser His Tyr Ser Asn His Tyr Trp
    770                 775                 780

Ala Thr Val Asp Pro Tyr Arg Leu Pro Gly Thr Thr Thr Thr Lys Asp
785                 790                 795                 800

Lys Arg Glu Asp Gly Ser Gly Glu Val Thr Leu Ala Ser Asp Phe Val
                805                 810                 815

Gly Ala Ser Gln Leu Gly Asn Arg Leu Ala Thr Ile Ala Met Asp Phe
            820                 825                 830

Asn Asn Trp Asn Asn Ser Leu Thr Ala Arg Lys Ala Trp Ile Val Leu
        835                 840                 845

Gly Asn Lys Ile Val Phe Leu Gly Thr Asp Ile Gln His Gln Ser Ala
    850                 855                 860

Gln Gly Ala Glu Thr Thr Ile Glu Asn Arg Lys Leu Leu Thr Gly Glu
865                 870                 875                 880

Lys Tyr Ser Tyr Tyr Ile Asn Gly Gln Pro Val Asp Leu Ser Lys Glu
                885                 890                 895

Val Val Thr Asp Lys Thr Gln Ser Phe Tyr Met Thr Asn Gly Lys Asp
            900                 905                 910

Asn Gln Ser Ile Gly Tyr Val Phe Leu Asn Gln Leu Pro Thr His Ala
        915                 920                 925

Lys Leu Asp Gln Arg Thr Gly Lys Trp Ser Asp Ile Asn Tyr Asn Gln
    930                 935                 940

Ser Lys Glu Glu Val Ser Asn Ser Phe Val Ser Leu Trp His Glu His
945                 950                 955                 960

Ala Gln Thr Ser Ser Asn Tyr Ala Tyr Val Leu Val Pro Asn Gln Ser
                965                 970                 975

Met Glu Lys Val Asn Gln Ala Ala Ala Ser Val Lys Leu Leu His Gln
            980                 985                 990

Asp Arg Asp Leu Gln Val Val Tyr  Asp Gln Glu Gln Asn  Val Trp Gly
        995                 1000                1005

Val Val  Lys Tyr Thr Asp Thr  Ala Tyr Lys Leu Thr  Asp Asp Ile
    1010                1015                1020

Thr Leu  Thr Asp Ala Gly Leu  Tyr Thr Ile Gln Lys  Val Glu Gly
    1025                1030                1035

Gly Tyr  Arg Ile Ala Phe Tyr  Asn Pro Ser Thr Arg  Thr Val Lys
    1040                1045                1050

Asn Gly  Ile Glu Leu Thr Lys  Ala Gly Ser Ser Leu  Thr Val Glu
    1055                1060                1065

Met Glu  Pro Thr Ala Ala Tyr  Pro Ser Thr Val Trp  Lys Val Thr
    1070                1075                1080

Met Pro  Glu Gly Ser Asp Lys  Gln Thr Gly Ser Val  Glu Lys Thr
    1085                1090                1095

Glu Lys  Glu Glu Lys Gln Leu  Lys Glu Asn Gln Pro  Ser Ser Glu
    1100                1105                1110

Val Lys  Gln Val Val His His  Ala Ala Glu Lys Thr  Lys Pro Ser
    1115                1120                1125
```

Lys Pro Arg Leu Pro Gln Thr Gly Glu Glu Ala Ser Leu Gly Leu
    1130                1135                1140

Gly Phe Leu Gly Leu Leu Thr Leu Gly Ala Val Val Asp Phe Lys
    1145                1150                1155

Cys Arg Arg Ser His Ser
    1160

<210> SEQ ID NO 93
<211> LENGTH: 1164
<212> TYPE: PRT
<213> ORGANISM: Streptococcus suis

<400> SEQUENCE: 93

Met Gly Phe Phe Ile Ser Gln Ser Lys Gln His Tyr Gly Ile Arg Lys
1               5                   10                  15

Tyr Lys Val Gly Val Cys Ser Ala Leu Ile Ala Leu Ser Ile Leu Gly
            20                  25                  30

Thr Arg Val Ala Ala Asn Gln Leu Pro Ser Thr Glu Thr Ala Ser Pro
        35                  40                  45

Gln Ser Ser Gln Leu Val Glu Thr Thr Pro Glu Thr Thr Glu Ala Val
    50                  55                  60

Met Thr Ser Glu Val Ser Ser Glu Val Ser Pro Val Thr Ser Thr Glu
65                  70                  75                  80

Thr Gln Pro Ser Ser Thr Thr Ala Glu Thr Leu Ala Ser Pro Gln Ala
                85                  90                  95

Val Gln Ala Thr Lys Glu Glu Lys Asn Leu Val Ala Asn Gly Glu Phe
            100                 105                 110

Ile Ser Thr Thr Ala Pro Ser Gly Asn Trp Lys Glu Leu Ala Ala Thr
        115                 120                 125

Asn Trp Glu Thr Trp Ile Pro Ala Asn Val Lys Lys Glu Asn Gly Gln
    130                 135                 140

Val Arg Ile Asp Glu Gly Arg Leu His Ile Ser Ser Thr Ala Ser Tyr
145                 150                 155                 160

Arg Val Ala Val His Gln Thr Val Asp Val Asp Pro Asn Lys Arg Tyr
                165                 170                 175

Leu Phe Ser Tyr Asp Val Glu Thr Lys Asp Leu Lys Gly Ser Gly Val
            180                 185                 190

Arg Val Arg Leu Arg Ser Leu Thr Ala Glu Gly Lys Asp Leu Ser Pro
        195                 200                 205

Gln Glu Phe Ala Tyr Thr Pro Tyr Lys Asn Gly Ser Gln Ala Glu His
    210                 215                 220

Ile Glu Gln Ile Leu Thr Val Ser Pro Glu Thr Arg Lys Leu Lys Val
225                 230                 235                 240

Glu Leu Phe Phe Glu Asn Ser Val Gly Gln Ala Trp Leu Asp Asn Ile
                245                 250                 255

Ser Leu Val Glu Tyr Val Glu Lys Thr Pro Glu Thr Pro Glu Gln Ser
            260                 265                 270

Pro Glu Leu Val Gln Pro Glu Thr Gly Gln Ile Ser Leu Ala Ser Asn
        275                 280                 285

Lys Val Tyr Leu Pro Val Arg Pro Asp Leu Thr Tyr Arg Ile Ala Asp
    290                 295                 300

Ala Ala Val Ala Thr Val Glu Lys Asn Met Ile Arg Pro Leu Ala Ala
305                 310                 315                 320

Gly Lys Thr Gln Val Asp Val Tyr Asp Lys Asp Thr Lys Leu Ser Ser
                325                 330                 335

-continued

```
Phe Glu Leu Ile Val Thr Glu His Gln Ala Thr Val Phe Asp Thr Leu
            340                 345                 350

Arg Asn Asn Trp Glu Asp Ile Ser Leu Ala Asn Lys Arg Tyr Gln Ser
        355                 360                 365

Asn Asp Ala Gln Met Lys Ala Phe Leu Gly Arg Leu Asp Ala Gly Val
    370                 375                 380

Ala Ser Ser Leu Glu Lys Trp Val Glu Pro Thr Glu Gln Ser Lys Thr
385                 390                 395                 400

Ile Phe Asn Asp Ile Asp Phe Ser Lys Ser Ser His Leu Thr Thr Val
                405                 410                 415

Tyr Arg Arg Leu Glu Gln Met Ala Gln Val Val Glu Asn Pro Asp Ser
            420                 425                 430

Ala Tyr Tyr His Asp Arg Ser Leu Ile Asp Leu Val Arg Lys Gly Met
        435                 440                 445

Asn Trp Leu Tyr Thr Asn Val Tyr Asn Glu Asn Lys Ser Ile Asp Gly
    450                 455                 460

Asn Trp Trp Asp Tyr Glu Ile Gly Thr Pro Arg Ala Val Val Asn Thr
465                 470                 475                 480

Leu Ile Tyr Met His Pro Tyr Phe Ser Gln Glu Glu Ile Leu Thr Tyr
                485                 490                 495

Thr Lys Pro Ile Ser Lys Phe Val Pro Asp Pro Thr Thr Ile Arg Lys
            500                 505                 510

Thr Leu Thr Asn Pro Val Pro Ala Val Gly Gly Asn Gln Thr Asp Leu
        515                 520                 525

Ser Lys Val Ala Ile Leu Glu Gly Ala Leu Arg Glu Asp Ala Asp Arg
    530                 535                 540

Val Arg Ala Gly Ala Gln Gly Leu Thr Thr Ile Met Lys Phe Val Asp
545                 550                 555                 560

Lys Gly Glu Gly Phe Tyr Arg Asp Gly Ser Phe Ile Asp His Thr Asn
                565                 570                 575

Val Ala Tyr Thr Gly Ala Tyr Gly Asn Val Leu Ile Glu Gly Phe Ser
            580                 585                 590

Gln Leu Leu Pro Val Ile Gln Pro Thr Glu Phe Ala Leu Lys Glu Glu
        595                 600                 605

Gln Thr Asn Ile Leu Tyr Glu Trp Ile Glu Lys Ala Phe Met Pro Ile
    610                 615                 620

Leu Val Arg Gly Glu Leu Met Asp Met Thr Arg Gly Arg Ser Ile Ser
625                 630                 635                 640

Arg Ala Thr Gly Glu Ser His Val Gln Ala Met Glu Ile Leu Arg Ser
                645                 650                 655

Leu Val Arg Ile Ala Glu Ser Ala Gln Pro Glu Gln Lys Thr Lys Leu
            660                 665                 670

Leu Ser Phe Val Lys Ala Gln Leu Thr Ser Asp Thr Phe Tyr Asp Ser
        675                 680                 685

Tyr Arg Ser Leu Lys Ser Tyr Lys Asp Ile Asp Leu Val Asn Lys Leu
    690                 695                 700

Leu Ala Asp Asn Gln Ile Pro Ala Glu Val Asp Lys Asp Tyr Ile Ala
705                 710                 715                 720

Ala Phe Asn Asn Met Asp Lys Phe Val Tyr Arg Ser Ala Gln Glu Gly
                725                 730                 735

Phe Thr Phe Ala Leu Ser Met Tyr Ser Ser Arg Thr Gln Asn Tyr Glu
            740                 745                 750
```

```
Asp Met Asn Asn Glu Asn Arg Lys Gly Trp Tyr Thr Ala Asp Gly Met
        755                 760                 765

Val Tyr Leu Tyr Asn Asp Asp Leu Ser His Tyr Ser Asn His Tyr Trp
    770                 775                 780

Ala Thr Val Asp Pro Tyr Arg Leu Pro Gly Thr Thr Thr Thr Lys Asp
785                 790                 795                 800

Lys Arg Glu Asp Gly Ser Gly Glu Val Thr Leu Ala Ser Asp Phe Val
                805                 810                 815

Gly Ala Ser Gln Leu Gly Asn Arg Leu Ala Thr Ile Ala Met Asp Phe
            820                 825                 830

Asn Asn Trp Asn Asn Ser Leu Thr Ala Arg Lys Ala Trp Ile Val Leu
        835                 840                 845

Gly Asn Lys Ile Val Phe Leu Gly Thr Asp Ile Gln His Gln Ser Ala
    850                 855                 860

Gln Gly Ala Glu Thr Thr Ile Glu Asn Arg Lys Leu Leu Thr Gly Glu
865                 870                 875                 880

Lys Tyr Ser Tyr Tyr Ile Asn Gly Gln Pro Val Asp Leu Ser Lys Glu
                885                 890                 895

Val Val Thr Asp Lys Thr Gln Ser Phe Tyr Met Thr Asn Gly Lys Asp
            900                 905                 910

Asn Gln Ser Ile Gly Tyr Val Phe Leu Asn Gln Leu Pro Thr His Ala
        915                 920                 925

Lys Leu Asp Gln Arg Thr Gly Lys Trp Ser Asp Ile Asn Tyr Asn Gln
    930                 935                 940

Ser Lys Glu Glu Val Ser Asn Ser Phe Val Ser Leu Trp His Glu His
945                 950                 955                 960

Ala Gln Thr Ser Ser Asn Tyr Ala Tyr Val Leu Val Pro Asn Gln Ser
                965                 970                 975

Met Glu Lys Val Asn Gln Ala Ala Ala Ser Val Lys Leu Leu His Gln
            980                 985                 990

Asp Arg Asp Leu Gln Val Val Tyr  Asp Gln Glu Gln Asn  Val Trp Gly
        995                 1000                 1005

Val Val  Lys Tyr Thr Asp Thr  Ala Tyr Lys Leu Thr  Asp Asp Ile
    1010                 1015                 1020

Thr Leu  Thr Asp Ala Gly Leu  Tyr Thr Ile Gln Lys  Val Glu Gly
    1025                 1030                 1035

Gly Tyr  Arg Ile Ala Phe Tyr  Asn Pro Ser Thr Arg  Thr Val Lys
    1040                 1045                 1050

Asn Gly  Ile Glu Leu Thr Lys  Ala Gly Ser Ser Leu  Thr Val Glu
    1055                 1060                 1065

Met Glu  Pro Thr Ala Ala Tyr  Pro Ser Thr Val Trp  Lys Val Thr
    1070                 1075                 1080

Met Pro  Glu Gly Ser Asp Lys  Gln Thr Gly Ser Val  Glu Lys Thr
    1085                 1090                 1095

Glu Lys  Glu Glu Lys Gln Leu  Lys Glu Asn Gln Pro  Ser Ser Glu
    1100                 1105                 1110

Val Lys  Gln Val Val His His  Ala Ala Glu Lys Thr  Lys Pro Ser
    1115                 1120                 1125

Lys Pro  Arg Leu Pro Gln Thr  Gly Glu Glu Ala Ser  Leu Gly Leu
    1130                 1135                 1140

Gly Phe  Leu Gly Leu Leu Thr  Leu Gly Ala Val Val  Asp Phe Lys
    1145                 1150                 1155

Cys Arg  Arg Ser His Ser
```

1160

<210> SEQ ID NO 94
<211> LENGTH: 802
<212> TYPE: PRT
<213> ORGANISM: Vibrio fischeri

<400> SEQUENCE: 94

Met Tyr Met Ile Lys Lys His Arg Leu Asn Thr Ile Ala Leu Ser Met
1 5 10 15

Leu Phe Leu Phe Thr Gly Asn Ala Tyr Ala Ala Lys Asn Thr Gln Thr
20 25 30

Pro Gln Tyr Leu Pro Ser Asp Phe Glu Gln Val Arg Glu Asn Trp Ala
35 40 45

Glu Asn Tyr Leu Gly Asp Pro Ala Ile Thr Phe Asp Gln Thr Leu Lys
50 55 60

Asn Met Val Thr Ser Thr Asn Ser Ser Ala Gln Lys His Trp Asp Ser
65 70 75 80

Met Thr Pro Gln Pro Asn Ala Ser Gly Ile Trp Asp Asp Leu Pro Leu
85 90 95

Ile Asp Lys Asp Thr Thr Leu Gly Pro Asn Ile Arg Asn Ser Tyr Gln
100 105 110

Arg Leu Phe Thr Met Ala Lys Ala Tyr Arg Leu Arg Asp Gly Asn Leu
115 120 125

Glu Asn Asn Gln Leu Met Leu Asn Asp Ile Met Thr Ala Met Asn Tyr
130 135 140

Ile Asn Gln Asn Phe Tyr Phe Val Asn Gln Leu Glu Tyr Gly Asn Trp
145 150 155 160

Trp Gln Trp Glu Leu Ala Ile Pro Lys Asp Ile His Asn Ile Leu Val
165 170 175

Leu Leu Phe Asp Asp Ile Lys Asp Asn Tyr Gln Thr Ile Ile Thr Asn
180 185 190

His Leu Asn Ala Thr Arg Tyr Phe Thr Pro Asp Pro Thr His Leu Gly
195 200 205

Val Ser Pro Gly Ala Ala Glu Ser Thr Asn Pro Asn Tyr Arg Glu Ser
210 215 220

Thr Gly Gly Asn Arg Thr Asp Asn Ala Gln Val Val Leu Ile Arg Gly
225 230 235 240

Met Leu Glu Asn Asn Ser Glu Glu Ile Ser Gln Ala Ile Ala Ala Leu
245 250 255

Pro Ala Val Ile Glu Tyr Val Ser Glu Gly Asp Gly Tyr Tyr Thr Asp
260 265 270

Gly Ser Phe Leu Gln His Ser Asp Ile Ala Tyr Asn Gly Thr Tyr Gly
275 280 285

Asn Val Leu Leu Gly Gly Leu Gly Ile Gln Met Asn Ala Val Ala Gly
290 295 300

Ser Pro Trp Ser Met Asp Asn Gln Thr Ile Ser Asn Val Tyr Asn Ile
305 310 315 320

Ile Asn Gln Ser Tyr Glu Pro Leu Leu Tyr Lys Gly Ala Met Met Asp
325 330 335

Met Val Asn Gly Arg Ser Ile Ser Arg Ser Ala Glu Gln Asn His Asp
340 345 350

Val Gly Leu Asn Ile Val Asn Ser Met Leu Phe Tyr Thr Asn Gly Pro
355 360 365

-continued

```
Asp Ser Asp Lys Asn Lys Gln Leu Ser Ser Leu Ile Lys Thr Gln Ile
    370                 375                 380

Thr Asp Asp Thr Tyr Gln Asn Phe Phe Asp Lys Ile Tyr Tyr Val Ser
385                 390                 395                 400

Thr Tyr Gln Ala Ala Gln His Ile Val Asn Asp Pro Thr Val Ser Leu
                405                 410                 415

Lys Asp Pro Leu Ile Gly Asn Phe Ser Tyr Pro Ser Met Asp Arg Ile
            420                 425                 430

Val His Arg Arg Thr Asp Trp Ala Phe Ala Leu Ala Met His Ser Tyr
        435                 440                 445

Arg Ile Gly Asn Tyr Glu Cys Met Asn Gly Glu Asn Leu Lys Gly Trp
    450                 455                 460

Phe Thr Gly Asp Gly Met Ile Tyr Leu Tyr Asn Asp Gln Leu Asp His
465                 470                 475                 480

Tyr Thr Gly Tyr Trp Pro Thr Val Asn Ala Ser Arg Met Pro Gly Thr
                485                 490                 495

Thr Val Asp Ser Gln Ile Met Ala Asp Cys Ser Gly Glu Arg Val Gly
            500                 505                 510

Gly Asn Val Asn Thr Asn Met Gln Trp Val Gly Ser Thr Ser Leu Asn
        515                 520                 525

Asn Tyr Gly Ile Ala Gly Met Gln Phe Tyr Asn Trp Ser Asp Thr Leu
    530                 535                 540

Ser Ala Tyr Lys Ser Trp Phe Met Phe Asp Asn Glu Val Val Met Leu
545                 550                 555                 560

Gly Ser Asn Ile Lys Asp Gln Ser Asn Ala Asn Asn Ile Thr Thr Ile
                565                 570                 575

Glu Asn Arg Lys Arg Leu Ala Glu Thr Lys Leu Phe Ile Asp Gly Thr
            580                 585                 590

Glu Gln Ala Ala Leu Pro Tyr Gln Gly Ala Pro Ala Thr Phe Ser Ile
        595                 600                 605

Arg Asn Lys Thr Leu Ala Asn Ser Asp Leu Ser Tyr Val Met Leu Thr
    610                 615                 620

Pro Lys Thr Ile Ser Ile Ser Gln Asn Asp Val Asp Gly Asn Trp Ser
625                 630                 635                 640

Asp Ile Gly Asn Ser Lys Gly Asp Val Ser Asp Ser Tyr Leu Gln Ala
                645                 650                 655

Thr Leu Thr Gln Val Asp Gln Ala Asp Tyr Gln Tyr Ala Leu Leu Pro
            660                 665                 670

Asn Gln Asn Asn Asp Thr Val Gln Asn Tyr Ala Gln His Pro Asp Val
        675                 680                 685

Thr Val Leu Arg Gln Asp Glu Gln Ala His Ala Val Gln Glu Asn Thr
    690                 695                 700

Leu Asn Ile Ile Ala Ala Asn Asn Trp Lys Asn Asn Pro Val Asn Ile
705                 710                 715                 720

Thr Asp Thr Ile Thr Leu Asn Ser Met Met Gly Phe Met Ile Lys Glu
                725                 730                 735

Glu Ser Ser Asn Thr Phe Thr Val Ala Val Ser Glu Pro Ile Gln Thr
            740                 745                 750

Ile Asp Ser Val Asn Phe Thr Phe Asp Lys Gln Gly Ile Val Ile Lys
        755                 760                 765

Glu Asp Ile Glu Asn Arg Val Val Leu Asn Gly Thr Thr Leu Thr Ile
    770                 775                 780

Asn Thr Ser Gly Leu Gln Gly Gln Ser Tyr Ser Phe Gln Val Thr Ile
```

785 790 795 800

Gln Asp

<210> SEQ ID NO 95
<211> LENGTH: 489
<212> TYPE: PRT
<213> ORGANISM: Hirudo nipponia

<400> SEQUENCE: 95

Met Lys Glu Ile Ala Val Thr Ile Asp Asp Lys Asn Val Ile Ala Ser
1 5 10 15

Val Ser Glu Ser Phe His Gly Val Ala Phe Asp Ala Ser Leu Phe Ser
20 25 30

Pro Lys Gly Leu Trp Ser Phe Val Asp Ile Thr Ser Pro Lys Leu Phe
35 40 45

Lys Leu Leu Glu Gly Leu Ser Pro Gly Tyr Phe Arg Val Gly Gly Thr
50 55 60

Phe Ala Asn Trp Leu Phe Phe Asp Leu Asp Glu Asn Asn Lys Trp Lys
65 70 75 80

Asp Tyr Trp Ala Phe Lys Asp Lys Thr Pro Glu Thr Ala Thr Ile Thr
85 90 95

Arg Arg Trp Leu Phe Arg Lys Gln Asn Asn Leu Lys Lys Glu Thr Phe
100 105 110

Asp Asp Leu Val Lys Leu Thr Lys Gly Ser Lys Met Arg Leu Leu Phe
115 120 125

Asp Leu Asn Ala Glu Val Arg Thr Gly Tyr Glu Ile Gly Lys Lys Met
130 135 140

Thr Ser Thr Trp Asp Ser Ser Glu Ala Glu Lys Leu Phe Lys Tyr Cys
145 150 155 160

Val Ser Lys Gly Tyr Gly Asp Asn Ile Asp Trp Glu Leu Gly Asn Glu
165 170 175

Pro Asp His Thr Ser Ala His Asn Leu Thr Glu Lys Gln Val Gly Glu
180 185 190

Asp Phe Lys Ala Leu His Lys Val Leu Glu Lys Tyr Pro Thr Leu Asn
195 200 205

Lys Gly Ser Leu Val Gly Pro Asp Val Gly Trp Met Gly Val Ser Tyr
210 215 220

Val Lys Gly Leu Ala Asp Gly Ala Gly Asp His Val Thr Ala Phe Thr
225 230 235 240

Leu His Gln Tyr Tyr Phe Asp Gly Asn Thr Ser Asp Val Ser Thr Tyr
245 250 255

Leu Asp Ala Thr Tyr Phe Lys Lys Leu Gln Gln Leu Phe Asp Lys Val
260 265 270

Lys Asp Val Leu Lys Asn Ser Pro His Lys Asp Lys Pro Leu Trp Leu
275 280 285

Gly Glu Thr Ser Ser Gly Tyr Asn Ser Gly Thr Lys Asp Val Ser Asp
290 295 300

Arg Tyr Val Ser Gly Phe Leu Thr Leu Asp Lys Leu Gly Leu Ser Ala
305 310 315 320

Ala Asn Asn Val Lys Val Val Ile Arg Gln Thr Ile Tyr Asn Gly Tyr
325 330 335

Tyr Gly Leu Leu Asp Lys Asn Thr Leu Glu Pro Asn Pro Asp Tyr Trp
340 345 350

Leu Met His Val His Asn Ser Leu Val Gly Asn Thr Val Phe Lys Val

```
        355                 360                 365

Asp Val Ser Asp Pro Thr Asn Lys Ala Arg Val Tyr Ala Gln Cys Thr
    370                 375                 380

Lys Thr Asn Ser Lys His Thr Gln Ser Arg Tyr Tyr Lys Gly Ser Leu
385                 390                 395                 400

Thr Ile Phe Ala Leu Asn Val Gly Asp Glu Asp Val Thr Leu Lys Ile
                405                 410                 415

Asp Gln Tyr Ser Gly Lys Lys Ile Tyr Ser Tyr Ile Leu Thr Pro Glu
            420                 425                 430

Gly Gly Gln Leu Thr Ser Gln Lys Val Leu Leu Asn Gly Lys Glu Leu
        435                 440                 445

Lys Leu Val Ser Asp Gln Leu Pro Glu Leu Asn Ala Asp Glu Ser Lys
    450                 455                 460

Thr Ser Phe Thr Leu Ser Pro Lys Thr Phe Gly Phe Phe Val Val Ser
465                 470                 475                 480

Asp Ala Asn Val Glu Ala Cys Lys Lys
                485


<210> SEQ ID NO 96
<211> LENGTH: 815
<212> TYPE: PRT
<213> ORGANISM: Staphylococcus aureus

<400> SEQUENCE: 96

Met Thr Tyr Arg Met Lys Lys Trp Gln Lys Leu Ser Thr Ile Thr Leu
1               5                   10                  15

Leu Met Ala Gly Ala Ile Thr Leu Asn Gly Gly Glu Phe Arg Ser Ile
            20                  25                  30

Asp Lys His Gln Ile Ala Val Ala Asp Thr Asn Val Gln Thr Pro Asp
        35                  40                  45

Tyr Glu Lys Leu Arg Asn Thr Trp Leu Asn Val Asn Tyr Gly Tyr Asp
    50                  55                  60

Gln Tyr Asp Glu Lys Asn Asp Ala Met Lys Lys Lys Phe Asp Ala Thr
65                  70                  75                  80

Glu Lys Glu Ala Glu Lys Leu Leu Ser Ser Met Lys Thr Glu Ser Gly
                85                  90                  95

Arg Thr Tyr Leu Trp Asp Ser Ala Lys Asp Leu Asp Asn Lys Ser Ala
            100                 105                 110

Asp Met Thr Arg Thr Tyr Arg Asn Ile Glu Lys Ile Ala Glu Ala Met
        115                 120                 125

Lys His Lys Asp Thr Lys Leu Asn Thr Pro Asp Asn Lys Asn Lys Val
    130                 135                 140

Lys Asp Ala Leu Glu Trp Leu His Lys Asn Ala Tyr Gly Lys Glu Pro
145                 150                 155                 160

Val Lys Lys Leu Glu Glu Leu Lys Thr Asn Phe Ser Lys Ser Ala Pro
                165                 170                 175

Gln Lys Asn Thr Asn Leu Asn Trp Trp Asp Tyr Glu Ile Gly Thr Pro
            180                 185                 190

Arg Ala Leu Thr Asn Thr Leu Ile Leu Leu Lys Glu Asp Phe Thr Asp
        195                 200                 205

Glu Glu Lys Lys Lys Tyr Thr Ala Pro Ile Lys Thr Phe Ala Pro Lys
    210                 215                 220

Ser Asp Glu Ile Leu Ser Ser Val Gly Lys Ala Glu Pro Ala Lys Gly
225                 230                 235                 240
```

```
Gly Asn Leu Val Asp Ile Ser Lys Val Lys Leu Leu Glu Ser Ile Ile
                245                 250                 255

Glu Glu Asp Ala Thr Met Met Lys Glu Ser Ile Glu Ala Phe Asn Lys
            260                 265                 270

Val Phe Thr Tyr Val Gln Ser Asn Ala Thr Gly Lys Glu Arg Asn Gly
        275                 280                 285

Phe Tyr Lys Asp Gly Ser Tyr Ile Asp His Gln Asp Val Pro Tyr Thr
    290                 295                 300

Gly Ala Tyr Gly Val Val Leu Leu Glu Gly Ile Ser Gln Met Met Pro
305                 310                 315                 320

Met Ile Lys Glu Thr Pro Phe Lys Asp Ser Asn Gln Asn Asp Thr Thr
                325                 330                 335

Leu Lys Ser Trp Ile Asp Glu Gly Phe Met Pro Leu Ile Tyr Lys Gly
            340                 345                 350

Glu Met Met Asp Leu Ser Arg Gly Arg Ala Ile Ser Arg Glu Asn Glu
        355                 360                 365

Thr Ser His Ser Thr Ser Ala Thr Val Met Lys Ser Leu Leu Arg Leu
    370                 375                 380

Ser Asp Ala Met Asp Glu Ser Thr Lys Ala Lys Tyr Lys Gln Ile Val
385                 390                 395                 400

Lys Thr Ser Val Lys Ser Asp Ser Ser Tyr Lys Gln Asn Asp Tyr Leu
                405                 410                 415

Ser Ser Tyr Ser Asp Ile Ser Lys Met Lys Ser Leu Ile Glu Asp Ser
            420                 425                 430

Thr Ile Ser Thr Asn Gly Leu Thr Gln Gln Leu Lys Ile Tyr Asn Asp
        435                 440                 445

Met Asn Arg Val Thr Tyr His Asn Lys Asp Leu Asp Phe Ala Phe Gly
    450                 455                 460

Leu Ser Met Thr Ser Lys Asn Val Ala His Tyr Glu Ser Ile Asn Gly
465                 470                 475                 480

Glu Asn Leu Lys Gly Trp His Thr Gly Ala Gly Met Ser Tyr Leu Tyr
                485                 490                 495

Asn Ser Asp Val Lys His Tyr Arg Asp Asn Phe Trp Ala Thr Ala Asp
            500                 505                 510

Met Lys Arg Leu Ala Gly Thr Thr Thr Leu Asp Asn Glu Glu Pro Lys
        515                 520                 525

Glu Asn Lys Asn Ser Asp Lys Thr Phe Val Gly Gly Thr Lys Phe Asp
    530                 535                 540

Asp Gln His Ala Ser Ile Gly Met Asp Phe Glu Asn Gln Asp Lys Thr
545                 550                 555                 560

Leu Thr Ala Lys Lys Ser Tyr Phe Ile Leu Asn Asp Lys Ile Val Phe
                565                 570                 575

Leu Gly Thr Gly Ile Lys Ser Thr Asp Ser Ser Lys Asn Pro Val Thr
            580                 585                 590

Thr Ile Glu Asn Arg Lys Ser Asn Gly Tyr Thr Leu Phe Thr Asp Asp
        595                 600                 605

Lys Gln Thr Thr Ala Ser Asn Ile Asn Asp Gln Glu Thr Asn Ser Val
    610                 615                 620

Phe Leu Glu Ser Thr Asp Thr Lys Lys Asn Ile Gly Tyr His Phe Leu
625                 630                 635                 640

Asn Glu Ser Lys Ile Thr Val Lys Lys Glu Ser His Thr Gly Lys Trp
                645                 650                 655

Ser Asp Ile Asn Lys Ser Gln Lys Ser Asp Asp Lys Thr Asp Glu Tyr
```

```
            660                 665                 670

Tyr Glu Val Thr Gln Lys His Ser Asn Thr Asp Asp Lys Tyr Ala Tyr
        675                 680                 685

Val Leu Tyr Pro Gly Leu Ser Lys Asp Asn Phe Lys Ser Lys Ala Ser
    690                 695                 700

Gln Val Thr Ile Val Lys Gln Asp Asp Asp Phe His Ile Val Lys Asp
705                 710                 715                 720

Asn Glu Ser Val Trp Ala Gly Val Asn Tyr Ser Asn Ser Thr Gln Thr
                725                 730                 735

Phe Asp Ile Asn Asn Thr Lys Val Glu Val Lys Ala Lys Gly Met Phe
            740                 745                 750

Ile Leu Lys Asn Lys Asp Asp Asn Thr Tyr Glu Cys Ser Phe Tyr Asn
        755                 760                 765

Pro Glu Ser Thr Asn Thr Ala Ser Asp Ile Glu Ser Lys Ile Ser Met
    770                 775                 780

Thr Gly Tyr Ser Ile Thr Asn Lys Asn Thr Ser Thr Ser Asn Glu Ser
785                 790                 795                 800

Gly Val Arg Phe Glu Leu Gln Gln Thr Leu Asn Lys Asp Asp Asn
                805                 810                 815


<210> SEQ ID NO 97
<211> LENGTH: 400
<212> TYPE: PRT
<213> ORGANISM: Loxosceles intermedia

<400> SEQUENCE: 97

Met Gln Thr Ile Leu Val Leu Thr Thr Phe Leu Ser Ala Trp Phe Leu
1               5                   10                  15

Ala Val Gly Phe Asp Val Phe Trp Asn Val Pro Ser Gln Gln Cys Lys
            20                  25                  30

Lys Tyr Gly Met Lys Phe Val Pro Leu Leu Glu Gln Tyr Ser Ile Leu
        35                  40                  45

Val Asn Lys Glu Asp Asn Phe Lys Gly Asp Lys Ile Thr Ile Phe Tyr
    50                  55                  60

Glu Ser Gln Leu Gly Leu Tyr Pro His Ile Gly Ala Asn Asp Glu Ser
65                  70                  75                  80

Phe Asn Gly Gly Ile Pro Gln Leu Gly Asp Leu Lys Ala His Leu Glu
                85                  90                  95

Lys Ser Ala Val Asp Ile Arg Arg Asp Ile Leu Asp Lys Ser Ala Thr
            100                 105                 110

Gly Leu Arg Ile Ile Asp Trp Glu Ala Trp Arg Pro Ile Trp Glu Phe
        115                 120                 125

Asn Trp Ser Ser Leu Arg Lys Tyr Gln Asp Lys Met Lys Lys Val Val
    130                 135                 140

Arg Gln Phe Asn Pro Thr Ala His Glu Ser Thr Val Ala Lys Leu Ala
145                 150                 155                 160

His Asn Glu Trp Glu Asn Ser Ser Lys Ser Trp Met Leu Ser Thr Leu
                165                 170                 175

Gln Leu Gly Lys Gln Leu Arg Pro Asn Ser Val Trp Cys Tyr Tyr Leu
            180                 185                 190

Phe Pro Asp Cys Tyr Asn Tyr Asp Gly Asn Ser Val Gln Glu Phe Gln
        195                 200                 205

Cys Ser Glu Ala Ile Arg Lys Gly Asn Asp Arg Leu Lys Trp Leu Trp
    210                 215                 220
```

```
Glu Glu Ser Thr Ala Val Cys Pro Ser Ile Tyr Ile Lys Glu Gly Gln
225                 230                 235                 240

Leu Thr Asn Tyr Thr Leu Gln Lys Arg Ile Trp Phe Thr Asn Gly Arg
                245                 250                 255

Leu Gln Glu Ala Leu Arg Val Ala Gln Pro Lys Ala Arg Ile Tyr Pro
            260                 265                 270

Tyr Ile Asn Tyr Ser Ile Lys Pro Gly Met Met Val Pro Glu Val Glu
        275                 280                 285

Phe Trp Arg Leu Ile Ala Gln Ile Ala Ser Leu Gly Met Asp Gly Ala
    290                 295                 300

Val Ile Trp Gly Ser Ser Ala Ser Val Gly Ser Lys Asn His Cys Ala
305                 310                 315                 320

Gln Leu Met Lys Tyr Ile Ala Asp Val Leu Gly Pro Ala Thr Leu Arg
                325                 330                 335

Ile Lys Glu Asn Val Ala Arg Cys Ser Lys Gln Ala Cys Ser Gly Arg
            340                 345                 350

Gly Arg Cys Thr Trp Pro Lys Asp Thr Ser Val Ile Ala Trp Lys Phe
        355                 360                 365

Leu Val Glu Lys Glu Asp Tyr Asp Phe Tyr Leu Gly Asp Ile Glu Cys
    370                 375                 380

Lys Cys Val Glu Gly Tyr Glu Gly Arg Tyr Cys Glu Gln Lys Thr Lys
385                 390                 395                 400


<210> SEQ ID NO 98

<400> SEQUENCE: 98

000


<210> SEQ ID NO 99
<211> LENGTH: 247
<212> TYPE: PRT
<213> ORGANISM: Streptomyces koganeiensis

<400> SEQUENCE: 99

Met Pro Val Ala Arg Arg Leu Phe Leu Gly Ser Phe Thr Ala Gly Ala
1               5                   10                  15

Val Thr Val Ala Thr Ala Ala Ala Thr Gly Thr Ala Ser Ala Ala Gly
            20                  25                  30

Glu Asn Gly Ala Thr Thr Thr Phe Asp Gly Pro Val Ala Ala Glu Arg
        35                  40                  45

Phe Ser Ala Asp Thr Thr Leu Glu Ala Ala Phe Leu Lys Thr Thr Ser
    50                  55                  60

Glu Thr Asn His Ala Ala Thr Ile Tyr Gln Ala Gly Thr Ser Gly Asp
65                  70                  75                  80

Gly Ala Ala Leu Asn Val Ile Ser Asp Asn Pro Gly Thr Ser Ala Met
                85                  90                  95

Tyr Leu Ser Gly Thr Glu Thr Ala Arg Gly Thr Leu Lys Ile Thr His
            100                 105                 110

Arg Gly Tyr Ala Asp Gly Ser Asp Lys Asp Ala Ala Ala Leu Ser Leu
        115                 120                 125

Asp Leu Arg Val Ala Gly Thr Ala Ala Gln Gly Ile Tyr Val Thr Ala
    130                 135                 140

Thr Asn Gly Pro Thr Lys Gly Asn Leu Ile Ala Leu Arg Asn Asn Thr
145                 150                 155                 160

Gly Leu Asp Asp Phe Val Val Lys Gly Thr Gly Arg Ile Gly Val Gly
```

```
                165                 170                 175

Ile Asp Arg Ala Ala Thr Pro Arg Ala Gln Val His Ile Val Gln Arg
            180                 185                 190

Gly Asp Ala Leu Ala Ala Leu Leu Val Glu Gly Ser Val Arg Ile Gly
        195                 200                 205

Asn Ala Ala Thr Val Pro Thr Ser Val Asp Ser Ser Gly Gly Gly Ala
    210                 215                 220

Leu Tyr Ala Ser Gly Gly Ala Leu Leu Trp Arg Gly Ser Asn Gly Thr
225                 230                 235                 240

Val Thr Thr Ile Ala Pro Ala
                245


<210> SEQ ID NO 100
<211> LENGTH: 239
<212> TYPE: PRT
<213> ORGANISM: Mycobacterium tuberculosis

<400> SEQUENCE: 100

Met Thr Glu Ser Arg Pro Val Phe Ala Val Val Ile Ser Ala Gly Leu
1               5                   10                  15

Ser Ala Ile Pro Met Val Gly Gly Pro Leu Gln Thr Val Phe Asp Ala
            20                  25                  30

Ile Glu Glu Arg Thr Arg His Arg Ala Glu Thr Thr Thr Arg Glu Ile
        35                  40                  45

Cys Glu Ser Val Gly Gly Ala Asp Thr Val Leu Ser Arg Ile Asp Lys
    50                  55                  60

Asn Pro Glu Leu Glu Pro Leu Leu Ser Gln Ala Ile Glu Ala Ala Thr
65                  70                  75                  80

Arg Thr Ser Met Glu Ala Lys Arg Arg Leu Leu Ala Gln Ala Ala Ala
                85                  90                  95

Ala Ala Leu Glu Asp Asp Gln Lys Val Glu Pro Ala Ser Leu Ile Val
            100                 105                 110

Ala Thr Leu Ser Gln Leu Glu Pro Val His Ile His Ala Leu Val Arg
        115                 120                 125

Leu Ala Lys Ala Ala Lys Ser Ser Pro Asp Gln Asp Glu Ile Gln Arg
    130                 135                 140

Arg Glu Val Met Arg Ala Ala Ser Lys Val Glu Pro Val Pro Val Leu
145                 150                 155                 160

Ala Ala Leu Ile Gln Thr Gly Val Ala Ile Ala Thr Thr Thr Val Trp
                165                 170                 175

His Gly Asn Gly Thr Gly Thr Pro Ala Glu Glu Ser Gly His Ile Leu
            180                 185                 190

Ile His Asp Val Ser Asp Phe Gly His Arg Leu Leu Ala Tyr Leu Arg
        195                 200                 205

Ala Ala Asp Ala Gly Ala Glu Leu Leu Ile Leu Pro Ser Gly Gly Ser
    210                 215                 220

Ala Pro Thr Gly Asp His Pro Thr Pro His Pro Ser Thr Ser Arg
225                 230                 235


<210> SEQ ID NO 101
<211> LENGTH: 507
<212> TYPE: PRT
<213> ORGANISM: Hirudo nipponia

<400> SEQUENCE: 101

Met Asp Trp Thr Trp Ile Leu Phe Leu Val Ala Ala Ala Thr Arg Val
```

-continued

```
1               5                   10                  15

His Ser Gly Arg Lys Glu Ile Ala Val Thr Ile Asp Asp Lys Asn Val
            20                  25                  30

Ile Ala Ser Val Ser Glu Ser Phe His Gly Val Ala Phe Asp Ala Ser
        35                  40                  45

Leu Phe Ser Pro Lys Gly Leu Trp Ser Phe Val Asp Ile Thr Ser Pro
    50                  55                  60

Lys Leu Phe Lys Leu Leu Glu Gly Leu Ser Pro Gly Tyr Phe Arg Val
65                  70                  75                  80

Gly Gly Thr Phe Ala Asn Trp Leu Phe Phe Asp Leu Asp Glu Asn Asn
                85                  90                  95

Lys Trp Lys Asp Tyr Trp Ala Phe Lys Asp Lys Thr Pro Glu Thr Ala
            100                 105                 110

Thr Ile Thr Arg Arg Trp Leu Phe Arg Lys Gln Asn Asn Leu Lys Lys
        115                 120                 125

Glu Thr Phe Asp Asp Leu Val Lys Leu Thr Lys Gly Ser Lys Met Arg
    130                 135                 140

Leu Leu Phe Asp Leu Asn Ala Glu Val Arg Thr Gly Tyr Glu Ile Gly
145                 150                 155                 160

Lys Lys Met Thr Ser Thr Trp Asp Ser Ser Glu Ala Glu Lys Leu Phe
                165                 170                 175

Lys Tyr Cys Val Ser Lys Gly Tyr Gly Asp Asn Ile Asp Trp Glu Leu
            180                 185                 190

Gly Asn Glu Pro Asp His Thr Ser Ala His Asn Leu Thr Glu Lys Gln
        195                 200                 205

Val Gly Glu Asp Phe Lys Ala Leu His Lys Val Leu Glu Lys Tyr Pro
    210                 215                 220

Thr Leu Asn Lys Gly Ser Leu Val Gly Pro Asp Val Gly Trp Met Gly
225                 230                 235                 240

Val Ser Tyr Val Lys Gly Leu Ala Asp Gly Ala Gly Asp His Val Thr
                245                 250                 255

Ala Phe Thr Leu His Gln Tyr Tyr Phe Asp Gly Asn Thr Ser Asp Val
            260                 265                 270

Ser Thr Tyr Leu Asp Ala Thr Tyr Phe Lys Lys Leu Gln Gln Leu Phe
        275                 280                 285

Asp Lys Val Lys Asp Val Leu Lys Asn Ser Pro His Lys Asp Lys Pro
    290                 295                 300

Leu Trp Leu Gly Glu Thr Ser Ser Gly Tyr Asn Ser Gly Thr Lys Asp
305                 310                 315                 320

Val Ser Asp Arg Tyr Val Ser Gly Phe Leu Thr Leu Asp Lys Leu Gly
                325                 330                 335

Leu Ser Ala Ala Asn Asn Val Lys Val Val Ile Arg Gln Thr Ile Tyr
            340                 345                 350

Asn Gly Tyr Tyr Gly Leu Leu Asp Lys Asn Thr Leu Glu Pro Asn Pro
        355                 360                 365

Asp Tyr Trp Met His Val His Asn Ser Leu Val Gly Asn Thr Val Phe
    370                 375                 380

Lys Val Asp Val Ser Asp Pro Thr Asn Lys Ala Arg Val Tyr Ala Gln
385                 390                 395                 400

Cys Thr Lys Thr Asn Ser Lys His Thr Gln Ser Arg Tyr Tyr Lys Gly
                405                 410                 415

Ser Leu Thr Ile Phe Ala Leu Asn Val Gly Asp Glu Asp Val Thr Leu
            420                 425                 430
```

```
Lys Ile Asp Gln Tyr Ser Gly Lys Lys Ile Tyr Ser Tyr Ile Leu Thr
        435                 440                 445

Pro Glu Gly Gly Gln Leu Thr Ser Gln Lys Val Leu Leu Asn Gly Lys
    450                 455                 460

Glu Leu Lys Leu Val Ser Asp Gln Leu Pro Glu Leu Asn Ala Asp Glu
465                 470                 475                 480

Ser Lys Thr Ser Phe Thr Leu Ser Pro Lys Thr Phe Gly Phe Phe Val
                485                 490                 495

Val Ser Asp Ala Asn Val Glu Ala Cys Lys Lys
            500                 505


<210> SEQ ID NO 102
<211> LENGTH: 787
<212> TYPE: PRT
<213> ORGANISM: Staphylococcus aureus

<400> SEQUENCE: 102

Met Asp Trp Thr Trp Ile Leu Phe Leu Val Ala Ala Ala Thr Arg Val
1               5                   10                  15

His Ser Gly Arg Asp Thr Asn Val Gln Thr Pro Asp Tyr Glu Lys Leu
            20                  25                  30

Arg Asn Thr Trp Leu Asn Val Asn Tyr Gly Tyr Asp Gln Tyr Asp Glu
        35                  40                  45

Lys Asn Asp Ala Met Lys Lys Lys Phe Asp Ala Thr Glu Lys Glu Ala
    50                  55                  60

Glu Lys Leu Leu Ser Ser Met Lys Thr Glu Ser Gly Arg Thr Tyr Leu
65                  70                  75                  80

Trp Asp Ser Ala Lys Asp Leu Asp Asn Lys Ser Ala Asp Met Thr Arg
                85                  90                  95

Thr Tyr Arg Asn Ile Glu Lys Ile Ala Glu Ala Met Lys His Lys Asp
            100                 105                 110

Thr Lys Leu Asn Thr Pro Asp Asn Lys Asn Lys Val Lys Asp Ala Leu
        115                 120                 125

Glu Trp Leu His Lys Asn Ala Tyr Gly Lys Glu Pro Val Lys Lys Leu
    130                 135                 140

Glu Glu Leu Lys Thr Asn Phe Ser Lys Ser Ala Pro Gln Lys Asn Thr
145                 150                 155                 160

Asn Leu Asn Trp Trp Asp Tyr Glu Ile Gly Thr Pro Arg Ala Leu Thr
                165                 170                 175

Asn Thr Leu Ile Leu Leu Lys Glu Asp Phe Thr Asp Glu Glu Lys Lys
            180                 185                 190

Lys Tyr Thr Ala Pro Ile Lys Thr Phe Ala Pro Lys Ser Asp Glu Ile
        195                 200                 205

Leu Ser Ser Val Gly Lys Ala Glu Pro Ala Lys Gly Gly Asn Leu Val
    210                 215                 220

Asp Ile Ser Lys Val Lys Leu Leu Glu Ser Ile Ile Glu Glu Asp Ala
225                 230                 235                 240

Thr Met Met Lys Glu Ser Ile Glu Ala Phe Asn Lys Val Phe Thr Tyr
                245                 250                 255

Val Gln Ser Asn Ala Thr Gly Lys Glu Arg Asn Gly Phe Tyr Lys Asp
            260                 265                 270

Gly Ser Tyr Ile Asp His Gln Asp Val Pro Tyr Thr Gly Ala Tyr Gly
        275                 280                 285

Val Val Leu Leu Glu Gly Ile Ser Gln Met Met Pro Met Ile Lys Glu
```

-continued

```
    290                 295                 300

Thr Pro Phe Lys Asp Ser Asn Gln Asn Asp Thr Thr Leu Lys Ser Trp
305                 310                 315                 320

Ile Asp Glu Gly Phe Met Pro Leu Ile Tyr Lys Gly Glu Met Met Asp
                325                 330                 335

Leu Ser Arg Gly Arg Ala Ile Ser Arg Glu Asn Glu Thr Ser His Ser
            340                 345                 350

Thr Ser Ala Thr Val Met Lys Ser Leu Leu Arg Leu Ser Asp Ala Met
        355                 360                 365

Asp Glu Ser Thr Lys Ala Lys Tyr Lys Gln Ile Val Lys Thr Ser Val
    370                 375                 380

Lys Ser Asp Ser Ser Tyr Lys Gln Asn Asp Tyr Leu Ser Ser Tyr Ser
385                 390                 395                 400

Asp Ile Ser Met Lys Ser Leu Ile Glu Asp Ser Thr Ile Ser Thr Asn
                405                 410                 415

Gly Leu Thr Gln Gln Leu Lys Ile Tyr Asn Asp Met Asn Arg Val Thr
            420                 425                 430

Tyr His Asn Lys Asp Leu Asp Phe Ala Phe Gly Leu Ser Met Thr Ser
        435                 440                 445

Lys Asn Val Ala His Tyr Glu Ser Ile Asn Gly Glu Asn Leu Lys Gly
    450                 455                 460

Trp His Thr Gly Ala Gly Met Ser Tyr Leu Tyr Asn Ser Asp Val Lys
465                 470                 475                 480

His Tyr Arg Asp Asn Phe Trp Ala Thr Ala Asp Met Lys Arg Leu Ala
                485                 490                 495

Gly Thr Thr Thr Leu Asp Asn Glu Glu Pro Lys Glu Asn Lys Asn Ser
            500                 505                 510

Asp Lys Thr Phe Val Gly Gly Thr Lys Phe Asp Asp Gln His Ala Ser
        515                 520                 525

Ile Gly Met Asp Phe Glu Asn Gln Asp Lys Thr Leu Thr Ala Lys Lys
    530                 535                 540

Ser Tyr Phe Ile Leu Asn Asp Lys Ile Val Phe Leu Gly Thr Gly Ile
545                 550                 555                 560

Lys Ser Thr Asp Ser Ser Lys Asn Pro Val Thr Thr Ile Glu Asn Arg
                565                 570                 575

Lys Ser Asn Gly Tyr Thr Leu Phe Thr Asp Asp Lys Gln Thr Thr Ala
            580                 585                 590

Ser Asn Ile Asn Asp Gln Glu Thr Asn Ser Val Phe Leu Glu Ser Thr
        595                 600                 605

Asp Thr Lys Lys Asn Ile Gly Tyr His Phe Leu Asn Glu Ser Lys Ile
    610                 615                 620

Thr Val Lys Lys Glu Ser His Thr Gly Lys Trp Ser Asp Ile Asn Lys
625                 630                 635                 640

Ser Gln Lys Ser Asp Asp Lys Thr Asp Glu Tyr Tyr Glu Val Thr Gln
                645                 650                 655

Lys His Ser Asn Thr Asp Asp Lys Tyr Ala Tyr Val Leu Tyr Pro Gly
            660                 665                 670

Leu Ser Lys Asp Asn Phe Lys Ser Lys Ala Ser Gln Val Thr Ile Val
        675                 680                 685

Lys Gln Asp Asp Asp Phe His Ile Val Lys Asp Asn Glu Ser Val Trp
    690                 695                 700

Ala Gly Val Asn Tyr Ser Asn Ser Thr Gln Thr Phe Asp Ile Asn Asn
705                 710                 715                 720
```

```
Thr Lys Val Glu Val Lys Ala Lys Gly Met Phe Ile Leu Lys Asn Lys
                725                 730                 735

Asp Asp Asn Thr Tyr Glu Cys Ser Phe Tyr Asn Pro Glu Ser Thr Asn
            740                 745                 750

Thr Ala Ser Asp Ile Glu Ser Lys Ile Ser Met Thr Gly Tyr Ser Ile
        755                 760                 765

Thr Asn Lys Asn Thr Ser Thr Ser Asn Glu Ser Gly Val His Phe Glu
    770                 775                 780

Leu Thr Lys
785


<210> SEQ ID NO 103
<211> LENGTH: 400
<212> TYPE: PRT
<213> ORGANISM: Loxosceles intermedia

<400> SEQUENCE: 103

Met Asp Trp Thr Trp Ile Leu Phe Leu Val Ala Ala Ala Thr Arg Val
1               5                   10                  15

His Ser Gly Arg Asp Val Phe Trp Asn Val Pro Ser Gln Gln Cys Lys
            20                  25                  30

Lys Tyr Gly Met Lys Phe Val Pro Leu Leu Glu Gln Tyr Ser Ile Leu
        35                  40                  45

Val Asn Lys Glu Asp Asn Phe Lys Gly Asp Lys Ile Thr Ile Phe Tyr
    50                  55                  60

Glu Ser Gln Leu Gly Leu Tyr Pro His Ile Gly Ala Asn Asp Glu Ser
65                  70                  75                  80

Phe Asn Gly Gly Ile Pro Gln Leu Gly Asp Leu Lys Ala His Leu Glu
                85                  90                  95

Lys Ser Ala Val Asp Ile Arg Arg Asp Ile Leu Asp Lys Ser Ala Thr
            100                 105                 110

Gly Leu Arg Ile Ile Asp Trp Glu Ala Trp Arg Pro Ile Trp Glu Phe
        115                 120                 125

Asn Trp Ser Ser Leu Arg Lys Tyr Gln Asp Lys Met Lys Lys Val Val
    130                 135                 140

Arg Gln Phe Asn Pro Thr Ala His Glu Ser Thr Val Ala Lys Leu Ala
145                 150                 155                 160

His Asn Glu Trp Glu Asn Ser Ser Lys Ser Trp Met Leu Ser Thr Leu
                165                 170                 175

Gln Leu Gly Lys Gln Leu Arg Pro Asn Ser Val Trp Cys Tyr Tyr Leu
            180                 185                 190

Phe Pro Asp Cys Tyr Asn Tyr Asp Gly Asn Ser Val Gln Glu Phe Gln
        195                 200                 205

Cys Ser Glu Ala Ile Arg Lys Gly Asn Asp Arg Leu Lys Trp Leu Trp
    210                 215                 220

Glu Glu Ser Thr Ala Val Cys Pro Ser Ile Tyr Ile Lys Glu Gly Gln
225                 230                 235                 240

Leu Thr Asn Tyr Thr Leu Gln Lys Arg Ile Trp Phe Thr Asn Gly Arg
                245                 250                 255

Leu Gln Glu Ala Leu Arg Val Ala Gln Pro Lys Ala Arg Ile Tyr Pro
            260                 265                 270

Tyr Ile Asn Tyr Ser Ile Lys Pro Gly Met Met Val Pro Glu Val Glu
        275                 280                 285

Phe Trp Arg Leu Ile Ala Gln Ile Ala Ser Leu Gly Met Asp Gly Ala
```

```
    290                 295                 300

Val Ile Trp Gly Ser Ser Ala Ser Val Gly Ser Lys Asn His Cys Ala
305                 310                 315                 320

Gln Leu Met Lys Tyr Ile Ala Asp Val Leu Gly Pro Ala Thr Leu Arg
                325                 330                 335

Ile Lys Glu Asn Val Ala Arg Cys Ser Lys Gln Ala Cys Ser Gly Arg
            340                 345                 350

Gly Arg Cys Thr Trp Pro Lys Asp Thr Ser Val Ile Ala Trp Lys Phe
        355                 360                 365

Leu Val Glu Lys Glu Asp Tyr Asp Phe Tyr Leu Gly Asp Ile Glu Cys
    370                 375                 380

Lys Cys Val Glu Gly Tyr Glu Gly Arg Tyr Cys Glu Gln Lys Thr Lys
385                 390                 395                 400


<210> SEQ ID NO 104
<211> LENGTH: 244
<212> TYPE: PRT
<213> ORGANISM: Streptomyces koganeiensis

<400> SEQUENCE: 104

Met Asp Trp Thr Trp Ile Leu Phe Leu Val Ala Ala Ala Thr Arg Val
1               5                   10                  15

His Ser Gly Arg Ala Thr Gly Thr Ala Ser Ala Ala Gly Glu Asn Gly
            20                  25                  30

Ala Thr Thr Thr Phe Asp Gly Pro Val Ala Ala Glu Arg Phe Ser Ala
        35                  40                  45

Asp Thr Thr Leu Glu Ala Ala Phe Leu Lys Thr Thr Ser Glu Thr Asn
    50                  55                  60

His Ala Ala Thr Ile Tyr Gln Ala Gly Thr Ser Gly Asp Gly Ala Ala
65                  70                  75                  80

Leu Asn Val Ile Ser Asp Asn Pro Gly Thr Ser Ala Met Tyr Leu Ser
                85                  90                  95

Gly Thr Glu Thr Ala Arg Gly Thr Leu Lys Ile Thr His Arg Gly Tyr
            100                 105                 110

Ala Asp Gly Ser Asp Lys Asp Ala Ala Ala Leu Ser Leu Asp Leu Arg
        115                 120                 125

Val Ala Gly Thr Ala Ala Gln Gly Ile Tyr Val Thr Ala Thr Asn Gly
    130                 135                 140

Pro Thr Lys Gly Asn Leu Ile Ala Leu Arg Asn Asn Thr Gly Leu Asp
145                 150                 155                 160

Asp Phe Val Val Lys Gly Thr Gly Arg Ile Gly Val Gly Ile Asp Arg
                165                 170                 175

Ala Ala Thr Pro Arg Ala Gln Val His Ile Val Gln Arg Gly Asp Ala
            180                 185                 190

Leu Ala Ala Leu Leu Val Glu Gly Ser Val Arg Ile Gly Asn Ala Ala
        195                 200                 205

Thr Val Pro Thr Ser Val Asp Ser Ser Gly Gly Gly Ala Leu Tyr Ala
    210                 215                 220

Ser Gly Gly Ala Leu Leu Trp Arg Gly Ser Asn Gly Thr Val Thr Thr
225                 230                 235                 240

Ile Ala Pro Ala


<210> SEQ ID NO 105
<211> LENGTH: 230
<212> TYPE: PRT
```

<213> ORGANISM: Mycobacterium tuberculosis

<400> SEQUENCE: 105

Met Asp Trp Thr Trp Ile Leu Phe Leu Val Ala Ala Ala Thr Arg Val
1 5 10 15

His Ser Gly Arg Gly Ser Ala Ile Glu Glu Arg Thr Arg His Arg Ala
20 25 30

Glu Thr Thr Thr Arg Glu Ile Cys Glu Ser Val Gly Gly Ala Asp Thr
35 40 45

Val Leu Ser Arg Ile Asp Lys Asn Pro Glu Leu Glu Pro Leu Leu Ser
50 55 60

Gln Ala Ile Glu Ala Ala Thr Arg Thr Ser Met Glu Ala Lys Arg Arg
65 70 75 80

Leu Leu Ala Gln Ala Ala Ala Ala Ala Leu Glu Asp Asp Gln Lys Val
85 90 95

Glu Pro Ala Ser Leu Ile Val Ala Thr Leu Ser Gln Leu Glu Pro Val
100 105 110

His Ile His Ala Leu Val Arg Leu Ala Lys Ala Ala Lys Ser Ser Pro
115 120 125

Asp Gln Asp Glu Ile Gln Arg Arg Glu Val Met Arg Ala Ala Ser Lys
130 135 140

Val Glu Pro Val Pro Val Leu Ala Ala Leu Ile Gln Thr Gly Val Ala
145 150 155 160

Ile Ala Thr Thr Thr Val Trp His Gly Asn Gly Thr Gly Thr Pro Ala
165 170 175

Glu Glu Ser Gly His Ile Leu Ile His Asp Val Ser Asp Phe Gly His
180 185 190

Arg Leu Leu Ala Tyr Leu Arg Ala Ala Asp Ala Gly Ala Glu Leu Leu
195 200 205

Ile Leu Pro Ser Gly Gly Ser Ala Pro Thr Gly Asp His Pro Thr Pro
210 215 220

His Pro Ser Thr Ser Arg
225 230

<210> SEQ ID NO 106
<211> LENGTH: 435
<212> TYPE: PRT
<213> ORGANISM: Homo sapiens

<400> SEQUENCE: 106

Met Ala Ala His Leu Leu Pro Ile Cys Ala Leu Phe Leu Thr Leu Leu
1 5 10 15

Asp Met Ala Gln Gly Phe Arg Gly Pro Leu Leu Pro Asn Arg Pro Phe
20 25 30

Thr Thr Val Trp Asn Ala Asn Thr Gln Trp Cys Leu Glu Arg His Gly
35 40 45

Val Asp Val Asp Val Ser Val Phe Asp Val Val Ala Asn Pro Gly Gln
50 55 60

Thr Phe Arg Gly Pro Asp Met Thr Ile Phe Tyr Ser Ser Gln Leu Gly
65 70 75 80

Thr Tyr Pro Tyr Tyr Thr Pro Thr Gly Glu Pro Val Phe Gly Gly Leu
85 90 95

Pro Gln Asn Ala Ser Leu Ile Ala His Leu Ala Arg Thr Phe Gln Asp
100 105 110

Ile Leu Ala Ala Ile Pro Ala Pro Asp Phe Ser Gly Leu Ala Val Ile

```
        115                 120                 125

Asp Trp Glu Ala Trp Arg Pro Arg Trp Ala Phe Asn Trp Asp Thr Lys
    130                 135                 140

Asp Ile Tyr Arg Gln Arg Ser Arg Ala Leu Val Gln Ala Gln His Pro
145                 150                 155                 160

Asp Trp Pro Ala Pro Gln Val Glu Ala Val Ala Gln Asp Gln Phe Gln
                165                 170                 175

Gly Ala Ala Arg Ala Trp Met Ala Gly Thr Leu Gln Leu Gly Arg Ala
            180                 185                 190

Leu Arg Pro Arg Gly Leu Trp Gly Phe Tyr Gly Phe Pro Asp Cys Tyr
        195                 200                 205

Asn Tyr Asp Phe Leu Ser Pro Asn Tyr Thr Gly Gln Cys Pro Ser Gly
    210                 215                 220

Ile Arg Ala Gln Asn Asp Gln Leu Gly Trp Leu Trp Gly Gln Ser Arg
225                 230                 235                 240

Ala Leu Tyr Pro Ser Ile Tyr Met Pro Ala Val Leu Glu Gly Thr Gly
                245                 250                 255

Lys Ser Gln Met Tyr Val Gln His Arg Val Ala Glu Ala Phe Arg Val
            260                 265                 270

Ala Val Ala Ala Gly Asp Pro Asn Leu Pro Val Leu Pro Tyr Val Gln
        275                 280                 285

Ile Phe Tyr Asp Thr Thr Asn His Phe Leu Pro Leu Asp Glu Leu Glu
    290                 295                 300

His Ser Leu Gly Glu Ser Ala Ala Gln Gly Ala Ala Gly Val Val Leu
305                 310                 315                 320

Trp Val Ser Trp Glu Asn Thr Arg Thr Lys Glu Ser Cys Gln Ala Ile
                325                 330                 335

Lys Glu Tyr Met Asp Thr Thr Leu Gly Pro Phe Ile Leu Asn Val Thr
            340                 345                 350

Ser Gly Ala Leu Leu Cys Ser Gln Ala Leu Cys Ser Gly His Gly Arg
        355                 360                 365

Cys Val Arg Arg Thr Ser His Pro Lys Ala Leu Leu Leu Leu Asn Pro
    370                 375                 380

Ala Ser Phe Ser Ile Gln Leu Thr Pro Gly Gly Gly Pro Leu Ser Leu
385                 390                 395                 400

Arg Gly Ala Leu Ser Leu Glu Asp Gln Ala Gln Met Ala Val Glu Phe
                405                 410                 415

Lys Cys Arg Cys Tyr Pro Gly Trp Gln Ala Pro Trp Cys Glu Arg Lys
            420                 425                 430

Ser Met Trp
        435


<210> SEQ ID NO 107
<211> LENGTH: 473
<212> TYPE: PRT
<213> ORGANISM: Homo sapiens

<400> SEQUENCE: 107

Met Arg Ala Gly Pro Gly Pro Thr Val Thr Leu Ala Leu Val Leu Ala
1               5                   10                  15

Val Ala Trp Ala Met Glu Leu Lys Pro Thr Ala Pro Pro Ile Phe Thr
            20                  25                  30

Gly Arg Pro Phe Val Val Ala Trp Asp Val Pro Thr Gln Asp Cys Gly
        35                  40                  45
```

-continued

```
Pro Arg Leu Lys Val Pro Leu Asp Leu Asn Ala Phe Asp Val Gln Ala
    50                  55                  60

Ser Pro Asn Glu Gly Phe Val Asn Gln Asn Ile Thr Ile Phe Tyr Arg
65                  70                  75                  80

Asp Arg Leu Gly Leu Tyr Pro Arg Phe Asp Ser Ala Gly Arg Ser Val
                85                  90                  95

His Gly Gly Val Pro Gln Asn Val Ser Leu Trp Ala His Arg Lys Met
            100                 105                 110

Leu Gln Lys Arg Val Glu His Tyr Ile Arg Thr Gln Glu Ser Ala Gly
        115                 120                 125

Leu Ala Val Ile Asp Trp Glu Asp Trp Arg Pro Val Trp Val Arg Asn
    130                 135                 140

Trp Gln Asp Lys Asp Val Tyr Arg Arg Leu Ser Arg Gln Leu Val Ala
145                 150                 155                 160

Ser Arg His Pro Asp Trp Pro Pro Asp Arg Ile Val Lys Gln Ala Gln
                165                 170                 175

Tyr Glu Phe Glu Phe Ala Ala Gln Gln Phe Met Leu Glu Thr Leu Arg
            180                 185                 190

Tyr Val Lys Ala Val Arg Pro Arg His Leu Trp Gly Phe Tyr Leu Phe
        195                 200                 205

Pro Asp Cys Tyr Asn His Asp Tyr Val Gln Asn Trp Glu Ser Tyr Thr
    210                 215                 220

Gly Arg Cys Pro Asp Val Glu Val Ala Arg Asn Asp Gln Leu Ala Trp
225                 230                 235                 240

Leu Trp Ala Glu Ser Thr Ala Leu Phe Pro Ser Val Tyr Leu Asp Glu
                245                 250                 255

Thr Leu Ala Ser Ser Arg His Gly Arg Asn Phe Val Ser Phe Arg Val
            260                 265                 270

Gln Glu Ala Leu Arg Val Ala Arg Thr His His Ala Asn His Ala Leu
        275                 280                 285

Pro Val Tyr Val Phe Thr Arg Pro Thr Tyr Ser Arg Arg Leu Thr Gly
    290                 295                 300

Leu Ser Glu Met Asp Leu Ile Ser Thr Ile Gly Glu Ser Ala Ala Leu
305                 310                 315                 320

Gly Ala Ala Gly Val Ile Leu Trp Gly Asp Ala Gly Tyr Thr Thr Ser
                325                 330                 335

Thr Glu Thr Cys Gln Tyr Leu Lys Asp Tyr Leu Thr Arg Leu Leu Val
            340                 345                 350

Pro Tyr Val Val Asn Val Ser Trp Ala Thr Gln Tyr Cys Ser Arg Ala
        355                 360                 365

Gln Cys His Gly His Gly Arg Cys Val Arg Arg Asn Pro Ser Ala Ser
    370                 375                 380

Thr Phe Leu His Leu Ser Thr Asn Ser Phe Arg Leu Val Pro Gly His
385                 390                 395                 400

Ala Pro Gly Glu Pro Gln Leu Arg Pro Val Gly Glu Leu Ser Trp Ala
                405                 410                 415

Asp Ile Asp His Leu Gln Thr His Phe Arg Cys Gln Cys Tyr Leu Gly
            420                 425                 430

Trp Ser Gly Glu Gln Cys Gln Trp Asp His Arg Gln Ala Ala Gly Gly
        435                 440                 445

Ala Ser Glu Ala Trp Ala Gly Ser His Leu Thr Ser Leu Leu Ala Leu
    450                 455                 460

Ala Ala Leu Ala Phe Thr Trp Thr Leu
```

```
465                 470


<210> SEQ ID NO 108
<211> LENGTH: 417
<212> TYPE: PRT
<213> ORGANISM: Homo sapiens

<400> SEQUENCE: 108

Met Thr Thr Gln Leu Gly Pro Ala Leu Val Leu Gly Val Ala Leu Cys
1               5                   10                  15

Leu Gly Cys Gly Gln Pro Leu Pro Gln Val Pro Glu Arg Pro Phe Ser
            20                  25                  30

Val Leu Trp Asn Val Pro Ser Ala His Cys Glu Ala Arg Phe Gly Val
        35                  40                  45

His Leu Pro Leu Asn Ala Leu Gly Ile Ile Ala Asn Arg Gly Gln His
    50                  55                  60

Phe His Gly Gln Asn Met Thr Ile Phe Tyr Lys Asn Gln Leu Gly Leu
65                  70                  75                  80

Tyr Pro Tyr Phe Gly Pro Arg Gly Thr Ala His Asn Gly Gly Ile Pro
                85                  90                  95

Gln Ala Leu Pro Leu Asp Arg His Leu Ala Leu Ala Ala Tyr Gln Ile
            100                 105                 110

His His Ser Leu Arg Pro Gly Phe Ala Gly Pro Ala Val Leu Asp Trp
        115                 120                 125

Glu Glu Trp Cys Pro Leu Trp Ala Gly Asn Trp Gly Arg Arg Arg Ala
    130                 135                 140

Tyr Gln Ala Ala Ser Trp Ala Trp Ala Gln Gln Val Phe Pro Asp Leu
145                 150                 155                 160

Asp Pro Gln Glu Gln Leu Tyr Lys Ala Tyr Thr Gly Phe Glu Gln Ala
                165                 170                 175

Ala Arg Ala Leu Met Glu Asp Thr Leu Arg Val Ala Gln Ala Leu Arg
            180                 185                 190

Pro His Gly Leu Trp Gly Phe Tyr His Tyr Pro Ala Cys Gly Asn Gly
        195                 200                 205

Trp His Ser Met Ala Ser Asn Tyr Thr Gly Arg Cys His Ala Ala Thr
    210                 215                 220

Leu Ala Arg Asn Thr Gln Leu His Trp Leu Trp Ala Ala Ser Ser Ala
225                 230                 235                 240

Leu Phe Pro Ser Ile Tyr Leu Pro Pro Arg Leu Pro Pro Ala His His
                245                 250                 255

Gln Ala Phe Val Arg His Arg Leu Glu Glu Ala Phe Arg Val Ala Leu
            260                 265                 270

Val Gly His Arg His Pro Leu Pro Val Leu Ala Tyr Val Arg Leu Thr
        275                 280                 285

His Arg Arg Ser Gly Arg Phe Leu Ser Gln Asp Asp Leu Val Gln Ser
    290                 295                 300

Ile Gly Val Ser Ala Ala Leu Gly Ala Ala Gly Val Val Leu Trp Gly
305                 310                 315                 320

Asp Leu Ser Leu Ser Ser Ser Glu Glu Glu Cys Trp His Leu His Asp
                325                 330                 335

Tyr Leu Val Asp Thr Leu Gly Pro Tyr Val Ile Asn Val Thr Arg Ala
            340                 345                 350

Ala Met Ala Cys Ser His Gln Arg Cys His Gly His Gly Arg Cys Ala
        355                 360                 365
```

```
Arg Arg Asp Pro Gly Gln Met Glu Ala Phe Leu His Leu Trp Pro Asp
    370                 375                 380

Gly Ser Leu Gly Asp Trp Lys Ser Phe Ser Cys His Cys Tyr Trp Gly
385                 390                 395                 400

Trp Ala Gly Pro Thr Cys Gln Glu Pro Arg Pro Gly Pro Lys Glu Ala
                405                 410                 415

Val


<210> SEQ ID NO 109
<211> LENGTH: 481
<212> TYPE: PRT
<213> ORGANISM: Homo sapiens

<400> SEQUENCE: 109

Met Lys Val Leu Ser Glu Gly Gln Leu Lys Leu Cys Val Val Gln Pro
1               5                   10                  15

Val His Leu Thr Ser Trp Leu Leu Ile Phe Phe Ile Leu Lys Ser Ile
            20                  25                  30

Ser Cys Leu Lys Pro Ala Arg Leu Pro Ile Tyr Gln Arg Lys Pro Phe
        35                  40                  45

Ile Ala Ala Trp Asn Ala Pro Thr Asp Gln Cys Leu Ile Lys Tyr Asn
    50                  55                  60

Leu Arg Leu Asn Leu Lys Met Phe Pro Val Ile Gly Ser Pro Leu Ala
65                  70                  75                  80

Lys Ala Arg Gly Gln Asn Val Thr Ile Phe Tyr Val Asn Arg Leu Gly
                85                  90                  95

Tyr Tyr Pro Trp Tyr Thr Ser Gln Gly Val Pro Ile Asn Gly Gly Leu
            100                 105                 110

Pro Gln Asn Ile Ser Leu Gln Val His Leu Glu Lys Ala Asp Gln Asp
        115                 120                 125

Ile Asn Tyr Tyr Ile Pro Ala Glu Asp Phe Ser Gly Leu Ala Val Ile
    130                 135                 140

Asp Trp Glu Tyr Trp Arg Pro Gln Trp Ala Arg Asn Trp Asn Ser Lys
145                 150                 155                 160

Asp Val Tyr Arg Gln Lys Ser Arg Lys Leu Ile Ser Asp Met Gly Lys
                165                 170                 175

Asn Val Ser Ala Thr Asp Ile Glu Tyr Leu Ala Lys Val Thr Phe Glu
            180                 185                 190

Glu Ser Ala Lys Ala Phe Met Lys Glu Thr Ile Lys Leu Gly Ile Lys
        195                 200                 205

Ser Arg Pro Lys Gly Leu Trp Gly Tyr Tyr Leu Tyr Pro Asp Cys His
    210                 215                 220

Asn Tyr Asn Val Tyr Ala Pro Asn Tyr Ser Gly Ser Cys Pro Glu Asp
225                 230                 235                 240

Glu Val Leu Arg Asn Asn Glu Leu Ser Trp Leu Trp Asn Ser Ser Ala
                245                 250                 255

Ala Leu Tyr Pro Ser Ile Gly Val Trp Lys Ser Leu Gly Asp Ser Glu
            260                 265                 270

Asn Ile Leu Arg Phe Ser Lys Phe Arg Val His Glu Ser Met Arg Ile
        275                 280                 285

Ser Thr Met Thr Ser His Asp Tyr Ala Leu Pro Val Phe Val Tyr Thr
    290                 295                 300

Arg Leu Gly Tyr Arg Asp Glu Pro Leu Phe Phe Leu Ser Lys Gln Asp
305                 310                 315                 320
```

Leu Val Ser Thr Ile Gly Glu Ser Ala Ala Leu Gly Ala Ala Gly Ile
325 330 335

Val Ile Trp Gly Asp Met Asn Leu Thr Ala Ser Lys Ala Asn Cys Thr
340 345 350

Lys Val Lys Gln Phe Val Ser Ser Asp Leu Gly Ser Tyr Ile Ala Asn
355 360 365

Val Thr Arg Ala Ala Glu Val Cys Ser Leu His Leu Cys Arg Asn Asn
370 375 380

Gly Arg Cys Ile Arg Lys Met Trp Asn Ala Pro Ser Tyr Leu His Leu
385 390 395 400

Asn Pro Ala Ser Tyr His Ile Glu Ala Ser Glu Asp Gly Glu Phe Thr
405 410 415

Val Lys Gly Lys Ala Ser Asp Thr Asp Leu Ala Val Met Ala Asp Thr
420 425 430

Phe Ser Cys His Cys Tyr Gln Gly Tyr Glu Gly Ala Asp Cys Arg Glu
435 440 445

Ile Lys Thr Ala Asp Gly Cys Ser Gly Val Ser Pro Ser Pro Gly Ser
450 455 460

Leu Met Thr Leu Cys Leu Leu Leu Leu Ala Ser Tyr Arg Ser Ile Gln
465 470 475 480

Leu

<210> SEQ ID NO 110
<211> LENGTH: 360
<212> TYPE: PRT
<213> ORGANISM: Homo sapiens

<400> SEQUENCE: 110

Met Glu Asp Phe Asn Met Glu Ser Asp Ser Phe Glu Asp Phe Trp Lys
1 5 10 15

Gly Glu Asp Leu Ser Asn Tyr Ser Tyr Ser Ser Thr Leu Pro Pro Phe
20 25 30

Leu Leu Asp Ala Ala Pro Cys Glu Pro Glu Ser Leu Glu Ile Asn Lys
35 40 45

Tyr Phe Val Val Ile Ile Tyr Ala Leu Val Phe Leu Leu Ser Leu Leu
50 55 60

Gly Asn Ser Leu Val Met Leu Val Ile Leu Tyr Ser Arg Val Gly Arg
65 70 75 80

Ser Val Thr Asp Val Tyr Leu Leu Asn Leu Ala Leu Ala Asp Leu Leu
85 90 95

Phe Ala Leu Thr Leu Pro Ile Trp Ala Ala Ser Lys Val Asn Gly Trp
100 105 110

Ile Phe Gly Thr Phe Leu Cys Lys Val Val Ser Leu Leu Lys Glu Val
115 120 125

Asn Phe Tyr Ser Gly Ile Leu Leu Leu Ala Cys Ile Ser Val Asp Arg
130 135 140

Tyr Leu Ala Ile Val His Ala Thr Arg Thr Leu Thr Gln Lys Arg Tyr
145 150 155 160

Leu Val Lys Phe Ile Cys Leu Ser Ile Trp Gly Leu Ser Leu Leu Leu
165 170 175

Ala Leu Pro Val Leu Leu Phe Arg Arg Thr Val Tyr Ser Ser Asn Val
180 185 190

Ser Pro Ala Cys Tyr Glu Asp Met Gly Asn Asn Thr Ala Asn Trp Arg
195 200 205

-continued

```
Met Leu Leu Arg Ile Leu Pro Gln Ser Phe Gly Phe Ile Val Pro Leu
    210                 215                 220

Leu Ile Met Leu Phe Cys Tyr Gly Phe Thr Leu Arg Thr Leu Phe Lys
225                 230                 235                 240

Ala His Met Gly Gln Lys His Arg Ala Met Arg Val Ile Phe Ala Val
                245                 250                 255

Val Leu Ile Phe Leu Leu Cys Trp Leu Pro Tyr Asn Leu Val Leu Leu
            260                 265                 270

Ala Asp Thr Leu Met Arg Thr Gln Val Ile Gln Glu Thr Cys Glu Arg
        275                 280                 285

Arg Asn His Ile Asp Arg Ala Leu Asp Ala Thr Glu Ile Leu Gly Ile
    290                 295                 300

Leu His Ser Cys Leu Asn Pro Leu Ile Tyr Ala Phe Ile Gly Gln Lys
305                 310                 315                 320

Phe Arg His Gly Leu Leu Lys Ile Leu Ala Ile His Gly Leu Ile Ser
                325                 330                 335

Lys Asp Ser Leu Pro Lys Asp Ser Arg Pro Ser Phe Val Gly Ser Ser
            340                 345                 350

Ser Gly His Thr Ser Thr Thr Leu
        355                 360


<210> SEQ ID NO 111
<211> LENGTH: 374
<212> TYPE: PRT
<213> ORGANISM: Homo sapiens

<400> SEQUENCE: 111

Met Leu Ser Thr Ser Arg Ser Arg Phe Ile Arg Asn Thr Asn Glu Ser
1               5                   10                  15

Gly Glu Glu Val Thr Thr Phe Phe Asp Tyr Asp Tyr Gly Ala Pro Cys
            20                  25                  30

His Lys Phe Asp Val Lys Gln Ile Gly Ala Gln Leu Leu Pro Pro Leu
        35                  40                  45

Tyr Ser Leu Val Phe Ile Phe Gly Phe Val Gly Asn Met Leu Val Val
    50                  55                  60

Leu Ile Leu Ile Asn Cys Lys Lys Leu Lys Cys Leu Thr Asp Ile Tyr
65                  70                  75                  80

Leu Leu Asn Leu Ala Ile Ser Asp Leu Leu Phe Leu Ile Thr Leu Pro
                85                  90                  95

Leu Trp Ala His Ser Ala Ala Asn Glu Trp Val Phe Gly Asn Ala Met
            100                 105                 110

Cys Lys Leu Phe Thr Gly Leu Tyr His Ile Gly Tyr Phe Gly Gly Ile
        115                 120                 125

Phe Phe Ile Ile Leu Leu Thr Ile Asp Arg Tyr Leu Ala Ile Val His
    130                 135                 140

Ala Val Phe Ala Leu Lys Ala Arg Thr Val Thr Phe Gly Val Val Thr
145                 150                 155                 160

Ser Val Ile Thr Trp Leu Val Ala Val Phe Ala Ser Val Pro Gly Ile
                165                 170                 175

Ile Phe Thr Lys Cys Gln Lys Glu Asp Ser Val Tyr Val Cys Gly Pro
            180                 185                 190

Tyr Phe Pro Arg Gly Trp Asn Asn Phe His Thr Ile Met Arg Asn Ile
        195                 200                 205

Leu Gly Leu Val Leu Pro Leu Leu Ile Met Val Ile Cys Tyr Ser Gly
    210                 215                 220
```

```
Ile Leu Lys Thr Leu Leu Arg Cys Arg Asn Glu Lys Lys Arg His Arg
225                 230                 235                 240

Ala Val Arg Val Ile Phe Thr Ile Met Ile Val Tyr Phe Leu Phe Trp
                245                 250                 255

Thr Pro Tyr Asn Ile Val Ile Leu Leu Asn Thr Phe Gln Glu Phe Phe
            260                 265                 270

Gly Leu Ser Asn Cys Glu Ser Thr Ser Gln Leu Asp Gln Ala Thr Gln
        275                 280                 285

Val Thr Glu Thr Leu Gly Met Thr His Cys Cys Ile Asn Pro Ile Ile
    290                 295                 300

Tyr Ala Phe Val Gly Glu Lys Phe Arg Ser Leu Phe His Ile Ala Leu
305                 310                 315                 320

Gly Cys Arg Ile Ala Pro Leu Gln Lys Pro Val Cys Gly Gly Pro Gly
                325                 330                 335

Val Arg Pro Gly Lys Asn Val Lys Val Thr Thr Gln Gly Leu Leu Asp
            340                 345                 350

Gly Arg Gly Lys Gly Lys Ser Ile Gly Arg Ala Pro Glu Ala Ser Leu
        355                 360                 365

Gln Asp Lys Glu Gly Ala
    370


<210> SEQ ID NO 112
<211> LENGTH: 91
<212> TYPE: PRT
<213> ORGANISM: Homo sapiens

<400> SEQUENCE: 112

Met Lys Val Ser Ala Ala Ala Leu Ala Val Ile Leu Ile Ala Thr Ala
1               5                   10                  15

Leu Cys Ala Pro Ala Ser Ala Ser Pro Tyr Ser Ser Asp Thr Thr Pro
            20                  25                  30

Cys Cys Phe Ala Tyr Ile Ala Arg Pro Leu Pro Arg Ala His Ile Lys
        35                  40                  45

Glu Tyr Phe Tyr Thr Ser Gly Lys Cys Ser Asn Pro Ala Val Val Phe
    50                  55                  60

Val Thr Arg Lys Asn Arg Gln Val Cys Ala Asn Pro Glu Lys Lys Trp
65                  70                  75                  80

Val Arg Glu Tyr Ile Asn Ser Leu Glu Met Ser
                85                  90


<210> SEQ ID NO 113
<211> LENGTH: 352
<212> TYPE: PRT
<213> ORGANISM: Homo sapiens

<400> SEQUENCE: 113

Met Asp Tyr Gln Val Ser Ser Pro Ile Tyr Asp Ile Asn Tyr Tyr Thr
1               5                   10                  15

Ser Glu Pro Cys Gln Lys Ile Asn Val Lys Gln Ile Ala Ala Arg Leu
            20                  25                  30

Leu Pro Pro Leu Tyr Ser Leu Val Phe Ile Phe Gly Phe Val Gly Asn
        35                  40                  45

Met Leu Val Ile Leu Ile Leu Ile Asn Cys Lys Arg Leu Lys Ser Met
    50                  55                  60

Thr Asp Ile Tyr Leu Leu Asn Leu Ala Ile Ser Asp Leu Phe Phe Leu
65                  70                  75                  80
```

-continued

```
Leu Thr Val Pro Phe Trp Ala His Tyr Ala Ala Ala Gln Trp Asp Phe
                85                  90                  95

Gly Asn Thr Met Cys Gln Leu Leu Thr Gly Leu Tyr Phe Ile Gly Phe
            100                 105                 110

Phe Ser Gly Ile Phe Phe Ile Ile Leu Leu Thr Ile Asp Arg Tyr Leu
        115                 120                 125

Ala Val Val His Ala Val Phe Ala Leu Lys Ala Arg Thr Val Thr Phe
    130                 135                 140

Gly Val Val Thr Ser Val Ile Thr Trp Val Val Ala Val Phe Ala Ser
145                 150                 155                 160

Leu Pro Gly Ile Ile Phe Thr Arg Ser Gln Lys Glu Gly Leu His Tyr
                165                 170                 175

Thr Cys Ser Ser His Phe Pro Tyr Ser Gln Tyr Gln Phe Trp Lys Asn
            180                 185                 190

Phe Gln Thr Leu Lys Ile Val Ile Leu Gly Leu Val Leu Pro Leu Leu
        195                 200                 205

Val Met Val Ile Cys Tyr Ser Gly Ile Leu Lys Thr Leu Leu Arg Cys
    210                 215                 220

Arg Asn Glu Lys Lys Arg His Arg Ala Val Arg Leu Ile Phe Thr Ile
225                 230                 235                 240

Met Ile Val Tyr Phe Leu Phe Trp Ala Pro Tyr Asn Ile Val Leu Leu
                245                 250                 255

Leu Asn Thr Phe Gln Glu Phe Phe Gly Leu Asn Asn Cys Ser Ser Ser
            260                 265                 270

Asn Arg Leu Asp Gln Ala Met Gln Val Thr Glu Thr Leu Gly Met Thr
        275                 280                 285

His Cys Cys Ile Asn Pro Ile Ile Tyr Ala Phe Val Gly Glu Lys Phe
    290                 295                 300

Arg Asn Tyr Leu Leu Val Phe Phe Gln Lys His Ile Ala Lys Arg Phe
305                 310                 315                 320

Cys Lys Cys Cys Ser Ile Phe Gln Gln Glu Ala Pro Glu Arg Ala Ser
                325                 330                 335

Ser Val Tyr Thr Arg Ser Thr Gly Glu Gln Glu Ile Ser Val Gly Leu
            340                 345                 350


<210> SEQ ID NO 114
<211> LENGTH: 215
<212> TYPE: PRT
<213> ORGANISM: Homo sapiens

<400> SEQUENCE: 114

Met Gly Lys Gly Asp Pro Lys Lys Pro Arg Gly Lys Met Ser Ser Tyr
1               5                   10                  15

Ala Phe Phe Val Gln Thr Cys Arg Glu Glu His Lys Lys Lys His Pro
            20                  25                  30

Asp Ala Ser Val Asn Phe Ser Glu Phe Ser Lys Lys Cys Ser Glu Arg
        35                  40                  45

Trp Lys Thr Met Ser Ala Lys Glu Lys Gly Lys Phe Glu Asp Met Ala
    50                  55                  60

Lys Ala Asp Lys Ala Arg Tyr Glu Arg Glu Met Lys Thr Tyr Ile Pro
65                  70                  75                  80

Pro Lys Gly Glu Thr Lys Lys Lys Phe Lys Asp Pro Asn Ala Pro Lys
                85                  90                  95

Arg Pro Pro Ser Ala Phe Phe Leu Phe Cys Ser Glu Tyr Arg Pro Lys
```

```
            100                 105                 110

Ile Lys Gly Glu His Pro Gly Leu Ser Ile Gly Asp Val Ala Lys Lys
        115                 120                 125

Leu Gly Glu Met Trp Asn Asn Thr Ala Ala Asp Asp Lys Gln Pro Tyr
    130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Pro Asp Ala Ala Lys Lys Gly Val Val
                165                 170                 175

Lys Ala Glu Lys Ser Lys Lys Lys Lys Glu Glu Glu Glu Asp Glu Glu
            180                 185                 190

Asp Glu Glu Asp Glu Glu Glu Glu Glu Asp Glu Glu Asp Glu Asp Glu
        195                 200                 205

Glu Glu Asp Asp Asp Asp Glu
    210                 215


<210> SEQ ID NO 115
<211> LENGTH: 628
<212> TYPE: PRT
<213> ORGANISM: Homo sapiens

<400> SEQUENCE: 115

Met Ala Glu Leu Gly Glu Leu Lys His Met Val Met Ser Phe Arg Val
1               5                   10                  15

Ser Glu Leu Gln Val Leu Leu Gly Phe Ala Gly Arg Asn Lys Ser Gly
            20                  25                  30

Arg Lys His Glu Leu Leu Ala Lys Ala Leu His Leu Leu Lys Ser Ser
        35                  40                  45

Cys Ala Pro Ser Val Gln Met Lys Ile Lys Glu Leu Tyr Arg Arg Arg
    50                  55                  60

Phe Pro Arg Lys Thr Leu Gly Pro Ser Asp Leu Ser Leu Leu Ser Leu
65                  70                  75                  80

Pro Pro Gly Thr Ser Pro Val Gly Ser Pro Gly Pro Leu Ala Pro Ile
                85                  90                  95

Pro Pro Thr Leu Leu Ala Pro Gly Thr Leu Leu Gly Pro Lys Arg Glu
            100                 105                 110

Val Asp Met His Pro Pro Leu Pro Gln Pro Val His Pro Asp Val Thr
        115                 120                 125

Met Lys Pro Leu Pro Phe Tyr Glu Val Tyr Gly Glu Leu Ile Arg Pro
    130                 135                 140

Thr Thr Leu Ala Ser Thr Ser Ser Gln Arg Phe Glu Glu Ala His Phe
145                 150                 155                 160

Thr Phe Ala Leu Thr Pro Gln Gln Val Gln Gln Ile Leu Thr Ser Arg
                165                 170                 175

Glu Val Leu Pro Gly Ala Lys Cys Asp Tyr Thr Ile Gln Val Gln Leu
            180                 185                 190

Arg Phe Cys Leu Cys Glu Thr Ser Cys Pro Gln Glu Asp Tyr Phe Pro
        195                 200                 205

Pro Asn Leu Phe Val Lys Val Asn Gly Lys Leu Cys Pro Leu Pro Gly
    210                 215                 220

Tyr Leu Pro Pro Thr Lys Asn Gly Ala Glu Pro Lys Arg Pro Ser Arg
225                 230                 235                 240

Pro Ile Asn Ile Thr Pro Leu Ala Arg Leu Ser Ala Thr Val Pro Asn
                245                 250                 255
```

```
Thr Ile Val Val Asn Trp Ser Ser Glu Phe Gly Arg Asn Tyr Ser Leu
            260                 265                 270

Ser Val Tyr Leu Val Arg Gln Leu Thr Ala Gly Thr Leu Leu Gln Lys
        275                 280                 285

Leu Arg Ala Lys Gly Ile Arg Asn Pro Asp His Ser Arg Ala Leu Ile
    290                 295                 300

Lys Glu Lys Leu Thr Ala Asp Pro Asp Ser Glu Val Ala Thr Thr Ser
305                 310                 315                 320

Leu Arg Val Ser Leu Met Cys Pro Leu Gly Lys Met Arg Leu Thr Val
                325                 330                 335

Pro Cys Arg Ala Leu Thr Cys Ala His Leu Gln Ser Phe Asp Ala Ala
            340                 345                 350

Leu Tyr Leu Gln Met Asn Glu Lys Lys Pro Thr Trp Thr Cys Pro Val
        355                 360                 365

Cys Asp Lys Lys Ala Pro Tyr Glu Ser Leu Ile Ile Asp Gly Leu Phe
    370                 375                 380

Met Glu Ile Leu Ser Ser Cys Ser Asp Cys Asp Glu Ile Gln Phe Met
385                 390                 395                 400

Glu Asp Gly Ser Trp Cys Pro Met Lys Pro Lys Lys Glu Ala Ser Glu
                405                 410                 415

Val Cys Pro Pro Pro Gly Tyr Gly Leu Asp Gly Leu Gln Tyr Ser Pro
            420                 425                 430

Val Gln Gly Gly Asp Pro Ser Glu Asn Lys Lys Lys Val Glu Val Ile
        435                 440                 445

Asp Leu Thr Ile Glu Ser Ser Ser Asp Glu Glu Asp Leu Pro Pro Thr
    450                 455                 460

Lys Lys His Cys Ser Val Thr Ser Ala Ala Ile Pro Ala Leu Pro Gly
465                 470                 475                 480

Ser Lys Gly Val Leu Thr Ser Gly His Gln Pro Ser Ser Val Leu Arg
                485                 490                 495

Ser Pro Ala Met Gly Thr Leu Gly Gly Asp Phe Leu Ser Ser Leu Pro
            500                 505                 510

Leu His Glu Tyr Pro Pro Ala Phe Pro Leu Gly Ala Asp Ile Gln Gly
        515                 520                 525

Leu Asp Leu Phe Ser Phe Leu Gln Thr Glu Ser Gln His Tyr Gly Pro
    530                 535                 540

Ser Val Ile Thr Ser Leu Asp Glu Gln Asp Ala Leu Gly His Phe Phe
545                 550                 555                 560

Gln Tyr Arg Gly Thr Pro Ser His Phe Leu Gly Pro Leu Ala Pro Thr
                565                 570                 575

Leu Gly Ser Ser His Cys Ser Ala Thr Pro Ala Pro Pro Pro Gly Arg
            580                 585                 590

Val Ser Ser Ile Val Ala Pro Gly Gly Ala Leu Arg Glu Gly His Gly
        595                 600                 605

Gly Pro Leu Pro Ser Gly Pro Ser Leu Thr Gly Cys Arg Ser Asp Ile
    610                 615                 620

Ile Ser Leu Asp
625
```

<210> SEQ ID NO 116
<211> LENGTH: 162
<212> TYPE: PRT
<213> ORGANISM: Homo sapiens

<400> SEQUENCE: 116

Met Arg Ile Ser Lys Pro His Leu Arg Ser Ile Ser Ile Gln Cys Tyr
1 5 10 15

Leu Cys Leu Leu Leu Asn Ser His Phe Leu Thr Glu Ala Gly Ile His
20 25 30

Val Phe Ile Leu Gly Cys Phe Ser Ala Gly Leu Pro Lys Thr Glu Ala
35 40 45

Asn Trp Val Asn Val Ile Ser Asp Leu Lys Lys Ile Glu Asp Leu Ile
50 55 60

Gln Ser Met His Ile Asp Ala Thr Leu Tyr Thr Glu Ser Asp Val His
65 70 75 80

Pro Ser Cys Lys Val Thr Ala Met Lys Cys Phe Leu Leu Glu Leu Gln
85 90 95

Val Ile Ser Leu Glu Ser Gly Asp Ala Ser Ile His Asp Thr Val Glu
100 105 110

Asn Leu Ile Ile Leu Ala Asn Asn Ser Leu Ser Ser Asn Gly Asn Val
115 120 125

Thr Glu Ser Gly Cys Lys Glu Cys Glu Glu Leu Glu Glu Lys Asn Ile
130 135 140

Lys Glu Phe Leu Gln Ser Phe Val His Ile Val Gln Met Phe Ile Asn
145 150 155 160

Thr Ser

<210> SEQ ID NO 117
<211> LENGTH: 807
<212> TYPE: PRT
<213> ORGANISM: Staphylococcus aureus

<400> SEQUENCE: 117

Met Thr Tyr Arg Ile Lys Lys Trp Gln Lys Leu Ser Thr Ile Thr Leu
1 5 10 15

Leu Met Ala Gly Val Ile Thr Leu Asn Gly Gly Glu Phe Arg Ser Val
20 25 30

Asp Lys His Gln Ile Ala Val Ala Asp Thr Asn Val Gln Thr Pro Asp
35 40 45

Tyr Glu Lys Leu Arg Asn Thr Trp Leu Asp Val Asn Tyr Gly Tyr Asp
50 55 60

Lys Tyr Asp Glu Asn Asn Pro Asp Met Lys Lys Lys Phe Asp Ala Thr
65 70 75 80

Glu Lys Glu Ala Thr Asn Leu Leu Lys Glu Met Lys Thr Glu Ser Gly
85 90 95

Arg Lys Tyr Leu Trp Ser Gly Ala Glu Thr Leu Glu Thr Asn Ser Ser
100 105 110

His Met Thr Arg Thr Tyr Arg Asn Ile Glu Lys Ile Ala Glu Ala Met
115 120 125

Arg Asn Pro Lys Thr Thr Leu Asn Thr Asp Glu Asn Lys Lys Lys Val
130 135 140

Lys Asp Ala Leu Glu Trp Leu His Lys Asn Ala Tyr Gly Lys Glu Pro
145 150 155 160

Asp Lys Lys Val Lys Glu Leu Ser Glu Asn Phe Thr Lys Thr Thr Gly
165 170 175

Lys Asn Thr Asn Leu Asn Trp Trp Asp Tyr Glu Ile Gly Thr Pro Lys
180 185 190

Ser Leu Thr Asn Thr Leu Ile Leu Leu Asn Asp Gln Phe Ser Asn Glu
195 200 205

```
Glu Lys Lys Lys Phe Thr Ala Pro Ile Lys Thr Phe Ala Pro Asp Ser
    210                 215                 220

Asp Lys Ile Leu Ser Ser Val Gly Lys Ala Glu Leu Ala Lys Gly Gly
225                 230                 235                 240

Asn Leu Val Asp Ile Ser Lys Val Lys Leu Leu Glu Cys Ile Ile Glu
                245                 250                 255

Glu Asp Lys Asp Met Met Lys Lys Ser Ile Asp Ser Phe Asn Lys Val
            260                 265                 270

Phe Thr Tyr Val Gln Asp Ser Ala Thr Gly Lys Glu Arg Asn Gly Phe
        275                 280                 285

Tyr Lys Asp Gly Ser Tyr Ile Asp His Gln Asp Val Pro Tyr Thr Gly
    290                 295                 300

Ala Tyr Gly Val Val Leu Leu Glu Gly Ile Ser Gln Met Met Pro Met
305                 310                 315                 320

Ile Lys Glu Thr Pro Phe Asn Asp Lys Thr Gln Asn Asp Thr Thr Leu
                325                 330                 335

Lys Ser Trp Ile Asp Asp Gly Phe Met Pro Leu Ile Tyr Lys Gly Glu
            340                 345                 350

Met Met Asp Leu Ser Arg Gly Arg Ala Ile Ser Arg Glu Asn Glu Thr
        355                 360                 365

Ser His Ser Ala Ser Ala Thr Val Met Lys Ser Leu Leu Arg Leu Ser
    370                 375                 380

Asp Ala Met Asp Asp Ser Thr Lys Ala Lys Tyr Lys Lys Ile Val Lys
385                 390                 395                 400

Ser Ser Val Glu Ser Asp Ser Ser Tyr Lys Gln Asn Asp Tyr Leu Asn
                405                 410                 415

Ser Tyr Ser Asp Ile Asp Lys Met Lys Ser Leu Met Thr Asp Asn Ser
            420                 425                 430

Ile Ser Lys Asn Gly Leu Thr Gln Gln Leu Lys Ile Tyr Asn Asp Met
        435                 440                 445

Asp Arg Val Thr Tyr His Asn Lys Asp Leu Asp Phe Ala Phe Gly Leu
    450                 455                 460

Ser Met Thr Ser Lys Asn Val Ala Arg Tyr Glu Ser Ile Asn Gly Glu
465                 470                 475                 480

Asn Leu Lys Gly Trp His Thr Gly Ala Gly Met Ser Tyr Leu Tyr Asn
                485                 490                 495

Ser Asp Val Lys His Tyr His Asp Asn Phe Trp Val Thr Ala Asp Met
            500                 505                 510

Lys Arg Leu Ser Gly Thr Thr Thr Leu Asp Asn Glu Ile Leu Lys Asp
        515                 520                 525

Thr Asp Asp Lys Lys Ser Ser Lys Thr Phe Val Gly Gly Thr Lys Val
    530                 535                 540

Asp Asp Gln His Ala Ser Ile Gly Met Asp Phe Glu Asn Gln Asp Lys
545                 550                 555                 560

Thr Leu Thr Ala Lys Lys Ser Tyr Phe Ile Leu Asn Asp Lys Ile Val
                565                 570                 575

Phe Leu Gly Thr Gly Ile Lys Ser Thr Asp Ser Ser Lys Asn Pro Val
            580                 585                 590

Thr Thr Ile Glu Asn Arg Lys Ala Asn Gly Tyr Thr Leu Tyr Thr Asp
        595                 600                 605

Asp Lys Gln Thr Thr Asn Ser Asp Asn Gln Glu Asn Asn Ser Val Phe
    610                 615                 620
```

Leu Glu Ser Thr Asp Thr Lys Lys Asn Ile Gly Tyr His Phe Leu Asn
625 630 635 640

Lys Pro Lys Ile Thr Val Lys Lys Glu Ser His Thr Gly Lys Trp Lys
645 650 655

Glu Ile Asn Lys Ser Gln Lys Asp Thr Gln Lys Thr Asp Glu Tyr Tyr
660 665 670

Glu Val Thr Gln Lys His Ser Asn Ser Asp Asn Lys Tyr Gly Tyr Val
675 680 685

Leu Tyr Pro Gly Leu Ser Lys Asp Val Phe Lys Thr Lys Lys Asp Glu
690 695 700

Val Thr Val Val Lys Gln Glu Asp Asp Phe His Val Val Lys Asp Asn
705 710 715 720

Glu Ser Val Trp Ala Gly Val Asn Tyr Ser Asn Ser Thr Gln Thr Phe
725 730 735

Asp Ile Asn Asn Thr Lys Val Glu Val Lys Ala Lys Gly Met Phe Ile
740 745 750

Leu Lys Lys Lys Asp Asp Asn Thr Tyr Glu Cys Ser Phe Tyr Asn Pro
755 760 765

Glu Ser Thr Asn Ser Ala Ser Asp Ile Glu Ser Lys Ile Ser Met Thr
770 775 780

Gly Tyr Ser Ile Thr Asn Lys Asn Thr Ser Thr Ser Asn Glu Ser Gly
785 790 795 800

Val His Phe Glu Leu Thr Lys
805

<210> SEQ ID NO 118
<211> LENGTH: 493
<212> TYPE: PRT
<213> ORGANISM: Sus scrofa

<400> SEQUENCE: 118

Met Gly Val Gln Arg Leu Gln His Ile Ser Phe Arg Ser Phe Phe Val
1 5 10 15

Pro Ser Gly Ala Pro Gln Val Val Phe Thr Phe Leu Leu Ile Pro Cys
20 25 30

Cys Leu Ala Leu Asp Phe Arg Ala Ser Pro Ile Ile Pro Asn Thr Thr
35 40 45

Phe Leu Trp Val Trp Asn Ala Pro Thr Glu Ser Cys Ala Lys Lys Phe
50 55 60

Tyr Met Pro Pro Asp Leu Ser Leu Phe Ser Phe Val Thr Ser Pro Arg
65 70 75 80

Ala Ser Val Thr Gly Gln Phe Leu Thr Leu Phe Tyr Ala Asn Arg Leu
85 90 95

Gly Tyr Tyr Pro His Val Asp Glu Asn Thr Gly Lys Asn Val Asn Gly
100 105 110

Gly Ile Pro Gln Leu Gly Ser Leu Gln Arg His Leu Asp Lys Ala Glu
115 120 125

Lys Asp Ile Leu His Tyr Met Gln Ile Asp Lys Val Gly Leu Ser Val
130 135 140

Ile Asp Trp Glu Asn Trp Arg Pro Thr Trp Glu Arg Asn Trp Lys Glu
145 150 155 160

Lys Ala Ile Tyr Arg Arg Gln Ser Ile Glu Leu Val Gln Gln Lys Asn
165 170 175

Ile Lys Leu Thr Pro Ala Ala Ala Thr Lys Leu Ala Lys Arg Glu Phe
180 185 190

Glu Lys Ala Gly Lys Thr Phe Met Gln Glu Thr Leu Lys Leu Gly Lys
195 200 205

Leu Leu Arg Pro Asn His Leu Trp Gly Tyr Tyr Leu Phe Pro Asp Cys
210 215 220

Tyr Asn His Asn Tyr His Lys Pro Gly Tyr Asn Gly Ser Cys Leu Asp
225 230 235 240

Ile Glu Lys Arg Arg Asn Asp Ala Leu Asp Trp Leu Trp Lys Glu Ser
245 250 255

Thr Ala Leu Phe Pro Ser Ile Tyr Leu Asn Thr Arg Leu Lys Pro Ser
260 265 270

Gln Val Ala Leu Phe Val Arg Asn Arg Val Gln Glu Ala Ile Arg Val
275 280 285

Ser Lys Val Ala Asn Ala Gln Ser Pro Leu Pro Val Phe Val Tyr Thr
290 295 300

Arg Pro Val Phe Ser Gly Ala Ser Ser Arg Tyr Leu Ser Gln Asp Asp
305 310 315 320

Leu Val Asn Thr Ile Gly Glu Thr Val Ala Leu Gly Ala Ser Gly Ile
325 330 335

Val Met Trp Gly Ser Leu Asn Leu Ser Leu Thr Met Gln Ser Cys Met
340 345 350

Asn Leu Gly Ser Tyr Leu Lys Thr Thr Leu Asn Pro Tyr Leu Ile Asn
355 360 365

Val Thr Leu Ala Ala Lys Met Cys Ser Gln Val Leu Cys Gln Glu Gln
370 375 380

Gly Val Cys Thr Arg Lys His Trp Asn Ser Ser Asp Tyr Leu His Leu
385 390 395 400

Asn Pro Ala Asn Phe Ala Ile Arg Thr Gly Lys Gly Asn Lys Tyr Ile
405 410 415

Val His Gly Lys Pro Thr Leu Glu Asp Leu Lys Glu Phe Ser Lys Asn
420 425 430

Phe Tyr Cys Ser Cys Phe Ala Asn Phe His Cys Lys Glu Arg Ala Asp
435 440 445

Ile Glu Asn Ile His Ala Ile Asn Val Cys Ile Thr Glu Asp Val Cys
450 455 460

Val Glu Ala Phe Leu Asn Ser Glu Pro Glu Leu Pro Asp Glu Val Gln
465 470 475 480

Gln Asp Asn Gln Pro Pro Cys Gly Gly Ser Gly Arg Cys
485 490

<210> SEQ ID NO 119
<211> LENGTH: 240
<212> TYPE: PRT
<213> ORGANISM: Homo sapiens

<400> SEQUENCE: 119

Met Glu Glu Ser Val Val Arg Pro Ser Val Phe Val Val Asp Gly Gln
1 5 10 15

Thr Asp Ile Pro Phe Thr Arg Leu Gly Arg Ser His Arg Arg Gln Ser
20 25 30

Cys Ser Val Ala Arg Val Gly Leu Gly Leu Leu Leu Leu Leu Met Gly
35 40 45

Ala Gly Leu Ala Val Gln Gly Trp Phe Leu Leu Gln Leu His Trp Arg
50 55 60

Leu Gly Glu Met Val Thr Arg Leu Pro Asp Gly Pro Ala Gly Ser Trp

```
65                  70                  75                  80

Glu Gln Leu Ile Gln Glu Arg Arg Ser His Glu Val Asn Pro Ala Ala
                85                  90                  95

His Leu Thr Gly Ala Asn Ser Ser Leu Thr Gly Ser Gly Gly Pro Leu
            100                 105                 110

Leu Trp Glu Thr Gln Leu Gly Leu Ala Phe Leu Arg Gly Leu Ser Tyr
        115                 120                 125

His Asp Gly Ala Leu Val Val Thr Lys Ala Gly Tyr Tyr Tyr Ile Tyr
    130                 135                 140

Ser Lys Val Gln Leu Gly Gly Val Gly Cys Pro Leu Gly Leu Ala Ser
145                 150                 155                 160

Thr Ile Thr His Gly Leu Tyr Lys Arg Thr Pro Arg Tyr Pro Glu Glu
                165                 170                 175

Leu Glu Leu Leu Val Ser Gln Gln Ser Pro Cys Gly Arg Ala Thr Ser
            180                 185                 190

Ser Ser Arg Val Trp Trp Asp Ser Ser Phe Leu Gly Gly Val Val His
        195                 200                 205

Leu Glu Ala Gly Glu Lys Val Val Val Arg Val Leu Asp Glu Arg Leu
    210                 215                 220

Val Arg Leu Arg Asp Gly Thr Arg Ser Tyr Phe Gly Ala Phe Met Val
225                 230                 235                 240


<210> SEQ ID NO 120
<211> LENGTH: 94
<212> TYPE: PRT
<213> ORGANISM: Homo sapiens

<400> SEQUENCE: 120

Met Ser Val Lys Gly Met Ala Ile Ala Leu Ala Val Ile Leu Cys Ala
1               5                   10                  15

Thr Val Val Gln Gly Phe Pro Met Phe Lys Arg Gly Arg Cys Leu Cys
            20                  25                  30

Ile Gly Pro Gly Val Lys Ala Val Lys Val Ala Asp Ile Glu Lys Ala
        35                  40                  45

Ser Ile Met Tyr Pro Ser Asn Asn Cys Asp Lys Ile Glu Val Ile Ile
    50                  55                  60

Thr Leu Lys Glu Asn Lys Gly Gln Arg Cys Leu Asn Pro Lys Ser Lys
65                  70                  75                  80

Gln Ala Arg Leu Ile Ile Lys Lys Val Glu Arg Lys Asn Phe
                85                  90


<210> SEQ ID NO 121
<211> LENGTH: 397
<212> TYPE: PRT
<213> ORGANISM: Homo sapiens

<400> SEQUENCE: 121

Met Ala Pro Ile Ser Leu Ser Trp Leu Leu Arg Leu Ala Thr Phe Cys
1               5                   10                  15

His Leu Thr Val Leu Leu Ala Gly Gln His His Gly Val Thr Lys Cys
            20                  25                  30

Asn Ile Thr Cys Ser Lys Met Thr Ser Lys Ile Pro Val Ala Leu Leu
        35                  40                  45

Ile His Tyr Gln Gln Asn Gln Ala Ser Cys Gly Lys Arg Ala Ile Ile
    50                  55                  60

Leu Glu Thr Arg Gln His Arg Leu Phe Cys Ala Asp Pro Lys Glu Gln
```

```
65                  70                  75                  80

Trp Val Lys Asp Ala Met Gln His Leu Asp Arg Gln Ala Ala Ala Leu
                85                  90                  95

Thr Arg Asn Gly Gly Thr Phe Glu Lys Gln Ile Gly Glu Val Lys Pro
            100                 105                 110

Arg Thr Thr Pro Ala Ala Gly Gly Met Asp Glu Ser Val Val Leu Glu
        115                 120                 125

Pro Glu Ala Thr Gly Glu Ser Ser Ser Leu Glu Pro Thr Pro Ser Ser
    130                 135                 140

Gln Glu Ala Gln Arg Ala Leu Gly Thr Ser Pro Glu Leu Pro Thr Gly
145                 150                 155                 160

Val Thr Gly Ser Ser Gly Thr Arg Leu Pro Pro Thr Pro Lys Ala Gln
                165                 170                 175

Asp Gly Gly Pro Val Gly Thr Glu Leu Phe Arg Val Pro Pro Val Ser
            180                 185                 190

Thr Ala Ala Thr Trp Gln Ser Ser Ala Pro His Gln Pro Gly Pro Ser
        195                 200                 205

Leu Trp Ala Glu Ala Lys Thr Ser Glu Ala Pro Ser Thr Gln Asp Pro
    210                 215                 220

Ser Thr Gln Ala Ser Thr Ala Ser Ser Pro Ala Pro Glu Glu Asn Ala
225                 230                 235                 240

Pro Ser Glu Gly Gln Arg Val Trp Gly Gln Gly Gln Ser Pro Arg Pro
                245                 250                 255

Glu Asn Ser Leu Glu Arg Glu Glu Met Gly Pro Val Pro Ala His Thr
            260                 265                 270

Asp Ala Phe Gln Asp Trp Gly Pro Gly Ser Met Ala His Val Ser Val
        275                 280                 285

Val Pro Val Ser Ser Glu Gly Thr Pro Ser Arg Glu Pro Val Ala Ser
    290                 295                 300

Gly Ser Trp Thr Pro Lys Ala Glu Glu Pro Ile His Ala Thr Met Asp
305                 310                 315                 320

Pro Gln Arg Leu Gly Val Leu Ile Thr Pro Val Pro Asp Ala Gln Ala
                325                 330                 335

Ala Thr Arg Arg Gln Ala Val Gly Leu Leu Ala Phe Leu Gly Leu Leu
            340                 345                 350

Phe Cys Leu Gly Val Ala Met Phe Thr Tyr Gln Ser Leu Gln Gly Cys
        355                 360                 365

Pro Arg Lys Met Ala Gly Glu Met Ala Glu Gly Leu Arg Tyr Ile Pro
    370                 375                 380

Arg Ser Cys Gly Ser Asn Ser Tyr Val Leu Val Pro Val
385                 390                 395


<210> SEQ ID NO 122
<211> LENGTH: 788
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

Met Asp Trp Thr Trp Ile Leu Phe Leu Val Ala Ala Ala Thr Arg Val
1               5                   10                  15

His Ser Gly Arg Asp Thr Asn Val Gln Thr Pro Asp Tyr Glu Lys Leu
            20                  25                  30
```

```
Arg Asn Thr Trp Leu Asn Val Asn Tyr Gly Tyr Asp Gln Tyr Asp Glu
        35                  40                  45

Lys Asn Asp Ala Met Lys Lys Lys Phe Asp Ala Thr Glu Lys Glu Ala
    50                  55                  60

Glu Lys Leu Leu Ser Ser Met Lys Thr Glu Ser Gly Arg Thr Tyr Leu
65                  70                  75                  80

Trp Asp Ser Ala Lys Asp Leu Asp Asn Lys Ser Ala Asp Met Thr Arg
                85                  90                  95

Thr Tyr Arg Asn Ile Glu Lys Ile Ala Glu Ala Met Lys His Lys Asp
            100                 105                 110

Thr Lys Leu Asn Thr Pro Asp Asn Lys Asn Lys Val Lys Asp Ala Leu
        115                 120                 125

Glu Trp Leu His Lys Asn Ala Tyr Gly Lys Glu Pro Val Lys Lys Leu
    130                 135                 140

Glu Glu Leu Lys Thr Asn Phe Ser Lys Ser Ala Pro Gln Lys Asn Thr
145                 150                 155                 160

Asn Leu Asn Trp Trp Asp Tyr Glu Ile Gly Thr Pro Arg Ala Leu Thr
                165                 170                 175

Asn Thr Leu Ile Leu Leu Lys Glu Asp Phe Thr Asp Glu Glu Lys Lys
            180                 185                 190

Lys Tyr Thr Ala Pro Ile Lys Thr Phe Ala Pro Lys Ser Asp Glu Ile
        195                 200                 205

Leu Ser Ser Val Gly Lys Ala Glu Pro Ala Lys Gly Gly Asn Leu Val
    210                 215                 220

Asp Ile Ser Lys Val Lys Leu Leu Glu Ser Ile Ile Glu Glu Asp Ala
225                 230                 235                 240

Thr Met Met Lys Glu Ser Ile Glu Ala Phe Asn Lys Val Phe Thr Tyr
                245                 250                 255

Val Gln Ser Asn Ala Thr Gly Lys Glu Arg Asn Gly Phe Tyr Lys Asp
            260                 265                 270

Gly Ser Tyr Ile Asp His Gln Asp Val Pro Tyr Thr Gly Ala Tyr Gly
        275                 280                 285

Val Val Leu Leu Glu Gly Ile Ser Gln Met Met Pro Met Ile Lys Glu
    290                 295                 300

Thr Pro Phe Lys Asp Ser Asn Gln Asn Asp Thr Thr Leu Lys Ser Trp
305                 310                 315                 320

Ile Asp Glu Gly Phe Met Pro Leu Ile Tyr Lys Gly Glu Met Met Asp
                325                 330                 335

Leu Ser Arg Gly Arg Ala Ile Ser Arg Glu Asn Glu Thr Ser His Ser
            340                 345                 350

Thr Ser Ala Thr Val Met Lys Ser Leu Leu Arg Leu Ser Asp Ala Met
        355                 360                 365

Asp Glu Ser Thr Lys Ala Lys Tyr Lys Gln Ile Val Lys Thr Ser Val
    370                 375                 380

Lys Ser Asp Ser Ser Tyr Lys Gln Asn Asp Tyr Leu Ser Ser Tyr Ser
385                 390                 395                 400

Asp Ile Ser Lys Met Lys Ser Leu Ile Glu Asp Ser Thr Ile Ser Thr
                405                 410                 415

Asn Gly Leu Thr Gln Gln Leu Lys Ile Tyr Asn Asp Met Asn Arg Val
            420                 425                 430

Thr Tyr His Asn Lys Asp Leu Asp Phe Ala Phe Gly Leu Ser Met Thr
        435                 440                 445

Ser Lys Asn Val Ala His Tyr Glu Ser Ile Asn Gly Glu Asn Leu Lys
```

```
    450                 455                 460

Gly Trp His Thr Gly Ala Gly Met Ser Tyr Leu Tyr Asn Ser Asp Val
465                 470                 475                 480

Lys His Tyr Arg Asp Asn Phe Trp Ala Thr Ala Asp Met Lys Arg Leu
                485                 490                 495

Ala Gly Thr Thr Thr Leu Asp Asn Glu Glu Pro Lys Glu Asn Lys Asn
            500                 505                 510

Ser Asp Lys Thr Phe Val Gly Gly Thr Lys Phe Asp Asp Gln His Ala
        515                 520                 525

Ser Ile Gly Met Asp Phe Glu Asn Gln Asp Lys Thr Leu Thr Ala Lys
    530                 535                 540

Lys Ser Tyr Phe Ile Leu Asn Asp Lys Ile Val Phe Leu Gly Thr Gly
545                 550                 555                 560

Ile Lys Ser Thr Asp Ser Ser Lys Asn Pro Val Thr Thr Ile Glu Asn
                565                 570                 575

Arg Lys Ser Asn Gly Tyr Thr Leu Phe Thr Asp Asp Lys Gln Thr Thr
            580                 585                 590

Ala Ser Asn Ile Asn Asp Gln Glu Thr Asn Ser Val Phe Leu Glu Ser
        595                 600                 605

Thr Asp Thr Lys Lys Asn Ile Gly Tyr His Phe Leu Asn Glu Ser Lys
    610                 615                 620

Ile Thr Val Lys Lys Glu Ser His Thr Gly Lys Trp Ser Asp Ile Asn
625                 630                 635                 640

Lys Ser Gln Lys Ser Asp Asp Lys Thr Asp Glu Tyr Tyr Glu Val Thr
                645                 650                 655

Gln Lys His Ser Asn Thr Asp Asp Lys Tyr Ala Tyr Val Leu Tyr Pro
            660                 665                 670

Gly Leu Ser Lys Asp Asn Phe Lys Ser Lys Ala Ser Gln Val Thr Ile
        675                 680                 685

Val Lys Gln Asp Asp Asp Phe His Ile Val Lys Asp Asn Glu Ser Val
    690                 695                 700

Trp Ala Gly Val Asn Tyr Ser Asn Ser Thr Gln Thr Phe Asp Ile Asn
705                 710                 715                 720

Asn Thr Lys Val Glu Val Lys Ala Lys Gly Met Phe Ile Leu Lys Asn
                725                 730                 735

Lys Asp Asp Asn Thr Tyr Glu Cys Ser Phe Tyr Asn Pro Glu Ser Thr
            740                 745                 750

Asn Thr Ala Ser Asp Ile Glu Ser Lys Ile Ser Met Thr Gly Tyr Ser
        755                 760                 765

Ile Thr Asn Lys Asn Thr Ser Thr Ser Asn Glu Ser Gly Val His Phe
    770                 775                 780

Glu Leu Thr Lys
785


<210> SEQ ID NO 123
<211> LENGTH: 807
<212> TYPE: PRT
<213> ORGANISM: Staphylococcus aureus

<400> SEQUENCE: 123

Met Thr Tyr Arg Ile Lys Lys Trp Gln Lys Leu Ser Thr Ile Thr Leu
1               5                   10                  15

Leu Met Ala Gly Val Ile Thr Leu Asn Gly Gly Glu Phe Arg Ser Val
            20                  25                  30
```

```
Asp Lys His Gln Ile Ala Val Ala Asp Thr Asn Val Gln Thr Pro Asp
        35                  40                  45

Tyr Glu Lys Leu Arg Asn Thr Trp Leu Asp Val Asn Tyr Gly Tyr Asp
    50                  55                  60

Lys Tyr Asp Glu Asn Asn Pro Asp Met Lys Lys Lys Phe Asp Ala Thr
65                  70                  75                  80

Glu Lys Glu Ala Thr Asn Leu Leu Lys Glu Met Lys Thr Glu Ser Gly
                85                  90                  95

Arg Lys Tyr Leu Trp Ser Gly Ala Glu Thr Leu Glu Thr Asn Ser Ser
            100                 105                 110

His Met Thr Arg Thr Tyr Arg Asn Ile Glu Lys Ile Ala Glu Ala Met
        115                 120                 125

Arg Asn Pro Lys Thr Thr Leu Asn Thr Asp Glu Asn Lys Lys Lys Val
    130                 135                 140

Lys Asp Ala Leu Glu Trp Leu His Lys Asn Ala Tyr Gly Lys Glu Pro
145                 150                 155                 160

Asp Lys Lys Val Lys Glu Leu Ser Glu Asn Phe Thr Lys Thr Thr Gly
                165                 170                 175

Lys Asn Thr Asn Leu Asn Trp Trp Asp Tyr Glu Ile Gly Thr Pro Lys
            180                 185                 190

Ser Leu Thr Asn Thr Leu Ile Leu Leu Asn Asp Gln Phe Ser Asn Glu
        195                 200                 205

Glu Lys Lys Lys Phe Thr Ala Pro Ile Lys Thr Phe Ala Pro Asp Ser
    210                 215                 220

Asp Lys Ile Leu Ser Ser Val Gly Lys Ala Glu Leu Ala Lys Gly Gly
225                 230                 235                 240

Asn Leu Val Asp Ile Ser Lys Val Lys Leu Leu Glu Cys Ile Ile Glu
                245                 250                 255

Glu Asp Lys Asp Met Met Lys Lys Ser Ile Asp Ser Phe Asn Lys Val
            260                 265                 270

Phe Thr Tyr Val Gln Asp Ser Ala Thr Gly Lys Glu Arg Asn Gly Phe
        275                 280                 285

Tyr Lys Asp Gly Ser Tyr Ile Asp His Gln Asp Val Pro Tyr Thr Gly
    290                 295                 300

Ala Tyr Gly Val Val Leu Leu Glu Gly Ile Ser Gln Met Met Pro Met
305                 310                 315                 320

Ile Lys Glu Thr Pro Phe Asn Asp Lys Thr Gln Asn Asp Thr Thr Leu
                325                 330                 335

Lys Ser Trp Ile Asp Asp Gly Phe Met Pro Leu Ile Tyr Lys Gly Glu
            340                 345                 350

Met Met Asp Leu Ser Arg Gly Arg Ala Ile Ser Arg Glu Asn Glu Thr
        355                 360                 365

Ser His Ser Ala Ser Ala Thr Val Met Lys Ser Leu Leu Arg Leu Ser
    370                 375                 380

Asp Ala Met Asp Asp Ser Thr Lys Ala Lys Tyr Lys Lys Ile Val Lys
385                 390                 395                 400

Ser Ser Val Glu Ser Asp Ser Ser Tyr Lys Gln Asn Asp Tyr Leu Asn
                405                 410                 415

Ser Tyr Ser Asp Ile Asp Lys Met Lys Ser Leu Met Thr Asp Asn Ser
            420                 425                 430

Ile Ser Lys Asn Gly Leu Thr Gln Gln Leu Lys Ile Tyr Asn Asp Met
        435                 440                 445

Asp Arg Val Thr Tyr His Asn Lys Asp Leu Asp Phe Ala Phe Gly Leu
```

```
    450                 455                 460

Ser Met Thr Ser Lys Asn Val Ala Arg Tyr Glu Ser Ile Asn Gly Glu
465                 470                 475                 480

Asn Leu Lys Gly Trp His Thr Gly Ala Gly Met Ser Tyr Leu Tyr Asn
                485                 490                 495

Ser Asp Val Lys His Tyr His Asp Asn Phe Trp Val Thr Ala Asp Met
            500                 505                 510

Lys Arg Leu Ser Gly Thr Thr Thr Leu Asp Asn Glu Ile Leu Lys Asp
        515                 520                 525

Thr Asp Asp Lys Lys Ser Ser Lys Thr Phe Val Gly Gly Thr Lys Val
    530                 535                 540

Asp Asp Gln His Ala Ser Ile Gly Met Asp Phe Glu Asn Gln Asp Lys
545                 550                 555                 560

Thr Leu Thr Ala Lys Lys Ser Tyr Phe Ile Leu Asn Asp Lys Ile Val
                565                 570                 575

Phe Leu Gly Thr Gly Ile Lys Ser Thr Asp Ser Ser Lys Asn Pro Val
            580                 585                 590

Thr Thr Ile Glu Asn Arg Lys Ala Asn Gly Tyr Thr Leu Tyr Thr Asp
        595                 600                 605

Asp Lys Gln Thr Thr Asn Ser Asp Asn Gln Glu Asn Asn Ser Val Phe
    610                 615                 620

Leu Glu Ser Thr Asp Thr Lys Lys Asn Ile Gly Tyr His Phe Leu Asn
625                 630                 635                 640

Lys Pro Lys Ile Thr Val Lys Lys Glu Ser His Thr Gly Lys Trp Lys
                645                 650                 655

Glu Ile Asn Lys Ser Gln Lys Asp Thr Gln Lys Thr Asp Glu Tyr Tyr
            660                 665                 670

Glu Val Thr Gln Lys His Ser Asn Ser Asp Asn Lys Tyr Gly Tyr Val
        675                 680                 685

Leu Tyr Pro Gly Leu Ser Lys Asp Val Phe Lys Thr Lys Lys Asp Glu
    690                 695                 700

Val Thr Val Val Lys Gln Glu Asp Asp Phe His Val Val Lys Asp Asn
705                 710                 715                 720

Glu Ser Val Trp Ala Gly Val Asn Tyr Ser Asn Ser Thr Gln Thr Phe
                725                 730                 735

Asp Ile Asn Asn Thr Lys Val Glu Val Lys Ala Lys Gly Met Phe Ile
            740                 745                 750

Leu Lys Lys Lys Asp Asp Asn Thr Tyr Glu Cys Ser Phe Tyr Asn Pro
        755                 760                 765

Glu Ser Thr Asn Ser Ala Ser Asp Ile Glu Ser Lys Ile Ser Met Thr
    770                 775                 780

Gly Tyr Ser Ile Thr Asn Lys Asn Thr Ser Thr Ser Asn Glu Ser Gly
785                 790                 795                 800

Val His Phe Glu Leu Thr Lys
                805


<210> SEQ ID NO 124
<211> LENGTH: 400
<212> TYPE: PRT
<213> ORGANISM: Loxosceles intermedia

<400> SEQUENCE: 124

Met Asp Trp Thr Trp Ile Leu Phe Leu Val Ala Ala Ala Thr Arg Val
1               5                   10                  15
```

-continued

```
His Ser Gly Arg Asp Val Phe Trp Asn Val Pro Ser Gln Gln Cys Lys
            20                  25                  30

Lys Tyr Gly Met Lys Phe Val Pro Leu Leu Glu Gln Tyr Ser Ile Leu
        35                  40                  45

Val Asn Lys Glu Asp Asn Phe Lys Gly Asp Lys Ile Thr Ile Phe Tyr
    50                  55                  60

Glu Ser Gln Leu Gly Leu Tyr Pro His Ile Gly Ala Asn Asp Glu Ser
65                  70                  75                  80

Phe Asn Gly Gly Ile Pro Gln Leu Gly Asp Leu Lys Ala His Leu Glu
                85                  90                  95

Lys Ser Ala Val Asp Ile Arg Arg Asp Ile Leu Asp Lys Ser Ala Thr
            100                 105                 110

Gly Leu Arg Ile Ile Asp Trp Glu Ala Trp Arg Pro Ile Trp Glu Phe
        115                 120                 125

Asn Trp Ser Ser Leu Arg Lys Tyr Gln Asp Lys Met Lys Lys Val Val
    130                 135                 140

Arg Gln Phe Asn Pro Thr Ala His Glu Ser Thr Val Ala Lys Leu Ala
145                 150                 155                 160

His Asn Glu Trp Glu Asn Ser Ser Lys Ser Trp Met Leu Ser Thr Leu
                165                 170                 175

Gln Leu Gly Lys Gln Leu Arg Pro Asn Ser Val Trp Cys Tyr Tyr Leu
            180                 185                 190

Phe Pro Asp Cys Tyr Asn Tyr Asp Gly Asn Ser Val Gln Glu Phe Gln
        195                 200                 205

Cys Ser Glu Ala Ile Arg Lys Gly Asn Asp Arg Leu Lys Trp Leu Trp
    210                 215                 220

Glu Glu Ser Thr Ala Val Cys Pro Ser Ile Tyr Ile Lys Glu Gly Gln
225                 230                 235                 240

Leu Thr Asn Tyr Thr Leu Gln Lys Arg Ile Trp Phe Thr Asn Gly Arg
                245                 250                 255

Leu Gln Glu Ala Leu Arg Val Ala Gln Pro Lys Ala Arg Ile Tyr Pro
            260                 265                 270

Tyr Ile Asn Tyr Ser Ile Lys Pro Gly Met Met Val Pro Glu Val Glu
        275                 280                 285

Phe Trp Arg Leu Ile Ala Gln Ile Ala Ser Leu Gly Met Asp Gly Ala
    290                 295                 300

Val Ile Trp Gly Ser Ser Ala Ser Val Gly Ser Lys Asn His Cys Ala
305                 310                 315                 320

Gln Leu Met Lys Tyr Ile Ala Asp Val Leu Gly Pro Ala Thr Leu Arg
                325                 330                 335

Ile Lys Glu Asn Val Ala Arg Cys Ser Lys Gln Ala Cys Ser Gly Arg
            340                 345                 350

Gly Arg Cys Thr Trp Pro Lys Asp Thr Ser Val Ile Ala Trp Lys Phe
        355                 360                 365

Leu Val Glu Lys Glu Asp Tyr Asp Phe Tyr Leu Gly Asp Ile Glu Cys
    370                 375                 380

Lys Cys Val Glu Gly Tyr Glu Gly Arg Tyr Cys Glu Gln Lys Thr Lys
385                 390                 395                 400
```

<210> SEQ ID NO 125
<211> LENGTH: 230
<212> TYPE: PRT
<213> ORGANISM: Mycobacterium tuberculosis

<400> SEQUENCE: 125

```
Met Asp Trp Thr Trp Ile Leu Phe Leu Val Ala Ala Ala Thr Arg Val
1               5                   10                  15

His Ser Gly Arg Gly Ser Ala Ile Glu Glu Arg Thr Arg His Arg Ala
            20                  25                  30

Glu Thr Thr Thr Arg Glu Ile Cys Glu Ser Val Gly Gly Ala Asp Thr
        35                  40                  45

Val Leu Ser Arg Ile Asp Lys Asn Pro Glu Leu Glu Pro Leu Leu Ser
    50                  55                  60

Gln Ala Ile Glu Ala Ala Thr Arg Thr Ser Met Glu Ala Lys Arg Arg
65                  70                  75                  80

Leu Leu Ala Gln Ala Ala Ala Ala Ala Leu Glu Asp Asp Gln Lys Val
                85                  90                  95

Glu Pro Ala Ser Leu Ile Val Ala Thr Leu Ser Gln Leu Glu Pro Val
            100                 105                 110

His Ile His Ala Leu Val Arg Leu Ala Lys Ala Ala Lys Ser Ser Pro
        115                 120                 125

Asp Gln Asp Glu Ile Gln Arg Arg Glu Val Met Arg Ala Ala Ser Lys
    130                 135                 140

Val Glu Pro Val Pro Val Leu Ala Ala Leu Ile Gln Thr Gly Val Ala
145                 150                 155                 160

Ile Ala Thr Thr Thr Val Trp His Gly Asn Gly Thr Gly Thr Pro Ala
                165                 170                 175

Glu Glu Ser Gly His Ile Leu Ile His Asp Val Ser Asp Phe Gly His
            180                 185                 190

Arg Leu Leu Ala Tyr Leu Arg Ala Ala Asp Ala Gly Ala Glu Leu Leu
        195                 200                 205

Ile Leu Pro Ser Gly Gly Ser Ala Pro Thr Gly Asp His Pro Thr Pro
    210                 215                 220

His Pro Ser Thr Ser Arg
225                 230
```

<210> SEQ ID NO 126
<211> LENGTH: 244
<212> TYPE: PRT
<213> ORGANISM: Streptomyces koganeiensis

<400> SEQUENCE: 126

```
Met Asp Trp Thr Trp Ile Leu Phe Leu Val Ala Ala Ala Thr Arg Val
1               5                   10                  15

His Ser Gly Arg Ala Thr Gly Thr Ala Ser Ala Ala Gly Glu Asn Gly
            20                  25                  30

Ala Thr Thr Thr Phe Asp Gly Pro Val Ala Ala Glu Arg Phe Ser Ala
        35                  40                  45

Asp Thr Thr Leu Glu Ala Ala Phe Leu Lys Thr Thr Ser Glu Thr Asn
    50                  55                  60

His Ala Ala Thr Ile Tyr Gln Ala Gly Thr Ser Gly Asp Gly Ala Ala
65                  70                  75                  80

Leu Asn Val Ile Ser Asp Asn Pro Gly Thr Ser Ala Met Tyr Leu Ser
                85                  90                  95

Gly Thr Glu Thr Ala Arg Gly Thr Leu Lys Ile Thr His Arg Gly Tyr
            100                 105                 110

Ala Asp Gly Ser Asp Lys Asp Ala Ala Ala Leu Ser Leu Asp Leu Arg
        115                 120                 125

Val Ala Gly Thr Ala Ala Gln Gly Ile Tyr Val Thr Ala Thr Asn Gly
```

```
    130                 135                 140

Pro Thr Lys Gly Asn Leu Ile Ala Leu Arg Asn Asn Thr Gly Leu Asp
145                 150                 155                 160

Asp Phe Val Val Lys Gly Thr Gly Arg Ile Gly Val Gly Ile Asp Arg
                165                 170                 175

Ala Ala Thr Pro Arg Ala Gln Val His Ile Val Gln Arg Gly Asp Ala
            180                 185                 190

Leu Ala Ala Leu Leu Val Glu Gly Ser Val Arg Ile Gly Asn Ala Ala
        195                 200                 205

Thr Val Pro Thr Ser Val Asp Ser Ser Gly Gly Gly Ala Leu Tyr Ala
    210                 215                 220

Ser Gly Gly Ala Leu Leu Trp Arg Gly Ser Asn Gly Thr Val Thr Thr
225                 230                 235                 240

Ile Ala Pro Ala


<210> SEQ ID NO 127
<211> LENGTH: 400
<212> TYPE: PRT
<213> ORGANISM: Loxosceles intermedia

<400> SEQUENCE: 127

Met Gln Thr Ile Leu Val Leu Thr Thr Phe Leu Ser Ala Trp Phe Leu
1               5                   10                  15

Ala Val Gly Phe Asp Val Phe Trp Asn Val Pro Ser Gln Gln Cys Lys
            20                  25                  30

Lys Tyr Gly Met Lys Phe Val Pro Leu Leu Glu Gln Tyr Ser Ile Leu
        35                  40                  45

Val Asn Lys Glu Asp Asn Phe Lys Gly Asp Lys Ile Thr Ile Phe Tyr
    50                  55                  60

Glu Ser Gln Leu Gly Leu Tyr Pro His Ile Gly Ala Asn Asp Glu Ser
65                  70                  75                  80

Phe Asn Gly Gly Ile Pro Gln Leu Gly Asp Leu Lys Ala His Leu Glu
                85                  90                  95

Lys Ser Ala Val Asp Ile Arg Arg Asp Ile Leu Asp Lys Ser Ala Thr
            100                 105                 110

Gly Leu Arg Ile Ile Asp Trp Glu Ala Trp Arg Pro Ile Trp Glu Phe
        115                 120                 125

Asn Trp Ser Ser Leu Arg Lys Tyr Gln Asp Lys Met Lys Lys Val Val
    130                 135                 140

Arg Gln Phe Asn Pro Thr Ala His Glu Ser Thr Val Ala Lys Leu Ala
145                 150                 155                 160

His Asn Glu Trp Glu Asn Ser Ser Lys Ser Trp Met Leu Ser Thr Leu
                165                 170                 175

Gln Leu Gly Lys Gln Leu Arg Pro Asn Ser Val Trp Cys Tyr Tyr Leu
            180                 185                 190

Phe Pro Asp Cys Tyr Asn Tyr Asp Gly Asn Ser Val Gln Glu Phe Gln
        195                 200                 205

Cys Ser Glu Ala Ile Arg Lys Gly Asn Asp Arg Leu Lys Trp Leu Trp
    210                 215                 220

Glu Glu Ser Thr Ala Val Cys Pro Ser Ile Tyr Ile Lys Glu Gly Gln
225                 230                 235                 240

Leu Thr Asn Tyr Thr Leu Gln Lys Arg Ile Trp Phe Thr Asn Gly Arg
                245                 250                 255

Leu Gln Glu Ala Leu Arg Val Ala Gln Pro Lys Ala Arg Ile Tyr Pro
```

```
            260                 265                 270

Tyr Ile Asn Tyr Ser Ile Lys Pro Gly Met Met Val Pro Glu Val Glu
        275                 280                 285

Phe Trp Arg Leu Ile Ala Gln Ile Ala Ser Leu Gly Met Asp Gly Ala
    290                 295                 300

Val Ile Trp Gly Ser Ser Ala Ser Val Gly Ser Lys Asn His Cys Ala
305                 310                 315                 320

Gln Leu Met Lys Tyr Ile Ala Asp Val Leu Gly Pro Ala Thr Leu Arg
                325                 330                 335

Ile Lys Glu Asn Val Ala Arg Cys Ser Lys Gln Ala Cys Ser Gly Arg
            340                 345                 350

Gly Arg Cys Thr Trp Pro Lys Asp Thr Ser Val Ile Ala Trp Lys Phe
        355                 360                 365

Leu Val Glu Lys Glu Asp Tyr Asp Phe Tyr Leu Gly Asp Ile Glu Cys
    370                 375                 380

Lys Cys Val Glu Gly Tyr Glu Gly Arg Tyr Cys Glu Gln Lys Thr Lys
385                 390                 395                 400


<210> SEQ ID NO 128
<211> LENGTH: 239
<212> TYPE: PRT
<213> ORGANISM: Mycobacterium tuberculosis

<400> SEQUENCE: 128

Met Thr Glu Pro Arg Pro Val Phe Ala Val Val Ile Ser Ala Gly Leu
1               5                   10                  15

Ser Ala Ile Pro Met Val Gly Gly Pro Leu Gln Thr Val Phe Asp Ala
            20                  25                  30

Ile Glu Glu Arg Thr Arg His Arg Ala Glu Thr Thr Thr Arg Glu Ile
        35                  40                  45

Cys Glu Ser Val Gly Gly Ala Asp Thr Val Leu Ser Arg Ile Asp Lys
    50                  55                  60

Asn Pro Glu Leu Glu Pro Leu Leu Ser Gln Ala Ile Glu Ala Ala Thr
65                  70                  75                  80

Arg Thr Ser Met Glu Ala Lys Arg Arg Leu Leu Ala Gln Ala Ala Ala
                85                  90                  95

Ala Ala Leu Glu Asp Asp Gln Lys Val Glu Pro Ala Ser Leu Ile Val
            100                 105                 110

Ala Thr Leu Ser Gln Leu Glu Pro Val His Ile His Ala Leu Val Arg
        115                 120                 125

Leu Ala Lys Ala Ala Lys Ser Ser Pro Asp Gln Asp Glu Ile Gln Arg
    130                 135                 140

Arg Glu Val Met Arg Ala Ala Ser Lys Val Glu Pro Val Pro Val Leu
145                 150                 155                 160

Ala Ala Leu Ile Gln Thr Gly Val Ala Ile Ala Thr Thr Thr Val Trp
                165                 170                 175

His Gly Asn Gly Thr Gly Thr Pro Ala Glu Glu Ser Gly His Ile Leu
            180                 185                 190

Ile His Asp Val Ser Asp Phe Gly His Arg Leu Leu Ala Tyr Leu Arg
        195                 200                 205

Ala Ala Asp Ala Gly Ala Glu Leu Leu Ile Leu Pro Ser Gly Gly Ser
    210                 215                 220

Ala Pro Thr Gly Asp His Pro Thr Pro His Pro Ser Thr Ser Arg
225                 230                 235
```

<210> SEQ ID NO 129
<211> LENGTH: 247
<212> TYPE: PRT
<213> ORGANISM: Streptomyces koganeiensis

<400> SEQUENCE: 129

```
Met Pro Val Ala Arg Arg Leu Phe Leu Gly Ser Phe Thr Ala Gly Ala
1               5                   10                  15

Val Thr Val Ala Thr Ala Ala Ala Thr Gly Thr Ala Ser Ala Ala Gly
            20                  25                  30

Glu Asn Gly Ala Thr Thr Thr Phe Asp Gly Pro Val Ala Ala Glu Arg
        35                  40                  45

Phe Ser Ala Asp Thr Thr Leu Glu Ala Ala Phe Leu Lys Thr Thr Ser
    50                  55                  60

Glu Thr Asn His Ala Ala Thr Ile Tyr Gln Ala Gly Thr Ser Gly Asp
65                  70                  75                  80

Gly Ala Ala Leu Asn Val Ile Ser Asp Asn Pro Gly Thr Ser Ala Met
                85                  90                  95

Tyr Leu Ser Gly Thr Glu Thr Ala Arg Gly Thr Leu Lys Ile Thr His
            100                 105                 110

Arg Gly Tyr Ala Asp Gly Ser Asp Lys Asp Ala Ala Ala Leu Ser Leu
        115                 120                 125

Asp Leu Arg Val Ala Gly Thr Ala Ala Gln Gly Ile Tyr Val Thr Ala
    130                 135                 140

Thr Asn Gly Pro Thr Lys Gly Asn Leu Ile Ala Leu Arg Asn Asn Thr
145                 150                 155                 160

Gly Leu Asp Asp Phe Val Val Lys Gly Thr Gly Arg Ile Gly Val Gly
                165                 170                 175

Ile Asp Arg Ala Ala Thr Pro Arg Ala Gln Val His Ile Val Gln Arg
            180                 185                 190

Gly Asp Ala Leu Ala Ala Leu Leu Val Glu Gly Ser Val Arg Ile Gly
        195                 200                 205

Asn Ala Ala Thr Val Pro Thr Ser Val Asp Ser Ser Gly Gly Gly Ala
    210                 215                 220

Leu Tyr Ala Ser Gly Gly Ala Leu Leu Trp Arg Gly Ser Asn Gly Thr
225                 230                 235                 240

Val Thr Thr Ile Ala Pro Ala
                245
```

<210> SEQ ID NO 130
<211> LENGTH: 489
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 130

```
Met Gly Val Leu Lys Phe Lys His Ile Phe Phe Arg Ser Phe Val Lys
1               5                   10                  15

Ser Ser Gly Val Ser Gln Ile Val Phe Thr Phe Leu Leu Ile Pro Cys
            20                  25                  30

Cys Leu Thr Leu Asn Phe Arg Ala Pro Pro Val Ile Pro Asn Val Pro
        35                  40                  45

Phe Leu Trp Ala Trp Asn Ala Pro Ser Glu Phe Cys Leu Gly Lys Phe
    50                  55                  60
```

-continued

```
Asp Glu Pro Leu Asp Met Ser Leu Phe Ser Phe Ile Gly Ser Pro Arg
65                  70                  75                  80

Ile Asn Ala Thr Gly Gln Gly Val Thr Ile Phe Tyr Val Asp Arg Leu
                85                  90                  95

Gly Tyr Tyr Pro Tyr Ile Asp Ser Ile Thr Gly Val Thr Val Asn Gly
            100                 105                 110

Gly Ile Pro Gln Lys Ile Ser Leu Gln Asp His Leu Asp Lys Ala Lys
        115                 120                 125

Lys Asp Ile Thr Phe Tyr Met Pro Val Asp Asn Leu Gly Met Ala Val
    130                 135                 140

Ile Asp Trp Glu Glu Trp Arg Pro Thr Trp Ala Arg Asn Trp Lys Pro
145                 150                 155                 160

Lys Asp Val Tyr Lys Asn Arg Ser Ile Glu Leu Val Gln Gln Gln Asn
                165                 170                 175

Val Gln Leu Ser Leu Thr Glu Ala Thr Glu Lys Ala Lys Gln Glu Phe
            180                 185                 190

Glu Lys Ala Gly Lys Asp Phe Leu Val Glu Thr Ile Lys Leu Gly Lys
        195                 200                 205

Leu Leu Arg Pro Asn His Leu Trp Gly Tyr Tyr Leu Phe Pro Asp Cys
    210                 215                 220

Tyr Asn His His Tyr Lys Lys Pro Gly Tyr Asn Gly Ser Cys Phe Asn
225                 230                 235                 240

Val Glu Ile Lys Arg Asn Asp Asp Leu Ser Trp Leu Trp Asn Glu Ser
                245                 250                 255

Thr Ala Leu Tyr Pro Ser Ile Tyr Leu Asn Thr Gln Gln Ser Pro Val
            260                 265                 270

Ala Ala Thr Leu Tyr Val Arg Asn Arg Val Arg Glu Ala Ile Arg Val
        275                 280                 285

Ser Lys Ile Pro Asp Ala Lys Ser Pro Leu Pro Val Phe Ala Tyr Thr
    290                 295                 300

Arg Ile Val Phe Thr Asp Gln Val Leu Lys Phe Leu Ser Gln Asp Glu
305                 310                 315                 320

Leu Val Tyr Thr Phe Gly Glu Thr Val Ala Leu Gly Ala Ser Gly Ile
                325                 330                 335

Val Ile Trp Gly Thr Leu Ser Ile Met Arg Ser Met Lys Ser Cys Leu
            340                 345                 350

Leu Leu Asp Asn Tyr Met Glu Thr Ile Leu Asn Pro Tyr Ile Ile Asn
        355                 360                 365

Val Thr Leu Ala Ala Lys Met Cys Ser Gln Val Leu Cys Gln Glu Gln
    370                 375                 380

Gly Val Cys Ile Arg Lys Asn Trp Asn Ser Ser Asp Tyr Leu His Leu
385                 390                 395                 400

Asn Pro Asp Asn Phe Ala Ile Gln Leu Glu Lys Gly Gly Lys Phe Thr
                405                 410                 415

Val Arg Gly Lys Pro Thr Leu Glu Asp Leu Glu Gln Phe Ser Glu Lys
            420                 425                 430

Phe Tyr Cys Ser Cys Tyr Ser Thr Leu Ser Cys Lys Glu Lys Ala Asp
        435                 440                 445

Val Lys Asp Thr Asp Ala Val Asp Val Cys Ile Ala Asp Gly Val Cys
    450                 455                 460

Ile Asp Ala Phe Leu Lys Pro Pro Met Glu Thr Glu Glu Pro Gln Ile
465                 470                 475                 480
```

-continued

```
Phe Tyr Asn Ala Ser Pro Ser Thr Leu
                485


<210> SEQ ID NO 131
<211> LENGTH: 4
<212> TYPE: PRT
<213> ORGANISM: Unknown
<220> FEATURE:
<223> OTHER INFORMATION: Description of Unknown:
      DEAD-box helicase peptide

<400> SEQUENCE: 131

Asp Glu Ala Asp
1
```